US012767692B2

(12) United States Patent
Gutierrez et al.

(10) Patent No.: US 12,767,692 B2
(45) Date of Patent: Oct. 20, 2026

(54) MOLECULES FOR CONTROLLING AUTOIMMUNE RESPONSE

(71) Applicant: Merida Biosciences, Inc., Cambridge, MA (US)

(72) Inventors: Dario A. Gutierrez, Belmont, MA (US); Meike E. W. Logtenberg, Cambridge, MA (US); Allan D. Capili, Somerville, MA (US); Adrienne Marie Rothschilds, San Francisco, CA (US)

(73) Assignee: Merida Biosciences, Inc., Cambridge, MA (US)

( * ) Notice: Subject to any disclaimer, the term of this patent is extended or adjusted under 35 U.S.C. 154(b) by 0 days.

(21) Appl. No.: 19/358,364

(22) Filed: Oct. 14, 2025

(65) Prior Publication Data

US 2026/0167684 A1 Jun. 18, 2026

Related U.S. Application Data

(63) Continuation of application No. PCT/US2024/040515, filed on Aug. 1, 2024.

(60) Provisional application No. 63/517,101, filed on Aug. 1, 2023.

(51) Int. Cl.
*C07K 14/47* (2006.01)
*A61K 38/00* (2006.01)
*A61P 37/06* (2006.01)

(52) U.S. Cl.
CPC .............. *C07K 14/47* (2013.01); *A61P 37/06* (2018.01); *A61K 38/00* (2013.01); *C07K 2319/02* (2013.01)

(58) Field of Classification Search
None
See application file for complete search history.

(56) References Cited

U.S. PATENT DOCUMENTS 4,816,567 A 3/1989 Cabilly et al.
5,571,894 A 11/1996 Wels et al.
5,587,458 A 12/1996 King et al.
5,624,821 A 4/1997 Winter et al.
5,641,640 A 6/1997 Hanning
5,648,237 A 7/1997 Carter
5,789,199 A 8/1998 Joly et al.
5,840,523 A 11/1998 Simmons et al.
5,869,046 A 2/1999 Presta et al.
5,959,177 A 9/1999 Hein et al.
6,040,498 A 3/2000 Stomp et al.
6,194,551 B1 2/2001 Idusogie et al.
6,248,516 B1 6/2001 Winter et al.
6,417,429 B1 7/2002 Hein et al.
6,420,548 B1 7/2002 Vezina et al.
6,933,364 B1 8/2005 Hattori et al.
7,083,784 B2 8/2006 Dall'Acqua et al.
7,125,978 B1 10/2006 Vezina et al.
8,088,376 B2 1/2012 Chamberlain et al.
8,163,881 B2 4/2012 Ober
8,216,805 B2 7/2012 Carter et al.
8,399,618 B2 3/2013 Lazar et al.
8,802,823 B2 8/2014 Lazar et al.
8,834,871 B2 9/2014 Ober
8,883,147 B2 11/2014 Lazar et al.
8,969,526 B2 3/2015 Baehner et al.
9,051,373 B2 6/2015 Lazar et al.
9,243,071 B2 1/2016 Homma et al.
9,409,989 B2 8/2016 Arathoon et al.
9,657,106 B2 5/2017 Lazar et al.
9,663,582 B2 5/2017 Lazar et al.
9,714,282 B2 7/2017 Lazar et al.
9,862,772 B2 1/2018 Radbruch et al.
9,902,773 B2 2/2018 Chu et al.
10,183,999 B2 1/2019 Lazar et al.
11,459,375 B2 10/2022 Holthoff et al.
11,479,596 B2 10/2022 Song et al.
11,732,026 B2 8/2023 Rees Smith et al.
12,404,339 B2 9/2025 Ober et al.
12,410,233 B2 9/2025 Sung et al.
2004/0180046 A1 9/2004 Himawan
2012/0156207 A1 6/2012 Chu et al.
2014/0093496 A1* 4/2014 Mimoto .................. A61P 27/02 435/69.6
2015/0010584 A1 1/2015 Marshak-Rothstein et al.
2017/0204159 A1* 7/2017 Rees Smith ............ A61P 37/02
2018/0208668 A1 7/2018 Lazar et al.
2021/0221869 A1 7/2021 Song et al.
2021/0332411 A1 10/2021 Ma et al.
2022/0002409 A1 1/2022 Viney et al.

(Continued)

FOREIGN PATENT DOCUMENTS

WO WO-93/01161 A1 1/1993
WO WO-96/27011 A1 9/1996

(Continued)

OTHER PUBLICATIONS

Anania, J.C. et al., The human FcγRII (CD32) family of leukocyte FcR in health and disease, Front Immunol, 10:464 1-17 (2019).
Beneduce, C. et al., Inhibitory Fc-Gamma IIb Receptor Signaling Induced by Multivalent IgG-Fc Is Dependent on Sialylation, Cells, 12(2130):1-17 (2023).
Burch, H.B. and Cooper, D.S., Management of Graves Disease, JAMA, 314(23): 2544-2554 (2015).
Cheng, Q. et al., Selective depletion of plasma cells in vivo based on the specificity of their secreted antibodies, Eur J Immunol, 50: 284-291 (2020).
Chistiakov, D.A. Thyroid-stimulating hormone receptor and its role in Graves disease, Mol Genet Metab, 80(3):377-388 (2003).

(Continued)

*Primary Examiner* — Peter J Reddig
(74) *Attorney, Agent, or Firm* — Choate, Hall & Stewart LLP; Dana M. Daukss; Stephany Foster

(57) ABSTRACT

The present disclosure provides inter alia, molecules comprising an autoantibody-binding domain and at least one modified Fc domain. The present disclosure also provides methods and compositions that allow for selective depletion and/or neutralization of pathogenic autoantibodies.

30 Claims, 59 Drawing Sheets

Specification includes a Sequence Listing.

(56) References Cited

U.S. PATENT DOCUMENTS

| | | | | |
|---|---|---|---|---|
| 2022/0098271 | A1 | 3/2022 | Gill et al. | |
| 2022/0119533 | A1 | 4/2022 | Cheung et al. | |
| 2023/0174655 | A1 | 6/2023 | Mimoto et al. | |
| 2023/0280340 | A1 | 9/2023 | Kornau et al. | |
| 2024/0043498 | A1 | 2/2024 | Rees Smith et al. | |
| 2025/0059255 | A1 | 2/2025 | Oved et al. | |
| 2025/0114440 | A1 | 4/2025 | Desjarlais et al. | |
| 2025/0376502 | A1* | 12/2025 | Oved .................... | C07K 14/72 |

FOREIGN PATENT DOCUMENTS

| | | | |
|---|---|---|---|
| WO | WO-98/050431 | A2 | 11/1998 |
| WO | WO-99/029344 | A1 | 6/1999 |
| WO | WO-2001/085798 | A2 | 11/2001 |
| WO | WO-2002/016414 | A2 | 2/2002 |
| WO | WO-2003/040169 | A2 | 5/2003 |
| WO | WO-2003/068822 | A2 | 8/2003 |
| WO | WO-2004/091543 | A2 | 10/2004 |
| WO | WO-2004/099249 | A2 | 11/2004 |
| WO | WO-2005/070959 | A2 | 8/2005 |
| WO | WO-2006/073748 | A2 | 7/2006 |
| WO | WO-2007/035857 | A2 | 3/2007 |
| WO | WO-2007/057778 | A2 | 5/2007 |
| WO | WO-2008/097870 | A2 | 8/2008 |
| WO | WO-2008/098145 | A1 | 8/2008 |
| WO | WO-2009/078796 | A1 | 6/2009 |
| WO | WO-2010/033736 | A1 | 3/2010 |
| WO | WO-2010/141658 | A1 | 12/2010 |
| WO | WO-2011/097527 | A2 | 8/2011 |
| WO | WO-2012/057671 | A1 | 5/2012 |
| WO | WO-2013/047748 | A1 | 4/2013 |
| WO | WO-2013/047752 | A1 | 4/2013 |
| WO | WO-2013/125667 | A1 | 8/2013 |
| WO | WO-2013/160865 | A1 | 10/2013 |
| WO | WO-2014/023709 | A1 | 2/2014 |
| WO | WO-2014/030728 | A1 | 2/2014 |
| WO | WO-2014/037519 | A2 | 3/2014 |
| WO | WO-2014/163101 | A1 | 10/2014 |
| WO | WO-2014/204762 | A1 | 12/2014 |
| WO | WO-2015/051379 | A2 | 4/2015 |
| WO | WO-2015/112749 | A2 | 7/2015 |
| WO | WO-2015/168613 | A2 | 11/2015 |
| WO | WO-2016/064899 | A1 | 4/2016 |
| WO | WO-2019/197607 | A1 | 10/2019 |
| WO | WO-2021/008890 | A1 | 1/2021 |
| WO | WO-2021/142377 | A2 | 7/2021 |
| WO | WO-2021/155317 | A1 | 8/2021 |
| WO | WO-2021/263060 | A2 | 12/2021 |
| WO | WO-2021/263061 | A2 | 12/2021 |
| WO | WO-2022/035997 | A9 | 3/2022 |
| WO | WO-2022/200388 | A1 | 9/2022 |
| WO | WO-2022/200390 | A2 | 9/2022 |
| WO | WO-2022/235699 | A2 | 11/2022 |
| WO | WO-2022/260579 | A2 | 12/2022 |
| WO | WO-2022/271981 | A2 | 12/2022 |
| WO | WO-2022/272307 | A1 | 12/2022 |
| WO | WO-2023/288015 | A1 | 1/2023 |
| WO | WO-2023/288033 | A1 | 1/2023 |
| WO | WO-2023/009554 | A1 | 2/2023 |
| WO | WO-2023/028338 | A2 | 3/2023 |
| WO | WO-2023/070100 | A1 | 4/2023 |
| WO | WO-2023/112028 | A1 | 6/2023 |
| WO | WO-2023/183477 | A1 | 9/2023 |
| WO | WO-2024/035955 | A2 | 2/2024 |
| WO | WO-2024/091999 | A1 | 5/2024 |
| WO | WO-2024/092031 | A1 | 5/2024 |
| WO | WO-2024/098039 | A2 | 5/2024 |
| WO | WO-2024/108137 | A2 | 5/2024 |
| WO | WO-2024/068768 | A9 | 6/2024 |
| WO | WO-2024/127398 | A1 | 6/2024 |
| WO | WO-2024/147111 | A1 | 7/2024 |
| WO | WO-2024/147112 | A1 | 7/2024 |
| WO | WO-2024/147113 | A1 | 7/2024 |
| WO | WO-2024/148276 | A1 | 7/2024 |
| WO | WO-2024/155746 | A1 | 7/2024 |
| WO | WO-2024/155747 | A2 | 7/2024 |
| WO | WO-2024/155748 | A1 | 7/2024 |
| WO | WO-2024/155750 | A1 | 7/2024 |
| WO | WO-2024/182772 | A2 | 9/2024 |
| WO | WO-2024/186255 | A1 | 9/2024 |
| WO | WO-2024/189620 | A1 | 9/2024 |
| WO | WO-2024/218743 | A1 | 10/2024 |
| WO | WO-2024/226943 | A1 | 10/2024 |
| WO | WO-2024/231929 | A1 | 11/2024 |
| WO | WO-2024/231930 | A1 | 11/2024 |
| WO | WO-2024/231931 | A1 | 11/2024 |
| WO | WO-2025/030000 | A1 | 2/2025 |
| WO | WO-2025/030003 | A2 | 2/2025 |
| WO | WO-2025/030009 | A1 | 2/2025 |
| WO | WO-2025/035040 | A1 | 2/2025 |
| WO | WO-2025/035052 | A1 | 2/2025 |
| WO | WO-2025/117848 | A1 | 6/2025 |
| WO | WO-2025/126210 | A1 | 6/2025 |
| WO | WO-2025/126216 | A1 | 6/2025 |
| WO | WO-2025/181697 | A1 | 9/2025 |
| WO | WO-2025/186694 | A1 | 9/2025 |
| WO | WO-2025/207934 | A1 | 10/2025 |
| WO | WO-2025/259945 | A1 | 12/2025 |

OTHER PUBLICATIONS

Chu, S.Y. et al., Inhibition of B cell receptor-mediated activation of primary human B cells by coengagement of CD19 and FcγRIIb with Fc-engineered antibodies, Mol Immunol, 45(15):3926-3933 (2008).

Cole, S. et al., Integrative analysis reveals CD38 as a therapeutic target for plasma cell-rich pre-disease and established rheumatoid arthritis and systemic lupus erythematosus, Arthritis Research and Therapy, 20(85): 1-14 (2018).

Davies, T.F. et al., Graves' disease, Nat Rev Dis Primers, 6(52): 1-23 (2020).

Duan, J. et al., Hormone- and antibody-mediated activation of the thyrotropin receptor, Nature, 609: 854-859 (2022).

Dunford, P. et al., PREVAIL 1: A multiple ascending dose study in normal healthy volunteers of PRV-3279, a novel bispecific DART molecule targeting CD32B and CD79B on B cells, with potential for treatment of SLE, Arthritis & Rheumatology, 72(Suppl 10): Abstract 0860 (2020). https://acrabstracts.org/abstract/prevail-1-a-multiple-ascending-dose-study-in-normal-healthy-volunteers-of-prv-3279-a-novel-bispecific-dart-molecule-targeting-cd32b-and-cd79b-on-b-cells-with-potential-for-treatment-of-sle/. Accessed Aug. 21, 2025.

Evans, M. et al., Monoclonal autoantibodies to the TSH receptor, one with stimulating activity and one with blocking activity, obtained from the same blood sample, Clinical Endocrinology, 73(3): 404-412 (2010).

Faust, B. et al., Autoantibody mimicry of hormone action at the thyrotropin receptor, Nature, 609(7928): 846-853 (2022).

Ganesan, L.P et al., FcγRIIb on liver sinusoidal endothelium clears small immune complexes, Journal of Immunology, 189(10): 4981-4988 (2012).

George, A. et al., Stimulatory Thyrotropin Receptor Antibodies Are a Biomarker for Graves' Orbitopathy, Front Endocrinol, 11(629925): 1-6 (2021).

Gerngross, T.U., Advances in the production of human therapeutic proteins in yeasts and filamentous fungi, Nat. Biotech, 22:1409-1414 (2004).

Gershengorn, M. C. and Neumann, S., Update in TSH Receptor Agonists and Antagonists, J Clin Endocrinol Metabolism, 97: 4287-4292 (2012).

Graham, F.L. et al., Characteristics of a human cell line transformed by DNA from human adenovirus type 5, J. Gen Virol. 36(1):59-74 (1977).

Gupta, S. and Douglas, R.S., The pathophysiology of thyroid eye disease (TED): Implications for immunotherapy, Current Opinion in Ophthalmology, 22(5): 385-390 (2011).

Ha, J-H. et al., Immunoglobulin Fc Heterodimer Platform Technology: From Design to Applications in Therapeutic Antibodies and Proteins, Frontiers in Immunology, 7(394):1-16 (2016).

(56) References Cited

OTHER PUBLICATIONS

Hanouske, A-R. et al., Phase1b Dose Escalation Study of Erlotinib in Combination with Infusional 5-Fluorouracil, Leucovorin, and Oxaliplatin in Patients with Advanced Solid Tumors, Clin Cancer Res, 13(2):523-531 (2007).
Hansen, M. et al., Characterizing the Interplay of Lymphocytes in Graves' Disease, International Journal of Molecular Sciences, 24(6835):1-13 (2023).
Hetherington, S. et al., Phase I Dose Escalation Study To Evaluate the Safety and Pharmacokinetic Profile of Tefibazumab in Subjects with End-Stage Renal Disease Requiring Hemodialysis, Antimicrobial Agents and Chemotherapy, 50(10):3499-3500 (2006).
Höchst, B. et al., Liver sinusoidal endothelial cells contribute to CD8 T cell tolerance toward circulating carcinoembryonic antigen in mice, Hepatology, 56(5): 1924-1933 (2012).
Hollinger, P. et al., "Diabodies": Small bivalent and bispecific antibody fragments, Proc. Natl. Acad. Sci. USA, 90: 6444-6448 (1993).
Holthoff, H-P. et al., Thyroid-stimulating hormone receptor (TSHR) fusion proteins in Graves' disease, Jrnl. Endocrin., 246(2):135-147 (2020).
Hudson, P.J. and Souriau, C., Engineered antibodies, Nat. Med., 9:129-134 (2003).
International Search Report for PCT/US2024/040515, 4 pages (mailed Jan. 21, 2025).
International Search Report for PCT/US2024/040519, 5 pages (mailed Feb. 25, 2025).
International Search Report for PCT/US2024/040527, 5 pages (mailed Jan. 10, 2025).
Invitation to Pay Additional Fees for PCT/US2024/040519, 3 pages (mailed Jan. 3, 2025).
Iwata, Y. et al., Preclinical in vitro evaluation of immune suppression induced by GYM329, Fc-engineered sweeping antibody, Jrnl. Toxicol. Sci., 48(7):399-409 (2023).
Kendall-Taylor, P., The pathogenesis of Graves' ophthalmopathy, Clinics in Endocrinology and Metabolism, 14(2): 331-349 (1985).
Kerntke, C. et al., There is (Scientific) strength in numbers: A comprehensive quantitation of Fc gamma receptor numbers on human and murine peripheral blood leukocytes, Frontiers in Immunology, 11(118): 1-17 (2020).
Klugewitz, K. et al., Immunomodulatory effects of the liver: Deletion of activated CD4 effector cells and suppression of IFN-γ-producing cells after intravenous protein immunization, Journal of Immunology, 169(5): 2407-2413 (2002).
Lazaridis, K. et al., A recombinant acetylcholine receptor a1 subunit extracellular domain is a promising new drug candidate for treatment of myasthenia gravis, Frontiers in Immunology, 13(809106): 1-12 (2022).
Li, H. et al., Optimization of humanized IgGs in glycoengineered Pichia pastoris, Nat. Biotech, 24(2):210-215 (2006).
Limmer, A. et al., Cross-presentation of oral antigens by liver sinusoidal endothelial cells leads to CD8 T cell tolerance, European Journal of Immunology, 35(10): 2970-2981 (2005).
Liu, R. et al., Fc-Engineering for Modulated Effector Functions—Improving Antibodies for Cancer Treatment, Antibodies 9(4): 64, 1-34 (2020).
Miller-Gallacher, J. et al., Crystal structure of a ligand-free stable TSH receptor leucine-rich repeat domain, Journal of Molecular Endocrinology, 62(3): 117-128 (2019).
Mimoto, F. et al., Engineered antibody Fc variant with selectively enhanced FcγRIIb binding over both FcγRIIbR131 and FcγRIIbH131, Protein Engineering, Design & Selection, 26(10): 589-598 (2013).
Oostindie, S.C. et al., Avidity in antibody effector functions and biotherapeutic drug design, Nature Reviews Drug Discovery, 21: 715-734 (2022).
Perugino, C.A. et al., Evaluation of the safety, efficacy, and mechanism of action of obexelimab for the treatment of patients with IgG4-related disease: an open-label, single-arm, single-centre, phase 2 pilot trial, The Lancet Rheumatology, 5(8): e442-e450 (2023).
Pluckthun, A., Antibodies from *Escherichia coli*, The Pharmacology of Monoclonal Antibodies, Chapter 11, 113: 269-270 (1994).
Rees Smith, B. et al., TSH receptor-autoantibody interactions, Hormone and Metabolic Research, 41(6): 448-455 (2009).
Ridgway, J.B.B, et al., 'Knobs-into-holes' engineering of antibody CH3 domains for heavy chain heterodimerization, Protein Eng, 9(7):617-621 (1996).
Rojko, J.L. et al., Formation, clearance, deposition, pathogenicity, and identification of biopharmaceutical-related immune complexes: Review and case studies, Toxicologic Pathology, 42(4): 725-764 (2014).
Sanders, J. et al., Characteristics of a human monoclonal autoantibody to the thyrotropin receptor: Sequence, structure and function, Thyroid, 14(8): 560-570 (2004).
Sanders, J. et al., Human monoclonal thyroid stimulating autoantibody, Lancet, 362(9378): 126-128 (2003).
Schildberg, F.A. et al., Liver sinusoidal endothelial cells veto CD8 T cell activation by antigen-presenting dendritic cells, European Journal of Immunology, 38(4): 957-967 (2008).
Van Gurp, E. et al., Phase 1 Dose-Escalation Study of CP-690 550 in Stable Renal Allograft Recipients: Preliminary Findings of Safety, Tolerability, Effects on Lymphocyte Subsets and Pharmacokinetics, Am J Transplantation, 8(8):1711-1718 (2008).
Volkov, M. et al., Comprehensive Overview of Autoantibody Isotype and Subclass Distribution, Journal of Allergy and Clinical Immunology, 150(5): 999-1010 (2022).
Weetman, A.P. et al., Thyroid-stimulating Antibody Activity between Different Immunoglobulin G Subclasses, Journal of Clinical Investigation, 86(3): 723-727 (1990).
Written Opinion for PCT/US2024/040515, 10 pages (mailed Jan. 21, 2025).
Written Opinion for PCT/US2024/040519, 9 pages (mailed Feb. 25, 2025).
Written Opinion for PCT/US2024/040527, 11 pages (mailed Jan. 10, 2025).
Acqua, W. F. D. et al., Increasing the Affinity of a Human IgG1 for the Neonatal Fc Receptor: Biological Consequences, Jrnl. Immunol., 169(9):5171-5180 (2002).
Boysen, M. et al., SEC Based Method for Size Determination of Immune Complexes of Therapeutic Antibodies in Animal Matrix, Journal of Immunology Research, 2016(2):1-9 (2016).
Saunders, K. O., Conceptual Approaches to Modulating Antibody Effector Functions and Circulation Half-Life, Front. Immunol., 10(1296):1-20 (2019).

* cited by examiner

A and A' = Antigen
L and L' = Linker
Fc1 = Fc domain 1
Fc2 = Fc domain 2

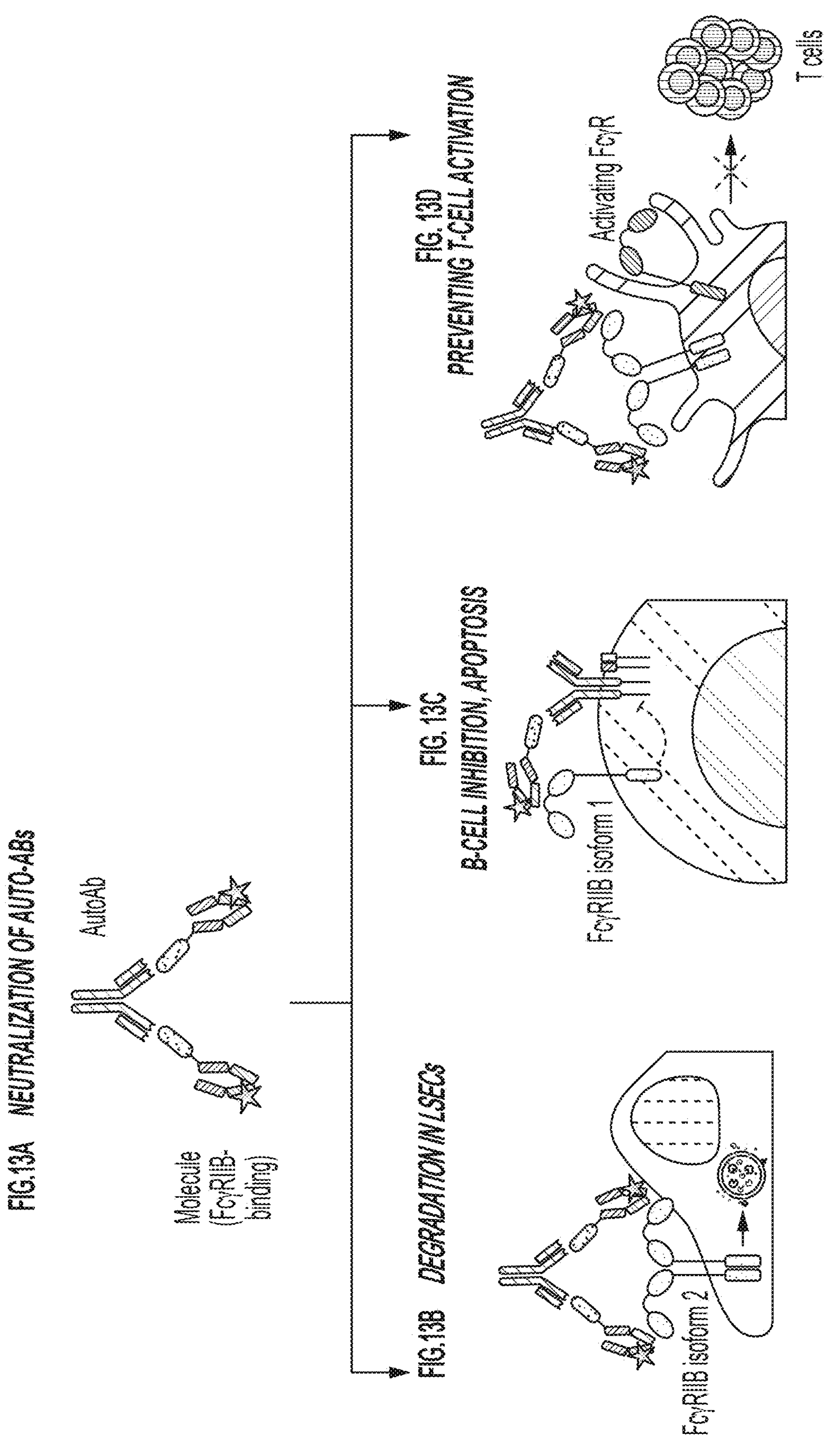
FIG.13A NEUTRALIZATION OF AUTO-ABs
FIG.13B DEGRADATION IN LSECs
FIG. 13C B-CELL INHIBITION, APOPTOSIS
FIG. 13D PREVENTING T-CELL ACTIVATION FcγRIIB FcγRIIA167H FcγRIIB

| Reaction | Variant D3 % Area | Complex 1 % Area | Complex 2 % Area |
|---|---|---|---|
| GD007: 2 nM Variant D3 | n/a | n/a | n/a |
| GD007: 8 nM Variant D3 | 34 | 28 | 38 |
| GD007: 16 nM Variant D3 | 33 | 29 | 38 |

| Tm onset(°C) | DSC Tm1 (°C) | DSC Tm2 (°C) |
|---|---|---|
| 49.3 | 59.0 | 81.9 |

| Tm onset(°C) | DSC Tm1 (°C) | DSC Tm2 (°C) |
|---|---|---|
| 48.4 | 58.2 | 77.6 |

FIG. 47A
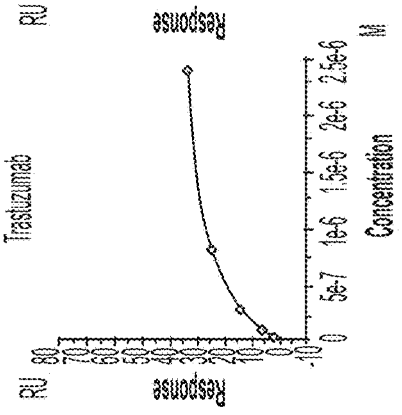
FIG. 47B
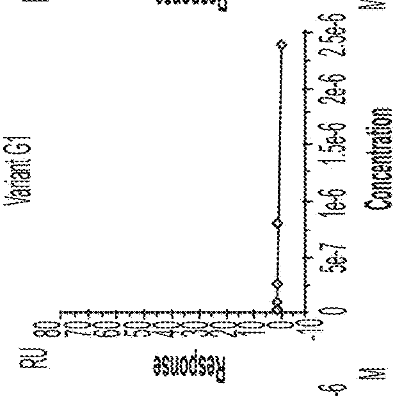
FIG. 47C
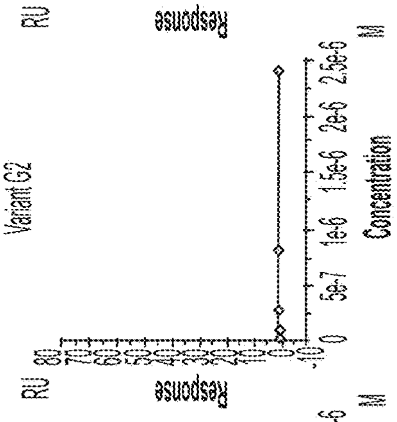
FIG. 47D
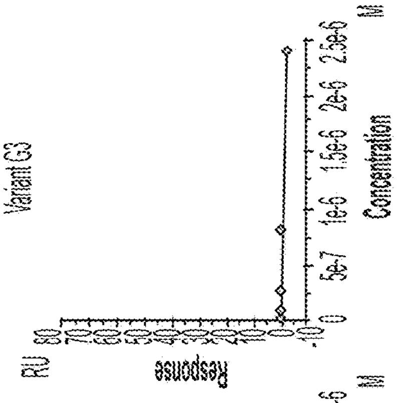
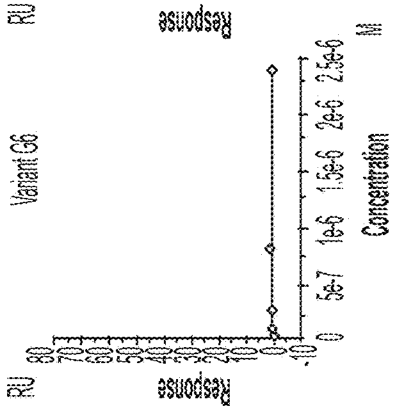
FIG. 47E
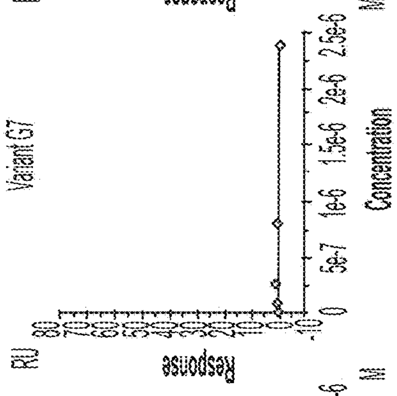
FIG. 47F
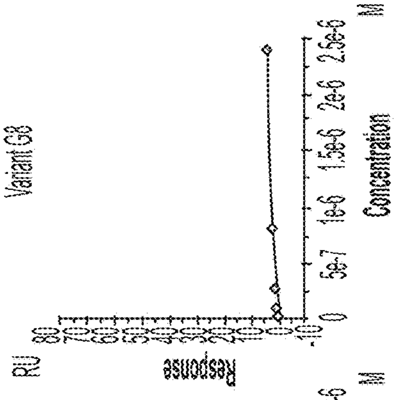
FIG. 47G FIG. 48A
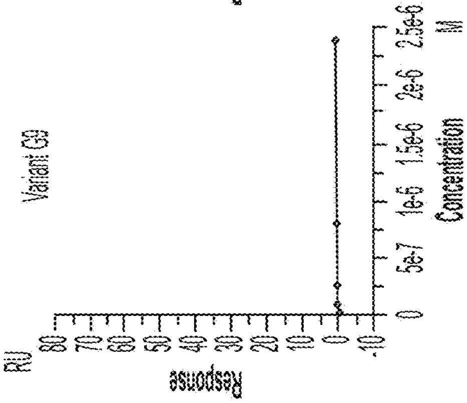
FIG. 48B
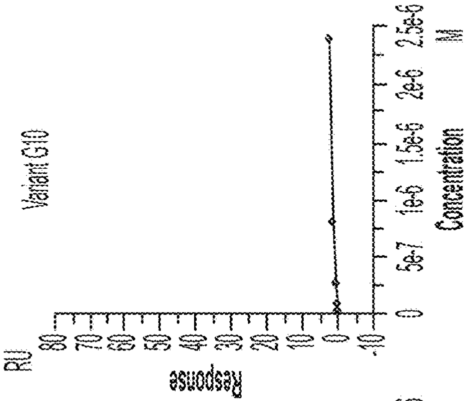
FIG. 48C
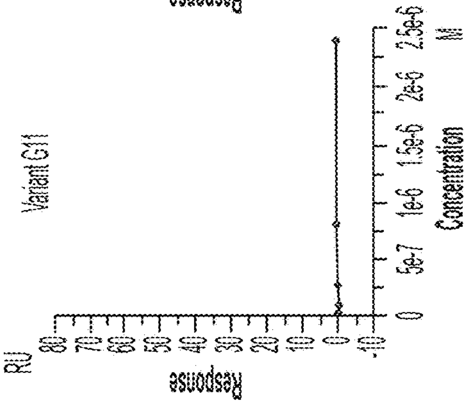
FIG. 48D
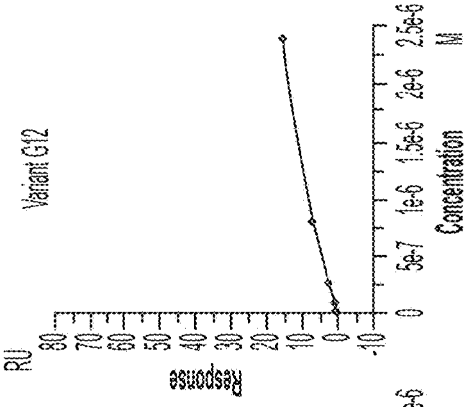
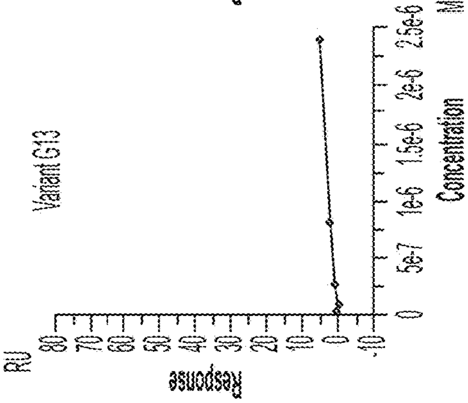
FIG. 48E
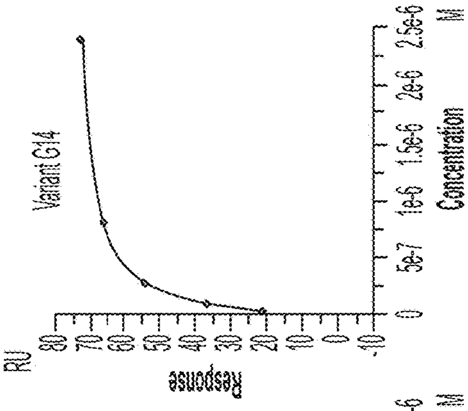
FIG. 48F
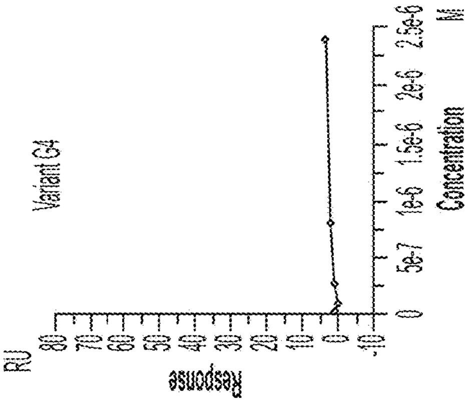
FIG. 48G

MOLECULES FOR CONTROLLING AUTOIMMUNE RESPONSE

CROSS REFERENCE TO RELATED APPLICATIONS

This application is a continuation of International Patent Application No. PCT/US24/40515, filed Aug. 1, 2024, which claims the benefit of U.S. Provisional Application No. 63/517,101, filed Aug. 1, 2023. The contents of the aforementioned applications are hereby incorporated by reference in their entirety.

SEQUENCE LISTING

The present application contains a Sequence Listing, which has been submitted electronically through USPTO Patent Center in XML format and is hereby incorporated by reference in its entirety. Said XML copy, created on Nov. 10, 2024, is named "2017420-0029_SL.xml" and is 256,763 bytes in size.

BACKGROUND

Autoimmune disease develops when the body's immune system attacks its own healthy cells. There are various types of autoimmune diseases, for instance, Graves' Disease, type 1 diabetes, rheumatoid arthritis, systemic lupus erythematosus, inflammatory bowel disease, pre-eclampsia, multiple sclerosis, and vasculitis. Autoantibodies are antibodies that target self-antigens and healthy cells, and are produced by pathogenic plasma cells. Autoantibodies are considered markers of immune disease, and methods of targeting and depleting autoantibodies in patients with autoimmune disease have been explored. However, therapeutic approaches for autoimmune disease oftentimes do not selectively deplete pathogenic autoantibodies and lead to depletion of antibodies that provide appropriate immune response to invading pathogens.

SUMMARY

Among other things, in some embodiments, the present disclosure provides a molecule that selectively targets and neutralizes and/or depletes pathogenic autoantibodies in a subject.

Molecules described herein comprise a first polypeptide and a second polypeptide, wherein the first polypeptide comprises an autoantibody-binding domain and a first Fc domain and the second polypeptide comprises a second Fc domain. As described herein, such molecules neutralize and deplete specific pathogenic autoantibodies. In some embodiments, targeting and depletion of autoantibodies is through a mechanism of targeting immune complexes including the autoantibodies to the lysosome of a cell for degradation.

Molecules described herein may be used for treatment of autoimmune diseases such as Graves' Disease, Thyroid Eye Disease, and/or other autoimmune diseases implicated by autoantibodies that target thyroid stimulating hormone receptor (TSHR). In some embodiments, a molecule comprises an autoantigen domain that is a TSHR autoantigen domain, or a fragment or variant thereof.

In addition to including an autoantibody-binding domain that targets autoantibodies, a molecule described herein may also include modifications to target specific internalizing receptors. In some embodiments, a molecule described herein includes an Fc domain that binds to a receptor on a cell that causes internalization of the bound molecule. Such molecules allow for binding of anti-TSHR autoantibodies through the autoantigen domain and targeting to the lysosome for degradation through binding of an internalizing receptor. In some embodiments, a molecule may include in its first and/or second Fc domains, a modification that increases its binding affinity to the Fc-gamma-RIIB (FcγRIIB). In some embodiments, a first and/or second Fc domain of a molecule may include a modification that increases its binding affinity to the human neonatal Fc receptor (FcRn).

In some embodiments, molecules described herein include an antigen-binding domain, wherein the antigen-binding domain binds to a receptor on a cell that internalizes the bound molecule (e.g., see FIG. 3). In some embodiments, an antigen-binding domain binds to an internalizing receptor such as FcγRIIB, ASPGR and/or FcRn. A molecule that targets an internalizing receptor such as FcγRIIB may inhibit/deplete autoantigen-specific B cells on which the autoantibody is expressed on the cell surface (e.g., as described in Chu et al., *Mol Immunol* 45:3926-3933 (2008), which is herein incorporated by reference in its entirety).

All of such strategies aim to deplete certain autoantibodies implicated in autoimmune disease. In some embodiments, an autoantibody is an anti-TSHR autoantibody and the disease is Graves' Disease, Graves' Orbitopathy (Thyroid Eye Disease) or another autoimmune disease caused by anti-TSHR autoantibodies. Molecules may include a TSHR autoantigen domain that targets anti-TSHR autoantibodies and an Fc domain and/or an antigen-binding domain that targets the complex (molecule and autoantibody) to the lysosome of a cell for selective degradation.

In one aspect, the present disclosure provides, a molecule comprising: a first polypeptide comprising a first Fc domain and an autoantibody-binding domain that binds to anti-TSHR autoantibodies; and a second polypeptide comprising a second Fc domain; wherein the first Fc domain and the second Fc domain form a homodimer or heterodimer of the first polypeptide and the second polypeptide. In some embodiments, the second polypeptide further comprises an autoantibody-binding domain that binds to anti-TSHR autoantibodies and the molecule is a homodimer. In some embodiments, the second polypeptide further comprises an autoantibody-binding domain that binds to anti-TSHR autoantibodies and the molecule is a heterodimer. In some embodiments, the second polypeptide does not comprise an autoantibody-binding domain that binds to anti-TSHR autoantibodies and the molecule is a heterodimer.

In some embodiments, the autoantibody-binding domain is covalently linked to the first Fc domain. In some embodiments, the C-terminus of the autoantibody-binding domain is covalently linked to the N-terminus of the first Fc domain. In some embodiments, the N-terminus of the autoantibody-binding domain is covalently linked to the C-terminus of the first Fc domain.

In some embodiments, the first and second Fc domains form a heterodimer as a result of knobs-in-holes (KIH) mutations. In some embodiments, the KIH mutations comprise Y349T and T394F, according to EU numbering scheme. In some embodiments, the first Fc domain comprises the Y349T mutation and the second Fc domain comprises the T394F mutation. In some embodiments, the KIH mutations comprise T366W, S354C, T366S, L368A, Y407V, and Y349C, according to the EU numbering scheme. In some embodiments, the first Fc domain comprises the T366W, and S354C mutations and the second Fc domain comprises the T366S, L368A, Y407V, and Y349C mutations, according to the EU numbering scheme.

In some embodiments, the first and/or second Fc domains comprise an IgG1 isotype. In some embodiments, the first and/or second Fc domains comprise a human IgG1 isotype.

In some embodiments, the first and/or second Fc domain comprises one or more mutated amino acid residues that increase half-life. In some embodiments, the first and/or second Fc domain comprises one of the following mutated amino acid residues: M252Y, S254T, and T256E, according to the EU numbering scheme. In some embodiments, the first and/or second Fc domain comprises a combination of the following mutated amino acid residues: M252Y, S254T, and T256E, according to the EU numbering scheme. In some embodiments, the first and/or second Fc domain comprises one of the following mutated amino acid residues: M428L and N434S, according to the EU numbering scheme. In some embodiments, the first and/or second Fc domain comprises a combination of the following mutated amino acid residues: M428L and N434S, according to the EU numbering scheme.

In some embodiments, the first and/or second Fc domain comprises one or more mutated amino acid residues that alters its binding to an internalizing receptor on a cell, where the internalizing receptor is capable of shuttling its cargo to the lysosome of the cell leading to degradation. In some embodiments, the altered binding to the internalizing receptor comprises increased binding to an internalizing receptor. In some embodiments, the molecule that is bound to an autoantibody through the autoantibody-binding domain binds to the internalizing receptor on a cell, the internalizing receptor internalizes the molecule and the autoantibody is shuttled to the lysosome of the cell for degradation. In some embodiments, the internalizing receptor comprises one of the following: FcγRIIB, FcRn, ASGPR, CD38, or BCMA.

In some embodiments, the first and/or second Fc domain comprises one or more mutated amino acid residues that increases binding to FcγRIIB relative to a corresponding wildtype Fc domain.

In some embodiments, the first and/or second Fc domain comprising one or more mutated amino acid residues does not have increased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, the first and/or second Fc domain comprising one or more mutated amino acid residues has decreased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, the first and/or second Fc domain comprising one or more mutated amino acid residues has substantially no binding affinity to FcγRI, FcγRIIA167H, FcγRIIA167R, FcγRIIIA176F, FcγRIIIA176V, FcγRIIIB, and/or FcRn relative to the corresponding wild-type Fc domain.

In some embodiments, upon binding of two molecules to an anti-TSHR autoantibody, an immune complex is formed that has enhanced binding kinetics with FcγRIIB relative to an immune complex that comprises the anti-TSHR autoantibody and two corresponding molecules with wild-type Fc domains. In some embodiments, upon binding of two molecules to an anti-TSHR autoantibody, an immune complex is formed that has enhanced binding kinetics with FcγRIIB relative to an immune complex that comprises the anti-TSHR autoantibody bound to only a single molecule. In some embodiments, upon binding of two molecules to an anti-TSHR autoantibody, an immune complex is formed that has enhanced binding kinetics with FcγRIIB relative to the anti-TSHR autoantibody alone. In some embodiments, the enhanced binding kinetics comprise an increase in the rate of association, a decrease in the rate of disassociation, and/or a change in the equilibrium dissociation constant. In some embodiments, the enhanced binding kinetics produce an increase in avidity, stability, strength, frequency, and/or duration of binding between the immune complex and FcγRIIB.

In some embodiments, the enhanced binding kinetics comprises at least 10% greater binding affinity of the immune complex to FcγRIIB. In some embodiments, the at least 10% greater binding affinity comprises at least 15%, at least 20%, at least 25%, at least 30%, at least 35%, at least 40%, at least 45%, or at least 50% or greater binding affinity. In some embodiments, the molecule binds to FcγRIIB with an affinity within the range of about 1 μM to 0.001 μM. In some embodiments, the molecule binds to FcγRIIB with an affinity within the range of about 1 μM to 0.001 μM. In some embodiments, the molecule binds to FcγRIIB with an affinity within the range of about 0.1 μM to 0.01 μM. In some embodiments, the binding affinity comprises binding affinity to a cell line (e.g., a CHO cell line) overexpressing FcγRIIB measured by flow cytometry.

In some embodiments, the molecule does not bind to complement (C1q).

In some embodiments, the molecule preferentially binds to immune cells expressing FcγRIIB over immune cells expressing FcγRIIA. In some embodiments, the molecule comprises substantially no binding affinity for cells that do not express FcγRIIB. In some embodiments, the immune cells expressing FcγRIIB comprise B cells, monocytes and/or basophils. In some embodiments, the immune cells that do not express FcγRIIB comprise T cells, NK cells, neutrophils, and/or eosinophils.

In some embodiments, the molecule does not activate immune cells (e.g., does not activate immune cells to secrete pro-inflammatory cytokines, e.g., IL-6).

In some embodiments, the molecule inhibits B cells by cross-linking FcγRIIB with a B cell receptor. In some embodiments, the molecule cross-links FcγRIIB with a B cell receptor. In some embodiments, an immune complex of one or two molecules with an anti-TSHR autoantibody cross-links FcγRIIB with a B cell receptor.

In some embodiments, the one or more mutated amino acid residues that increases binding to FcγRIIB comprises one or more of the following amino acid mutations, according to the EU numbering scheme: E233V, L234D, L235F, G236R, G237D, S239L, S267D, H268P, S298G, T299A, A327L, L328A, A330H, E333I, R292Q, E233P, P238D, H268D, P271G, A330R, L234Y, T250V, V264I, T307P, Q311R, A330K, P343R, M428L, N434A, Y436T, Q438R, S440E, G236N, S267E, L235R, D270E, E233D, and G237D.

In some embodiments, the one or more mutated amino acid residues that increases binding to FcγRIIB comprises one or more of the following sets of amino acid mutations, according to the EU numbering scheme: (i) E233V, L234D, L235F, G236R, G237D, S239L, S267D, H268P, S298G, T299A, A327L, L328A, A330H, and E333I; (ii) E233V, L234D, L235F, G236R, G237D, S239L, S267D, R292Q, H268P, S298G, T299A, A327L, L328A, A330H, and E333I; (iii) E233V, L234D, L235F, G236R, G237D, S239L, H268P, R292Q, S298G, T299A, A327L, L328A, A330H, and E333I; (iv) E233P, G237D, P238D, H268D, P271G, and A330R; (v) L234Y, P238D, T250V, V264I, T307P, Q311R, A330K, P343R, M428L, N434A, Y436T, Q438R, and S440E; (vi) L234D, G236N, and S267E; (vii) L235R; (viii) G236N and S267E; (ix) P238D and D270E; (x) P238D and P271G; (xi) P238D, D270E, and P271G; (xii) G237D, P238D, P271G, and A330R; (xiii) G237D, P238D, D270E, P271G, and A330R; (xiv) E233D, G237D, P238D, H268D, P271G, and A330R; and (xv) P238D. In some embodiments, the one or more mutated amino acid residues comprises the mutated amino acid residue P238D, according to the EU numbering scheme. In some embodiments, the one or more mutated amino acid residues does not comprise the following mutated amino acid residues: S267E and L328F, according to the EU numbering scheme.

In some embodiments, the first and/or second Fc domain comprises the following mutated amino acid residues: L234A, L235A, and P238D, according to the EU numbering scheme. In some embodiments, the first and/or second Fc domain comprises the following mutated amino acid residues: L234A, L235A, P238D and P329G, according to the EU numbering scheme.

In some embodiments, the first and/or second Fc domain comprises the following mutated amino acid residues: M428L, N434S, and P238D, according to the EU numbering scheme.

In some embodiments, the first and/or second Fc domain comprises at least one of the following mutated amino acid residues: S267E and L328F, according to the EU numbering scheme. In some embodiments, the first and/or second Fc domain comprise a combination of the following mutated amino acid residues: S267E and L328F, according to the EU numbering scheme.

In some embodiments, the first and/or second Fc domain comprises one or more mutated amino acid residues that increase binding to FcRn. In some embodiments, the first and/or second Fc domain comprises one or more mutated amino acid residues that increase binding to FcRn at a neutral or near-neutral pH (e.g., pH between about 6.8 and 7.5).

In some embodiments, the first and second Fc domain comprises a human IgG1 isotype and remains bound to FcRn upon entry into an environment having an acidic pH and/or having low calcium concentration (e.g., into an endosome of a cell). In some embodiments, the first and/or second Fc domain comprises at least one of the following mutated amino acid residues: M252Y, S254T, T256E, H433K, and N434F, according to the EU numbering scheme. In some embodiments, the first and/or second Fc domain comprises a combination of the following mutated amino acid residues: M252Y, S254T, T256E, H433K, and N434F, according to the EU numbering scheme.

In some embodiments, the first and/or second Fc domain comprises at least one mutated amino acid sequence that decreases binding to one or more Fc-gamma receptors (FcγRs). In some embodiments, the first and/or second Fc domain comprises at least one of the following mutated amino acid residues: G236R and L328R, according to the EU numbering scheme. In some embodiments, the first and/or second Fc domain comprises the following mutated amino acid residues: G236R and L328R, according to the EU numbering scheme.

In some embodiments, the first Fc domain comprises a sequence selected from SEQ ID NOs: 103, 105, 107, 109, 111-113, 115, 117, 119, 121, 123, 125, 127, 129, 131, 133, 135, 137, 139-149, 163-164, 374-376, 378, or a fragment or variant thereof (e.g., a sequence selected from SEQ ID NOs: 107, 109, 113, 115, 119, 131, 139, 140, 142, 148, 374, or 378). In some embodiments, the second Fc domain comprises a sequence selected from SEQ ID NOs: 104, 106, 108, 110, 111, 112, 114, 116, 118, 120, 122, 124, 126, 128, 130, 132, 134, 136, 138, 139-149, 163-164, 374-375, 377, 379, or a fragment or variant thereof (e.g., a sequence selected from SEQ ID NOs: 108, 110, 114, 116, 120, 132, 139, 140, 142, 148, 374, or 379).

In some embodiments, the autoantibody-binding domain is covalently linked to the first Fc domain through a linker. In some embodiments, the linker comprises the amino acid sequence of SEQ ID NO: 150 (GGGGS), SEQ ID NO: 151 (GGGGSGGGGS), SEQ ID NO: 152 (GGGGSGGGGSGGGGS), SEQ ID NO: 153 (VDGGGGSGGGGSGGGGSG), SEQ ID NO: 154 (GGGGSGGGGSGGGGSGGGGS), SEQ ID NO: 155 (GGGGSGGGGSGGGGSGGGGSSGGGGS), SEQ ID NO: 156 (GSGGS), SEQ ID NO: 157 (GGSG), SEQ ID NO: 158 (GGSGG), SEQ ID NO: 159 (GSGSG), SEQ ID NO: 160 (GSGGG), SEQ ID NO: 161 (GGGSG), or SEQ ID NO: 162 (GSSSG).

In some embodiments, the autoantibody-binding domain comprises an autoantigen, or a fragment or variant thereof. In some embodiments, the autoantigen comprises a TSHR autoantigen domain, or a fragment or variant thereof. In some embodiments, the TSHR autoantigen domain comprises an amino acid sequence that is at least 90% identical to the amino acid sequence of SEQ ID NO: 1 or SEQ ID NO: 5. In some embodiments, the TSHR autoantigen domain comprises the amino acid sequence of SEQ ID NO: 1 or SEQ ID NO: 5. In some embodiments, the autoantibody-binding domain comprises a TSHR autoantigen domain variant that includes one or more of the following mutations relative to the amino acid sequence of SEQ ID NO: 1 or SEQ ID NO: 5: R112P, D143P, V169R, I253R, H63S, or any combination thereof. In some embodiments, the autoantibody-binding domain comprises a TSHR autoantigen domain variant that includes the following mutations relative to the amino acid sequence of SEQ ID NO: 1 or SEQ ID NO: 5: R112P and D143P. In some embodiments, the autoantibody-binding domain comprises a TSHR autoantigen domain variant that includes the following mutations relative to the amino acid sequence of SEQ ID NO: 1 or SEQ ID NO: 5: R112P, D143P, V169R, and I253R. In some embodiments, the autoantibody-binding domain comprises a TSHR autoantigen domain variant that includes the following mutations relative to the amino acid sequence of SEQ ID NO: 1 or SEQ ID NO: 5: R112P, D143P, and H63S. In some embodiments, the autoantibody-binding domain comprises a TSHR autoantigen domain variant that comprises the sequence of any one of SEQ ID NOs: 1-8. In some embodiments, the autoantibody-binding domain comprises a TSHR autoantigen domain variant that comprises the sequence of any one of SEQ ID NOs: 307-317.

In some embodiments, the first polypeptide comprises: an amino acid sequence that is at least 90% identical to SEQ ID NO: 1 and an amino acid sequence that is at least 90% identical to SEQ ID NO: 103; an amino acid sequence that is at least 90% identical to SEQ ID NO: 2 and an amino acid sequence that is at least 90% identical to SEQ ID NO: 103; an amino acid sequence that is at least 90% identical to SEQ ID NO: 3 and an amino acid sequence that is at least 90% identical to SEQ ID NO: 103; an amino acid sequence that is at least 90% identical to SEQ ID NO: 4 and an amino acid sequence that is at least 90% identical to SEQ ID NO: 103; an amino acid sequence that is at least 90% identical to SEQ ID NO: 5 and an amino acid sequence that is at least 90% identical to SEQ ID NO: 103; an amino acid sequence that is at least 90% identical to SEQ ID NO: 6 and an amino acid sequence that is at least 90% identical to SEQ ID NO: 103;

an amino acid sequence that is at least 90% identical to SEQ ID NO: 7 and an amino acid sequence that is at least 90% identical to SEQ ID NO: 103; an amino acid sequence that is at least 90% identical to SEQ ID NO: 8 and an amino acid sequence that is at least 90% identical to SEQ ID NO: 103; an amino acid sequence that is at least 90% identical to SEQ ID NO: 307 and an amino acid sequence that is at least 90% identical to SEQ ID NO: 103; an amino acid sequence that is at least 90% identical to SEQ ID NO: 308 and an amino acid sequence that is at least 90% identical to SEQ ID NO: 103; an amino acid sequence that is at least 90% identical to SEQ ID NO: 309 and an amino acid sequence that is at least 90% identical to SEQ ID NO: 103; an amino acid sequence that is at least 90% identical to SEQ ID NO: 310 and an amino acid sequence that is at least 90% identical to SEQ ID NO: 103; an amino acid sequence that is at least 90% identical to SEQ ID NO: 311 and an amino acid sequence that is at least 90% identical to SEQ ID NO: 103; an amino acid sequence that is at least 90% identical to SEQ ID NO: 312 and an amino acid sequence that is at least 90% identical to SEQ ID NO: 103; an amino acid sequence that is at least 90% identical to SEQ ID NO: 313 and an amino acid sequence that is at least 90% identical to SEQ ID NO: 103; an amino acid sequence that is at least 90% identical to SEQ ID NO: 314 and an amino acid sequence that is at least 90% identical to SEQ ID NO: 103; an amino acid sequence that is at least 90% identical to SEQ ID NO: 315 and an amino acid sequence that is at least 90% identical to SEQ ID NO: 103; an amino acid sequence that is at least 90% identical to SEQ ID NO: 316 and an amino acid sequence that is at least 90% identical to SEQ ID NO: 103; an amino acid sequence that is at least 90% identical to SEQ ID NO: 317 and an amino acid sequence that is at least 90% identical to SEQ ID NO: 103; an amino acid sequence that is at least 90% identical to SEQ ID NO: 1 and an amino acid sequence that is at least 90% identical to SEQ ID NO: 105; an amino acid sequence that is at least 90% identical to SEQ ID NO: 2 and an amino acid sequence that is at least 90% identical to SEQ ID NO: 105; an amino acid sequence that is at least 90% identical to SEQ ID NO: 3 and an amino acid sequence that is at least 90% identical to SEQ ID NO: 105; an amino acid sequence that is at least 90% identical to SEQ ID NO: 4 and an amino acid sequence that is at least 90% identical to SEQ ID NO: 105; an amino acid sequence that is at least 90% identical to SEQ ID NO: 5 and an amino acid sequence that is at least 90% identical to SEQ ID NO: 105; an amino acid sequence that is at least 90% identical to SEQ ID NO: 6 and an amino acid sequence that is at least 90% identical to SEQ ID NO: 105; an amino acid sequence that is at least 90% identical to SEQ ID NO: 7 and an amino acid sequence that is at least 90% identical to SEQ ID NO: 105; an amino acid sequence that is at least 90% identical to SEQ ID NO: 8 and an amino acid sequence that is at least 90% identical to SEQ ID NO: 105; an amino acid sequence that is at least 90% identical to SEQ ID NO: 307 and an amino acid sequence that is at least 90% identical to SEQ ID NO: 105; an amino acid sequence that is at least 90% identical to SEQ ID NO: 308 and an amino acid sequence that is at least 90% identical to SEQ ID NO: 105; an amino acid sequence that is at least 90% identical to SEQ ID NO: 309 and an amino acid sequence that is at least 90% identical to SEQ ID NO: 105; an amino acid sequence that is at least 90% identical to SEQ ID NO: 310 and an amino acid sequence that is at least 90% identical to SEQ ID NO: 105; an amino acid sequence that is at least 90% identical to SEQ ID NO: 311 and an amino acid sequence that is at least 90% identical to SEQ ID NO: 105; an amino acid sequence that is at least 90% identical to SEQ ID NO: 312 and an amino acid sequence that is at least 90% identical to SEQ ID NO: 105; an amino acid sequence that is at least 90% identical to SEQ ID NO: 313 and an amino acid sequence that is at least 90% identical to SEQ ID NO: 105; an amino acid sequence that is at least 90% identical to SEQ ID NO: 314 and an amino acid sequence that is at least 90% identical to SEQ ID NO: 105; an amino acid sequence that is at least 90% identical to SEQ ID NO: 315 and an amino acid sequence that is at least 90% identical to SEQ ID NO: 105; an amino acid sequence that is at least 90% identical to SEQ ID NO: 316 and an amino acid sequence that is at least 90% identical to SEQ ID NO: 105; an amino acid sequence that is at least 90% identical to SEQ ID NO: 317 and an amino acid sequence that is at least 90% identical to SEQ ID NO: 105; an amino acid sequence that is at least 90% identical to SEQ ID NO: 4, an amino acid sequence that is at least 90% identical to SEQ ID NO: 209, an amino acid sequence that is at least 90% identical to SEQ ID NO: 210, and an amino acid sequence that is at least 90% identical to SEQ ID NO: 105; or an amino acid sequence that is at least 90% identical to SEQ ID NO: 1 and an amino acid sequence that is at least 90% identical to SEQ ID NO: 107; an amino acid sequence that is at least 90% identical to SEQ ID NO: 2 and an amino acid sequence that is at least 90% identical to SEQ ID NO: 107; an amino acid sequence that is at least 90% identical to SEQ ID NO: 3 and an amino acid sequence that is at least 90% identical to SEQ ID NO: 107; an amino acid sequence that is at least 90% identical to SEQ ID NO: 4 and an amino acid sequence that is at least 90% identical to SEQ ID NO: 107; an amino acid sequence that is at least 90% identical to SEQ ID NO: 5 and an amino acid sequence that is at least 90% identical to SEQ ID NO: 107; an amino acid sequence that is at least 90% identical to SEQ ID NO: 6 and an amino acid sequence that is at least 90% identical to SEQ ID NO: 107; an amino acid sequence that is at least 90% identical to SEQ ID NO: 7 and an amino acid sequence that is at least 90% identical to SEQ ID NO: 107; an amino acid sequence that is at least 90% identical to SEQ ID NO: 8 and an amino acid sequence that is at least 90% identical to SEQ ID NO: 107; an amino acid sequence that is at least 90% identical to SEQ ID NO: 307 and an amino acid sequence that is at least 90% identical to SEQ ID NO: 107; an amino acid sequence that is at least 90% identical to SEQ ID NO: 308 and an amino acid sequence that is at least 90% identical to SEQ ID NO: 107; an amino acid sequence that is at least 90% identical to SEQ ID NO: 309 and an amino acid sequence that is at least 90% identical to SEQ ID NO: 107; an amino acid sequence that is at least 90% identical to SEQ ID NO: 310 and an amino acid sequence that is at least 90% identical to SEQ ID NO: 107; an amino acid sequence that is at least 90% identical to SEQ ID NO: 311 and an amino acid sequence that is at least 90% identical to SEQ ID NO: 107; an amino acid sequence that is at least 90% identical to SEQ ID NO: 312 and an amino acid sequence that is at least 90% identical to SEQ ID NO: 107; an amino acid sequence that is at least 90% identical to SEQ ID NO: 313 and an amino acid sequence that is at least 90% identical to SEQ ID NO: 107; an amino acid sequence that is at least 90% identical to SEQ ID NO: 314 and an amino acid sequence that is at least 90% identical to SEQ ID NO: 107; an amino acid sequence that is at least 90% identical to SEQ ID NO: 315 and an amino acid sequence that is at least 90% identical to SEQ ID NO: 107; an amino acid sequence that is at least 90% identical to SEQ ID NO: 316 and an amino acid sequence that is at least 90% identical to SEQ ID NO: 107; an amino acid sequence that is at least 90% identical to SEQ ID NO: 317 and an amino acid sequence that is at least 90% identical to SEQ ID NO: 107; an amino acid sequence that is at least 90% identical to SEQ ID NO: 1 and an amino acid sequence that is at least 90% identical to SEQ ID NO: 109; an amino acid sequence that is at least 90% identical to SEQ ID NO: 2 and an amino acid sequence that is at least 90% identical to SEQ ID NO: 109; an amino acid sequence that is at least 90% identical to SEQ ID NO: 3 and an amino acid sequence that is at least 90% identical to SEQ ID NO: 109; an amino acid sequence that is at least 90% identical to SEQ ID NO: 4 and an amino acid sequence that is at least 90% identical to SEQ ID NO: 109; an amino acid sequence that is at least 90% identical to SEQ ID NO: 5 and an amino acid sequence that is at least 90% identical to SEQ ID NO: 109; an amino acid sequence that is at least 90% identical to SEQ ID NO: 6 and an amino acid sequence that is at least 90% identical to SEQ ID NO: 109; an amino acid sequence that is at least 90% identical to SEQ ID NO: 7 and an amino acid sequence that is at least 90% identical to SEQ ID NO: 109; an amino acid sequence that is at least 90% identical to SEQ ID NO: 8 and an amino acid sequence that is at least 90% identical to SEQ ID NO: 109; an amino acid sequence that is at least 90% identical to SEQ ID NO: 307 and an amino acid sequence that is at least 90% identical to SEQ ID NO: 109; an amino acid sequence that is at least 90% identical to SEQ ID NO: 308 and an amino acid sequence that is at least 90% identical to SEQ ID NO: 109; an amino acid sequence that is at least 90% identical to SEQ ID NO: 309 and an amino acid sequence that is at least 90% identical to SEQ ID NO: 109; an amino acid sequence that is at least 90% identical to SEQ ID NO: 310 and an amino acid sequence that is at least 90% identical to SEQ ID NO: 109; an amino acid sequence that is at least 90% identical to SEQ ID NO: 311 and an amino acid sequence that is at least 90% identical to SEQ ID NO: 109; an amino acid sequence that is at least 90% identical to SEQ ID NO: 312 and an amino acid sequence that is at least 90% identical to SEQ ID NO: 109; an amino acid sequence that is at least 90% identical to SEQ ID NO: 313 and an amino acid sequence that is at least 90% identical to SEQ ID NO: 109; an amino acid sequence that is at least 90% identical to SEQ ID NO: 314 and an amino acid sequence that is at least 90% identical to SEQ ID NO: 109; an amino acid sequence that is at least 90% identical to SEQ ID NO: 315 and an amino acid sequence that is at least 90% identical to SEQ ID NO: 109; an amino acid sequence that is at least 90% identical to SEQ ID NO: 316 and an amino acid sequence that is at least 90% identical to SEQ ID NO: 109; an amino acid sequence that is at least 90% identical to SEQ ID NO: 317 and an amino acid sequence that is at least 90% identical to SEQ ID NO: 109; an amino acid sequence that is at least 90% identical to SEQ ID NO: 1 and an amino acid sequence that is at least 90% identical to SEQ ID NO: 113; an amino acid sequence that is at least 90% identical to SEQ ID NO: 2 and an amino acid sequence that is at least 90% identical to SEQ ID NO: 113; an amino acid sequence that is at least 90% identical to SEQ ID NO: 3 and an amino acid sequence that is at least 90% identical to SEQ ID NO: 113; an amino acid sequence that is at least 90% identical to SEQ ID NO: 4 and an amino acid sequence that is at least 90% identical to SEQ ID NO: 113; an amino acid sequence that is at least 90% identical to SEQ ID NO: 5 and an amino acid sequence that is at least 90% identical to SEQ ID NO: 113; an amino acid sequence that is at least 90% identical to SEQ ID NO: 6 and an amino acid sequence that is at least 90% identical to SEQ ID NO: 113; an amino acid sequence that is at least 90% identical to SEQ ID NO: 7 and an amino acid sequence that is at least 90% identical to SEQ ID NO: 113; an amino acid sequence that is at least 90% identical to SEQ ID NO: 8 and an amino acid sequence that is at least 90% identical to SEQ ID NO: 113; an amino acid sequence that is at least 90% identical to SEQ ID NO: 307 and an amino acid sequence that is at least 90% identical to SEQ ID NO: 113; an amino acid sequence that is at least 90% identical to SEQ ID NO: 308 and an amino acid sequence that is at least 90% identical to SEQ ID NO: 113; an amino acid sequence that is at least 90% identical to SEQ ID NO: 309 and an amino acid sequence that is at least 90% identical to SEQ ID NO: 113; an amino acid sequence that is at least 90% identical to SEQ ID NO: 310 and an amino acid sequence that is at least 90% identical to SEQ ID NO: 113; an amino acid sequence that is at least 90% identical to SEQ ID NO: 311 and an amino acid sequence that is at least 90% identical to SEQ ID NO: 113; an amino acid sequence that is at least 90% identical to SEQ ID NO: 312 and an amino acid sequence that is at least 90% identical to SEQ ID NO: 113; an amino acid sequence that is at least 90% identical to SEQ ID NO: 313 and an amino acid sequence that is at least 90% identical to SEQ ID NO: 113; an amino acid sequence that is at least 90% identical to SEQ ID NO: 314 and an amino acid sequence that is at least 90% identical to SEQ ID NO: 113; an amino acid sequence that is at least 90% identical to SEQ ID NO: 315 and an amino acid sequence that is at least 90% identical to SEQ ID NO: 113; an amino acid sequence that is at least 90% identical to SEQ ID NO: 316 and an amino acid sequence that is at least 90% identical to SEQ ID NO: 113; an amino acid sequence that is at least 90% identical to SEQ ID NO: 317 and an amino acid sequence that is at least 90% identical to SEQ ID NO: 113; an amino acid sequence that is at least 90% identical to SEQ ID NO: 1 and an amino acid sequence that is at least 90% identical to SEQ ID NO: 115; an amino acid sequence that is at least 90% identical to SEQ ID NO: 2 and an amino acid sequence that is at least 90% identical to SEQ ID NO: 115; an amino acid sequence that is at least 90% identical to SEQ ID NO: 3 and an amino acid sequence that is at least 90% identical to SEQ ID NO: 115; an amino acid sequence that is at least 90% identical to SEQ ID NO: 4 and an amino acid sequence that is at least 90% identical to SEQ ID NO: 115; an amino acid sequence that is at least 90% identical to SEQ ID NO: 5 and an amino acid sequence that is at least 90% identical to SEQ ID NO: 115; an amino acid sequence that is at least 90% identical to SEQ ID NO: 6 and an amino acid sequence that is at least 90% identical to SEQ ID NO: 115; an amino acid sequence that is at least 90% identical to SEQ ID NO: 7 and an amino acid sequence that is at least 90% identical to SEQ ID NO: 115; an amino acid sequence that is at least 90% identical to SEQ ID NO: 8 and an amino acid sequence that is at least 90% identical to SEQ ID NO: 115; an amino acid sequence that is at least 90% identical to SEQ ID NO: 307 and an amino acid sequence that is at least 90% identical to SEQ ID NO: 115; an amino acid sequence that is at least 90% identical to SEQ ID NO: 308 and an amino acid sequence that is at least 90% identical to SEQ ID NO: 115; an amino acid sequence that is at least 90% identical to SEQ ID NO: 309 and an amino acid sequence that is at least 90% identical to SEQ ID NO: 115; an amino acid sequence that is at least 90% identical to SEQ ID NO: 310 and an amino acid sequence that is at least 90% identical to SEQ ID NO: 115; an amino acid sequence that is at least 90% identical to SEQ ID NO: 311 and an amino acid sequence that is at least 90% identical to SEQ ID NO: 115; an amino acid sequence that is at least 90% identical to SEQ ID NO: 312 and an amino acid sequence that is at least 90% identical to SEQ ID NO: 115; an amino acid sequence that is at least 90% identical to SEQ ID NO:

313 and an amino acid sequence that is at least 90% identical to SEQ ID NO: 115; an amino acid sequence that is at least 90% identical to SEQ ID NO: 314 and an amino acid sequence that is at least 90% identical to SEQ ID NO: 115; an amino acid sequence that is at least 90% identical to SEQ ID NO: 315 and an amino acid sequence that is at least 90% identical to SEQ ID NO: 115; an amino acid sequence that is at least 90% identical to SEQ ID NO: 316 and an amino acid sequence that is at least 90% identical to SEQ ID NO: 115; an amino acid sequence that is at least 90% identical to SEQ ID NO: 317 and an amino acid sequence that is at least 90% identical to SEQ ID NO: 115; an amino acid sequence that is at least 90% identical to SEQ ID NO: 1 and an amino acid sequence that is at least 90% identical to SEQ ID NO: 117; an amino acid sequence that is at least 90% identical to SEQ ID NO: 2 and an amino acid sequence that is at least 90% identical to SEQ ID NO: 117; an amino acid sequence that is at least 90% identical to SEQ ID NO: 3 and an amino acid sequence that is at least 90% identical to SEQ ID NO: 117; an amino acid sequence that is at least 90% identical to SEQ ID NO: 4 and an amino acid sequence that is at least 90% identical to SEQ ID NO: 117; an amino acid sequence that is at least 90% identical to SEQ ID NO: 5 and an amino acid sequence that is at least 90% identical to SEQ ID NO: 117; an amino acid sequence that is at least 90% identical to SEQ ID NO: 6 and an amino acid sequence that is at least 90% identical to SEQ ID NO: 117; an amino acid sequence that is at least 90% identical to SEQ ID NO: 7 and an amino acid sequence that is at least 90% identical to SEQ ID NO: 117; an amino acid sequence that is at least 90% identical to SEQ ID NO: 8 and an amino acid sequence that is at least 90% identical to SEQ ID NO: 117; an amino acid sequence that is at least 90% identical to SEQ ID NO: 307 and an amino acid sequence that is at least 90% identical to SEQ ID NO: 117; an amino acid sequence that is at least 90% identical to SEQ ID NO: 308 and an amino acid sequence that is at least 90% identical to SEQ ID NO: 117; an amino acid sequence that is at least 90% identical to SEQ ID NO: 309 and an amino acid sequence that is at least 90% identical to SEQ ID NO: 117; an amino acid sequence that is at least 90% identical to SEQ ID NO: 310 and an amino acid sequence that is at least 90% identical to SEQ ID NO: 117; an amino acid sequence that is at least 90% identical to SEQ ID NO: 311 and an amino acid sequence that is at least 90% identical to SEQ ID NO: 117; an amino acid sequence that is at least 90% identical to SEQ ID NO: 312 and an amino acid sequence that is at least 90% identical to SEQ ID NO: 117; an amino acid sequence that is at least 90% identical to SEQ ID NO: 313 and an amino acid sequence that is at least 90% identical to SEQ ID NO: 117; an amino acid sequence that is at least 90% identical to SEQ ID NO: 314 and an amino acid sequence that is at least 90% identical to SEQ ID NO: 117; an amino acid sequence that is at least 90% identical to SEQ ID NO: 315 and an amino acid sequence that is at least 90% identical to SEQ ID NO: 117; an amino acid sequence that is at least 90% identical to SEQ ID NO: 316 and an amino acid sequence that is at least 90% identical to SEQ ID NO: 117; an amino acid sequence that is at least 90% identical to SEQ ID NO: 317 and an amino acid sequence that is at least 90% identical to SEQ ID NO: 117; an amino acid sequence that is at least 90% identical to SEQ ID NO: 1 and an amino acid sequence that is at least 90% identical to SEQ ID NO: 119; an amino acid sequence that is at least 90% identical to SEQ ID NO: 2 and an amino acid sequence that is at least 90% identical to SEQ ID NO: 119; an amino acid sequence that is at least 90% identical to SEQ ID NO: 3 and an amino acid sequence that is at least 90% identical to SEQ ID NO: 119; an amino acid sequence that is at least 90% identical to SEQ ID NO: 4 and an amino acid sequence that is at least 90% identical to SEQ ID NO: 119; an amino acid sequence that is at least 90% identical to SEQ ID NO: 5 and an amino acid sequence that is at least 90% identical to SEQ ID NO: 119; an amino acid sequence that is at least 90% identical to SEQ ID NO: 6 and an amino acid sequence that is at least 90% identical to SEQ ID NO: 119; an amino acid sequence that is at least 90% identical to SEQ ID NO: 7 and an amino acid sequence that is at least 90% identical to SEQ ID NO: 119; an amino acid sequence that is at least 90% identical to SEQ ID NO: 8 and an amino acid sequence that is at least 90% identical to SEQ ID NO: 119; an amino acid sequence that is at least 90% identical to SEQ ID NO: 307 and an amino acid sequence that is at least 90% identical to SEQ ID NO: 119; an amino acid sequence that is at least 90% identical to SEQ ID NO: 308 and an amino acid sequence that is at least 90% identical to SEQ ID NO: 119; an amino acid sequence that is at least 90% identical to SEQ ID NO: 309 and an amino acid sequence that is at least 90% identical to SEQ ID NO: 119; an amino acid sequence that is at least 90% identical to SEQ ID NO: 310 and an amino acid sequence that is at least 90% identical to SEQ ID NO: 119; an amino acid sequence that is at least 90% identical to SEQ ID NO: 311 and an amino acid sequence that is at least 90% identical to SEQ ID NO: 119; an amino acid sequence that is at least 90% identical to SEQ ID NO: 312 and an amino acid sequence that is at least 90% identical to SEQ ID NO: 119; an amino acid sequence that is at least 90% identical to SEQ ID NO: 313 and an amino acid sequence that is at least 90% identical to SEQ ID NO: 119; an amino acid sequence that is at least 90% identical to SEQ ID NO: 314 and an amino acid sequence that is at least 90% identical to SEQ ID NO: 119; an amino acid sequence that is at least 90% identical to SEQ ID NO: 315 and an amino acid sequence that is at least 90% identical to SEQ ID NO: 119; an amino acid sequence that is at least 90% identical to SEQ ID NO: 316 and an amino acid sequence that is at least 90% identical to SEQ ID NO: 119; an amino acid sequence that is at least 90% identical to SEQ ID NO: 317 and an amino acid sequence that is at least 90% identical to SEQ ID NO: 119; an amino acid sequence that is at least 90% identical to SEQ ID NO: 1 and an amino acid sequence that is at least 90% identical to SEQ ID NO: 121; an amino acid sequence that is at least 90% identical to SEQ ID NO: 2 and an amino acid sequence that is at least 90% identical to SEQ ID NO: 121; an amino acid sequence that is at least 90% identical to SEQ ID NO: 3 and an amino acid sequence that is at least 90% identical to SEQ ID NO: 121; an amino acid sequence that is at least 90% identical to SEQ ID NO: 4 and an amino acid sequence that is at least 90% identical to SEQ ID NO: 121; an amino acid sequence that is at least 90% identical to SEQ ID NO: 5 and an amino acid sequence that is at least 90% identical to SEQ ID NO: 121; an amino acid sequence that is at least 90% identical to SEQ ID NO: 6 and an amino acid sequence that is at least 90% identical to SEQ ID NO: 121; an amino acid sequence that is at least 90% identical to SEQ ID NO: 7 and an amino acid sequence that is at least 90% identical to SEQ ID NO: 121; an amino acid sequence that is at least 90% identical to SEQ ID NO: 8 and an amino acid sequence that is at least 90% identical to SEQ ID NO: 121; an amino acid sequence that is at least 90% identical to SEQ ID NO: 307 and an amino acid sequence that is at least 90% identical to SEQ ID NO: 121; an amino acid sequence that is at least 90% identical to SEQ ID NO: 308 and an amino acid sequence that is at least 90% identical to SEQ ID NO: 121; an amino acid sequence that is at least 90% identical to SEQ ID NO: 309 and an amino acid sequence that is at least 90% identical to SEQ ID NO: 121; an amino acid sequence that is at least 90% identical to SEQ ID NO: 310 and an amino acid sequence that is at least 90% identical to SEQ ID NO: 121; an amino acid sequence that is at least 90% identical to SEQ ID NO: 311 and an amino acid sequence that is at least 90% identical to SEQ ID NO: 121; an amino acid sequence that is at least 90% identical to SEQ ID NO: 312 and an amino acid sequence that is at least 90% identical to SEQ ID NO: 121; an amino acid sequence that is at least 90% identical to SEQ ID NO: 313 and an amino acid sequence that is at least 90% identical to SEQ ID NO: 121; an amino acid sequence that is at least 90% identical to SEQ ID NO: 314 and an amino acid sequence that is at least 90% identical to SEQ ID NO: 121; an amino acid sequence that is at least 90% identical to SEQ ID NO: 315 and an amino acid sequence that is at least 90% identical to SEQ ID NO: 121; an amino acid sequence that is at least 90% identical to SEQ ID NO: 316 and an amino acid sequence that is at least 90% identical to SEQ ID NO: 121; an amino acid sequence that is at least 90% identical to SEQ ID NO: 317 and an amino acid sequence that is at least 90% identical to SEQ ID NO: 121; an amino acid sequence that is at least 90% identical to SEQ ID NO: 1 and an amino acid sequence that is at least 90% identical to SEQ ID NO: 123; an amino acid sequence that is at least 90% identical to SEQ ID NO: 2 and an amino acid sequence that is at least 90% identical to SEQ ID NO: 123; an amino acid sequence that is at least 90% identical to SEQ ID NO: 3 and an amino acid sequence that is at least 90% identical to SEQ ID NO: 123; an amino acid sequence that is at least 90% identical to SEQ ID NO: 4 and an amino acid sequence that is at least 90% identical to SEQ ID NO: 123; an amino acid sequence that is at least 90% identical to SEQ ID NO: 5 and an amino acid sequence that is at least 90% identical to SEQ ID NO: 123; an amino acid sequence that is at least 90% identical to SEQ ID NO: 6 and an amino acid sequence that is at least 90% identical to SEQ ID NO: 123; an amino acid sequence that is at least 90% identical to SEQ ID NO: 7 and an amino acid sequence that is at least 90% identical to SEQ ID NO: 123; an amino acid sequence that is at least 90% identical to SEQ ID NO: 8 and an amino acid sequence that is at least 90% identical to SEQ ID NO: 123; an amino acid sequence that is at least 90% identical to SEQ ID NO: 307 and an amino acid sequence that is at least 90% identical to SEQ ID NO: 123; an amino acid sequence that is at least 90% identical to SEQ ID NO: 308 and an amino acid sequence that is at least 90% identical to SEQ ID NO: 123; an amino acid sequence that is at least 90% identical to SEQ ID NO: 309 and an amino acid sequence that is at least 90% identical to SEQ ID NO: 123; an amino acid sequence that is at least 90% identical to SEQ ID NO: 310 and an amino acid sequence that is at least 90% identical to SEQ ID NO: 123; an amino acid sequence that is at least 90% identical to SEQ ID NO: 311 and an amino acid sequence that is at least 90% identical to SEQ ID NO: 123; an amino acid sequence that is at least 90% identical to SEQ ID NO: 312 and an amino acid sequence that is at least 90% identical to SEQ ID NO: 123; an amino acid sequence that is at least 90% identical to SEQ ID NO: 313 and an amino acid sequence that is at least 90% identical to SEQ ID NO: 123; an amino acid sequence that is at least 90% identical to SEQ ID NO: 314 and an amino acid sequence that is at least 90% identical to SEQ ID NO: 123; an amino acid sequence that is at least 90% identical to SEQ ID NO: 315 and an amino acid sequence that is at least 90% identical to SEQ ID NO: 123; an amino acid sequence that is at least 90% identical to SEQ ID NO: 316 and an amino acid sequence that is at least 90% identical to SEQ ID NO: 123; an amino acid sequence that is at least 90% identical to SEQ ID NO: 317 and an amino acid sequence that is at least 90% identical to SEQ ID NO: 123; an amino acid sequence that is at least 90% identical to SEQ ID NO: 1 and an amino acid sequence that is at least 90% identical to SEQ ID NO: 125; an amino acid sequence that is at least 90% identical to SEQ ID NO: 2 and an amino acid sequence that is at least 90% identical to SEQ ID NO: 125; an amino acid sequence that is at least 90% identical to SEQ ID NO: 3 and an amino acid sequence that is at least 90% identical to SEQ ID NO: 125; an amino acid sequence that is at least 90% identical to SEQ ID NO: 4 and an amino acid sequence that is at least 90% identical to SEQ ID NO: 125; an amino acid sequence that is at least 90% identical to SEQ ID NO: 5 and an amino acid sequence that is at least 90% identical to SEQ ID NO: 125; an amino acid sequence that is at least 90% identical to SEQ ID NO: 6 and an amino acid sequence that is at least 90% identical to SEQ ID NO: 125; an amino acid sequence that is at least 90% identical to SEQ ID NO: 7 and an amino acid sequence that is at least 90% identical to SEQ ID NO: 125; an amino acid sequence that is at least 90% identical to SEQ ID NO: 8 and an amino acid sequence that is at least 90% identical to SEQ ID NO: 125; an amino acid sequence that is at least 90% identical to SEQ ID NO: 307 and an amino acid sequence that is at least 90% identical to SEQ ID NO: 125; an amino acid sequence that is at least 90% identical to SEQ ID NO: 308 and an amino acid sequence that is at least 90% identical to SEQ ID NO: 125; an amino acid sequence that is at least 90% identical to SEQ ID NO: 309 and an amino acid sequence that is at least 90% identical to SEQ ID NO: 125; an amino acid sequence that is at least 90% identical to SEQ ID NO: 310 and an amino acid sequence that is at least 90% identical to SEQ ID NO: 125; an amino acid sequence that is at least 90% identical to SEQ ID NO: 311 and an amino acid sequence that is at least 90% identical to SEQ ID NO: 125; an amino acid sequence that is at least 90% identical to SEQ ID NO: 312 and an amino acid sequence that is at least 90% identical to SEQ ID NO: 125; an amino acid sequence that is at least 90% identical to SEQ ID NO: 313 and an amino acid sequence that is at least 90% identical to SEQ ID NO: 125; an amino acid sequence that is at least 90% identical to SEQ ID NO: 314 and an amino acid sequence that is at least 90% identical to SEQ ID NO: 125; an amino acid sequence that is at least 90% identical to SEQ ID NO: 315 and an amino acid sequence that is at least 90% identical to SEQ ID NO: 125; an amino acid sequence that is at least 90% identical to SEQ ID NO: 316 and an amino acid sequence that is at least 90% identical to SEQ ID NO: 125; an amino acid sequence that is at least 90% identical to SEQ ID NO: 317 and an amino acid sequence that is at least 90% identical to SEQ ID NO: 125; an amino acid sequence that is at least 90% identical to SEQ ID NO: 1 and an amino acid sequence that is at least 90% identical to SEQ ID NO: 127; an amino acid sequence that is at least 90% identical to SEQ ID NO: 2 and an amino acid sequence that is at least 90% identical to SEQ ID NO: 127; an amino acid sequence that is at least 90% identical to SEQ ID NO: 3 and an amino acid sequence that is at least 90% identical to SEQ ID NO: 127; an amino acid sequence that is at least 90% identical to SEQ ID NO: 4 and an amino acid sequence that is at least 90% identical to SEQ ID NO: 127; an amino acid sequence that is at least 90% identical to SEQ ID NO: 5 and an amino acid sequence that is at least 90% identical to SEQ ID NO: 127; an amino acid sequence that is at least 90% identical to SEQ ID NO: 6 and an amino acid sequence that is at least 90% identical to SEQ ID NO:

127; an amino acid sequence that is at least 90% identical to SEQ ID NO: 7 and an amino acid sequence that is at least 90% identical to SEQ ID NO: 127; an amino acid sequence that is at least 90% identical to SEQ ID NO: 8 and an amino acid sequence that is at least 90% identical to SEQ ID NO: 127; an amino acid sequence that is at least 90% identical to SEQ ID NO: 307 and an amino acid sequence that is at least 90% identical to SEQ ID NO: 127; an amino acid sequence that is at least 90% identical to SEQ ID NO: 308 and an amino acid sequence that is at least 90% identical to SEQ ID NO: 127; an amino acid sequence that is at least 90% identical to SEQ ID NO: 309 and an amino acid sequence that is at least 90% identical to SEQ ID NO: 127; an amino acid sequence that is at least 90% identical to SEQ ID NO: 310 and an amino acid sequence that is at least 90% identical to SEQ ID NO: 127; an amino acid sequence that is at least 90% identical to SEQ ID NO: 311 and an amino acid sequence that is at least 90% identical to SEQ ID NO: 127; an amino acid sequence that is at least 90% identical to SEQ ID NO: 312 and an amino acid sequence that is at least 90% identical to SEQ ID NO: 127; an amino acid sequence that is at least 90% identical to SEQ ID NO: 313 and an amino acid sequence that is at least 90% identical to SEQ ID NO: 127; an amino acid sequence that is at least 90% identical to SEQ ID NO: 314 and an amino acid sequence that is at least 90% identical to SEQ ID NO: 127; an amino acid sequence that is at least 90% identical to SEQ ID NO: 315 and an amino acid sequence that is at least 90% identical to SEQ ID NO: 127; an amino acid sequence that is at least 90% identical to SEQ ID NO: 316 and an amino acid sequence that is at least 90% identical to SEQ ID NO: 127; an amino acid sequence that is at least 90% identical to SEQ ID NO: 317 and an amino acid sequence that is at least 90% identical to SEQ ID NO: 127; an amino acid sequence that is at least 90% identical to SEQ ID NO: 1 and an amino acid sequence that is at least 90% identical to SEQ ID NO: 129; an amino acid sequence that is at least 90% identical to SEQ ID NO: 2 and an amino acid sequence that is at least 90% identical to SEQ ID NO: 129; an amino acid sequence that is at least 90% identical to SEQ ID NO: 3 and an amino acid sequence that is at least 90% identical to SEQ ID NO: 129; an amino acid sequence that is at least 90% identical to SEQ ID NO: 4 and an amino acid sequence that is at least 90% identical to SEQ ID NO: 129; an amino acid sequence that is at least 90% identical to SEQ ID NO: 5 and an amino acid sequence that is at least 90% identical to SEQ ID NO: 129; an amino acid sequence that is at least 90% identical to SEQ ID NO: 6 and an amino acid sequence that is at least 90% identical to SEQ ID NO: 129; an amino acid sequence that is at least 90% identical to SEQ ID NO: 7 and an amino acid sequence that is at least 90% identical to SEQ ID NO: 129; an amino acid sequence that is at least 90% identical to SEQ ID NO: 8 and an amino acid sequence that is at least 90% identical to SEQ ID NO: 129; an amino acid sequence that is at least 90% identical to SEQ ID NO: 307 and an amino acid sequence that is at least 90% identical to SEQ ID NO: 129; an amino acid sequence that is at least 90% identical to SEQ ID NO: 308 and an amino acid sequence that is at least 90% identical to SEQ ID NO: 129; an amino acid sequence that is at least 90% identical to SEQ ID NO: 309 and an amino acid sequence that is at least 90% identical to SEQ ID NO: 129; an amino acid sequence that is at least 90% identical to SEQ ID NO: 310 and an amino acid sequence that is at least 90% identical to SEQ ID NO: 129; an amino acid sequence that is at least 90% identical to SEQ ID NO: 311 and an amino acid sequence that is at least 90% identical to SEQ ID NO: 129; an amino acid sequence that is at least 90% identical to SEQ ID NO: 312 and an amino acid sequence that is at least 90% identical to SEQ ID NO: 129; an amino acid sequence that is at least 90% identical to SEQ ID NO: 313 and an amino acid sequence that is at least 90% identical to SEQ ID NO: 129; an amino acid sequence that is at least 90% identical to SEQ ID NO: 314 and an amino acid sequence that is at least 90% identical to SEQ ID NO: 129; an amino acid sequence that is at least 90% identical to SEQ ID NO: 315 and an amino acid sequence that is at least 90% identical to SEQ ID NO: 129; an amino acid sequence that is at least 90% identical to SEQ ID NO: 316 and an amino acid sequence that is at least 90% identical to SEQ ID NO: 129; an amino acid sequence that is at least 90% identical to SEQ ID NO: 317 and an amino acid sequence that is at least 90% identical to SEQ ID NO: 129; an amino acid sequence that is at least 90% identical to SEQ ID NO: 1 and an amino acid sequence that is at least 90% identical to SEQ ID NO: 131; an amino acid sequence that is at least 90% identical to SEQ ID NO: 2 and an amino acid sequence that is at least 90% identical to SEQ ID NO: 131; an amino acid sequence that is at least 90% identical to SEQ ID NO: 3 and an amino acid sequence that is at least 90% identical to SEQ ID NO: 131; an amino acid sequence that is at least 90% identical to SEQ ID NO: 4 and an amino acid sequence that is at least 90% identical to SEQ ID NO: 131; an amino acid sequence that is at least 90% identical to SEQ ID NO: 5 and an amino acid sequence that is at least 90% identical to SEQ ID NO: 131; an amino acid sequence that is at least 90% identical to SEQ ID NO: 6 and an amino acid sequence that is at least 90% identical to SEQ ID NO: 131; an amino acid sequence that is at least 90% identical to SEQ ID NO: 7 and an amino acid sequence that is at least 90% identical to SEQ ID NO: 131; an amino acid sequence that is at least 90% identical to SEQ ID NO: 8 and an amino acid sequence that is at least 90% identical to SEQ ID NO: 131; an amino acid sequence that is at least 90% identical to SEQ ID NO: 307 and an amino acid sequence that is at least 90% identical to SEQ ID NO: 131; an amino acid sequence that is at least 90% identical to SEQ ID NO: 308 and an amino acid sequence that is at least 90% identical to SEQ ID NO: 131; an amino acid sequence that is at least 90% identical to SEQ ID NO: 309 and an amino acid sequence that is at least 90% identical to SEQ ID NO: 131; an amino acid sequence that is at least 90% identical to SEQ ID NO: 310 and an amino acid sequence that is at least 90% identical to SEQ ID NO: 131; an amino acid sequence that is at least 90% identical to SEQ ID NO: 311 and an amino acid sequence that is at least 90% identical to SEQ ID NO: 131; an amino acid sequence that is at least 90% identical to SEQ ID NO: 312 and an amino acid sequence that is at least 90% identical to SEQ ID NO: 131; an amino acid sequence that is at least 90% identical to SEQ ID NO: 313 and an amino acid sequence that is at least 90% identical to SEQ ID NO: 131; an amino acid sequence that is at least 90% identical to SEQ ID NO: 314 and an amino acid sequence that is at least 90% identical to SEQ ID NO: 131; an amino acid sequence that is at least 90% identical to SEQ ID NO: 315 and an amino acid sequence that is at least 90% identical to SEQ ID NO: 131; an amino acid sequence that is at least 90% identical to SEQ ID NO: 316 and an amino acid sequence that is at least 90% identical to SEQ ID NO: 131; an amino acid sequence that is at least 90% identical to SEQ ID NO: 317 and an amino acid sequence that is at least 90% identical to SEQ ID NO: 131; an amino acid sequence that is at least 90% identical to SEQ ID NO: 1 and an amino acid sequence that is at least 90% identical to SEQ ID NO: 133; an amino acid sequence that is at least 90% identical to SEQ ID NO: 2 and an amino acid sequence that is at least 90% identical to SEQ ID NO: 133; an amino acid sequence that is at least 90% identical to SEQ ID NO: 3 and an amino acid sequence that is at least 90% identical to SEQ ID NO: 133; an amino acid sequence that is at least 90% identical to SEQ ID NO: 4 and an amino acid sequence that is at least 90% identical to SEQ ID NO: 133; an amino acid sequence that is at least 90% identical to SEQ ID NO: 5 and an amino acid sequence that is at least 90% identical to SEQ ID NO: 133; an amino acid sequence that is at least 90% identical to SEQ ID NO: 6 and an amino acid sequence that is at least 90% identical to SEQ ID NO: 133; an amino acid sequence that is at least 90% identical to SEQ ID NO: 7 and an amino acid sequence that is at least 90% identical to SEQ ID NO: 133; an amino acid sequence that is at least 90% identical to SEQ ID NO: 8 and an amino acid sequence that is at least 90% identical to SEQ ID NO: 133; an amino acid sequence that is at least 90% identical to SEQ ID NO: 307 and an amino acid sequence that is at least 90% identical to SEQ ID NO: 133; an amino acid sequence that is at least 90% identical to SEQ ID NO: 308 and an amino acid sequence that is at least 90% identical to SEQ ID NO: 133; an amino acid sequence that is at least 90% identical to SEQ ID NO: 309 and an amino acid sequence that is at least 90% identical to SEQ ID NO: 133; an amino acid sequence that is at least 90% identical to SEQ ID NO: 310 and an amino acid sequence that is at least 90% identical to SEQ ID NO: 133; an amino acid sequence that is at least 90% identical to SEQ ID NO: 311 and an amino acid sequence that is at least 90% identical to SEQ ID NO: 133; an amino acid sequence that is at least 90% identical to SEQ ID NO: 312 and an amino acid sequence that is at least 90% identical to SEQ ID NO: 133; an amino acid sequence that is at least 90% identical to SEQ ID NO: 313 and an amino acid sequence that is at least 90% identical to SEQ ID NO: 133; an amino acid sequence that is at least 90% identical to SEQ ID NO: 314 and an amino acid sequence that is at least 90% identical to SEQ ID NO: 133; an amino acid sequence that is at least 90% identical to SEQ ID NO: 315 and an amino acid sequence that is at least 90% identical to SEQ ID NO: 133; an amino acid sequence that is at least 90% identical to SEQ ID NO: 316 and an amino acid sequence that is at least 90% identical to SEQ ID NO: 133; an amino acid sequence that is at least 90% identical to SEQ ID NO: 317 and an amino acid sequence that is at least 90% identical to SEQ ID NO: 133; an amino acid sequence that is at least 90% identical to SEQ ID NO: 1 and an amino acid sequence that is at least 90% identical to SEQ ID NO: 135; an amino acid sequence that is at least 90% identical to SEQ ID NO: 2 and an amino acid sequence that is at least 90% identical to SEQ ID NO: 135; an amino acid sequence that is at least 90% identical to SEQ ID NO: 3 and an amino acid sequence that is at least 90% identical to SEQ ID NO: 135; an amino acid sequence that is at least 90% identical to SEQ ID NO: 4 and an amino acid sequence that is at least 90% identical to SEQ ID NO: 135; an amino acid sequence that is at least 90% identical to SEQ ID NO: 5 and an amino acid sequence that is at least 90% identical to SEQ ID NO: 135; an amino acid sequence that is at least 90% identical to SEQ ID NO: 6 and an amino acid sequence that is at least 90% identical to SEQ ID NO: 135; an amino acid sequence that is at least 90% identical to SEQ ID NO: 7 and an amino acid sequence that is at least 90% identical to SEQ ID NO: 135; an amino acid sequence that is at least 90% identical to SEQ ID NO: 8 and an amino acid sequence that is at least 90% identical to SEQ ID NO: 135; an amino acid sequence that is at least 90% identical to SEQ ID NO: 307 and an amino acid sequence that is at least 90% identical to SEQ ID NO: 135; an amino acid sequence that is at least 90% identical to SEQ ID NO: 308 and an amino acid sequence that is at least 90% identical to SEQ ID NO: 135; an amino acid sequence that is at least 90% identical to SEQ ID NO: 309 and an amino acid sequence that is at least 90% identical to SEQ ID NO: 135; an amino acid sequence that is at least 90% identical to SEQ ID NO: 310 and an amino acid sequence that is at least 90% identical to SEQ ID NO: 135; an amino acid sequence that is at least 90% identical to SEQ ID NO: 311 and an amino acid sequence that is at least 90% identical to SEQ ID NO: 135; an amino acid sequence that is at least 90% identical to SEQ ID NO: 312 and an amino acid sequence that is at least 90% identical to SEQ ID NO: 135; an amino acid sequence that is at least 90% identical to SEQ ID NO: 313 and an amino acid sequence that is at least 90% identical to SEQ ID NO: 135; an amino acid sequence that is at least 90% identical to SEQ ID NO: 314 and an amino acid sequence that is at least 90% identical to SEQ ID NO: 135; an amino acid sequence that is at least 90% identical to SEQ ID NO: 315 and an amino acid sequence that is at least 90% identical to SEQ ID NO: 135; an amino acid sequence that is at least 90% identical to SEQ ID NO: 316 and an amino acid sequence that is at least 90% identical to SEQ ID NO: 135; an amino acid sequence that is at least 90% identical to SEQ ID NO: 317 and an amino acid sequence that is at least 90% identical to SEQ ID NO: 135; an amino acid sequence that is at least 90% identical to SEQ ID NO: 1 and an amino acid sequence that is at least 90% identical to SEQ ID NO: 137; an amino acid sequence that is at least 90% identical to SEQ ID NO: 2 and an amino acid sequence that is at least 90% identical to SEQ ID NO: 137; an amino acid sequence that is at least 90% identical to SEQ ID NO: 3 and an amino acid sequence that is at least 90% identical to SEQ ID NO: 137; an amino acid sequence that is at least 90% identical to SEQ ID NO: 4 and an amino acid sequence that is at least 90% identical to SEQ ID NO: 137; an amino acid sequence that is at least 90% identical to SEQ ID NO: 5 and an amino acid sequence that is at least 90% identical to SEQ ID NO: 137; an amino acid sequence that is at least 90% identical to SEQ ID NO: 6 and an amino acid sequence that is at least 90% identical to SEQ ID NO: 137; an amino acid sequence that is at least 90% identical to SEQ ID NO: 7 and an amino acid sequence that is at least 90% identical to SEQ ID NO: 137; an amino acid sequence that is at least 90% identical to SEQ ID NO: 8 and an amino acid sequence that is at least 90% identical to SEQ ID NO: 137; an amino acid sequence that is at least 90% identical to SEQ ID NO: 307 and an amino acid sequence that is at least 90% identical to SEQ ID NO: 137; an amino acid sequence that is at least 90% identical to SEQ ID NO: 308 and an amino acid sequence that is at least 90% identical to SEQ ID NO: 137; an amino acid sequence that is at least 90% identical to SEQ ID NO: 309 and an amino acid sequence that is at least 90% identical to SEQ ID NO: 137; an amino acid sequence that is at least 90% identical to SEQ ID NO: 310 and an amino acid sequence that is at least 90% identical to SEQ ID NO: 137; an amino acid sequence that is at least 90% identical to SEQ ID NO: 311 and an amino acid sequence that is at least 90% identical to SEQ ID NO: 137; an amino acid sequence that is at least 90% identical to SEQ ID NO: 312 and an amino acid sequence that is at least 90% identical to SEQ ID NO: 137; an amino acid sequence that is at least 90% identical to SEQ ID NO: 313 and an amino acid sequence that is at least 90% identical to SEQ ID NO: 137; an amino acid sequence that is at least 90% identical to SEQ ID NO: 314 and an amino acid sequence that is at least 90% identical to SEQ ID NO: 137; an amino acid sequence that is at least 90% identical to SEQ ID NO: 315 and an amino acid sequence that is at least 90% identical to SEQ ID NO: 137; an amino acid sequence that is at least 90% identical to SEQ ID NO: 316 and an amino acid sequence that is at least 90% identical to SEQ ID NO: 137; an amino acid sequence that is at least 90% identical to SEQ ID NO: 317 and an amino acid sequence that is at least 90% identical to SEQ ID NO: 137; an amino acid sequence that is at least 90% identical to SEQ ID NO: 1 and an amino acid sequence that is at least 90% identical to SEQ ID NO: 376; an amino acid sequence that is at least 90% identical to SEQ ID NO: 2 and an amino acid sequence that is at least 90% identical to SEQ ID NO: 376; an amino acid sequence that is at least 90% identical to SEQ ID NO: 3 and an amino acid sequence that is at least 90% identical to SEQ ID NO: 376; an amino acid sequence that is at least 90% identical to SEQ ID NO: 4 and an amino acid sequence that is at least 90% identical to SEQ ID NO: 376; an amino acid sequence that is at least 90% identical to SEQ ID NO: 5 and an amino acid sequence that is at least 90% identical to SEQ ID NO: 376; an amino acid sequence that is at least 90% identical to SEQ ID NO: 6 and an amino acid sequence that is at least 90% identical to SEQ ID NO: 376; an amino acid sequence that is at least 90% identical to SEQ ID NO: 7 and an amino acid sequence that is at least 90% identical to SEQ ID NO: 376; an amino acid sequence that is at least 90% identical to SEQ ID NO: 8 and an amino acid sequence that is at least 90% identical to SEQ ID NO: 376; an amino acid sequence that is at least 90% identical to SEQ ID NO: 307 and an amino acid sequence that is at least 90% identical to SEQ ID NO: 376; an amino acid sequence that is at least 90% identical to SEQ ID NO: 308 and an amino acid sequence that is at least 90% identical to SEQ ID NO: 376; an amino acid sequence that is at least 90% identical to SEQ ID NO: 309 and an amino acid sequence that is at least 90% identical to SEQ ID NO: 376; an amino acid sequence that is at least 90% identical to SEQ ID NO: 310 and an amino acid sequence that is at least 90% identical to SEQ ID NO: 376; an amino acid sequence that is at least 90% identical to SEQ ID NO: 311 and an amino acid sequence that is at least 90% identical to SEQ ID NO: 376; an amino acid sequence that is at least 90% identical to SEQ ID NO: 312 and an amino acid sequence that is at least 90% identical to SEQ ID NO: 376; an amino acid sequence that is at least 90% identical to SEQ ID NO: 313 and an amino acid sequence that is at least 90% identical to SEQ ID NO: 376; an amino acid sequence that is at least 90% identical to SEQ ID NO: 314 and an amino acid sequence that is at least 90% identical to SEQ ID NO: 376; an amino acid sequence that is at least 90% identical to SEQ ID NO: 315 and an amino acid sequence that is at least 90% identical to SEQ ID NO: 376; an amino acid sequence that is at least 90% identical to SEQ ID NO: 316 and an amino acid sequence that is at least 90% identical to SEQ ID NO: 376; an amino acid sequence that is at least 90% identical to SEQ ID NO: 317 and an amino acid sequence that is at least 90% identical to SEQ ID NO: 376; an amino acid sequence that is at least 90% identical to SEQ ID NO: 1 and an amino acid sequence that is at least 90% identical to SEQ ID NO: 378; an amino acid sequence that is at least 90% identical to SEQ ID NO: 2 and an amino acid sequence that is at least 90% identical to SEQ ID NO: 378; an amino acid sequence that is at least 90% identical to SEQ ID NO: 3 and an amino acid sequence that is at least 90% identical to SEQ ID NO: 378; an amino acid sequence that is at least 90% identical to SEQ ID NO: 4 and an amino acid sequence that is at least 90% identical to SEQ ID NO: 378; an amino acid sequence that is at least 90% identical to SEQ ID NO: 5 and an amino acid sequence that is at least 90% identical to SEQ ID NO: 378; an amino acid sequence that is at least 90% identical to SEQ ID NO: 6 and an amino acid sequence that is at least 90% identical to SEQ ID NO: 378; an amino acid sequence that is at least 90% identical to SEQ ID NO: 7 and an amino acid sequence that is at least 90% identical to SEQ ID NO: 378; an amino acid sequence that is at least 90% identical to SEQ ID NO: 8 and an amino acid sequence that is at least 90% identical to SEQ ID NO: 378; an amino acid sequence that is at least 90% identical to SEQ ID NO: 307 and an amino acid sequence that is at least 90% identical to SEQ ID NO: 378; an amino acid sequence that is at least 90% identical to SEQ ID NO: 308 and an amino acid sequence that is at least 90% identical to SEQ ID NO: 378; an amino acid sequence that is at least 90% identical to SEQ ID NO: 309 and an amino acid sequence that is at least 90% identical to SEQ ID NO: 378; an amino acid sequence that is at least 90% identical to SEQ ID NO: 310 and an amino acid sequence that is at least 90% identical to SEQ ID NO: 378; an amino acid sequence that is at least 90% identical to SEQ ID NO: 311 and an amino acid sequence that is at least 90% identical to SEQ ID NO: 378; an amino acid sequence that is at least 90% identical to SEQ ID NO: 312 and an amino acid sequence that is at least 90% identical to SEQ ID NO: 378; an amino acid sequence that is at least 90% identical to SEQ ID NO: 313 and an amino acid sequence that is at least 90% identical to SEQ ID NO: 378; an amino acid sequence that is at least 90% identical to SEQ ID NO: 314 and an amino acid sequence that is at least 90% identical to SEQ ID NO: 378; an amino acid sequence that is at least 90% identical to SEQ ID NO: 315 and an amino acid sequence that is at least 90% identical to SEQ ID NO: 378; an amino acid sequence that is at least 90% identical to SEQ ID NO: 316 and an amino acid sequence that is at least 90% identical to SEQ ID NO: 378; an amino acid sequence that is at least 90% identical to SEQ ID NO: 317 and an amino acid sequence that is at least 90% identical to SEQ ID NO: 378.

In some embodiments, the first polypeptide comprises: the amino acid sequence of SEQ ID NO: 1 and the amino acid sequence of SEQ ID NO: 103; the amino acid sequence of SEQ ID NO: 2 and the amino acid sequence of SEQ ID NO: 103; the amino acid sequence of SEQ ID NO: 3 and the amino acid sequence of SEQ ID NO: 103; the amino acid sequence of SEQ ID NO: 4 and the amino acid sequence of SEQ ID NO: 103; the amino acid sequence of SEQ ID NO: 5 and the amino acid sequence of SEQ ID NO: 103; the amino acid sequence of SEQ ID NO: 6 and the amino acid sequence of SEQ ID NO: 103; the amino acid sequence of SEQ ID NO: 7 and the amino acid sequence of SEQ ID NO: 103; the amino acid sequence of SEQ ID NO: 8 and the amino acid sequence of SEQ ID NO: 103; the amino acid sequence of SEQ ID NO: 307 and the amino acid sequence of SEQ ID NO: 103; the amino acid sequence of SEQ ID NO: 308 and the amino acid sequence of SEQ ID NO: 103; the amino acid sequence of SEQ ID NO: 309 and the amino acid sequence of SEQ ID NO: 103; the amino acid sequence of SEQ ID NO: 310 and the amino acid sequence of SEQ ID NO: 103; the amino acid sequence of SEQ ID NO: 311 and the amino acid sequence of SEQ ID NO: 103; the amino acid sequence of SEQ ID NO: 312 and the amino acid sequence of SEQ ID NO: 103; the amino acid sequence of SEQ ID NO: 313 and the amino acid sequence of SEQ ID NO: 103; the amino acid sequence of SEQ ID NO: 314 and the amino acid sequence of SEQ ID NO: 103; the amino acid sequence of SEQ ID NO: 315 and the amino acid sequence of SEQ ID NO: 103; the amino acid sequence of SEQ ID NO: 316 and the amino acid sequence of SEQ ID NO: 103; the amino acid sequence of SEQ ID NO: 317 and the amino acid sequence of SEQ ID NO: 103; the amino acid sequence of SEQ ID NO: 1 and the amino acid sequence of SEQ ID NO: 105; the amino acid sequence of SEQ ID NO: 2 and the amino acid sequence of SEQ ID NO: 105; the amino acid sequence of SEQ ID NO: 3 and the amino acid sequence of SEQ ID NO: 105; the amino acid sequence of SEQ ID NO: 4 and the amino acid sequence of SEQ ID NO: 105; the amino acid sequence of SEQ ID NO: 5 and the amino acid sequence of SEQ ID NO: 105; the amino acid sequence of SEQ ID NO: 6 and the amino acid sequence of SEQ ID NO: 105; the amino acid sequence of SEQ ID NO: 7 and the amino acid sequence of SEQ ID NO: 105; the amino acid sequence of SEQ ID NO: 8 and the amino acid sequence of SEQ ID NO: 105; the amino acid sequence of SEQ ID NO: 307 and the amino acid sequence of SEQ ID NO: 105; the amino acid sequence of SEQ ID NO: 308 and the amino acid sequence of SEQ ID NO: 105; the amino acid sequence of SEQ ID NO: 309 and the amino acid sequence of SEQ ID NO: 105; the amino acid sequence of SEQ ID NO: 310 and the amino acid sequence of SEQ ID NO: 105; the amino acid sequence of SEQ ID NO: 311 and the amino acid sequence of SEQ ID NO: 105; the amino acid sequence of SEQ ID NO: 312 and the amino acid sequence of SEQ ID NO: 105; the amino acid sequence of SEQ ID NO: 313 and the amino acid sequence of SEQ ID NO: 105; the amino acid sequence of SEQ ID NO: 314 and the amino acid sequence of SEQ ID NO: 105; the amino acid sequence of SEQ ID NO: 315 and the amino acid sequence of SEQ ID NO: 105; the amino acid sequence of SEQ ID NO: 316 and the amino acid sequence of SEQ ID NO: 105; the amino acid sequence of SEQ ID NO: 317 and the amino acid sequence of SEQ ID NO: 105; the amino acid sequence of SEQ ID NO: 4, the amino acid sequence of SEQ ID NO: 209, the amino acid sequence of SEQ ID NO: 210, and the amino acid sequence of SEQ ID NO: 105; the amino acid sequence of SEQ ID NO: 1 and the amino acid sequence of SEQ ID NO: 107; the amino acid sequence of SEQ ID NO: 2 and the amino acid sequence of SEQ ID NO: 107; the amino acid sequence of SEQ ID NO: 3 and the amino acid sequence of SEQ ID NO: 107; the amino acid sequence of SEQ ID NO: 4 and the amino acid sequence of SEQ ID NO: 107; the amino acid sequence of SEQ ID NO: 5 and the amino acid sequence of SEQ ID NO: 107; the amino acid sequence of SEQ ID NO: 6 and the amino acid sequence of SEQ ID NO: 107; the amino acid sequence of SEQ ID NO: 7 and the amino acid sequence of SEQ ID NO: 107; the amino acid sequence of SEQ ID NO: 8 and the amino acid sequence of SEQ ID NO: 107; the amino acid sequence of SEQ ID NO: 307 and the amino acid sequence of SEQ ID NO: 107; the amino acid sequence of SEQ ID NO: 308 and the amino acid sequence of SEQ ID NO: 107; the amino acid sequence of SEQ ID NO: 309 and the amino acid sequence of SEQ ID NO: 107; the amino acid sequence of SEQ ID NO: 310 and the amino acid sequence of SEQ ID NO: 107; the amino acid sequence of SEQ ID NO: 311 and the amino acid sequence of SEQ ID NO: 107; the amino acid sequence of SEQ ID NO: 312 and the amino acid sequence of SEQ ID NO: 107; the amino acid sequence of SEQ ID NO: 313 and the amino acid sequence of SEQ ID NO: 107; the amino acid sequence of SEQ ID NO: 314 and the amino acid sequence of SEQ ID NO: 107; the amino acid sequence of SEQ ID NO: 315 and the amino acid sequence of SEQ ID NO: 107; the amino acid sequence of SEQ ID NO: 316 and the amino acid sequence of SEQ ID NO: 107; the amino acid sequence of SEQ ID NO: 317 and the amino acid sequence of SEQ ID NO: 107; the amino acid sequence of SEQ ID NO: 1 and the amino acid sequence of SEQ ID NO: 109; the amino acid sequence of SEQ ID NO: 2 and the amino acid sequence of SEQ ID NO: 109; the amino acid sequence of SEQ ID NO: 3 and the amino acid sequence of SEQ ID NO: 109; the amino acid sequence of SEQ ID NO: 4 and the amino acid sequence of SEQ ID NO: 109; the amino acid sequence of SEQ ID NO: 5 and the amino acid sequence of SEQ ID NO: 109; the amino acid sequence of SEQ ID NO: 6 and the amino acid sequence of SEQ ID NO: 109; the amino acid sequence of SEQ ID NO: 7 and the amino acid sequence of SEQ ID NO: 109; the amino acid sequence of SEQ ID NO: 8 and the amino acid sequence of SEQ ID NO: 109; the amino acid sequence of SEQ ID NO: 307 and the amino acid sequence of SEQ ID NO: 109; the amino acid sequence of SEQ ID NO: 308 and the amino acid sequence of SEQ ID NO: 109; the amino acid sequence of SEQ ID NO: 309 and the amino acid sequence of SEQ ID NO: 109; the amino acid sequence of SEQ ID NO: 310 and the amino acid sequence of SEQ ID NO: 109; the amino acid sequence of SEQ ID NO: 311 and the amino acid sequence of SEQ ID NO: 109; the amino acid sequence of SEQ ID NO: 312 and the amino acid sequence of SEQ ID NO: 109; the amino acid sequence of SEQ ID NO: 313 and the amino acid sequence of SEQ ID NO: 109; the amino acid sequence of SEQ ID NO: 314 and the amino acid sequence of SEQ ID NO: 109; the amino acid sequence of SEQ ID NO: 315 and the amino acid sequence of SEQ ID NO: 109; the amino acid sequence of SEQ ID NO: 316 and the amino acid sequence of SEQ ID NO: 109; the amino acid sequence of SEQ ID NO: 317 and the amino acid sequence of SEQ ID NO: 109; the amino acid sequence of SEQ ID NO: 1 and the amino acid sequence of SEQ ID NO: 113; the amino acid sequence of SEQ ID NO: 2 and the amino acid sequence of SEQ ID NO: 113; the amino acid sequence of SEQ ID NO: 3 and the amino acid sequence of SEQ ID NO: 113; the amino acid sequence of SEQ ID NO: 4 and the amino acid sequence of SEQ ID NO: 113; the amino acid sequence of SEQ ID NO: 5 and the amino acid sequence of SEQ ID NO: 113; the amino acid sequence of SEQ ID NO: 6 and the amino acid sequence of SEQ ID NO: 113; the amino acid sequence of SEQ ID NO: 7 and the amino acid sequence of SEQ ID NO: 113; the amino acid sequence of SEQ ID NO: 8 and the amino acid sequence of SEQ ID NO: 113; the amino acid sequence of SEQ ID NO: 307 and the amino acid sequence of SEQ ID NO: 113; the amino acid sequence of SEQ ID NO: 308 and the amino acid sequence of SEQ ID NO: 113; the amino acid sequence of SEQ ID NO: 309 and the amino acid sequence of SEQ ID NO: 113; the amino acid sequence of SEQ ID NO: 310 and the amino acid sequence of SEQ ID NO: 113; the amino acid sequence of SEQ ID NO: 311 and the amino acid sequence of SEQ ID NO: 113; the amino acid sequence of SEQ ID NO: 312 and the amino acid sequence of SEQ ID NO: 113; the amino acid sequence of SEQ ID NO: 313 and the amino acid sequence of SEQ ID NO: 113; the amino acid sequence of SEQ ID NO: 314 and the amino acid sequence of SEQ ID NO: 113; the amino acid sequence of SEQ ID NO: 315 and the amino acid sequence of SEQ ID NO: 113; the amino acid sequence of SEQ ID NO: 316 and the amino acid sequence of SEQ ID NO: 113; the amino acid sequence of SEQ ID NO: 317 and the amino acid sequence of SEQ ID NO: 113; the amino acid sequence of SEQ ID NO: 1 and the amino acid sequence of SEQ ID NO: 115; the amino acid sequence of SEQ ID NO: 2 and the amino acid sequence of SEQ ID NO: 115; the amino acid sequence of SEQ ID NO: 3 and the amino acid sequence of SEQ ID NO: 115; the amino acid sequence of SEQ ID NO: 4 and the amino acid sequence of SEQ ID NO: 115; the amino acid sequence of SEQ ID NO: 5 and the amino acid sequence of SEQ ID NO:

115; the amino acid sequence of SEQ ID NO: 6 and the amino acid sequence of SEQ ID NO: 115; the amino acid sequence of SEQ ID NO: 7 and the amino acid sequence of SEQ ID NO: 115; the amino acid sequence of SEQ ID NO: 8 and the amino acid sequence of SEQ ID NO: 115; the amino acid sequence of SEQ ID NO: 307 and the amino acid sequence of SEQ ID NO: 115; the amino acid sequence of SEQ ID NO: 308 and the amino acid sequence of SEQ ID NO: 115; the amino acid sequence of SEQ ID NO: 309 and the amino acid sequence of SEQ ID NO: 115; the amino acid sequence of SEQ ID NO: 310 and the amino acid sequence of SEQ ID NO: 115; the amino acid sequence of SEQ ID NO: 311 and the amino acid sequence of SEQ ID NO: 115; the amino acid sequence of SEQ ID NO: 312 and the amino acid sequence of SEQ ID NO: 115; the amino acid sequence of SEQ ID NO: 313 and the amino acid sequence of SEQ ID NO: 115; the amino acid sequence of SEQ ID NO: 314 and the amino acid sequence of SEQ ID NO: 115; the amino acid sequence of SEQ ID NO: 315 and the amino acid sequence of SEQ ID NO: 115; the amino acid sequence of SEQ ID NO: 316 and the amino acid sequence of SEQ ID NO: 115; the amino acid sequence of SEQ ID NO: 317 and the amino acid sequence of SEQ ID NO: 115; the amino acid sequence of SEQ ID NO: 1 and the amino acid sequence of SEQ ID NO: 117; the amino acid sequence of SEQ ID NO: 2 and the amino acid sequence of SEQ ID NO: 117; the amino acid sequence of SEQ ID NO: 3 and the amino acid sequence of SEQ ID NO: 117; the amino acid sequence of SEQ ID NO: 4 and the amino acid sequence of SEQ ID NO: 117; the amino acid sequence of SEQ ID NO: 5 and the amino acid sequence of SEQ ID NO: 117; the amino acid sequence of SEQ ID NO: 6 and the amino acid sequence of SEQ ID NO: 117; the amino acid sequence of SEQ ID NO: 7 and the amino acid sequence of SEQ ID NO: 117; the amino acid sequence of SEQ ID NO: 8 and the amino acid sequence of SEQ ID NO: 117; the amino acid sequence of SEQ ID NO: 307 and the amino acid sequence of SEQ ID NO: 117; the amino acid sequence of SEQ ID NO: 308 and the amino acid sequence of SEQ ID NO: 117; the amino acid sequence of SEQ ID NO: 309 and the amino acid sequence of SEQ ID NO: 117; the amino acid sequence of SEQ ID NO: 310 and the amino acid sequence of SEQ ID NO: 117; the amino acid sequence of SEQ ID NO: 311 and the amino acid sequence of SEQ ID NO: 117; the amino acid sequence of SEQ ID NO: 312 and the amino acid sequence of SEQ ID NO: 117; the amino acid sequence of SEQ ID NO: 313 and the amino acid sequence of SEQ ID NO: 117; the amino acid sequence of SEQ ID NO: 314 and the amino acid sequence of SEQ ID NO: 117; the amino acid sequence of SEQ ID NO: 315 and the amino acid sequence of SEQ ID NO: 117; the amino acid sequence of SEQ ID NO: 316 and the amino acid sequence of SEQ ID NO: 117; the amino acid sequence of SEQ ID NO: 317 and the amino acid sequence of SEQ ID NO: 117; the amino acid sequence of SEQ ID NO: 1 and the amino acid sequence of SEQ ID NO: 119; the amino acid sequence of SEQ ID NO: 2 and the amino acid sequence of SEQ ID NO: 119; the amino acid sequence of SEQ ID NO: 3 and the amino acid sequence of SEQ ID NO: 119; the amino acid sequence of SEQ ID NO: 4 and the amino acid sequence of SEQ ID NO: 119; the amino acid sequence of SEQ ID NO: 5 and the amino acid sequence of SEQ ID NO: 119; the amino acid sequence of SEQ ID NO: 6 and the amino acid sequence of SEQ ID NO: 119; the amino acid sequence of SEQ ID NO: 7 and the amino acid sequence of SEQ ID NO: 119; the amino acid sequence of SEQ ID NO: 8 and the amino acid sequence of SEQ ID NO: 119; the amino acid sequence of SEQ ID NO: 307 and the amino acid sequence of SEQ ID NO: 119; the amino acid sequence of SEQ ID NO: 308 and the amino acid sequence of SEQ ID NO: 119; the amino acid sequence of SEQ ID NO: 309 and the amino acid sequence of SEQ ID NO: 119; the amino acid sequence of SEQ ID NO: 310 and the amino acid sequence of SEQ ID NO: 119; the amino acid sequence of SEQ ID NO: 311 and the amino acid sequence of SEQ ID NO: 119; the amino acid sequence of SEQ ID NO: 312 and the amino acid sequence of SEQ ID NO: 119; the amino acid sequence of SEQ ID NO: 313 and the amino acid sequence of SEQ ID NO: 119; the amino acid sequence of SEQ ID NO: 314 and the amino acid sequence of SEQ ID NO: 119; the amino acid sequence of SEQ ID NO: 315 and the amino acid sequence of SEQ ID NO: 119; the amino acid sequence of SEQ ID NO: 316 and the amino acid sequence of SEQ ID NO: 119; the amino acid sequence of SEQ ID NO: 317 and the amino acid sequence of SEQ ID NO: 119; the amino acid sequence of SEQ ID NO: 1 and the amino acid sequence of SEQ ID NO: 121; the amino acid sequence of SEQ ID NO: 2 and the amino acid sequence of SEQ ID NO: 121; the amino acid sequence of SEQ ID NO: 3 and the amino acid sequence of SEQ ID NO: 121; the amino acid sequence of SEQ ID NO: 4 and the amino acid sequence of SEQ ID NO: 121; the amino acid sequence of SEQ ID NO: 5 and the amino acid sequence of SEQ ID NO: 121; the amino acid sequence of SEQ ID NO: 6 and the amino acid sequence of SEQ ID NO: 121; the amino acid sequence of SEQ ID NO: 7 and the amino acid sequence of SEQ ID NO: 121; the amino acid sequence of SEQ ID NO: 8 and the amino acid sequence of SEQ ID NO: 121; the amino acid sequence of SEQ ID NO: 307 and the amino acid sequence of SEQ ID NO: 121; the amino acid sequence of SEQ ID NO: 308 and the amino acid sequence of SEQ ID NO: 121; the amino acid sequence of SEQ ID NO: 309 and the amino acid sequence of SEQ ID NO: 121; the amino acid sequence of SEQ ID NO: 310 and the amino acid sequence of SEQ ID NO: 121; the amino acid sequence of SEQ ID NO: 311 and the amino acid sequence of SEQ ID NO: 121; the amino acid sequence of SEQ ID NO: 312 and the amino acid sequence of SEQ ID NO: 121; the amino acid sequence of SEQ ID NO: 313 and the amino acid sequence of SEQ ID NO: 121; the amino acid sequence of SEQ ID NO: 314 and the amino acid sequence of SEQ ID NO: 121; the amino acid sequence of SEQ ID NO: 315 and the amino acid sequence of SEQ ID NO: 121; the amino acid sequence of SEQ ID NO: 316 and the amino acid sequence of SEQ ID NO: 121; the amino acid sequence of SEQ ID NO: 317 and the amino acid sequence of SEQ ID NO: 121; the amino acid sequence of SEQ ID NO: 1 and the amino acid sequence of SEQ ID NO: 123; the amino acid sequence of SEQ ID NO: 2 and the amino acid sequence of SEQ ID NO: 123; the amino acid sequence of SEQ ID NO: 3 and the amino acid sequence of SEQ ID NO: 123; the amino acid sequence of SEQ ID NO: 4 and the amino acid sequence of SEQ ID NO: 123; the amino acid sequence of SEQ ID NO: 5 and the amino acid sequence of SEQ ID NO: 123; the amino acid sequence of SEQ ID NO: 6 and the amino acid sequence of SEQ ID NO: 123; the amino acid sequence of SEQ ID NO: 7 and the amino acid sequence of SEQ ID NO: 123; the amino acid sequence of SEQ ID NO: 8 and the amino acid sequence of SEQ ID NO: 123; the amino acid sequence of SEQ ID NO: 307 and the amino acid sequence of SEQ ID NO: 123; the amino acid sequence of SEQ ID NO: 308 and the amino acid sequence of SEQ ID NO: 123; the amino acid sequence of SEQ ID NO: 309 and the amino acid sequence of SEQ ID NO: 123; the amino acid sequence of SEQ ID NO: 310 and the amino acid sequence of SEQ ID NO: 123; the amino acid sequence of SEQ ID NO: 311 and the amino acid sequence of SEQ ID NO: 123; the amino acid sequence of SEQ ID NO: 312 and the amino acid sequence of SEQ ID NO: 123; the amino acid sequence of SEQ ID NO: 313 and the amino acid sequence of SEQ ID NO: 123; the amino acid sequence of SEQ ID NO: 314 and the amino acid sequence of SEQ ID NO: 123; the amino acid sequence of SEQ ID NO: 315 and the amino acid sequence of SEQ ID NO: 123; the amino acid sequence of SEQ ID NO: 316 and the amino acid sequence of SEQ ID NO: 123; the amino acid sequence of SEQ ID NO: 317 and the amino acid sequence of SEQ ID NO: 123; the amino acid sequence of SEQ ID NO: 1 and the amino acid sequence of SEQ ID NO: 125; the amino acid sequence of SEQ ID NO: 2 and the amino acid sequence of SEQ ID NO: 125; the amino acid sequence of SEQ ID NO: 3 and the amino acid sequence of SEQ ID NO: 125; the amino acid sequence of SEQ ID NO: 4 and the amino acid sequence of SEQ ID NO: 125; the amino acid sequence of SEQ ID NO: 5 and the amino acid sequence of SEQ ID NO: 125; the amino acid sequence of SEQ ID NO: 6 and the amino acid sequence of SEQ ID NO: 125; the amino acid sequence of SEQ ID NO: 7 and the amino acid sequence of SEQ ID NO: 125; the amino acid sequence of SEQ ID NO: 8 and the amino acid sequence of SEQ ID NO: 125; the amino acid sequence of SEQ ID NO: 307 and the amino acid sequence of SEQ ID NO: 125; the amino acid sequence of SEQ ID NO: 308 and the amino acid sequence of SEQ ID NO: 125; the amino acid sequence of SEQ ID NO: 309 and the amino acid sequence of SEQ ID NO: 125; the amino acid sequence of SEQ ID NO: 310 and the amino acid sequence of SEQ ID NO: 125; the amino acid sequence of SEQ ID NO: 311 and the amino acid sequence of SEQ ID NO: 125; the amino acid sequence of SEQ ID NO: 312 and the amino acid sequence of SEQ ID NO: 125; the amino acid sequence of SEQ ID NO: 313 and the amino acid sequence of SEQ ID NO: 125; the amino acid sequence of SEQ ID NO: 314 and the amino acid sequence of SEQ ID NO: 125; the amino acid sequence of SEQ ID NO: 315 and the amino acid sequence of SEQ ID NO: 125; the amino acid sequence of SEQ ID NO: 316 and the amino acid sequence of SEQ ID NO: 125; the amino acid sequence of SEQ ID NO: 317 and the amino acid sequence of SEQ ID NO: 125; the amino acid sequence of SEQ ID NO: 1 and the amino acid sequence of SEQ ID NO: 127; the amino acid sequence of SEQ ID NO: 2 and the amino acid sequence of SEQ ID NO: 127; the amino acid sequence of SEQ ID NO: 3 and the amino acid sequence of SEQ ID NO: 127; the amino acid sequence of SEQ ID NO: 4 and the amino acid sequence of SEQ ID NO: 127; the amino acid sequence of SEQ ID NO: 5 and the amino acid sequence of SEQ ID NO: 127; the amino acid sequence of SEQ ID NO: 6 and the amino acid sequence of SEQ ID NO: 127; the amino acid sequence of SEQ ID NO: 7 and the amino acid sequence of SEQ ID NO: 127; the amino acid sequence of SEQ ID NO: 8 and the amino acid sequence of SEQ ID NO: 127; the amino acid sequence of SEQ ID NO: 307 and the amino acid sequence of SEQ ID NO: 127; the amino acid sequence of SEQ ID NO: 308 and the amino acid sequence of SEQ ID NO: 127; the amino acid sequence of SEQ ID NO: 309 and the amino acid sequence of SEQ ID NO: 127; the amino acid sequence of SEQ ID NO: 310 and the amino acid sequence of SEQ ID NO: 127; the amino acid sequence of SEQ ID NO: 311 and the amino acid sequence of SEQ ID NO: 127; the amino acid sequence of SEQ ID NO: 312 and the amino acid sequence of SEQ ID NO: 127; the amino acid sequence of SEQ ID NO: 313 and the amino acid sequence of SEQ ID NO: 127; the amino acid sequence of SEQ ID NO: 314 and the amino acid sequence of SEQ ID NO: 127; the amino acid sequence of SEQ ID NO: 315 and the amino acid sequence of SEQ ID NO: 127; the amino acid sequence of SEQ ID NO: 316 and the amino acid sequence of SEQ ID NO: 127; the amino acid sequence of SEQ ID NO: 317 and the amino acid sequence of SEQ ID NO: 127; the amino acid sequence of SEQ ID NO: 1 and the amino acid sequence of SEQ ID NO: 129; the amino acid sequence of SEQ ID NO: 2 and the amino acid sequence of SEQ ID NO: 129; the amino acid sequence of SEQ ID NO: 3 and the amino acid sequence of SEQ ID NO: 129; the amino acid sequence of SEQ ID NO: 4 and the amino acid sequence of SEQ ID NO: 129; the amino acid sequence of SEQ ID NO: 5 and the amino acid sequence of SEQ ID NO: 129; the amino acid sequence of SEQ ID NO: 6 and the amino acid sequence of SEQ ID NO: 129; the amino acid sequence of SEQ ID NO: 7 and the amino acid sequence of SEQ ID NO: 129; the amino acid sequence of SEQ ID NO: 8 and the amino acid sequence of SEQ ID NO: 129; the amino acid sequence of SEQ ID NO: 307 and the amino acid sequence of SEQ ID NO: 129; the amino acid sequence of SEQ ID NO: 308 and the amino acid sequence of SEQ ID NO: 129; the amino acid sequence of SEQ ID NO: 309 and the amino acid sequence of SEQ ID NO: 129; the amino acid sequence of SEQ ID NO: 310 and the amino acid sequence of SEQ ID NO: 129; the amino acid sequence of SEQ ID NO: 311 and the amino acid sequence of SEQ ID NO: 129; the amino acid sequence of SEQ ID NO: 312 and the amino acid sequence of SEQ ID NO: 129; the amino acid sequence of SEQ ID NO: 313 and the amino acid sequence of SEQ ID NO: 129; the amino acid sequence of SEQ ID NO: 314 and the amino acid sequence of SEQ ID NO: 129; the amino acid sequence of SEQ ID NO: 315 and the amino acid sequence of SEQ ID NO: 129; the amino acid sequence of SEQ ID NO: 316 and the amino acid sequence of SEQ ID NO: 129; the amino acid sequence of SEQ ID NO: 317 and the amino acid sequence of SEQ ID NO: 129; the amino acid sequence of SEQ ID NO: 1 and the amino acid sequence of SEQ ID NO: 131; the amino acid sequence of SEQ ID NO: 2 and the amino acid sequence of SEQ ID NO: 131; the amino acid sequence of SEQ ID NO: 3 and the amino acid sequence of SEQ ID NO: 131; the amino acid sequence of SEQ ID NO: 4 and the amino acid sequence of SEQ ID NO: 131; the amino acid sequence of SEQ ID NO: 5 and the amino acid sequence of SEQ ID NO: 131; the amino acid sequence of SEQ ID NO: 6 and the amino acid sequence of SEQ ID NO: 131; the amino acid sequence of SEQ ID NO: 7 and the amino acid sequence of SEQ ID NO: 131; the amino acid sequence of SEQ ID NO: 8 and the amino acid sequence of SEQ ID NO: 131; the amino acid sequence of SEQ ID NO: 307 and the amino acid sequence of SEQ ID NO: 131; the amino acid sequence of SEQ ID NO: 308 and the amino acid sequence of SEQ ID NO: 131; the amino acid sequence of SEQ ID NO: 309 and the amino acid sequence of SEQ ID NO: 131; the amino acid sequence of SEQ ID NO: 310 and the amino acid sequence of SEQ ID NO: 131; the amino acid sequence of SEQ ID NO: 311 and the amino acid sequence of SEQ ID NO: 131; the amino acid sequence of SEQ ID NO: 312 and the amino acid sequence of SEQ ID NO: 131; the amino acid sequence of SEQ ID NO: 313 and the amino acid sequence of SEQ ID NO: 131; the amino acid sequence of SEQ ID NO: 314 and the amino acid sequence of SEQ ID NO: 131; the amino acid sequence of SEQ ID NO: 315 and the amino acid sequence of SEQ ID NO: 131; the amino acid sequence of SEQ ID NO: 316 and the amino acid sequence of SEQ ID NO: 131; the amino acid sequence of SEQ ID NO: 317 and the amino acid sequence of SEQ ID NO: 131; the amino acid sequence of SEQ ID NO: 1 and the amino acid sequence of SEQ ID NO: 133; the amino acid sequence of SEQ ID NO:

2 and the amino acid sequence of SEQ ID NO: 133; the amino acid sequence of SEQ ID NO: 3 and the amino acid sequence of SEQ ID NO: 133; the amino acid sequence of SEQ ID NO: 4 and the amino acid sequence of SEQ ID NO: 133; the amino acid sequence of SEQ ID NO: 5 and the amino acid sequence of SEQ ID NO: 133; the amino acid sequence of SEQ ID NO: 6 and the amino acid sequence of SEQ ID NO: 133; the amino acid sequence of SEQ ID NO: 7 and the amino acid sequence of SEQ ID NO: 133; the amino acid sequence of SEQ ID NO: 8 and the amino acid sequence of SEQ ID NO: 133; the amino acid sequence of SEQ ID NO: 307 and the amino acid sequence of SEQ ID NO: 133; the amino acid sequence of SEQ ID NO: 308 and the amino acid sequence of SEQ ID NO: 133; the amino acid sequence of SEQ ID NO: 309 and the amino acid sequence of SEQ ID NO: 133; the amino acid sequence of SEQ ID NO: 310 and the amino acid sequence of SEQ ID NO: 133; the amino acid sequence of SEQ ID NO: 311 and the amino acid sequence of SEQ ID NO: 133; the amino acid sequence of SEQ ID NO: 312 and the amino acid sequence of SEQ ID NO: 133; the amino acid sequence of SEQ ID NO: 313 and the amino acid sequence of SEQ ID NO: 133; the amino acid sequence of SEQ ID NO: 314 and the amino acid sequence of SEQ ID NO: 133; the amino acid sequence of SEQ ID NO: 315 and the amino acid sequence of SEQ ID NO: 133; the amino acid sequence of SEQ ID NO: 316 and the amino acid sequence of SEQ ID NO: 133; the amino acid sequence of SEQ ID NO: 317 and the amino acid sequence of SEQ ID NO: 133; the amino acid sequence of SEQ ID NO: 1 and the amino acid sequence of SEQ ID NO: 135; the amino acid sequence of SEQ ID NO: 2 and the amino acid sequence of SEQ ID NO: 135; the amino acid sequence of SEQ ID NO: 3 and the amino acid sequence of SEQ ID NO: 135; the amino acid sequence of SEQ ID NO: 4 and the amino acid sequence of SEQ ID NO: 135; the amino acid sequence of SEQ ID NO: 5 and the amino acid sequence of SEQ ID NO: 135; the amino acid sequence of SEQ ID NO: 6 and the amino acid sequence of SEQ ID NO: 135; the amino acid sequence of SEQ ID NO: 7 and the amino acid sequence of SEQ ID NO: 135; the amino acid sequence of SEQ ID NO: 8 and the amino acid sequence of SEQ ID NO: 135; the amino acid sequence of SEQ ID NO: 307 and the amino acid sequence of SEQ ID NO: 135; the amino acid sequence of SEQ ID NO: 308 and the amino acid sequence of SEQ ID NO: 135; the amino acid sequence of SEQ ID NO: 309 and the amino acid sequence of SEQ ID NO: 135; the amino acid sequence of SEQ ID NO: 310 and the amino acid sequence of SEQ ID NO: 135; the amino acid sequence of SEQ ID NO: 311 and the amino acid sequence of SEQ ID NO: 135; the amino acid sequence of SEQ ID NO: 312 and the amino acid sequence of SEQ ID NO: 135; the amino acid sequence of SEQ ID NO: 313 and the amino acid sequence of SEQ ID NO: 135; the amino acid sequence of SEQ ID NO: 314 and the amino acid sequence of SEQ ID NO: 135; the amino acid sequence of SEQ ID NO: 315 and the amino acid sequence of SEQ ID NO: 135; the amino acid sequence of SEQ ID NO: 316 and the amino acid sequence of SEQ ID NO: 135; the amino acid sequence of SEQ ID NO: 317 and the amino acid sequence of SEQ ID NO: 135; the amino acid sequence of SEQ ID NO: 1 and the amino acid sequence of SEQ ID NO: 137; the amino acid sequence of SEQ ID NO: 2 and the amino acid sequence of SEQ ID NO: 137; the amino acid sequence of SEQ ID NO: 3 and the amino acid sequence of SEQ ID NO: 137; the amino acid sequence of SEQ ID NO: 4 and the amino acid sequence of SEQ ID NO: 137; the amino acid sequence of SEQ ID NO: 5 and the amino acid sequence of SEQ ID NO: 137; the amino acid sequence of SEQ ID NO: 6 and the amino acid sequence of SEQ ID NO: 137; the amino acid sequence of SEQ ID NO: 7 and the amino acid sequence of SEQ ID NO: 137; the amino acid sequence of SEQ ID NO: 8 and the amino acid sequence of SEQ ID NO: 137; the amino acid sequence of SEQ ID NO: 307 and the amino acid sequence of SEQ ID NO: 137; the amino acid sequence of SEQ ID NO: 308 and the amino acid sequence of SEQ ID NO: 137; the amino acid sequence of SEQ ID NO: 309 and the amino acid sequence of SEQ ID NO: 137; the amino acid sequence of SEQ ID NO: 310 and the amino acid sequence of SEQ ID NO: 137; the amino acid sequence of SEQ ID NO: 311 and the amino acid sequence of SEQ ID NO: 137; the amino acid sequence of SEQ ID NO: 312 and the amino acid sequence of SEQ ID NO: 137; the amino acid sequence of SEQ ID NO: 313 and the amino acid sequence of SEQ ID NO: 137; the amino acid sequence of SEQ ID NO: 314 and the amino acid sequence of SEQ ID NO: 137; the amino acid sequence of SEQ ID NO: 315 and the amino acid sequence of SEQ ID NO: 137; the amino acid sequence of SEQ ID NO: 316 and the amino acid sequence of SEQ ID NO: 137; the amino acid sequence of SEQ ID NO: 317 and the amino acid sequence of SEQ ID NO: 137; the amino acid sequence of SEQ ID NO: 1 and the amino acid sequence of SEQ ID NO: 376; the amino acid sequence of SEQ ID NO: 2 and the amino acid sequence of SEQ ID NO: 376; the amino acid sequence of SEQ ID NO: 3 and the amino acid sequence of SEQ ID NO: 376; the amino acid sequence of SEQ ID NO: 4 and the amino acid sequence of SEQ ID NO: 376; the amino acid sequence of SEQ ID NO: 5 and the amino acid sequence of SEQ ID NO: 376; the amino acid sequence of SEQ ID NO: 6 and the amino acid sequence of SEQ ID NO: 376; the amino acid sequence of SEQ ID NO: 7 and the amino acid sequence of SEQ ID NO: 376; the amino acid sequence of SEQ ID NO: 8 and the amino acid sequence of SEQ ID NO: 376; the amino acid sequence of SEQ ID NO: 307 and the amino acid sequence of SEQ ID NO: 376; the amino acid sequence of SEQ ID NO: 308 and the amino acid sequence of SEQ ID NO: 376; the amino acid sequence of SEQ ID NO: 309 and the amino acid sequence of SEQ ID NO: 376; the amino acid sequence of SEQ ID NO: 310 and the amino acid sequence of SEQ ID NO: 376; the amino acid sequence of SEQ ID NO: 311 and the amino acid sequence of SEQ ID NO: 376; the amino acid sequence of SEQ ID NO: 312 and the amino acid sequence of SEQ ID NO: 376; the amino acid sequence of SEQ ID NO: 313 and the amino acid sequence of SEQ ID NO: 376; the amino acid sequence of SEQ ID NO: 314 and the amino acid sequence of SEQ ID NO: 376; the amino acid sequence of SEQ ID NO: 315 and the amino acid sequence of SEQ ID NO: 376; the amino acid sequence of SEQ ID NO: 316 and the amino acid sequence of SEQ ID NO: 376; the amino acid sequence of SEQ ID NO: 317 and the amino acid sequence of SEQ ID NO: 376; the amino acid sequence of SEQ ID NO: 1 and the amino acid sequence of SEQ ID NO: 378; the amino acid sequence of SEQ ID NO: 2 and the amino acid sequence of SEQ ID NO: 378; the amino acid sequence of SEQ ID NO: 3 and the amino acid sequence of SEQ ID NO: 378; the amino acid sequence of SEQ ID NO: 4 and the amino acid sequence of SEQ ID NO: 378; the amino acid sequence of SEQ ID NO: 5 and the amino acid sequence of SEQ ID NO: 378; the amino acid sequence of SEQ ID NO: 6 and the amino acid sequence of SEQ ID NO: 378; the amino acid sequence of SEQ ID NO: 7 and the amino acid sequence of SEQ ID NO: 378; the amino acid sequence of SEQ ID NO: 8 and the amino acid sequence of SEQ ID NO: 378; the amino acid sequence of SEQ ID NO: 307 and the amino acid sequence of SEQ ID NO: 378; the amino acid sequence of SEQ ID NO: 308 and the amino acid sequence of SEQ ID NO: 378; the amino acid sequence of SEQ ID NO: 309 and the amino acid sequence of SEQ ID NO: 378; the amino acid sequence of SEQ ID NO: 310 and the amino acid sequence of SEQ ID NO: 378; the amino acid sequence of SEQ ID NO: 311 and the amino acid sequence of SEQ ID NO: 378; the amino acid sequence of SEQ ID NO: 312 and the amino acid sequence of SEQ ID NO: 378; the amino acid sequence of SEQ ID NO: 313 and the amino acid sequence of SEQ ID NO: 378; the amino acid sequence of SEQ ID NO: 314 and the amino acid sequence of SEQ ID NO: 378; the amino acid sequence of SEQ ID NO: 315 and the amino acid sequence of SEQ ID NO: 378; the amino acid sequence of SEQ ID NO: 316 and the amino acid sequence of SEQ ID NO: 378; the amino acid sequence of SEQ ID NO: 317 and the amino acid sequence of SEQ ID NO: 378.

In some embodiments, the second polypeptide comprises: (i) an amino acid sequence that is at least 90% identical to SEQ ID NO: 104; (ii) an amino acid sequence that is at least 90% identical to SEQ ID NO: 106; (iii) an amino acid sequence that is at least 90% identical to SEQ ID NO: 108; (iv) an amino acid sequence that is at least 90% identical to SEQ ID NO: 110; (v) an amino acid sequence that is at least 90% identical to SEQ ID NO: 209, an amino acid sequence that is at least 90% identical to SEQ ID NO: 210, and an amino acid sequence that is at least 90% identical to SEQ ID NO: 106; (vi) an amino acid sequence that is at least 90% identical to SEQ ID NO: 114; (vii) an amino acid sequence that is at least 90% identical to SEQ ID NO: 116; (viii) an amino acid sequence that is at least 90% identical to SEQ ID NO: 118; (ix) an amino acid sequence that is at least 90% identical to SEQ ID NO: 120; (x) an amino acid sequence that is at least 90% identical to SEQ ID NO: 122; (xi) an amino acid sequence that is at least 90% identical to SEQ ID NO: 124; (xii) an amino acid sequence that is at least 90% identical to SEQ ID NO: 126; (xiii) an amino acid sequence that is at least 90% identical to SEQ ID NO: 128; (xiv) an amino acid sequence that is at least 90% identical to SEQ ID NO: 130; (xv) an amino acid sequence that is at least 90% identical to SEQ ID NO: 132; (xvi) an amino acid sequence that is at least 90% identical to SEQ ID NO: 134; (xvii) an amino acid sequence that is at least 90% identical to SEQ ID NO: 136; (xviii) an amino acid sequence that is at least 90% identical to SEQ ID NO: 138; (xix) the amino acid sequence that is at least 90% identical to SEQ ID NO: 377; or (xx) the amino acid sequence that is at least 90% identical to SEQ ID NO: 379.

In some embodiments, the second polypeptide comprises: (i) the amino acid sequence of SEQ ID NO: 104; (ii) the amino acid sequence of SEQ ID NO: 106; (iii) the amino acid sequence of SEQ ID NO: 108; (iv) the amino acid sequence of SEQ ID NO: 110; (v) the amino acid sequence of SEQ ID NO: 209, the amino acid sequence of SEQ ID NO: 210, and the amino acid sequence of SEQ ID NO: 106; (vi) the amino acid sequence of SEQ ID NO: 114; (vii) the amino acid sequence of SEQ ID NO: 116; (viii) the amino acid sequence of SEQ ID NO: 118; (ix) the amino acid sequence of SEQ ID NO: 120; (x) the amino acid sequence of SEQ ID NO: 122; (xi) the amino acid sequence of SEQ ID NO: 124; (xii) the amino acid sequence of SEQ ID NO: 126; (xiii) the amino acid sequence of SEQ ID NO: 128; (xiv) the amino acid sequence of SEQ ID NO: 130; (xv) the amino acid sequence of SEQ ID NO: 132; (xvi) the amino acid sequence of SEQ ID NO: 134; (xvii) the amino acid sequence of SEQ ID NO: 136; (xviii) the amino acid sequence of SEQ ID NO: 138; (xix) the amino acid sequence of SEQ ID NO: 377; or (xx) the amino acid sequence of SEQ ID NO: 379.

In some embodiments, (i) the first polypeptide comprises the amino acid sequence of SEQ ID NO: 211 and the second polypeptide comprises the amino acid sequence of SEQ ID NO: 218; (ii) the first polypeptide comprises the amino acid sequence of SEQ ID NO: 212 and the second polypeptide comprises the amino acid sequence of SEQ ID NO: 219; (iii) the first polypeptide comprises the amino acid sequence of SEQ ID NO: 213 and the second polypeptide comprises the amino acid sequence of SEQ ID NO: 220; (iv) the first polypeptide comprises the amino acid sequence of SEQ ID NO: 214 and the second polypeptide comprises the amino acid sequence of SEQ ID NO: 221; (v) the first polypeptide comprises the amino acid sequence of SEQ ID NO: 215 and the second polypeptide comprises the amino acid sequence of SEQ ID NO: 222; (vi) the first polypeptide comprises the amino acid sequence of SEQ ID NO: 216 and the second polypeptide comprises the amino acid sequence of SEQ ID NO: 223; (vii) the first polypeptide comprises the amino acid sequence of SEQ ID NO: 217 and the second polypeptide comprises the amino acid sequence of SEQ ID NO: 224; (viii) the first polypeptide comprises the amino acid sequence of SEQ ID NO: 225 and the second polypeptide comprises the amino acid sequence of SEQ ID NO: 228; (ix) the first polypeptide comprises the amino acid sequence of SEQ ID NO: 226 and the second polypeptide comprises the amino acid sequence of SEQ ID NO: 229; (x) the first polypeptide comprises the amino acid sequence of SEQ ID NO: 227 and the second polypeptide comprises the amino acid sequence of SEQ ID NO: 230; (xi) the first polypeptide comprises the amino acid sequence of SEQ ID NO: 231 and the second polypeptide comprises the amino acid sequence of SEQ ID NO: 238; (xii) the first polypeptide comprises the amino acid sequence of SEQ ID NO: 232 and the second polypeptide comprises the amino acid sequence of SEQ ID NO: 239; (xiii) the first polypeptide comprises the amino acid sequence of SEQ ID NO: 233 and the second polypeptide comprises the amino acid sequence of SEQ ID NO: 240; (xiv) the first polypeptide comprises the amino acid sequence of SEQ ID NO: 234 and the second polypeptide comprises the amino acid sequence of SEQ ID NO: 241; (xv) the first polypeptide comprises the amino acid sequence of SEQ ID NO: 235 and the second polypeptide comprises the amino acid sequence of SEQ ID NO: 242; (xvi) the first polypeptide comprises the amino acid sequence of SEQ ID NO: 236 and the second polypeptide comprises the amino acid sequence of SEQ ID NO: 243; (xvii) the first polypeptide comprises the amino acid sequence of SEQ ID NO: 237 and the second polypeptide comprises the amino acid sequence of SEQ ID NO: 244; (xviii) the first polypeptide comprises the amino acid sequence of SEQ ID NO: 245 and the second polypeptide comprises the amino acid sequence of SEQ ID NO: 248; (xix) the first polypeptide comprises the amino acid sequence of SEQ ID NO: 246 and the second polypeptide comprises the amino acid sequence of SEQ ID NO: 249; (xx) the first polypeptide comprises the amino acid sequence of SEQ ID NO: 247 and the second polypeptide comprises the amino acid sequence of SEQ ID NO: 250; (xxi) the first polypeptide comprises the amino acid sequence of SEQ ID NO: 318 and the second polypeptide comprises the amino acid sequence of SEQ ID NO: 332; (xxi) the first polypeptide comprises the amino acid sequence of SEQ ID NO: 319 and the second polypeptide comprises the amino acid sequence of SEQ ID NO: 333; (xxii) the first polypeptide comprises the amino acid sequence of SEQ ID NO: 320 and the second polypeptide comprises the amino acid sequence of SEQ ID NO: 334; (xxiii) the first polypeptide comprises the amino acid sequence of SEQ ID NO: 321 and the second polypeptide comprises the amino acid sequence of SEQ ID NO: 335; (xxiv) the first polypeptide comprises the amino acid sequence of SEQ ID NO: 322 and the second polypeptide comprises the amino acid sequence of SEQ ID NO: 336; (xxv) the first polypeptide comprises the amino acid sequence of SEQ ID NO: 323 and the second polypeptide comprises the amino acid sequence of SEQ ID NO: 337; (xxvi) the first polypeptide comprises the amino acid sequence of SEQ ID NO: 324 and the second polypeptide comprises the amino acid sequence of SEQ ID NO: 338; (xxvii) the first polypeptide comprises the amino acid sequence of SEQ ID NO: 325 and the second polypeptide comprises the amino acid sequence of SEQ ID NO: 339; (xxviii) the first polypeptide comprises the amino acid sequence of SEQ ID NO: 326 and the second polypeptide comprises the amino acid sequence of SEQ ID NO: 340; (xxix) the first polypeptide comprises the amino acid sequence of SEQ ID NO: 327 and the second polypeptide comprises the amino acid sequence of SEQ ID NO: 341; (xxx) the first polypeptide comprises the amino acid sequence of SEQ ID NO: 329 and the second polypeptide comprises the amino acid sequence of SEQ ID NO: 343; (xxxi) the first polypeptide comprises the amino acid sequence of SEQ ID NO: 330 and the second polypeptide comprises the amino acid sequence of SEQ ID NO: 344; (xxxii) the first polypeptide comprises the amino acid sequence of SEQ ID NO: 331 and the second polypeptide comprises the amino acid sequence of SEQ ID NO: 345; (xxxiii) the first polypeptide comprises the amino acid sequence of SEQ ID NO: 346 and the second polypeptide comprises the amino acid sequence of SEQ ID NO: 360; (xxxiv) the first polypeptide comprises the amino acid sequence of SEQ ID NO: 347 and the second polypeptide comprises the amino acid sequence of SEQ ID NO: 361; (xxxv) the first polypeptide comprises the amino acid sequence of SEQ ID NO: 348 and the second polypeptide comprises the amino acid sequence of SEQ ID NO: 362; (xxxvi) the first polypeptide comprises the amino acid sequence of SEQ ID NO: 349 and the second polypeptide comprises the amino acid sequence of SEQ ID NO: 363; (xxxvii) the first polypeptide comprises the amino acid sequence of SEQ ID NO: 350 and the second polypeptide comprises the amino acid sequence of SEQ ID NO: 364; (xxxviii) the first polypeptide comprises the amino acid sequence of SEQ ID NO: 351 and the second polypeptide comprises the amino acid sequence of SEQ ID NO: 365; (xxxix) the first polypeptide comprises the amino acid sequence of SEQ ID NO: 352 and the second polypeptide comprises the amino acid sequence of SEQ ID NO: 366; (xl) the first polypeptide comprises the amino acid sequence of SEQ ID NO: 353 and the second polypeptide comprises the amino acid sequence of SEQ ID NO: 367; (xli) the first polypeptide comprises the amino acid sequence of SEQ ID NO: 350 and the second polypeptide comprises the amino acid sequence of SEQ ID NO: 368; (xlii) the first polypeptide comprises the amino acid sequence of SEQ ID NO: 355 and the second polypeptide comprises the amino acid sequence of SEQ ID NO: 369; (xliii) the first polypeptide comprises the amino acid sequence of SEQ ID NO: 356 and the second polypeptide comprises the amino acid sequence of SEQ ID NO: 370; (xliv) the first polypeptide comprises the amino acid sequence of SEQ ID NO: 357 and the second polypeptide comprises the amino acid sequence of SEQ ID NO: 371; (xlv) the first polypeptide comprises the amino acid sequence of SEQ ID NO: 358 and the second polypeptide comprises the amino acid sequence of SEQ ID NO: 372; or (xlvi) the first polypeptide comprises the amino acid sequence of SEQ ID NO: 359 and the second polypeptide comprises the amino acid sequence of SEQ ID NO: 373.

In some embodiments, the molecule further comprises an antigen-binding domain. In some embodiments, the antigen-binding domain is covalently linked to the second Fc domain. In some embodiments, the C-terminus of the antigen-binding domain is covalently linked to the N-terminus of the second Fc domain. In some embodiments, the N-terminus of the antigen-binding domain is covalently linked to the C-terminus of the second Fc domain. In some embodiments, the antigen-binding domain is covalently linked to the first Fc domain. In some embodiments, the C-terminus of the antigen-binding domain is covalently linked to the N-terminus of the first Fc domain. In some embodiments, the N-terminus of the antigen-binding domain is covalently linked to the C-terminus of the first Fc domain. In some embodiments, the antigen-binding domain is selected from the group consisting of a Fab, Fab', Fab'2, Fab2, Fab3, F(ab')2, Fd, Fv, sdAb, scFv, SMIP, diabody, triabody, tetrabody, minibody, nanobody, maxibody, tandab, DVD, BiTe, TandAb, or any combination thereof. In some embodiments, the antigen-binding domain binds to an internalizing receptor expressed on the surface of a cell. In some embodiments, the internalizing receptor is selected from the group consisting of FcγRIIB, FcRn, ASGPR, CD38, SLAMF7, GPCR5D, and BCMA. In some embodiments, the internalizing receptor is ASGPR. In some embodiments, the antigen-binding domain comprises a Fab. In some embodiments, the Fab comprises an antibody heavy chain sequence that is at least 90% identical to the amino acid sequence of SEQ ID NO: 209 and an antibody light chain sequence that is at least 90% identical to the amino acid sequence of SEQ ID NO: 210. In some embodiments, the Fab comprises the antibody heavy chain sequence of SEQ ID NO: 209 and the antibody light chain sequence of SEQ ID NO: 210.

In some embodiments, the second Fc domain further comprises a second autoantibody-binding domain. In some embodiments, the N-terminus of the second Fc domain is covalently linked to the C-terminus of the second autoantibody-binding domain. In some embodiments, the C-terminus of the second Fc domain is covalently linked to the C-terminus of the second autoantibody-binding domain. In some embodiments, the second autoantibody-binding domain binds to anti-TSHR autoantibodies.

In some embodiments, the molecule is capable of selectively depleting anti-TSHR autoantibodies that bind to the autoantibody-binding domain when administered to a subject. In some embodiments, the anti-TSHR autoantibodies that bind to the autoantibody-binding domain are selectively depleted by uptake into cells and shuttling of the autoantibodies to the lysosome for degradation.

In some embodiments, the second polypeptide does not comprise an autoantibody-binding domain that binds to anti-TSHR autoantibodies.

In another aspect, the present disclosure provides a nucleic acid comprising a nucleotide sequence encoding a molecule of the present disclosure.

In another aspect, the present disclosure provides a host cell containing a nucleic acid comprising a nucleotide sequence encoding a molecule of the present disclosure.

In another aspect, the present disclosure provides a vector comprising a nucleic acid comprising a nucleotide sequence encoding a molecule of the present disclosure. In some embodiments, the vector comprises a viral vector. In some embodiments, the viral vector comprises a retroviral vector, a lentiviral vector, an adeno-associated viral (AAV) vector, or an adenoviral vector.

In another aspect, the present disclosure provides a pharmaceutical composition comprising a molecule of the present disclosure or a nucleic acid encoding a molecule and a pharmaceutically acceptable carrier.

In another aspect, the present disclosure provides a method of making a molecule of the present disclosure, the method comprising expressing a nucleic acid comprising a nucleotide sequence encoding a molecule in a host cell, and recovering the molecule.

In another aspect, the present disclosure provides a method of treating a subject suffering from or susceptible to an autoimmune disease, the method comprising: administering to the subject a pharmaceutical composition comprising a molecule of the present disclosure or a nucleic acid encoding the molecule. In some embodiments, the autoimmune disease is Graves' Disease (GD), Thyroid Eye Disease, or another autoimmune disease involving anti-TSHR autoantibodies.

In another aspect, the present disclosure provides a method of treating a subject suffering from or susceptible to an autoimmune disease, the method comprising: administering to the subject a first pharmaceutical composition comprising a molecule of the present disclosure or a nucleic acid encoding the molecule; and administering to the subject a second pharmaceutical composition that selectively depletes plasma cells producing autoantibodies that are targeted by the autoantibody-binding domain. In some embodiments, the autoimmune disease is Graves' Disease (GD), Thyroid Eye Disease, or another autoimmune disease involving anti-TSHR autoantibodies. In some embodiments, the first pharmaceutical composition is administered before the second pharmaceutical composition. In some embodiments, the first pharmaceutical composition is administered after the second pharmaceutical composition. In some embodiments, the first pharmaceutical composition and the second pharmaceutical composition are co-administered.

In some embodiments, the level of anti-TSHR autoantibodies in the subject or in a biological sample from the subject after administration is reduced relative to a level before administration. In some embodiments, the level of anti-TSHR autoantibodies is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a level before the administration. In some embodiments, the reduced level of anti-TSHR autoantibodies is sustained over time. In some embodiments, a sustained period of time comprises at least 1 day, 2 days, 3 days, 4 days, 5 days, 6 days, 1 week, 2 weeks, 3 weeks, 4 weeks, 5 weeks, 6 weeks, 7 weeks, 8 weeks, 10 weeks, 12 weeks, or longer. In some embodiments, the pharmaceutical composition is administered intravenously, intramuscularly, or subcutaneously to the subject. In some embodiments, the subject is a human.

In another aspect, the present disclosure provides a method of selectively depleting anti-TSHR autoantibodies in a subject, the method comprising administering to the subject a pharmaceutical composition comprising a molecule of the present disclosure or a nucleic acid encoding the molecule.

In another aspect, the present disclosure provides a method of treating a human subject suffering from or susceptible to Graves' Disease (GD), Thyroid Eye Disease, or another autoimmune disease involving anti-TSHR autoantibodies, the method comprising administering to the subject a pharmaceutical composition comprising a molecule of the present disclosure or a nucleic acid encoding the molecule.

In another aspect, the present disclosure provides a pharmaceutical composition comprising: a molecule of the present disclosure or a nucleic acid encoding the molecule; a molecule that selectively depletes plasma cells producing the autoantibodies that are targeted by the autoantibody-binding domain, or a nucleic acid encoding the same; and a pharmaceutically acceptable carrier.

In another aspect, the present disclosure provides a composition for decreasing the titer of anti-TSHR autoantibodies in the blood serum of a subject in need thereof, the composition comprising: a plurality of molecules, each molecule comprising (a) a first polypeptide comprising a first Fc domain and an autoantibody-binding domain that binds to anti-TSHR autoantibodies; and (b) a second polypeptide comprising a second Fc domain, wherein the first Fc domain and the second Fc domain form a homodimer or heterodimer of the first polypeptide and the second polypeptide; wherein the first and/or second Fc domain comprises one or more mutated amino acid residues and has increased binding affinity to FcγRIIB relative to a corresponding wild-type Fc domain, and wherein, upon administration of the plurality of molecules, the molecules bind to anti-TSHR autoantibodies to form immune complexes comprising two molecules bound to an anti-TSHR autoantibody, and wherein the immune complex binds with higher avidity to FcγRIIB expressed on the surface of liver sinusoidal endothelial cells (LSECs) and are endocytosed thereby decreasing the titer of the anti-TSHR autoantibodies in the subject's blood serum, wherein the higher avidity is relative to an immune complex comprising two corresponding molecules with wild-type Fc domains.

In another aspect, the present disclosure provides an immune complex comprising an anti-TSHR autoantibody and two molecules of the present disclosure, wherein the immune complex has enhanced binding kinetics with FcγRIIB relative to an immune complex that comprises the anti-TSHR autoantibody bound to two corresponding molecules with wild-type Fc domains.

In another aspect, the present disclosure provides an immune complex comprising: (i) an anti-TSHR autoantibody; and (ii) two molecules, wherein each molecule comprises: a first polypeptide comprising a first Fc domain, and an autoantibody-binding domain that binds to the anti-TSHR autoantibody; and a second polypeptide comprising a second Fc domain; wherein the first Fc domain and the second Fc domain form a homodimer or heterodimer of the first polypeptide and the second polypeptide; wherein the first and/or second Fc domain comprises one or more mutated amino acid residues and has increased binding affinity to FcγRIIB relative to a corresponding wild-type Fc domain; and wherein the immune complex has enhanced binding kinetics with FcγRIIB relative to an immune complex that comprises the anti-TSHR autoantibody bound to two corresponding molecules with wild-type Fc domains. In some embodiments, the immune complex has enhanced binding kinetics with FcγRIIB relative to an immune complex that comprises the anti-TSHR autoantibody and only a single molecule. In some embodiments, the immune complex has enhanced binding kinetics with FcγRIIB relative to the anti-TSHR autoantibody alone. In some embodiments, the autoantibody-binding domain of each of the two molecules is bound to the anti-TSHR autoantibody.

In some embodiments, the enhanced binding kinetics comprise an increase in the rate of association, a decrease in the rate of disassociation, and/or a change in the equilibrium dissociation constant.

In some embodiments, the enhanced binding kinetics produce an increase in avidity, stability, strength, frequency, and/or duration of the binding between the immune complex and FcγRIIB.

In some embodiments, the first and/or second Fc domain comprising one or more mutated amino acid residues does not have increased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, the first and/or second Fc domain comprising one or more mutated amino acid residues has decreased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, the first and/or second Fc domain comprising one or more mutated amino acid residues has negligible or no binding affinity to FcγRI, FcγRIIA167H, FcγRIIA167R, FcγRIIIA176F, FcγRIIIA176V, FcγRIIIB, and/or FcRn relative to the corresponding wild-type Fc domain.

In some embodiments, the enhanced binding kinetics comprises at least 10% greater binding affinity of the immune complex to FcγRIIB. In some embodiments, the at least 10% greater binding affinity comprises at least 15%, at least 20%, at least 25%, at least 30%, at least 35%, at least 40%, at least 45%, or at least 50% or greater binding affinity.

In some embodiments, the binding affinity comprises binding affinity to a cell line (e.g., a CHO cell line) over-expressing FcγRIIB measured by flow cytometry. In some embodiments, the immune complex preferentially binds to immune cells expressing FcγRIIB over immune cells expressing FcγRIIA. In some embodiments, the immune complex cross-links FcγRIIB with a B cell receptor on a B cell.

BRIEF DESCRIPTION OF THE DRAWING

FIG. 6A shows that M22 binds to TSHR260 variants 2P, 2P2R, and 2P1S at pH 7.4 using single-cycle kinetics. FIG. 6B shows that K1-70 binds to TSHR260 variants 2P, 2P2R, and 2P1S at pH 7.4 using single-cycle kinetics.

FIGS. 13A-13D show some exemplary mechanisms of action of molecules described herein that contain mutations in the Fc domain to increase affinity for FcγRIIB including neutralization of autoantibodies (FIG. 13A), clearing of autoantibodies by targeting FcγRIIB isoform 2 on liver sinusoidal endothelial cells (FIG. 13B), targeting pathogenic B cells producing target autoantibodies (e.g., anti-TSHR autoantibodies), by targeting FcγRIIB isoform 1 to the B cell receptor (BCR), which leads to B cell apoptosis and inhibition (FIG. 13C), and binding FcγRIIB on T cells and preventing T-cell activation (FIG. 13D).

FIG. 22A is adapted from Kerntke, et al., (2020) Frontiers in immunology. 11: 489401, which is herein incorporated by reference and shows that B cells have high expression of FcγRIIB. FIG. 22B shows that immune complexes of M22 and an exemplary molecule bound most strongly to B cells and unlabeled cells. Unlabeled cells represent cells that were negative for CD16, CD19, CD56, and CD3 and therefore could not be categorized as monocytes, B cells, NK cells, or T cells. Such cells may be non-classical monocytes or basophils.

FIG. 28A shows a dosing schematic of exemplary molecules in wildtype BALB/c mice (M22 antibodies were administered 1 day prior to administration of an exemplary molecule).

FIG. 28B shows serum concentration of M22 antibodies (ng/mL) measured over time when different exemplary molecules were administered at t=0. FIG. 28C shows serum concentration of M22 antibodies (ng/mL) measured over time when different exemplary molecules were administered at t=0 in the same experiment as shown in FIG. 28B over earlier timepoints.

FIG. 29A shows a dosing schematic of exemplary molecules in wildtype BALB/c mice (M22 antibodies were administered 1 day prior to administration of an exemplary molecule). FIG. 29B shows serum concentration of the exemplary molecules ("ASP") (ng/mL) measured over time when different exemplary molecules were administered at t=0. FIG. 29C shows serum concentration of the exemplary molecules ("ASP") (ng/mL) measured over time when different exemplary molecules were administered at t=0 in the same experiment as shown in FIG. 29B over earlier timepoints.

FIG. 31A shows a dosing schematic of exemplary molecules in B-hFcRn mice (mice that contain a human FcRn gene) (M22 antibodies were administered 1 day prior to administration of an exemplary molecule). FIG. 31B shows serum concentration of M22 antibodies (ng/mL) measured over time when different exemplary molecules were administered at t=0. FIG. 31C shows serum concentration of M22 antibodies (ng/mL) measured over time when different exemplary molecules were administered at t=0 in the same experiment as shown in FIG. 31B over earlier timepoints.

FIG. 32A shows a dosing schematic of exemplary molecule in B-hFcRn mice (mice that contain a human FcRn gene) (M22 antibodies were administered 1 day prior to administration of an exemplary molecule). FIG. 32B shows serum concentration of the exemplary molecules ("ASP") (ng/mL) measured over time when different exemplary molecules were administered at t=0. FIG. 32C shows serum concentration of the exemplary molecules ("ASP") (ng/mL) measured over time when different exemplary molecules were administered at t=0 in the same experiment as shown in FIG. 32B over earlier timepoints.

FIG. 34A shows a dosing schematic of exemplary molecules in huFcγR-huFcRn mice (mice that contain human FcRn and FcγR genes) (M22 antibodies were administered 1 day prior to administration of an exemplary molecule). FIG. 34B shows serum concentration of M22 antibodies (ng/mL) measured over time when different exemplary molecules were administered at t=0. FIG. 34C shows serum concentration of M22 antibodies (ng/mL) measured over time when different exemplary molecules were administered at t=0 in the same experiment as shown in FIG. 34B over earlier timepoints.

FIG. 35A shows a dosing schematic of exemplary molecule in huFcγR-huFcRn mice (mice that contain a human FcRn and FcγR genes) (M22 antibodies were administered 1 day prior to administration of an exemplary molecule). FIG. 35B shows serum concentration of the exemplary molecules ("ASP") (ng/mL) measured over time when different exemplary molecules were administered at t=0. FIG. 35C shows serum concentration of the exemplary molecules ("ASP") (ng/mL) measured over time when different exemplary molecules were administered at t=0 in the same experiment as FIG. 35B.

FIG. 39A shows level of IL-6 secreted into supernatant of human PBMCs cultured with exemplary molecules and M22 antibody. FIG. 39B shows level of MCP-1 secreted into supernatant of human PBMCs cultured with exemplary molecules and M22 antibody.

FIGS. 47A-47G show results from binding assays measuring binding activity of Trastuzumab control (FIG. 47A), Variant G1 (FIG. 47B), Variant G2 (FIG. 47C), Variant G3 (FIG. 47D), Variant G6 (FIG. 47E), Variant G7 (FIG. 47F), and Variant G8 (FIG. 47G) to activating receptor FcγRIIA167H when molecules were captured onto an SPR sensor chip and FcγR used as the analyte.

FIGS. 48A-48G show results from binding assays measuring binding activity of Variant G9 (FIG. 48A), Variant G10 (FIG. 48B), Variant G11 (FIG. 48C), Variant G12 (FIG. 48D), Variant G13 (FIG. 48E), Variant G14 (FIG. 48F), and Variant G4 (FIG. 48G) to activating receptor FcγRIIA167H when molecules were captured onto an SPR sensor chip and FcγR used as the analyte.

DEFINITIONS

Figure 1:
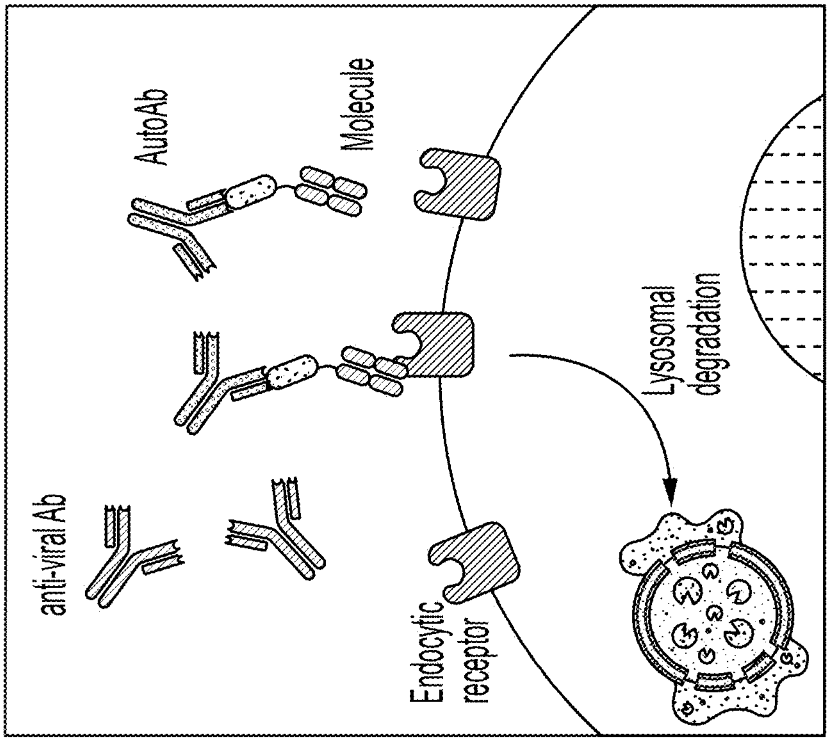
FIG. 1 shows a schematic of an exemplary molecule described herein for selective depletion of autoantibodies targeted by an autoantibody-binding domain.

In order for the present disclosure to be more readily understood, certain terms are first defined below. Additional definitions for the following terms and other terms are set forth throughout the specification. The publications and other reference materials referenced herein to describe the background and to provide additional detail regarding its practice are hereby incorporated by reference.

The articles "a" and "an" are used herein to refer to one or to more than one (i.e., to at least one) of the grammatical object of the article. By way of example, “an element” means one element or more than one element.

Administration: As used herein, typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some particular embodiments, administration may be parenteral (e.g., by intravenous injection). In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, “affinity” is a measure of the tightness with which two or more binding partners associate with one another (e.g., an antibody and target antigen). Those skilled in the art are aware of a variety of assays that can be used to assess affinity, and will furthermore be aware of appropriate controls for such assays. In some embodiments, affinity is assessed in a quantitative assay. In some embodiments, affinity is assessed over a plurality of concentrations (e.g., of one binding partner at a time). In some embodiments, affinity is assessed in the presence of one or more potential competitor entities (e.g., that might be present in a relevant—e.g., physiological—setting). In some embodiments, affinity is assessed relative to a reference (e.g., that has a known affinity above a particular threshold—a “positive control” reference—or that has a known affinity below a particular threshold—a “negative control” reference”). In some embodiments, affinity may be assessed relative to a contemporaneous reference. In some embodiments, affinity may be assessed relative to a historical reference. Typically, when affinity is assessed relative to a reference, it is assessed under comparable conditions.

Approximately or about: As used herein and as applied to one or more values of interest, refers to a value that is similar to a stated reference value. In some embodiments, the term “approximately” or “about” refers to a range of values that fall within 20% in either direction (greater than or less than) of the stated reference value unless otherwise stated or otherwise evident from the context (except where such number would exceed 100% of a possible reference value).

Antibody: As used herein, refers to a polypeptide that includes canonical immunoglobulin sequence elements sufficient to confer specific binding to a particular target antigen. As is known in the art, intact antibodies as produced in nature are tetrameric agents comprising two identical heavy chain polypeptides and two identical light chain polypeptides that associate with each other into what is commonly referred to as a “Y-shaped” structure. Each heavy chain comprises at least four domains—an amino-terminal variable (VH) domain (located at the tips of the Y structure), followed by three constant domains: CH1, CH2, and the carboxy-terminal CH3 (located at the base of the Y’s stem). A short region, known as the “switch”, connects the heavy chain variable and constant regions. The “hinge” connects CH2 and CH3 domains to the rest of the antibody. Two disulfide bonds in this hinge region connect the two heavy chain polypeptides to one another in an intact antibody. Each light chain comprises two domains—an amino-terminal variable (VL) domain, followed by a carboxy-terminal constant (CL) domain, separated from one another by another “switch”. Intact antibody tetramers comprise two heavy chain-light chain dimers in which the heavy and light chains are linked to one another by a single disulfide bond; two other disulfide bonds connect the heavy chain hinge regions to one another, so that the dimers are connected to one another and a tetramer is formed. Naturally produced antibodies are also glycosylated, typically on the CH2 domain. Each domain in a natural antibody has a structure characterized by an “immunoglobulin fold” formed from two beta sheets (e.g., 3-, 4-, or 5-stranded sheets) packed against each other in a compressed antiparallel beta barrel. Each variable domain contains three hypervariable loops known as “complementarity determining regions” or “CDRs” (CDR1, CDR2, and CDR3) and four somewhat invariant “framework” regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally occurring antibodies is located at the bottom of the Y structure and binds to elements of the complement system, and also to receptors on effector cells, including, for example, effector cells that mediate cytotoxicity. Affinity and/or other binding attributes of Fc regions for Fc receptors can be modulated through glycosylation or other modification. In some embodiments, antibodies produced and/or utilized in accordance with the present disclosure include glycosylated Fc domains, including Fc domains with modified or engineered glycosylation. In some embodiments, any polypeptide or complex of polypeptides that includes sufficient immunoglobulin domain sequences as found in natural antibodies can be referred to and/or used as an “antibody”, whether such polypeptide is naturally produced (e.g., generated by an organism reacting to an antigen), or produced by recombinant engineering, chemical synthesis, or other artificial system or methodology. In some embodiments, an antibody is polyclonal. In some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term “antibody”, as used herein, can refer in appropriate embodiments (unless otherwise stated or clear from context) to any of the art-known or developed constructs or formats for utilizing antibody structural and functional features in alternative presentation. For example, in some embodiments, an antibody utilized in accordance with the present disclosure is in a format selected from, but not limited to, intact IgA, IgG, IgE or IgM antibodies; bi- or multi-specific antibodies; antibody fragments such as is used herein in the broadest sense and encompasses various antibody structures (preferably those fragments that exhibit the desired antigen-binding activity). For example, an antibody described herein can be an immunoglobulin, heavy chain antibody, light chain antibody, LRR-based antibody, or other protein scaffold with antibody-like properties, as well as any other immunological binding moiety known in the art, including, e.g., a Fab, Fab', Fab'2, Fab2, Fab3, F(ab')2, Fd, Fv, sdAb, scFv, SMIP, diabody, triabody, tetrabody, minibody, nanobody, maxibody, tandab, DVD, BiTe, TandAb, or the like, or any combination thereof. The subunit structures and three-dimensional configurations of different classes of antibodies are known in the art. In some embodiments, an antibody may lack a covalent modification (e.g., attachment of a glycan) that it would have if produced naturally. In some embodiments, an antibody may contain a covalent modification, e.g., attachment of a glycan, a cargo moiety (e.g., a detectable moiety, a therapeutic moiety, a catalytic moiety, etc.), or other pendant group (e.g., polyethylene glycol, etc.).

Antigen-binding domain: An "antigen-binding domain" refers to a portion of an antibody that binds the antigen to which the intact antibody binds. An antigen-binding domain of an antibody includes any naturally occurring, enzymatically obtainable, synthetic, or genetically engineered polypeptide or glycoprotein that specifically binds an antigen to form a complex. Exemplary antigen-binding domains include, but are not limited to, a Fab, Fab', Fab'2, Fab2, Fab3, F(ab')2, Fd, Fv, sdAb, scFv, SMIP, diabody, triabody, tetrabody, minibody, nanobody, maxibody, tandab, DVD, BiTe, TandAb, or the like, or any combination thereof. In some embodiments, the antigen-binding domain of the antibodies described herein are scFvs. In some embodiments, the antigen-binding domains of the antibodies described herein are VHH domains only. As with full antibody molecules, antigen-binding domains may be mono-specific or multispecific (e.g., bispecific). A multispecific antigen-binding domain of an antibody may comprise at least two different variable domains, wherein each variable domain is capable of specifically binding to a separate antigen or to a different epitope of the same antigen.

Antibody heavy chain: As used herein, refers to the larger of the two types of polypeptide chains present in intact antibodies as produced in nature.

Antibody light chain: As used herein, refers to the smaller of the two types of polypeptide chains present in intact antibodies as produced in nature.

Synthetic antibody: As used herein, refers to an antibody that is generated using recombinant DNA technology. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

Antigen: The term "antigen", as used herein, refers to a molecule (e.g., a peptide, a polypeptide or a polysaccharide) that elicits a specific immune response. Antigen-specific immunological responses, also known as adaptive immune responses, are mediated by lymphocytes (e.g., T cells, B cells, NK cells) that express antigen receptors (e.g., T cell receptors, B cell receptors). In some embodiments, an antigen is a T cell antigen, and elicits a cellular immune response. In some embodiments, an antigen is a B cell antigen, and elicits a humoral (i.e., antibody) response. In some embodiments, an antigen is both a T cell antigen and a B cell antigen. As used herein, the term "antigen" encompasses both a full-length polypeptide as well as a portion or immunogenic fragment of the polypeptide, and a peptide epitope within the polypeptides (e.g., a peptide epitope bound by a Major Histocompatibility Complex (MHC) molecule (e.g., MHC class I, or MHC class II)). In some embodiments, an antigen is an autoantigen. In some embodiments, an antigen is tissue-specific or non-specific, e.g., identified from a cell or tissue that is a target of an autoimmune response, or from a healthy cell or tissue.

Autoantigen: An "autoantigen" as used herein refers to antigen that elicits an autoimmune response. An autoantigen refers to an endogenous (self) antigen that is recognized by an immune system as non-self, i.e., a foreign pathogen. An autoantigen may be a protein or an immunogenic fragment of a protein, or complexes of proteins recognized by the immune system of a subject suffering from or susceptible to an autoimmune disease.

Autoimmune disease: An "autoimmune disease" as used herein refers to an immune response directed against an autoantigen or self-antigen.

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of, susceptibility to, severity of, stage of, etc. the disease, disorder, or condition (e.g., across a relevant population).

Binding domain: As used herein, refers to a moiety or entity that specifically binds to a target moiety or entity. Typically, the interaction between a binding domain and its target is non-covalent. In some embodiments, a binding domain may be or comprise a moiety or entity of any chemical class including, for example, a carbohydrate, a lipid, a nucleic acid, a metal, a polypeptide, a small molecule. In some embodiments, a binding domain may be or comprise a polypeptide (or complex thereof). In some embodiments, a binding domain may be or comprise a target-binding portion of an antibody agent, a cytokine, a ligand (e.g., a receptor ligand), a receptor, a toxin, etc. In some embodiments, a binding domain may be or comprise an aptamer. In some embodiments, a binding domain may be or comprise a peptide nucleic acid (PNA). In some embodiments, a binding domain may be a antigen (e.g., an autoantigen). In some embodiments, a binding domain binds an antibody (i.e., a "target antibody").

Effective amount: As used herein with reference to a dose of an agent, refers to a dose that is adequate to prevent or treat a target disease or disorder in a subject. Amounts effective for a therapeutic or prophylactic use will depend on, for example, the stage and severity of the disease or disorder being treated, the age, weight, and general state of health of the subject, and the judgment of the prescribing physician. The size of the dose will also be determined by the agent selected, method of administration, timing and frequency of administration, the existence, nature, and extent of any adverse side effects that might accompany the administration of a particular agent, and the desired physiological effect. It will be appreciated by one of skill in the art that various diseases or disorders could require prolonged treatment involving multiple administrations, perhaps using the inventive molecules in each or various rounds of administration.

Encoding: As used herein, "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Epitope: as used herein, refers to a moiety that is specifically recognized by an immunoglobulin (e.g., antibody) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized or denatured).

Expression: As used herein, the term "expression" of a nucleic acid sequence refers to generation of any gene product from a nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and (4) post-translational modification of a polypeptide or protein.

Fragment: As used herein, the terms "fragment" or "portion" refers to a structure that includes a discrete portion of the whole, but lacks one or more moieties found in the whole structure. In some embodiments, a fragment consists of such a discrete portion. In some embodiments, a fragment consists of or comprises a characteristic structural element or moiety found in the whole. In some embodiments, a nucleotide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, or more monomeric units (e.g., nucleic acids) as found in the whole nucleotide. In some embodiments, a nucleotide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99%, or more of the monomeric units (e.g., nucleic acids) found in the whole nucleotide. In some embodiments, a polypeptide or protein fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500, or more monomeric units (e.g., amino acids) as found in the whole polypeptide or protein. In some embodiments, a polypeptide or protein fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99%, or more of the monomeric units (e.g., amino acids) found in the whole polypeptide or protein. The whole material or entity may, in some embodiments, be referred to as the "parent" of the fragment.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In some embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Human antibody: As used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

Immune cell: As used herein, refers to a cell that is involved in an immune response, e.g., promotion of an immune response. Examples of immune cells include, but are not limited to, T-lymphocytes, natural killer (NK) cells, macrophages, monocytes, dendritic cells, neutrophils, eosinophils, mast cells, platelets, large granular lymphocytes, Langerhans' cells, plasma cells, or B-lymphocytes. A source of immune cells (e.g., T lymphocytes) can be obtained from a subject.

Immune mediator: As used herein, the term "immune mediator" refers to any molecule that affects the cells and processes involved in immune responses. Immune mediators include cytokines, chemokines, soluble proteins, enzymes, and cell surface markers.

Immune response: As used herein, refers to a cellular and/or systemic response to an antigen that occurs when an immune cell identifies an antigenic molecule as foreign and induces the formation of antibodies and/or activates itself or other immune cells to remove the antigen.

Immunoglobulin or Ig: As used herein, refers to a class of proteins that function as antibodies. Antibodies expressed by B cells are sometimes referred to as a BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is an immunoglobulin that has no known antibody function, but may serve as an antigen receptor. IgE is an immunoglobulin that mediates immediate hypersensitivity by causing release of mediators from mast cells and basophils upon exposure to allergen.

Improved, increased or reduced: As used herein, the terms "improved", "increased" or "reduced", or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Isolated: As used herein, refers to something altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or polypeptide can exist in substantially purified form, or can exist in a non-native environment such as, for example, a host cell.

$K_D$: As used herein, refers to the dissociation constant of a binding agent (e.g., an antibody or binding component thereof) from a complex with its partner (e.g., the epitope to which the antibody or binding component thereof binds).

$K_{off}$: As used herein, refers to the off rate constant for dissociation of a binding agent (e.g., an antibody or binding component thereof) from a complex with its partner (e.g., the epitope to which the antibody or binding component thereof binds).

$K_{on}$: As used herein, refers to the on rate constant for association of a binding agent (e.g., an antibody or binding component thereof) with its partner (e.g., the epitope to which the antibody or binding component thereof binds).

Modulating: As used herein the term "modulating," refers to mediating a detectable increase or decrease in the level of a response and/or a change in the nature of a response in a subject compared with the level and/or nature of a response in the subject in the absence of a treatment, and/or compared with the level and/or nature of a response in an otherwise identical but untreated subject. The term encompasses perturbing and/or affecting a native signal or response thereby mediating a beneficial therapeutic response in a subject, preferably, a human.

Nucleic acid: As used herein, refers to a polymer of at least three nucleotides. In some embodiments, a nucleic acid comprises DNA. In some embodiments, a nucleic acid comprises RNA. In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises one or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyluridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long.

Operably linked: As used herein, refers to functional linkage between, for example, a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutical composition: As used herein, refers to an active agent, formulated together with one or more pharmaceutically acceptable carriers. In some embodiments, an active agent of interest is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polynucleotide: As used herein, refers to a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

Protein: As used herein, refers to a polypeptide (i.e., a string of at least two amino acids linked to one another by peptide bonds). Thus, proteins and polypeptides as used herein are interchangeable. Proteins may include moieties other than amino acids (e.g., may be glycoproteins, proteoglycans, etc.) and/or may be otherwise processed or modified. Those of ordinary skill in the art will appreciate that a "protein" can be a complete polypeptide as produced by a cell (with or without a signal sequence), or can be a characteristic portion thereof. Those of ordinary skill will appreciate that a protein can sometimes include more than one polypeptide, for example linked by one or more disulfide bonds or associated by other covalent or non-covalent means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Specifically binds: As used herein, the term "specifically binds," with respect to an antigen-binding domain, such as those found in an antibody, refers to an antigen-binding domain which recognizes a specific antigen, but does not substantially recognize or bind other molecules in a sample. For example, an antigen-binding domain that specifically binds to an antigen from one species may also bind to that antigen from one or more other species. But, such cross-species reactivity does not itself alter the classification of an antigen-binding domain as specific. In another example, an antigen-binding domain that specifically binds to an antigen may also bind to different allelic forms of the antigen. However, such cross reactivity does not itself alter the classification of an antigen-binding domain as specific. In some instances, the terms "specific binding" or "specifically binding," can be used in reference to the interaction of an antigen binding domain with a second chemical species, to mean that the interaction is dependent upon the presence of a particular structure (e.g., an antigenic determinant or epitope) on the chemical species; for example, an antigen binding domain recognizes and binds to a specific protein structure rather than to proteins generally. If an antigen binding domain is specific for epitope "A", the presence of a molecule containing epitope A (or free, unlabeled A), in a reaction containing labeled "A" and the antigen binding domain, will reduce the amount of labeled A bound to the antigen binding domain.

Subject: As used herein, refers to an organism, for example, a mammal (e.g., a human, a non-human mammal, a non-human primate, a primate, a laboratory animal, a mouse, a rat, a hamster, a gerbil, a cat, or a dog). In some embodiments a human subject is an adult, adolescent, or pediatric subject. In some embodiments, a subject is suffering from a disease, disorder or condition, e.g., a disease, disorder, or condition that can be treated as provided herein, e.g., a an autoimmune disease. In some embodiments, a subject is susceptible to a disease, disorder, or condition; in some embodiments, a susceptible subject is predisposed to and/or shows an increased risk (as compared to the average risk observed in a reference subject or population) of developing the disease, disorder, or condition. In some embodiments, a subject displays one or more symptoms of a disease, disorder, or condition. In some embodiments, a subject does not display a particular symptom (e.g., clinical manifestation of disease) or characteristic of a disease, disorder, or condition. In some embodiments, a subject does not display any symptom or characteristic of a disease, disorder, or condition. In some embodiments, a subject is a patient. In some embodiments, a subject is an individual to whom diagnosis and/or therapy is and/or has been administered.

Target: As used herein, refers to a cell, tissue, organ, or site within the body that is the subject of provided methods, systems, and/or compositions, for example, a cell, tissue, organ or site within a body that is in need of treatment or is preferentially bound by, for example, a molecule described herein.

Treat: As used herein, the term "treat," "treatment," or "treating" refers to partial or complete alleviation, amelioration, delay of onset of, inhibition, prevention, relief, and/or reduction in incidence and/or severity of one or more symptoms or features of a disease, disorder, and/or condition. In some embodiments, treatment may be administered to a subject who does not exhibit signs or features of a disease, disorder, and/or condition (e.g., may be prophylactic). In some embodiments, treatment may be administered to a subject who exhibits only early or mild signs or features of the disease, disorder, and/or condition, for example for the purpose of decreasing the risk of developing pathology associated with the disease, disorder, and/or condition. In some embodiments, treatment may be administered to a subject who exhibits established, severe, and/or late-stage signs of the disease, disorder, or condition. As used herein, a "therapeutic" is any agent used to treat a subject.

Vector: As used herein, the term "vector" refers to a composition of matter that comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral components which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Throughout this disclosure, various aspects can be presented in a range format. It should be understood that the description in range format is merely for convenience and brevity and should not be construed as an inflexible limitation on scope. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DETAILED DESCRIPTION

Certain autoimmune diseases are driven by autoantibodies that mount an immune response to self-antigens (i.e., autoantigens). Despite the identification of certain autoantibody-antigen pairs and their implication in autoimmune diseases (e.g., TSHR and Graves' Disease), many are poorly controlled with current treatments. Current standards of care involve tamping down the autoimmune response by inhibiting or depleting complete immune components or cell populations, including those essential for a healthy immune response to foreign pathogens. Current treatments include glucocorticoids, antibodies that target plasma cells, antibodies that target FcRn "FcRn inhibitors", and plasmapheresis. FcRn inhibitors result in pan IgG depletion, and often an incomplete depletion of autoantibodies.

The present disclosure encompasses molecules for selectively depleting autoantibodies (i.e., anti-TSHR autoantibodies), to treat autoimmune diseases (e.g., Graves' Disease and Thyroid Eye Disease). Molecules described herein in some embodiments include a first polypeptide comprising a first Fc domain and an autoantibody-binding domain that binds to autoantibodies (i.e., anti-TSHR autoantibodies); and a second polypeptide comprising a second Fc domain; wherein the first Fc domain and the second Fc domain form a homodimer or heterodimer of the first polypeptide and the second polypeptide. In some embodiments, the second polypeptide further comprises an autoantibody-binding domain that binds to autoantibodies (i.e., anti-TSHR autoantibodies). In some embodiments, the autoantibody-binding domains in the first and second polypeptides are identical and the molecule is a homodimer. In some embodiments, the autoantibody-binding domains in the first and second polypeptides are different and the molecule is a heterodimer. In some embodiments, the second polypeptide does not further comprise an autoantibody-binding domain that binds to autoantibodies (i.e., anti-TSHR autoantibodies) and the molecule is a heterodimer.

The disclosure provides, among other things, molecules that selectively target and deplete autoantibodies, for example, by targeting them to internalizing receptors which bind to and internalize the complex into a cell for lysosomal degradation. In some embodiments, the autoantibody-binding domain comprises an autoantigen. For example, if the particular autoantibodies to be targeted are anti-TSHR autoantibodies (e.g., for treatment of Graves' Disease and Thyroid Eye Disease), an autoantigen domain may comprise a TSHR autoantigen domain. In addition to including an autoantibody-binding domain, a molecule may also include in its first and/or second Fc domains, a modification that increases its binding to an internalizing receptor or endocytic receptor on a cell surface (e.g., that internalizes its ligands and targets them to the lysosome). In some embodiments, a molecule may include an antigen-binding domain that binds to an internalizing receptor or endocytic receptor on a cell surface (e.g., that internalizes its ligands and targets them to the lysosome).

Graves' Disease, Thyroid Eye Disease and TSHR

In some embodiments, molecules described herein may be used for the treatment of Graves' Disease, Thyroid Eye Disease, and other autoimmune diseases implicated by autoantibodies that target thyroid stimulating hormone receptor (TSHR) by including an autoantibody binding domain that comprises a TSHR autoantigen domain, or a fragment or variant thereof.

Graves' Disease is an autoimmune thyroid disorder caused by antibodies stimulating thyrotropin or thyroid-stimulating hormone (TSH) receptor (TSHR) localized on thyroid follicle cells or thyrocytes. These antibodies may bind to TSH receptors in retroorbital tissues and lead to Graves' Orbitopathy or thyroid eye disease (see Burch and Cooper, *JAMA* 314(23): 2544 (2015)). As such, stimulating thyrotropin receptor antibodies are the main cause of Graves' Disease and GO, and are an important measurement in diagnosis and predicting clinical severity.

Graves' Disease is prevalent, affecting 20-30 per 100,000 people (see Burch and Cooper, *JAMA* 314(23): 2544 (2015)). Graves' Disease is largely seen in women. About 3% of all women and 0.5% of men will develop Graves' Disease during their lifetime, and approximately 25-50% of those with Graves' Disease develop Graves' Orbitopathy (GO) (see Burch and Cooper, *JAMA* 314(23): 2544 (2015); and George et al., *Front Endocrinol*, 11: 629925 (2021), which are herein incorporated by reference in their entirety). Current treatments for Graves' Disease and GO aim to reduce symptoms but do not target the root cause of the disease.

Thyrotropin receptor or thyroid stimulating hormone receptor (TSHR) is the main autoantigen that causes Graves' hyperthyroidism and related eye diseases (Graves' Orbitopathy or Thyroid Eye Disease). TSHR peptides are recognized by the immune system through ingestion and are displayed on antigen-presenting cells (APCs) through MHC class II. T-helper cells recognize the TSHR autoantigen domain, by binding to its fragments on the APCs. The T-helper cell is activated and binds to a B cell, causing the B cell to mature into a TSHR antibody-secreting plasma cell via inflammatory cytokines interleukin II and gamma interferon. The synthesized TSHR antibodies bind to the TSH-R expressed by thyrocytes and orbital target cells (fibroblasts, pre-adipocytes). This activates pathways such as Gas adenylyl cyclase (AC) pathway and stimulates protein kinase A, inducing gene activation through the cAMP responsive element binding (CREB) protein. Additional pathways including the Gαq protein kinase C (PKC) pathway are also activated, leading to activation of protein kinase B (Akt) and induction of the mammalian target of rapamycin (mTOR). This induction of gene expression leads to differentiation into pre-adipocytes and synthesis of glycosaminoglycans in the orbital space and can cause edema and later fibrosis, which are the clinical phenotype of thyroid eye disease (see George et al., *Front Endocrinol,* 11: 629925 (2021); and Hansen et al., *International Journal of Molecular Sciences* 24.7: 6835 (2023)).

Graves' Disease can be diagnosed through clinical features, high levels of thyroxine (T4) and triiodothyronine (T3), and undetectable levels of TSH. Level of TSHR antibodies is also an important indicator (see Burch and Cooper, *JAMA* 314(23): 2544 (2015)). The standard of care for treating hyperthyroidism due to Graves' Disease includes antithyroid drugs to normalize thyroid hormone production, destruction of the thyroid using RAI, or surgical removal of the thyroid (see Burch and Cooper, *JAMA* 314(23): 2544 (2015)). However, these therapies do not target the stimulating TSHR antibodies, which implicate the disease.

Thyroid Eye Disease (also called Graves' Orbitopathy) manifests as a protrusion of the eyes, upper lid retraction, diplopia, and irritation of the periorbital tissue and conjunctiva (see George et al., *Front Endocrinol,* 11: 629925 (2021)). As most patients with Graves' Disease have hyperthyroidism, characteristic symptoms of patients with Graves' Disease include palpitations, tremulousness, heat intolerance, weight loss, and anxiety.

Other recently developed treatments for Graves' Disease and other autoimmune diseases involving pathogenic plasma cells producing autoantibodies include antibodies that target B cell/plasma cell markers such as anti-CD20 antibodies (e.g., Rituximab), anti-CD19 antibodies, anti-CD38 antibodies (e.g., Daratumumab), FcRn inhibitors, and plasmapheresis. Such strategies, however, target all B cells or plasma cells, rather than the cells producing pathogenic autoantibodies. In the case of CD38, targeting such target also depletes other CD38+ cells including monocytes, T cells and NK cells. FcRn inhibitors result in pan IgG depletion, and often incomplete depletion of autoantibodies.

The present disclosure recognizes that further selectively can be introduced in order to preserve essential immunity and increase efficacy of, e.g., antibodies that target foreign pathogens such as viral antigens. Molecules described herein include a further selectivity to target autoantibodies that implicate autoimmune disease. This strategy includes, in some embodiments, utilizing a TSHR autoantigen domain, or a fragment or variant thereof, for targeted destruction of anti-TSHR autoantibodies, thus removing the autoimmune response that implicates Graves' Disease and Thyroid Eye Disease.

Exemplary Molecules

The present disclosure provides molecules for selectively depleting and/neutralizing autoantibodies (i.e., anti-TSHR autoantibodies), to treat autoimmune diseases (e.g., Graves' Disease). Molecules described herein in some embodiments include a first polypeptide comprising a first Fc domain and an autoantibody-binding domain that binds to autoantibodies (i.e., anti-TSHR autoantibodies); and a second polypeptide comprising a second Fc domain; wherein the first Fc domain and the second Fc domain form a homodimer or heterodimer of the first polypeptide and the second polypeptide. In some embodiments, the second polypeptide further comprises an autoantibody-binding domain that binds to anti-TSHR autoantibodies and the molecule is a homodimer. In some embodiments, the second polypeptide further comprises an autoantibody-binding domain that binds to anti-TSHR autoantibodies and the molecule is a heterodimer. In some embodiments, the second polypeptide does not comprise an autoantibody-binding domain that binds to anti-TSHR autoantibodies and the molecule is a heterodimer.

In some embodiments, the first and/or second polypeptide further comprises an antigen-binding domain (e.g., a Fab domain).

In some embodiments, a first and second polypeptide of a molecule described herein can be in the form of a fusion protein. In some embodiments, a first and second polypeptide of a molecule described herein can be in the form of a chemically conjugated molecule.

In some embodiments, the first and/or second Fc domain comprises one or more mutated amino acid residues and has increased binding affinity to an internalizing receptor (e.g., FcγRIIB) relative to a corresponding wild-type Fc domain.

In some embodiments, upon binding of one or two molecules to an autoantibody (i.e., anti-TSHR autoantibody), an immune complex is formed. In some embodiments, immune complexes formed with one molecule described herein and an autoantibody (i.e., anti-TSHR autoantibody) have enhanced binding kinetics with FcγRIIB relative to an immune complex that comprises the autoantibody (i.e., anti-TSHR autoantibody) bound to one corresponding molecule with wild-type Fc domains. In some embodiments, immune complexes formed with two molecules described herein and an autoantibody (i.e., anti-TSHR autoantibody) have enhanced binding kinetics with FcγRIIB relative to an immune complex that comprises the autoantibody (i.e., anti-TSHR autoantibody) bound to two corresponding molecules with wild-type Fc domains. Such enhanced binding kinetics increases clearance of the immune complex.

Autoantibody-Binding Domain

The present disclosure provides molecules that include an autoantibody-binding domain. An autoantibody-binding domain may include any domain that binds to autoantibodies that drive an autoimmune disease (e.g., anti-TSHR antibodies). In some embodiments, the autoantibody-binding domain comprises an autoantigen, or a fragment or variant thereof (e.g., a TSHR autoantigen domain, or fragment or variant thereof). In some embodiments, the autoantibody-binding domain comprises a binding domain that targets any portion or region or epitope on an autoantibody. In some embodiments, the autoantibody-binding domain comprises a Fab domain, scFv domain, VHH, Fc domain, peptide sequence, mimotope, and/or any part of an autoantigen domain that the autoantibody targets.

In some embodiments, the autoantibody-binding domain described herein prevents binding of an autoantibody to its cognate autoantigen (e.g., autoantibodies to TSHR autoantigens).

Autoantigens

In some embodiments a molecule comprises an autoantibody-binding domain that comprises an autoantigen, or a fragment or variant thereof. Such autoantigen domains target autoantibodies that are implicated in various autoimmune diseases. For example, a TSHR autoantigen domain (or a fragment or variant thereof) may be used in a molecule in order to target anti-TSHR autoantibodies that are known to cause autoimmune diseases such as Graves' Disease and Thyroid Eye Disease.

TSHR belongs to a family of leucine-rich repeat-containing class A G-protein coupled receptors including follicle-stimulating hormone. The first 21 amino acids (as shown in SEQ ID NO: 9) is a signal peptide, which is ultimately cleaved. The remaining amino acid sequence include an N-terminal leucine-rich repeat domain (LRD, amino acids 22-281), a hinge or cleavage domain (CD, amino acids 282-409) and a transmembrane domain (TMD, amino acids 410-764). TSHR stimulating autoantibodies, responsible for Graves' Disease and hyperthyroidism, bind to the LRD (see Miller-Gallacher et al., *Journal of Molecular Endocrinology* 62(3): 117 (2019), which is herein incorporated by reference in its entirety).

In some embodiments, an autoantigen domain includes a thyroid stimulating hormone receptor (TSHR), or a fragment or variant thereof. In some embodiments, a TSHR autoantigen domain comprises a fragment or variant of SEQ ID NO: 9. In some embodiments, a TSHR autoantigen domain comprises a TSHR leucine-rich repeat domain, corresponding to amino acids 22-260 of SEQ ID NO: 9 or "TSHR260" as represented in SEQ ID NO: 1. Such a domain is known to interact with certain stimulating antibodies, including an autoantibody known as M22 (see Miller-Gallacher et al., *Journal of Molecular Endocrinology* 62(3): 117-128 (2019)). Such domains are also known to interact with antagonistic antibodies such as K1-70 (see Miller-Gallacher et al., *Journal of Molecular Endocrinology* 62(3): 117-128 (2019)). In some embodiments, a TSHR autoantigen domain comprises a fragment of TSHR that corresponds to amino acids 22-289 of SEQ ID NO: 9 (human wildtype TSHR) or "TSHR289" as represented in SEQ ID NO: 5. In some embodiments, an autoantigen domain comprises an amino acid sequence that is at least 90% identical to the amino acid sequence SEQ ID NO: 1 or SEQ ID NO: 5, or a fragment thereof. In some embodiments, an autoantigen domain comprises the amino acid sequence of SEQ ID NO: 1 or SEQ ID NO: 5, or a fragment thereof.

In some embodiments, a TSHR autoantigen domain comprises one or more mutations that increase stability while preserving binding of stimulating anti-TSHR autoantibodies (e.g., M22) or TSH-blocking anti-TSHR autoantibodies (e.g., K1-70). Certain mutations introduced in TSHR260 have been shown to produce a TSHR260 mutant approximately 900 times more thermostable than wildtype TSHR and TSHR260 (see Miller-Gallacher et al., *Journal of Molecular Endocrinology* 62(3): 117-128 (2019)).

In some embodiments, an autoantigen domain comprises a human TSHR autoantigen domain variant that includes one or more of the following mutations relative to the amino acid sequence of SEQ ID NO: 1 or SEQ ID NO: 5: R112P, D143P, V169R, I253R, H63S, or any combination thereof. In some embodiments, an autoantigen domain comprises a human TSHR autoantigen domain variant that includes the following mutations relative to the amino acid sequence of SEQ ID NO: 1 or SEQ ID NO: 5: R112P and D143P (see e.g., SEQ ID NOs: 2 and 6). In some embodiments, an autoantigen domain comprises a human TSHR autoantigen domain variant that includes the following mutations relative to the amino acid sequence of SEQ ID NO: 1 or SEQ ID NO: 5: R112P, D143P, V169R, and I253R (see e.g., SEQ ID NOs: 3 and 7). In some embodiments, an autoantigen domain comprises a human TSHR autoantigen domain variant that includes the following mutations relative to the amino acid sequence of SEQ ID NO: 1 or SEQ ID NO: 5: R112P, D143P, and H63S (see e.g., SEQ ID NOs: 4 and 8).

In some embodiments, an autoantigen domain comprises a human TSHR autoantigen domain variant that includes one or more of the following mutations relative to the amino acid sequence of SEQ ID NO: 1 or SEQ ID NO: 5: S94, G194P, K218P, V87P, G137P, G188P, or any combination thereof. In some embodiments, an autoantigen domain comprises a human TSHR autoantigen domain variant that includes the mutation S94P relative to the amino acid sequence of SEQ ID NO: 1 or SEQ ID NO: 5 (see e.g., SEQ ID NO: 307). In some embodiments, an autoantigen domain comprises a human TSHR autoantigen domain variant that includes the following mutations relative to the amino acid sequence of SEQ ID NO: 1 or SEQ ID NO: 5: S94P and G194P (see e.g., SEQ ID NO: 308). In some embodiments, an autoantigen domain comprises a human TSHR autoantigen domain variant that includes the following mutations relative to the amino acid sequence of SEQ ID NO: 1 or SEQ ID NO: 5: S94P, G194P, and K218P (see e.g., SEQ ID NO: 309). In some embodiments, an autoantigen domain comprises a human TSHR autoantigen domain variant that includes the following mutations relative to the amino acid sequence of SEQ ID NO: 1 or SEQ ID NO: 5: V87P, S94P, G194P, and K218P (see e.g., SEQ ID NO: 310). In some embodiments, an autoantigen domain comprises a human TSHR autoantigen domain variant that includes the following mutations relative to the amino acid sequence of SEQ ID NO: 1 or SEQ ID NO: 5: V87P, S94P, and G194P (see e.g., SEQ ID NO: 311). In some embodiments, an autoantigen domain comprises a human TSHR autoantigen domain variant that includes the following mutations relative to the amino acid sequence of SEQ ID NO: 1 or SEQ ID NO: 5: V87P, G194P, and K218P (see e.g., SEQ ID NO: 312). In some embodiments, an autoantigen domain comprises a human TSHR autoantigen domain variant that includes the following mutations relative to the amino acid sequence of SEQ ID NO: 1 or SEQ ID NO: 5: V87P and G194P (see e.g., SEQ ID NO: 313). In some embodiments, an autoantigen domain comprises a human TSHR autoantigen domain variant that includes the mutation G194P relative to the amino acid sequence of SEQ ID NO: 1 or SEQ ID NO: 5 (see e.g., SEQ ID NO: 314). In some embodiments, an autoantigen domain comprises a human TSHR autoantigen domain variant that includes the following mutations relative to the amino acid sequence of SEQ ID NO: 1 or SEQ ID NO: 5: G194P and K218P (see e.g., SEQ ID NO: 315). In some embodiments, an autoantigen domain comprises a human TSHR autoantigen domain variant that includes the following mutations relative to the amino acid sequence of SEQ ID NO: 1 or SEQ ID NO: 5: V87P, S94P, G137P, G194P, and K218P (see e.g., SEQ ID NO: 316). In some embodiments, an autoantigen domain comprises a human TSHR autoantigen domain variant that includes the following mutations relative to the amino acid sequence of SEQ ID NO: 1 or SEQ ID NO: 5: V87P, S94P, G137P, G188P, G194P, and K218P (see e.g., SEQ ID NO: 317).

In some embodiments, an autoantigen domain comprises a human TSHR autoantigen domain variant that comprises a sequence that is at least 90% identical to any one of SEQ ID NOs: 1-8 and 307-317 (shown below in Table 1). In some embodiments, an autoantigen domain comprises a human TSHR autoantigen domain variant that comprises a sequence selected from SEQ ID NOs: 1-8 and 307-317 (shown below in Table 1).

TABLE 1

Exemplary TSHR Antigen Sequences

| Antigen | | Sequences | SEQ ID NO |
|---|---|---|---|
| TSHR260 WT | — | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 1 |
| TSHR260 2P | R112P<br>D143P | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LIKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 2 |
| TSHR260 2P2R | R112P<br>D143P<br>V169R<br>I253R | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIP**R**NAFQGLCN<br>ETLTLKLYNNGFTSVQGYAFNGTKLDAVYLNKNKYLTVI<br>DKDAFGGVYSGPSLLDVSQTSVTALPSKGLEHLKEL**R**AR<br>NTWTL | 3 |
| TSHR260 2P1S | R112P<br>D143P<br>H63S | MGCSSPPCECHQEEDFRVTCKDIQRIPSLPPSTQTLKLI<br>ET**S**LRTIPSHAFSNLPNISRIYVSIDVTLQQLESHSFYN<br>LSKVTHIEIRNT**P**NLTYIDPDALKELPLLKELGIFNTGL<br>KMFP**P**LTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 4 |
| TSHR289 WT | — | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTLKKLPLSLSFLHLTRADLSYPSHCCAFKNQ | 5 |
| TSHR289 2P | R112P<br>D143P | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTLKKLPLSLSFLHLTRADLSYPSHCCAFKNQ | 6 |
| TSHR289 2P2R | R112P<br>D143P<br>V169R<br>I253R | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIP**R**NAFQGLCN<br>ETLTLKLYNNGFTSVQGYAFNGTKLDAVYLNKNKYLTVI<br>DKDAFGGVYSGPSLLDVSQTSVTALPSKGLEHLKEL**R**AR<br>NTWTLKKLPLSLSFLHLTRADLSYPSHCCAFKNQ | 7 |
| TSHR289 2P1S | R112P<br>D143P<br>H63S | MGCSSPPCECHQEEDFRVTCKDIQRIPSLPPSTQTLKLI<br>ET**S**LRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTLKKLPLSLSFLHLTRADLSYPSHCCAFKNQ | 8 |
| TSHR WT | — | MRPADLLQLVLLLDLPRDLGGMGCSSPPCECHQEEDERV<br>TCKDIQRIPSLPPSTQTLKLIETHLRTIPSHAFSNLPNI<br>SRIYVSIDVTLQQLESHSFYNLSKVTHIEIRNTRNLTYI<br>DPDALKELPLLKFLGIFNTGLKMFPDLTKVYSTDIFFIL<br>EITDNPYMTSIPVNAFQGLCNETLTLKLYNNGFTSVQGY<br>AFNGTKLDAVYLNKNKYLTVIDKDAFGGVYSGPSLLDVS | 9 |

TABLE 1-continued

Exemplary TSHR Antigen Sequences

| Antigen | | Sequences | SEQ ID NO |
|---|---|---|---|
| | | QTSVTALPSKGLEHLKELIARNTWTLKKLPLSLSFLHLT<br>RADLSYPSHCCAFKNQKKIRGILESLMCNESSMQSLRQR<br>KSVNALNSPLHQEYEENLGDSIVGYKEKSKFQDTHNNAH<br>YYVFFEEQEDEIIGFGQELKNPQEETLQAFDSHYDYTIC<br>GDSEDMVCTPKSDEFNPCEDIMGYKFLRIVVWFVSLLAL<br>LGNVFVLLILLTSHYKLNVPRFLMCNLAFADFCMGMYLL<br>LIASVDLYTHSEYYNHAIDWQTGPGCNTAGFFTVFASEL<br>SVYTLTVITLERWYAITFAMRLDRKIRLRHACAIMVGGW<br>VCCFLLALLPLVGISSYAKVSICLPMDTETPLALAYIVE<br>VLTLNIVAFVIVCCCYVKIYITVRNPQYNPGDKDTKIAK<br>RMAVLIFTDFICMAPISFYALSAILNKPLITVSNSKILL<br>VLFYPLNSCANPFLYAIFTKAFQRDVFILLSKFGICKRQ<br>AQAYRGQRVPPKNSTDIQVQKVTHDMRQGLHNMEDVYEL<br>IENSHLTPKKQGQISEEYMQTVL | |
| TSHR260<br>SP | S94P | MGCSSPPCECHQEEDFRVTCKDIQRIPSLPPSTQTLKLI<br>ETHLRTIPSHAFSNLPNISRIYVSIDVTLQQLE**P**HSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 307 |
| TSHR260<br>SP GP | S94P<br>G194P | MGCSSPPCECHQEEDFRVTCKDIQRIPSLPPSTQTLKLI<br>ETHLRTIPSHAFSNLPNISRIYVSIDVTLQQLE**P**HSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>DKDAFGGVYSGPSLLDVSQTSVTALPSKGLEHLKELIAR<br>NTWTL | 308 |
| TSHR260<br>SP GP KP | S94P<br>G194P<br>K218P | MGCSSPPCECHQEEDFRVTCKDIQRIPSLPPSTQTLKLI<br>ETHLRTIPSHAFSNLPNISRIYVSIDVTLQQLE**P**HSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>D**P**DAFGGVYSGPSLLDVSQTSVTALPSKGLEHLKELIAR<br>NTWTL | 309 |
| TSHR260<br>VP SP GP<br>KP | V87P<br>S94P<br>G194P<br>K218P | MGCSSPPCECHQEEDFRVTCKDIQRIPSLPPSTQTLKLI<br>ETHLRTIPSHAFSNLPNISRIYVSID**P**TLQQLE**P**HSFYN<br>LSKVTHIEIRNTRNLTYIDPDALKELPLLKELGIFNTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>D**P**DAFGGVYSGPSLLDVSQTSVTALPSKGLEHLKELIAR<br>NTWTL | 310 |
| TSHR260<br>VP SP GP | V87P<br>S94P<br>G194P | MGCSSPPCECHQEEDERVTCKDIQRIPSLPPSTQTLKLI<br>ETHLRTIPSHAFSNLPNISRIYVSID**P**TLQQLE**P**HSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>DKDAFGGVYSGPSLLDVSQTSVTALPSKGLEHLKELIAR<br>NTWTL | 311 |
| TSHR260<br>VP GP KP | V87P<br>G194P<br>K218P | MGCSSPPCECHQEEDFRVTCKDIQRIPSLPPSTQTLKLI<br>ETHLRTIPSHAFSNLPNISRIYVSID**P**TLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>D**P**DAFGGVYSGPSLLDVSQTSVTALPSKGLEHLKELIAR<br>NTWTL | 312 |
| TSHR260<br>VP GP | V87P<br>G194P | MGCSSPPCECHQEEDFRVTCKDIQRIPSLPPSTQTLKLI<br>ETHLRTIPSHAFSNLPNISRIYVSID**P**TLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>DKDAFGGVYSGPSLLDVSQTSVTALPSKGLEHLKELIAR<br>NTWTL | 313 |

TABLE 1-continued

| Exemplary TSHR Antigen Sequences | | | |
|---|---|---|---|
| Antigen | | Sequences | SEQ ID NO |
| TSHR260<br>GP | G194P | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>DKDAFGGVYSGPSLLDVSQTSVTALPSKGLEHLKELIAR<br>NTWTL | 314 |
| TSHR260<br>GP KP | G194P<br>K218P | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQ**P**YAFNGTKLDAVYLNKNKYLTVI<br>D**P**DAFGGVYSGPSLLDVSQTSVTALPSKGLEHLKELIAR<br>NTWTL | 315 |
| TSHR260<br>VP SP GP<br>GP KP | V87P<br>S94P<br>G137P<br>G194P<br>K218P | MGCSSPPCECHQEEDFRVTCKDIQRIPSLPPSTQTLKLI<br>ETHLRTIPSHAFSNLPNISRIYVSID**P**TLQQLE**P**HSFYN<br>LSKVTHIEIRNTRNLTYIDPDALKELPLLKELGIENT**P**L<br>KMFPDLTKVYSTDIFFILEITDNPYMTSIPVNAFQGLCN<br>ETLTLKLYNNGFTSVQ**P**YAFNGTKLDAVYLNKNKYLTVI<br>D**P**DAFGGVYSGPSLLDVSQTSVTALPSKGLEHLKELIAR<br>NTWTL | 316 |
| TSHR260<br>VP SP GP<br>GP GP KP | V87P<br>S94P<br>G137P<br>G188P<br>G194P<br>K218P | MGCSSPPCECHQEEDFRVTCKDIQRIPSLPPSTQTLKLI<br>ETHLRTIPSHAFSNLPNISRIYVSID**P**TLQQLE**P**HSFYN<br>LSKVTHIEIRNTRNLTYIDPDALKELPLLKELGIENT**P**L<br>KMFPDLTKVYSTDIFFILEITDNPYMTSIPVNAFQGLCN<br>ETLTLKLYNN**P**FTSVQ**P**YAFNGTKLDAVYLNKNKYLTVI<br>D**P**DAFGGVYSGPSLLDVSQTSVTALPSKGLEHLKELIAR<br>NTWTL | 317 |

Antigen-Binding Domains

Figure 3:
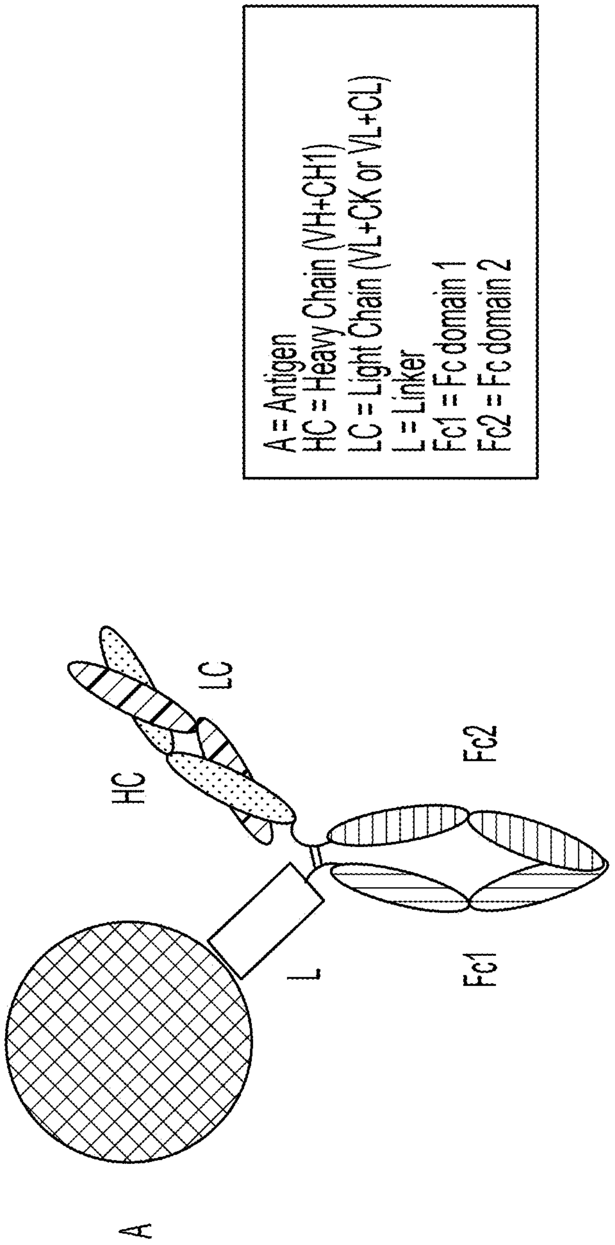
FIG. 3 shows an exemplary molecule format described herein.

In some embodiments, a molecule provided herein includes one or more antigen-binding domains (e.g., as shown in FIG. 3). In some embodiments, an antigen-binding domain binds to an internalizing receptor (e.g., FcγRIIB, FcRn, ASGPR, BCMA, CD38, SLAMF7, GPCR5D, and/or CD138).

An antigen-binding domain can include, but is not limited to, a monoclonal antibody, a synthetic antibody, a human antibody, a humanized antibody, a non-human antibody, and any fragment thereof. Thus, in one embodiment, the antigen-binding domain portion comprises a mammalian antibody or a fragment thereof. In some embodiments, an antigen-binding domain included in a molecule can be any binding polypeptide such as, but not limited protein scaffold with antibody-like properties (e.g., an antibody variable domain), as well as any other immunological binding moiety known in the art, including, e.g., a Fab, Fab', Fab'2, Fab2, Fab3, F(ab')2, Fd, Fv, sdAb, scFv, SMIP, diabody, triabody, tetrabody, minibody, nanobody, maxibody, tandab, DVD, BiTe, TandAb, VHH, peptide sequence, or mimotope, or any combination thereof.

In some embodiments, an antigen-binding domain binds to an autoantibody (e.g., an anti-TSHR autoantibody). In some embodiments, an antigen-binding domain binds to an internalizing receptor (e.g., FcγRIIB, FcRn, ASGPR, BCMA, CD38, SLAMF7, GPCR5D, and/or CD138).

In some embodiments, a molecule described herein includes an antigen-binding domain that targets two or more targets. In some embodiments an antigen-binding domain is a bispecific antigen-binding domain. In some embodiments, an antigen-binding domain comprises a trispecific antigen-binding domain. In some embodiments, an antigen-binding domain targets two non-overlapping epitopes on the same target (e.g., two non-overlapping epitopes on FcγRIIB, FcRn, ASGPR, BCMA, CD38, SLAMF7, GPCR5D, and/or CD138 in the case of antigen-binding domain that targets an internalizing receptor or two-non-overlapping epitopes of an autoantibody).

In some embodiments, a molecule may include a first antigen-binding domain and a second antigen-binding domain such that each antigen-binding domain is capable of binding to the same or different target antigen. In some embodiments, a first antigen-binding domain targets an autoantibody (e.g., an anti-TSHR autoantibody) and a second antigen-binding domain targets an internalizing receptor (e.g., FcγRIIB, FcRn, ASGPR, BCMA, CD38, SLAMF7, GPCR5D, and/or CD138).

In some embodiments, an antigen-binding domain comprises a Fab comprising a heavy chain and light chain antibody component. In some embodiments, an antigen-binding domain comprises a Fab that comprises any of the following particular heavy chain and light chain antibody sequences shown in Table 2.

In some embodiments, an antigen-binding domain is a Fab that comprises an antibody heavy chain sequence that is at least 90% identical to SEQ ID NO: 209, and/or an antibody light chain sequence that is at least 90% identical to SEQ ID NO: 210. In some embodiments, an antigen-binding domain is a Fab that comprises an antibody heavy chain sequence SEQ ID NO: 209 and/or an antibody light chain sequence SEQ ID NO: 210.

TABLE 2

Exemplary Additional Antigen-binding domain sequences

| Fab Targeting Arm | | Sequences | SEQ ID NO |
|---|---|---|---|
| 4F3 Anti-ASGPR Fab | HC (Heavy Chain) | EVQLLESGGGLVQPGGSLRLSCAASGFTESSYAMSWVRQAPGKGLEWVSAISGSGGSTYYADSVKGRFTISRDNSKNTLYLQMNSLRAEDTAVYYCAKDESSRRWYLEYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC | 209 |
| | LC (Light Chain) | SSELTQDPAVSVALGQTVRITCQGDSLRSYYASWYQQKPGQAPVLVIYGKNNRPSGIPDRESGSSSGNTASLTITGAQAEDEADYYCNSLERIGYLSYVFGGGTKLTVLGQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS | 210 |

Fc Domains

In some embodiments, a molecule described herein includes a first polypeptide comprising an autoantigen domain comprising a TSHR autoantigen domain or fragment or variant thereof linked to a first Fc domain and a second polypeptide comprising a second Fc domain. A TSHR autoantigen domain or fragment or variant thereof targets anti-TSHR autoantibodies and upon binding, the complexes are targeted to an internalizing receptor and shuttled to the lysosome for degradation of the anti-TSHR autoantibodies.

In some embodiments, an Fc domain described herein includes one or more mutations that alter its binding affinity to certain Fc receptors (e.g., FcγRIIB, FcγRI, FcγRIIA167H, FcγRIIA167R, FcγRIIIA176F, FcγRIIIA176V, FcγRIIIB, and/or FcRn).

In some embodiments, a first Fc domain and a second Fc domain are the same (e.g., in the case of a homodimeric molecule). In some embodiments, a first Fc domain and a second Fc domain are different (e.g., in the case of a heterodimeric molecule).

In some embodiments, an Fc domain includes one or more mutated amino acid residues and has decreased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, an Fc domain includes one or more mutated amino acid residues and has substantially no binding affinity to FcγRI, FcγRIIA167H, FcγRIIA167R, FcγRIIIA176F, FcγRIIIA176V, FcγRIIIB, and/or FcRn relative to the corresponding wild-type Fc domain.

In some embodiments, a first and/or second Fc domain of a molecule comprise a modification (e.g., one or more mutations) that enhances binding to an internalizing receptor. In some embodiments, a first and/or second Fc domain of a molecule comprise a modification (e.g., one or more mutations) that decrease binding to certain Fc-receptors. In some embodiments, a first and/or second Fc domain of a molecule comprise a modification (e.g., one or more mutations) that enhances other characteristics of a molecule described herein (e.g., increased half-life, heterodimerization, etc.).

An Fc domain included in a molecule may comprise any one of the five major classes of antibodies: IgA, IgD, IgE, IgG, and IgM. In some embodiments, a conventional antibody comprises an IgG antibody. In some embodiments, an Fc domain described herein comprises a particular isotype selected from the group of IgG isotypes: IgG1, IgG2, IgG3, IgG4. In some embodiments, a molecule comprises a first and/or second Fc domains that are an IgG1 isotype. In some embodiments, a molecule comprises a first and/or second Fc domains that are a human IgG1 isotype. Additionally, in some embodiments, an Fc domain may include any particular heavy chain constant domains that correspond to the different classes of immunoglobulins which include α, δ, ε, γ, and μ, respectively. In some embodiments, a conventional antibody is an intact IgG1 antibody or other antibody class or isotype as described herein (see, e.g., Hudson et al., *Nat. Med.* 9:129 (2003); Pluckthun, *The Pharmacology of Monoclonal Antibodies,* 113:269 (1994); Hollinger et al., *Proc. Natl. Acad. Sci. USA* 90: 6444 (1993); WO 1993/01161; and U.S. Pat. Nos. 5,571,894, 5,869,046, 6,248,516, and 5,587,458, each of which are herein incorporated by reference).

The Fc region of an antibody and included in molecules described herein may bind to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, a molecule described herein includes glycosylated Fc domains, including Fc domains with modified or engineered glycosylation. In some embodiments, a molecule is naturally produced (e.g., generated by an organism reacting to an antigen), or produced by recombinant engineering, chemical synthesis, or other artificial system or methodology.

In some embodiments, one or more modifications made to an Fc domain increases clearance of an immune complex formed by one or more molecules described herein bound to an autoantibody (e.g., an anti-TSHR autoantibody). In some embodiments, one or more modifications made to an Fc domain may induce selective targeting and/or clearance of an immune complex formed by one or more molecules described herein bound to a target antibody. For example, in some embodiments, wherein upon binding of two molecules to an autoantibody (e.g., an anti-TSHR autoantibody), an immune complex is formed that has enhanced binding kinetics with one or more Fc receptors (e.g., FcγRIIB) relative to an immune complex that comprises the autoantibody (e.g., anti-TSHR autoantibody) bound to two corresponding molecules with wild-type Fc domains. Binding kinetics may be characterized by, e.g., an increase rate of association, a decrease in the rate of disassociation, and/or a change in the equilibrium dissociation constant. In some embodiments, an Fc domain preferentially binds to immune cells expressing FcγRIIB over immune cells expressing FcγRIIA. In some embodiments, an Fc domain comprises substantially no binding affinity for cells that do not express FcγRIIB (e.g., T cells, NK cells, neutrophils, and/or eosinophils). In some embodiment, cells that express FcγRIIB are B cells, monocytes and/or basophils.

In some embodiments, enhanced binding kinetics comprises at least 10% greater binding affinity of the immune complex to one or more Fc receptors (e.g., FcγRIIB). In some embodiments, enhanced binding kinetics comprises at least 15%, at least 20%, at least 25%, at least 30%, at least 35%, at least 40%, at least 45%, or at least 50% or greater binding affinity.

In some embodiments, the molecule binds to FcγRIIB with an affinity within the range of about 1 μM to 0.001 μM. In some embodiments, the molecule binds to FcγRIIB with an affinity within the range of about 1 μM to 0.01 μM. In some embodiments, the molecule binds to FcγRIIB with an affinity within the range of about 0.1 μM to 0.01 μM.

In some embodiments, an Fc domain described herein comprises one or more modifications such that a molecule described herein does not activate immune cells (e.g., does not activate immune cells to secrete pro-inflammatory cytokines, e.g., IL-6).

Exemplary Fc domain sequences for use in accordance with the present disclosure are shown below in Table 3. It will be understood that any of these Fc domain sequences can be used in a first or second polypeptide of a molecule of the present disclosure. It will also be understood that any of the exemplary Fc domain sequences with knob mutations (identified with a "Knob" reference) can be used with any of the exemplary Fc domain sequences with hole mutations (identified with a "Hole" reference) in preparing a heterodimeric molecule. In some embodiments, Fc domain sequences shown in Table 3 can be used in pairs in preparing a heterodimeric molecule, e.g., without limitation based on the numerical references found in Table 3 (e.g., Human IgG1 Fc 1.1 Knob can be used with Human IgG1 Fc 1.1 Hole, Human IgG1 Fc 1.2 Knob can be used with Human IgG1 Fc 1.2 Hole, etc.). It will also be understood that references in Table 3 to an Fc domain sequence being useful for an "Antigen Arm for Ag Depletion" (i.e., in a polypeptide that also includes an autoantibody-binding domain) or a "Free arm for Ag Depletion" (i.e., in a polypeptide that does not include an autoantibody-binding domain) is intended to be exemplary and non-limiting, i.e., an Fc domain sequence that is identified in Table 3 as being useful for an "Antigen Arm for Ag Depletion" can, in some embodiments, be used in a "Free arm for Ag Depletion" and an Fc domain sequence that is noted in Table 3 as being useful for a "Free arm for Ag Depletion" can, in some embodiments, be used in an "Antigen Arm for Ag Depletion".

TABLE 3

Exemplary Fc Domain Sequences

| Fc Sequences | | Sequences | SEQ ID NO |
|---|---|---|---|
| Human IgG1 Fc 1.1 Knob S354C/T366W, G236R/L328R, M252Y/S254T/ T256E, H433K/N434F | Antigen Arm for Ag Depletion | DKTHTCPPCPAPELLRGPSVELFPPKPKDTLYITR<br>EPEVTCVVVDVSHEDPEVKENWYVDGVEVHNAKTK<br>PREEQYNSTYRVVSVLTVLHQDWLNGKEYKCKVSN<br>KARPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALKFHYTQKSLSLSPGK | 103 |
| Human IgG1 Fc 1.1 Hole T366S/L368A/ Y407V/Y349C, G236R/L328R, M252Y/S254T/ T256E, H433K/N434F | Free Arm for Ag Depletion | DKTHTCPPCPAPELLRGPSVFLFPPKPKDTLYITR<br>EPEVTCVVVDVSHEDPEVKENWYVDGVEVHNAKTK<br>PREEQYNSTYRVVSVLTVLHQDWLNGKEYKCKVSN<br>KARPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALKFHYTQKSLSLSPGK | 104 |
| Human IgG1 Fc 1.2 Knob S354C/T366W, S267E/L328F | Antigen Arm for Ag Depletion | DKTHTCPPCPAPELLGGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KAFPAPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 105 |
| Human IgG1 Fc 1.2 Hole T366S/L368A/ Y407V/Y349C, S267E/L328F | Free Arm for Ag Depletion | DKTHTCPPCPAPELLGGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KAFPAPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 106 |
| Human IgG1 Fc 1.3a Knob S354C/T366W, P238D | Antigen Arm for Ag Depletion | DKTHTCPPCPAPELLGGDSVELFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 107 |

TABLE 3-continued

| Exemplary Fc Domain Sequences | | | |
|---|---|---|---|
| Fc Sequences | | Sequences | SEQ ID NO |
| Human IgG1 Fc 1.3a Hole T366S/L368A/ Y407V/Y349C, P238D | Free Arm for Ag Depletion | DKTHTCPPCPAPELLGGDSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 108 |
| Human IgG1 Fc 1.3b Knob S354C/T366W, P238D | Antigen Arm for Ag Depletion | EPKSSDKTHTCPPCPAPELLGGDSVELFPPKPKDT<br>LMISRTPEVTCVVVDVSHEDPEVKENWYVDGVEVH<br>NAKTKPREEQYNSTYRVVSVLTVLHQDWLNGKEYK<br>CKVSNKALPAPIEKTISKAKGQPREPQVYTLPPCR<br>DELTKNQVSLWCLVKGFYPSDIAVEWESNGQPENN<br>YKTTPPVLDSDGSFFLYSKLTVDKSRWQQGNVFSC<br>SVMHEALHNHYTQKSLSLSPGK | 378 |
| Human IgG1 Fc 1.3b Hole T366S/L368A/ Y407V/Y349C, P238D | Free Arm for Ag Depletion | EPKSSDKTHTCPPCPAPELLGGDSVELFPPKPKDT<br>LMISRTPEVTCVVVDVSHEDPEVKENWYVDGVEVH<br>NAKTKPREEQYNSTYRVVSVLTVLHQDWLNGKEYK<br>CKVSNKALPAPIEKTISKAKGQPREPQVCTLPPSR<br>DELTKNQVSLSCAVKGFYPSDIAVEWESNGQPENN<br>YKTTPPVLDSDGSFFLVSKLTVDKSRWQQGNVESC<br>SVMHEALHNHYTQKSLSLSPGK | 379 |
| Human IgG1 Fc 1.4 Knob S354C/T366W, P238D/M428L/ N434S | Antigen Arm for Ag Depletion | DKTHTCPPCPAPELLGGDSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVLHE<br>ALHSHYTQKSLSLSPGK | 109 |
| Human IgG1 Fc 1.4 Hole T366S/L368A/ Y407V/Y349C, P238D/M428L/ N434S | Free Arm for Ag Depletion | DKTHTCPPCPAPELLGGDSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVLHE<br>ALHSHYTQKSLSLSPGK | 110 |
| Human IgG1 Fc (wild-type) | Bivalent Fc | DKTHTCPPCPAPELLGGPSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 111 |
| Human IgG1 Fc G236R/L328R, M252Y/S254T/ T256E, H433K/N434F | Bivalent Fc | DKTHTCPPCPAPELLRGPSVFLFPPKPKDTLYITR<br>EPEVTCVVVDVSHEDPEVKENWYVDGVEVHNAKTK<br>PREEQYNSTYRVVSVLTVLHQDWLNGKEYKCKVSN<br>KARPAPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVESCSVMHE<br>ALKFHYTQKSLSLSPGK | 112 |
| Human IgG1 Fc 1.5 Knob S354C/T366W, E233V/L234D/ L235F/G236R/ G237D/S239L/ S267D/H268P/ S298G/T299A/ A327L/L328A/ A330H/E333I | Antigen Arm for Ag Depletion | DKTHTCPPCPAPVDFRDPLVFLFPPKPKDTLMISR<br>TPEVTCVVVDVDPEDPEVKENWYVDGVEVHNAKTK<br>PREEQYNGAYRVVSVLTVLHQDWLNGKEYKCKVSN<br>KLAPHPIIKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 113 |
| Human IgG1 Fc 1.5 Hole T366S/L368A/ Y407V/Y349C, E233V/L234D/ L235F/G236R/ G237D/S239L/ | Free Arm for Ag Depletion | DKTHTCPPCPAPVDFRDPLVFLFPPKPKDTLMISR<br>TPEVTCVVVDVDPEDPEVKENWYVDGVEVHNAKTK<br>PREEQYNGAYRVVSVLTVLHQDWLNGKEYKCKVSN<br>KLAPHPIIKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 114 |

TABLE 3-continued

| Exemplary Fc Domain Sequences | | | |
|---|---|---|---|
| Fc Sequences | | Sequences | SEQ ID NO |
| S267D/H268P/S298G/T299A/A327L/L328A/A330H/E333I | | | |
| Human IgG1 Fc 1.6 Knob S354C/T366W, E233V/L234D/L235F/G236R/G237D/S239L/S267D/R292Q/H268P/S298G/T299A/A327L/L328A/A330H/E333I | Antigen Arm for Ag Depletion | DKTHTCPPCPAPVDFRDPLVFLFPPKPKDTLMISRTPEVTCVVVDVDPEDPEVKENWYVDGVEVHNAKTKPQEEQYNGAYRVVSVLTVLHQDWLNGKEYKCKVSNKLAPHPIIKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 115 |
| Human IgG1 Fc 1.6 Hole T366S/L368A/Y407V/Y349C, E233V/L234D/L235F/G236R/G237D/S239L/S267D/R292Q/H268P/S298G/T299A/A327L/L328A/A330H/E333I | Free Arm for Ag Depletion | DKTHTCPPCPAPVDFRDPLVFLFPPKPKDTLMISRTPEVTCVVVDVDPEDPEVKENWYVDGVEVHNAKTKPQEEQYNGAYRVVSVLTVLHQDWLNGKEYKCKVSNKLAPHPIIKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 116 |
| Human IgG1 Fc 1.7 Knob S354C/T366W, E233V/L234D/L235F/G236R/G237D/S239L/H268P/R292Q/S298G/T299A/A327L/L328A/A330H/E333I | Antigen Arm for Ag Depletion | DKTHTCPPCPAPVDFRDPLVFLFPPKPKDTLMISRTPEVTCVVVDVSPEDPEVKENWYVDGVEVHNAKTKPQEEQYNGAYRVVSVLTVLHQDWLNGKEYKCKVSNKLAPHPIIKTISKAKGQPREPQVYTLPPCRDELTKNQVSLWCLVKGFYPSDIAVEWESNGQPENNYKTTPPVLDSDGSFFLYSKLTVDKSRWQQGNVESCSVMHEALHNHYTQKSLSLSPGK | 117 |
| Human IgG1 Fc 1.7 Hole T366S/L368A/Y407V/Y349C, E233V/L234D/L235F/G236R/G237D/S239L/H268P/R292Q/S298G/T299A/A327L/L328A/A330H/E333I | Free Arm for Ag Depletion | DKTHTCPPCPAPVDFRDPLVFLFPPKPKDTLMISRTPEVTCVVVDVSPEDPEVKENWYVDGVEVHNAKTKPQEEQYNGAYRVVSVLTVLHQDWLNGKEYKCKVSNKLAPHPIIKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 118 |
| Human IgG1 Fc 1.8 Knob S354C/T366W, L234Y/P238D/T250V/V264I/T307P/Q311R/A330K/P343R/M428L/N434A/Y436T/Q438R/S440E | Antigen Arm for Ag Depletion | DKTHTCPPCPAPEYLGGDSVFLFPPKPKDVLMISRTPEVTCVVIDVSHEDPEVKENWYVDGVEVHNAKTKPREEQYNSTYRVVSVLPVLHRDWLNGKEYKCKVSNKALPKPIEKTISKAKGQRREPQVYTLPPCREEMTKNQVSLWCLVKGFYPSDIAVEWESNGQPENNYKTTPPVLDSDGSFFLYSKLTVDKSRWQQGNVFSCSVLHEALHAHTTRKELSLSPGK | 119 |
| Human IgG1 Fc 1.8 Hole T366S/L368A/Y407V/Y349C, L234Y/P238D/T250V/V264I/T307P/Q311R/A330K/P343R/M428L/N434A/Y436T/Q438R/S440E | Free Arm for Ag Depletion | DKTHTCPPCPAPEYLGGDSVFLFPPKPKDVLMISRTPEVTCVVIDVSHEDPEVKENWYVDGVEVHNAKTKPREEQYNSTYRVVSVLPVLHRDWLNGKEYKCKVSNKALPKPIEKTISKAKGQRREPQVCTLPPSREEMTKNQVSLSCAVKGFYPSDIAVEWESNGQPENNYKTTPPVLDSDGSFFLVSKLTVDKSRWQQGNVESCSVLHEALHAHTTRKELSLSPGK | 120 |

TABLE 3-continued

| Exemplary Fc Domain Sequences | | | |
|---|---|---|---|
| Fc Sequences | | Sequences | SEQ ID NO |
| Human IgG1 Fc 1.9 Knob S354C/T366W, L234D/G236N/ S267E | Antigen Arm for Ag Depletion | DKTHTCPPCPAPEDLNGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 121 |
| Human IgG1 Fc 1.9 Hole T366S/L368A/ Y407V/Y349C, L234D/G236N/ S267E | Free Arm for Ag Depletion | DKTHTCPPCPAPEDLNGPSVELFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 122 |
| Human IgG1 Fc 1.10 Knob S354C/T366W, L235R | Antigen Arm for Ag Depletion | DKTHTCPPCPAPELRGGPSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 123 |
| Human IgG1 Fc 1.10 Hole T366S/L368A/ Y407V/Y349C, L235R | Free Arm for Ag Depletion | DKTHTCPPCPAPELRGGPSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 124 |
| Human IgG1 Fc 1.11 Knob S354C/T366W, G236N/S267E | Antigen Arm for Ag Depletion | DKTHTCPPCPAPELLNGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 125 |
| Human IgG1 Fc 1.11 Hole T366S/L368A/ Y407V/Y349C, G236N/S267E | Free Arm for Ag Depletion | DKTHTCPPCPAPELLNGPSVELFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 126 |
| Human IgG1 Fc 1.12 Knob S354C/T366W, P238D/D270E | Antigen Arm for Ag Depletion | DKTHTCPPCPAPELLGGDSVFLFPPKPKDTLMISR<br>TPEVTCVVVDVSHEEPEVKENWYVDGVEVHNAKTK<br>PREEQYNSTYRVVSVLTVLHQDWLNGKEYKCKVSN<br>KALPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 127 |
| Human IgG1 Fc 1.12 Hole T366S/L368A/ Y407V/Y349C, P238D/D270E | Free Arm for Ag Depletion | DKTHTCPPCPAPELLGGDSVFLFPPKPKDTLMISR<br>TPEVTCVVVDVSHEEPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 128 |
| Human IgG1 Fc 1.13 Knob S354C/T366W, P238D/P271G | Antigen Arm for Ag Depletion | DKTHTCPPCPAPELLGGDSVFLFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPAPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 129 |

TABLE 3-continued

| Exemplary Fc Domain Sequences | | | |
|---|---|---|---|
| Fc Sequences | | Sequences | SEQ ID NO |
| Human IgG1 Fc 1.13 Hole T366S/L368A/ Y407V/Y349C, P238D/P271G | Free Arm for Ag Depletion | DKTHTCPPCPAPELLGGDSVELFPPKPKDTLMISRTPEVTCVVVDVSHEDGEVKENWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | 130 |
| Human IgG1 Fc 1.14 Knob S354C/T366W, P238D/D270E/ P271G | Antigen Arm for Ag Depletion | DKTHTCPPCPAPELLGGDSVELFPPKPKDTLMISRTPEVTCVVVDVSHEEGEVKENWYVDGVEVHNAKTKPREEQYNSTYRVVSVLTVLHQDWLNGKEYKCKVSNKALPAPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK | 131 |
| Human IgG1 Fc 1.14 Hole T366S/L368A/ Y407V/Y349C, P238D/D270E/ P271G | Free Arm for Ag Depletion | DKTHTCPPCPAPELLGGDSVELFPPKPKDTLMISRTPEVTCVVVDVSHEEGEVKENWYVDGVEVHNAKTKPREEQYNSTYRVVSVLTVLHQDWLNGKEYKCKVSNKALPAPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | 132 |
| Human IgG1 Fc 1.15 Knob S354C/T366W, G237D/P238D/ P271G/A330R | Antigen Arm for Ag Depletion | DKTHTCPPCPAPELLGDDSVFLFPPKPKDTLMISRTPEVTCVVVDVSHEDGEVKENWYVDGVEVHNAKTKPREEQYNSTYRVVSVLTVLHQDWLNGKEYKCKVSNKALPRPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK | 133 |
| Human IgG1 Fc 1.15 Hole T366S/L368A/ Y407V/Y349C, G237D/P238D/ P271G/A330R | Free Arm for Ag Depletion | DKTHTCPPCPAPELLGDDSVFLFPPKPKDTLMISRTPEVTCVVVDVSHEDGEVKENWYVDGVEVHNAKTKPREEQYNSTYRVVSVLTVLHQDWLNGKEYKCKVSNKALPRPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | 134 |
| Human IgG1 Fc 1.16 Knob S354C/T366W, G237D/P238D/ D270E/P271G/ A330R | Antigen Arm for Ag Depletion | DKTHTCPPCPAPELLGDDSVFLFPPKPKDTLMISRTPEVTCVVVDVSHEEGEVKENWYVDGVEVHNAKTKPREEQYNSTYRVVSVLTVLHQDWLNGKEYKCKVSNKALPRPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK | 135 |
| Human IgG1 Fc 1.16 Hole T366S/L368A/ Y407V/Y349C, G237D/P238D/ D270E/P271G/ A330R | Free Arm for Ag Depletion | DKTHTCPPCPAPELLGDDSVFLFPPKPKDTLMISRTPEVTCVVVDVSHEEGEVKENWYVDGVEVHNAKTKPREEQYNSTYRVVSVLTVLHQDWLNGKEYKCKVSNKALPRPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | 136 |
| Human IgG1 Fc 1.17 Knob S354C/T366W, E233D/G237D/ P238D/H268D/ P271G/A330R | Antigen Arm for Ag Depletion | DKTHTCPPCPAPDLLGDDSVFLFPPKPKDTLMISRTPEVTCVVVDVSDEDGEVKENWYVDGVEVHNAKTKPREEQYNSTYRVVSVLTVLHQDWLNGKEYKCKVSNKALPRPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 137 |
| Human IgG1 Fc 1.17 Hole T366S/L368A/ Y407V/Y349C, E233D/G237D/ P238D/H268D/ P271G/A330R | Free Arm for Ag Depletion | DKTHTCPPCPAPDLLGDDSVFLFPPKPKDTLMISRTPEVTCVVVDVSDEDGEVKENWYVDGVEVHNAKTKPREEQYNSTYRVVSVLTVLHQDWLNGKEYKCKVSNKALPRPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 138 |

TABLE 3-continued

| Exemplary Fc Domain Sequences | | | |
|---|---|---|---|
| Fc Sequences | | Sequences | SEQ ID NO |
| Human IgG1 Fc E233V/L234D/ L235F/G236R/ G237D/S239L/ S267D/H268P/ S298G/T299A/ A327L/L328A/ A330H/E333I | Bivalent Fc | DKTHTCPPCPAPVDFRDPLVFLFPPKPKDTLMISR TPEVTCVVVDVDPEDPEVKENWYVDGVEVHNAKTK PREEQYNGAYRVVSVLTVLHQDWLNGKEYKCKVSN KLAPHPIIKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 139 |
| Human IgG1 Fc E233V/L234D/ L235F/G236R/ G237D/S239L/ S267D/R292Q/ H268P/S298G/ T299A/A327L/ L328A/A330H/ E333I | Bivalent Fc | DKTHTCPPCPAPVDFRDPLVFLFPPKPKDTLMISR TPEVTCVVVDVDPEDPEVKENWYVDGVEVHNAKTK POEEQYNGAYRVVSVLTVLHQDWLNGKEYKCKVSN KLAPHPIIKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 140 |
| Human IgG1 Fc E233V/L234D/ L235F/G236R/ G237D/S239L/ H268P/R292Q/ S298G/T299A/ A327L/L328A/ A330H/E333I | Bivalent Fc | DKTHTCPPCPAPVDFRDPLVFLFPPKPKDTLMISR TPEVTCVVVDVSPEDPEVKENWYVDGVEVHNAKTK PQEEQYNGAYRVVSVLTVLHQDWLNGKEYKCKVSN KLAPHPIIKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 14 |
| Human IgG1 Fc L234Y/P238D/ T250V/V264I/ T307P/Q311R/ A330K/P343R/ M428L/N434A/ Y436T/Q438R/ S440E | Bivalent Fc | DKTHTCPPCPAPEYLGGDSVFLFPPKPKDVLMISR TPEVTCVVIDVSHEDPEVKENWYVDGVEVHNAKTK PREEQYNSTYRVVSVLPVLHRDWLNGKEYKCKVSN KALPKPIEKTISKAKGQRREPQVYTLPPSREEMTK NQVSLTCLVKGFYPSDIAVEWESNGQPENNYKTTP PVLDSDGSFFLYSKLTVDKSRWQQGNVESCSVLHE ALHAHTTRKELSLSPGK | 142 |
| Human IgG1 Fc L234D/G236N/ S267E | Bivalent Fc | DKTHTCPPCPAPEDLNGPSVFLFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 143 |
| Human IgG1 Fc L235R | Bivalent Fc | DKTHTCPPCPAPELRGGPSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 144 |
| Human IgG1 Fc G236N/S267E | Bivalent Fc | DKTHTCPPCPAPELLNGPSVFLFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 145 |
| Human IgG1 Fc P238D/D270E | Bivalent Fc | DKTHTCPPCPAPELLGGDSVFLFPPKPKDTLMISR TPEVTCVVVDVSHEEPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 146 |
| Human IgG1 Fc P238D/P271G | Bivalent Fc | DKTHTCPPCPAPELLGGDSVFLFPPKPKDTLMISR TPEVTCVVVDVSHEDGEVKENWYVDGVEVHNAKTK PREEQYNSTYRVVSVLTVLHQDWLNGKEYKCKVSN KALPAPIEKTISKAKGQPREPQVYTLPPSREEMTK | 147 |

TABLE 3-continued

| Exemplary Fc Domain Sequences | | | |
|---|---|---|---|
| Fc Sequences | | Sequences | SEQ ID NO |
| | | NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | |
| Human IgG1 Fc P238D/D270E/ P271G | Bivalent Fc | DKTHTCPPCPAPELLGGDSVELFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPAPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 148 |
| Human IgG1 Fc G237D/P238D/ P271G/A330R | Bivalent Fc | DKTHTCPPCPAPELLGDDSVELFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPRPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 149 |
| Human IgG1 Fc G237D/P238D/ D270E/P271G/ A330R | Bivalent Fc | DKTHTCPPCPAPELLGDDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPRPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 163 |
| Human IgG1 Fc E233D/G237D/ P238D/H268D/ P271G/A330R | Bivalent Fc | DKTHTCPPCPAPDLLGDDSVFLFPPKPKDTLMISR<br>TPEVTCVVVDVSDEDGEVKENWYVDGVEVHNAKTK<br>PREEQYNSTYRVVSVLTVLHQDWLNGKEYKCKVSN<br>KALPRPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 164 |
| Human IgG1 Fc P238D | Bivalent Fc | DKTHTCPPCPAPELLGGDSVFLFPPKPKDTLMISR<br>TPEVTCVVVDVSHEDPEVKENWYVDGVEVHNAKTK<br>PREEQYNSTYRVVSVLTVLHQDWLNGKEYKCKVSN<br>KALPAPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 374 |
| Human IgG1 Fc S239D/H268D/ L328W | Bivalent Fc | DKTHTCPPCPAPELLGGPDVFLFPPKPKDTLMISR<br>TPEVTCVVVDVSDEDPEVKENWYVDGVEVHNAKTK<br>PREEQYNSTYRVVSVLTVLHQDWLNGKEYKCKVSN<br>KAWPAPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 375 |
| Human IgG1 Fc 1.18 Knob S354C/T366W, S239D/H268D/ L328W | Antigen Arm for Ag Depletion | DKTHTCPPCPAPELLGGPDVFLFPPKPKDTLMISR<br>TPEVTCVVVDVSDEDPEVKENWYVDGVEVHNAKTK<br>PREEQYNSTYRVVSVLTVLHQDWLNGKEYKCKVSN<br>KAWPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 376 |
| Human IgG1 Fc 1.18 Hole T366S/L368A/ Y407V/Y349C, S239D/H268D/ L328W | Free arm for Ag Depletion | DKTHTCPPCPAPELLGGPDVFLFPPKPKDTLMISR<br>TPEVTCVVVDVSDEDPEVKENWYVDGVEVHNAKTK<br>PREEQYNSTYRVVSVLTVLHQDWLNGKEYKCKVSN<br>KAWPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 377 |

In some embodiments, a first Fc domain comprises a sequence selected from SEQ ID NO: 103, SEQ ID NO: 105, SEQ ID NO: 107, SEQ ID NO: 109, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 376, and SEQ ID NO: 378 and a second Fc domain comprises a sequence selected from SEQ ID NO: 104, SEQ ID NO: 106, SEQ ID NO: 108, SEQ ID NO: 110, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 377, and SEQ ID NO: 379.

In some embodiments, a first Fc domain comprises a sequence selected from SEQ ID NO: 103, SEQ ID NO: 105, SEQ ID NO: 113, SEQ ID NO: 115, SEQ ID NO: 117, SEQ ID NO: 121, SEQ ID NO: 123, SEQ ID NO:125, SEQ ID NO: 376, and SEQ ID NO: 378, and a second Fc domain comprises a sequence selected from SEQ ID NO: 104, SEQ ID NO: 106, SEQ ID NO: 114, SEQ ID NO: 116, SEQ ID NO: 118, SEQ ID NO: 122, SEQ ID NO: 124, SEQ ID NO: 126, SEQ ID NO: 377, and SEQ ID NO: 379.

In some embodiments, a first Fc domain comprises a sequence selected from SEQ ID NO: 107, SEQ ID NO: 109, SEQ ID NO: 119, SEQ ID NO: 127, SEQ ID NO: 129, SEQ ID NO: 131, SEQ ID NO: 133, SEQ ID NO: 135, and SEQ ID NO: 137, and a second Fc domain comprises a sequence selected from SEQ ID NO: 108, SEQ ID NO: 110, SEQ ID NO: 120, SEQ ID NO: 128, SEQ ID NO: 130, SEQ ID NO: 132, SEQ ID NO: 134, SEQ ID NO: 136, and SEQ ID NO: 138.

In some embodiments, a first Fc domain comprises a sequence of SEQ ID NO: 103 and a second Fc domain comprises a sequence of SEQ ID NO: 104. In some embodiments, a first Fc domain comprises a sequence of SEQ ID NO: 105 and a second Fc domain comprises a sequence of SEQ ID NO: 106. In some embodiments, a first Fc domain comprises a sequence of SEQ ID NO: 107 and a second Fc domain comprises a sequence of SEQ ID NO: 108. In some embodiments, a first Fc domain comprises a sequence of SEQ ID NO: 109 and a second Fc domain comprises a sequence of SEQ ID NO: 110. In some embodiments, a first Fc domain comprises a sequence of SEQ ID NO: 113 and a second Fc domain comprises a sequence of SEQ ID NO: 114. In some embodiments, a first Fc domain comprises a sequence of SEQ ID NO: 115 and a second Fc domain comprises a sequence of SEQ ID NO: 116. In some embodiments, a first Fc domain comprises a sequence of SEQ ID NO: 117 and a second Fc domain comprises a sequence of SEQ ID NO: 118. In some embodiments, a first Fc domain comprises a sequence of SEQ ID NO: 119 and a second Fc domain comprises a sequence of SEQ ID NO: 120. In some embodiments, a first Fc domain comprises a sequence of SEQ ID NO: 121 and a second Fc domain comprises a sequence of SEQ ID NO: 122. In some embodiments, a first Fc domain comprises a sequence of SEQ ID NO: 123 and a second Fc domain comprises a sequence of SEQ ID NO: 124. In some embodiments, a first Fc domain comprises a sequence of SEQ ID NO: 125 and a second Fc domain comprises a sequence of SEQ ID NO: 126. In some embodiments, a first Fc domain comprises a sequence of SEQ ID NO: 127 and a second Fc domain comprises a sequence of SEQ ID NO: 128. In some embodiments, a first Fc domain comprises a sequence of SEQ ID NO: 129 and a second Fc domain comprises a sequence of SEQ ID NO: 130. In some embodiments, a first Fc domain comprises a sequence of SEQ ID NO: 131 and a second Fc domain comprises a sequence of SEQ ID NO: 132. In some embodiments, a first Fc domain comprises a sequence of SEQ ID NO: 133 and a second Fc domain comprises a sequence of SEQ ID NO: 134. In some embodiments, a first Fc domain comprises a sequence of SEQ ID NO: 135 and a second Fc domain comprises a sequence of SEQ ID NO: 136. In some embodiments, a first Fc domain comprises a sequence of SEQ ID NO: 137 and a second Fc domain comprises a sequence of SEQ ID NO: 138. In some embodiments, a first Fc domain comprises a sequence of SEQ ID NO: 376 and a second Fc domain comprises a sequence of SEQ ID NO: 377. In some embodiments, a first Fc domain comprises a sequence of SEQ ID NO: 378 and a second Fc domain comprises a sequence of SEQ ID NO: 379. In some embodiments, a first Fc domain comprises a sequence of SEQ ID NO: 111 and a second Fc domain comprises a sequence of SEQ ID NO: 111. In some embodiments, a first Fc domain comprises a sequence of SEQ ID NO: 139 and a second Fc domain comprises a sequence of SEQ ID NO: 139. In some embodiments, a first Fc domain comprises a sequence of SEQ ID NO: 140 and a second Fc domain comprises a sequence of SEQ ID NO: 140. In some embodiments, a first Fc domain comprises a sequence of SEQ ID NO: 141 and a second Fc domain comprises a sequence of SEQ ID NO: 141. In some embodiments, a first Fc domain comprises a sequence of SEQ ID NO: 142 and a second Fc domain comprises a sequence of SEQ ID NO: 142. In some embodiments, a first Fc domain comprises a sequence of SEQ ID NO: 143 and a second Fc domain comprises a sequence of SEQ ID NO: 143. In some embodiments, a first Fc domain comprises a sequence of SEQ ID NO: 144 and a second Fc domain comprises a sequence of SEQ ID NO: 144. In some embodiments, a first Fc domain comprises a sequence of SEQ ID NO: 145 and a second Fc domain comprises a sequence of SEQ ID NO: 145. In some embodiments, a first Fc domain comprises a sequence of SEQ ID NO: 146 and a second Fc domain comprises a sequence of SEQ ID NO: 146. In some embodiments, a first Fc domain comprises a sequence of SEQ ID NO: 147 and a second Fc domain comprises a sequence of SEQ ID NO: 147. In some embodiments, a first Fc domain comprises a sequence of SEQ ID NO: 148 and a second Fc domain comprises a sequence of SEQ ID NO: 148. In some embodiments, a first Fc domain comprises a sequence of SEQ ID NO: 149 and a second Fc domain comprises a sequence of SEQ ID NO: 149. In some embodiments, a first Fc domain comprises a sequence of SEQ ID NO: 163 and a second Fc domain comprises a sequence of SEQ ID NO: 163. In some embodiments, a first Fc domain comprises a sequence of SEQ ID NO: 164 and a second Fc domain comprises a sequence of SEQ ID NO: 164. In some embodiments, a first Fc domain comprises a sequence of SEQ ID NO: 374 and a second Fc domain comprises a sequence of SEQ ID NO: 374. In some embodiments, a first Fc domain comprises a sequence of SEQ ID NO: 375 and a second Fc domain comprises a sequence of SEQ ID NO: 375.

Hinge Sequences

In some embodiments, an Fc domain comprises a hinge sequence. In some embodiments, an Fc domain comprises the amino acid sequence of SEQ ID NO: 299 (DKTHTCPPCP). In some embodiments, an Fc domain comprises the amino acid sequence of SEQ ID NO: 300 (EPKSSDKTHTCPPCP). In some embodiments, an Fc domain comprises the amino acid sequence of SEQ ID NO: 301 (ERKCCVECPPCP). In some embodiments, an Fc domain comprises the amino acid sequence of SEQ ID NO: 302 (ELKTRPLGDTTHTCPPCP). In some embodiments, an Fc domain comprises the amino acid sequence of SEQ ID NO: 303 (ELKTRPLGDTTHTCPRCP (EPKSCDTPPPCPRCP)3). In some embodiments, an Fc domain comprises the amino acid sequence of SEQ ID NO: 304 (ESKYGPPCPPCP).

In this context, it is to be understood that any of the exemplary Fc domain sequences provided in Table 3 can be modified by replacing the hinge sequence of SEQ ID NO: 299 (DKTHTCPPCP) or SEQ ID NO: 300 (EPKSSDKTH-TCPPCP) with the hinge sequence of SEQ ID NO: 301 (ERKCCVECPPCP), SEQ ID NO: 302 (ELKTR-PLGDTTHTCPPCP), SEQ ID NO: 303 (ELKTR-PLGDTTHTCPRCP(EPKSCDTPPPCPRCP)3), SEQ ID NO: 304 (ESKYGPPCPPCP) or any other suitable hinge sequence including variants of the hinge sequences of SEQ ID NOs: 299-304 that include 1, 2, 3, 4, 5 or more mutations.

Mutations to Increase Binding to Internalizing Receptors

In some embodiments, additional mutations are introduced into Fc domains of molecules described herein in order to target cell surface receptors that bind and internalize ligands and target them to the lysosome (i.e., internalizing receptors or endocytic receptors). By modifying Fc domains to increase binding to internalizing receptors, molecules described herein and their bound autoantibodies are targeted for internalization and lysosomal degradation.

In some embodiments, a molecule comprises a first and/or second Fc domain that comprises one of more mutated amino acid residues that alters its binding to an internalizing receptor on a cell, where the internalizing receptor is capable of shuttling its cargo to the lysosome of the cell leading to degradation. In some embodiments, altered binding to the internalizing receptor comprises increased binding to an internalizing receptor. Without wishing to be bound to any theory, once a molecule bound to an autoantibody binds to an internalizing receptor on a cell, the internalizing receptor internalizes the molecule and the autoantibody is shuttled to the lysosome of the cell for degradation.

Exemplary internalizing receptors include but are not limited to FcγRIIB, FcRn, ASGPR, BCMA, CD38, SLAMF7, GPCR5D, or CD138.

In some embodiments, a first and/or second Fc domain comprises one or more mutated amino acid residues that increase binding to the human FcγR, specifically FcγRIIB. In some embodiments, such a mutation comprises at least one of the following mutated amino acid residues: S267E and L328F, according to the EU numbering scheme. In some embodiments, a first and/or second Fc domain comprise a combination of the following mutated amino acid residues: S267E and L328F, according to the EU numbering scheme. In some embodiments, a first and/or second Fc domain comprises the mutated amino acid residue P238D, according to the EU numbering scheme. In some embodiments, a first and/or second Fc domain comprises at least one of the following mutated amino acid residues: L234A, L235A, and P238D, according to the EU numbering scheme. In some embodiments, a first and/or second Fc domain comprises the following mutated amino acid residues: L234A, L235A, and P238D, according to the EU numbering scheme. In some embodiments, a first and/or second Fc domain comprises at least one of the following mutated amino acid residues: L234A, L235A, P238D and P329G, according to the EU numbering scheme. In some embodiments, a first and/or second Fc domain comprises the following mutated amino acid residues: L234A, L235A, P238D and P329G, according to the EU numbering scheme. In some embodiments, a first and/or second Fc domain comprises at least one of the following mutated amino acid residues: L234A, L235A, and P238D, according to the EU numbering scheme. In some embodiments, a first and/or second Fc domain comprises the following mutated amino acid residues: L234A, L235A, and P238D, according to the EU numbering scheme. In some embodiments, a first and/or second Fc domain comprises at least one of the following mutated amino acid residues: N297A and P238D, according to the EU numbering scheme. In some embodiments, a first and/or second Fc domain comprises the following mutated amino acid residues: N297A and P238D, according to the EU numbering scheme.

In some embodiments, one or more Fc mutations are introduced in order to increase binding to the human neonatal receptor (FcRn). In some embodiments, an Fc domain is an IgG1 Fc domain. Human IgG1 naturally binds FcRn at an acidic pH, which allows it to, upon binding FcRn and internalization into a cell, be recycled back to the surface of the cell and not to be degraded in the lysosome. In some embodiments, Fc mutations comprise mutation that increase binding to FcRn in neutral pH environments (e.g., extracellular environment). Without wishing to be bound by any theory, such mutations are included in the molecules described herein in order to increase binding of the Fc domain to FcRn on the surface of a cell in a neutral pH environment, such that there will be increased receptor-mediated internalization into cells and shuttling of the autoantibodies (bound to the molecule) to the lysosome.

In some embodiments, a first and/or second Fc domain comprises one or more mutated amino acid residues that increase binding to FcRn at a neutral or near-neutral pH (e.g., pH between about 6.8 and 7.5). In some embodiments, a first and/or second Fc domain comprises a human IgG1 isotype and has remains bound to FcRn upon entry into an environment having an acidic pH and/or having low calcium concentration (e.g., into an endosome of a cell). In some embodiments, a first and/or second Fc domain comprises at least one of the following mutated amino acid residues: M252Y, S254T, T256E, H433K, and N434F, according to the EU numbering scheme. In some embodiments, such mutations include a combination that includes the following mutations: M252Y, S254T, T256E, H433K, N434F (i.e., “MST-HN”), according to the EU numbering scheme. In some embodiments, the first and/or second Fc domain comprises a combination of the following mutated amino acid residues: M252Y, S254T, T256E, H433K, and N434F (i.e., “MST-HN”), according to the EU numbering scheme.

In some embodiments, a first and/or second Fc domain comprises at least one mutated amino acid sequence that decreases binding to one or more Fc-gamma receptors (FcγRs). Such modifications may prevent immune crosslinking (i.e., of a molecule, autoantibody, FcγRs) that leads to inflammatory responses. Such mutations may focus the primary mechanism of action of the molecules, i.e., to the targeted internalization and subsequent degradation of autoantibodies. In some embodiments, a first and/or second Fc domain comprises at least one of the following mutated amino acid residues: G236R and L328R, according to the EU numbering scheme. In some embodiments, a first and/or second Fc domain comprises the following mutated amino acid residues: G236R and L328R, according to the EU numbering scheme.

In some embodiments, a molecule described herein may include any combination of the above-described Fc mutations that alter binding to an internalizing receptor or Fc receptor. In some embodiments, a molecule described herein includes an Fc domain that comprises an “MST-HN” modification described herein in combination with an “RR” mutation described herein. In some embodiments, a molecule described herein includes an Fc domain that comprises an “MST-HN” modification described herein in combination with the “P238D” mutation described herein. In some embodiments, a molecule described herein includes an Fc domain that comprises an “MST-HN” modification described herein in combination with an "RR" mutation and "P238D" mutation described herein.

i. Exemplary FcγRIIB Mutations

In some embodiments, an Fc domain comprises one or more amino acid mutations that increase affinity for FcγRIIB. In some embodiments FcγRIIB is human FcγRIIB. In some embodiments, FcγRIIB is murine FcγRIIB.

In some embodiments, an Fc domain is utilized in a molecule described herein that comprises one or more mutations that enhances binding kinetics of an immune complex comprising the one or more molecules bound to a target antibody to FcγRIIB. In some embodiments, enhanced binding kinetics comprises at least 15%, at least 20%, at least 25%, at least 30%, at least 35%, at least 40%, at least 45%, or at least 50% or greater binding affinity. In some embodiments, enhanced binding kinetics comprises an increase in avidity, stability, strength, frequency, and/or duration of binding between the immune complex and FcγRIIB. In some embodiments, enhanced binding kinetics comprise an increase in the rate of association, a decrease in the rate of disassociation, and/or a change in the equilibrium dissociation constant.

In some embodiments, molecules described herein having a first and second Fc domain comprise one or more mutations in the first and/or second Fc domain to increase binding to FcγRIIB, wherein upon binding of two molecules to the target antibody, an immune complex is formed that has enhanced binding kinetics with FcγRIIB relative to an immune complex that comprises the target antibody bound to two corresponding molecules with wild-type Fc domains. Without wishing to be bound by any theory, a molecule described herein may have one or more mutations that increase binding affinity for FcγRIIB, but the binding affinity of the molecule alone to FcγRIIB is moderate. In some embodiments, a molecule binds to FcγRIIB with an affinity within the range of about 1 μM to 0.001 μM. In some embodiments, a molecule binds to FcγRIIB with an affinity within the range of about 1 μM to 0.01 μM. In some embodiments, a molecule binds to FcγRIIB with an affinity within the range of about 0.1 μM to 0.01 μM. In some embodiments, such mutations when introduced into an Fc domain of a molecule described herein confer an avidity-mediated binding effect to FcγRIIB when two or more molecules are present in an immune complex with a target antibody. In some embodiments, a molecule described herein has increased binding to FcγRIIB when the immune complex comprises two molecules bound to a target antibody compared to an immune complex with only one molecule bound to the target antibody. Without wishing to be bound by any theory, such avidity-mediated effects allow for selective binding and depletion of immune complexes and weaker binding (and hence depletion) of molecules when they are not part of an immune complex. These characteristics allow for molecules described herein to remain circulating longer in the bloodstream of a subject before being cleared by FcγRIIB-mediated internalization and degradation.

Additionally, the present disclosure provides Fc domain mutations that achieve the binding affinity to FcγRIIB to confer avidity-mediated effects to take advantage of the benefits and additional selectively described herein. Exemplary Fc domain mutations that may be used to achieve these binding kinetics with FcγRIIB include, e.g., in some embodiments, one or more of the following mutations: E233V, L234D, L235F, G236R, G237D, S239L, S267D, H268P, S298G, T299A, A327L, L328A, A330H, E333I, R292Q, E233P, P238D, H268D, P271G, A330R, L234Y, T250V, V264I, T307P, Q311R, A330K, P343R, M428L, N434A, Y436T, Q438R, S440E, G236N, S267E, L235R, D270E, E233D, and G237D, according to the EU numbering scheme.

In some embodiments, an Fc domain mutation comprises one or more of the following mutations: E233V, L234D, L235F, G236R, G237D, S239L, S267D, H268P, S298G, T299A, A327L, L328A, A330H, or E333I. In some embodiments, an Fc domain comprises the following set of mutations: E233V, L234D, L235F, G236R, G237D, S239L, S267D, H268P, S298G, T299A, A327L, L328A, A330H, and E333I, according to the EU numbering scheme (e.g., see SEQ ID NOs: 113, 114, and 139).

In some embodiments, an Fc domain mutation comprises one or more of the following mutations: E233V, L234D, L235F, G236R, G237D, S239L, S267D, R292Q, H268P, S298G, T299A, A327L, L328A, A330H, or E333I, according to the EU numbering scheme. In some embodiments, an Fc domain comprises the following set of mutations: E233V, L234D, L235F, G236R, G237D, S239L, S267D, R292Q, H268P, S298G, T299A, A327L, L328A, A330H, and E333I, according to the EU numbering scheme (e.g., see SEQ ID NOs: 115, 116, and 140).

In some embodiments, an Fc domain mutation comprises one or more of the following mutations: E233V, L234D, L235F, G236R, G237D, S239L, H268P, R292Q, S298G, T299A, A327L, L328A, A330H, or E333I, according to the EU numbering scheme. In some embodiments, an Fc domain comprises the following set of mutations: E233V, L234D, L235F, G236R, G237D, S239L, H268P, R292Q, S298G, T299A, A327L, L328A, A330H, and E333I, according to the EU numbering scheme (e.g., see SEQ ID NOs: 117, 118, and 141).

In some embodiments, an Fc domain mutation comprises one or more of the following mutations: L234Y, P238D, T250V, V264I, T307P, Q311R, A330K, P343R, M428L, N434A, Y436T, Q438R, or S440E, according to the EU numbering scheme. In some embodiments, an Fc domain comprises the following set of mutations: L234Y, P238D, T250V, V264I, T307P, Q311R, A330K, P343R, M428L, N434A, Y436T, Q438R, and S440E, according to the EU numbering scheme (e.g., see SEQ ID NOs: 119, 120, and 142).

In some embodiments, an Fc domain mutation comprises one or more of the following mutations: L234D, G236N, or S267E, according to the EU numbering scheme. In some embodiments, an Fc domain comprises the following set of mutations: L234D, G236N, and S267E, according to the EU numbering scheme (e.g., see SEQ ID NOs: 121, 122, and 143).

In some embodiments, an Fc domain mutation comprises L235R, according to the EU numbering scheme (e.g., see SEQ ID NOs: 123, 124, and 144).

In some embodiments, an Fc domain mutation comprises one or both of the following mutations G236N and S267E, according to the EU numbering scheme. In some embodiments, an Fc domain comprises the following set of mutations: G236N and S267E, according to the EU numbering scheme (e.g., see SEQ ID NOs: 125, 126, and 145).

In some embodiments, an Fc domain mutation comprises one or both of the following mutations P238D and D270E, according to the EU numbering scheme. In some embodiments, an Fc domain comprises the following set of mutations: P238D and D270E, according to the EU numbering scheme (e.g., see SEQ ID NOs: 127, 128, and 146).

In some embodiments, an Fc domain mutation comprises one or both of the following mutations P238D and P271G, according to the EU numbering scheme. In some embodiments, an Fc domain comprises the following set of mutations: P238D and P271G, according to the EU numbering scheme (e.g., see SEQ ID NOs: 129, 130, and 147).

In some embodiments, an Fc domain mutation comprises one or more of the following mutations: P238D, D270E, or P271G, according to the EU numbering scheme. In some embodiments, an Fc domain comprises the following set of mutations: P238D, D270E, and P271G, according to the EU numbering scheme (e.g., see SEQ ID NOs: 131, 132, and 148).

In some embodiments, an Fc domain mutation comprises one or more of the following mutations: G237D, P238D, P271G, or A330R, according to the EU numbering scheme. In some embodiments, an Fc domain comprises the following set of mutations: G237D, P238D, P271G, and A330R, according to the EU numbering scheme (e.g., see SEQ ID NOs: 133, 134, and 149).

In some embodiments, an Fc domain mutation comprises one or more of the following mutations: G237D, P238D, D270E, P271G, or A330R, according to the EU numbering scheme. In some embodiments, an Fc domain comprises the following set of mutations: G237D, P238D, D270E, P271G, and A330R, according to the EU numbering scheme (e.g., see SEQ ID NOs: 135, 136, and 163).

In some embodiments, an Fc domain mutation comprises one or more of the following mutations: E233D, G237D, P238D, H268D, P271G, or A330R, according to the EU numbering scheme. In some embodiments, an Fc domain comprises the following set of mutations: E233D, G237D, P238D, H268D, P271G, and A330R, according to the EU numbering scheme (e.g., see SEQ ID NOs: 137, 138, and 164).

In some embodiments, an Fc domain mutation comprises P238D, according to the EU numbering scheme (e.g., see SEQ ID NOs: 107 and 108).

In some embodiments, Fc domains with mutations that increase binding affinity for FcγRIIB also have decreased or undetectable binding to certain activating Fc receptors. In some embodiments, an activating Fc receptor includes one or more of FcγRI, FcγRIIA167H, FcγRIIA167R, FcγRIIIA176F, FcγRIIIA176V, FcγRIIIB, and/or FcRn. Such binding properties lead to additional beneficial properties of molecules described herein including, e.g., a low risk of toxicity as there is less risk of activating the innate immune response (through activating Fc receptors) in response to molecules being introduced.

In some embodiments, an Fc domain described herein comprises one or more modifications such that a molecule described herein does not activate immune cells (e.g., does not activate immune cells to secrete pro-inflammatory cytokines, e.g., IL-6).

Mutations for Heterodimerization

In some embodiments, Fc mutations are introduced to promote heterodimerization of the two polypeptides, where each polypeptide comprises an Fc domain, and the first and second Fc domains heterodimerize in order to generate the full molecule.

Challenges exist in producing heterodimerized Fc domains of two different polypeptides from a single composition, particularly because the random pairing of different polypeptides can yield undesired species. Due to the presence of mispaired byproducts, and significantly reduced production yields, sophisticated purification procedures are required to isolate the desired antibody agent in those situations. In general, the same problem of mispaired byproducts remains if recombinant expression techniques are used. One approach to solve the problem of mispaired byproducts is known as "knob-into-holes technology" (KIH), which aims to force the pairing of two different polypeptides containing Fc domains by introducing mutations into the CH3 regions of the Fc domains to modify the contact interface. On one CH3 region, bulky amino acids are replaced by amino acids with short side chains to create a "hole" and amino acids with large side chains are introduced into the other CH3 region, to create a "knob". For example, co-expressing two heavy chains of an antibody with such a modification with two light chains, leads to high yields of heterodimer formation versus homodimer was observed (see Ridgway et al., Protein Eng. 9:617 (1996); and WO 1996/027011, which are herein incorporated by reference). In some embodiments, a molecule described herein utilizes KIH technology as described in, e.g., WO 1998/050431, which is herein incorporated by reference in its entirety.

As described herein, a molecule comprises a first Fc domain and a second Fc domain. In some embodiments a first Fc domain and/or a second Fc domain comprises a CH2 region variant and/or a CH3 region variant, wherein such variants each independently comprise at least one different amino acid substitution such that a heterodimeric domain pair is generated such that heterodimerization of the first and second Fc domains of the inventive molecule is favored over homodimerization.

As described herein, a first and/or second Fc domain in a molecule described herein may comprise certain mutations that utilize KIH technology that include, but are not limited to, a CH3 modification. In some embodiments, a molecule comprises first and second Fc domains that form a heterodimer using knobs-in-holes (KIH) modifications. In some embodiments, a KIH mutation comprises Y349T and T394F, according to the EU numbering scheme. In some embodiments, the first Fc domain comprises the Y349T mutation and the second Fc domain comprises the T394F mutation. In some embodiments, the first Fc domain comprises the T394F mutation and the second Fc domain comprises the Y349T mutation. In some embodiments, a KIH mutation comprises T366W, S354C, T366S, L368A, Y407V, and Y349C, according to the EU numbering scheme. In some embodiments, the first Fc domain comprises the T366W and S354C mutations and the second Fc domain comprises the T366S, L368A, Y407V, and Y349C mutations. In some embodiments, the first Fc domain comprises the T366S, L368A, Y407V, and Y349C mutations and the second Fc domain comprises the T366W and S354C mutations.

One of skill in the art will understand that other known KIH mutations or other Fc modifications are known in the art to promote heterodimerization and may be used in the molecules described herein, such as charge-to-charge swap design (e.g., "DD-KK" mutation pairs) and isotype strand swap design (e.g., "SEED Fc") (see Ha et al., *Frontiers in Immunology* 7: 394 (2016), which is herein incorporated by reference in its entirety).

Mutations for Half-Life Extension

In some embodiments, a first and/or second Fc domain in a molecule includes one or more mutated amino acid residues that increase half-life. In some embodiments, a first and/or second Fc domain comprises one of the following mutated amino acid residues: M252Y, S254T, and T256E ("MST" or "YTE"), according to the EU numbering scheme to increase half-life. In some embodiments, a first and/or second Fc domain comprises a combination of the following mutated amino acid residues: M252Y, S254T, and T256E, according to the EU numbering scheme to increase half-life. In some embodiments, a first and/or second Fc domain comprises one of the following mutated amino acid residues: M428L and N434S ("L/S"), according to the EU numbering scheme. In some embodiments, a first and/or second Fc domain comprises a combination of the following mutated amino acid residues: M428L and N434S, according to the EU numbering scheme.

In some embodiments, a first and/or second Fc domain comprises one of the following mutated amino acid residues: T250Q and M428L ("QL"), according to the EU numbering scheme to increase half-life. In some embodiments, a first and/or second Fc domain comprises one of the following mutated amino acid residues: H433K and N434F ("KF"), according to the EU numbering scheme to increase half-life. In some embodiments, a first and/or second Fc domain comprises one of the following mutated amino acid residues: T307A, E380A and N434A ("AAA"), according to the EU numbering scheme to increase half-life. In some embodiments, a first and/or second Fc domain comprises the following mutated amino acid residues: V308P, according to the EU numbering scheme to increase half-life. In some embodiments, a first and/or second Fc domain comprises one of the following mutated amino acid residues: M252Y, V308P, and N434Y ("YPY"), according to the EU numbering scheme to increase half-life. In some embodiments, a first and/or second Fc domain comprises one of the following mutated amino acid residues: H285D, T307Q, and A378V ("DQV"), according to the EU numbering scheme to increase half-life. In some embodiments, a first and/or second Fc domain comprises one of the following mutated amino acid residues: L309D, Q311H, N434S ("DHS"), according to the EU numbering scheme to increase half-life. Exemplary Fc mutations are described in e.g., Liu et al., *Antibodies* 9(4): 64 (2020), which is hereby incorporated by reference in its entirety.

Linkers

Molecules described herein include an Fc domain linked to an autoantibody-binding domain. In some embodiments, the autoantibody-binding domain is connected directly to an Fc domain. In some embodiments, the autoantibody-binding domain is connected to an Fc domain through a linker. Various linkers are contemplated to be used in molecules described herein. While linkers may be between an autoantibody-binding domain and an Fc domain they may also be between other domains of the molecule, e.g., connecting one or more autoantigen domains within the autoantibody-binding domain.

In some embodiments, a linker includes a flexible linker so as to provide flexibility in a molecule (e.g., between an autoantigen domain and a Fc domain). In some embodiments, a flexible linker contains at least 1 flexible amino acid (e.g., Gly).

Exemplary flexible linkers include glycine polymers $(G)_n$, glycine-serine polymers (including, for example, $(GS)_n$, (GSGGS: SEQ ID NO: $156)_n$ and (GGGS: SEQ ID NO: $380)_n$, where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, *Rev. Computational Chem.* 11:173-142 (1992)). In some embodiments, a linker comprises the amino acid sequence of SEQ ID NO: 150 (GGGGS), SEQ ID NO: 151 (GGGGSGGGGS), SEQ ID NO: 152 (GGGGSGGGGSGGGGS) or SEQ ID NO: 153 (VDGGGGSGGGGSGGGGSG).

Additional exemplary flexible linkers include, but are not limited to, SEQ ID NO: 157 (GGSG), SEQ ID NO: 158 (GGSGG), SEQ ID NO: 159 (GSGSG), SEQ ID NO: 160 (GSGGG), SEQ ID NO: 161 (GGGSG), SEQ ID NO: 162 (GSSSG), and the like. Additional exemplary linkers also include the following: GGGGSGGGGSGGGGSGGGGS (SEQ ID NO: 154) and GGGGSGGGGSGGGGSGGGGSSGGGGS (SEQ ID NO: 155).

The ordinarily skilled artisan will recognize that the design of a molecule described herein can include a linker that is all or partially flexible, such that the linker can include a flexible linker as well as one or more portions that confer less flexible structure to provide for a desired molecule structure.

Suitable linkers can be readily selected and can be of various lengths, such as from 1 amino acid (e.g., Gly) to 20 amino acids or more, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids (e.g., at least 1, 2, 3, 4, 5, 6, 7, 8, 9, 10, 11, 12, 13, 14, 15, 16, 17, 18, or 19 amino acids).

In some embodiments a linker may be or comprise a synthetic linker that does not comprise amino acids, e.g., a polyethylene (PEG) linker or other known synthetic linkers that are commonly used for chemical conjugation, e.g., in antibody-drug conjugates. In this context, it is also to be understood that the molecules described herein encompass molecules where the components of the first or second polypeptides (i.e., autoantigen domain, antigen-binding domain, Fc domains) are linked via chemical conjugation, e.g., "click" or other chemistry, optionally with an intervening amino acid or synthetic linker.

In some embodiments, a molecule described herein is a fusion protein wherein the first and second polypeptides can be encoded by a single nucleic acid sequence. In some embodiments, a molecule described herein is a chemically conjugated molecule that includes components conjugated using synthetic chemistry.

Exemplary Configurations

Various configurations of molecules as described herein are contemplated. Such configurations include various elements of molecules as described herein including a first polypeptide comprising an autoantibody-binding domain linked to a first Fc domain, and a second polypeptide comprising a second Fc domain. Exemplary autoantibody-binding domains, antigen-binding domains, Fc domains, and linkers are described. Such components may be assembled in different configurations to generate a molecule as described herein.

Exemplary combinations of specific autoantigen domains, antigen-binding domains, Fc domains, and linkers are provided in Table 4 below. In some embodiments, any one of the combinations in Table 4 may be included in a molecule configuration as shown, e.g., in FIG. 2. In such a configuration, the C-terminus of an autoantigen domain (A) is linked to the N-terminus of a first Fc domain (Fc1) through an optional linker (L) (first polypeptide) and forms a heterodimer with a second Fc domain (Fc2) of the second polypeptide.

In some embodiments, any one of the combinations in Table 4 may be included in a molecule configuration as shown, e.g., in FIG. 3. In such a configuration, the C-terminus of an autoantigen domain (A) is linked to the N-terminus of a first Fc domain (Fc1) though an optional linker (L) (first polypeptide) and the molecule also includes an antigen-binding domain, where the C-terminus of the antigen-binding domain (HC/LC Fab) is linked to the N-terminus of a second Fc domain (Fc2) (second polypeptide). In some embodiments (not shown), the N-terminus of the antigen-binding domain (HC/LC Fab) is instead linked to the C-terminus of a second Fc domain (Fc2) (second polypeptide). In some embodiments (not shown), the C-terminus of a first Fc domain (Fc1) is instead linked to the N-terminus of a first autoantigen domain (A) through an optional linker (L) (first polypeptide). In some embodiments (not shown), the C-terminus of a first Fc domain (Fc1) is instead linked to the N-terminus of a first autoantigen domain (A) through an optional linker (L) (first polypeptide) and the N-terminus of the antigen-binding domain (HC/LC Fab) is instead linked to the C-terminus of a second Fc domain (Fc2) (second polypeptide).

Figure 4:
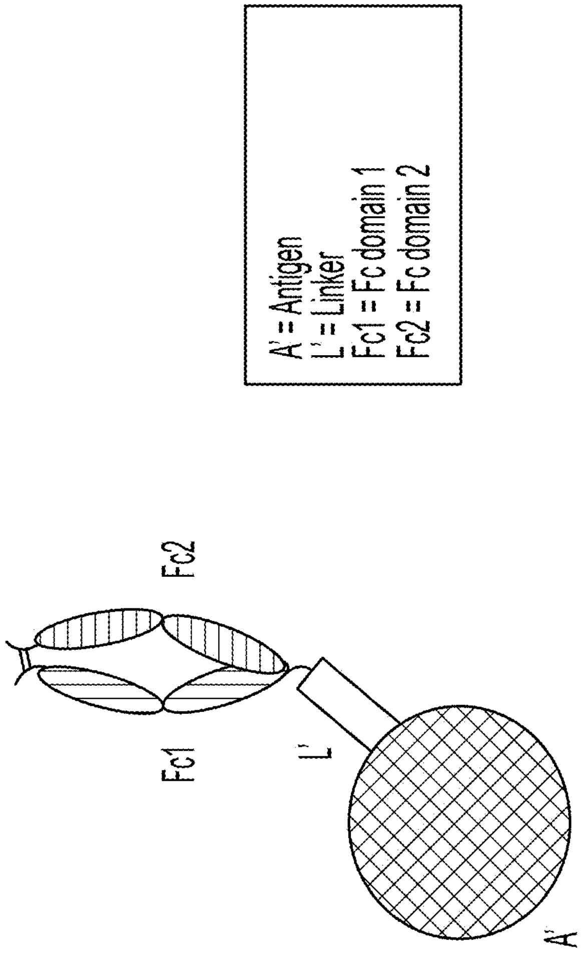
FIG. 4 shows an exemplary molecule format described herein.

In some embodiments, any one of the combinations in Table 4 may be included in a molecule configuration as shown, e.g., in FIG. 4. In such a configuration, the C-terminus of a first Fc domain (Fc1) is linked to the N-terminus of an autoantigen domain (A) through an optional linker (L) (first polypeptide) and forms a heterodimer with a second Fc domain (Fc2) of the second polypeptide.

Figure 5A:
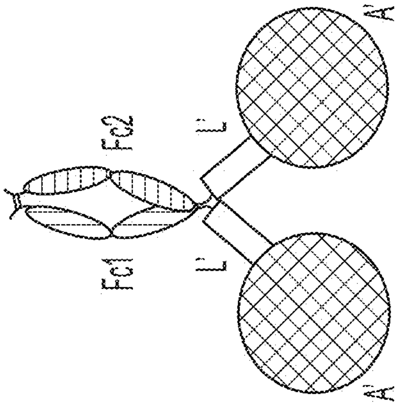
FIGS. 5A-5B show exemplary molecule formats described herein.

In some embodiments, any one of the combinations in Table 4 may be included in a molecule configuration as shown, e.g., in FIG. 5A. In such a configuration, a molecule includes two autoantigen domains, where the C-terminus of a first Fc domain (Fc1) is linked to the N-terminus of a first autoantigen domain (A') through an optional linker (L') (first polypeptide) and the C-terminus of a second Fc domain (Fc2) is linked to the N-terminus of a second autoantigen domain (A') through an optional linker (L') (second polypeptide). In some embodiments, the two autoantigen domains are the same (e.g., in a homodimeric molecule of the present disclosure). In some embodiments, the two autoantigen domains are different (e.g., in a heterodimeric molecule of the present disclosure).

Figure 5B:
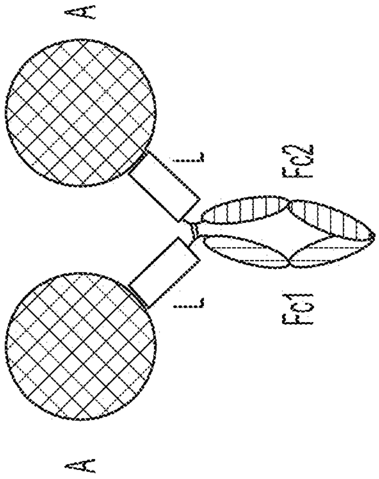

In some embodiments, any one of the combinations in Table 4 may be included in a molecule configuration as shown, e.g., in FIG. 5B. In such a configuration, a molecule includes two autoantigen domains, where the C-terminus of a first autoantigen domain (A) is linked to the N-terminus of a first Fc domain (Fc1) through an optional linker (L) (first polypeptide) and the C-terminus of a second autoantigen domain (A) is linked to the N-terminus of a second Fc domain (Fc2) through an optional linker (L) (second polypeptide). In some embodiments, the two autoantigen domains are the same (e.g., in a homodimeric molecule of the present disclosure). In some embodiments, the two autoantigen domains are different (e.g., in a heterodimeric molecule of the present disclosure).

Where FIGS. 2-5 label "A" or "A'" as an antigen (e.g., any antigen described herein), the present disclosure also encompasses any domain that targets an autoantibody for this component in the molecules described herein.

Additionally or alternatively, in some embodiments, a molecule may include a first antigen-binding domain and a second antigen-binding domain such that each antigen-binding domain is capable of binding to the same or different target antigen. In some embodiments, a first and/or second polypeptide of a molecule comprises an antigen binding domain. In some embodiments, a first polypeptide of a molecule comprises an antigen-binding domain. In some embodiments, a second polypeptide of a molecule comprises an antigen-binding domain. In some embodiments, both a first and second polypeptide of a molecule comprise an antigen-binding domain. In some embodiments, a first antigen-binding domain targets an anti-TSHR autoantibody and a second antigen-binding domain targets an internalizing receptor (e.g., ASPGR).

TABLE 4

Exemplary TSHR Antibody Depletion Combinations

| Molecule ID | Name | A or A' | HC | LC | L | Fc1 | Fc2 |
|---|---|---|---|---|---|---|---|
| Variant A1 | TSHR260 WT huIgG1 Fc MST-HN/RR | 1 | n/a | n/a | n/a | 103 | 104 |
| Variant A2 | TSHR260 2P huIgG1 Fc MST-HN/RR | 2 | n/a | n/a | n/a | 103 | 104 |
| Variant A3 | TSHR260 2P2R huIgG1 Fc MST-HN/RR | 3 | n/a | n/a | n/a | 103 | 104 |
| Variant A4 | TSHR260 2P1S huIgG1 Fc MST-HN/RR | 4 | n/a | n/a | n/a | 103 | 104 |
| Variant A5 | TSHR289 WT huIgG1 Fc MST-HN/RR | 5 | n/a | n/a | n/a | 103 | 104 |
| Variant A6 | TSHR 289 2P huIgG1 Fc MST-HN/RR | 6 | n/a | n/a | n/a | 103 | 104 |
| Variant A7 | TSHR289 2P2R huIgG1 Fc MST-HN/RR | 7 | n/a | n/a | n/a | 103 | 104 |
| Variant A8 | TSHR289 2P1S huIgG1 Fc MST-HN/RR | 8 | n/a | n/a | n/a | 103 | 104 |
| Variant B1 | TSHR260 WT huIgG1 Fc S267E/L328F | 1 | n/a | n/a | n/a | 105 | 106 |
| Variant B2 | TSHR260 2P huIgG1 Fc | 2 | n/a | n/a | n/a | 105 | 106 |
| Variant B3 | TSHR260 2P2R huIgG1 Fc S267E/L328F | 3 | n/a | n/a | n/a | 105 | 106 |
| Variant B4 | TSHR260 2P1S huIgG1 Fc S267E/L328F | 4 | n/a | n/a | n/a | 105 | 106 |
| Variant B5 | TSHR289 WT huIgG1 Fc S267E/L328F | 5 | n/a | n/a | n/a | 105 | 106 |
| Variant B6 | TSHR289 2P huIgG1 Fc S267E/L328F | 6 | n/a | n/a | n/a | 105 | 106 |
| Variant B7 | TSHR289 2P2R huIgG1 Fc S267E/L328F | 7 | n/a | n/a | n/a | 105 | 106 |
| Variant B8 | TSHR289 2P1S huIgG1 Fc S267E/L328F | 8 | n/a | n/a | n/a | 105 | 106 |
| Variant C1 | TSHR260 WT × 4F3 huIgG1 Fc | 1 | 209 | 210 | n/a | 105 | 106 |
| Variant C2 | TSHR260 2P × 4F3 huIgG1 Fc S267E/L328F | 2 | 209 | 210 | n/a | 105 | 106 |
| Variant C3 | TSHR260 2P2R × 4F3 huIgG1 Fc S267E/L328F | 3 | 209 | 210 | n/a | 105 | 106 |
| Variant C4 | TSHR260 2P1S × 4F3 huIgG1 Fc S267E/L328F | 4 | 209 | 210 | n/a | 105 | 106 |
| Variant C5 | TSHR289 WT × 4F3 huIgG1 Fc S267E/L328F | 5 | 209 | 210 | n/a | 105 | 106 |
| Variant C6 | TSHR289 2P × 4F3 huIgG1 Fc S267E/L328F | 6 | 209 | 210 | n/a | 105 | 106 |
| Variant C7 | TSHR289 2P2R × 4F3 huIgG1 Fc S267E/L328F | 7 | 209 | 210 | n/a | 105 | 106 |
| Variant C8 | TSHR289 2P1S × 4F3 huIgG1 Fc S267E/L328F | 8 | 209 | 210 | n/a | 105 | 106 |
| Variant D1 | TSHR260 WT huIgG1 Fc P238D | 1 | n/a | n/a | n/a | 107 | 108 |
| Variant D2 | TSHR260 2P huIgG1 Fc P238D | 2 | n/a | n/a | n/a | 107 | 108 |
| Variant D3 | TSHR260 2P2R huIgG1 Fc P238D | 3 | n/a | n/a | n/a | 107 | 108 |
| Variant D4 | TSHR260 2P1S huIgG1 Fc P238D | 4 | n/a | n/a | n/a | 107 | 108 |
| Variant D5 | TSHR289 WT huIgG1 Fc P238D | 5 | n/a | n/a | n/a | 107 | 108 |
| Variant D6 | TSHR289 2P huIgG1 Fc P238D | 6 | n/a | n/a | n/a | 107 | 108 |
| Variant D7 | TSHR289 2P2R huIgG1 Fc P238D | 7 | n/a | n/a | n/a | 107 | 108 |
| Variant D8 | TSHR289 2P1S huIgG1 Fc P238D | 8 | n/a | n/a | n/a | 107 | 108 |
| Variant E1 | TSHR260 WT huIgG1 Fc P238D/LS | 1 | n/a | n/a | n/a | 109 | 110 |
| Variant E2 | TSHR260 2P huIgG1 Fc P238D/LS | 2 | n/a | n/a | n/a | 109 | 110 |
| Variant E3 | TSHR260 2P2R huIgG1 Fc P238D/LS | 3 | n/a | n/a | n/a | 109 | 110 |

TABLE 4-continued

| Exemplary TSHR Antibody Depletion Combinations | | | | | | | |
|---|---|---|---|---|---|---|---|
| Molecule ID | Name | A or A' | HC | LC | L | Fc1 | Fc2 |
| Variant E4 | TSHR260 2P1S huIgG1 Fc P238D/LS | 4 | n/a | n/a | n/a | 109 | 110 |
| Variant E5 | TSHR289 WT huIgG1 Fc P238D/LS | 5 | n/a | n/a | n/a | 109 | 110 |
| Variant E6 | TSHR 289 2P huIgG1 Fc P238D/LS | 6 | n/a | n/a | n/a | 109 | 110 |
| Variant E7 | TSHR289 2P2R huIgG1 Fc P238D/LS | 7 | n/a | n/a | n/a | 109 | 110 |
| Variant E8 | TSHR289 2P1S huIgG1 Fc P238D/LS | 8 | n/a | n/a | n/a | 109 | 110 |
| Variant G1 | TSHR260 2P2R huIgG1 Fc E233V/L234D/L235F/G236R/G237D/S239L/S267D/H268P/S298G/T299A/A327L/L328A/A330H/E333I | 3 | n/a | n/a | n/a | 113 | 114 |
| Variant G2 | TSHR260 2P2R huIgG1 Fc E233V/L234D/L235F/G236R/G237D/S239L/S267D/R292Q/H268P/S298G/T299A/A327L/L328A/A330H/E333I | 3 | n/a | n/a | n/a | 115 | 116 |
| Variant G3 | TSHR260 2P2R huIgG1 Fc E233V/L234D/L235F/G236R/G237D/S239L/H268P/R292Q/S298G/T299A/A327L/L328A/A330H/E333I | 3 | n/a | n/a | n/a | 117 | 118 |
| Variant G4 | TSHR260 2P2R huIgG1 Fc E233D/G237D/P238D/H268D/P271G/A330R | 3 | n/a | n/a | n/a | 137 | 138 |
| Variant G5 | TSHR260 2P2R huIgG1 Fc L234Y/P238D/T250V/V264I/T307P/Q311R/A330K/P343R/M428L/N434A/Y436T/Q438R/S440E | 3 | n/a | n/a | n/a | 119 | 120 |
| Variant G6 | TSHR260 2P2R huIgG1 Fc L234D/G236N/S267E | 3 | n/a | n/a | n/a | 121 | 122 |
| Variant G7 | TSHR260 2P2R huIgG1 Fc L235R | 3 | n/a | n/a | n/a | 123 | 124 |
| Variant G8 | TSHR260 2P2R huIgG1 Fc G236N/S267E | 3 | n/a | n/a | n/a | 125 | 126 |
| Variant G9 | TSHR260 2P2R huIgG1 Fc P238D/D270E | 3 | n/a | n/a | n/a | 127 | 128 |
| Variant G10 | TSHR260 2P2R huIgG1 Fc P238D/P271G | 3 | n/a | n/a | n/a | 129 | 130 |
| Variant G11 | TSHR260 2P2R huIgG1 Fc P238D/D270E/P271G | 3 | n/a | n/a | n/a | 131 | 132 |
| Variant G12 | TSHR260 2P2R huIgG1 Fc G237D/P238D/P271G/A330R | 3 | n/a | n/a | n/a | 133 | 134 |
| Variant G13 | TSHR260 2P2R huIgG1 Fc G237D/P238D/D270E/P271G/A330R | 3 | n/a | n/a | n/a | 135 | 136 |
| Variant G14 | TSHR260 2P2R huIgG1 Fc S239D/H268D/L328W | 3 | n/a | n/a | n/a | 376 | 377 |
| Variant H1 | TSHR289 2P2R huIgG1 Fc E233V/L234D/L235F/G236R/G237D/S239L/S267D/H268P/S298G/T299A/A327L/L328A/A330H/E333I | 7 | n/a | n/a | n/a | 113 | 114 |
| Variant H2 | TSHR289 2P2R huIgG1 Fc E233V/L234D/L235F/G236R/G237D/S239L/S267D/R292Q/H268P/S298G/T299A/A327L/L328A/A330H/E333I | 7 | n/a | n/a | n/a | 115 | 116 |
| Variant H3 | TSHR289 2P2R huIgG1 Fc E233V/L234D/L235F/G236R/G237D/S239L/H268P/R292Q/S298G/T299A/A327L/L328A/A330H/E333I | 7 | n/a | n/a | n/a | 117 | 118 |
| Variant H4 | TSHR289 2P2R huIgG1 Fc E233D/G237D/P238D/H268D/P271G/A330R | 7 | n/a | n/a | n/a | 137 | 138 |
| Variant H5 | TSHR289 2P2R huIgG1 Fc L234Y/P238D/T250V/V264I/T307P/Q311R/A330K/P343R/M428L/N434A/Y436T/Q438R/S440E | 7 | n/a | n/a | n/a | 119 | 120 |
| Variant H6 | TSHR289 2P2R huIgG1 Fc L234D/G236N/S267E | 7 | n/a | n/a | n/a | 121 | 122 |
| Variant H7 | TSHR289 2P2R huIgG1 Fc L235R | 7 | n/a | n/a | n/a | 123 | 124 |
| Variant H8 | TSHR289 2P2R huIgG1 Fc G236N/S267E | 7 | n/a | n/a | n/a | 125 | 126 |
| Variant H9 | TSHR289 2P2R huIgG1 Fc P238D/D270E | 7 | n/a | n/a | n/a | 127 | 128 |
| Variant H10 | TSHR289 2P2R huIgG1 Fc P238D/P271G | 7 | n/a | n/a | n/a | 129 | 130 |
| Variant H11 | TSHR289 2P2R huIgG1 Fc P238D/D270E/P271G | 7 | n/a | n/a | n/a | 131 | 132 |
| Variant H12 | TSHR289 2P2R huIgG1 Fc G237D/P238D/P271G/A330R | 7 | n/a | n/a | n/a | 133 | 134 |
| Variant H13 | TSHR289 2P2R huIgG1 Fc G237D/P238D/D270E/P271G/A330R | 7 | n/a | n/a | n/a | 135 | 136 |
| Variant H14 | TSHR289 2P2R huIgG1 Fc S239D/H268D/L328W | 7 | n/a | n/a | n/a | 376 | 377 |

In some embodiments, a molecule comprises an amino acid sequence comprising any of the combinations of sequences shown in Table 4. In some embodiments, a molecule comprises an amino acid sequence comprising any of the combinations of sequences shown in Table 4 and includes a linker (L) between the autoantigen domain and Fc domain (e.g., as shown in any one of the configurations in FIGS. 2-5).

In some embodiments, a molecule comprises a first polypeptide, wherein the first polypeptide comprises: (i) an amino acid sequence that is at least 90% identical to SEQ ID NO: 1 and an amino acid sequence that is at least 90% identical to SEQ ID NO: 103; (ii) an amino acid sequence that is at least 90% identical to SEQ ID NO: 2 and an amino acid sequence that is at least 90% identical to SEQ ID NO: 103; (iii) an amino acid sequence that is at least 90% identical to SEQ ID NO: 3 and an amino acid sequence that is at least 90% identical to SEQ ID NO: 103; (iv) an amino acid sequence that is at least 90% identical to SEQ ID NO: 4 and an amino acid sequence that is at least 90% identical to SEQ ID NO: 103; (v) an amino acid sequence that is at least 90% identical to SEQ ID NO: 1 and an amino acid sequence that is at least 90% identical to SEQ ID NO: 105; (vi) an amino acid sequence that is at least 90% identical to SEQ ID NO: 2 and an amino acid sequence that is at least 90% identical to SEQ ID NO: 105; (vii) an amino acid sequence that is at least 90% identical to SEQ ID NO: 3 and an amino acid sequence that is at least 90% identical to SEQ ID NO: 105; (viii) S an amino acid sequence that is at least 90% identical to EQ ID NO: 4 and an amino acid sequence that is at least 90% identical to SEQ ID NO: 105; or (ix) an amino acid sequence that is at least 90% identical to SEQ ID NO: 4, an amino acid sequence that is at least 90% identical to SEQ ID NO: 209, an amino acid sequence that is at least 90% identical to SEQ ID NO: 210, and an amino acid sequence that is at least 90% identical to SEQ ID NO: 105. In some embodiments a molecule comprises a first polypeptide, wherein the first polypeptide comprises: (i) the amino acid sequence of SEQ ID NO: 1 and the amino acid sequence of SEQ ID NO: 103; (ii) the amino acid sequence of SEQ ID NO: 2 and the amino acid sequence of SEQ ID NO: 103; (iii) the amino acid sequence of SEQ ID NO: 3 and the amino acid sequence of SEQ ID NO: 103; (iv) the amino acid sequence of SEQ ID NO: 4 and the amino acid sequence of SEQ ID NO: 103; (v) the amino acid sequence of SEQ ID NO: 1 and the amino acid sequence of SEQ ID NO: 105; (vi) the amino acid sequence of SEQ ID NO: 2 and the amino acid sequence of SEQ ID NO: 105; (vii) the amino acid sequence of SEQ ID NO: 3 and the amino acid sequence of SEQ ID NO: 105; (viii) the amino acid sequence of SEQ ID NO: 4 and the amino acid sequence of SEQ ID NO: 105; or (ix) the amino acid sequence of SEQ ID NO: 4, the amino acid sequence of SEQ ID NO: 209, the amino acid sequence of SEQ ID NO: 210, and the amino acid sequence of SEQ ID NO: 105, (x) the amino acid sequence of SEQ ID NO: 5 and the amino acid sequence of SEQ ID NO: 103; (xi) the amino acid sequence of SEQ ID NO: 6 and the amino acid sequence of SEQ ID NO: 103.

In some embodiments, a molecule comprises a second polypeptide, wherein the second polypeptide comprises: (i) an amino acid sequence that is at least 90% identical to SEQ ID NO: 104, (ii) an amino acid sequence that is at least 90% identical to SEQ ID NO: 106, (iii) an amino acid sequence that is at least 90% identical to SEQ ID NO: 108, (iv) an amino acid sequence that is at least 90% identical to SEQ ID NO: 110 or (v) an amino acid sequence that is at least 90% identical to SEQ ID NO: 209, an amino acid sequence that is at least 90% identical to SEQ ID NO: 210, and an amino acid sequence that is at least 90% identical to SEQ ID NO: 106. In some embodiments, a second polypeptide comprises: (i) the amino acid sequence of SEQ ID NO: 104, (ii) the amino acid sequence SEQ ID NO: 106, (iii) the amino acid sequence of SEQ ID NO: 108, (iv) the amino acid sequence of SEQ ID NO: 110, or (v) the amino acid sequence SEQ ID NO: 209, the amino acid sequence SEQ ID NO: 210, and the amino acid sequence SEQ ID NO: 106.

In some embodiments, a molecule comprises a first and second polypeptide wherein, (i) the first polypeptide comprises an amino acid sequence comprising SEQ ID NO: 1 and SEQ ID NO: 103, and the second polypeptide comprises the amino acid sequence of SEQ ID NO: 104; or (ii) the first polypeptide comprises an amino acid sequence comprising SEQ ID NO: 1 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 2 and SEQ ID NO: 103, and the second polypeptide comprises the amino acid sequence of SEQ ID NO: 104; or (ii) the first polypeptide comprises an amino acid sequence comprising SEQ ID NO: 2 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 3 and SEQ ID NO: 103, and the second polypeptide comprises the amino acid sequence of SEQ ID NO: 104; or (ii) the first polypeptide comprises an amino acid sequence comprising SEQ ID NO: 3 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 4 and SEQ ID NO: 103, and the second polypeptide comprises the amino acid sequence of SEQ ID NO: 104; or (ii) the first polypeptide comprises an amino acid sequence comprising SEQ ID NO: 4 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 5 and SEQ ID NO: 103, and the second polypeptide comprises the amino acid sequence of SEQ ID NO: 104; or (ii) the first polypeptide comprises an amino acid sequence comprising SEQ ID NO: 5 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 6 and SEQ ID NO: 103, and the second polypeptide comprises the amino acid sequence of SEQ ID NO: 104; or (ii) the first polypeptide comprises an amino acid sequence comprising SEQ ID NO: 6 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 7 and SEQ ID NO: 103, and the second polypeptide comprises the amino acid sequence of SEQ ID NO: 104; or (ii) the first polypeptide comprises an amino acid sequence comprising SEQ ID NO: 7 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 8 and SEQ ID NO: 103, and the second polypeptide comprises the amino acid sequence of SEQ ID NO: 104; or (ii) the first polypeptide comprises an amino acid sequence comprising SEQ ID NO: 8 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 307 and SEQ ID NO: 103, and the second polypeptide comprises the amino acid sequence of SEQ ID NO: 104; or (ii) the first polypeptide comprises an amino acid sequence comprising SEQ ID NO: 307 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 308 and SEQ ID NO: 103, and the second polypeptide comprises the amino acid sequence of SEQ ID NO: 104; or (ii) the first polypeptide comprises an amino acid sequence comprising SEQ ID NO: 308 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 309 and SEQ ID NO: 103, and the second polypeptide comprises the amino acid sequence of SEQ ID NO: 104; or (ii) the first polypeptide comprises an amino acid sequence comprising SEQ ID NO: 309 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 310 and SEQ ID NO: 103, and the second polypeptide comprises the amino acid sequence of SEQ ID NO: 104; or (ii) the first polypeptide comprises an amino acid sequence comprising SEQ ID NO: 310 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 311 and SEQ ID NO: 103, and the second polypeptide comprises the amino acid sequence of SEQ ID NO: 104; or (ii) the first polypeptide comprises an amino acid sequence comprising SEQ ID NO: 311 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 312 and SEQ ID NO: 103, and the second polypeptide comprises the amino acid sequence of SEQ ID NO: 104; or (ii) the first polypeptide comprises an amino acid sequence comprising SEQ ID NO: 312 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 313 and SEQ ID NO: 103, and the second polypeptide comprises the amino acid sequence of SEQ ID NO: 104; or (ii) the first polypeptide comprises an amino acid sequence comprising SEQ ID NO: 313 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 314 and SEQ ID NO: 103, and the second polypeptide comprises the amino acid sequence of SEQ ID NO: 104; or (ii) the first polypeptide comprises an amino acid sequence comprising SEQ ID NO: 314 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 315 and SEQ ID NO: 103, and the second polypeptide comprises the amino acid sequence of SEQ ID NO: 104; or (ii) the first polypeptide comprises an amino acid sequence comprising SEQ ID NO: 315 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 316 and SEQ ID NO: 103, and the second polypeptide comprises the amino acid sequence of SEQ ID NO: 104; or (ii) the first polypeptide comprises an amino acid sequence comprising SEQ ID NO: 316 and SEQ ID NO: 104, and the second polypeptide comprises the amino acid sequence of SEQ ID NO: 103. In some embodiments, a molecule comprises a first and second polypeptide wherein, (i) the first polypeptide comprises an amino acid sequence comprising SEQ ID NO: 317 and SEQ ID NO: 103, and the second polypeptide comprises the amino acid sequence of SEQ ID NO: 104; or (ii) the first polypeptide comprises an amino acid sequence comprising SEQ ID NO: 317 and SEQ ID NO: 104, and the second polypeptide comprises the amino acid sequence of SEQ ID NO: 103.

In some embodiments, a molecule comprises a first and second polypeptide wherein, (i) the first polypeptide comprises an amino acid sequence comprising SEQ ID NO: 1 and SEQ ID NO: 105, and the second polypeptide comprises the amino acid sequence of SEQ ID NO: 106; or (ii) the first polypeptide comprises an amino acid sequence comprising SEQ ID NO: 1 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 2 and SEQ ID NO: 105, and the second polypeptide comprises the amino acid sequence of SEQ ID NO: 106; or (ii) the first polypeptide comprises an amino acid sequence comprising SEQ ID NO: 2 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 3 and SEQ ID NO: 105, and the second polypeptide comprises the amino acid sequence of SEQ ID NO: 106; or (ii) the first polypeptide comprises an amino acid sequence comprising SEQ ID NO: 3 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 4 and SEQ ID NO: 105, and the second polypeptide comprises the amino acid sequence of SEQ ID NO: 106; or (ii) the first polypeptide comprises an amino acid sequence comprising SEQ ID NO: 4 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 5 and SEQ ID NO: 105, and the second polypeptide comprises the amino acid sequence of SEQ ID NO: 106; or (ii) the first polypeptide comprises an amino acid sequence comprising SEQ ID NO: 5 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 6 and SEQ ID NO: 105, and the second polypeptide comprises the amino acid sequence of SEQ ID NO: 106; or (ii) the first polypeptide comprises an amino acid sequence comprising SEQ ID NO: 6 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 7 and SEQ ID NO: 105, and the second polypeptide comprises the amino acid sequence of SEQ ID NO: 106; or (ii) the first polypeptide comprises an amino acid sequence comprising SEQ ID NO: 7 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 8 and SEQ ID NO: 105, and the second polypeptide comprises the amino acid sequence of SEQ ID NO: 106; or (ii) the first polypeptide comprises an amino acid sequence comprising SEQ ID NO: 8 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 307 and SEQ ID NO: 105, and the second polypeptide comprises the amino acid sequence of SEQ ID NO: 106; or (ii) the first polypeptide comprises an amino acid sequence comprising SEQ ID NO: 307 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 308 and SEQ ID NO: 105, and the second polypeptide comprises the amino acid sequence of SEQ ID NO: 106; or (ii) the first polypeptide comprises an amino acid sequence comprising SEQ ID NO: 308 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 309 and SEQ ID NO: 105, and the second polypeptide comprises the amino acid sequence of SEQ ID NO: 106; or (ii) the first polypeptide comprises an amino acid sequence comprising SEQ ID NO: 309 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 310 and SEQ ID NO: 105, and the second polypeptide comprises the amino acid sequence of SEQ ID NO: 106; or (ii) the first polypeptide comprises an amino acid sequence comprising SEQ ID NO: 310 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 311 and SEQ ID NO: 105, and the second polypeptide comprises the amino acid sequence of SEQ ID NO: 106; or (ii) the first polypeptide comprises an amino acid sequence comprising SEQ ID NO: 311 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 312 and SEQ ID NO: 105, and the second polypeptide comprises the amino acid sequence of SEQ ID NO: 106; or (ii) the first polypeptide comprises an amino acid sequence comprising SEQ ID NO: 312 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 313 and SEQ ID NO: 105, and the second polypeptide comprises the amino acid sequence of SEQ ID NO: 106; or (ii) the first polypeptide comprises an amino acid sequence comprising SEQ ID NO: 313 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 314 and SEQ ID NO: 105, and the second polypeptide comprises the amino acid sequence of SEQ ID NO: 106; or (ii) the first polypeptide comprises an amino acid sequence comprising SEQ ID NO: 314 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 315 and SEQ ID NO: 105, and the second polypeptide comprises the amino acid sequence of SEQ ID NO: 106; or (ii) the first polypeptide comprises an amino acid sequence comprising SEQ ID NO: 315 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 316 and SEQ ID NO: 105, and the second polypeptide comprises the amino acid sequence of SEQ ID NO: 106; or (ii) the first polypeptide comprises an amino acid sequence comprising SEQ ID NO: 316 and SEQ ID NO: 106, and the second polypeptide comprises the amino acid sequence of SEQ ID NO: 105. In some embodiments, a molecule comprises a first and second polypeptide wherein, (i) the first polypeptide comprises an amino acid sequence comprising SEQ ID NO: 317 and SEQ ID NO: 105, and the second polypeptide comprises the amino acid sequence of SEQ ID NO: 106; or (ii) the first polypeptide comprises an amino acid sequence comprising SEQ ID NO: 317 and SEQ ID NO: 106, and the second polypeptide comprises the amino acid sequence of SEQ ID NO: 105.

In some embodiments, a molecule comprises a first and second polypeptide wherein, (i) the first polypeptide comprises an amino acid sequence comprising SEQ ID NO: 1 and SEQ ID NO: 107, and the second polypeptide comprises the amino acid sequence of SEQ ID NO: 108; or (ii) the first polypeptide comprises an amino acid sequence comprising SEQ ID NO: 1 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 2 and SEQ ID NO: 107, and the second polypeptide comprises the amino acid sequence of SEQ ID NO: 108; or (ii) the first polypeptide comprises an amino acid sequence comprising SEQ ID NO: 2 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 3 and SEQ ID NO: 107, and the second polypeptide comprises the amino acid sequence of SEQ ID NO: 108; or (ii) the first polypeptide comprises an amino acid sequence comprising SEQ ID NO: 3 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 4 and SEQ ID NO: 107, and the second polypeptide comprises the amino acid sequence of SEQ ID NO: 108; or (ii) the first polypeptide comprises an amino acid sequence comprising SEQ ID NO: 4 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 5 and SEQ ID NO: 107, and the second polypeptide comprises the amino acid sequence of SEQ ID NO: 108; or (ii) the first polypeptide comprises an amino acid sequence comprising SEQ ID NO: 5 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 6 and SEQ ID NO: 107, and the second polypeptide comprises the amino acid sequence of SEQ ID NO: 108; or (ii) the first polypeptide comprises an amino acid sequence comprising SEQ ID NO: 6 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 7 and SEQ ID NO: 107, and the second polypeptide comprises the amino acid sequence of SEQ ID NO: 108; or (ii) the first polypeptide comprises an amino acid sequence comprising SEQ ID NO: 7 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 8 and SEQ ID NO: 107, and the second polypeptide comprises the amino acid sequence of SEQ ID NO: 108; or (ii) the first polypeptide comprises an amino acid sequence comprising SEQ ID NO: 8 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 307 and SEQ ID NO: 107, and the second polypeptide comprises the amino acid sequence of SEQ ID NO: 108; or (ii) the first polypeptide comprises an amino acid sequence comprising SEQ ID NO: 307 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 308 and SEQ ID NO: 107, and the second polypeptide comprises the amino acid sequence of SEQ ID NO: 108; or (ii) the first polypeptide comprises an amino acid sequence comprising SEQ ID NO: 308 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 309 and SEQ ID NO: 107, and the second polypeptide comprises the amino acid sequence of SEQ ID NO: 108; or (ii) the first polypeptide comprises an amino acid sequence comprising SEQ ID NO: 309 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 310 and SEQ ID NO: 107, and the second polypeptide comprises the amino acid sequence of SEQ ID NO: 108; or (ii) the first polypeptide comprises an amino acid sequence comprising SEQ ID NO: 310 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 311 and SEQ ID NO: 107, and the second polypeptide comprises the amino acid sequence of SEQ ID NO: 108; or (ii) the first polypeptide comprises an amino acid sequence comprising SEQ ID NO: 311 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 312 and SEQ ID NO: 107, and the second polypeptide comprises the amino acid sequence of SEQ ID NO: 108; or (ii) the first polypeptide comprises an amino acid sequence comprising SEQ ID NO: 312 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 313 and SEQ ID NO: 107, and the second polypeptide comprises the amino acid sequence of SEQ ID NO: 108; or (ii) the first polypeptide comprises an amino acid sequence comprising SEQ ID NO: 313 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 314 and SEQ ID NO: 107, and the second polypeptide comprises the amino acid sequence of SEQ ID NO: 108; or (ii) the first polypeptide comprises an amino acid sequence comprising SEQ ID NO: 314 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 315 and SEQ ID NO: 107, and the second polypeptide comprises the amino acid sequence of SEQ ID NO: 108; or (ii) the first polypeptide comprises an amino acid sequence comprising SEQ ID NO: 315 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 316 and SEQ ID NO: 107, and the second polypeptide comprises the amino acid sequence of SEQ ID NO: 108; or (ii) the first polypeptide comprises an amino acid sequence comprising SEQ ID NO: 316 and SEQ ID NO: 108, and the second polypeptide comprises the amino acid sequence of SEQ ID NO: 107. In some embodiments, a molecule comprises a first and second polypeptide wherein, (i) the first polypeptide comprises an amino acid sequence comprising SEQ ID NO: 317 and SEQ ID NO: 107, and the second polypeptide comprises the amino acid sequence of SEQ ID NO: 108; or (ii) the first polypeptide comprises an amino acid sequence comprising SEQ ID NO: 317 and SEQ ID NO: 108, and the second polypeptide comprises the amino acid sequence of SEQ ID NO: 107.

In some embodiments, a molecule comprises a first and second polypeptide wherein, (i) the first polypeptide comprises an amino acid sequence comprising SEQ ID NO: 1 and SEQ ID NO: 109, and the second polypeptide comprises the amino acid sequence of SEQ ID NO: 110; or (ii) the first polypeptide comprises an amino acid sequence comprising SEQ ID NO: 1 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 2 and SEQ ID NO: 109, and the second polypeptide comprises the amino acid sequence of SEQ ID NO: 110; or (ii) the first polypeptide comprises an amino acid sequence comprising SEQ ID NO: 2 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 3 and SEQ ID NO: 109, and the second polypeptide comprises the amino acid sequence of SEQ ID NO: 110; or (ii) the first polypeptide comprises an amino acid sequence comprising SEQ ID NO: 3 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 4 and SEQ ID NO: 109, and the second polypeptide comprises the amino acid sequence of SEQ ID NO: 110; or (ii) the first polypeptide comprises an amino acid sequence comprising SEQ ID NO: 4 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 5 and SEQ ID NO: 109, and the second polypeptide comprises the amino acid sequence of SEQ ID NO: 110; or (ii) the first polypeptide comprises an amino acid sequence comprising SEQ ID NO: 5 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 6 and SEQ ID NO: 109, and the second polypeptide comprises the amino acid sequence of SEQ ID NO: 110; or (ii) the first polypeptide comprises an amino acid sequence comprising SEQ ID NO: 6 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 7 and SEQ ID NO: 109, and the second polypeptide comprises the amino acid sequence of SEQ ID NO: 110; or (ii) the first polypeptide comprises an amino acid sequence comprising SEQ ID NO: 7 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 8 and SEQ ID NO: 109, and the second polypeptide comprises the amino acid sequence of SEQ ID NO: 110; or (ii) the first polypeptide comprises an amino acid sequence comprising SEQ ID NO: 8 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 307 and SEQ ID NO: 109, and the second polypeptide comprises the amino acid sequence of SEQ ID NO: 110; or (ii) the first polypeptide comprises an amino acid sequence comprising SEQ ID NO: 307 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 308 and SEQ ID NO: 109, and the second polypeptide comprises the amino acid sequence of SEQ ID NO: 110; or (ii) the first polypeptide comprises an amino acid sequence comprising SEQ ID NO: 308 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 309 and SEQ ID NO: 109, and the second polypeptide comprises the amino acid sequence of SEQ ID NO: 110; or (ii) the first polypeptide comprises an amino acid sequence comprising SEQ ID NO: 309 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 310 and SEQ ID NO: 109, and the second polypeptide comprises the amino acid sequence of SEQ ID NO: 110; or (ii) the first polypeptide comprises an amino acid sequence comprising SEQ ID NO: 310 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 311 and SEQ ID NO: 109, and the second polypeptide comprises the amino acid sequence of SEQ ID NO: 110; or (ii) the first polypeptide comprises an amino acid sequence comprising SEQ ID NO: 311 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 312 and SEQ ID NO: 109, and the second polypeptide comprises the amino acid sequence of SEQ ID NO: 110; or (ii) the first polypeptide comprises an amino acid sequence comprising SEQ ID NO: 312 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 313 and SEQ ID NO: 109, and the second polypeptide comprises the amino acid sequence of SEQ ID NO: 110; or (ii) the first polypeptide comprises an amino acid sequence comprising SEQ ID NO: 313 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 314 and SEQ ID NO: 109, and the second polypeptide comprises the amino acid sequence of SEQ ID NO: 110; or (ii) the first polypeptide comprises an amino acid sequence comprising SEQ ID NO: 314 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 315 and SEQ ID NO: 109, and the second polypeptide comprises the amino acid sequence of SEQ ID NO: 110; or (ii) the first polypeptide comprises an amino acid sequence comprising SEQ ID NO: 315 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 316 and SEQ ID NO: 109, and the second polypeptide comprises the amino acid sequence of SEQ ID NO: 110; or (ii) the first polypeptide comprises an amino acid sequence comprising SEQ ID NO: 316 and SEQ ID NO: 110, and the second polypeptide comprises the amino acid sequence of SEQ ID NO: 109. In some embodiments, a molecule comprises a first and second polypeptide wherein, (i) the first polypeptide comprises an amino acid sequence comprising SEQ ID NO: 317 and SEQ ID NO: 109, and the second polypeptide comprises the amino acid sequence of SEQ ID NO: 110; or (ii) the first polypeptide comprises an amino acid sequence comprising SEQ ID NO: 317 and SEQ ID NO: 110, and the second polypeptide comprises the amino acid sequence of SEQ ID NO: 109.

In some embodiments, a molecule comprises a first and second polypeptide wherein, (i) the first polypeptide comprises an amino acid sequence comprising SEQ ID NO: 1 and SEQ ID NO: 113, and the second polypeptide comprises the amino acid sequence of SEQ ID NO: 114; or (ii) the first polypeptide comprises an amino acid sequence comprising SEQ ID NO: 1 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO:

2 and SEQ ID NO: 113, and the second polypeptide comprises the amino acid sequence of SEQ ID NO: 114; or (ii) the first polypeptide comprises an amino acid sequence comprising SEQ ID NO: 2 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 3 and SEQ ID NO: 113, and the second polypeptide comprises the amino acid sequence of SEQ ID NO: 114; or (ii) the first polypeptide comprises an amino acid sequence comprising SEQ ID NO: 3 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 4 and SEQ ID NO: 113, and the second polypeptide comprises the amino acid sequence of SEQ ID NO: 114; or (ii) the first polypeptide comprises an amino acid sequence comprising SEQ ID NO: 4 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 5 and SEQ ID NO: 113, and the second polypeptide comprises the amino acid sequence of SEQ ID NO: 114; or (ii) the first polypeptide comprises an amino acid sequence comprising SEQ ID NO: 5 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 6 and SEQ ID NO: 113, and the second polypeptide comprises the amino acid sequence of SEQ ID NO: 114; or (ii) the first polypeptide comprises an amino acid sequence comprising SEQ ID NO: 6 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 7 and SEQ ID NO: 113, and the second polypeptide comprises the amino acid sequence of SEQ ID NO: 114; or (ii) the first polypeptide comprises an amino acid sequence comprising SEQ ID NO: 7 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 8 and SEQ ID NO: 113, and the second polypeptide comprises the amino acid sequence of SEQ ID NO: 114; or (ii) the first polypeptide comprises an amino acid sequence comprising SEQ ID NO: 8 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 307 and SEQ ID NO: 113, and the second polypeptide comprises the amino acid sequence of SEQ ID NO: 114; or (ii) the first polypeptide comprises an amino acid sequence comprising SEQ ID NO: 307 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 308 and SEQ ID NO: 113, and the second polypeptide comprises the amino acid sequence of SEQ ID NO: 114; or (ii) the first polypeptide comprises an amino acid sequence comprising SEQ ID NO: 308 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 309 and SEQ ID NO: 113, and the second polypeptide comprises the amino acid sequence of SEQ ID NO: 114; or (ii) the first polypeptide comprises an amino acid sequence comprising SEQ ID NO: 309 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 310 and SEQ ID NO: 113, and the second polypeptide comprises the amino acid sequence of SEQ ID NO: 114; or (ii) the first polypeptide comprises an amino acid sequence comprising SEQ ID NO: 310 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 311 and SEQ ID NO: 113, and the second polypeptide comprises the amino acid sequence of SEQ ID NO: 114; or (ii) the first polypeptide comprises an amino acid sequence comprising SEQ ID NO: 311 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 312 and SEQ ID NO: 113, and the second polypeptide comprises the amino acid sequence of SEQ ID NO: 114; or (ii) the first polypeptide comprises an amino acid sequence comprising SEQ ID NO: 312 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 313 and SEQ ID NO: 113, and the second polypeptide comprises the amino acid sequence of SEQ ID NO: 114; or (ii) the first polypeptide comprises an amino acid sequence comprising SEQ ID NO: 313 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 314 and SEQ ID NO: 113, and the second polypeptide comprises the amino acid sequence of SEQ ID NO: 114; or (ii) the first polypeptide comprises an amino acid sequence comprising SEQ ID NO: 314 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 315 and SEQ ID NO: 113, and the second polypeptide comprises the amino acid sequence of SEQ ID NO: 114; or (ii) the first polypeptide comprises an amino acid sequence comprising SEQ ID NO: 315 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 316 and SEQ ID NO: 113, and the second polypeptide comprises the amino acid sequence of SEQ ID NO: 114; or (ii) the first polypeptide comprises an amino acid sequence comprising SEQ ID NO: 316 and SEQ ID NO: 114, and the second polypeptide comprises the amino acid sequence of SEQ ID NO: 113. In some embodiments, a molecule comprises a first and second polypeptide wherein, (i) the first polypeptide comprises an amino acid sequence comprising SEQ ID NO: 317 and SEQ ID NO: 113, and the second polypeptide comprises the amino acid sequence of SEQ ID NO: 114; or (ii) the first polypeptide comprises an amino acid sequence comprising SEQ ID NO: 317 and SEQ ID NO: 114, and the second polypeptide comprises the amino acid sequence of SEQ ID NO: 113.

In some embodiments, a molecule comprises a first and second polypeptide wherein, (i) the first polypeptide comprises an amino acid sequence comprising SEQ ID NO: 1 and SEQ ID NO: 115, and the second polypeptide comprises the amino acid sequence of SEQ ID NO: 116; or (ii) the first polypeptide comprises an amino acid sequence comprising SEQ ID NO: 1 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 2 and SEQ ID NO: 115, and the second polypeptide comprises the amino acid sequence of SEQ ID NO: 116; or (ii) the first polypeptide comprises an amino acid sequence comprising SEQ ID NO: 2 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 3 and SEQ ID NO: 115, and the second polypeptide comprises the amino acid sequence of SEQ ID NO: 116; or (ii) the first polypeptide comprises an amino acid sequence comprising SEQ ID NO: 3 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 4 and SEQ ID NO: 115, and the second polypeptide comprises the amino acid sequence of SEQ ID NO: 116; or (ii) the first polypeptide comprises an amino acid sequence comprising SEQ ID NO: 4 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 5 and SEQ ID NO: 115, and the second polypeptide comprises the amino acid sequence of SEQ ID NO: 116; or (ii) the first polypeptide comprises an amino acid sequence comprising SEQ ID NO: 5 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 6 and SEQ ID NO: 115, and the second polypeptide comprises the amino acid sequence of SEQ ID NO: 116; or (ii) the first polypeptide comprises an amino acid sequence comprising SEQ ID NO: 6 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 7 and SEQ ID NO: 115, and the second polypeptide comprises the amino acid sequence of SEQ ID NO: 116; or (ii) the first polypeptide comprises an amino acid sequence comprising SEQ ID NO: 7 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 8 and SEQ ID NO: 115, and the second polypeptide comprises the amino acid sequence of SEQ ID NO: 116; or (ii) the first polypeptide comprises an amino acid sequence comprising SEQ ID NO: 8 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 307 and SEQ ID NO: 115, and the second polypeptide comprises the amino acid sequence of SEQ ID NO: 116; or (ii) the first polypeptide comprises an amino acid sequence comprising SEQ ID NO: 307 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 308 and SEQ ID NO: 115, and the second polypeptide comprises the amino acid sequence of SEQ ID NO: 116; or (ii) the first polypeptide comprises an amino acid sequence comprising SEQ ID NO: 308 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 309 and SEQ ID NO: 115, and the second polypeptide comprises the amino acid sequence of SEQ ID NO: 116; or (ii) the first polypeptide comprises an amino acid sequence comprising SEQ ID NO: 309 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 310 and SEQ ID NO: 115, and the second polypeptide comprises the amino acid sequence of SEQ ID NO: 116; or (ii) the first polypeptide comprises an amino acid sequence comprising SEQ ID NO: 310 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 311 and SEQ ID NO: 115, and the second polypeptide comprises the amino acid sequence of SEQ ID NO: 116; or (ii) the first polypeptide comprises an amino acid sequence comprising SEQ ID NO: 311 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 312 and SEQ ID NO: 115, and the second polypeptide comprises the amino acid sequence of SEQ ID NO: 116; or (ii) the first polypeptide comprises an amino acid sequence comprising SEQ ID NO: 312 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 313 and SEQ ID NO: 115, and the second polypeptide comprises the amino acid sequence of SEQ ID NO: 116; or (ii) the first polypeptide comprises an amino acid sequence comprising SEQ ID NO: 313 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 314 and SEQ ID NO: 115, and the second polypeptide comprises the amino acid sequence of SEQ ID NO: 116; or (ii) the first polypeptide comprises an amino acid sequence comprising SEQ ID NO: 314 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 315 and SEQ ID NO: 115, and the second polypeptide comprises the amino acid sequence of SEQ ID NO: 116; or (ii) the first polypeptide comprises an amino acid sequence comprising SEQ ID NO: 315 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 316 and SEQ ID NO: 115, and the second polypeptide comprises the amino acid sequence of SEQ ID NO: 116; or (ii) the first polypeptide comprises an amino acid sequence comprising SEQ ID NO: 316 and SEQ ID NO: 116, and the second polypeptide comprises the amino acid sequence of SEQ ID NO: 115. In some embodiments, a molecule comprises a first and second polypeptide wherein, (i) the first polypeptide comprises an amino acid sequence comprising SEQ ID NO: 317 and SEQ ID NO: 115, and the second polypeptide comprises the amino acid sequence of SEQ ID NO: 116; or (ii) the first polypeptide comprises an amino acid sequence comprising SEQ ID NO: 317 and SEQ ID NO: 116, and the second polypeptide comprises the amino acid sequence of SEQ ID NO: 115.

In some embodiments, a molecule comprises a first and second polypeptide wherein, (i) the first polypeptide comprises an amino acid sequence comprising SEQ ID NO: 1 and SEQ ID NO: 117, and the second polypeptide comprises the amino acid sequence of SEQ ID NO: 118; or (ii) the first polypeptide comprises an amino acid sequence comprising SEQ ID NO: 1 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 2 and SEQ ID NO: 117, and the second polypeptide comprises the amino acid sequence of SEQ ID NO: 118; or (ii) the first polypeptide comprises an amino acid sequence comprising SEQ ID NO: 2 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 3 and SEQ ID NO: 117, and the second polypeptide comprises the amino acid sequence of SEQ ID NO: 118; or (ii) the first polypeptide comprises an amino acid sequence comprising SEQ ID NO: 3 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 4 and SEQ ID NO: 117, and the second polypeptide comprises the amino acid sequence of SEQ ID NO: 118; or (ii) the first polypeptide comprises an amino acid sequence comprising SEQ ID NO: 4 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 5 and SEQ ID NO: 117, and the second polypeptide comprises the amino acid sequence of SEQ ID NO: 118; or (ii) the first polypeptide comprises an amino acid sequence comprising SEQ ID NO: 5 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 6 and SEQ ID NO: 117, and the second polypeptide comprises the amino acid sequence of SEQ ID NO: 118; or (ii) the first polypeptide comprises an amino acid sequence comprising SEQ ID NO: 6 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 7 and SEQ ID NO: 117, and the second polypeptide comprises the amino acid sequence of SEQ ID NO: 118; or (ii) the first polypeptide comprises an amino acid sequence comprising SEQ ID NO: 7 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 8 and SEQ ID NO: 117, and the second polypeptide comprises the amino acid sequence of SEQ ID NO: 118; or (ii) the first polypeptide comprises an amino acid sequence comprising SEQ ID NO: 8 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 307 and SEQ ID NO: 117, and the second polypeptide comprises the amino acid sequence of SEQ ID NO: 118; or (ii) the first polypeptide comprises an amino acid sequence comprising SEQ ID NO: 307 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 308 and SEQ ID NO: 117, and the second polypeptide comprises the amino acid sequence of SEQ ID NO: 118; or (ii) the first polypeptide comprises an amino acid sequence comprising SEQ ID NO: 308 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 309 and SEQ ID NO: 117, and the second polypeptide comprises the amino acid sequence of SEQ ID NO: 118; or (ii) the first polypeptide comprises an amino acid sequence comprising SEQ ID NO: 309 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 310 and SEQ ID NO: 117, and the second polypeptide comprises the amino acid sequence of SEQ ID NO: 118; or (ii) the first polypeptide comprises an amino acid sequence comprising SEQ ID NO: 310 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 311 and SEQ ID NO: 117, and the second polypeptide comprises the amino acid sequence of SEQ ID NO: 118; or (ii) the first polypeptide comprises an amino acid sequence comprising SEQ ID NO: 311 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 312 and SEQ ID NO: 117, and the second polypeptide comprises the amino acid sequence of SEQ ID NO: 118; or (ii) the first polypeptide comprises an amino acid sequence comprising SEQ ID NO: 312 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 313 and SEQ ID NO: 117, and the second polypeptide comprises the amino acid sequence of SEQ ID NO: 118; or (ii) the first polypeptide comprises an amino acid sequence comprising SEQ ID NO: 313 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 314 and SEQ ID NO: 117, and the second polypeptide comprises the amino acid sequence of SEQ ID NO: 118; or (ii) the first polypeptide comprises an amino acid sequence comprising SEQ ID NO: 314 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 315 and SEQ ID NO: 117, and the second polypeptide comprises the amino acid sequence of SEQ ID NO: 118; or (ii) the first polypeptide comprises an amino acid sequence comprising SEQ ID NO: 315 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 316 and SEQ ID NO: 117, and the second polypeptide comprises the amino acid sequence of SEQ ID NO: 118; or (ii) the first polypeptide comprises an amino acid sequence comprising SEQ ID NO: 316 and SEQ ID NO: 118, and the second polypeptide comprises the amino acid sequence of SEQ ID NO: 117. In some embodiments, a molecule comprises a first and second polypeptide wherein, (i) the first polypeptide comprises an amino acid sequence comprising SEQ ID NO: 317 and SEQ ID NO: 117, and the second polypeptide comprises the amino acid sequence of SEQ ID NO: 118; or (ii) the first polypeptide comprises an amino acid sequence comprising SEQ ID NO: 317 and SEQ ID NO: 118, and the second polypeptide comprises the amino acid sequence of SEQ ID NO: 117.

In some embodiments, a molecule comprises a first and second polypeptide wherein, (i) the first polypeptide comprises an amino acid sequence comprising SEQ ID NO: 1 and SEQ ID NO: 119, and the second polypeptide comprises the amino acid sequence of SEQ ID NO: 120; or (ii) the first polypeptide comprises an amino acid sequence comprising SEQ ID NO: 1 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 2 and SEQ ID NO: 119, and the second polypeptide comprises the amino acid sequence of SEQ ID NO: 120; or (ii) the first polypeptide comprises an amino acid sequence comprising SEQ ID NO: 2 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 3 and SEQ ID NO: 119, and the second polypeptide comprises the amino acid sequence of SEQ ID NO: 120; or (ii) the first polypeptide comprises an amino acid sequence comprising SEQ ID NO: 3 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 4 and SEQ ID NO: 119, and the second polypeptide comprises the amino acid sequence of SEQ ID NO: 120; or (ii) the first polypeptide comprises an amino acid sequence comprising SEQ ID NO: 4 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 5 and SEQ ID NO: 119, and the second polypeptide comprises the amino acid sequence of SEQ ID NO: 120; or (ii) the first polypeptide comprises an amino acid sequence comprising SEQ ID NO: 5 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 6 and SEQ ID NO: 119, and the second polypeptide comprises the amino acid sequence of SEQ ID NO: 120; or (ii) the first polypeptide comprises an amino acid sequence comprising SEQ ID NO: 6 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 7 and SEQ ID NO: 119, and the second polypeptide comprises the amino acid sequence of SEQ ID NO: 120; or (ii) the first polypeptide comprises an amino acid sequence comprising SEQ ID NO: 7 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 8 and SEQ ID NO: 119, and the second polypeptide comprises the amino acid sequence of SEQ ID NO: 120; or (ii) the first polypeptide comprises an amino acid sequence comprising SEQ ID NO: 8 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 307 and SEQ ID NO: 119, and the second polypeptide comprises the amino acid sequence of SEQ ID NO: 120; or (ii) the first polypeptide comprises an amino acid sequence comprising SEQ ID NO: 307 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 308 and SEQ ID NO: 119, and the second polypeptide comprises the amino acid sequence of SEQ ID NO: 120; or (ii) the first polypeptide comprises an amino acid sequence comprising SEQ ID NO: 308 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 309 and SEQ ID NO: 119, and the second polypeptide comprises the amino acid sequence of SEQ ID NO: 120; or (ii) the first polypeptide comprises an amino acid sequence comprising SEQ ID NO: 309 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 310 and SEQ ID NO: 119, and the second polypeptide comprises the amino acid sequence of SEQ ID NO: 120; or (ii) the first polypeptide comprises an amino acid sequence comprising SEQ ID NO: 310 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 311 and SEQ ID NO: 119, and the second polypeptide comprises the amino acid sequence of SEQ ID NO: 120; or (ii) the first polypeptide comprises an amino acid sequence comprising SEQ ID NO: 311 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 312 and SEQ ID NO: 119, and the second polypeptide comprises the amino acid sequence of SEQ ID NO: 120; or (ii) the first polypeptide comprises an amino acid sequence comprising SEQ ID NO: 312 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 313 and SEQ ID NO: 119, and the second polypeptide comprises the amino acid sequence of SEQ ID NO: 120; or (ii) the first polypeptide comprises an amino acid sequence comprising SEQ ID NO: 313 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 314 and SEQ ID NO: 119, and the second polypeptide comprises the amino acid sequence of SEQ ID NO: 120; or (ii) the first polypeptide comprises an amino acid sequence comprising SEQ ID NO: 314 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 315 and SEQ ID NO: 119, and the second polypeptide comprises the amino acid sequence of SEQ ID NO: 120; or (ii) the first polypeptide comprises an amino acid sequence comprising SEQ ID NO: 315 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 316 and SEQ ID NO: 119, and the second polypeptide comprises the amino acid sequence of SEQ ID NO: 120; or (ii) the first polypeptide comprises an amino acid sequence comprising SEQ ID NO: 316 and SEQ ID NO: 120, and the second polypeptide comprises the amino acid sequence of SEQ ID NO: 119. In some embodiments, a molecule comprises a first and second polypeptide wherein, (i) the first polypeptide comprises an amino acid sequence comprising SEQ ID NO: 317 and SEQ ID NO: 119, and the second polypeptide comprises the amino acid sequence of SEQ ID NO: 120; or (ii) the first polypeptide comprises an amino acid sequence comprising SEQ ID NO: 317 and SEQ ID NO: 120, and the second polypeptide comprises the amino acid sequence of SEQ ID NO: 119.

In some embodiments, a molecule comprises a first and second polypeptide wherein, (i) the first polypeptide comprises an amino acid sequence comprising SEQ ID NO: 1 and SEQ ID NO: 121, and the second polypeptide comprises the amino acid sequence of SEQ ID NO: 122; or (ii) the first polypeptide comprises an amino acid sequence comprising SEQ ID NO: 1 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 2 and SEQ ID NO: 121, and the second polypeptide comprises the amino acid sequence of SEQ ID NO: 122; or (ii) the first polypeptide comprises an amino acid sequence comprising SEQ ID NO: 2 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 3 and SEQ ID NO: 121, and the second polypeptide comprises the amino acid sequence of SEQ ID NO: 122; or (ii) the first polypeptide comprises an amino acid sequence comprising SEQ ID NO: 3 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 4 and SEQ ID NO: 121, and the second polypeptide comprises the amino acid sequence of SEQ ID NO: 122; or (ii) the first polypeptide comprises an amino acid sequence comprising SEQ ID NO: 4 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 5 and SEQ ID NO: 121, and the second polypeptide comprises the amino acid sequence of SEQ ID NO: 122; or (ii) the first polypeptide comprises an amino acid sequence comprising SEQ ID NO: 5 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 6 and SEQ ID NO: 121, and the second polypeptide comprises the amino acid sequence of SEQ ID NO: 122; or (ii) the first polypeptide comprises an amino acid sequence comprising SEQ ID NO: 6 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 7 and SEQ ID NO: 121, and the second polypeptide comprises the amino acid sequence of SEQ ID NO: 122; or (ii) the first polypeptide comprises an amino acid sequence comprising SEQ ID NO: 7 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 8 and SEQ ID NO: 121, and the second polypeptide comprises the amino acid sequence of SEQ ID NO: 122; or (ii) the first polypeptide comprises an amino acid sequence comprising SEQ ID NO: 8 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 307 and SEQ ID NO: 121, and the second polypeptide comprises the amino acid sequence of SEQ ID NO: 122; or (ii) the first polypeptide comprises an amino acid sequence comprising SEQ ID NO: 307 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 308 and SEQ ID NO: 121, and the second polypeptide comprises the amino acid sequence of SEQ ID NO: 122; or (ii) the first polypeptide comprises an amino acid sequence comprising SEQ ID NO: 308 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 309 and SEQ ID NO: 121, and the second polypeptide comprises the amino acid sequence of SEQ ID NO: 122; or (ii) the first polypeptide comprises an amino acid sequence comprising SEQ ID NO: 309 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 310 and SEQ ID NO: 121, and the second polypeptide comprises the amino acid sequence of SEQ ID NO: 122; or (ii) the first polypeptide comprises an amino acid sequence comprising SEQ ID NO: 310 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 311 and SEQ ID NO: 121, and the second polypeptide comprises the amino acid sequence of SEQ ID NO: 122; or (ii) the first polypeptide comprises an amino acid sequence comprising SEQ ID NO: 311 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 312 and SEQ ID NO: 121, and the second polypeptide comprises the amino acid sequence of SEQ ID NO: 122; or (ii) the first polypeptide comprises an amino acid sequence comprising SEQ ID NO: 312 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 313 and SEQ ID NO: 121, and the second polypeptide comprises the amino acid sequence of SEQ ID NO: 122; or (ii) the first polypeptide comprises an amino acid sequence comprising SEQ ID NO: 313 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 314 and SEQ ID NO: 121, and the second polypeptide comprises the amino acid sequence of SEQ ID NO: 122; or (ii) the first polypeptide comprises an amino acid sequence comprising SEQ ID NO: 314 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 315 and SEQ ID NO: 121, and the second polypeptide comprises the amino acid sequence of SEQ ID NO: 122; or (ii) the first polypeptide comprises an amino acid sequence comprising SEQ ID NO: 315 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 316 and SEQ ID NO: 121, and the second polypeptide comprises the amino acid sequence of SEQ ID NO: 122; or (ii) the first polypeptide comprises an amino acid sequence comprising SEQ ID NO: 316 and SEQ ID NO: 122, and the second polypeptide comprises the amino acid sequence of SEQ ID NO: 121. In some embodiments, a molecule comprises a first and second polypeptide wherein, (i) the first polypeptide comprises an amino acid sequence comprising SEQ ID NO: 317 and SEQ ID NO: 121, and the second polypeptide comprises the amino acid sequence of SEQ ID NO: 122; or (ii) the first polypeptide comprises an amino acid sequence comprising SEQ ID NO: 317 and SEQ ID NO: 122, and the second polypeptide comprises the amino acid sequence of SEQ ID NO: 121.

In some embodiments, a molecule comprises a first and second polypeptide wherein, (i) the first polypeptide comprises an amino acid sequence comprising SEQ ID NO: 1 and SEQ ID NO: 123, and the second polypeptide comprises the amino acid sequence of SEQ ID NO: 124; or (ii) the first polypeptide comprises an amino acid sequence comprising SEQ ID NO: 1 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 2 and SEQ ID NO: 123, and the second polypeptide comprises the amino acid sequence of SEQ ID NO: 124; or (ii) the first polypeptide comprises an amino acid sequence comprising SEQ ID NO: 2 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 3 and SEQ ID NO: 123, and the second polypeptide comprises the amino acid sequence of SEQ ID NO: 124; or (ii) the first polypeptide comprises an amino acid sequence comprising SEQ ID NO: 3 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 4 and SEQ ID NO: 123, and the second polypeptide comprises the amino acid sequence of SEQ ID NO: 124; or (ii) the first polypeptide comprises an amino acid sequence comprising SEQ ID NO: 4 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 5 and SEQ ID NO: 123, and the second polypeptide comprises the amino acid sequence of SEQ ID NO: 124; or (ii) the first polypeptide comprises an amino acid sequence comprising SEQ ID NO: 5 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 6 and SEQ ID NO: 123, and the second polypeptide comprises the amino acid sequence of SEQ ID NO: 124; or (ii) the first polypeptide comprises an amino acid sequence comprising SEQ ID NO: 6 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 7 and SEQ ID NO: 123, and the second polypeptide comprises the amino acid sequence of SEQ ID NO: 124; or (ii) the first polypeptide comprises an amino acid sequence comprising SEQ ID NO: 7 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 8 and SEQ ID NO: 123, and the second polypeptide comprises the amino acid sequence of SEQ ID NO: 124; or (ii) the first polypeptide comprises an amino acid sequence comprising SEQ ID NO: 8 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 307 and SEQ ID NO: 123, and the second polypeptide comprises the amino acid sequence of SEQ ID NO: 124; or (ii) the first polypeptide comprises an amino acid sequence comprising SEQ ID NO: 307 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 308 and SEQ ID NO: 123, and the second polypeptide comprises the amino acid sequence of SEQ ID NO: 124; or (ii) the first polypeptide comprises an amino acid sequence comprising SEQ ID NO: 308 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 309 and SEQ ID NO: 123, and the second polypeptide comprises the amino acid sequence of SEQ ID NO: 124; or (ii) the first polypeptide comprises an amino acid sequence comprising SEQ ID NO: 309 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 310 and SEQ ID NO: 123, and the second polypeptide comprises the amino acid sequence of SEQ ID NO: 124; or (ii) the first polypeptide comprises an amino acid sequence comprising SEQ ID NO: 310 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 311 and SEQ ID NO: 123, and the second polypeptide comprises the amino acid sequence of SEQ ID NO: 124; or (ii) the first polypeptide comprises an amino acid sequence comprising SEQ ID NO: 311 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 312 and SEQ ID NO: 123, and the second polypeptide comprises the amino acid sequence of SEQ ID NO: 124; or (ii) the first polypeptide comprises an amino acid sequence comprising SEQ ID NO: 312 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 313 and SEQ ID NO: 123, and the second polypeptide comprises the amino acid sequence of SEQ ID NO: 124; or (ii) the first polypeptide comprises an amino acid sequence comprising SEQ ID NO: 313 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 314 and SEQ ID NO: 123, and the second polypeptide comprises the amino acid sequence of SEQ ID NO: 124; or (ii) the first polypeptide comprises an amino acid sequence comprising SEQ ID NO: 314 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 315 and SEQ ID NO: 123, and the second polypeptide comprises the amino acid sequence of SEQ ID NO: 124; or (ii) the first polypeptide comprises an amino acid sequence comprising SEQ ID NO: 315 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 316 and SEQ ID NO: 123, and the second polypeptide comprises the amino acid sequence of SEQ ID NO: 124; or (ii) the first polypeptide comprises an amino acid sequence comprising SEQ ID NO: 316 and SEQ ID NO: 124, and the second polypeptide comprises the amino acid sequence of SEQ ID NO: 123. In some embodiments, a molecule comprises a first and second polypeptide wherein, (i) the first polypeptide comprises an amino acid sequence comprising SEQ ID NO: 317 and SEQ ID NO: 123, and the second polypeptide comprises the amino acid sequence of SEQ ID NO: 124; or (ii) the first polypeptide comprises an amino acid sequence comprising SEQ ID NO: 317 and SEQ ID NO: 124, and the second polypeptide comprises the amino acid sequence of SEQ ID NO: 123.

In some embodiments, a molecule comprises a first and second polypeptide wherein, (i) the first polypeptide comprises an amino acid sequence comprising SEQ ID NO: 1 and SEQ ID NO: 125, and the second polypeptide comprises the amino acid sequence of SEQ ID NO: 126; or (ii) the first polypeptide comprises an amino acid sequence comprising SEQ ID NO: 1 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 2 and SEQ ID NO: 125, and the second polypeptide comprises the amino acid sequence of SEQ ID NO: 126; or (ii) the first polypeptide comprises an amino acid sequence comprising SEQ ID NO: 2 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 3 and SEQ ID NO: 125, and the second polypeptide comprises the amino acid sequence of SEQ ID NO: 126; or (ii) the first polypeptide comprises an amino acid sequence comprising SEQ ID NO: 3 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 4 and SEQ ID NO: 125, and the second polypeptide comprises the amino acid sequence of SEQ ID NO: 126; or (ii) the first polypeptide comprises an amino acid sequence comprising SEQ ID NO: 4 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 5 and SEQ ID NO: 125, and the second polypeptide comprises the amino acid sequence of SEQ ID NO: 126; or (ii) the first polypeptide comprises an amino acid sequence comprising SEQ ID NO: 5 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 6 and SEQ ID NO: 125, and the second polypeptide comprises the amino acid sequence of SEQ ID NO: 126; or (ii) the first polypeptide comprises an amino acid sequence comprising SEQ ID NO: 6 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 7 and SEQ ID NO: 125, and the second polypeptide comprises the amino acid sequence of SEQ ID NO: 126; or (ii) the first polypeptide comprises an amino acid sequence comprising SEQ ID NO: 7 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 8 and SEQ ID NO: 125, and the second polypeptide comprises the amino acid sequence of SEQ ID NO: 126; or (ii) the first polypeptide comprises an amino acid sequence comprising SEQ ID NO: 8 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 307 and SEQ ID NO: 125, and the second polypeptide comprises the amino acid sequence of SEQ ID NO: 126; or (ii) the first polypeptide comprises an amino acid sequence comprising SEQ ID NO: 307 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 308 and SEQ ID NO: 125, and the second polypeptide comprises the amino acid sequence of SEQ ID NO: 126; or (ii) the first polypeptide comprises an amino acid sequence comprising SEQ ID NO: 308 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 309 and SEQ ID NO: 125, and the second polypeptide comprises the amino acid sequence of SEQ ID NO: 126; or (ii) the first polypeptide comprises an amino acid sequence comprising SEQ ID NO: 309 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 310 and SEQ ID NO: 125, and the second polypeptide comprises the amino acid sequence of SEQ ID NO: 126; or (ii) the first polypeptide comprises an amino acid sequence comprising SEQ ID NO: 310 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 311 and SEQ ID NO: 125, and the second polypeptide comprises the amino acid sequence of SEQ ID NO: 126; or (ii) the first polypeptide comprises an amino acid sequence comprising SEQ ID NO: 311 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 312 and SEQ ID NO: 125, and the second polypeptide comprises the amino acid sequence of SEQ ID NO: 126; or (ii) the first polypeptide comprises an amino acid sequence comprising SEQ ID NO: 312 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 313 and SEQ ID NO: 125, and the second polypeptide comprises the amino acid sequence of SEQ ID NO: 126; or (ii) the first polypeptide comprises an amino acid sequence comprising SEQ ID NO: 313 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 314 and SEQ ID NO: 125, and the second polypeptide comprises the amino acid sequence of SEQ ID NO: 126; or (ii) the first polypeptide comprises an amino acid sequence comprising SEQ ID NO: 314 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 315 and SEQ ID NO: 125, and the second polypeptide comprises the amino acid sequence of SEQ ID NO: 126; or (ii) the first polypeptide comprises an amino acid sequence comprising SEQ ID NO: 315 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 316 and SEQ ID NO: 125, and the second polypeptide comprises the amino acid sequence of SEQ ID NO: 126; or (ii) the first polypeptide comprises an amino acid sequence comprising SEQ ID NO: 316 and SEQ ID NO: 126, and the second polypeptide comprises the amino acid sequence of SEQ ID NO: 125. In some embodiments, a molecule comprises a first and second polypeptide wherein, (i) the first polypeptide comprises an amino acid sequence comprising SEQ ID NO: 317 and SEQ ID NO: 125, and the second polypeptide comprises the amino acid sequence of SEQ ID NO: 126; or (ii) the first polypeptide comprises an amino acid sequence comprising SEQ ID NO: 317 and SEQ ID NO: 126, and the second polypeptide comprises the amino acid sequence of SEQ ID NO: 125.

In some embodiments, a molecule comprises a first and second polypeptide wherein, (i) the first polypeptide comprises an amino acid sequence comprising SEQ ID NO: 1 and SEQ ID NO: 127, and the second polypeptide comprises the amino acid sequence of SEQ ID NO: 128; or (ii) the first polypeptide comprises an amino acid sequence comprising SEQ ID NO: 1 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 2 and SEQ ID NO: 127, and the second polypeptide comprises the amino acid sequence of SEQ ID NO: 128; or (ii) the first polypeptide comprises an amino acid sequence comprising SEQ ID NO: 2 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 3 and SEQ ID NO: 127, and the second polypeptide comprises the amino acid sequence of SEQ ID NO: 128; or (ii) the first polypeptide comprises an amino acid sequence comprising SEQ ID NO: 3 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 4 and SEQ ID NO: 127, and the second polypeptide comprises the amino acid sequence of SEQ ID NO: 128; or (ii) the first polypeptide comprises an amino acid sequence comprising SEQ ID NO: 4 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 5 and SEQ ID NO: 127, and the second polypeptide comprises the amino acid sequence of SEQ ID NO: 128; or (ii) the first polypeptide comprises an amino acid sequence comprising SEQ ID NO: 5 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 6 and SEQ ID NO: 127, and the second polypeptide comprises the amino acid sequence of SEQ ID NO: 128; or (ii) the first polypeptide comprises an amino acid sequence comprising SEQ ID NO: 6 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 7 and SEQ ID NO: 127, and the second polypeptide comprises the amino acid sequence of SEQ ID NO: 128; or (ii) the first polypeptide comprises an amino acid sequence comprising SEQ ID NO: 7 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 8 and SEQ ID NO: 127, and the second polypeptide comprises the amino acid sequence of SEQ ID NO: 128; or (ii) the first polypeptide comprises an amino acid sequence comprising SEQ ID NO: 8 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 307 and SEQ ID NO: 127, and the second polypeptide comprises the amino acid sequence of SEQ ID NO: 128; or (ii) the first polypeptide comprises an amino acid sequence comprising SEQ ID NO: 307 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 308 and SEQ ID NO: 127, and the second polypeptide comprises the amino acid sequence of SEQ ID NO: 128; or (ii) the first polypeptide comprises an amino acid sequence comprising SEQ ID NO: 308 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 309 and SEQ ID NO: 127, and the second polypeptide comprises the amino acid sequence of SEQ ID NO: 128; or (ii) the first polypeptide comprises an amino acid sequence comprising SEQ ID NO: 309 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 310 and SEQ ID NO: 127, and the second polypeptide comprises the amino acid sequence of SEQ ID NO: 128; or (ii) the first polypeptide comprises an amino acid sequence comprising SEQ ID NO: 310 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 311 and SEQ ID NO: 127, and the second polypeptide comprises the amino acid sequence of SEQ ID NO: 128; or (ii) the first polypeptide comprises an amino acid sequence comprising SEQ ID NO: 311 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 312 and SEQ ID NO: 127, and the second polypeptide comprises the amino acid sequence of SEQ ID NO: 128; or (ii) the first polypeptide comprises an amino acid sequence comprising SEQ ID NO: 312 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 313 and SEQ ID NO: 127, and the second polypeptide comprises the amino acid sequence of SEQ ID NO: 128; or (ii) the first polypeptide comprises an amino acid sequence comprising SEQ ID NO: 313 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 314 and SEQ ID NO: 127, and the second polypeptide comprises the amino acid sequence of SEQ ID NO: 128; or (ii) the first polypeptide comprises an amino acid sequence comprising SEQ ID NO: 314 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 315 and SEQ ID NO: 127, and the second polypeptide comprises the amino acid sequence of SEQ ID NO: 128; or (ii) the first polypeptide comprises an amino acid sequence comprising SEQ ID NO: 315 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 316 and SEQ ID NO: 127, and the second polypeptide comprises the amino acid sequence of SEQ ID NO: 128; or (ii) the first polypeptide comprises an amino acid sequence comprising SEQ ID NO: 316 and SEQ ID NO: 128, and the second polypeptide comprises the amino acid sequence of SEQ ID NO: 127. In some embodiments, a molecule comprises a first and second polypeptide wherein, (i) the first polypeptide comprises an amino acid sequence comprising SEQ ID NO: 317 and SEQ ID NO: 127, and the second polypeptide comprises the amino acid sequence of SEQ ID NO: 128; or (ii) the first polypeptide comprises an amino acid sequence comprising SEQ ID NO: 317 and SEQ ID NO: 128, and the second polypeptide comprises the amino acid sequence of SEQ ID NO: 127.

In some embodiments, a molecule comprises a first and second polypeptide wherein, (i) the first polypeptide comprises an amino acid sequence comprising SEQ ID NO: 1 and SEQ ID NO: 129, and the second polypeptide comprises the amino acid sequence of SEQ ID NO: 130; or (ii) the first polypeptide comprises an amino acid sequence comprising SEQ ID NO: 1 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 2 and SEQ ID NO: 129, and the second polypeptide comprises the amino acid sequence of SEQ ID NO: 130; or (ii) the first polypeptide comprises an amino acid sequence comprising SEQ ID NO: 2 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 3 and SEQ ID NO: 129, and the second polypeptide comprises the amino acid sequence of SEQ ID NO: 130; or (ii) the first polypeptide comprises an amino acid sequence comprising SEQ ID NO: 3 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 4 and SEQ ID NO: 129, and the second polypeptide comprises the amino acid sequence of SEQ ID NO: 130; or (ii) the first polypeptide comprises an amino acid sequence comprising SEQ ID NO: 4 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 5 and SEQ ID NO: 129, and the second polypeptide comprises the amino acid sequence of SEQ ID NO: 130; or (ii) the first polypeptide comprises an amino acid sequence comprising SEQ ID NO: 5 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 6 and SEQ ID NO: 129, and the second polypeptide comprises the amino acid sequence of SEQ ID NO: 130; or (ii) the first polypeptide comprises an amino acid sequence comprising SEQ ID NO: 6 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 7 and SEQ ID NO: 129, and the second polypeptide comprises the amino acid sequence of SEQ ID NO: 130; or (ii) the first polypeptide comprises an amino acid sequence comprising SEQ ID NO: 7 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 8 and SEQ ID NO: 129, and the second polypeptide comprises the amino acid sequence of SEQ ID NO: 130; or (ii) the first polypeptide comprises an amino acid sequence comprising SEQ ID NO: 8 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 307 and SEQ ID NO: 129, and the second polypeptide comprises the amino acid sequence of SEQ ID NO: 130; or (ii) the first polypeptide comprises an amino acid sequence comprising SEQ ID NO: 307 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 308 and SEQ ID NO: 129, and the second polypeptide comprises the amino acid sequence of SEQ ID NO: 130; or (ii) the first polypeptide comprises an amino acid sequence comprising SEQ ID NO: 308 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 309 and SEQ ID NO: 129, and the second polypeptide comprises the amino acid sequence of SEQ ID NO: 130; or (ii) the first polypeptide comprises an amino acid sequence comprising SEQ ID NO: 309 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 310 and SEQ ID NO: 129, and the second polypeptide comprises the amino acid sequence of SEQ ID NO: 130; or (ii) the first polypeptide comprises an amino acid sequence comprising SEQ ID NO: 310 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 311 and SEQ ID NO: 129, and the second polypeptide comprises the amino acid sequence of SEQ ID NO: 130; or (ii) the first polypeptide comprises an amino acid sequence comprising SEQ ID NO: 311 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 312 and SEQ ID NO: 129, and the second polypeptide comprises the amino acid sequence of SEQ ID NO: 130; or (ii) the first polypeptide comprises an amino acid sequence comprising SEQ ID NO: 312 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 313 and SEQ ID NO: 129, and the second polypeptide comprises the amino acid sequence of SEQ ID NO: 130; or (ii) the first polypeptide comprises an amino acid sequence comprising SEQ ID NO: 313 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 314 and SEQ ID NO: 129, and the second polypeptide comprises the amino acid sequence of SEQ ID NO: 130; or (ii) the first polypeptide comprises an amino acid sequence comprising SEQ ID NO: 314 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 315 and SEQ ID NO: 129, and the second polypeptide comprises the amino acid sequence of SEQ ID NO: 130; or (ii) the first polypeptide comprises an amino acid sequence comprising SEQ ID NO: 315 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 316 and SEQ ID NO: 129, and the second polypeptide comprises the amino acid sequence of SEQ ID NO: 130; or (ii) the first polypeptide comprises an amino acid sequence comprising SEQ ID NO: 316 and SEQ ID NO: 130, and the second polypeptide comprises the amino acid sequence of SEQ ID NO: 129. In some embodiments, a molecule comprises a first and second polypeptide wherein, (i) the first polypeptide comprises an amino acid sequence comprising SEQ ID NO: 317 and SEQ ID NO: 129, and the second polypeptide comprises the amino acid sequence of SEQ ID NO: 130; or (ii) the first polypeptide comprises an amino acid sequence comprising SEQ ID NO: 317 and SEQ ID NO: 130, and the second polypeptide comprises the amino acid sequence of SEQ ID NO: 129.

In some embodiments, a molecule comprises a first and second polypeptide wherein, (i) the first polypeptide comprises an amino acid sequence comprising SEQ ID NO: 1 and SEQ ID NO: 131, and the second polypeptide comprises the amino acid sequence of SEQ ID NO: 132; or (ii) the first polypeptide comprises an amino acid sequence comprising SEQ ID NO: 1 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 2 and SEQ ID NO: 131, and the second polypeptide comprises the amino acid sequence of SEQ ID NO: 132; or (ii) the first polypeptide comprises an amino acid sequence comprising SEQ ID NO: 2 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 3 and SEQ ID NO: 131, and the second polypeptide comprises the amino acid sequence of SEQ ID NO: 132; or (ii) the first polypeptide comprises an amino acid sequence comprising SEQ ID NO: 3 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 4 and SEQ ID NO: 131, and the second polypeptide comprises the amino acid sequence of SEQ ID NO: 132; or (ii) the first polypeptide comprises an amino acid sequence comprising SEQ ID NO: 4 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 5 and SEQ ID NO: 131, and the second polypeptide comprises the amino acid sequence of SEQ ID NO: 132; or (ii) the first polypeptide comprises an amino acid sequence comprising SEQ ID NO: 5 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 6 and SEQ ID NO: 131, and the second polypeptide comprises the amino acid sequence of SEQ ID NO: 132; or (ii) the first polypeptide comprises an amino acid sequence comprising SEQ ID NO: 6 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 7 and SEQ ID NO: 131, and the second polypeptide comprises the amino acid sequence of SEQ ID NO: 132; or (ii) the first polypeptide comprises an amino acid sequence comprising SEQ ID NO: 7 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 8 and SEQ ID NO: 131, and the second polypeptide comprises the amino acid sequence of SEQ ID NO: 132; or (ii) the first polypeptide comprises an amino acid sequence comprising SEQ ID NO: 8 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 307 and SEQ ID NO: 131, and the second polypeptide comprises the amino acid sequence of SEQ ID NO: 132; or (ii) the first polypeptide comprises an amino acid sequence comprising SEQ ID NO: 307 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 308 and SEQ ID NO: 131, and the second polypeptide comprises the amino acid sequence of SEQ ID NO: 132; or (ii) the first polypeptide comprises an amino acid sequence comprising SEQ ID NO: 308 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 309 and SEQ ID NO: 131, and the second polypeptide comprises the amino acid sequence of SEQ ID NO: 132; or (ii) the first polypeptide comprises an amino acid sequence comprising SEQ ID NO: 309 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 310 and SEQ ID NO: 131, and the second polypeptide comprises the amino acid sequence of SEQ ID NO: 132; or (ii) the first polypeptide comprises an amino acid sequence comprising SEQ ID NO: 310 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 311 and SEQ ID NO: 131, and the second polypeptide comprises the amino acid sequence of SEQ ID NO: 132; or (ii) the first polypeptide comprises an amino acid sequence comprising SEQ ID NO: 311 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 312 and SEQ ID NO: 131, and the second polypeptide comprises the amino acid sequence of SEQ ID NO: 132; or (ii) the first polypeptide comprises an amino acid sequence comprising SEQ ID NO: 312 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 313 and SEQ ID NO: 131, and the second polypeptide comprises the amino acid sequence of SEQ ID NO: 132; or (ii) the first polypeptide comprises an amino acid sequence comprising SEQ ID NO: 313 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 314 and SEQ ID NO: 131, and the second polypeptide comprises the amino acid sequence of SEQ ID NO: 132; or (ii) the first polypeptide comprises an amino acid sequence comprising SEQ ID NO: 314 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 315 and SEQ ID NO: 131, and the second polypeptide comprises the amino acid sequence of SEQ ID NO: 132; or (ii) the first polypeptide comprises an amino acid sequence comprising SEQ ID NO: 315 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 316 and SEQ ID NO: 131, and the second polypeptide comprises the amino acid sequence of SEQ ID NO: 132; or (ii) the first polypeptide comprises an amino acid sequence comprising SEQ ID NO: 316 and SEQ ID NO: 132, and the second polypeptide comprises the amino acid sequence of SEQ ID NO: 131. In some embodiments, a molecule comprises a first and second polypeptide wherein, (i) the first polypeptide comprises an amino acid sequence comprising SEQ ID NO: 317 and SEQ ID NO: 131, and the second polypeptide comprises the amino acid sequence of SEQ ID NO: 132; or (ii) the first polypeptide comprises an amino acid sequence comprising SEQ ID NO: 317 and SEQ ID NO: 132, and the second polypeptide comprises the amino acid sequence of SEQ ID NO: 131.

In some embodiments, a molecule comprises a first and second polypeptide wherein, (i) the first polypeptide comprises an amino acid sequence comprising SEQ ID NO: 1 and SEQ ID NO: 133, and the second polypeptide comprises the amino acid sequence of SEQ ID NO: 134; or (ii) the first polypeptide comprises an amino acid sequence comprising SEQ ID NO: 1 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 2 and SEQ ID NO: 133, and the second polypeptide comprises the amino acid sequence of SEQ ID NO: 134; or (ii) the first polypeptide comprises an amino acid sequence comprising SEQ ID NO: 2 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 3 and SEQ ID NO: 133, and the second polypeptide comprises the amino acid sequence of SEQ ID NO: 134; or (ii) the first polypeptide comprises an amino acid sequence comprising SEQ ID NO: 3 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 4 and SEQ ID NO: 133, and the second polypeptide comprises the amino acid sequence of SEQ ID NO: 134; or (ii) the first polypeptide comprises an amino acid sequence comprising SEQ ID NO: 4 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 5 and SEQ ID NO: 133, and the second polypeptide comprises the amino acid sequence of SEQ ID NO: 134; or (ii) the first polypeptide comprises an amino acid sequence comprising SEQ ID NO: 5 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 6 and SEQ ID NO: 133, and the second polypeptide comprises the amino acid sequence of SEQ ID NO: 134; or (ii) the first polypeptide comprises an amino acid sequence comprising SEQ ID NO: 6 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 7 and SEQ ID NO: 133, and the second polypeptide comprises the amino acid sequence of SEQ ID NO: 134; or (ii) the first polypeptide comprises an amino acid sequence comprising SEQ ID NO: 7 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 8 and SEQ ID NO: 133, and the second polypeptide comprises the amino acid sequence of SEQ ID NO: 134; or (ii) the first polypeptide comprises an amino acid sequence comprising SEQ ID NO: 8 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 307 and SEQ ID NO: 133, and the second polypeptide comprises the amino acid sequence of SEQ ID NO: 134; or (ii) the first polypeptide comprises an amino acid sequence comprising SEQ ID NO: 307 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 308 and SEQ ID NO: 133, and the second polypeptide comprises the amino acid sequence of SEQ ID NO: 134; or (ii) the first polypeptide comprises an amino acid sequence comprising SEQ ID NO: 308 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 309 and SEQ ID NO: 133, and the second polypeptide comprises the amino acid sequence of SEQ ID NO: 134; or (ii) the first polypeptide comprises an amino acid sequence comprising SEQ ID NO: 309 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 310 and SEQ ID NO: 133, and the second polypeptide comprises the amino acid sequence of SEQ ID NO: 134; or (ii) the first polypeptide comprises an amino acid sequence comprising SEQ ID NO: 310 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 311 and SEQ ID NO: 133, and the second polypeptide comprises the amino acid sequence of SEQ ID NO: 134; or (ii) the first polypeptide comprises an amino acid sequence comprising SEQ ID NO: 311 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 312 and SEQ ID NO: 133, and the second polypeptide comprises the amino acid sequence of SEQ ID NO: 134; or (ii) the first polypeptide comprises an amino acid sequence comprising SEQ ID NO: 312 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 313 and SEQ ID NO: 133, and the second polypeptide comprises the amino acid sequence of SEQ ID NO: 134; or (ii) the first polypeptide comprises an amino acid sequence comprising SEQ ID NO: 313 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 314 and SEQ ID NO: 133, and the second polypeptide comprises the amino acid sequence of SEQ ID NO: 134; or (ii) the first polypeptide comprises an amino acid sequence comprising SEQ ID NO: 314 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 315 and SEQ ID NO: 133, and the second polypeptide comprises the amino acid sequence of SEQ ID NO: 134; or (ii) the first polypeptide comprises an amino acid sequence comprising SEQ ID NO: 315 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 316 and SEQ ID NO: 133, and the second polypeptide comprises the amino acid sequence of SEQ ID NO: 134; or (ii) the first polypeptide comprises an amino acid sequence comprising SEQ ID NO: 316 and SEQ ID NO: 134, and the second polypeptide comprises the amino acid sequence of SEQ ID NO: 133. In some embodiments, a molecule comprises a first and second polypeptide wherein, (i) the first polypeptide comprises an amino acid sequence comprising SEQ ID NO: 317 and SEQ ID NO: 133, and the second polypeptide comprises the amino acid sequence of SEQ ID NO: 134; or (ii) the first polypeptide comprises an amino acid sequence comprising SEQ ID NO: 317 and SEQ ID NO: 134, and the second polypeptide comprises the amino acid sequence of SEQ ID NO: 133.

In some embodiments, a molecule comprises a first and second polypeptide wherein, (i) the first polypeptide comprises an amino acid sequence comprising SEQ ID NO: 1 and SEQ ID NO: 135, and the second polypeptide comprises the amino acid sequence of SEQ ID NO: 136; or (ii) the first polypeptide comprises an amino acid sequence comprising SEQ ID NO: 1 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 2 and SEQ ID NO: 135, and the second polypeptide comprises the amino acid sequence of SEQ ID NO: 136; or (ii) the first polypeptide comprises an amino acid sequence comprising SEQ ID NO: 2 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 3 and SEQ ID NO: 135, and the second polypeptide comprises the amino acid sequence of SEQ ID NO: 136; or (ii) the first polypeptide comprises an amino acid sequence comprising SEQ ID NO: 3 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 4 and SEQ ID NO: 135, and the second polypeptide comprises the amino acid sequence of SEQ ID NO: 136; or (ii) the first polypeptide comprises an amino acid sequence comprising SEQ ID NO: 4 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 5 and SEQ ID NO: 135, and the second polypeptide comprises the amino acid sequence of SEQ ID NO: 136; or (ii) the first polypeptide comprises an amino acid sequence comprising SEQ ID NO: 5 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 6 and SEQ ID NO: 135, and the second polypeptide comprises the amino acid sequence of SEQ ID NO: 136; or (ii) the first polypeptide comprises an amino acid sequence comprising SEQ ID NO: 6 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 7 and SEQ ID NO: 135, and the second polypeptide comprises the amino acid sequence of SEQ ID NO: 136; or (ii) the first polypeptide comprises an amino acid sequence comprising SEQ ID NO: 7 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 8 and SEQ ID NO: 135, and the second polypeptide comprises the amino acid sequence of SEQ ID NO: 136; or (ii) the first polypeptide comprises an amino acid sequence comprising SEQ ID NO: 8 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 307 and SEQ ID NO: 135, and the second polypeptide comprises the amino acid sequence of SEQ ID NO: 136; or (ii) the first polypeptide comprises an amino acid sequence comprising SEQ ID NO: 307 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 308 and SEQ ID NO: 135, and the second polypeptide comprises the amino acid sequence of SEQ ID NO: 136; or (ii) the first polypeptide comprises an amino acid sequence comprising SEQ ID NO: 308 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 309 and SEQ ID NO: 135, and the second polypeptide comprises the amino acid sequence of SEQ ID NO: 136; or (ii) the first polypeptide comprises an amino acid sequence comprising SEQ ID NO: 309 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 310 and SEQ ID NO: 135, and the second polypeptide comprises the amino acid sequence of SEQ ID NO: 136; or (ii) the first polypeptide comprises an amino acid sequence comprising SEQ ID NO: 310 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 311 and SEQ ID NO: 135, and the second polypeptide comprises the amino acid sequence of SEQ ID NO: 136; or (ii) the first polypeptide comprises an amino acid sequence comprising SEQ ID NO: 311 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 312 and SEQ ID NO: 135, and the second polypeptide comprises the amino acid sequence of SEQ ID NO: 136; or (ii) the first polypeptide comprises an amino acid sequence comprising SEQ ID NO: 312 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 313 and SEQ ID NO: 135, and the second polypeptide comprises the amino acid sequence of SEQ ID NO: 136; or (ii) the first polypeptide comprises an amino acid sequence comprising SEQ ID NO: 313 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 314 and SEQ ID NO: 135, and the second polypeptide comprises the amino acid sequence of SEQ ID NO: 136; or (ii) the first polypeptide comprises an amino acid sequence comprising SEQ ID NO: 314 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 315 and SEQ ID NO: 135, and the second polypeptide comprises the amino acid sequence of SEQ ID NO: 136; or (ii) the first polypeptide comprises an amino acid sequence comprising SEQ ID NO: 315 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 316 and SEQ ID NO: 135, and the second polypeptide comprises the amino acid sequence of SEQ ID NO: 136; or (ii) the first polypeptide comprises an amino acid sequence comprising SEQ ID NO: 316 and SEQ ID NO: 136, and the second polypeptide comprises the amino acid sequence of SEQ ID NO: 135. In some embodiments, a molecule comprises a first and second polypeptide wherein, (i) the first polypeptide comprises an amino acid sequence comprising SEQ ID NO: 317 and SEQ ID NO: 135, and the second polypeptide comprises the amino acid sequence of SEQ ID NO: 136; or (ii) the first polypeptide comprises an amino acid sequence comprising SEQ ID NO: 317 and SEQ ID NO: 136, and the second polypeptide comprises the amino acid sequence of SEQ ID NO: 135.

In some embodiments, a molecule comprises a first and second polypeptide wherein, (i) the first polypeptide comprises an amino acid sequence comprising SEQ ID NO: 1 and SEQ ID NO: 137, and the second polypeptide comprises the amino acid sequence of SEQ ID NO: 138; or (ii) the first polypeptide comprises an amino acid sequence comprising SEQ ID NO: 1 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 2 and SEQ ID NO: 137, and the second polypeptide comprises the amino acid sequence of SEQ ID NO: 138; or (ii) the first polypeptide comprises an amino acid sequence comprising SEQ ID NO: 2 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 3 and SEQ ID NO: 137, and the second polypeptide comprises the amino acid sequence of SEQ ID NO: 138; or (ii) the first polypeptide comprises an amino acid sequence comprising SEQ ID NO: 3 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 4 and SEQ ID NO: 137, and the second polypeptide comprises the amino acid sequence of SEQ ID NO: 138; or (ii) the first polypeptide comprises an amino acid sequence comprising SEQ ID NO: 4 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 5 and SEQ ID NO: 137, and the second polypeptide comprises the amino acid sequence of SEQ ID NO: 138; or (ii) the first polypeptide comprises an amino acid sequence comprising SEQ ID NO: 5 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 6 and SEQ ID NO: 137, and the second polypeptide comprises the amino acid sequence of SEQ ID NO: 138; or (ii) the first polypeptide comprises an amino acid sequence comprising SEQ ID NO: 6 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 7 and SEQ ID NO: 137, and the second polypeptide comprises the amino acid sequence of SEQ ID NO: 138; or (ii) the first polypeptide comprises an amino acid sequence comprising SEQ ID NO: 7 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 8 and SEQ ID NO: 137, and the second polypeptide comprises the amino acid sequence of SEQ ID NO: 138; or (ii) the first polypeptide comprises an amino acid sequence comprising SEQ ID NO: 8 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 307 and SEQ ID NO: 137, and the second polypeptide comprises the amino acid sequence of SEQ ID NO: 138; or (ii) the first polypeptide comprises an amino acid sequence comprising SEQ ID NO: 307 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 308 and SEQ ID NO: 137, and the second polypeptide comprises the amino acid sequence of SEQ ID NO: 138; or (ii) the first polypeptide comprises an amino acid sequence comprising SEQ ID NO: 308 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 309 and SEQ ID NO: 137, and the second polypeptide comprises the amino acid sequence of SEQ ID NO: 138; or (ii) the first polypeptide comprises an amino acid sequence comprising SEQ ID NO: 309 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 310 and SEQ ID NO: 137, and the second polypeptide comprises the amino acid sequence of SEQ ID NO: 138; or (ii) the first polypeptide comprises an amino acid sequence comprising SEQ ID NO: 310 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 311 and SEQ ID NO: 137, and the second polypeptide comprises the amino acid sequence of SEQ ID NO: 138; or (ii) the first polypeptide comprises an amino acid sequence comprising SEQ ID NO: 311 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 312 and SEQ ID NO: 137, and the second polypeptide comprises the amino acid sequence of SEQ ID NO: 138; or (ii) the first polypeptide comprises an amino acid sequence comprising SEQ ID NO: 312 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 313 and SEQ ID NO: 137, and the second polypeptide comprises the amino acid sequence of SEQ ID NO: 138; or (ii) the first polypeptide comprises an amino acid sequence comprising SEQ ID NO: 313 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 314 and SEQ ID NO: 137, and the second polypeptide comprises the amino acid sequence of SEQ ID NO: 138; or (ii) the first polypeptide comprises an amino acid sequence comprising SEQ ID NO: 314 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 315 and SEQ ID NO: 137, and the second polypeptide comprises the amino acid sequence of SEQ ID NO: 138; or (ii) the first polypeptide comprises an amino acid sequence comprising SEQ ID NO: 315 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 316 and SEQ ID NO: 137, and the second polypeptide comprises the amino acid sequence of SEQ ID NO: 138; or (ii) the first polypeptide comprises an amino acid sequence comprising SEQ ID NO: 316 and SEQ ID NO: 138, and the second polypeptide comprises the amino acid sequence of SEQ ID NO: 137. In some embodiments, a molecule comprises a first and second polypeptide wherein, (i) the first polypeptide comprises an amino acid sequence comprising SEQ ID NO: 317 and SEQ ID NO: 137, and the second polypeptide comprises the amino acid sequence of SEQ ID NO: 138; or (ii) the first polypeptide comprises an amino acid sequence comprising SEQ ID NO: 317 and SEQ ID NO: 138, and the second polypeptide comprises the amino acid sequence of SEQ ID NO: 137.

In some embodiments, a molecule comprises a first and second polypeptide wherein, (i) the first polypeptide comprises an amino acid sequence comprising SEQ ID NO: 1 and SEQ ID NO: 376, and the second polypeptide comprises the amino acid sequence of SEQ ID NO: 377; or (ii) the first polypeptide comprises an amino acid sequence comprising SEQ ID NO: 1 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 2 and SEQ ID NO: 376, and the second polypeptide comprises the amino acid sequence of SEQ ID NO: 377; or (ii) the first polypeptide comprises an amino acid sequence comprising SEQ ID NO: 2 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 3 and SEQ ID NO: 376, and the second polypeptide comprises the amino acid sequence of SEQ ID NO: 377; or (ii) the first polypeptide comprises an amino acid sequence comprising SEQ ID NO: 3 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 4 and SEQ ID NO: 376, and the second polypeptide comprises the amino acid sequence of SEQ ID NO: 377; or (ii) the first polypeptide comprises an amino acid sequence comprising SEQ ID NO: 4 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 5 and SEQ ID NO: 376, and the second polypeptide comprises the amino acid sequence of SEQ ID NO: 377; or (ii) the first polypeptide comprises an amino acid sequence comprising SEQ ID NO: 5 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 6 and SEQ ID NO: 376, and the second polypeptide comprises the amino acid sequence of SEQ ID NO: 377; or (ii) the first polypeptide comprises an amino acid sequence comprising SEQ ID NO: 6 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 7 and SEQ ID NO: 376, and the second polypeptide comprises the amino acid sequence of SEQ ID NO: 377; or (ii) the first polypeptide comprises an amino acid sequence comprising SEQ ID NO: 7 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 8 and SEQ ID NO: 376, and the second polypeptide comprises the amino acid sequence of SEQ ID NO: 377; or (ii) the first polypeptide comprises an amino acid sequence comprising SEQ ID NO: 8 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 307 and SEQ ID NO: 376, and the second polypeptide comprises the amino acid sequence of SEQ ID NO: 377; or (ii) the first polypeptide comprises an amino acid sequence comprising SEQ ID NO: 307 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 308 and SEQ ID NO: 376, and the second polypeptide comprises the amino acid sequence of SEQ ID NO: 377; or (ii) the first polypeptide comprises an amino acid sequence comprising SEQ ID NO: 308 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 309 and SEQ ID NO: 376, and the second polypeptide comprises the amino acid sequence of SEQ ID NO: 377; or (ii) the first polypeptide comprises an amino acid sequence comprising SEQ ID NO: 309 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 310 and SEQ ID NO: 376, and the second polypeptide comprises the amino acid sequence of SEQ ID NO: 377; or (ii) the first polypeptide comprises an amino acid sequence comprising SEQ ID NO: 310 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 311 and SEQ ID NO: 376, and the second polypeptide comprises the amino acid sequence of SEQ ID NO: 377; or (ii) the first polypeptide comprises an amino acid sequence comprising SEQ ID NO: 311 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 312 and SEQ ID NO: 376, and the second polypeptide comprises the amino acid sequence of SEQ ID NO: 377; or (ii) the first polypeptide comprises an amino acid sequence comprising SEQ ID NO: 312 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 313 and SEQ ID NO: 376, and the second polypeptide comprises the amino acid sequence of SEQ ID NO: 377; or (ii) the first polypeptide comprises an amino acid sequence comprising SEQ ID NO: 313 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 314 and SEQ ID NO: 376, and the second polypeptide comprises the amino acid sequence of SEQ ID NO: 377; or (ii) the first polypeptide comprises an amino acid sequence comprising SEQ ID NO: 314 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 315 and SEQ ID NO: 376, and the second polypeptide comprises the amino acid sequence of SEQ ID NO: 377; or (ii) the first polypeptide comprises an amino acid sequence comprising SEQ ID NO: 315 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 316 and SEQ ID NO: 376, and the second polypeptide comprises the amino acid sequence of SEQ ID NO: 377; or (ii) the first polypeptide comprises an amino acid sequence comprising SEQ ID NO: 316 and SEQ ID NO: 377, and the second polypeptide comprises the amino acid sequence of SEQ ID NO: 376. In some embodiments, a molecule comprises a first and second polypeptide wherein, (i) the first polypeptide comprises an amino acid sequence comprising SEQ ID NO: 317 and SEQ ID NO: 376, and the second polypeptide comprises the amino acid sequence of SEQ ID NO: 377; or (ii) the first polypeptide comprises an amino acid sequence comprising SEQ ID NO: 317 and SEQ ID NO: 377, and the second polypeptide comprises the amino acid sequence of SEQ ID NO: 376.

In some embodiments, a molecule comprises a first and second polypeptide wherein, (i) the first polypeptide comprises an amino acid sequence comprising SEQ ID NO: 1 and SEQ ID NO: 378, and the second polypeptide comprises the amino acid sequence of SEQ ID NO: 379; or (ii) the first polypeptide comprises an amino acid sequence comprising SEQ ID NO: 1 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 2 and SEQ ID NO: 378, and the second polypeptide comprises the amino acid sequence of SEQ ID NO: 379; or (ii) the first polypeptide comprises an amino acid sequence comprising SEQ ID NO: 2 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 3 and SEQ ID NO: 378, and the second polypeptide comprises the amino acid sequence of SEQ ID NO: 379; or (ii) the first polypeptide comprises an amino acid sequence comprising SEQ ID NO: 3 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 4 and SEQ ID NO: 378, and the second polypeptide comprises the amino acid sequence of SEQ ID NO: 379; or (ii) the first polypeptide comprises an amino acid sequence comprising SEQ ID NO: 4 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 5 and SEQ ID NO: 378, and the second polypeptide comprises the amino acid sequence of SEQ ID NO: 379; or (ii) the first polypeptide comprises an amino acid sequence comprising SEQ ID NO: 5 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 6 and SEQ ID NO: 378, and the second polypeptide comprises the amino acid sequence of SEQ ID NO: 379; or (ii) the first polypeptide comprises an amino acid sequence comprising SEQ ID NO: 6 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 7 and SEQ ID NO: 378, and the second polypeptide comprises the amino acid sequence of SEQ ID NO: 379; or (ii) the first polypeptide comprises an amino acid sequence comprising SEQ ID NO: 7 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 8 and SEQ ID NO: 378, and the second polypeptide comprises the amino acid sequence of SEQ ID NO: 379; or (ii) the first polypeptide comprises an amino acid sequence comprising SEQ ID NO: 8 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 307 and SEQ ID NO: 378, and the second polypeptide comprises the amino acid sequence of SEQ ID NO: 379; or (ii) the first polypeptide comprises an amino acid sequence comprising SEQ ID NO: 307 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 308 and SEQ ID NO: 378, and the second polypeptide comprises the amino acid sequence of SEQ ID NO: 379; or (ii) the first polypeptide comprises an amino acid sequence comprising SEQ ID NO: 308 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 309 and SEQ ID NO: 378, and the second polypeptide comprises the amino acid sequence of SEQ ID NO: 379; or (ii) the first polypeptide comprises an amino acid sequence comprising SEQ ID NO: 309 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 310 and SEQ ID NO: 378, and the second polypeptide comprises the amino acid sequence of SEQ ID NO: 379; or (ii) the first polypeptide comprises an amino acid sequence comprising SEQ ID NO: 310 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 311 and SEQ ID NO: 378, and the second polypeptide comprises the amino acid sequence of SEQ ID NO: 379; or (ii) the first polypeptide comprises an amino acid sequence comprising SEQ ID NO: 311 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 312 and SEQ ID NO: 378, and the second polypeptide comprises the amino acid sequence of SEQ ID NO: 379; or (ii) the first polypeptide comprises an amino acid sequence comprising SEQ ID NO: 312 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 313 and SEQ ID NO: 378, and the second polypeptide comprises the amino acid sequence of SEQ ID NO: 379; or (ii) the first polypeptide comprises an amino acid sequence comprising SEQ ID NO: 313 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 314 and SEQ ID NO: 378, and the second polypeptide comprises the amino acid sequence of SEQ ID NO: 379; or (ii) the first polypeptide comprises an amino acid sequence comprising SEQ ID NO: 314 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 315 and SEQ ID NO: 378, and the second polypeptide comprises the amino acid sequence of SEQ ID NO: 379; or (ii) the first polypeptide comprises an amino acid sequence comprising SEQ ID NO: 315 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 316 and SEQ ID NO: 378, and the second polypeptide comprises the amino acid sequence of SEQ ID NO: 379; or (ii) the first polypeptide comprises an amino acid sequence comprising SEQ ID NO: 316 and SEQ ID NO: 379, and the second polypeptide comprises the amino acid sequence of SEQ ID NO: 378. In some embodiments, a molecule comprises a first and second polypeptide wherein, (i) the first polypeptide comprises an amino acid sequence comprising SEQ ID NO: 317 and SEQ ID NO: 378, and the second polypeptide comprises the amino acid sequence of SEQ ID NO: 379; or (ii) the first polypeptide comprises an amino acid sequence comprising SEQ ID NO: 317 and SEQ ID NO: 379, and the second polypeptide comprises the amino acid sequence of SEQ ID NO: 378.

In some embodiments, a molecule comprises (a) a first polypeptide, wherein the first polypeptide comprises: (i) an amino acid sequence that is at least 90% identical to any one of SEQ ID NOs: 1-8 or 307-317 and (ii) an amino acid sequence that is at least 90% identical to any one of SEQ ID NOs: 103, 105, 107, 109, 111-113, 115, 117, 119, 121, 123, 125, 127, 129, 131, 133, 135, 137, 139-149, 163-164, 374-376, or 378 (e.g., a sequence selected from SEQ ID NOs: 107, 109, 113, 115, 119, 131, 139, 140, 142, 148, 374, or 378), and (b) a second polypeptide, wherein the second polypeptide comprises: an amino acid sequence that is at least 90% identical to any one of SEQ ID NOs: 104, 106, 108, 110, 111, 112, 114, 116, 118, 120, 122, 124, 126, 128, 130, 132, 134, 136, 138, 139-149, 163-164, 374-375, 377, or 379 (e.g., a sequence selected from SEQ ID NOs: 108, 110, 114, 116, 120, 132, 139, 140, 142, 148, 374, or 379).

In some embodiments, a molecule comprises (a) a first polypeptide, wherein the first polypeptide comprises: (i) the amino acid sequence of any one of SEQ ID NOs: 1-8 or 307-317 and (ii) the amino acid sequence of any one of SEQ ID NOs: 103, 105, 107, 109, 111-113, 115, 117, 119, 121, 123, 125, 127, 129, 131, 133, 135, 137, 139-149, 163-164, 374-376, or 378 (e.g., a sequence selected from SEQ ID NOs: 107, 109, 113, 115, 119, 131, 139, 140, 142, 148, 374, or 378) and (b) a second polypeptide, wherein the second polypeptide comprises: the amino acid sequence of any one of SEQ ID NOs: 104, 106, 108, 110, 111, 112, 114, 116, 118, 120, 122, 124, 126, 128, 130, 132, 134, 136, 138, 139-149, 163-164, 374-375, 377, or 379 (e.g., a sequence selected from SEQ ID NOs: 108, 110, 114, 116, 120, 132, 139, 140, 142, 148, 374, or 379).

In some embodiments, a molecule comprises (a) a first polypeptide, wherein the first polypeptide comprises: (i) an amino acid sequence that is at least 90% identical to any one of SEQ ID NOs: 1-8 or 307-317 and (ii) an amino acid sequence that is at least 90% identical to any one of SEQ ID NOs: 104, 106, 108, 110, 111, 112, 114, 116, 118, 120, 122, 124, 126, 128, 130, 132, 134, 136, 138, 139-149, 163-164, 374-375, 377, or 379 (e.g., a sequence selected from SEQ ID NOs: 108, 110, 114, 116, 120, 132, 139, 140, 142, 148, 374, or 379) and (b) a second polypeptide, wherein the second polypeptide comprises: an amino acid sequence that is at least 90% identical to any one of SEQ ID NOs: 103, 105, 107, 109, 111-113, 115, 117, 119, 121, 123, 125, 127, 129, 131, 133, 135, 137, 139-149, 163-164, 374-376, or 378 (e.g., a sequence selected from SEQ ID NOs: 107, 109, 113, 115, 119, 131, 139, 140, 142, 148, 374, or 378).

In some embodiments, a molecule comprises (a) a first polypeptide, wherein the first polypeptide comprises: (i) the amino acid sequence of any one of SEQ ID NOs: 1-8 or 307-317 and (ii) the amino acid sequence of any one of SEQ ID NOs: 104, 106, 108, 110, 111, 112, 114, 116, 118, 120, 122, 124, 126, 128, 130, 132, 134, 136, 138, 139-149, 163-164, 374-375, 377, or 379 (e.g., a sequence selected from SEQ ID NOs: 108, 110, 114, 116, 120, 132, 139, 140, 142, 148, 374, or 379) and (b) a second polypeptide, wherein the second polypeptide comprises: the amino acid sequence of any one of SEQ ID NOs: 103, 105, 107, 109, 111-113, 115, 117, 119, 121, 123, 125, 127, 129, 131, 133, 135, 137, 139-149, 163-164, 374-376, or 378 (e.g., a sequence selected from SEQ ID NOs: 107, 109, 113, 115, 119, 131, 139, 140, 142, 148, 374, or 378).

In some embodiments, a molecule comprises a first and second polypeptide wherein, the first polypeptide comprises the amino acid sequence of any one of SEQ ID NOs: 211-217, 225-227, 231-237, 245-247, 318-331, or 346-359 and the second polypeptide comprises the amino acid sequence of any one of SEQ ID NOs: 218-224, 228-230, 238-244, 248-250, 332-345, or 360-373.

Characteristics of Exemplary Molecules

Molecules described herein may be identified, assessed, and/or characterized for one or more of their physical/chemical properties and/or biological activities. Those skilled in the art will be aware of a variety of approaches, including particular assays, that may be utilized for such identification, assessment, and/or characterization. Antigen-binding domains and autoantigen domains of molecules described herein may be selected according to various criteria including, but not limited to, binding affinity, or the potency of the response (e.g., neutralization/removal of autoantibodies).

Binding Properties

Antigen-binding domains and autoantigens can be selected based on, among other things, their binding properties for their targets. The binding properties of an antigen-binding domain of molecules described herein can be measured by methods known in the art, e.g., one of the following methods: BIACORE analysis, Enzyme Linked Immunosorbent Assay (ELISA), x-ray crystallography, sequence analysis and scanning mutagenesis. The binding interaction of an antibody and target antigen can be analyzed using surface plasmon resonance (SPR). SPR or Biomolecular Interaction Analysis (BIA) detects bio-specific interactions in real time, without labeling any of the interactants. Changes in the mass at the binding surface (indicative of a binding event) of the BIA chip result in alterations of the refractive index of light near the surface. The changes in the refractivity generate a detectable signal, which are measured as an indication of real-time reactions between biological molecules. Methods for using SPR are described, for example, in U.S. Pat. No. 5,641,640; Raether (1988) Surface Plasmons Springer Verlag; Sjolander and Urbaniczky, *Anal. Chem.* 63:2338-2345 (1991); Szabo et al., *Curr. Opin. Struct. Biol.* 5:699-705 (1995) and on-line resources provided by BIAcore (Cytiva, USA). Additionally, a KinExA (Kinetic Exclusion Assay) assay, available from Sapidyne Instruments (Boise, Idaho), and/or an Octet BLI (Bio-Layer Interferometry) from Sartorius (Goettingen, Germany) can also be used.

Information from SPR or from similar BIA methods can be used to provide an accurate and quantitative measure of the equilibrium dissociation constant ($K_D$), and kinetic parameters, including $K_{on}$ and $K_{off}$, for the binding of an antigen-binding domain to a target antigen. Such data can be used to compare different molecules. Information from SPR can also be used to develop structure-activity relationships (SAR). Variant amino acids at given positions can be identified that correlate with particular binding parameters, e.g., high affinity.

In some embodiments, an antigen-binding domain described herein exhibits high affinity for binding for an autoantibody or an internalizing receptor. In various embodiments, $K_D$ of an antigen-binding domain as described herein for a target antigen is less than about $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$M or any range there between. In certain instances, $K_D$ of an antigen-binding domain as described herein for an immune cell target is between 0.001 and 1 nM, e.g., 0.001 nM, 0.005 nM, 0.01 nM, 0.05 nM, 0.1 nM, 0.5 nM, or 1 nM or any range there between.

In some embodiments, an autoantigen domain binds to an autoantibody with a high binding affinity. In various embodiments, $K_D$ of an autoantigen domain as described herein for an autoantibody is less than about $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or 10–$^{15}$ M or any range there between. In some embodiments, an autoantigen domain binds to an autoantibody with a binding affinity that is comparable or higher than an affinity of a natural autoantigen domain to an autoantibody. In certain instances, $K_D$ of an autoantigen domain for an autoantibody is between 0.001 and 1 nM, e.g., 0.001 nM, 0.005 nM, 0.01 nM, 0.05 nM, 0.1 nM, 0.5 nM, or 1 nM or any range there between.

In some embodiments, a molecule is characterized in its ability to selectively reduce or deplete circulating autoantibodies in a sample or patient.

In some embodiments, levels of target autoantibodies (e.g., anti-TSHR autoantibodies) in a subject or in a biological sample from the subject after administration is reduced relative to a level before administration. In some embodiments, a level of target autoantibodies (e.g., anti-TSHR autoantibodies) is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a level before the administration of the molecule. In some embodiments, level of target autoantibodies (e.g., anti-TSHR autoantibodies) is sustained over time. In some embodiments, a sustained period of time comprises at least 1 day, 2 days, 3 days, 4 days, 5 days, 6 days, 1 week, 2 weeks, 3 weeks, 4 weeks, 5 weeks, 6 weeks, 7 weeks, 8 weeks, 10 weeks, 12 weeks, or longer.

In some embodiments, a molecule described herein has an increased affinity for FcγRIIB. In some embodiments FcγRIIB is human FcγRIIB. In some embodiments, FcγRIIB is murine FcγRIIB. In some embodiments, an increased affinity for FcγRIIB is provided by mutating one or both of the molecule's Fc domains, as described herein.

In some embodiments, a molecule described herein comprises one or more mutations in one of both of the Fc domains that enhances binding kinetics of an immune complex comprising one or more molecules and a target antibody to FcγRIIB. In some embodiments, enhanced binding kinetics comprises at least 15%, at least 20%, at least 25%, at least 30%, at least 35%, at least 40%, at least 45%, or at least 50% or greater binding affinity. In some embodiments, enhanced binding kinetics comprises an increase in avidity, stability, strength, frequency, and/or duration of binding between the immune complex and FcγRIIB. In some embodiments, enhanced binding kinetics comprise an increase in the rate of association, a decrease in the rate of disassociation, and/or a change in the equilibrium dissociation constant.

In some embodiments, molecules described herein having a first and second Fc domain comprise one or more mutations in the first and/or second Fc domain to increase binding to FcγRIIB, wherein upon binding of two molecules to an autoantibody (e.g., an anti-TSHR autoantibody), an immune complex is formed that has enhanced binding kinetics with FcγRIIB relative to an immune complex that comprises the autoantibody (e.g., an anti-TSHR autoantibody) bound to two corresponding molecules with wild-type Fc domains.

In some embodiments, a molecule described herein that is not present in an immune complex has a moderate binding affinity to FcγRIIB (e.g., where the Fc domains of the molecule have slightly increased binding affinity to FcγRIIB compared to a molecule comprising wildtype Fc domains). In some embodiments, a molecule binds to FcγRIIB with an affinity within the range of about 1 μM to 0.001 μM. In some embodiments, a molecule binds to FcγRIIB with an affinity within the range of about 1 μM to 0.01 μM. In some embodiments, a molecule binds to FcγRIIB with an affinity within the range of about 0.1 μM to 0.01 μM. In some embodiments, a molecule described herein exhibits avidity-mediated binding to FcγRIIB when part of an immune complex comprising two molecules bound to an autoantibody (e.g., an anti-TSHR autoantibody). In some embodiments, a molecule described herein has increased binding to FcγRIIB when the molecule is present in an immune complex with two molecules bound to an autoantibody (e.g., an anti-TSHR autoantibody) compared to the same immune complex with only one molecule bound to the autoantibody (e.g., the anti-TSHR autoantibody). In some embodiments, a molecule described herein has increased binding to FcγRIIB when the molecule is present in an immune complex with two molecules bound to an autoantibody (e.g., an anti-TSHR autoantibody) compared to the autoantibody (e.g., an anti-TSHR autoantibody) alone. Without wishing to be bound by any theory, such avidity-mediated effects allow for selective binding and depletion of immune complexes, i.e., two molecules described herein and one autoantibody (e.g., an anti-TSHR autoantibody) and weaker binding to the molecules when they are not part of an immune complex. These characteristics allow for molecules described herein to remain circulating longer in the bloodstream of a subject before being cleared by FcγRIIB-mediated internalization and degradation.

Additionally, the present disclosure provides molecules comprising Fc domains that that have increased binding affinity for FcγRIIB and also have decreased or undetectable binding to certain activating Fc receptors. In some embodiments, an activating Fc receptor includes one or more of FcγRI, FcγRIIA167H, FcγRIIA167R, FcγRIIIA176F, FcγRIIIA176V, FcγRIIIB, and/or FcRn. In some embodiments, Fc domains of molecules described herein have decreased binding affinity to FcγRI, FcγRIIA167H, FcγRIIA167R, FcγRIIIA176F, FcγRIIIA176V, FcγRIIIB, and/or FcRn relative to the corresponding wild-type Fc domain. In some embodiments, Fc domains of molecules described herein have substantially no binding affinity to FcγRI, FcγRIIA167H, FcγRIIA167R, FcγRIIIA176F, FcγRIIIA176V, FcγRIIIB, and/or FcRn relative to the corresponding wild-type Fc domain. Such binding properties are beneficial in molecules described herein and may lessen risk of toxicity as there is less risk of activating the innate immune response (through activating Fc receptors) in response to the molecules being introduced into the body of a subject.

In some embodiments, a molecule described herein preferentially binds to immune cells expressing FcγRIIB over immune cells expressing FcγRIIA. In some embodiments, a molecule described herein has substantially no binding affinity for cells that do not express FcγRIIB (e.g., T cells, NK cells, neutrophils, and/or eosinophils). Immune cells known to express FcγRIIB include B cells, monocytes and/or basophils.

In some embodiments, a molecule described herein prevents binding of autoantibody (e.g., an anti-TSHR autoantibody) to its cognate autoantigen (e.g., TSHR autoantigen). In some embodiments, a molecule described herein neutralizes an autoantibody (e.g., an anti-TSHR autoantibody). In some embodiments, one or more molecules described herein form an immune complex with an autoantibody (e.g., an anti-TSHR autoantibody) and the immune complex is internalized and degraded by an immune cell expressing FcγRIIB. In some embodiments, an immune complex comprises one or more molecules (e.g., two or more molecules) bound to an autoantibody (e.g., an anti-TSHR autoantibody) and is cleared from circulation, e.g., destroyed, by any one of the mechanisms contemplated in FIG. 13. FcγRIIB is an internalizing receptor that binds to its target, internalizes the complex and shuttles the target to the lysosome for degradation. Without wishing to be bound by any theory, molecules described herein that have increased FcγRIIB binding may deplete target autoantibodies and/or antigen-specific B cells producing autoantibodies through various mechanisms including those shown in FIGS. 13A-D. FIG. 13B shows a potential mechanism of action which includes clearing autoantibodies by targeting FcγRIIB isoform 2 on liver sinusoidal endothelial cells (LSECs). In this exemplary mechanism of action, the binding domain of the molecule (e.g., an antigen domain) binds to target autoantibodies and the Fc domain binds to FcγRIIB isoform 2 on liver sinusoidal endothelial cells. Target autoantibodies are internalized into the liver sinusoidal endothelial cells and targeted to the lysosome for degradation. In another exemplary mechanism as shown in FIG. 13C, molecules described herein may target pathogenic B cells producing target autoantibodies, by targeting FcγRIIB isoform 1 on a B cell that comprises antigen-specific B cell receptor (BCR) (e.g., a target autoantibody expressed on the surface of the B cell), which leads to B cell apoptosis and inhibition. In another exemplary mechanism shown in FIG. 13D, molecules described herein may target FcγRIIB on T cells and prevent T-cell activation.

In some embodiments, an Fc domain described herein comprises one or more modifications such that a molecule described herein does not activate immune cells (e.g., does not activate immune cells to secrete pro-inflammatory cytokines, e.g., IL-6).

In some embodiments, molecules described herein do not bind to certain components of the complement system (e.g., C1q). In some embodiments, molecules described herein do not bind to C1q. In some embodiments, molecules described herein do not activate the complement system.

Methods of Generating Exemplary Molecules

The present disclosure features methods that include generating a molecule described herein.

Molecules as described herein may be produced using recombinant methods and compositions (see, e.g., U.S. Pat. No. 4,816,567). In some embodiments, an isolated nucleic acid encoding a molecule as described herein can be provided. Such nucleic acid may encode an amino acid sequence comprising the first and/or second polypeptide. In a further embodiment, one or more vectors comprising such nucleic acid can be provided. A vector can be a nucleic acid molecule capable of propagating another nucleic acid to which it is linked. The term can include the vector as a self-replicating nucleic acid structure as well as the vector incorporated into the genome of a host cell into which it has been introduced. Certain vectors can be capable of directing the expression of nucleic acids to which they are operatively linked.

In a further embodiment, a host cell comprising such nucleic acid can be provided. Host cells can be cells into which an exogenous nucleic acid has been introduced, including the progeny of such cells. Host cells can include "transformants" and "transformed cells," which can include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. In one such embodiment, a host cell can comprise (e.g., has been transformed with) a vector comprising a nucleic acid that encodes an amino acid sequence comprising a first polypeptide and a second polypeptide of a molecule. In some embodiments, a first vector comprises a nucleic acid that encodes an amino acid sequence comprising a first polypeptide of a molecule and a second vector comprising a nucleic acid that encodes an amino acid sequence comprising the second polypeptide of a molecule. In some embodiments, the host cell can be eukaryotic, e.g., a Chinese Hamster Ovary (CHO) cell, a lymphoid cell (e.g., Y0, NS0, Sp20 cell), or a Human Embryonic Kidney (HEK293) cell. In some embodiments, a method of making molecule and/or an antigen-binding domain described herein can be provided, wherein the method can comprise culturing a host cell comprising a nucleic acid encoding the molecule and/or an antigen-binding domain, as provided above, under conditions suitable for expression of the molecule and/or an antigen-binding domain, and optionally recovering the molecule from the host cell or host cell culture medium.

For recombinant production of a molecule and/or an antigen-binding domain, an isolated nucleic acid encoding a molecule and/or an antigen-binding domain, e.g., as described above, can be inserted into one or more vectors for further cloning and/or expression in a host cell. Such nucleic acid may be readily isolated and sequenced using conventional procedures.

Suitable host cells for cloning or expression of antibody-encoding vectors can include prokaryotic or eukaryotic cells described herein. For example, molecules and/or an antigen-binding domains may be produced in bacteria, e.g., when glycosylation and Fc effector function are not needed (see, e.g., U.S. Pat. Nos. 5,648,237, 5,789,199, and 5,840,523; Charlton, Methods in Molecular Biology 248:245-254 (2003)). After expression, the molecule and/or an antigen-binding domain may be isolated from the bacterial cell paste in a soluble fraction and can be further purified.

In addition to prokaryotes, eukaryotic microbes such as filamentous fungi or yeast can be suitable cloning or expression hosts for molecule and/or an antigen-binding domain-encoding vectors (see, e.g., Gerngross Nat. Biotech. 22:1409-1414 (2004) and Li et al. Nat. Biotech. 24:210-215 (2006)). Suitable host cells for the expression of glycosylated antibody can also be derived from multicellular organisms, including invertebrates and vertebrates. Examples of invertebrates can include plant and insect cells (see, e.g., U.S. Pat. Nos. 5,959,177, 6,040,498, 6,420,548, 7,125,978, and 6,417,429). Examples of vertebrate cells can include mammalian cell lines, monkey kidney CV1 line transformed by SV40 (COS-7); human embryonic kidney line (293 or 293T cells as described, e.g., in Graham et al. J. Gen Virol. 36:59-74 (1977)); baby hamster kidney cells (BHK); mouse sertoli cells (TM4 cells); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells; MRC 5 cells; FS4 cells; Chinese hamster ovary (CHO) cells, including DHFR-CHO cells; and myeloma cell lines such as Y0, NS0 and Sp2/0. (see, e.g., Yazaki and Wu, Methods in Molecular Biology 248: 255-268 (2003)).

Molecules described herein may be purified by any technique. For example, not wishing to be bound by theory, molecules described herein can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

As discussed herein, some or all of the components of a molecule may also be linked using "click" or other chemistry, optionally via an amino acid or synthetic linker. For such molecules some or all of the components of the molecule may be prepared recombinantly and then chemically modified for conjugation. Suitable methods are well known in the art, e.g., as used in the preparation of antibody-drug conjugates.

Purified molecules and antigen-binding domains included in such can be characterized by, for example, ELISA, ELISPOT, flow cytometry, immunocytology, BIACORE analysis, Octet BLI analysis, KINEXA kinetic exclusion assay, SDS-PAGE and Western blot, or by HPLC analysis as well as by a number of other functional assays disclosed herein. The contents of all cited references (including literature references, issued patents, published patent applications, and co-pending patent applications) cited throughout this application are hereby expressly incorporated by reference.

Applications

The present disclosure provides technologies for selective depletion of autoantibodies implicated in autoimmune disease such as Graves' Disease and Thyroid Eye Disease.

In some embodiments, a molecule can be administered in a pharmaceutical composition can be used in combination with, by administering before, concurrently or after administration of a second therapy.

In some embodiments, molecules of the present disclosure are used to treat a subject suffering from an autoimmune disease (an autoimmune disease caused by anti-TSHR autoantibodies) that would benefit from the selective neutralization and/or depletion of autoantibodies. Such molecules are generated such that they bind to an internalizing receptor and include an autoantibody-binding domain that binds to autoantibodies. Molecules may also include a modification to enhance binding to internalizing receptors (e.g., FcγRIIB).

For use in therapeutic methods, molecules of the present disclosure would be formulated, dosed, and administered in a fashion consistent with good medical practice. Factors for consideration in this context include the particular disease or disorder being treated, the particular subject being treated, the clinical condition of the individual subject, the cause of the disorder, the site of delivery of the agent, the method of administration, the scheduling of administration, and other factors known to medical practitioners.

In some embodiments, the present disclosure provides a method for treating a disease. In some embodiments, the method comprises administering to a subject having such disease a therapeutically effective amount of a molecule described herein. In some embodiments, a composition is administered to said subject, comprising a molecule described herein in a pharmaceutically acceptable form. In some embodiments, the disease to be treated is an autoimmune disease. In some embodiments, the autoimmune disease is caused by anti-TSHR antibodies. In some embodiments, the autoimmune disease is Graves' Disease, Graves' Orbitopathy (i.e., Thyroid Eye Disease). In some embodiments the method further comprises administering to the subject a therapeutically effective amount of at least one additional therapeutic agent. A "subject" may be a mammal, including a human.

Any of such methods can optionally comprise administering an effective amount of at least one composition or pharmaceutical composition comprising at least one molecule described herein to a subject in need of such modulation, treatment, diagnosis, and/or therapy (e.g., a subject suffering from an autoimmune disease such as Graves' Disease and Thyroid Eye Disease).

In some embodiments, provided methods include therapeutic methods that comprise administering an effective amount of a composition that comprises and/or delivers a molecule described herein to a subject such that the molecule binds an autoantibody and an internalizing receptor, such that the complex is internalized and targeted to the lysosome. In some embodiments an autoantibody is an anti-TSHR autoantibody and the internalizing receptor is FcγRIIB.

In some embodiments, provided methods include therapeutic methods that comprise administering an effective amount of a composition that comprises and/or delivers a molecule described herein to a subject such that the molecule binds a target autoantibody (e.g., anti-TSHR autoantibody) and an internalizing receptor (e.g., FcγRIIB) on a cell, such that the complex is internalized and targeted to the lysosome. In some embodiments, an effective amount of a composition comprises an effective amount of molecules described herein, wherein upon binding of two molecules to the target autoantibody (e.g., anti-TSHR autoantibody), an immune complex is formed that has enhanced binding kinetics with FcγRIIB relative to an immune complex that comprises the target antibody bound to two corresponding molecules with wild-type Fc domains. Such activity mediates clearance of immune complexes comprising the target antibody when bound to the molecule. In some embodiments, a molecule described herein may also include an antigen-binding domain (see FIG. 3). In some embodiments, an antigen-binding domain binds to an internalizing receptor such as FcγRIIB, ASPGR and/or FcRn. A molecule that targets an internalizing receptor such as FcγRIIB may inhibit B cells on which the auto-antibody is expressed (e.g., as described in Chu et al., *Mol Immunol* 45, 3926-3933 (2008), which is herein incorporated by reference in its entirety).

Therapeutic methods described herein can optionally further comprise co-administration or combination therapy for treating such diseases, wherein the administering a composition comprises a molecule described herein, further comprises administering, before concurrently, and/or after, at least one additional therapeutic agent.

The present disclosure also provides methods of treating a subject suffering from or susceptible to an autoimmune disease (e.g., Graves' Disease, Graves' Orbitopathy (also called Thyroid Eye Disease), or another autoimmune disease involving anti-TSHR antibodies), for example, by administering to the subject a pharmaceutical composition comprising a molecule described herein, a nucleic acid molecule encoding the molecule. In some embodiments, such a treatment decreases or ameliorates one or more signs or symptoms of an autoimmune disease. For example, in a subject with Graves' Disease, treatment with a pharmaceutical composition comprising a molecule described herein may decrease or ameliorate one or more signs or symptoms of Graves' Disease such as protrusion of the eyes, upper lid retraction, diplopia, and irritation of the periorbital tissue and conjunctiva (in Graves' Orbitopathy), hyperthyroidism, palpitations, tremulousness, heat intolerance, weight loss, and anxiety.

In some embodiments, treatment with a molecule described herein reduces the levels of target autoantibodies (e.g., anti-TSHR autoantibodies) in a subject or in a biological sample relative to a level before administration. In some embodiments, a level of target autoantibodies (e.g., anti-TSHR autoantibodies) is reduced by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% relative to a level before the administration. In some embodiments, treatment with a molecule described herein reduces target autoantibodies (e.g., anti-TSHR autoantibodies) in a subject for a sustained period of time, e.g., at least 1 day, 2 days, 3 days, 4 days, 5 days, 6 days, 1 week, 2 weeks, 3 weeks, 4 weeks, 5 weeks, 6 weeks, 7 weeks, 8 weeks, 10 weeks, 12 weeks, or longer.

Pharmaceutical Compositions

In some embodiments, a molecule described herein may be formulated as a pharmaceutical composition and administered to a subject (e.g., to treat an autoimmune disease). In various embodiments, molecules described herein can be incorporated into pharmaceutical compositions. Such a pharmaceutical composition can be useful, e.g., for the prevention and/or treatment of diseases, e.g., autoimmune diseases. Pharmaceutical compositions can be formulated by methods known to those skilled in the art (such as described in Remington's Pharmaceutical Sciences, 17th edition, ed. Alfonso R. Gennaro, Mack Publishing Company, Easton, Pa. (1985)).

In some embodiments, a pharmaceutical composition comprises a nucleic acid molecule comprising a nucleotide sequence encoding a molecule described herein and a pharmaceutically acceptable carrier. In some embodiments, a molecule is expressed in a host cell containing a nucleic acid molecule comprising a nucleotide sequence encoding a molecule described herein. In some embodiments, a molecule described herein is encoded by a vector (e.g., a viral vector such as a retroviral vector, a lentiviral vector, an adeno-associated viral (AAV) vector, or an adenoviral vector).

In some embodiments, a pharmaceutical composition comprises a first molecule described herein or a nucleic acid molecule encoding the molecule, and also comprises a therapeutic agent or a nucleic acid molecule encoding a second therapeutic agent that selectively depletes pathogenic plasma cells that produce the autoantibodies; and a pharmaceutically acceptable carrier.

In some embodiments, a pharmaceutical composition can be formulated to include a pharmaceutically acceptable carrier or excipient. Examples of pharmaceutically acceptable carriers include, without limitation, any and all solvents, dispersion media, coatings, antibacterial and antifungal agents, isotonic and absorption delaying agents, and the like that are physiologically compatible. Compositions of the present disclosure can include a pharmaceutically acceptable salt, e.g., an acid addition salt or a base addition salt.

In some embodiments, a composition including a molecule as described herein, e.g., a sterile formulation for injection, can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, such as, for example, an alcohol such as ethanol and/or a polyalcohol such as propylene glycol or polyethylene glycol, and/or a nonionic surfactant such as polysorbate 80 or HCO-50.

As disclosed herein, a pharmaceutical composition may be in any form known in the art. Such forms include, e.g., liquid, semi-solid and solid dosage forms, such as liquid solutions (e.g., injectable and infusible solutions), dispersions or suspensions, tablets, pills, powders, liposomes and suppositories.

Selection or use of any particular form may depend, in part, on the intended mode of administration and therapeutic application. For example, compositions containing a composition intended for systemic or local delivery can be in the form of injectable or infusible solutions. Accordingly, compositions can be formulated for administration by a parenteral mode (e.g., intravenous, subcutaneous, intraperitoneal, or intramuscular injection). As used herein, parenteral administration refers to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion.

Route of administration can be parenteral, for example, administration by injection, transnasal administration, transpulmonary administration, or transcutaneous administration. Administration can be systemic or local by intravenous injection, intramuscular injection, intraperitoneal injection, or subcutaneous injection.

In some embodiments, a pharmaceutical composition of the present disclosure can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

In some embodiments, a composition described herein can be therapeutically delivered to a subject by way of local administration. As used herein, "local administration" or "local delivery," can refer to delivery that does not rely upon transport of the composition or agent to its intended target tissue or site via the vascular system. For example, the composition may be delivered by injection or implantation of the composition or agent or by injection or implantation of a device containing the composition or agent. In some embodiments, following local administration in the vicinity of a target tissue or site, the composition or agent, or one or more components thereof, may diffuse to an intended target tissue or site that is not the site of administration.

In some embodiments, compositions can be formulated with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, administration of a molecule as described herein is achieved by administering to a subject a nucleic acid encoding the molecule. In some embodiments, a nucleic acid is an RNA (e.g., an mRNA). In some embodiments an RNA encoding a molecule described herein is associated with a delivery agent, i.e., a substance or entity that is non-covalently or covalently associated with a molecule or is co-administered with a molecule and serves one or more functions that increase the stability and/or efficacy of the biologically active agent beyond that which would result if the biologically active agent was delivered (e.g., administered to a subject) in the absence of the delivery agent. For example, a delivery agent may protect an RNA from degradation (e.g., in blood), may facilitate entry of an RNA into cells or into a cellular compartment of interest (e.g., the cytoplasm), and/or may enhance associations with particular cells containing the molecular target to be modulated. Those of ordinary skill in the art are aware of numerous delivery agents that may be used to deliver inhibitory RNA, e.g., mRNAs. See Kanasty, R., et al. Nat Mater. 12(11):967-77 (2013). In some embodiments, e.g., for administering an RNA systemically, the RNA may be associated with a delivery agent such as a nanoparticle, a dendrimer, a polymer, liposomes, or a cationic delivery system. Without wishing to be bound by any theory, positively charged cationic delivery systems are believed to facilitate binding of a negatively charged RNA and also enhance interactions at the negatively charged cell membrane to permit efficient uptake of an RNA by the cell. Lipids (e.g., cationic lipids, or neutral lipids), dendrimers, or polymers may be bound to an inhibitory RNA or may form a vesicle or micelle that encapsulates an inhibitory RNA. Methods for making and administering complexes comprising a cationic agent and an RNA are known in the art. In some embodiments it is particularly contemplated to use any of the delivery agents described in US Pub. 2016/0298124. In some embodiments an RNA encoding a molecule described herein is administered in association with a lipid or lipid-containing particle. In some embodiments an RNA is administered in association with a cationic polymer (which may be a polypeptide or a non-polypeptide polymer), a lipid, a peptide, PEG, cyclodextrin, or combination thereof, which may be in the form of a nanoparticle or microparticle. The lipid or peptide may be cationic. A nanoparticle may have a targeting moiety and/or cell-penetrating moiety or membrane active moiety covalently or noncovalently attached thereto. Nanoparticles, such as lipid nanoparticles, are described in, e.g., Tatiparti et al., *Nanomaterials* 7:77 (2017).

Nucleic acids encoding a molecule described herein can be incorporated into a gene construct to be used as a part of a gene therapy protocol to deliver nucleic acids that can be used to express and produce a molecule within cells. Expression constructs of such components may be administered in any therapeutically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1 (HSV-1), or recombinant bacterial or eukaryotic plasmids. Viral vectors can transfect cells directly; plasmid DNA can be delivered with the help of, for example, cationic liposomes (lipofectin) or derivatized, polylysine conjugates, gramicidin S, artificial viral envelopes or other such intracellular carriers, as well as direct injection of the gene construct or $CaPO_4$ precipitation (see, e.g., WO 2004/060407). Examples of suitable retroviruses include pLJ, pZIP, pWE and pEM which are known to those skilled in the art (see, e.g., Eglitis et al., *Science* 230:1395-1398 (1985); Danos and Mulligan *Proc. Natl. Acad Sci. USA* 85:6460-6464 (1988); Wilson et al., *Proc. Natl. Acad Sci. USA* 85:3014-3018 (1988); Armentano et al., *Proc. Natl. Acad Sci. USA* 87:6141-6145 (1990); Huber et al., *Proc. Natl. Acad Sci. USA* 88:8039-8043 (1991); Ferry et al., *Proc. Natl. Acad Sci. USA* 88:8377-8381 (1991); Chowdhury et al. *Science* 254:1802-1805 (1991); van Beusechem et al., *Proc. Natl. Acad Sci. USA* 89:7640-7644 (1992); Kay et al., *Human Gene Therapy* 3:641-647 (1992); Dai et al., *Proc. Natl. Acad Sci. USA* 89:10892-10895 (1992); Hwu et al., *J Immunol* 150:4104-4115 (1993); U.S. Pat. Nos. 4,868,116 and 4,980,286; and PCT Publication Nos. WO 1989/07136, WO 1989/02468, WO 1989/05345, and WO 1992/07573). Another viral gene delivery system utilizes adenovirus-derived vectors (see, e.g., Berkner et al., *BioTechniques* 6:616 (1988); Rosenfeld et al., *Science* 252:431-434 (1991); and Rosenfeld et al., *Cell* 68:143-155 (1992)). Suitable adenoviral vectors derived from the adenovirus strain Ad type 5 dl324 or other strains of adenovirus (e.g., Ad2, Ad3, Ad7, etc.) are known to those skilled in the art. Yet another viral vector system useful for delivery of the subject gene is the adeno-associated virus (AAV). See, e.g., Flotte et al., *Am J Respir Cell Mol Biol* 7:349-356 (1992); Samulski et al., *J Virol* 63:3822-3828 (1989); and McLaughlin et al., *J Virol* 62:1963-1973 (1989).

A pharmaceutical solution can include a therapeutically effective amount of a composition described herein. Such effective amounts can be readily determined by one of ordinary skill in the art based, in part, on the effect of the administered composition, or the combinatorial effect of the composition and one or more additional agents, if more than one agent is used. A therapeutically effective amount of a composition described herein can also vary according to factors such as the disease state, age, sex, and weight of the individual, and the ability of the composition (and one or more additional agents) to elicit a desired response in the individual, e.g., amelioration of at least one condition parameter, e.g., amelioration of at least one symptom of an autoimmune disease. For example, a therapeutically effective amount of a composition described herein can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the compositions described herein can further be evaluated in, e.g., Phase I dose escalation studies. See, e.g., van Gurp et al., *Am J Transplantation* 8(8):1711-1718 (2008); Hanouska et al., *Clin Cancer Res* 13(2, part 1):523-531 (2007); and Hetherington et al., *Antimicrobial Agents and Chemotherapy* 50(10): 3499-3500 (2006).

Toxicity and therapeutic efficacy of compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. A composition described herein that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

Those of skill in the art will appreciate that data obtained from cell culture assays and animal studies can be used in formulating a range of dosage for use in humans. Appropriate dosages of compositions described herein lie generally within a range of circulating concentrations of the compositions that include the $ED_{50}$ with little or no toxicity. The dosage may vary within this range depending upon the dosage form employed and the route of administration utilized. For a composition described herein, the therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art. Although methods and materials similar or equivalent to those described herein can be used, suitable methods and materials are described herein.

The disclosure is further illustrated by the following examples. The examples are provided for illustrative purposes only. They are not to be construed as limiting the scope or content of the disclosure in any way.

ADDITIONAL EMBODIMENTS

In some embodiments, molecules described herein comprise: a first polypeptide comprising a first Fc domain and an autoantibody-binding domain (e.g., an autoantigen domain, or fragment or variant thereof) that binds to autoantibodies; and a second polypeptide comprising a second Fc domain; wherein the first Fc domain and the second Fc domain form a homodimer or heterodimer of the first polypeptide and the second polypeptide; and wherein the first and/or second Fc domain comprises one or more mutated amino acid residues that increases binding to FcγRIIB. Molecules described herein comprising increased binding to FcγRIIB target and bind to particular autoantibodies that implicate various autoimmune diseases through the autoantigen-binding domain (e.g., an autoantigen domain, or fragment or variant thereof), and are shuttled to the lysosome of a cell for degradation through FcγRIIB.

Combining increased binding to the endocytic receptor FcγRIIB and also including a particular autoantigen (or fragment or variant thereof) allows for selective depletion of autoantibodies that target the autoantigen. One of skill in the art will appreciate that such molecules may be used to treat a variety of autoimmune diseases that are implicated by particular autoantibodies.

In some embodiments, a molecule described herein may be used to treat an autoimmune disease implicated by autoantibodies targeting thyroid stimulating hormone receptor (TSHR). Anti-TSHR autoantibodies in a subject can lead to development of autoimmune diseases such as Graves' Disease (GD) and Thyroid Eye Disease. In some embodiments, molecules described herein may be used in the treatment of GD or other autoimmune diseases caused by anti-TSHR autoantibodies. In some embodiments, a molecule described herein used to treat an autoimmune disease (e.g., GD) comprises a TSHR autoantigen domain (or a fragment or variant thereof) that targets anti-TSHR autoantibodies and an Fc domain that comprises one or more modifications that increase its binding to FcγRIIB, as described herein.

Other autoantibodies that are involved in the development of particular autoimmune diseases are known in the art, and molecules described herein may include all or a portion of the particular autoantigen domains that are targeted by these autoantibodies in order to selectively target and deplete these autoantibodies.

EXAMPLES

Example 1: Generation and Testing of Exemplary Molecules

The present Example demonstrates generation and testing of exemplary molecules described herein that target and selectively deplete circulating autoantibodies. In this Example, the targeted autoantibodies are anti-TSHR autoantibodies, which implicate various diseases like Graves' Disease (GD) and Thyroid Eye Disease.

Generation of Exemplary Molecules

Autoantibody Binding Domain: Exemplary molecules in this Example were designed to include an autoantigen domain as the autoantibody-binding domain. Specifically, human TSHR was selected as the autoantigen. Fragments and mutations in the human wild-type TSHR sequence were tested for their ability to selectively target and bind to anti-TSHR autoantibodies.

Two fragments of wildtype TSHR were used as a starting point (as shown in SEQ ID NO: 1 and SEQ ID NO: 5). The fragment noted as "260 WT" or "TSHR260" (SEQ ID NO: 1) is a fragment of full TSHR sequence (SEQ ID NO: 9) corresponding to amino acid positions 22-260 of SEQ ID NO: 9. The fragment noted as "289 WT" or "TSHR289" (SEQ ID NO: 5) is a fragment of full TSHR sequence (SEQ ID NO: 9) corresponding to amino acid positions 22-289 of SEQ ID NO: 9.

TSHR fragments were further mutated to optimize stability and expression. The mutations tested included: a "2P" mutation, which includes the following mutated amino acid residues: R112P, D143P; a "2P2R" mutation, which includes the following mutated amino acid residues: R112P, D143P, V169R, and I253R; a "2P1S" mutation, which includes the following mutated amino acid residues: R112P, D143P, H63S; and a "2P2R aglycosylated" mutation, which includes the "2P2R" mutation and mutation of N to Q at all N-linked glycosylation sites (with sequence motif NXS or NXT, where X can be any amino acid except for P) in order to eliminate glycosylation; each with respect to the wild-type TSHR sequence. THSR260 variants with these mutations (sequences for THSR260 wild-type and variants 2P, 2P2R and 2P1S are shown in Table 5A) were fused to an Fc domain, expressed in CHO cells, purified using standard protein A affinity capture, and assessed for both purity and titer as shown in Table 5B below.

TABLE 5A

Exemplary TSHR Antigen Sequences

| Antigen | Sequences | | SEQ ID NO |
|---|---|---|---|
| TSHR260 | WT | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNTRNLTYIDPDALKELPLLKELGIENTGL<br>KMFPDLTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 1 |
| TSHR260<br>2P | R112P<br>D143P | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIPVNAFQGLCN<br>ETLTLKLYNNGFTSVQGYAFNGTKLDAVYLNKNKYLTVI<br>DKDAFGGVYSGPSLLDVSQTSVTALPSKGLEHLKELIAR<br>NTWTL | 2 |
| TSHR260<br>2P2R | R112P<br>D143P<br>V169R<br>I253R | MGCSSPPCECHQEEDFRVTCKDIQRIPSLPPSTQTLKLI<br>ETHLRTIPSHAFSNLPNISRIYVSIDVTLQQLESHSFYN<br>LSKVTHIEIRNT**P**NLTYIDPDALKELPLLKELGIENTGL<br>KMFP**P**LTKVYSTDIFFILEITDNPYMTSIP**R**NAFQGLCN<br>ETLTLKLYNNGFTSVQGYAFNGTKLDAVYLNKNKYLTVI<br>DKDAFGGVYSGPSLLDVSQTSVTALPSKGLEHLKEL**R**AR<br>NTWTL | 3 |
| TSHR260<br>2P1S | R112P<br>D143P<br>H63S | MGCSSPPCECHQEEDFRVTCKDIQRIPSLPPSTQTLKLI<br>ET**S**LRTIPSHAFSNLPNISRIYVSIDVTLQQLESHSFYN<br>LSKVTHIEIRNT**P**NLTYIDPDALKELPLLKELGIFNTGL<br>KMFP**P**LTKVYSTDIFFILEITDNPYMTSIPVNAFQGLCN<br>ETLTLKLYNNGFTSVQGYAFNGTKLDAVYLNKNKYLTVI | 4 |

TABLE 5A-continued

| Exemplary TSHR Antigen Sequences | | |
|---|---|---|
| Antigen | Sequences | SEQ ID NO |
| | DKDAFGGVYSGPSLLDVSQTSVTALPSKGLEHLKELIAR NTWTL | |

Additional TSHR260 variants were generated by introducing an "SP" mutation, which includes the following mutated amino acid residue: S94P; an "SP GIP" mutation, which includes the following mutated amino acid residues: S94P, G194P; an "SP GIP KP" mutation, which includes the following mutated amino acid residues: S94P, G194P, K218P; a "VP SP KP" mutation, which includes the following mutated amino acid residues: V87P, S94P, K218P; a "VP SP GIP" mutation, which includes the following mutated amino acid residues: V87P, S94P, G194P; a "GIP KP" mutation, which includes the following mutated amino acid residues: G194P, K218P; a "VP SP LIP KP" mutation, which includes the following mutated amino acid residues: V87P, S94P, G137P, K218P; and an "SP GP GP KP" mutation, which includes the following mutated amino acid residues: S94P, G137P, G188P, K218P. THSR260 variants with these mutations were fused to an Fc domain, expressed in CHO cells, purified using standard protein A affinity capture, and assessed for both purity and titer as shown in Table 5B below.

TABLE 5B

| Purity and yield of exemplary TSHR260 variants (all based on TSHR260) fused to Fc domain | | |
|---|---|---|
| TSHR260 variant | Purity (%) | Yield (g/L) |
| WT | 21 | 0.058 |
| 2P | 62 | 0.175 |
| 2P2R | 76 | 0.678 |
| 2P1S | 51 | 0.680 |
| 2P2R aglycosylated | 41 | 0.105 |
| SP | 36 | 0.065 |
| SP GP | 42 | 0.092 |
| SP GP KP | 55 | 0.111 |
| VP SP KP | 59 | 0.179 |
| VP SP GP | 57 | 0.183 |
| GP KP | 65 | 0.112 |
| VP SP GP KP | 14 | 0.114 |
| SP GP GP KP | 12 | 0.144 |

Table 5B shows that the TSHR260 2P2R variant showed the highest purity and yield.

Select variants from those described above in Table 5B were also assessed as bispecific molecules. For this assessment each variant was fused to an Fc domain that included a Fab (from either a Daratumumab antibody, REA104, Belantamab, or Isatuximab), in order to improve initial expression. The individual constructs were transiently expressed in 100 mL culture of ExpiCHO cells for up to 9 days. The clarified supernatants were then purified by Protein A (MabSelect Sure) using standard procedures. The purified proteins were quantified using A280 and tested for purity using both SEC-HPLC and CD-SDS. The titer of each given TSHR autoantigen domain variant was determined by [total mg from pooled ProA fractions x % monomeric (HPLC-SEC)]/0.1 L culture. Results showed that again the TSHR260 2P2R variant showed the highest titer and purity, as well as the highest amount of product in monomeric molecules. The TSHR260 2P2R variant was further examined for expression titer and product quality when expressed as a Fc-fusion and purified by Protein A and preparative SEC. Results in Table 6 below show that this variant showed good titer and product quality after purification.

TABLE 6

| TSHR260 2P2R IgG1 characterization TSHR260 2P2R IgG1 | |
|---|---|
| Molecular Weight (kDa) | First polypeptide/ Second polypeptide 52.4/25.2 |
| Expression Host | CHO cells |
| Expression System | Transient |
| Expression Volume (ml) | 200 |
| Titer (g/L) | 0.80 |
| Conc. (mg/mL) | 5.56 |
| Volume (mL) | 12.33 |
| Yield (mg) | 68.55 |
| Purity by SEC-HPLC (%) | 99.26 |
| Formulation Buffer | 20 mM Histidine, 150 mM NaCl, pH 6.0 |

Figures 6A, 6B:
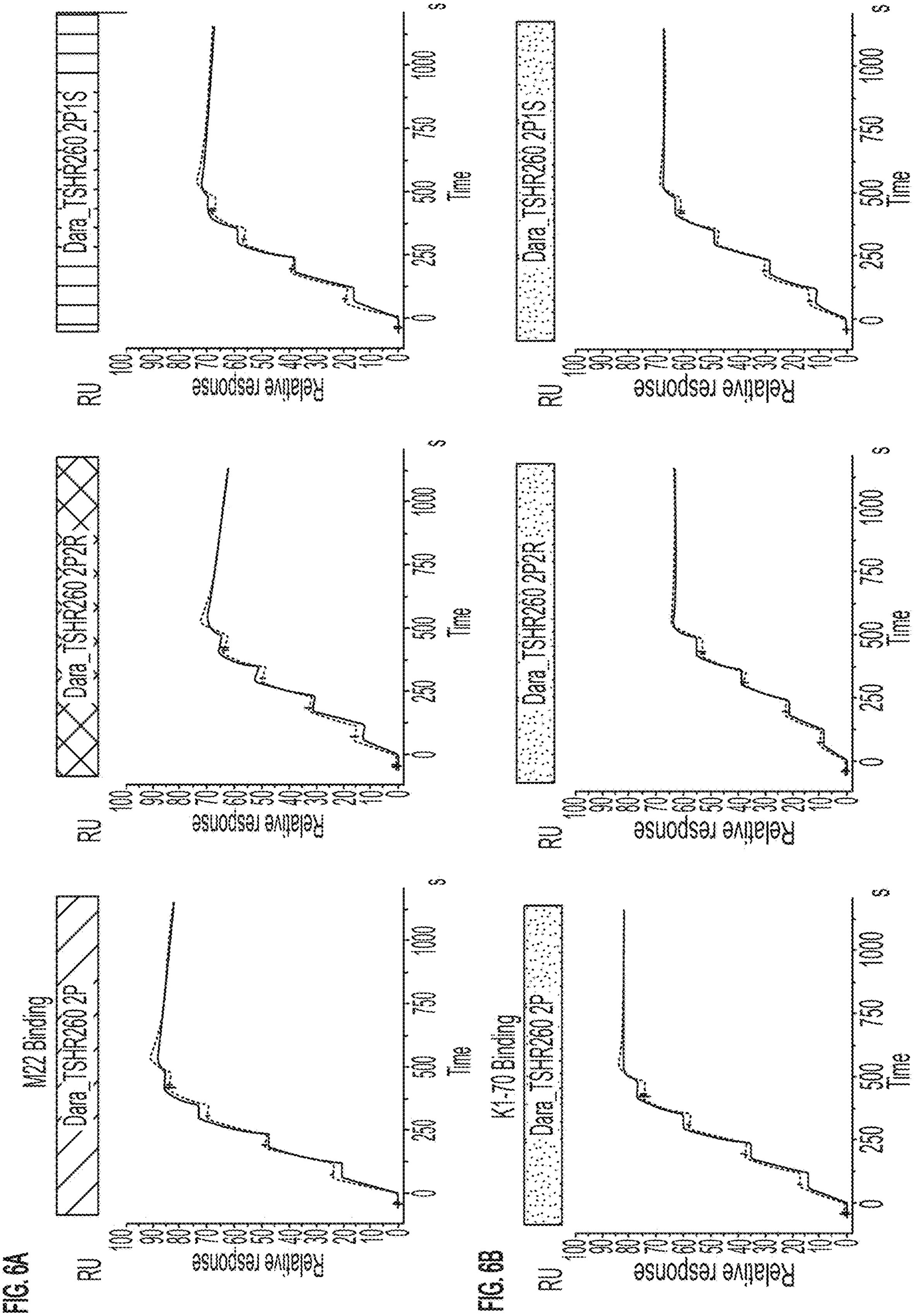
FIGS. 6A-6B show results from a binding assay with anti-TSHR autoantibodies M22 and K1-70 as Fab fragments.
Figure 7:
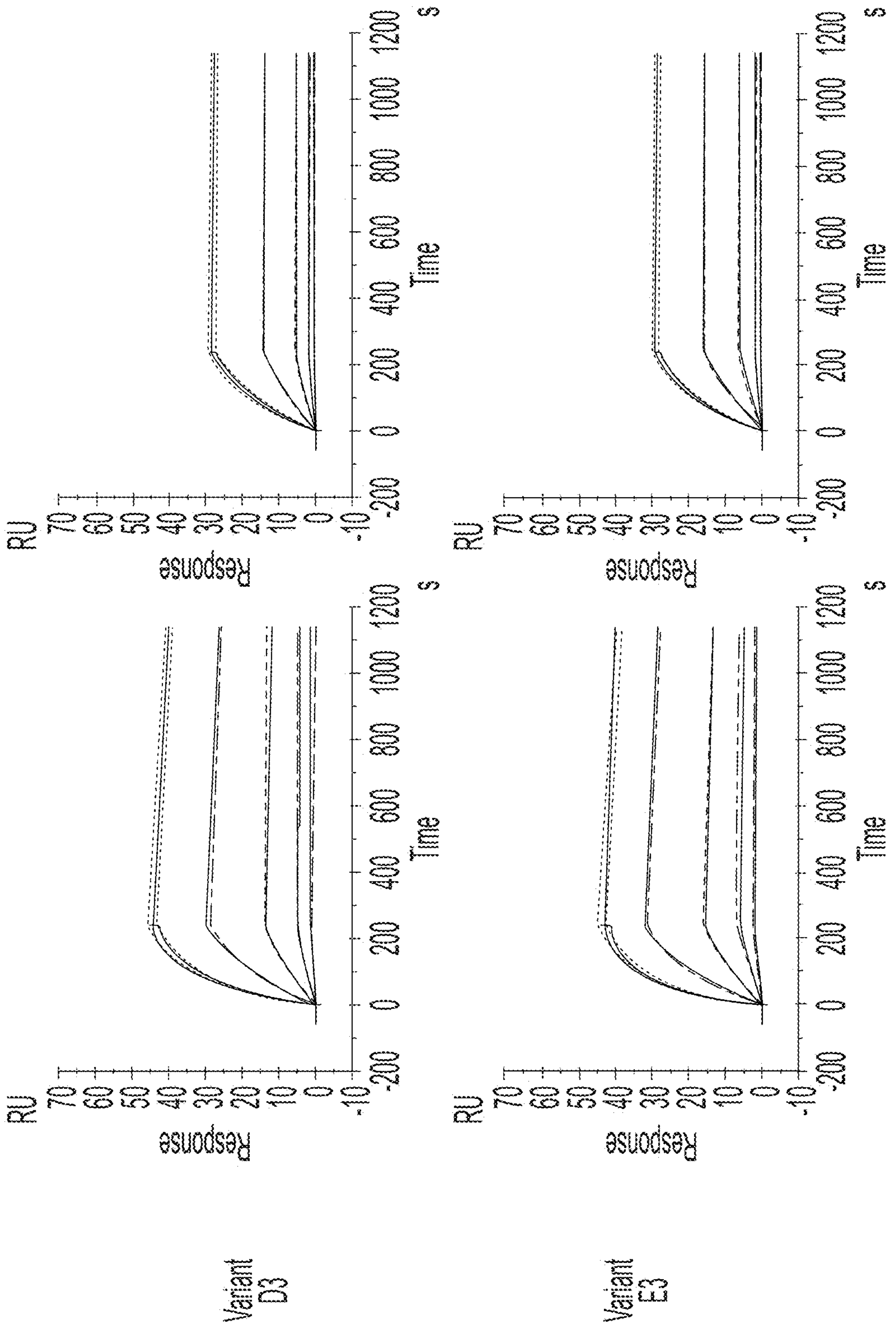
FIG. 7 shows results from a binding assay with anti-TSHR autoantibodies M22, K1-70, CS-17, and K1-18 as full length IgGs. It shows that M22, K1-70, CS-17, and K1-18 bind to TSHR260 variant 2P2R fused with various Fc domains (Variant D3 and Variant E3) using multi-cycle kinetics at pH 7.4.
Figure 7:
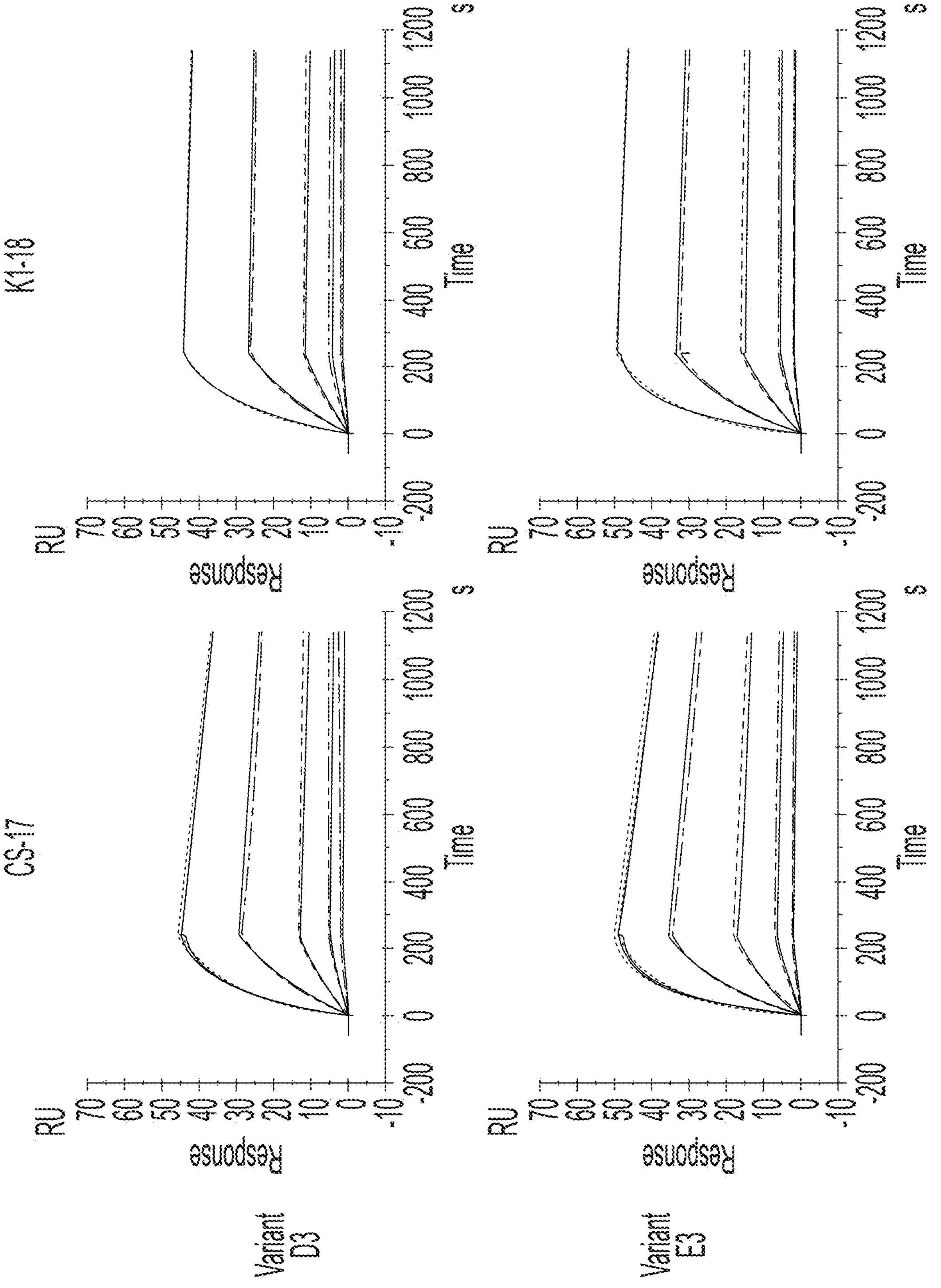

Select TSHR260 variants from those described above in Table 5B were also assessed for their ability to bind to anti-TSHR autoantibodies M22 and K1-70. For this experiment, TSHR260 variants (2P, 2P2R, and 2P1S) were fused with various Fc domains that also included a Fab (Daratumumab). Results in FIGS. 6A-6B show that both M22 (FIG. 6A) and K1-70 (FIG. 6B) Fab fragments bind to TSHR260 variants 2P, 2P2R, and 2P1S at pH 7.4 using single-cycle kinetics. Additionally, the results showed that binding was preserved at pH 6.0 (data not shown). FIG. 7 shows M22, K1-70, CS-17, and K1-18 as full length IgGs binding to TSHR260 variant 2P2R fused with various Fc domains (Variant D3 and Variant E3) using multi-cycle kinetics at pH 7.4.

Fc Domain: Exemplary molecules in this Example were designed to include Fc domains comprising particular mutations and modifications.

Human IgG1 Fc domains were chosen to be included in the molecules generated and tested in this Example. Human IgG1 naturally binds FcRn at an acidic pH, which allows it to, upon binding FcRn and internalization into a cell, be recycled back to the surface of the cell and not to be degraded in the lysosome.

In some molecules, Fc mutations were introduced to increase binding of the Fc domains to human FcγRIIB. Such mutations include: S267E and L328F and/or P238D, according to EU numbering. Such mutations allow for binding to FcγRIIB at neutral pH. Without wishing to be bound by any theory, upon binding, the molecule/autoantibody complex may be internalized into the cell and targeted to the lysosome for degradation. Such a mechanism destroys autoantibodies, while preserving free molecules in circulation.

In some molecules, Fc mutations were introduced to increase binding of the Fc domains to the human neonatal receptor (FcRn). Specifically, mutations were introduced to increase binding of the Fc domains to FcRn in neutral pH environments (e.g., extracellular environment). Such mutations include a combination that includes the following mutations: M252Y, S254T, T256E, H433K, N434F (i.e., "MST-HN"), according to EU numbering. Without wishing to be bound by any theory, such mutations may be included in the molecules described herein in order to increase binding of the Fc domain to FcRn on the surface of a cell in a neutral pH environment, such that there will be increased receptor-mediated internalization into cells and shuttling of the autoantibodies (bound to the molecule) to the lysosome.

In addition, mutations were also introduced with the MST-HN mutations to ablate binding affinity for human Fc-gamma receptors (FcγRs). Such mutations include the following mutations: G236R and L328R ("RR") and were introduced to decrease binding to one or more Fc-gamma receptors. This modification prevents immune crosslinking (i.e., of a molecule, autoantibody, FcγRs) that leads to inflammatory responses. Such mutations may focus the primary mechanism of action of the molecules to the targeted internalization and subsequent degradation of autoantibodies.

In this Example, Fc mutations were also introduced in certain molecules to promote heterodimerization of the two polypeptides, where each polypeptide comprises an Fc domain, and the first and second Fc domains heterodimerize in order to generate the full molecule. Such mutations are known as knobs-in-holes (KIH) modifications. The specific mutations used in this Example include: T366W, and S354C mutation (first Fc domain) and T366S, L368A, Y407V, and Y349C (second Fc domain). One of skill in the art will understand that the present disclosure encompasses molecules where the T366W and S354C mutations are included on second Fc domain (instead of the first Fc domain) and the T366S, L368A, Y407V, and Y349C mutations are included on the first Fc domain (instead of the second Fc domain). One of skill in the art will also understand that other known KIH mutations or other Fc modifications are known in the art to promote heterodimerization and may be used in the molecules described in this Example and as described in the disclosure.

In some molecules, Fc mutations were also introduced to increase the half-life of the molecule. The specific mutations used in this Example include the following mutations: M428L and N434S ("LS") and M252Y, S254T and T256E ("MST" or "YTE"). One of skill in the art will understand that other known mutations or modifications are known in the art to increase half-life and may be used in the molecules described in this Example and as described in the disclosure.

Exemplary Fc domain sequences used in the molecules made and tested in this Example are shown below in Table 7.

TABLE 7

Exemplary Fc Domain Sequences

| Fc Sequences | | Sequences | SEQ ID NO |
|---|---|---|---|
| Human IgG1 Fc 1.1 Knob S354C/T366W, G236R/L328R, M252Y/S254T/ T256E, H433K/N434F | Antigen Arm for Ag Depletion | DKTHTCPPCPAPELLRGPSVELFPPKPKDTLYITR<br>EPEVTCVVVDVSHEDPEVKENWYVDGVEVHNAKTK<br>PREEQYNSTYRVVSVLTVLHQDWLNGKEYKCKVSN<br>KARPAPIEKTISKAKGQPREPQVYTLPPCRDELTK<br>NQVSLWCLVKGFYPSDIAVEWESNGQPENNYKTTP<br>PVLDSDGSFFLYSKLTVDKSRWQQGNVFSCSVMHE<br>ALKFHYTQKSLSLSPGK | 103 |
| Human IgG1 Fc 1.1 Hole T366S/L368A/ Y407V/Y349C, G236R/L328R, M252Y/S254T/ T256E, H433K/N434F | Free Arm for Ag Depletion | DKTHTCPPCPAPELLRGPSVFLFPPKPKDTLYITR<br>EPEVTCVVVDVSHEDPEVKENWYVDGVEVHNAKTK<br>PREEQYNSTYRVVSVLTVLHQDWLNGKEYKCKVSN<br>KARPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALKFHYTQKSLSLSPGK | 104 |
| Human IgG1 Fc 1.2 Knob S354C/T366W, S267E/L328F | Antigen Arm for Ag Depletion | DKTHTCPPCPAPELLGGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KAFPAPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 105 |
| Human IgG1 Fc 1.2 Hole T366S/L368A/ Y407V/Y349C, S267E/L328F | Free Arm for Ag Depletion | DKTHTCPPCPAPELLGGPSVFLFPPKPKDTLMISR<br>TPEVTCVVVDVEHEDPEVKENWYVDGVEVHNAKTK<br>PREEQYNSTYRVVSVLTVLHQDWLNGKEYKCKVSN<br>KAFPAPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 106 |

TABLE 7-continued

Exemplary Fc Domain Sequences

| Fc Sequences | | Sequences | SEQ ID NO |
|---|---|---|---|
| Human IgG1 Fc 1.3 Knob S354C/T366W, P238D | Antigen Arm for Ag Depletion | DKTHTCPPCPAPELLGGDSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 107 |
| Human IgG1 Fc 1.3 Hole T366S/L368A/ Y407V/Y349C, P238D | Free Arm for Ag Depletion | DKTHTCPPCPAPELLGGDSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 108 |
| Human IgG1 Fc 1.3 Knob S354C/T366W, P238D/ M428L/N434S | Antigen Arm for Ag Depletion | DKTHTCPPCPAPELLGGDSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVFSCSVLHE ALHSHYTQKSLSLSPGK | 109 |
| Human IgG1 Fc 1.3 Hole T366S/L368A/ Y407V/Y349C, P238D/ M428L/N434S | Free Arm for Ag Depletion | DKTHTCPPCPAPELLGGDSVELFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVCTLPPSRDELTK NQVSLSCAVKGFYPSDIAVEWESNGQPENNYKTTP PVLDSDGSFFLVSKLTVDKSRWQQGNVFSCSVLHE ALHSHYTQKSLSLSPGK | 110 |
| Human IgG1 Fc (wild-type) | Bivalent Fc | DKTHTCPPCPAPELLGGPSVELFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 111 |
| Human IgG1 Fc G236R/L328R, M252Y/S254T/ T256E, H433K/N434F | Bivalent Fc | DKTHTCPPCPAPELLRGPSVELFPPKPKDTLYITR EPEVTCVVVDVSHEDPEVKENWYVDGVEVHNAKTK PREEQYNSTYRVVSVLTVLHQDWLNGKEYKCKVSN KARPAPIEKTISKAKGQPREPQVYTLPPSRDELTK NQVSLTCLVKGFYPSDIAVEWESNGQPENNYKTTP PVLDSDGSFFLYSKLTVDKSRWQQGNVESCSVMHE ALKFHYTQKSLSLSPGK | 112 |
| Human IgG1 Fc 1.5 Knob S354C/T366W, E233V/L234D/ L235F/G236R/ G237D/S239L/ S267D/H268P/ S298G/T299A/ A327L/L328A/ A330H/E333I | Antigen Arm for Ag Depletion | DKTHTCPPCPAPVDFRDPLVFLFPPKPKDTLMISR TPEVTCVVVDVDPEDPEVKENWYVDGVEVHNAKTK PREEQYNGAYRVVSVLTVLHQDWLNGKEYKCKVSN KLAPHPIIKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 113 |

TABLE 7-continued

Exemplary Fc Domain Sequences

| Fc Sequences | | Sequences | SEQ ID NO |
|---|---|---|---|
| Human IgG1 Fc 1.5 Hole T366S/L368A/ Y407V/Y349C, E233V/L234D/ L235F/G236R/ G237D/S239L/ S267D/H268P/ S298G/T299A/ A327L/L328A/ A330H/E333I | Free Arm for Ag Depletion | DKTHTCPPCPAPVDFRDPLVFLFPPKPKDTLMISR TPEVTCVVVDVDPEDPEVKENWYVDGVEVHNAKTK PREEQYNGAYRVVSVLTVLHQDWLNGKEYKCKVSN KLAPHPIIKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 114 |
| Human IgG1 Fc 1.6 Knob S354C/T366W, E233V/L234D/ L235F/G236R/ G237D/S239L/ S267D/R292Q/ H268P/S298G/ T299A/A327L/ L328A/A330H/ E333I | Antigen Arm for Ag Depletion | DKTHTCPPCPAPVDFRDPLVFLFPPKPKDTLMISR TPEVTCVVVDVDPEDPEVKENWYVDGVEVHNAKTK PQEEQYNGAYRVVSVLTVLHQDWLNGKEYKCKVSN KLAPHPIIKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 115 |
| Human IgG1 Fc 1.6 Hole T366S/L368A/ Y407V/Y349C, E233V/L234D/ L235F/G236R/ G237D/S239L/ S267D/R292Q/ H268P/S298G/ T299A/A327L/ L328A/A330H/ E333I | Free Arm for Ag Depletion | DKTHTCPPCPAPVDFRDPLVFLFPPKPKDTLMISR TPEVTCVVVDVDPEDPEVKENWYVDGVEVHNAKTK PQEEQYNGAYRVVSVLTVLHQDWLNGKEYKCKVSN KLAPHPIIKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 116 |
| Human IgG1 Fc 1.7 Knob S354C/T366W, E233V/L234D/ L235F/G236R/ G237D/S239L/ H268P/R292Q/ S298G/T299A/ A327L/L328A/ A330H/E333I | Antigen Arm for Ag Depletion | DKTHTCPPCPAPVDFRDPLVFLFPPKPKDTLMISR TPEVTCVVVDVSPEDPEVKENWYVDGVEVHNAKTK PQEEQYNGAYRVVSVLTVLHQDWLNGKEYKCKVSN KLAPHPIIKTISKAKGQPREPQVYTLPPCRDELTK NQVSLWCLVKGFYPSDIAVEWESNGQPENNYKTTP PVLDSDGSFFLYSKLTVDKSRWQQGNVESCSVMHE ALHNHYTQKSLSLSPGK | 117 |
| Human IgG1 Fc 1.7 Hole T366S/L368A/ Y407V/Y349C, E233V/L234D/ L235F/G236R/ G237D/S239L/ H268P/R292Q/ S298G/T299A/ A327L/L328A/ A330H/E333I | Free Arm for Ag Depletion | DKTHTCPPCPAPVDFRDPLVFLFPPKPKDTLMISR TPEVTCVVVDVSPEDPEVKENWYVDGVEVHNAKTK PQEEQYNGAYRVVSVLTVLHQDWLNGKEYKCKVSN KLAPHPIIKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 118 |
| Human IgG1 Fc 1.8 Knob S354C/T366W, L234Y/P238D/ T250V/V264I/ T307P/Q311R/ A330K/P343R/ M428L/N434A/ Y436T/Q438R/ S440E | Antigen Arm for Ag Depletion | DKTHTCPPCPAPEYLGGDSVELFPPKPKDVLMISR TPEVTCVVIDVSHEDPEVKENWYVDGVEVHNAKTK PREEQYNSTYRVVSVLPVLHRDWLNGKEYKCKVSN KALPKPIEKTISKAKGQRREPQVYTLPPCREEMTK NQVSLWCLVKGFYPSDIAVEWESNGQPENNYKTTP PVLDSDGSFFLYSKLTVDKSRWQQGNVESCSVLHE ALHAHTTRKELSLSPGK | 119 |

TABLE 7-continued

Exemplary Fc Domain Sequences

| Fc Sequences | | Sequences | SEQ ID NO |
|---|---|---|---|
| Human IgG1 Fc 1.8 Hole T366S/L368A/ Y407V/Y349C, L234Y/P238D/ T250V/V264I/ T307P/Q311R/ A330K/P343R/ M428L/N434A/ Y436T/Q438R/ S440E | Free Arm for Ag Depletion | DKTHTCPPCPAPEYLGGDSVFLFPPKPKDVLMISR TPEVTCVVIDVSHEDPEVKENWYVDGVEVHNAKTK PREEQYNSTYRVVSVLPVLHRDWLNGKEYKCKVSN KALPKPIEKTISKAKGQRREPQVCTLPPSREEMTK NQVSLSCAVKGFYPSDIAVEWESNGQPENNYKTTP PVLDSDGSFFLVSKLTVDKSRWQQGNVFSCSVLHE ALHAHTTRKELSLSPGK | 120 |
| Human IgG1 Fc 1.9 Knob S354C/T366W, L234D/G236N/ S267E | Antigen Arm for Ag Depletion | DKTHTCPPCPAPEDLNGPSVFLFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVESCSVMHE ALHNHYTQKSLSLSPGK | 121 |
| Human IgG1 Fc 1.9 Hole T366S/L368A/ Y407V/Y349C, L234D/G236N/ S267E | Free Arm for Ag Depletion | DKTHTCPPCPAPEDLNGPSVELFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 122 |
| Human IgG1 Fc 1.10 Knob S354C/T366W, L235R | Antigen Arm for Ag Depletion | DKTHTCPPCPAPELRGGPSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 123 |
| Human IgG1 Fc 1.10 Hole T366S/L368A/ Y407V/Y349C, L235R | Free Arm for Ag Depletion | DKTHTCPPCPAPELRGGPSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 124 |
| Human IgG1 Fc 1.11 Knob S354C/T366W, G236N/S267E | Antigen Arm for Ag Depletion | DKTHTCPPCPAPELLNGPSVELFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 125 |
| Human IgG1 Fc 1.11 Hole T366S/L368A/ Y407V/Y349C, G236N/S267E | Free Arm for Ag Depletion | DKTHTCPPCPAPELLNGPSVFLFPPKPKDTLMISR TPEVTCVVVDVEHEDPEVKENWYVDGVEVHNAKTK PREEQYNSTYRVVSVLTVLHQDWLNGKEYKCKVSN KALPAPIEKTISKAKGQPREPQVCTLPPSRDELTK NQVSLSCAVKGFYPSDIAVEWESNGQPENNYKTTP PVLDSDGSFFLVSKLTVDKSRWQQGNVFSCSVMHE ALHNHYTQKSLSLSPGK | 126 |
| Human IgG1 Fc 1.12 Knob S354C/T366W, P238D/D270E | Antigen Arm for Ag Depletion | DKTHTCPPCPAPELLGGDSVELFPPKPKDTLMISR TPEVTCVVVDVSHEEPEVKENWYVDGVEVHNAKTK PREEQYNSTYRVVSVLTVLHQDWLNGKEYKCKVSN KALPAPIEKTISKAKGQPREPQVYTLPPCRDELTK NQVSLWCLVKGFYPSDIAVEWESNGQPENNYKTTP PVLDSDGSFFLYSKLTVDKSRWQQGNVFSCSVMHE ALHNHYTQKSLSLSPGK | 127 |

TABLE 7-continued

Exemplary Fc Domain Sequences

| Fc Sequences | | Sequences | SEQ ID NO |
|---|---|---|---|
| Human IgG1 Fc 1.12 Hole T366S/L368A/ Y407V/Y349C, P238D/D270E | Free Arm for Ag Depletion | DKTHTCPPCPAPELLGGDSVFLFPPKPKDTLMISR<br>TPEVTCVVVDVSHEEPEVKENWYVDGVEVHNAKTK<br>PREEQYNSTYRVVSVLTVLHQDWLNGKEYKCKVSN<br>KALPAPIEKTISKAKGQPREPQVCTLPPSRDELTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 128 |
| Human IgG1 Fc 1.13 Knob S354C/T366W, P238D/P271G | Antigen Arm for Ag Depletion | DKTHTCPPCPAPELLGGDSVFLFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPAPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 129 |
| Human IgG1 Fc 1.13 Hole T366S/L368A/ Y407V/Y349C, P238D/P271G | Free Arm for Ag Depletion | DKTHTCPPCPAPELLGGDSVFLFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPAPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 130 |
| Human IgG1 Fc 1.14 Knob S354C/T366W, P238D/D270E/ P271G | Antigen Arm for Ag Depletion | DKTHTCPPCPAPELLGGDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPAPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 131 |
| Human IgG1 Fc 1.14 Hole T366S/L368A/ Y407V/Y349C, P238D/D270E/ P271G | Free Arm for Ag Depletion | DKTHTCPPCPAPELLGGDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPAPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 132 |
| Human IgG1 Fc 1.15 Knob S354C/T366W, G237D/P238D/ P271G/A330R | Antigen Arm for Ag Depletion | DKTHTCPPCPAPELLGDDSVELFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPRPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVFSCSVMHE<br>ALHNHYTQKSLSLSPGK | 133 |
| Human IgG1 Fc 1.15 Hole T366S/L368A/ Y407V/Y349C, G237D/P238D/ P271G/A330R | Free Arm for Ag Depletion | DKTHTCPPCPAPELLGDDSVFLFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPRPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 134 |
| Human IgG1 Fc 1.16 Knob S354C/T366W, G237D/P238D/ D270E/P271G/ A330R | Antigen Arm for Ag Depletion | DKTHTCPPCPAPELLGDDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPRPIEKTISKAKGQPREPQVYTLPPCREEMTK<br>NQVSLWCLVKGFYPSDIAVEWESNGQPENNYKTTP<br>PVLDSDGSFFLYSKLTVDKSRWQQGNVESCSVMHE<br>ALHNHYTQKSLSLSPGK | 135 |
| Human IgG1 Fc 1.16 Hole T366S/L368A/ Y407V/Y349C, G237D/P238D/ D270E/P271G/ A330R | Free Arm for Ag Depletion | DKTHTCPPCPAPELLGDDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPRPIEKTISKAKGQPREPQVCTLPPSREEMTK<br>NQVSLSCAVKGFYPSDIAVEWESNGQPENNYKTTP<br>PVLDSDGSFFLVSKLTVDKSRWQQGNVFSCSVMHE<br>ALHNHYTQKSLSLSPGK | 136 |

TABLE 7-continued

Exemplary Fc Domain Sequences

| Fc Sequences | | Sequences | SEQ ID NO |
|---|---|---|---|
| Human IgG1 Fc 1.17 Knob S354C/T366W, E233D/G237D/ P238D/H268D/ P271G/A330R | Antigen Arm for Ag Depletion | DKTHTCPPCPAP**D**LLG**DD**SVFLFPPKPKDTLMISR TPEVTCVVVDVS**D**ED**G**EVKENWYVDGVEVHNAKTK PREEQYNSTYRVVSVLTVLHQDWLNGKEYKCKVSN KALP**R**PIEKTISKAKGQPREPQVYTLPP**C**RDELTK NQVSL**W**CLVKGFYPSDIAVEWESNGQPENNYKTTP PVLDSDGSFFLYSKLTVDKSRWQQGNVFSCSVMHE ALHNHYTQKSLSLSPGK | 137 |
| Human IgG1 Fc 1.17 Hole T366S/L368A/ Y407V/Y349C, E233D/G237D/ P238D/H268D/ P271G/A330R | Free Arm for Ag Depletion | DKTHTCPPCPAP**D**LLG**DD**SVFLFPPKPKDTLMISR TPEVTCVVVDVS**D**ED**G**EVKENWYVDGVEVHNAKTK PREEQYNSTYRVVSVLTVLHQDWLNGKEYKCKVSN KALPRPIEKTISKAKGQPREPQV**C**TLPPSRDELTK NQVSL**S**C**A**VKGFYPSDIAVEWESNGQPENNYKTTP PVLDSDGSFFL**V**SKLTVDKSRWQQGNVFSCSVMHE ALHNHYTQKSLSLSPGK | 138 |
| Human IgG1 Fc E233V/L234D/ L235F/G236R/ G237D/S239L/ S267D/H268P/ S298G/T299A/ A327L/L328A/ A330H/E333I | Bivalent Fc | DKTHTCPPCPAP**VDFRD**P**L**VFLFPPKPKDTLMISR TPEVTCVVVDV**DP**EDPEVKENWYVDGVEVHNAKTK PREEQYN**GA**YRVVSVLTVLHQDWLNGKEYKCKVSN K**LA**P**H**PI**I**KTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 139 |
| Human IgG1 Fc E233V/L234D/ L235F/G236R/ G237D/S239L/ S267D/R292Q/ H268P/S298G/ T299A/A327L/ L328A/A330H/ E333I | Bivalent Fc | DKTHTCPPCPAP**VDFRD**P**L**VFLFPPKPKDTLMISR TPEVTCVVVDV**DP**EDPEVKENWYVDGVEVHNAKTK P**Q**EEQYN**GA**YRVVSVLTVLHQDWLNGKEYKCKVSN K**LA**P**H**PI**I**KTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 140 |
| Human IgG1 Fc E233V/L234D/ L235F/G236R/ G237D/S239L/ H268P/R292Q/ S298G/T299A/ A327L/L328A/ A330H/E333I | Bivalent Fc | DKTHTCPPCPAP**VDFRD**P**L**VFLFPPKPKDTLMISR TPEVTCVVVDVS**P**EDPEVKENWYVDGVEVHNAKTK P**Q**EEQYN**GA**YRVVSVLTVLHQDWLNGKEYKCKVSN K**LA**P**H**PI**I**KTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 141 |
| Human IgG1 Fc L234Y/P238D/ T250V/V264I/ T307P/Q311R/ A330K/P343R/ M428L/N434A/ Y436T/Q438R/ S440E | Bivalent Fc | DKTHTCPPCPAPE**Y**LGG**D**SVFLFPPKPKD**V**LMISR TPEVTCVV**I**DVSHEDPEVKENWYVDGVEVHNAKTK PREEQYNSTYRVVSVL**P**VLH**R**DWLNGKEYKCKVSN KALP**K**PIEKTISKAKGQ**R**REPQVYTLPPSREEMTK NQVSLTCLVKGFYPSDIAVEWESNGQPENNYKTTP PVLDSDGSFFLYSKLTVDKSRWQQGNVESCSV**L**HE ALH**A**H**T**T**R**K**E**LSLSPGK | 142 |
| Human IgG1 Fc L234D/G236N/ S267E | Bivalent Fc | DKTHTCPPCPAPE**D**L**N**GPSVELFPPKPKDTLMISR TPEVTCVVVDV**E**HEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVFSCSVMHE ALHNHYTQKSLSLSPGK | 143 |
| Human IgG1 Fc L235R | Bivalent Fc | DKTHTCPPCPAPEL**R**GGPSVFLFPPKPKDTLMISR TPEVTCVVVDVSHEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP PVLDSDGSFFLYSKLTVDKSRWQQGNVESCSVMHE ALHNHYTQKSLSLSPGK | 144 |
| Human IgG1 Fc G236N/S267E | Bivalent Fc | DKTHTCPPCPAPELL**N**GPSVELFPPKPKDTLMISR TPEVTCVVVDV**E**HEDPEVKENWYVDGVEVHNAKTK PREEQYNSTYRVVSVLTVLHQDWLNGKEYKCKVSN KALPAPIEKTISKAKGQPREPQVYTLPPSRDELTK NQVSLTCLVKGFYPSDIAVEWESNGQPENNYKTTP | 145 |

TABLE 7-continued

Exemplary Fc Domain Sequences

| Fc Sequences | | Sequences | SEQ ID NO |
|---|---|---|---|
| | | PVLDSDGSFFLYSKLTVDKSRWQQGNVFSCSVMHE<br>ALHNHYTQKSLSLSPGK | |
| Human IgG1 Fc<br>P238D/D270E | Bivalent<br>Fc | DKTHTCPPCPAPELLGGDSVELFPPKPKDTLMISR<br>TPEVTCVVVDVSHEEPEVKENWYVDGVEVHNAKTK<br>PREEQYNSTYRVVSVLTVLHQDWLNGKEYKCKVSN<br>KALPAPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 146 |
| Human IgG1 Fc<br>P238D/P271G | Bivalent<br>Fc | DKTHTCPPCPAPELLGGDSVELFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPAPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 147 |
| Human IgG1 Fc<br>P238D/D270E/P<br>271G | Bivalent<br>Fc | DKTHTCPPCPAPELLGGDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPAPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 148 |
| Human IgG1 Fc<br>G237D/P238D/P<br>271G/A330R | Bivalent<br>Fc | DKTHTCPPCPAPELLGDDSVELFPPKPKDTLMISR<br>TPEVTCVVVDVSHEDGEVKENWYVDGVEVHNAKTK<br>PREEQYNSTYRVVSVLTVLHQDWLNGKEYKCKVSN<br>KALPRPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 149 |
| Human IgG1 Fc<br>G237D/P238D/<br>D270E/P271G/<br>A330R | Bivalent<br>Fc | DKTHTCPPCPAPELLGDDSVFLFPPKPKDTLMISR<br>TPEVTCVVVDVSHEEGEVKENWYVDGVEVHNAKTK<br>PREEQYNSTYRVVSVLTVLHQDWLNGKEYKCKVSN<br>KALPRPIEKTISKAKGQPREPQVYTLPPSREEMTK<br>NQVSLTCLVKGFYPSDIAVEWESNGQPENNYKTTP<br>PVLDSDGSFFLYSKLTVDKSRWQQGNVESCSVMHE<br>ALHNHYTQKSLSLSPGK | 163 |
| Human IgG1 Fc<br>E233D/G237D/P<br>238D/H268D/P2<br>71G/A330R | Bivalent<br>Fc | DKTHTCPPCPAPDLLGDDSVFLFPPKPKDTLMISR<br>TPEVTCVVVDVSDEDGEVKENWYVDGVEVHNAKTK<br>PREEQYNSTYRVVSVLTVLHQDWLNGKEYKCKVSN<br>KALPRPIEKTISKAKGQPREPQVYTLPPSRDELTK<br>NQVSLTCLVKGFYPSDIAVEWESNGQPENNYKTTP<br>PVLDSDGSFFLYSKLTVDKSRWQQGNVFSCSVMHE<br>ALHNHYTQKSLSLSPGK | 164 |

Additional antigen-binding domain: In one exemplary molecule in this Example, an additional antigen-binding domain was included in the second polypeptide covalently linked to the second Fc domain. In this Example, a second antigen-binding domain specific for asialoglycoprotein receptor (ASGPR) was used. ASGPR is a membrane protein located on mammalian hepatocytes (liver cells) that targets and removes target glycoproteins from circulation. Without wishing to be bound by any theory, such an antigen-binding domain was introduced to provide a secondary mechanism by which the molecule can target autoantibodies for internalization and degradation in the lysosome. The molecule bound to a target autoantibody may target ASGPR on hepatocytes and binding to ASGPR will cause internalization of the complex (i.e., removal of target autoantibodies). Antigen-binding domain for ASGPR used in this Example includes an anti-ASGPR Fab (4F3) that includes a heavy chain sequence as shown in SEQ ID NO: 209 and a light chain sequence as shown in SEQ ID NO: 210 (see Table 2 above).

The first and second polypeptides with the modifications described above were used to generate exemplary molecules as described below in Table 8 based on the exemplary molecule formats shown in FIG. 2 (Variants A1-A4, B1-B4, D1-D4 and E1-E4) and FIG. 3 (Variant C which includes an anti-ASPGR Fab in second polypeptide). These sequences were encoded by expression plasmids (e.g., pTT5, pcDNA) then transfected into a suitable host cell (e.g., CHO, HEK293) and expressed using standard transfection techniques. After expression for 5-14 days or if cell viability dropped, cells were harvested. Conditioned media was then purified using standard chromatography techniques such as protein A affinity, ion exchange chromatography, and size exclusion chromatography to generate molecules with greater than 95% purity (as assessed by HPLC). Molecules were then buffer exchanged to a suitable formulation buffer and stored at 4 C or −80° C. prior to use.

TABLE 8

Figure 2:
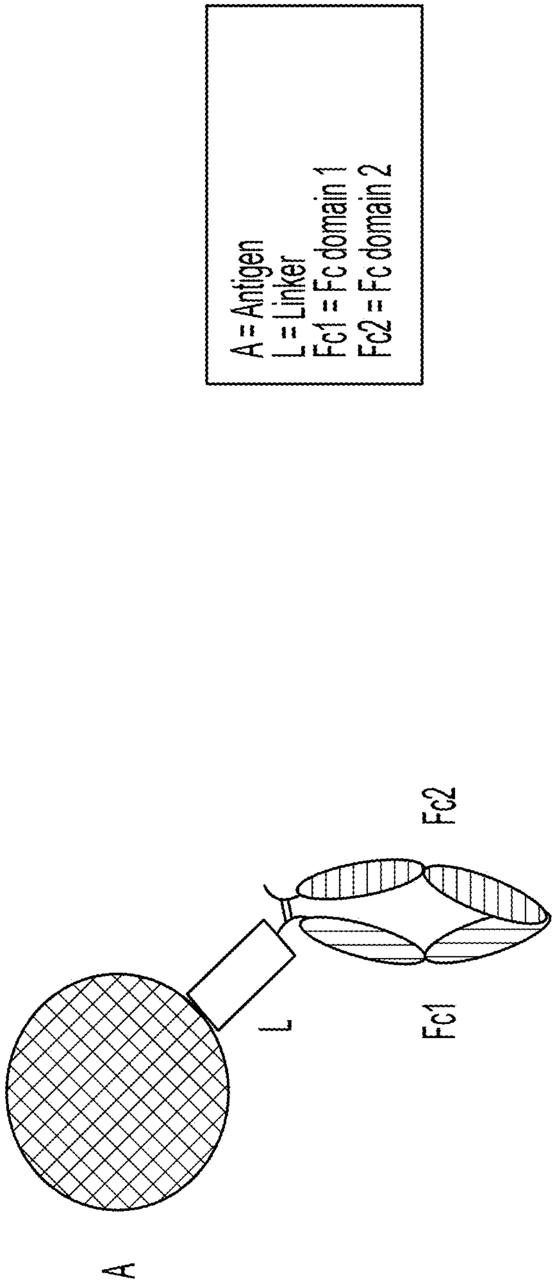
FIG. 2 shows an exemplary molecule format described herein.

Exemplary TSHR Antibody Depletion Combinations based on Formats in FIGS. 2 and 3 (where Linker L in first polypeptide is absent)

| Molecule ID | Name | A | HC | LC | L | Fc1 | Fc2 |
|---|---|---|---|---|---|---|---|
| Variant A1 | TSHR260 WT huIgG1 Fc MST-HN/RR | 1 | n/a | n/a | n/a | 103 | 104 |
| Variant A2 | TSHR260 2P huIgG1 Fc MST-HN/RR | 2 | n/a | n/a | n/a | 103 | 104 |
| Variant A3 | TSHR260 2P2R huIgG1 Fc MST-HN/RR | 3 | n/a | n/a | n/a | 103 | 104 |
| Variant A4 | TSHR260 2P1S huIgG1 Fc MST-HN/RR | 4 | n/a | n/a | n/a | 103 | 104 |
| Variant B1 | TSHR 260 WT huIgG1 Fc S267E/L328F | 1 | n/a | n/a | n/a | 105 | 106 |
| Variant B2 | TSHR 260 2P huIgG1 Fc S267E/L328F | 2 | n/a | n/a | n/a | 105 | 106 |
| Variant B3 | TSHR260 2P2R huIgG1 Fc S267E/L328F | 3 | n/a | n/a | n/a | 105 | 106 |
| Variant B4 | TSHR260 2P1S huIgG1 Fc S267E/L328F | 4 | n/a | n/a | n/a | 105 | 106 |
| Variant C1 | TSHR260 2P2R × 4F3 huIgG1 Fc S267E/L328F | 3 | 209 | 210 | n/a | 105 | 106 |
| Variant D1 | TSHR260 WT huIgG1 Fc P238D | 1 | n/a | n/a | n/a | 107 | 108 |

TABLE 8-continued

Exemplary TSHR Antibody Depletion Combinations based on Formats in FIGS. 2 and 3 (where Linker L in first polypeptide is absent)

| Molecule ID | Name | A | HC | LC | L | Fc1 | Fc2 |
|---|---|---|---|---|---|---|---|
| Variant D2 | TSHR260 2P huIgG1 Fc P238D | 2 | n/a | n/a | n/a | 107 | 108 |
| Variant D3 | TSHR260 2P2R huIgG1 Fc P238D | 3 | n/a | n/a | n/a | 107 | 108 |
| Variant D4 | TSHR260 2P1S huIgG1 Fc P238D | 4 | n/a | n/a | n/a | 107 | 108 |
| Variant E1 | TSHR260 WT huIgG1 Fc P238D/LS | 1 | n/a | n/a | n/a | 109 | 110 |
| Variant E2 | TSHR260 2P huIgG1 Fc P238D/LS | 2 | n/a | n/a | n/a | 109 | 110 |
| Variant E3 | TSHR260 2P2R huIgG1 Fc P238D/LS | 3 | n/a | n/a | n/a | 109 | 110 |
| Variant E4 | TSHR260 2P1S huIgG1 Fc P238D/LS | 4 | n/a | n/a | n/a | 109 | 110 |

Sequences of a subset of the exemplary molecules generated in this Example are shown below in Table 9A (with exemplary signal peptides) and Table 9B (without exemplary signal peptides). Tables 9A and 9B also include sequences for some additional exemplary molecules (Variants G1-G14) that were tested in Example 8 (see also Table 4 for components included in these other exemplary molecules).

TABLE 9A

Exemplary Molecules (including exemplary signal peptides which are underlined; all molecules also include KIH mutations)

| Molecule ID | Description | Knob Arm | SEQ ID NO: | Hole Arm | SEQ ID NO: |
|---|---|---|---|---|---|
| Variant A1 | TSHR260 WT huIgG1 with RR/MST-HN | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTR<br>NLTYIDPDALKELPLLKELGIF<br>NTGLKMFPDLTKVYSTDIFFIL<br>EITDNPYMTSIPVNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELIARNTWTLDKTHTC<br>PPCPAPELLRGPSVELFPPKPK<br>DTLYITREPEVTCVVVDVSHED<br>PEVKFNWYVDGVEVHNAKTKPR<br>EEQYNSTYRVVSVLTVLHQDWL<br>NGKEYKCKVSNKARPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALKFHYTQKSLSLSPG<br>K | 211 | MGWSLILLFLVAVATRVLSDKTHT<br>CPPCPAPELLRGPSVELFPPKPKD<br>TLYITREPEVTCVVVDVSHEDPEV<br>KFNWYVDGVEVHNAKTKPREEQYN<br>STYRVVSVLTVLHQDWLNGKEYKC<br>KVSNKARPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALKFHYTQKSL<br>SLSPGK | 218 |
| Variant A3 | TSHR260 2P2R huIgG1 with RR/MST-HN | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 212 | MGWSLILLELVAVATRVLSDKTHT<br>CPPCPAPELLRGPSVELFPPKPKD<br>TLYITREPEVTCVVVDVSHEDPEV<br>KFNWYVDGVEVHNAKTKPREEQYN<br>STYRVVSVLTVLHQDWINGKEYKC<br>KVSNKARPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALKFHYTQKSL<br>SLSPGK | 219 |

TABLE 9A-continued

Exemplary Molecules (including exemplary signal peptides which are underlined; all molecules also include KIH mutations)

| Molecule ID | Description | Knob Arm | SEQ ID NO: | Hole Arm | SEQ ID NO: |
|---|---|---|---|---|---|
| | | PPCPAPELLRGPSVELFPPKPK<br>DTLYITREPEVTCVVVDVSHED<br>PEVKFNWYVDGVEVHNAKTKPR<br>EEQYNSTYRVVSVLTVLHQDWL<br>NGKEYKCKVSNKARPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALKFHYTQKSLSLSPG<br>K | | | |
| Variant A4 | TSHR260 2P1S huIgG1 with RR/MST-HN | MGWSCIILFLVATATGVHSMGC<br>SSPPCECHQEEDFRVTCKDIQR<br>IPSLPPSTQTLKLIETSLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPVNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELIARNTWTLDKTHTC<br>PPCPAPELLRGPSVELFPPKPK<br>DTLYITREPEVTCVVVDVSHED<br>PEVKENWYVDGVEVHNAKTKPR<br>EEQYNSTYRVVSVLTVLHQDWL<br>NGKEYKCKVSNKARPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALKFHYTQKSLSLSPG<br>K | 213 | MGWSLILLFLVAVATRVLSDKTHT<br>CPPCPAPELLRGPSVELFPPKPKD<br>TLYITREPEVTCVVVDVSHEDPEV<br>KFNWYVDGVEVHNAKTKPREEQYN<br>STYRVVSVLTVLHQDWLNGKEYKC<br>KVSNKARPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALKFHYTQKSL<br>SLSPGK | 220 |
| Variant B1 | TSHR260 WT huIgG1 with S267E/L328F | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTR<br>NLTYIDPDALKELPLLKELGIF<br>NTGLKMFPDLTKVYSTDIFFIL<br>EITDNPYMTSIPVNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELIARNTWTLDKTHTC<br>PPCPAPELLGGPSVFLFPPKPK<br>DTLMISRTPEVTCVVVDVEHED<br>PEVKFNWYVDGVEVHNAKTKPR<br>EEQYNSTYRVVSVLTVLHQDWL<br>NGKEYKCKVSNKAFPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 214 | MGWSLILLFLVAVATRVLSDKTHT<br>CPPCPAPELLGGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKAFPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 221 |
| Variant B2 | TSHR260 2P huIgG1 with S267E/L328F | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPVNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELIARNTWTLDKTHTC | 215 | MGWSLILLELVAVATRVLSDKTHT<br>CPPCPAPELLGGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKAFPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 222 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | | PPCPAPELLGGPSVELFPPKPK<br>DTLMISRTPEVTCVVVDVEHED<br>PEVKFNWYVDGVEVHNAKTKPR<br>EEQYNSTYRVVSVLTVLHQDWL<br>NGKEYKCKVSNKAFPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant B3 | TSHR260<br>2P2R<br>huIgG1 with<br>S267E/L328F | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELRARNTWTLDKTHTC<br>PPCPAPELLGGPSVFLFPPKPK<br>DTLMISRTPEVTCVVVDVEHED<br>PEVKFNWYVDGVEVHNAKTKPR<br>EEQYNSTYRVVSVLTVLHQDWL<br>NGKEYKCKVSNKAFPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 216 | MGWSLILLFLVAVATRVLSDKTHT<br>CPPCPAPELLGGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKAFPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 223 |
| Variant B4 | TSHR260<br>2P1S<br>huIgG1 with<br>S267E/L328F | MGWSCIILFLVATATGVHSMGC<br>SSPPCECHQEEDERVTCKDIQR<br>IPSLPPSTQTLKLIETSLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPVNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELIARNTWTLDKTHTC<br>PPCPAPELLGGPSVFLFPPKPK<br>DTLMISRTPEVTCVVVDVEHED<br>PEVKENWYVDGVEVHNAKTKPR<br>EEQYNSTYRVVSVLTVLHQDWL<br>NGKEYKCKVSNKAFPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 217 | MGWSLILLFLVAVATRVLSDKTHT<br>CPPCPAPELLGGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKAFPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 224 |
| Variant D3 | TSHR260<br>2P2R<br>huIgG1 with<br>P238D | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 225 | MGWSLILLELVAVATRVLSDKTHT<br>CPPCPAPELLGGDSVFLFPPKPKD<br>TLMISRTPEVTCVVVDVSHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 228 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | | PPCPAPELLGGDSVELFPPKPK<br>DTLMISRTPEVTCVVVDVSHED<br>PEVKFNWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant E3 | TSHR260<br>2P2R<br>huIgG1 with<br>P238D and<br>LS | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELRARNTWTLDKTHTC<br>PPCPAPELLGGDSVELFPPKPK<br>DTLMISRTPEVTCVVVDVSHED<br>PEVKENWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVLHEALHSHYTQKSLSLSPG<br>K | 226 | MGWSLILLELVAVATRVLSDKTHT<br>CPPCPAPELLGGDSVELFPPKPKD<br>TLMISRTPEVTCVVVDVSHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVLHEALHSHYTQKSL<br>SLSPGK | 229 |
| Variant F3 | TSHR260<br>2P2R<br>huIgG1 with<br>LS | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPELLGGPSVFLFPPKPK<br>DTLMISRTPEVTCVVVDVSHED<br>PEVKFNWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVLHEALHSHYTQKSLSLSPG<br>K | 227 | MGWSLILLELVAVATRVLSDKTHT<br>CPPCPAPELLGGDSVELFPPKPKD<br>TLMISRTPEVTCVVVDVSHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVLHEALHSHYTQKSL<br>SLSPGK | 230 |
| Variant G1 | TSHR260<br>2P2R<br>huIgG1 with<br>E233V/<br>L234D/<br>L235F/<br>G236R/<br>G237D/<br>S239L/<br>S267D/<br>H268P/<br>S298G/ | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKFLGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 318 | MGWSCIILFLVATATGVHSDKTHT<br>CPPCPAPVDFRDPLVFLFPPKPKD<br>TLMISRTPEVTCVVVDVDPEDPEV<br>KFNWYVDGVEVHNAKTKPREEQYN<br>GAYRVVSVLTVLHQDWLNGKEYKC<br>KVSNKLAPHPIIKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 332 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | T299A/<br>A327L/<br>L328A/<br>A330H/<br>E333I | PPCPAPVDERDPLVELFPPKPK<br>DTLMISRTPEVTCVVVDVDPED<br>PEVKFNWYVDGVEVHNAKTKPR<br>EEQYNGAYRVVSVLTVLHQDWL<br>NGKEYKCKVSNKLAPHPIIKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant G2 | TSHR260<br>2P2R<br>huIgG1 with<br>E233V/<br>L234D/<br>L235F/<br>G236R/<br>G237D/<br>S239L/<br>S267D/<br>R292Q/<br>H268P/<br>S298G/<br>T299A/<br>A327L/<br>L328A/<br>A330H/<br>E333I | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPVDERDPLVFLFPPKPK<br>DTLMISRTPEVTCVVVDVDPED<br>PEVKFNWYVDGVEVHNAKTKPQ<br>EEQYNGAYRVVSVLTVLHQDWL<br>NGKEYKCKVSNKLAPHPIIKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 319 | MGWSCIILFLVATATGVHSDKTHT<br>CPPCPAPVDERDPLVELFPPKPKD<br>TLMISRTPEVTCVVVDVDPEDPEV<br>KFNWYVDGVEVHNAKTKPQEEQYN<br>GAYRVVSVLTVLHQDWLNGKEYKC<br>KVSNKLAPHPIIKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 333 |
| Variant G3 | TSHR260<br>2P2R<br>huIgG1 with<br>E233V/<br>L234D/<br>L235F/<br>G236R/<br>G237D/<br>S239L/<br>H268P/<br>R292Q/<br>S298G/<br>T299A/<br>A327L/<br>L328A/<br>A330H/<br>E333I | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPVDFRDPLVELFPPKPK<br>DTLMISRTPEVTCVVVDVSPED<br>PEVKENWYVDGVEVHNAKTKPQ<br>EEQYNGAYRVVSVLTVLHQDWL<br>NGKEYKCKVSNKLAPHPIIKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 320 | MGWSCIILFLVATATGVHSDKTHT<br>CPPCPAPVDFRDPLVFLFPPKPKD<br>TLMISRTPEVTCVVVDVSPEDPEV<br>KFNWYVDGVEVHNAKTKPQEEQYN<br>GAYRVVSVLTVLHQDWLNGKEYKC<br>KVSNKLAPHPIIKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 334 |
| Variant G4 | TSHR260<br>2P2R<br>huIgG1 with<br>E233D/<br>G237D/<br>P238D/<br>H268D/<br>P271G/<br>A330R | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKFLGIF<br>NTGLKMFPPLTKVYSTDIFFIL<br>EITDNPYMTSIPRNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELRARNTWTLDKTHTC | 321 | MGWSCIILFLVATATGVHSDKTHT<br>CPPCPAPDLLGDDSVELFPPKPKD<br>TLMISRTPEVTCVVVDVSDEDGEV<br>KFNWYVDGVEVHNAKTKPREEQYN<br>STYRVVSVLTVLHQDWLNGKEYKC<br>KVSNKALPRPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 335 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | | PPCPAPDLLGDDSVELFPPKPK<br>DTLMISRTPEVTCVVVDVSDED<br>GEVKENWYVDGVEVHNAKTKPR<br>EEQYNSTYRVVSVLTVLHQDWL<br>NGKEYKCKVSNKALPRPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant G5 | TSHR260 2P2R huIgG1 with L234Y/ P238D/ T250V/ V264I/ T307P/ Q311R/ A330K/ P343R/ M428L/ N434A/ Y436T/ Q438R/ S440E | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPEYLGGDSVELFPPKPK<br>DVLMISRTPEVTCVVIDVSHED<br>PEVKENWYVDGVEVHNAKTKPR<br>EEQYNSTYRVVSVLPVLHRDWL<br>NGKEYKCKVSNKALPKPIEKTI<br>SKAKGORREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVLHEALHAHTTRKELSLSPG<br>K | 322 | MGWSCIILFLVATATGVHSDKTHT<br>CPPCPAPEYLGGDSVFLFPPKPKD<br>VLMISRTPEVTCVVIDVSHEDPEV<br>KFNWYVDGVEVHNAKTKPREEQYN<br>STYRVVSVLPVLHRDWLNGKEYKC<br>KVSNKALPKPIEKTISKAKGQRRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMLEALHAHTTRKEL<br>SLSPGK | 336 |
| Variant G6 | TSHR260 2P2R huIgG1 with L234D/ G236N/S267E | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPEDLNGPSVELFPPKPK<br>DTLMISRTPEVTCVVVDVEHED<br>PEVKFNWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 323 | MGWSCIILFLVATATGVHSDKTHT<br>CPPCPAPEDLNGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 337 |
| Variant G7 | TSHR260 2P2R huIgG1 with L235R | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 324 | MGWSCIILFLVATATGVHSDKTHT<br>CPPCPAPELRGGPSVFLFPPKPKD<br>TLMISRTPEVTCVVVDVSHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 338 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | | PPCPAPELRGGPSVFLFPPKPK<br>DTLMISRTPEVTCVVVDVSHED<br>PEVKENWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant G8 | TSHR260 2P2R huIgG1 with G236N/S267E | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPELLNGPSVELFPPKPK<br>DTLMISRTPEVTCVVVDVEHED<br>PEVKENWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 325 | MGWSCIILFLVATATGVHSDKTHT<br>CPPCPAPELLNGPSVFLFPPKPKD<br>TLMISRTPEVTCVVVDVEHEDPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 339 |
| Variant G9 | TSHR260 2P2R huIgG1 with P238D/D270E | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPELLGGDSVELFPPKPK<br>DTLMISRTPEVTCVVVDVSHEE<br>PEVKENWYVDGVEVHNAKTKPR<br>EEQYNSTYRVVSVLTVLHQDWL<br>NGKEYKCKVSNKALPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 326 | MGWSCIILFLVATATGVHSDKTHT<br>CPPCPAPELLGGDSVFLFPPKPKD<br>TLMISRTPEVTCVVVDVSHEEPEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 340 |
| Variant G10 | TSHR260 2P2R huIgG1 with P238D/P271G | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 327 | MGWSCIILFLVATATGVHSDKTHT<br>CPPCPAPELLGGDSVFLFPPKPKD<br>TLMISRTPEVTCVVVDVSHEDGEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 341 |

TABLE 9A-continued

| Exemplary Molecules (including exemplary signal peptides which are underlined; all molecules also include KIH mutations) | | | | | |
|---|---|---|---|---|---|
| Molecule ID | Description | Knob Arm | SEQ ID NO: | Hole Arm | SEQ ID NO: |
| | | PPCPAPELLGGDSVELFPPKPK<br>DTLMISRTPEVTCVVVDVSHED<br>GEVKENWYVDGVEVHNAKTKPR<br>EEQYNSTYRVVSVLTVLHQDWL<br>NGKEYKCKVSNKALPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant G11 | TSHR260 2P2R huIgG1 with P238D/ D270E/P271G | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPELLGGDSVFLFPPKPK<br>DTLMISRTPEVTCVVVDVSHEE<br>GEVKFNWYVDGVEVHNAKTKPR<br>EEQYNSTYRVVSVLTVLHQDWL<br>NGKEYKCKVSNKALPAPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 328 | MGWSCIILFLVATATGVHSDKTHT<br>CPPCPAPELLGGDSVFLFPPKPKD<br>TLMISRTPEVTCVVVDVSHEEGEV<br>KFNWYVDGVEVHNAKTKPREEQYN<br>STYRVVSVLTVLHQDWLNGKEYKC<br>KVSNKALPAPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 342 |
| Variant G12 | TSHR260 2P2R huIgG1 with G237D/ P238D/ P271G/A330R | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKFLGIF<br>NTGLKMFPPLTKVYSTDIFFIL<br>EITDNPYMTSIPRNAFQGLCNE<br>TLTLKLYNNGFTSVQGYAENGT<br>KLDAVYLNKNKYLTVIDKDAFG<br>GVYSGPSLLDVSQTSVTALPSK<br>GLEHLKELRARNTWTLDKTHTC<br>PPCPAPELLGDDSVELFPPKPK<br>DTLMISRTPEVTCVVVDVSHED<br>GEVKFNWYVDGVEVHNAKTKPR<br>EEQYNSTYRVVSVLTVLHQDWL<br>NGKEYKCKVSNKALPRPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 329 | MGWSCIILFLVATATGVHSDKTHT<br>CPPCPAPELLGDDSVELFPPKPKD<br>TLMISRTPEVTCVVVDVSHEDGEV<br>KFNWYVDGVEVHNAKTKPREEQYN<br>STYRVVSVLTVLHQDWLNGKEYKC<br>KVSNKALPRPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 343 |
| Variant G13 | TSHR260 2P2R huIgG1 with G237D/ P238D/ D270E/ P271G/ A330R | MGWSCIILFLVATATGVHSMGC<br>SSPPCECHQEEDFRVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC | 330 | MGWSCIILFLVATATGVHSDKTHT<br>CPPCPAPELLGDDSVFLFPPKPKD<br>TLMISRTPEVTCVVVDVSHEEGEV<br>KFNWYVDGVEVHNAKTKPREEQYN<br>STYRVVSVLTVLHQDWLNGKEYKC<br>KVSNKALPRPIEKTISKAKGQPRE<br>PQVCTLPPSREEMTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 344 |

TABLE 9A-continued

Exemplary Molecules
(including exemplary signal peptides which are underlined;
all molecules also include KIH mutations)

| Molecule ID | Description | Knob Arm | SEQ ID NO: | Hole Arm | SEQ ID NO: |
|---|---|---|---|---|---|
| | | PPCPAPELLGDDSVFLFPPKPK<br>DTLMISRTPEVTCVVVDVSHEE<br>GEVKFNWYVDGVEVHNAKTKPR<br>EEQYNSTYRVVSVLTVLHQDWL<br>NGKEYKCKVSNKALPRPIEKTI<br>SKAKGQPREPQVYTLPPCREEM<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | | | |
| Variant G14 | TSHR260 2P2R huIgG1 with S239D/ H268D/L328W | MGWSCIILFLVATATGVHSMGC<br>SSPPCECHQEEDERVTCKDIQR<br>IPSLPPSTQTLKLIETHLRTIP<br>SHAFSNLPNISRIYVSIDVTLQ<br>QLESHSFYNLSKVTHIEIRNTP<br>NLTYIDPDALKELPLLKELGIF<br>NTGLKMFPPLTKVYSTDIFFIL<br>EITDNPYMTSIPRNAFQGLCNE<br>TLTLKLYNNGFTSVQGYAFNGT<br>KLDAVYLNKNKYLTVIDKDAFG<br>GVYSGPSLLDVSQTSVTALPSK<br>GLEHLKELRARNTWTLDKTHTC<br>PPCPAPELLGGPDVELFPPKPK<br>DTLMISRTPEVTCVVVDVSDED<br>PEVKENWYVDGVEVHNAKTKPR<br>EEQYNSTYRVVSVLTVLHQDWL<br>NGKEYKCKVSNKAWPAPIEKTI<br>SKAKGQPREPQVYTLPPCRDEL<br>TKNQVSLWCLVKGFYPSDIAVE<br>WESNGQPENNYKTTPPVLDSDG<br>SFFLYSKLTVDKSRWQQGNVES<br>CSVMHEALHNHYTQKSLSLSPG<br>K | 331 | MGWSCIILFLVATATGVHSDKTHT<br>CPPCPAPELLGGPDVFLFPPKPKD<br>TLMISRTPEVTCVVVDVSDEDPEV<br>KFNWYVDGVEVHNAKTKPREEQYN<br>STYRVVSVLTVLHQDWLNGKEYKC<br>KVSNKAWPAPIEKTISKAKGQPRE<br>PQVCTLPPSRDELTKNQVSLSCAV<br>KGFYPSDIAVEWESNGQPENNYKT<br>TPPVLDSDGSFFLVSKLTVDKSRW<br>QQGNVFSCSVMHEALHNHYTQKSL<br>SLSPGK | 345 |

TABLE 9B

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant A1 | TSHR260 WT huIgG1 with RR/MST-HN | MGCSSPPCECHQEEDFRVTCKD<br>IQRIPSLPPSTQTLKLIETHLR<br>TIPSHAFSNLPNISRIYVSIDV<br>TLQQLESHSFYNLSKVTHIEIR<br>NTRNLTYIDPDALKELPLLKEL<br>GIFNTGLKMFPDLTKVYSTDIF<br>FILEITDNPYMTSIPVNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELIARNTWTLDKT<br>HTCPPCPAPELLRGPSVELFPP<br>KPKDTLYITREPEVTCVVVDVS<br>HEDPEVKFNWYVDGVEVHNAKT<br>KPREEQYNSTYRVVSVLTVLHQ<br>DWLNGKEYKCKVSNKARPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALKFHYTQKSLSL<br>SPGK | 231 | DKTHTCPPCPAPELLRGPSVELEP<br>PKPKDTLYITREPEVTCVVVDVSH<br>EDPEVKENWYVDGVEVHNAKTKPR<br>EEQYNSTYRVVSVLTVLHQDWING<br>KEYKCKVSNKARPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALKFHY<br>TQKSLSLSPGK | 238 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant A3 | TSHR260 2P2R huIgG1 with RR/MST-HN | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPELLRGPSVELFPP<br>KPKDTLYITREPEVTCVVVDVS<br>HEDPEVKENWYVDGVEVHNAKT<br>KPREEQYNSTYRVVSVLTVLHQ<br>DWLNGKEYKCKVSNKARPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALKFHYTQKSLSL<br>SPGK | 232 | DKTHTCPPCPAPELLRGPSVELEP<br>PKPKDTLYITREPEVTCVVVDVSH<br>EDPEVKENWYVDGVEVHNAKTKPR<br>EEQYNSTYRVVSVLTVLHQDWING<br>KEYKCKVSNKARPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALKFHY<br>TQKSLSLSPGK | 239 |
| Variant A4 | TSHR260 2P1S huIgG1 with RR/MST-HN | MGCSSPPCECHQEEDERVTCKD<br>IQRIPSLPPSTQTLKLIETSLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPVNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELIARNTWTLDKT<br>HTCPPCPAPELLRGPSVELFPP<br>KPKDTLYITREPEVTCVVVDVS<br>HEDPEVKENWYVDGVEVHNAKT<br>KPREEQYNSTYRVVSVLTVLHQ<br>DWLNGKEYKCKVSNKARPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALKFHYTQKSLSL<br>SPGK | 233 | DKTHTCPPCPAPELLRGPSVELFP<br>PKPKDTLYITREPEVTCVVVDVSH<br>EDPEVKFNWYVDGVEVHNAKTKPR<br>EEQYNSTYRVVSVLTVLHQDWING<br>KEYKCKVSNKARPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALKFHY<br>TQKSLSLSPGK | 240 |
| Variant B1 | TSHR260 WT huIgG1 with S267E/ L328F | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTRNLTYIDPDALKELPLLKEL<br>GIFNTGLKMFPDLTKVYSTDIE<br>FILEITDNPYMTSIPVNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELIARNTWTLDKT<br>HTCPPCPAPELLGGPSVELFPP<br>KPKDTLMISRTPEVTCVVVDVE<br>HEDPEVKFNWYVDGVEVHNAKT<br>KPREEQYNSTYRVVSVLTVLHQ<br>DWLNGKEYKCKVSNKAFPAPIE<br>KTISKAKGQPREPQVYTLPPCR<br>EEMTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 234 | DKTHTCPPCPAPELLGGPSVELFP<br>PKPKDTLMISRTPEVTCVVVDVEH<br>EDPEVKFNWYVDGVEVHNAKTKPR<br>EEQYNSTYRVVSVLTVLHQDWING<br>KEYKCKVSNKAFPAPIEKTISKAK<br>GQPREPQVCTLPPSREEMTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 241 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant B2 | TSHR260 2P huIgG1 with S267E/ L328F | MGCSSPPCECHQEEDFRVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPVNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELIARNTWTLDKT<br>HTCPPCPAPELLGGPSVELFPP<br>KPKDTLMISRTPEVTCVVVDVE<br>HEDPEVKENWYVDGVEVHNAKT<br>KPREEQYNSTYRVVSVLTVLHQ<br>DWLNGKEYKCKVSNKAFPAPIE<br>KTISKAKGQPREPQVYTLPPCR<br>EEMTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 235 | DKTHTCPPCPAPELLGGPSVFLFP<br>PKPKDTLMISRTPEVTCVVVDVEH<br>EDPEVKFNWYVDGVEVHNAKTKPR<br>EEQYNSTYRVVSVLTVLHQDWLNG<br>KEYKCKVSNKAFPAPIEKTISKAK<br>GQPREPQVCTLPPSREEMTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 242 |
| Variant B3 | TSHR260 2P2R huIgG1 with S267E/L328F | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPELLGGPSVELEPP<br>KPKDTLMISRTPEVTCVVVDVE<br>HEDPEVKFNWYVDGVEVHNAKT<br>KPREEQYNSTYRVVSVLTVLHQ<br>DWLNGKEYKCKVSNKAFPAPIE<br>KTISKAKGQPREPQVYTLPPCR<br>EEMTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 236 | DKTHTCPPCPAPELLGGPSVELEP<br>PKPKDTLMISRTPEVTCVVVDVEH<br>EDPEVKFNWYVDGVEVHNAKTKPR<br>EEQYNSTYRVVSVLTVLHQDWING<br>KEYKCKVSNKAFPAPIEKTISKAK<br>GQPREPQVCTLPPSREEMTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 243 |
| Variant B4 | TSHR260 2P1S huIgG1 with S267E/L328F | MGCSSPPCECHQEEDERVTCKD<br>IQRIPSLPPSTQTLKLIETSLR<br>TIPSHAFSNLPNISRIYVSIDV<br>TLQQLESHSFYNLSKVTHIEIR<br>NTPNLTYIDPDALKELPLLKFL<br>GIFNTGLKMFPPLTKVYSTDIF<br>FILEITDNPYMTSIPVNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELIARNTWTLDKT<br>HTCPPCPAPELLGGPSVELEPP<br>KPKDTLMISRTPEVTCVVVDVE<br>HEDPEVKENWYVDGVEVHNAKT<br>KPREEQYNSTYRVVSVLTVLHQ<br>DWLNGKEYKCKVSNKAFPAPIE<br>KTISKAKGQPREPQVYTLPPCR<br>EEMTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 237 | DKTHTCPPCPAPELLGGPSVELEP<br>PKPKDTLMISRTPEVTCVVVDVEH<br>EDPEVKFNWYVDGVEVHNAKTKPR<br>EEQYNSTYRVVSVLTVLHQDWING<br>KEYKCKVSNKAFPAPIEKTISKAK<br>GQPREPQVCTLPPSREEMTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 244 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant D3 | TSHR260 2P2R huIgG1 with P238D | MGCSSPPCECHQEEDFRVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIE<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPELLGGDSVELFPP<br>KPKDTLMISRTPEVTCVVVDVS<br>HEDPEVKENWYVDGVEVHNAKT<br>KPREEQYNSTYRVVSVLTVLHQ<br>DWLNGKEYKCKVSNKALPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 245 | DKTHTCPPCPAPELLGGDSVELEP<br>PKPKDTLMISRTPEVTCVVVDVSH<br>EDPEVKFNWYVDGVEVHNAKTKPR<br>EEQYNSTYRVVSVLTVLHQDWLNG<br>KEYKCKVSNKALPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 248 |
| Variant E3 | TSHR260 2P2R huIgG1 with P238D and LS | MGCSSPPCECHQEEDFRVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPELLGGDSVELFPP<br>KPKDTLMISRTPEVTCVVVDVS<br>HEDPEVKENWYVDGVEVHNAKT<br>KPREEQYNSTYRVVSVLTVLHQ<br>DWLNGKEYKCKVSNKALPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVLHEALHSHYTQKSLSL<br>SPGK | 246 | DKTHTCPPCPAPELLGGDSVELEP<br>PKPKDTLMISRTPEVTCVVVDVSH<br>EDPEVKENWYVDGVEVHNAKTKPR<br>EEQYNSTYRVVSVLTVLHQDWING<br>KEYKCKVSNKALPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVLHEALHSHY<br>TQKSLSLSPGK | 249 |
| Variant F3 | TSHR260 2P2R huIgG1 with LS | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPELLGGPSVELFPP<br>KPKDTLMISRTPEVTCVVVDVS<br>HEDPEVKENWYVDGVEVHNAKT<br>KPREEQYNSTYRVVSVLTVLHQ<br>DWLNGKEYKCKVSNKALPAPIE<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVLHEALHSHYTQKSLSL<br>SPGK | 247 | DKTHTCPPCPAPELLGGDSVELEP<br>PKPKDTLMISRTPEVTCVVVDVSH<br>EDPEVKFNWYVDGVEVHNAKTKPR<br>EEQYNSTYRVVSVLTVLHQDWING<br>KEYKCKVSNKALPAPIEKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVLHEALHSHY<br>TQKSLSLSPGK | 250 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant G1 | TSHR260<br>2P2R huIgG1<br>with<br>E233V/<br>L234D/<br>L235F/<br>G236R/<br>G237D/<br>S239L/<br>S267D/<br>H268P/<br>S298G/<br>T299A/<br>A327L/<br>L328A/<br>A330H/<br>E333I | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPVDERDPLVELFPP<br>KPKDTLMISRTPEVTCVVVDVD<br>PEDPEVKFNWYVDGVEVHNAKT<br>KPREEQYNGAYRVVSVLTVLHQ<br>DWLNGKEYKCKVSNKLAPHPII<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 346 | DKTHTCPPCPAPVDERDPLVELFP<br>PKPKDTLMISRTPEVTCVVVDVDP<br>EDPEVKENWYVDGVEVHNAKTKPR<br>EEQYNGAYRVVSVLTVLHQDWING<br>KEYKCKVSNKLAPHPIIKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 360 |
| Variant G2 | TSHR260<br>2P2R<br>huIgG1 with<br>E233V/<br>L234D/<br>L235F/<br>G236R/<br>G237D/<br>S239L/<br>S267D/<br>R292Q/<br>H268P/<br>S298G/<br>T299A/<br>A327L/<br>L328A/<br>A330H/<br>E333I | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPVDERDPLVELFPP<br>KPKDTLMISRTPEVTCVVVDVD<br>PEDPEVKENWYVDGVEVHNAKT<br>KPQEEQYNGAYRVVSVLTVLHQ<br>DWLNGKEYKCKVSNKLAPHPII<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 347 | DKTHTCPPCPAPVDERDPLVELFP<br>PKPKDTLMISRTPEVTCVVVDVDP<br>EDPEVKENWYVDGVEVHNAKTKPQ<br>EEQYNGAYRVVSVLTVLHQDWING<br>KEYKCKVSNKLAPHPIIKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 361 |
| Variant G3 | TSHR260<br>2P2R<br>huIgG1 with<br>E233V/<br>L234D/<br>L235F/<br>G236R/<br>G237D/<br>S239L/<br>H268P/<br>R292Q/<br>S298G/<br>T299A/<br>A327L/<br>L328A/<br>A330H/<br>E333I | MGCSSPPCECHQEEDERVTCKD<br>IQRIPSLPPSTQTLKLIETHLR<br>TIPSHAFSNLPNISRIYVSIDV<br>TLQQLESHSFYNLSKVTHIEIR<br>NTPNLTYIDPDALKELPLLKEL<br>GIFNTGLKMFPPLTKVYSTDIF<br>FILEITDNPYMTSIPRNAFQGL<br>CNETLTLKLYNNGFTSVQGYAF<br>NGTKLDAVYLNKNKYLTVIDKD<br>AFGGVYSGPSLLDVSQTSVTAL<br>PSKGLEHLKELRARNTWTLDKT<br>HTCPPCPAPVDERDPLVELFPP<br>KPKDTLMISRTPEVTCVVVDVS<br>PEDPEVKENWYVDGVEVHNAKT<br>KPQEEQYNGAYRVVSVLTVLHQ<br>DWLNGKEYKCKVSNKLAPHPII<br>KTISKAKGQPREPQVYTLPPCR<br>DELTKNQVSLWCLVKGFYPSDI<br>AVEWESNGQPENNYKTTPPVLD<br>SDGSFFLYSKLTVDKSRWQQGN<br>VFSCSVMHEALHNHYTQKSLSL<br>SPGK | 348 | DKTHTCPPCPAPVDERDPLVFLFP<br>PKPKDTLMISRTPEVTCVVVDVSP<br>EDPEVKENWYVDGVEVHNAKTKPQ<br>EEQYNGAYRVVSVLTVLHQDWING<br>KEYKCKVSNKLAPHPIIKTISKAK<br>GQPREPQVCTLPPSRDELTKNQVS<br>LSCAVKGFYPSDIAVEWESNGQPE<br>NNYKTTPPVLDSDGSFFLVSKLTV<br>DKSRWQQGNVFSCSVMHEALHNHY<br>TQKSLSLSPGK | 362 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant G4 | TSHR260<br>2P2R<br>huIgG1 with<br>E233D/<br>G237D/<br>P238D/<br>H268D/<br>P271G/<br>A330R | MGCSSPPCECHQEEDERVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPDLLGDDSVELEPPKPKDTLMISRTPEVTCVVVDVSDEDGEVKENWYVDGVEVHNAKTKPREEQYNSTYRVVSVLTVLHQDWLNGKEYKCKVSNKALPRPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 349 | DKTHTCPPCPAPDLLGDDSVELEPPKPKDTLMISRTPEVTCVVVDVSDEDGEVKFNWYVDGVEVHNAKTKPREEQYNSTYRVVSVLTVLHQDWINGKEYKCKVSNKALPRPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 363 |
| Variant G5 | TSHR260<br>2P2R<br>huIgG1 with<br>L234Y/<br>P238D/<br>T250V/<br>V264I/<br>T307P/<br>Q311R/<br>A330K/<br>P343R/<br>M428L/<br>N434A/<br>Y436T/<br>Q438R/<br>S440E | MGCSSPPCECHQEEDFRVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPEYLGGDSVELFPPKPKDVLMISRTPEVTCVVIDVSHEDPEVKFNWYVDGVEVHNAKTKPREEQYNSTYRVVSVLPVLHRDWLNGKEYKCKVSNKALPKPIEKTISKAKGQRREPQVYTLPPCREEMTKNQVSLWCLVKGFYPSDIAVEWESNGQPENNYKTTPPVLDSDGSFFLYSKLTVDKSRWQQGNVFSCSVLHEALHAHTTRKELSLSPGK | 350 | DKTHTCPPCPAPEYLGGDSVELFPPKPKDVLMISRTPEVTCVVIDVSHEDPEVKENWYVDGVEVHNAKTKPREEQYNSTYRVVSVLPVLHRDWLNGKEYKCKVSNKALPKPIEKTISKAKGQRREPQVCTLPPSREEMTKNQVSLSCAVKGFYPSDIAVEWESNGQPENNYKTTPPVLDSDGSFFLVSKLTVDKSRWQQGNVFSCSVMLEALHAHTTRKELSLSPGK | 364 |
| Variant G6 | TSHR260<br>2P2R<br>huIgG1 with<br>L234D/<br>G236N/<br>S267E | MGCSSPPCECHQEEDFRVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPEDLNGPSVFLFPPKPKDTLMISRTPEVTCVVVDVEHEDPEVKENWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 351 | DKTHTCPPCPAPEDLNGPSVELEPPKPKDTLMISRTPEVTCVVVDVEHEDPEVKENWYVDGVEVHNAKTKPREEQYNSTYRVVSVLTVLHQDWINGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 365 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant G7 | TSHR260 2P2R huIgG1 with L235R | MGCSSPPCECHQEEDFRVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIEFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPELRGGPSVELFPPKPKDTLMISRTPEVTCVVVDVSHEDPEVKENWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 352 | DKTHTCPPCPAPELRGGPSVELEPPKPKDTLMISRTPEVTCVVVDVSHEDPEVKENWYVDGVEVHNAKTKPREEQYNSTYRVVSVLTVLHQDWINGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 366 |
| Variant G8 | TSHR260 2P2R huIgG1 with G236N/ S267E | MGCSSPPCECHQEEDERVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPELLNGPSVELFPPKPKDTLMISRTPEVTCVVVDVEHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 353 | DKTHTCPPCPAPELLNGPSVELFPPKPKDTLMISRTPEVTCVVVDVEHEDPEVKFNWYVDGVEVHNAKTKPREEQYNSTYRVVSVLTVLHQDWINGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 367 |
| Variant G9 | TSHR260 2P2R huIgG1 with P238D/ D270E | MGCSSPPCECHQEEDFRVTCKDIQRIPSLPPSTQTLKLIETHLRTIPSHAFSNLPNISRIYVSIDVTLQQLESHSFYNLSKVTHIEIRNTPNLTYIDPDALKELPLLKFLGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPELLGGDSVELFPPKPKDTLMISRTPEVTCVVVDVSHEEPEVKENWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 354 | DKTHTCPPCPAPELLGGDSVELFPPKPKDTLMISRTPEVTCVVVDVSHEEPEVKFNWYVDGVEVHNAKTKPREEQYNSTYRVVSVLTVLHQDWLNGKEYKCKVSNKALPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 368 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant G10 | TSHR260 2P2R huIgG1 with P238D/ P271G | MGCSSPPCECHQEEDFRVTCKD IQRIPSLPPSTQTLKLIETHLR TIPSHAFSNLPNISRIYVSIDV TLQQLESHSFYNLSKVTHIEIR NTPNLTYIDPDALKELPLLKEL GIFNTGLKMFPPLTKVYSTDIF FILEITDNPYMTSIPRNAFQGL CNETLTLKLYNNGFTSVQGYAF NGTKLDAVYLNKNKYLTVIDKD AFGGVYSGPSLLDVSQTSVTAL PSKGLEHLKELRARNTWTLDKT HTCPPCPAPELLGGDSVELFPP KPKDTLMISRTPEVTCVVVDVS HEDGEVKFNWYVDGVEVHNAKT KPREEQYNSTYRVVSVLTVLHQ DWLNGKEYKCKVSNKALPAPIE KTISKAKGQPREPQVYTLPPCR EEMTKNQVSLWCLVKGFYPSDI AVEWESNGQPENNYKTTPPVLD SDGSFFLYSKLTVDKSRWQQGN VFSCSVMHEALHNHYTQKSLSL SPGK | 355 | DKTHTCPPCPAPELLGGDSVELFP PKPKDTLMISRTPEVTCVVVDVSH EDGEVKFNWYVDGVEVHNAKTKPR EEQYNSTYRVVSVLTVLHQDWING KEYKCKVSNKALPAPIEKTISKAK GQPREPQVCTLPPSREEMTKNQVS LSCAVKGFYPSDIAVEWESNGQPE NNYKTTPPVLDSDGSFFLVSKLTV DKSRWQQGNVFSCSVMHEALHNHY TQKSLSLSPGK | 369 |
| Variant G11 | TSHR260 2P2R huIgG1 with P238D/ D270E/ P271G | MGCSSPPCECHQEEDERVTCKD IQRIPSLPPSTQTLKLIETHLR TIPSHAFSNLPNISRIYVSIDV TLQQLESHSFYNLSKVTHIEIR NTPNLTYIDPDALKELPLLKEL GIFNTGLKMFPPLTKVYSTDIF FILEITDNPYMTSIPRNAFQGL CNETLTLKLYNNGFTSVQGYAF NGTKLDAVYLNKNKYLTVIDKD AFGGVYSGPSLLDVSQTSVTAL PSKGLEHLKELRARNTWTLDKT HTCPPCPAPELLGGDSVELEPP KPKDTLMISRTPEVTCVVVDVS HEEGEVKENWYVDGVEVHNAKT KPREEQYNSTYRVVSVLTVLHQ DWLNGKEYKCKVSNKALPAPIE KTISKAKGQPREPQVYTLPPCR EEMTKNQVSLWCLVKGFYPSDI AVEWESNGQPENNYKTTPPVLD SDGSFFLYSKLTVDKSRWQQGN VFSCSVMHEALHNHYTQKSLSL SPGK | 356 | DKTHTCPPCPAPELLGGDSVELEP PKPKDTLMISRTPEVTCVVVDVSH EEGEVKENWYVDGVEVHNAKTKPR EEQYNSTYRVVSVLTVLHQDWING KEYKCKVSNKALPAPIEKTISKAK GQPREPQVCTLPPSREEMTKNQVS LSCAVKGFYPSDIAVEWESNGQPE NNYKTTPPVLDSDGSFFLVSKLTV DKSRWQQGNVFSCSVMHEALHNHY TQKSLSLSPGK | 370 |
| Variant G12 | TSHR260 2P2R huIgG1 with G237D/ P238D/ P271G/ A330R | MGCSSPPCECHQEEDERVTCKD IQRIPSLPPSTQTLKLIETHLR TIPSHAFSNLPNISRIYVSIDV TLQQLESHSFYNLSKVTHIEIR NTPNLTYIDPDALKELPLLKEL GIFNTGLKMFPPLTKVYSTDIF FILEITDNPYMTSIPRNAFQGL CNETLTLKLYNNGFTSVQGYAF NGTKLDAVYLNKNKYLTVIDKD AFGGVYSGPSLLDVSQTSVTAL PSKGLEHLKELRARNTWTLDKT HTCPPCPAPELLGDDSVELFPP KPKDTLMISRTPEVTCVVVDVS HEDGEVKENWYVDGVEVHNAKT KPREEQYNSTYRVVSVLTVLHQ DWLNGKEYKCKVSNKALPRPIE KTISKAKGQPREPQVYTLPPCR EEMTKNQVSLWCLVKGFYPSDI AVEWESNGQPENNYKTTPPVLD SDGSFFLYSKLTVDKSRWQQGN VESCSVMHEALHNHYTQKSLSL SPGK | 357 | DKTHTCPPCPAPELLGDDSVFLFP PKPKDTLMISRTPEVTCVVVDVSH EDGEVKFNWYVDGVEVHNAKTKPR EEQYNSTYRVVSVLTVLHQDWING KEYKCKVSNKALPRPIEKTISKAK GQPREPQVCTLPPSREEMTKNQVS LSCAVKGFYPSDIAVEWESNGQPE NNYKTTPPVLDSDGSFFLVSKLTV DKSRWQQGNVFSCSVMHEALHNHY TQKSLSLSPGK | 371 |

TABLE 9B-continued

Exemplary Molecules
(without exemplary signal peptides; all molecules also include KIH mutations)

| Molecule ID | Description | Knob Arm | SEQ ID NO: | Hole Arm | SEQ ID NO: |
|---|---|---|---|---|---|
| Variant G13 | TSHR260 2P2R huIgG1 with G237D/ P238D/ D270E/ P271G/ A330R | MGCSSPPCECHQEEDFRVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPELLGDDSVELFPPKPKDTLMISRTPEVTCVVVDVSHEEGEVKFNWYVDGVEVHNAKTKPREEQYNSTYRVVSVLTVLHQDWLNGKEYKCKVSNKALPRPIEKTISKAKGQPREPQVYTLPPCREEMTKNQVSLWCLVKGFYPSDIAVEWESNGQPENNYKTTPPVLDSDGSFFLYSKLTVDKSRWQQGNVFSCSVMHEALHNHYTQKSLSLSPGK | 358 | DKTHTCPPCPAPELLGDDSVELFPPKPKDTLMISRTPEVTCVVVDVSHEEGEVKENWYVDGVEVHNAKTKPREEQYNSTYRVVSVLTVLHQDWINGKEYKCKVSNKALPRPIEKTISKAKGQPREPQVCTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK | 372 |
| Variant G14 | TSHR260 2P2R huIgG1 with S239D/ H268D/ L328W | MGCSSPPCECHQEEDERVTCKDIQRIPSLPPSTQTLKLIETHLRTIPSHAFSNLPNISRIYVSIDVTLQQLESHSFYNLSKVTHIEIRNTPNLTYIDPDALKELPLLKELGIFNTGLKMFPPLTKVYSTDIFFILEITDNPYMTSIPRNAFQGLCNETLTLKLYNNGFTSVQGYAFNGTKLDAVYLNKNKYLTVIDKDAFGGVYSGPSLLDVSQTSVTALPSKGLEHLKELRARNTWTLDKTHTCPPCPAPELLGGPDVELFPPKPKDTLMISRTPEVTCVVVDVSDEDPEVKENWYVDGVEVHNAKTKPREEQYNSTYRVVSVLTVLHQDWLNGKEYKCKVSNKAWPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK | 359 | DKTHTCPPCPAPELLGGPDVFLFPPKPKDTLMISRTPEVTCVVVDVSDEDPEVKENWYVDGVEVHNAKTKPREEQYNSTYRVVSVLTVLHQDWINGKEYKCKVSNKAWPAPIEKTISKAKGQPREPQVCTLPPSRDELTKNQVSLSCAVKGFYPSDIAVEWESNGQPENNYKTTPPVLDSDGSFFLVSKLTVDKSRWQQGNVFSCSVMHEALHNHYTQKSLSLSPGK | 373 |

Example 2: In Vitro Neutralization of Anti-TSHR Autoantibodies

The present Example demonstrates the functionality of an exemplary molecule described in Example 1 (Variant D33). Specifically, the exemplary molecule was tested for its ability to target and neutralize patient-derived monoclonal anti-TSHR autoantibodies through the anti-TSHR autoantibody domain. The effect of the molecule on TSHR activity was also tested.

Figure 8B:
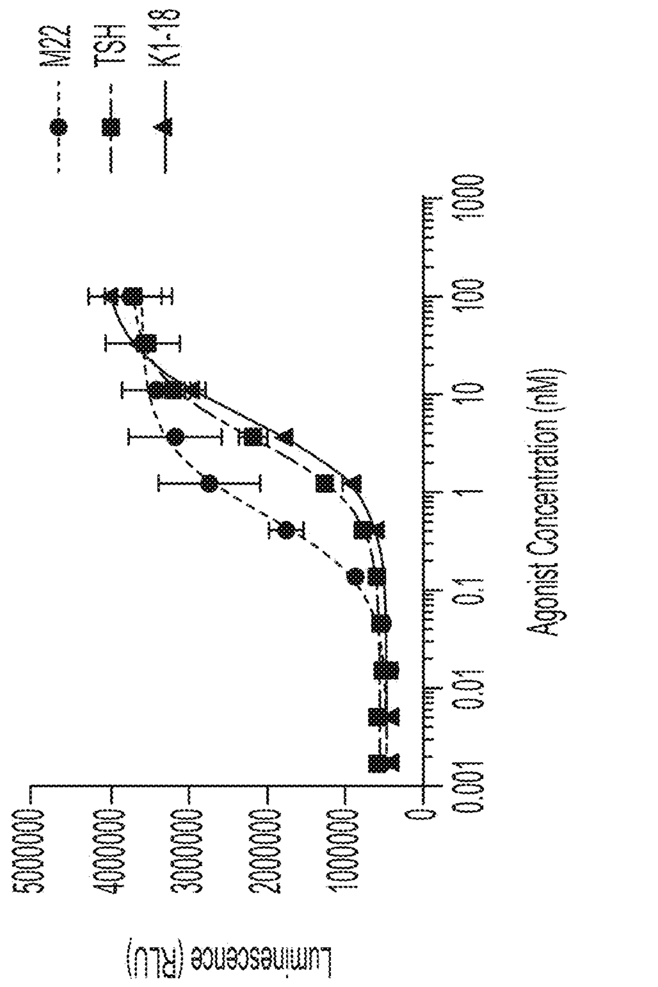
FIG. 8B shows results from a cAMP assay after addition of increasing concentration of agonist (M22, K1-18 and TSH).
Figure 8A:
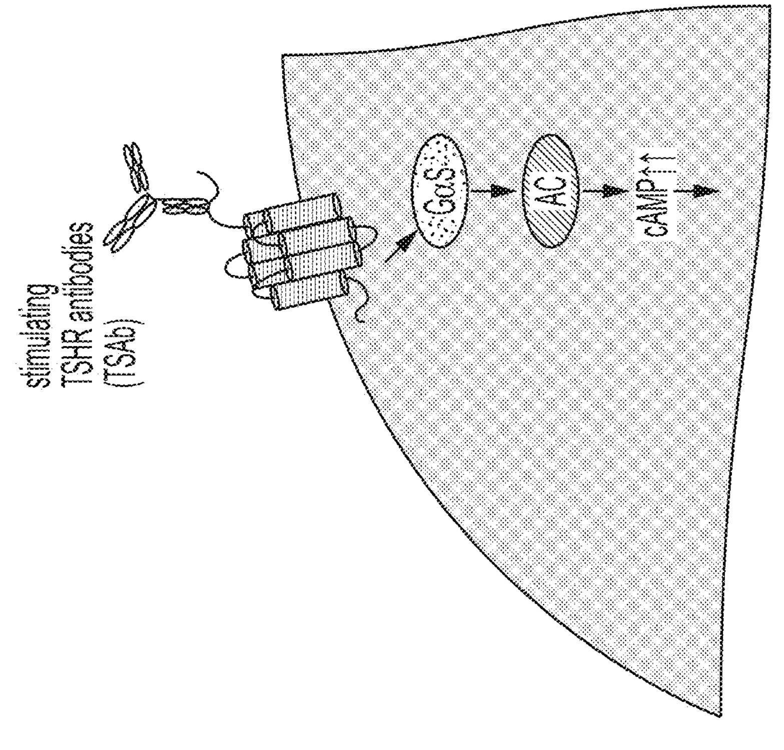
FIG. 8A shows an exemplary mechanism by which anti-TSHR autoantibodies stimulate cAMP production in a cell.

Determining the EC80 of Monoclonal Autoantibodies M22, K1-18, or Natural Ligand TSH in CHO-TSHR Cells To determine the potency of stimulating anti-TSHR autoantibodies or the natural ligand thyroid stimulating hormone (TSH), Chinese Hamster Ovary (CHO) cells over-expressing the wild type TSHR (Eurofins DiscoverX) were co-incubated with a titration of monoclonal autoantibodies M22 or K1-18, or TSH with an 11-point dilution curve (diluted in PBS) followed by a blank negative control. 16-20 hours prior to the assay, CHO-TSHR cells were detached with TrypLE™ (Thermo Fisher). Cells were then seeded at 20,000 cells per well in 100 ul in a 96-well flat bottom opaque white walled plate (Corning). After overnight culture at 37 C and 5% $CO_2$, monoclonal autoantibody or TSH serial dilutions were made in PBS, pH 7.4 at room temperature in a 96-well round bottom plate. The assay plate containing cells was then removed from the incubator, and the media from all wells was aspirated with a multichannel pipette. Serially diluted monoclonal autoantibodies or TSH were then added to the assay plate containing the CHO-TSHR cells, followed by a 30-minute incubation at 37 C. Next, the manufacturer's protocol for HitHunter® cAMP Assay for Biologics was followed to determine a luminescent signal that detects cAMP produced by the CHO-TSHR cells. Briefly, cells were lysed by adding 60 ul of "cAMP detection solution" containing the lysis buffer. The plate was then incubated at room temperature for 1 hour (protected from light) and then the "cAMP solution A" was added and the mixture was incubated for 3 hours at room temperature protected from light. Finally, the plate was read on a standard luminescence plate reader. A schematic of the anti-TSHR autoantibody-TSHR-cAMP pathway is shown in FIG. 8A. FIG. 8B shows cAMP activity from the addition of increasing concentration of agonist (M22, K1-18 or TSH).

Neutralization of Monoclonal Autoantibodies M22, K1-18 or Natural Ligand TSH with Molecule in CHO-TSHR Cells To determine the efficacy of the molecule Variant D3 in depleting the stimulatory activity of the monoclonal autoantibodies M22, K1-18 or the natural ligand thyroid stimulating hormone (TSH), cAMP levels were measured by ELISA produced by CHO cells overexpressing the wild type TSHR. 16-20 hours prior to the assay, CHO-TSHR cells were detached with TrypLE™ (Thermo Fisher). Cells were then seeded at 20,000 cells per well in 100 ul in a 96-well flat bottom opaque white walled plate (Corning). After overnight culture at 37 C in 5% $CO_2$, the molecule (Variant D3) was titrated in an 11-point 3-fold serial dilution curve, prior to mixing each dilution with a single concentration of M22, K1-18 or TSH that was previously determined as the EC80 for this assay. These mixtures were incubated at room temperature for 10 minutes prior to incubating with the CHO-TSHR cells. The assay plate containing cells was then removed from the incubator, and the media from all wells was aspirated with a multichannel pipette. 30 ul of PBS was then added to each well, and 15 ul of the 3× dilution mix was transferred to each well to a final 1× concentration. The cells were then incubated for 30 minutes at 37 C with immune complexes. Next, the manufacturer's protocol for HitHunter® cAMP Assay for Biologics was followed to determine a luminescent signal that detects cAMP produced by the CHO-TSHR cells. Briefly, cells were lysed by adding 60 ul of "cAMP detection solution" containing the lysis buffer. The plate was then incubated at room temperature for 1 hour (protected from light) and the "cAMP solution A" was added. The mixture was then incubated for 3 hours at room temperature protected from light. Finally, the plate was read on a standard luminescence plate reader.

Figure 9:
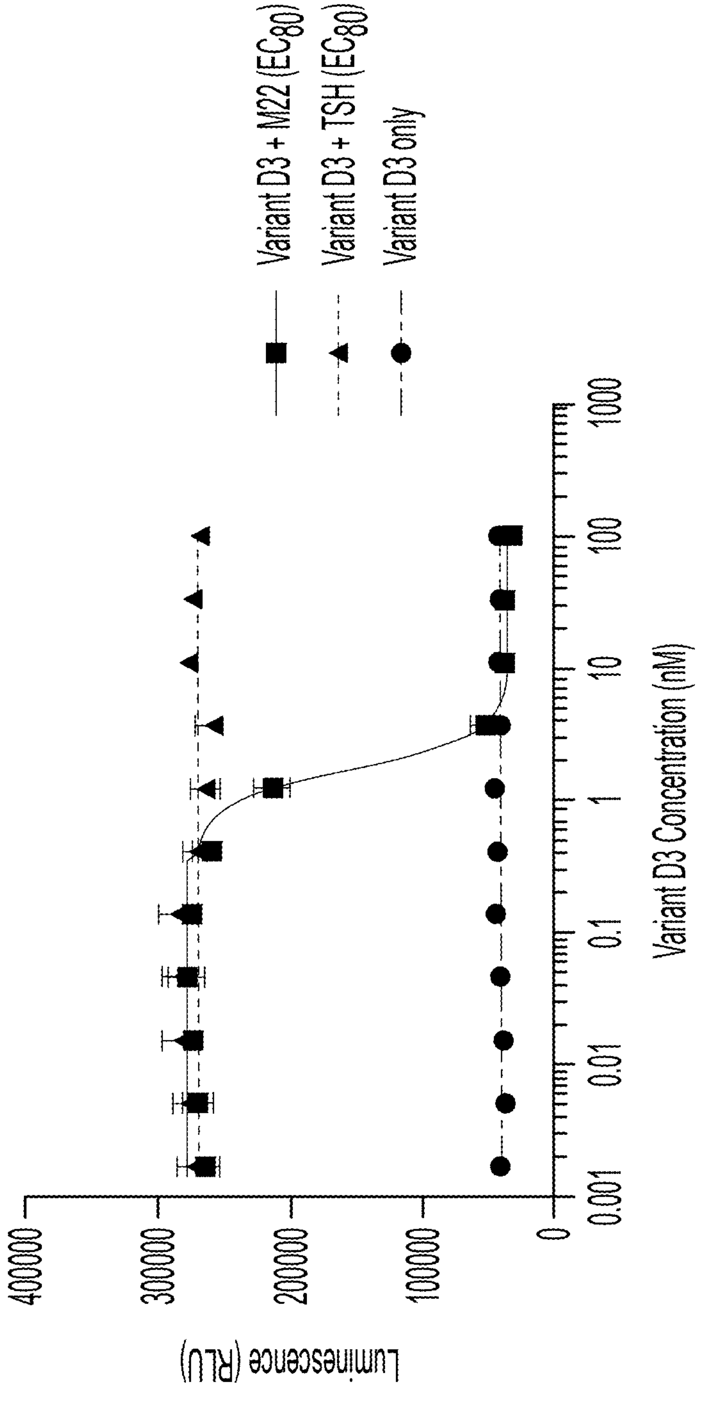
FIG. 9 shows results from a cAMP assay after administration of an exemplary molecule (Variant D3) alone, with anti-TSHR autoantibodies (M22) or with TSH.
Figure 10:
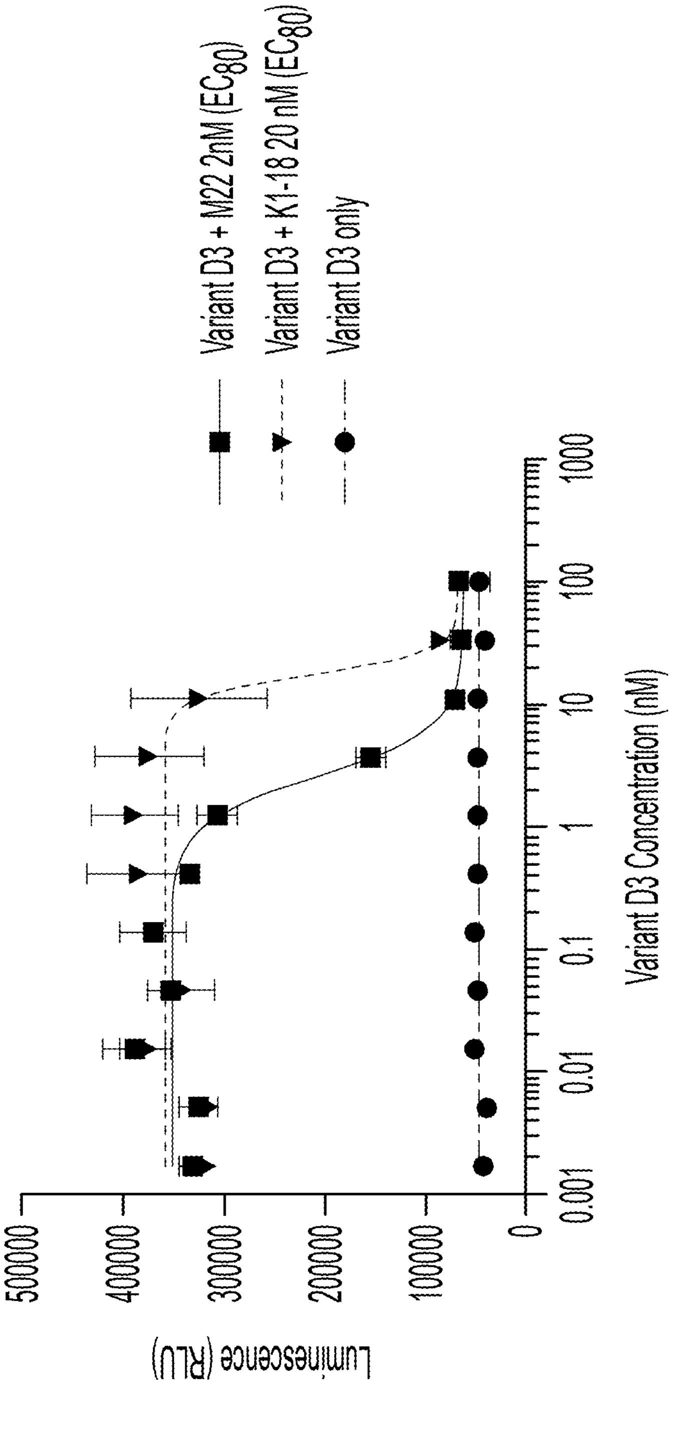
FIG. 10 shows results from a cAMP assay after administration of an exemplary molecule (Variant D3) alone or with anti-TSHR autoantibodies (M22 or K1-18).

Results from the cAMP assay are shown in FIG. 9 and FIG. 10. FIG. 9 shows that the exemplary molecule Variant D3 blocks TSHR-stimulating M22 autoantibody-induced cAMP signaling without affecting TSH signaling. FIG. 10 shows that the exemplary molecule Variant D3 also blocks TSHR-stimulating K1-18 autoantibody-induced cAMP signaling.

Neutralization of Polyclonal Patient Serum with Variant D3 in CHO-TSHR Cells

To determine the efficacy of exemplary molecule Variant D3 for depletion of the activity of polyclonal anti-TSHR antibodies in patient serum, Variant D3 was diluted to a final concentration of 200 nM in human serum at a 1:10 ratio. These mixtures were incubated at room temperature for 10 minutes prior to co-incubation with Chinese Hamster Ovary (CHO) cells overexpressing the wild type TSHR (Eurofins DiscoverX). 16-20 hours prior to the assay, CHO-TSHR cells were detached with TrypLE™ (Thermo Fisher). Cells were then seeded at 40,000 cells per well in 100 ul in a 96-well flat bottom opaque white walled plate (Corning). After overnight culture at 37C in 5% $CO_2$, Variant D3 dilutions were made with patient serum containing polyclonal anti-TSHR antibodies. The assay plate containing cells was then removed from the incubator, and the media from all wells was aspirated with a multichannel pipette. The cells were then incubated for 30 minutes at 37C with the molecule/patient serum mixture. Next, the manufacturer's protocol for Cyclic AMP XP Assay Kit (Cell Signaling Technologies) was followed to determine an absorbance signal that quantifies cAMP produced by the CHO-TSHR cells.

Briefly, cells were washed in PBS after co-incubation with molecule/patient serum, and then lysed with 1× lysis buffer. 50 ul of the cell lysates were then incubated at room temperature for 3 hours with 50 ul HRP-linked target solution in the provided antibody coated plate. The plate was then washed 4 times with 200 μl/well of 1× wash buffer, and 100 μl TMB substrate was added. After a 5-30 minute incubation at room temperature with TMB substrate, 100 ul/well of stop solution was added, and the plate was read on a plate reader at both 450 nm and 570 nm.

Figure 11:
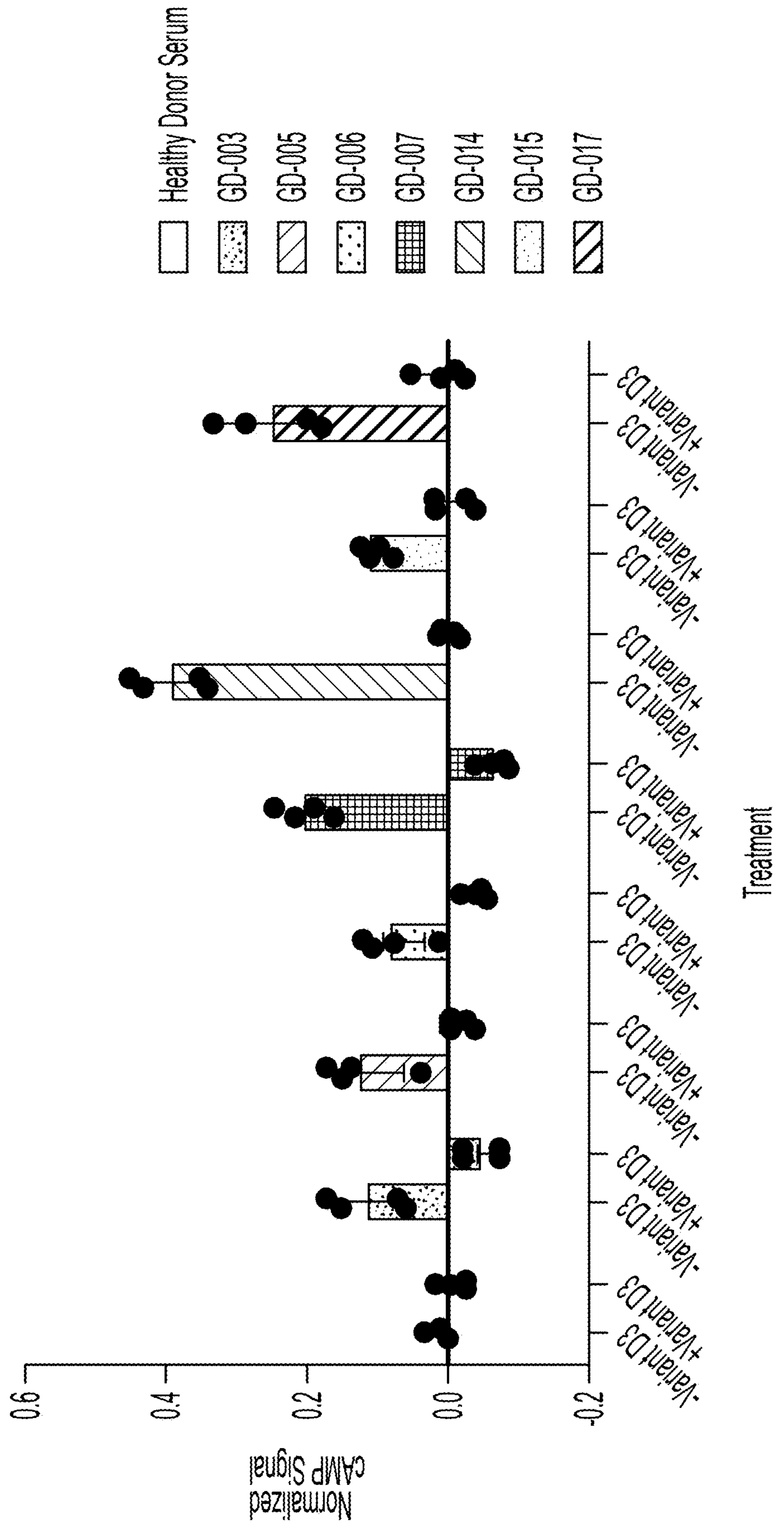
FIG. 11 shows results from a cAMP assay using healthy donor serum or patient serum samples containing anti-TSHR autoantibodies with and without an exemplary molecule (Variant D3).

Results from the cAMP assay are shown in FIG. 11. The data shows that the molecule Variant D3 neutralized polyclonal anti-TSHR antibodies in each patient's serum by way of diminished cAMP activity in each serum sample.

Neutralization of Polyclonal Patient Serum with Exemplary Molecule in CHO-TSHR Cells (Quidel Turbo TSI)

To determine the efficacy of exemplary molecule Variant D3 for depletion of the activity of patient serum containing polyclonal anti-TSHR antibodies, the molecule was diluted to a final concentration of 200 nM in human serum at a 1:10 ratio. These mixtures were incubated at room temperature for 10 minutes prior to co-incubation with Chinese Hamster Ovary (CHO) cells overexpressing the MC4 mutant TSHR (Thyretain Turbo TSI, Quidel Ortho). First, cAMP Reagent, Standard Panel, and Control were thawed at 37C for 7-10 minutes, and equilibrated to room temperature. Standards and samples were mixed by gentle pipetting, and 5 μl of each standard or sample was added to the bottom corner of each well in a white walled 96-well plate (Corning). Turbo TSI Cells were thawed in a 37C water bath for 2 minutes, and the entire contents were transferred to one bottle of 5 mL of cAMP Reagent and mixed by inverting. 50 ul of the cAMP Reagent and Turbo TSI Cells mixture was then transferred to each well of the white walled 96-well plate containing 5 μl of standard or samples. The cells and patient serum mixtures with or without molecule were incubated for 60 minutes at room temperature. The plate was then read on a standard plate reader or luminometer.

Figure 12B:
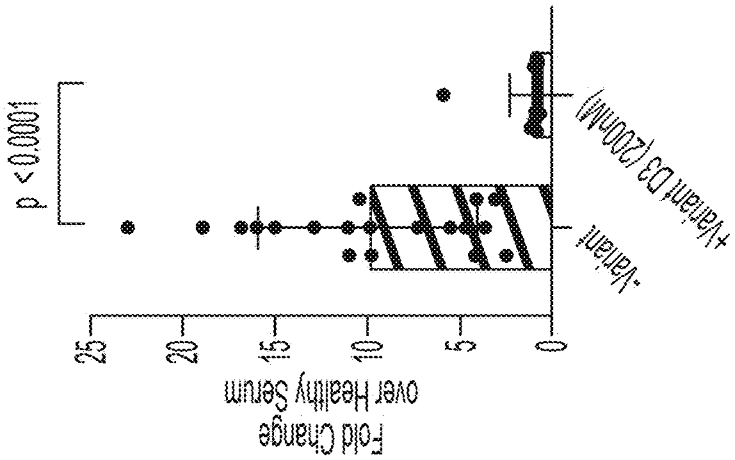
FIGS. 12A-12B show results from a cAMP assay where an exemplary molecule (Variant D3) reduced TSHR-activity (measured via downstream cAMP activity) in individual patient serum samples (FIG. 12A) and in pooled patient serum samples (FIG. 12B).
Figure 12A:
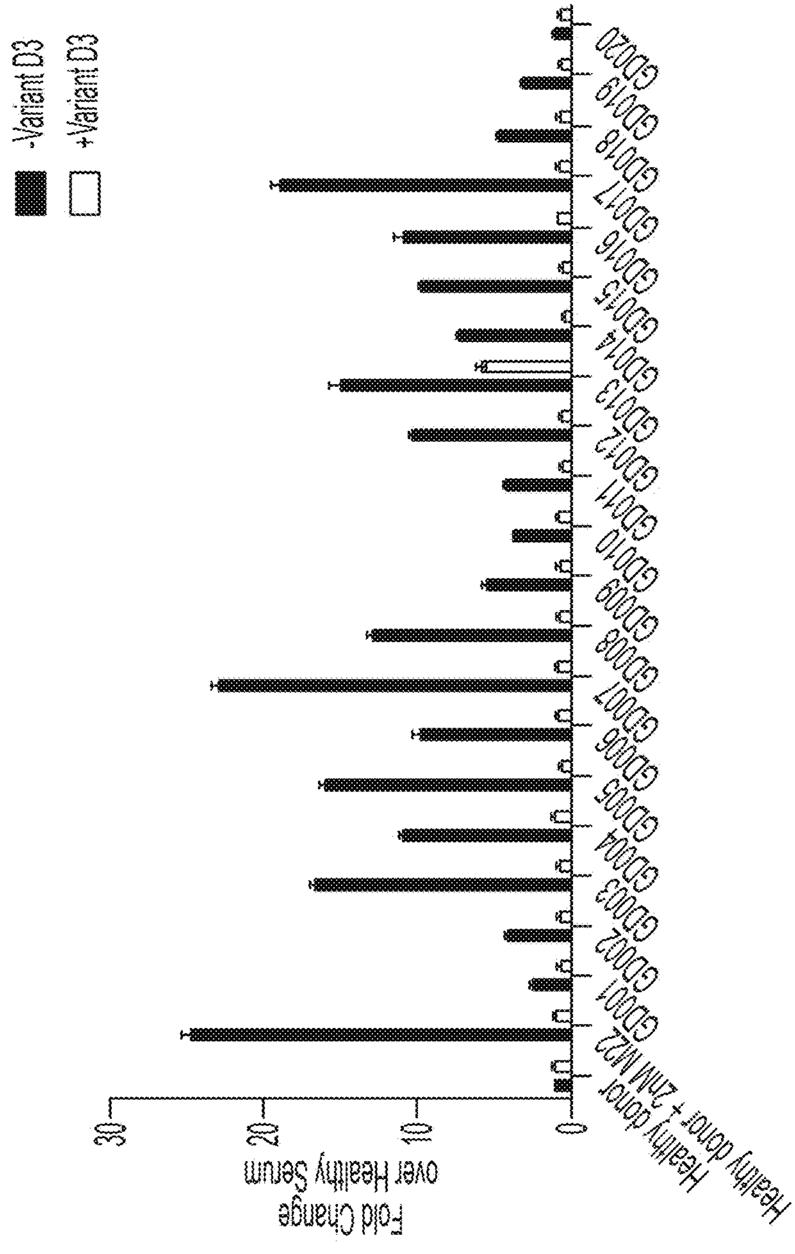
Figure 14A:
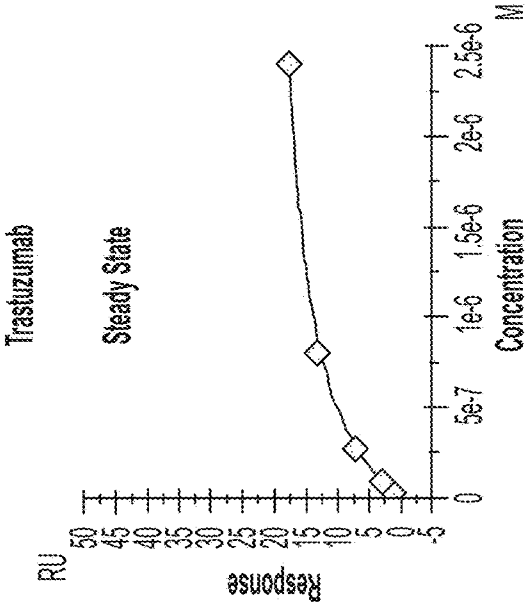
FIGS. 14A-14D show results from binding assays measuring binding activity of Trastuzumab control (FIG. 14A), Variant B3 (FIG. 14B), Variant D3 (FIG. 14C), and Variant E3 (FIG. 14D) to activating receptor FcγRIIA167H when the exemplary molecules were captured onto an SPR sensor chip and FcγR used as the analyte.
Figure 14B:
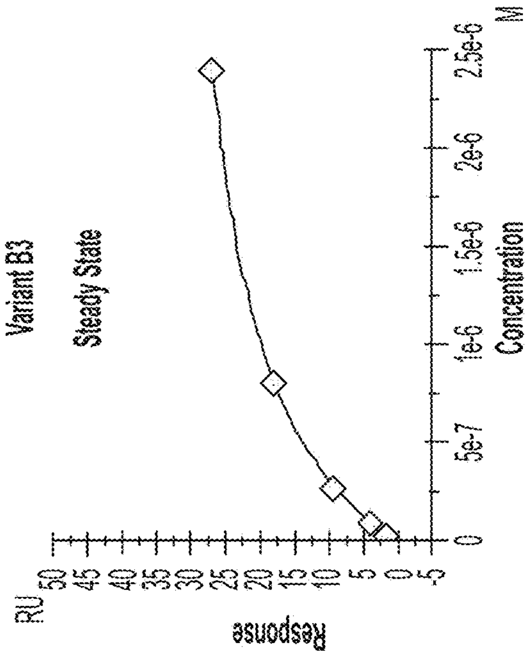
Figure 14C:
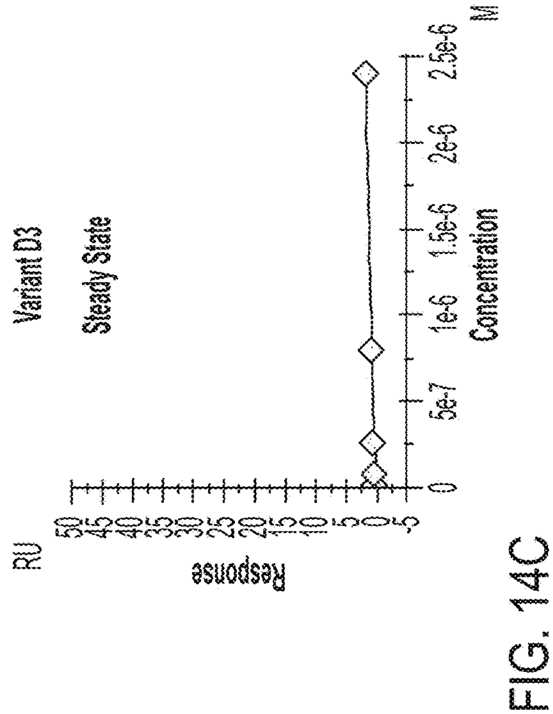
Figure 14D:
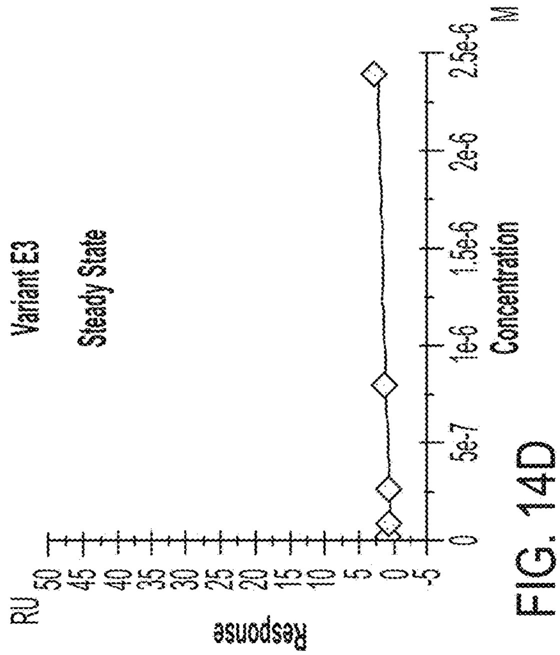
Figure 15A:
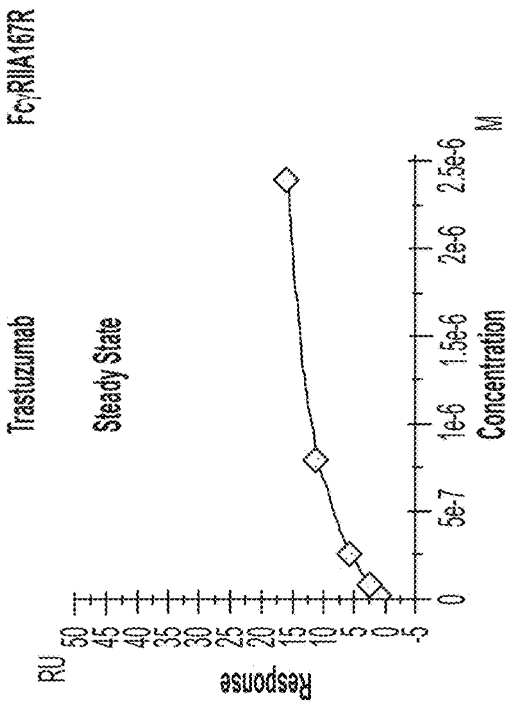
FIGS. 15A-15D show results from binding assays measuring binding activity of Trastuzumab control (FIG. 15A), Variant B3 (FIG. 15B), Variant D3 (FIG. 15C), and Variant E3 (FIG. 15D) to activating receptor FcγRIIA167R when the exemplary molecules were captured onto an SPR sensor chip and FcγR used as the analyte.
Figure 15B:
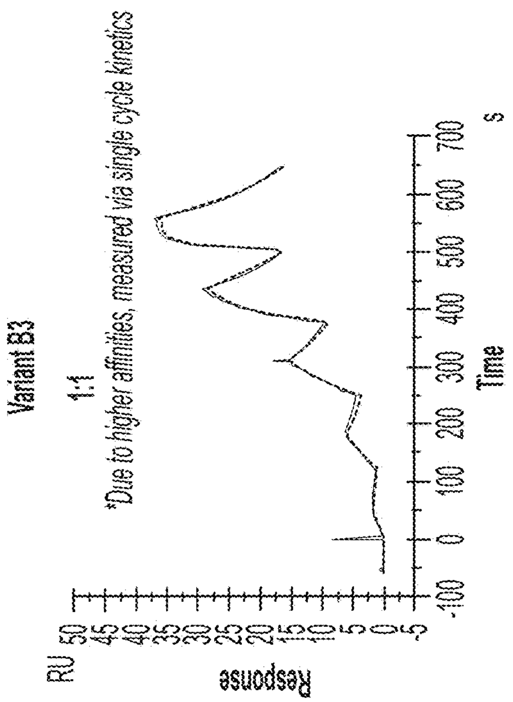
Figure 15C:
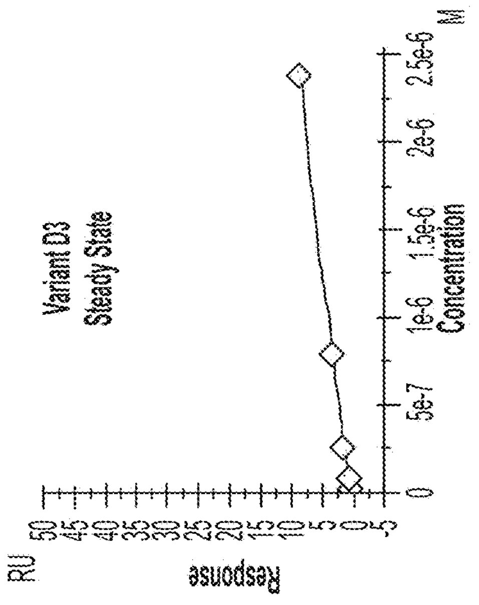
Figure 15D:
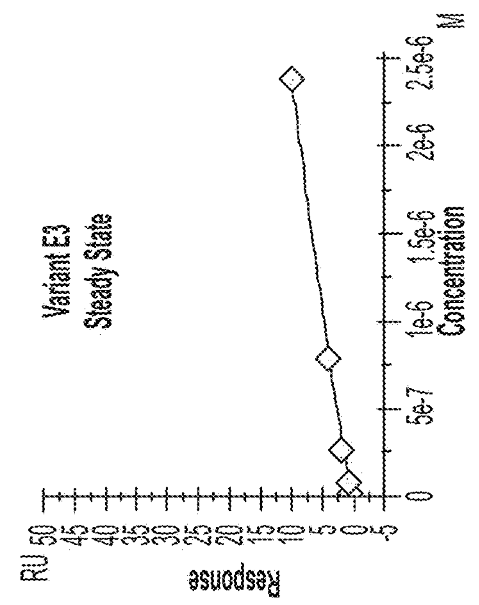
Figure 16A:
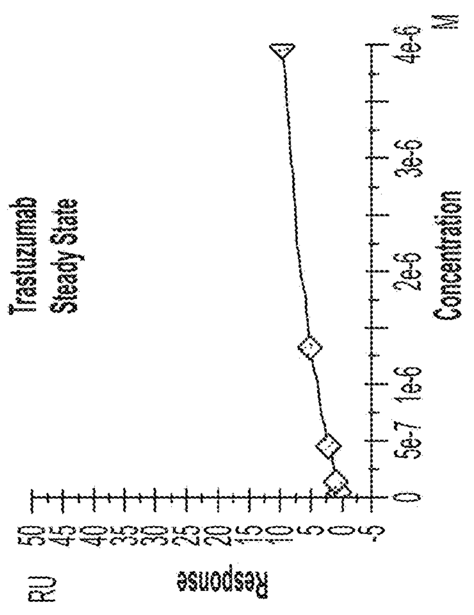
FIGS. 16A-16D show results from binding assays measuring binding activity of Trastuzumab control (FIG. 16A), Variant B3 (FIG. 16B), Variant D3 (FIG. 16C), and Variant E3 (FIG. 16D) to inhibitory receptor FcγRIIB when the exemplary molecules were captured onto an SPR sensor chip and FcγR used as the analyte.
Figure 16B:
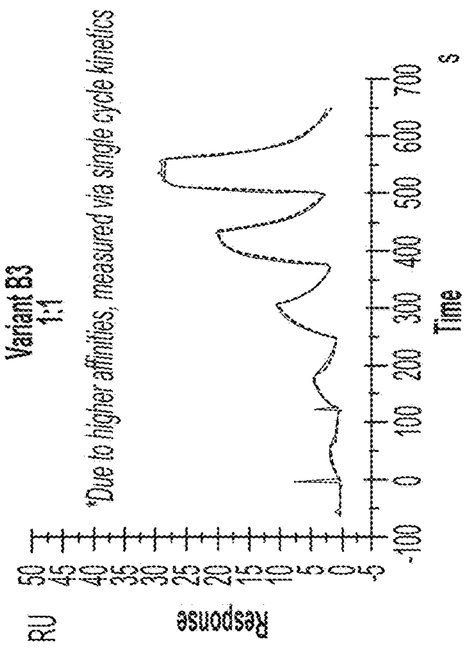
Figure 16C:
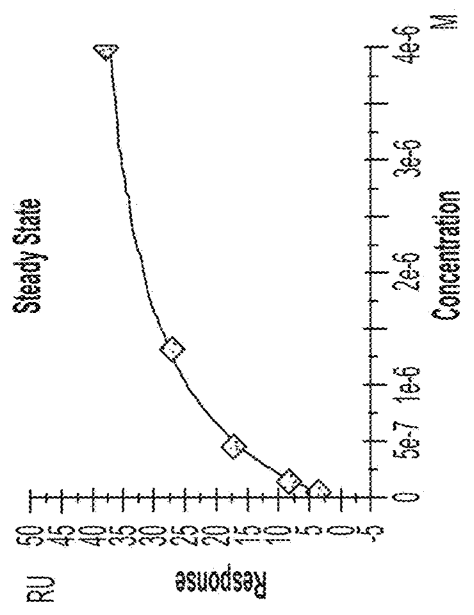
Figure 16D:
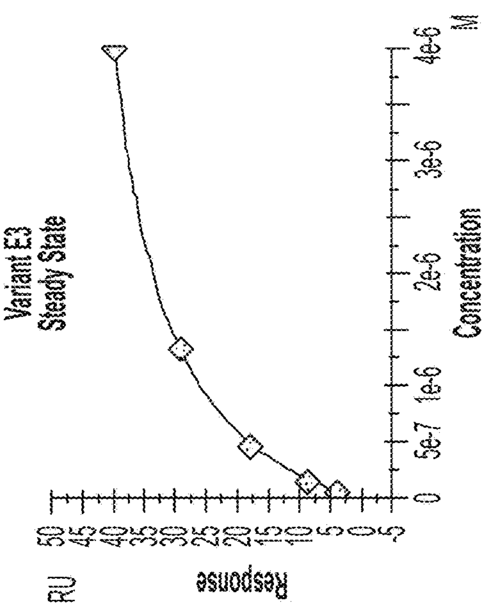
Figure 17A:
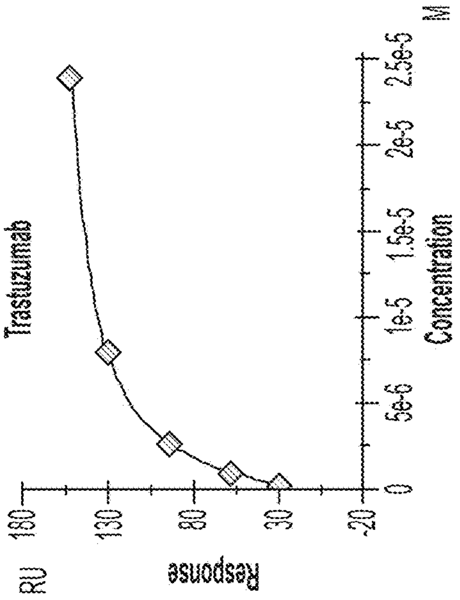
FIGS. 17A-17D show results from binding assays measuring binding activity of Trastuzumab control (FIG. 17A), Variant B3 (FIG. 17B), Variant D3 (FIG. 17C), and Variant E3 (FIG. 17D) to activating receptor FcγRIIA167H when His-Tagged FcγR was captured onto SPR sensor chip and the exemplary molecule used as the analyte.
Figure 17B:
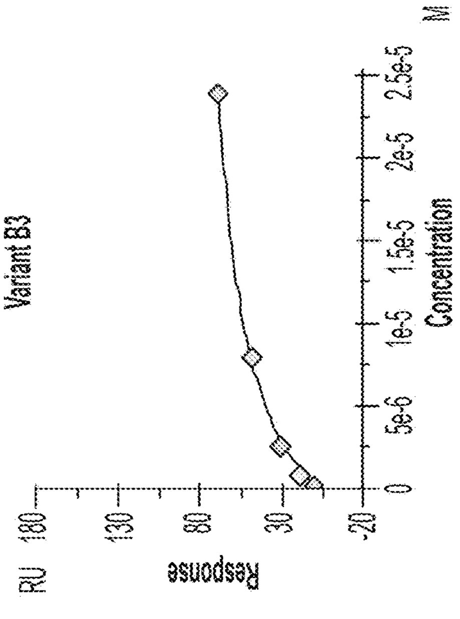
Figure 17C:
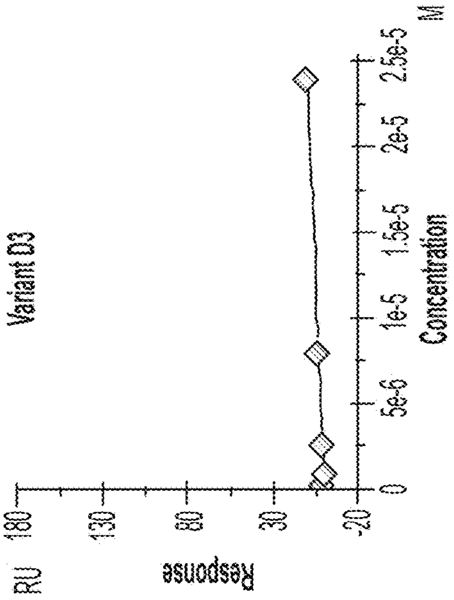
Figure 17D:
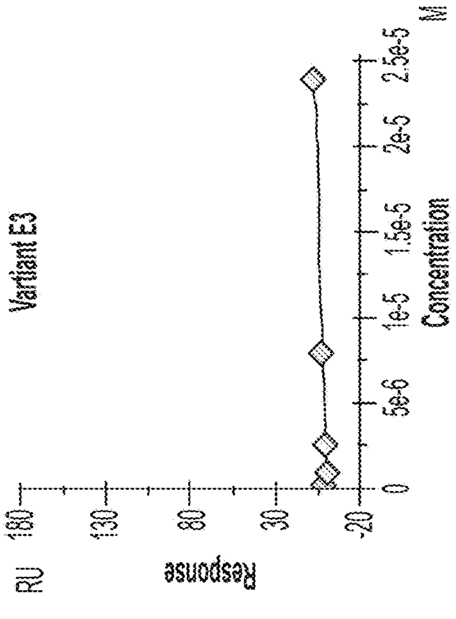
Figure 18A:
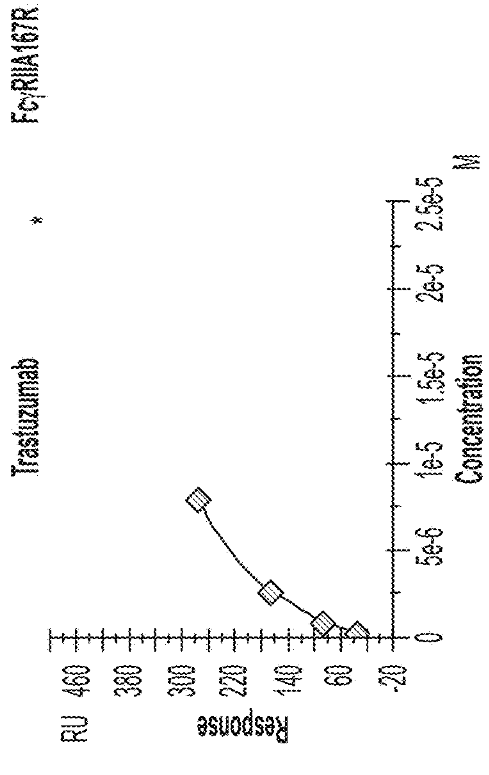
FIGS. 18A-18D show results from binding assays measuring binding activity of Trastuzumab control (FIG. 18A), Variant B3 (FIG. 18B), Variant D3 (FIG. 18C), and Variant E3 (FIG. 18D) to activating receptor FcγRIIA167R when His-Tagged FcγR was captured onto SPR sensor chip and the exemplary molecule used as the analyte.
Figure 18B:
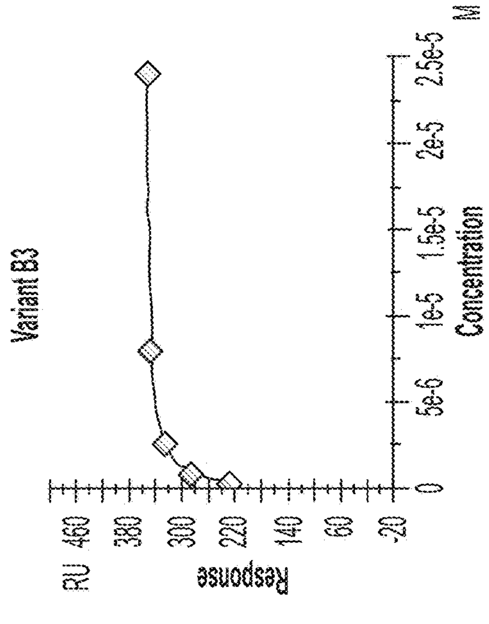
Figure 18C:
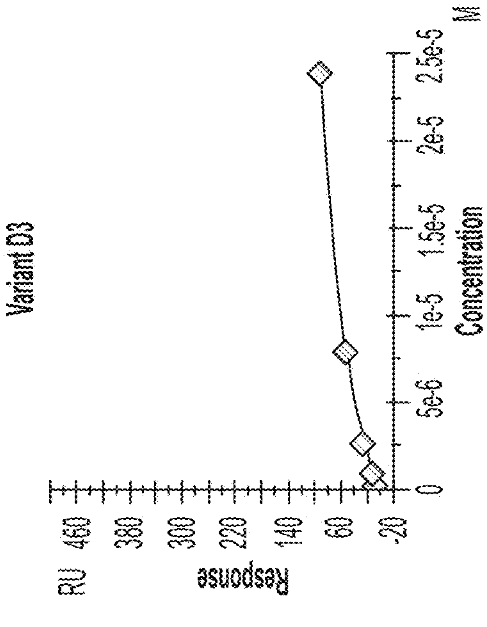
Figure 18D:
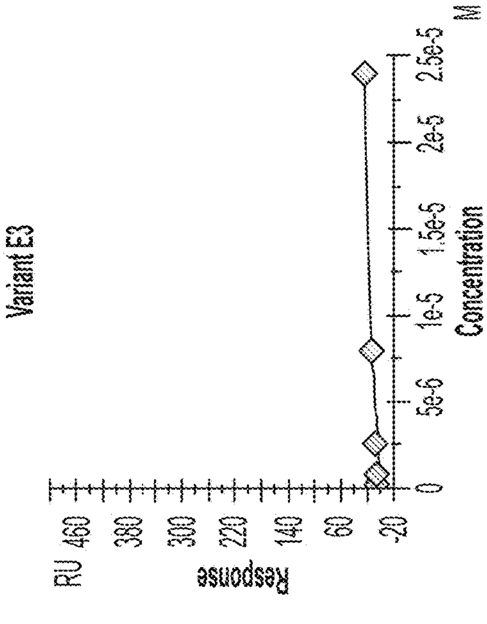
Figure 19A:
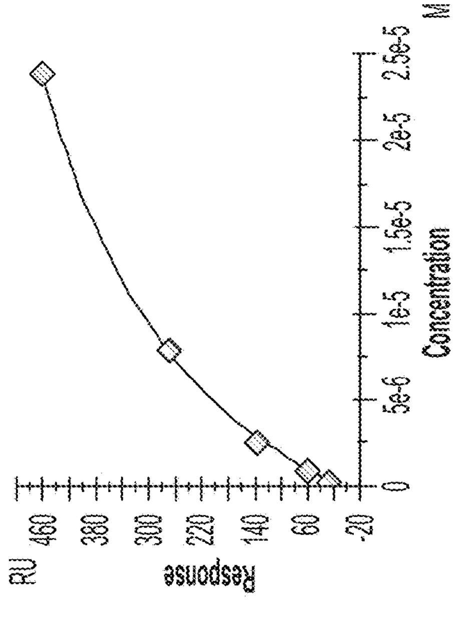
FIGS. 19A-19D show results from binding assays measuring binding activity of Trastuzumab control (FIG. 19A), Variant B3 (FIG. 19B), Variant D3 (FIG. 19C), and Variant E3 (FIG. 19D) to inhibitory receptor FcγRIIB when His-Tagged FcγR was captured onto SPR sensor chip and the exemplary molecule used as the analyte.
Figure 19B:
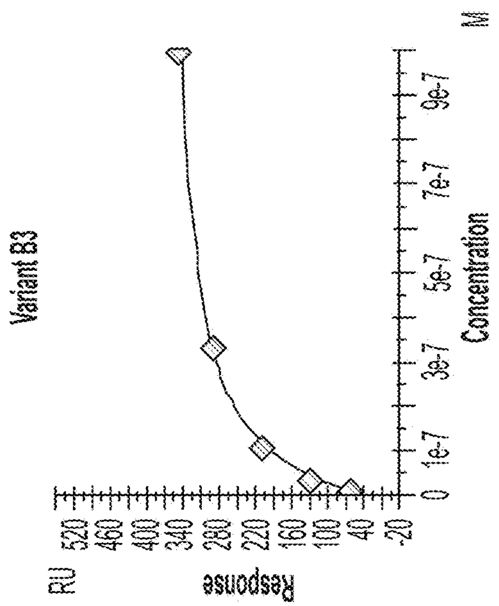
Figure 19C:
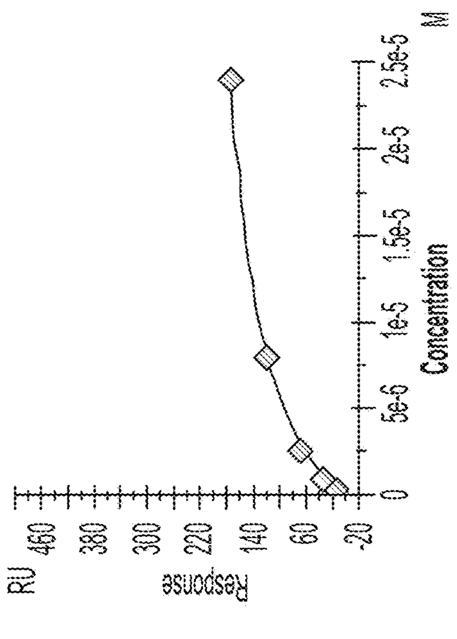
Figure 19D:
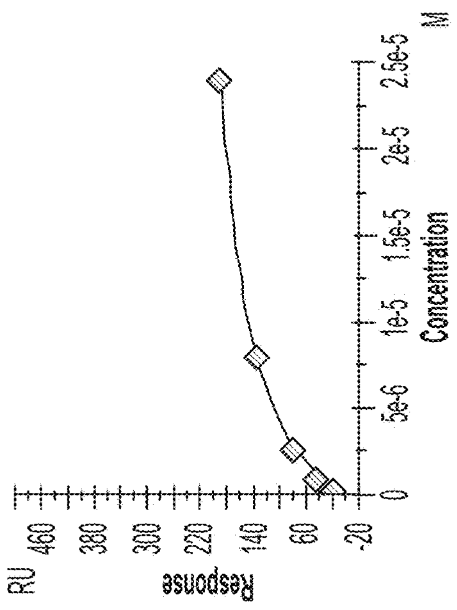

FIG. 12A shows that the exemplary molecule Variant D3 reduced TSHR-stimulating activity of patient serum autoantibodies in 19/19 patients, including reduction to background levels in 95% of donor sera (18/19 donors) and in the pooled samples (FIG. 12B).

Autoantibody-Molecule Complex Recycling Assay

Cells expressing FcRn, are seeded in a 96-well plate and incubated for 1 hour, followed by serum starvation and division into two groups—pH 6.0 and pH7.0. Varying dilutions of molecule comprising modifications that enhance FcRn binding as described above are added with varying dilutions of anti-TSHR autoantibodies (e.g., M22, K1-70, K-18) and are co-incubated with the cells for 4 hours. Cells are then washed in HBSS and the pH is adjusted to neutral (pH 7.4) and incubated at 37C for 4 hours or overnight. Cell supernatant is harvested and analyzed in anti-human IgG ELISA to quantify the amount of anti-TSHR autoantibody recycled into the supernatant.

The anti-TSHR monoclonal autoantibody M22 is labelled with a fluorescent tag (i.e., PE). A complex is then formed by co-incubating the molecule comprising modifications that enhance FcγRIIB binding as described above with labelled M22 for 15 minutes at room temperature at either a 1:1 or 4:1 ratio (molecule:autoantibody). Cells expressing FcγRIIB are seeded in a 96-well plate and stained with Live/Dead Violet Fixable Dye. Next, the pre-complexed molecule and autoantibody are incubated with the cells at various concentrations at either 4C (to assess binding) or 37C (to assess uptake). After incubation, cells are washed with PBS (binding) or acidic media to remove surface-bound complexes (uptake). Cellular fluorescence is determined by flow cytometry.

In Vitro SEC-Based Assessment of Immune Complexes

To assess the size of the immune complexes formed upon anti-TSHR autoantibody binding to molecule, molecule is incubated with Graves' Disease/Thyroid Eye Disease patient serum containing anti-TSHR autoantibodies, or with anti-TSHR monoclonal autoantibodies (M22, K1-70, K1-18, CS-17) as positive control. Analysis of the size of the immune complexes formed between molecule and autoantibodies present in patient serum is estimated using SEC-based method similar as described in Boysen et al., *Journal of Immunology Research* 2:1-9 (2016), which is herein incorporated by reference.

Example 3: Testing and Characterization of Exemplary Molecules

Identification of Fc Mutations that Confer Specific Binding to FcγRIIB

Exemplary molecules described above were tested for their ability to selectively bind to FcγRIIB through their Fc domains and to have decreased or no binding affinity for other Fc receptors FcγRIIA167H and FcγRIIA167R.

FcγRIIB isoform 2 is an endocytic receptor that binds to its target, internalizes the complex and shuttles the target to the lysosome for degradation. Without wishing to be bound by any theory, molecules described herein that have increased FcγRIIB binding may deplete anti-TSHR autoantibodies and/or antigen-specific B cells producing anti-TSHR autoantibodies through various mechanisms including those shown in FIGS. 13A-13D. FIG. 13B shows a potential mechanism of action which includes clearing autoantibodies by targeting FcγRIIB isoform 2 on liver sinusoidal endothelial cells (LSECs). In this exemplary mechanism of action, the autoantigen domain (TSHR or a fragment or variant thereof) binds to autoantibodies (anti-TSHR autoantibodies) and the Fc domain binds to FcγRIIB isoform 2 on liver sinusoidal endothelial cells. Autoantibodies are internalized into the liver sinusoidal endothelial cells and targeted to the lysosome for degradation. In another exemplary mechanism as shown in FIG. 13C, molecules described herein may target pathogenic B cells producing target autoantibodies (e.g., anti-TSHR autoantibodies), by targeting FcγRIIB isoform 1 to the B cell receptor (BCR), which leads to B cell apoptosis and inhibition. In another exemplary mechanism shown in FIG. 13D, molecule:autoantibody immune complexes described herein may target FcγRIIB on dendritic cells and reduce/inhibit antigen presentation to T cells.

Binding assays using SPR were performed to determine the binding affinity of the exemplary molecules. His-tagged FcγRIIA167H, FcγRIIA167R, or FcγRIIB were captured on a CM5 SPR chip previously coupled with an anti-His capture antibody by standard amine coupling. Increasing concentrations of molecules were subsequently injected over the captured FcγR and a single dissociation performed using single cycle kinetics. The data was then analyzed using steady state analysis which is suitable for low affinity interactions. In particular, a plot of response at equilibrium against the molecule concentration was generated. The $K_D$ value is equal to the concentration that gives 50% of the maximum response. The molecules represented include: a control IgG1 (Trastuzumab antibody), Variant B3, Variant D3, and Variant E3 for various Fc receptors: FcγRIIA167H, FcγRIIA167R and FcγRIIB. The molecule Variant B3 was designed to have enhanced binding to FcγRIIB (an inhibitory Fcγ receptor) by introducing the mutations S267E/L328F. The molecule Variant D3 includes the mutation P238D in its Fc domain to increase binding to FcγRIIB. The molecule Variant E3 includes the P238D mutation and the half-life extending LS mutation in its Fc domain. Trastuzumab and an exemplary molecule with a wild-type Fc domain (WT IgG1 Fc) were used as positive controls.

Results from the binding assays are shown in Table 10 and Table 11 below and FIGS. 14-19. Specifically, FIGS. 14-16 show binding activity of Trastuzumab (positive control) (A), Variant B3 (B), Variant D3 (C), and Variant E3 (D), to activating receptor FcγRIIA167H (FIGS. 14A-14D), activating receptor FcγRIIA167R (FIGS. 15 A-15D), and inhibitory receptor FcγRIIB (FIGS. 16 A-16D), when the exemplary molecules were captured onto an SPR sensor chip and FcγR used as the analyte. Table 11 shows the $K_D$ values for each assay.

FIGS. 17-19 and Table 10 show binding activity of Trastuzumab (positive control) (A), Variant B3 (B), Variant D3 (C), and Variant E3 (D), to FcγRIIA167H (FIGS. 17A-17D), FcγRIIA167R (FIGS. 18A-18D), and FcγRIIB (FIGS. 19A-19D), when His-Tagged FcγR was captured onto an SPR sensor chip and the exemplary molecules were used as the analyte. Table 10 shows the raw $K_D$ values for each assay.

The results show that exemplary molecule Variant D3 (P238D mutation) exhibits increased binding to FcγRIIB, with no or significantly reduced binding to FcγRIIA167R and FcγRIIA167H compared to control (wildtype IgG1 Fc). In contrast, exemplary molecule Variant B3 (SE/LF mutation) showed an increase in binding to both FcγRIIA167R and FcγRIIB.

Without wishing to be bound by any theory, the molecule Variant D3 having selective affinity for the inhibitory FcγRIIB presents certain advantages such as allowing for avidity-induced FcγRIIB-mediated intracellular uptake and degradation. Additionally, the molecule presents a low risk of toxicity in part due to the relatively small size of the molecule and little to no affinity for activating Fcγ receptors.

TABLE 10

His-Tagged FcγR captured onto SPR sensor chip and molecule used as analyte

| FcγR Immobilized | huIgG1 Fc | FcγRIIA167R KD (M) | Fold (WT/ Variant) | FcγRIIA167H KD (M) | Fold (WT/ Variant) | FcγRIIB KD(M) | Fold (WT/ Variant) |
|---|---|---|---|---|---|---|---|
| Trastuzumab | | 4.45E−06 | | 2.31E−06 | | 1.36E−05 | |
| WT IgG1 Fc | Wild-Type | 5.40E−06 | 1.0 | 5.02E−06 | 1.0 | 9.70E−06 | 1.0 |

TABLE 10-continued

His-Tagged FcγR captured onto SPR sensor chip and molecule used as analyte

| FcγR Immobilized | huIgG1 Fc | FcγRIIA167R KD (M) | Fold (WT/ Variant) | FcγRIIA167H KD (M) | Fold (WT/ Variant) | FcγRIIB KD(M) | Fold (WT/ Variant) |
|---|---|---|---|---|---|---|---|
| Variant B3 | SE/LF | 1.02E−07 | 52.9 | 7.51E−06 | 0.7 | 1.04E−07 | 93.3 |
| Variant D3 | P238D | 1.42E−05 | 0.4 | nb | | 7.74E−06 | 1.3 |

TABLE 11

Molecules captured onto SPR sensor chip and FcγR used as analyte

| Molecule Immobilized | huIgG1 Fc | FcγRIIA167R KD (M) | Fold (WT/ Variant) | FcγRIIA167H KD (M) | Fold (WT/ Variant) | FcγRIIB KD (M) | Fold (WT/ Variant) |
|---|---|---|---|---|---|---|---|
| Trastuzumab | | 6.85E−07 | | 5.46E−07 | | 3.24E−06 | |
| WT IgG1 Fc | Wild-Type | 4.64E−07 | 1.0 | 3.77E−07 | 1.0 | 2.10E−06 | 1.0 |
| Variant B3 | SE/LF | 9.06E−10 | 512.1 | 7.89E−07 | 0.5 | 5.35E−09 | 392.5 |
| Variant D3 | P238D | nb | | nb | | 8.93E−07 | 2.4 |

Complement Binding

Exemplary molecules Variant B3 and Variant D3 were tested for their ability to bind complement. The antibody Rituximab was used as a positive control. An IgG4 was used as a negative control. An additional molecule was generated using the TSHR260 2P2R autoantigen and an IgG1 Fc domain that includes an Fc mutation (LALAPG) that ablates effector activity ("Fc null" molecule).

Varying dilutions of each exemplary molecule or one of the controls were tested for binding to C1q by ELISA where serial dilutions of molecules or controls were coated on a plate (at 0.01 μg/mL, 0.1 μg/mL, 1.0 μg/mL, 10.0 μg/mL, 100.0 μg/mL, and 1000 μg/mL) overnight at 4 C. After blocking and subsequent wash steps, human C1q at 5 μg/mL was added to the ELISA plate for 1 hour at room temperature. The plate was washed and a sheep polyclonal anti-C1q HRP antibody at 1:200 dilution was added and incubated for an additional 1 hour. Development of the ELISA plate was carried out by addition of TMB. Color development was then stopped with addition of 3N HCl. Plate absorbance was read at 450 nm using a plate ready.

Figure 20B:
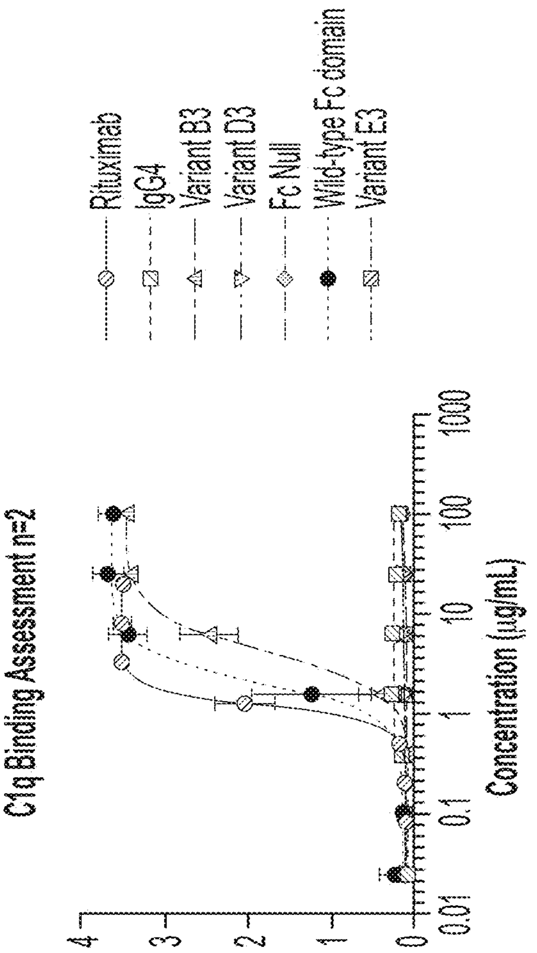
FIGS. 20A-20B shows results from an ELISA showing binding of exemplary molecules to C1q.
Figure 20A:
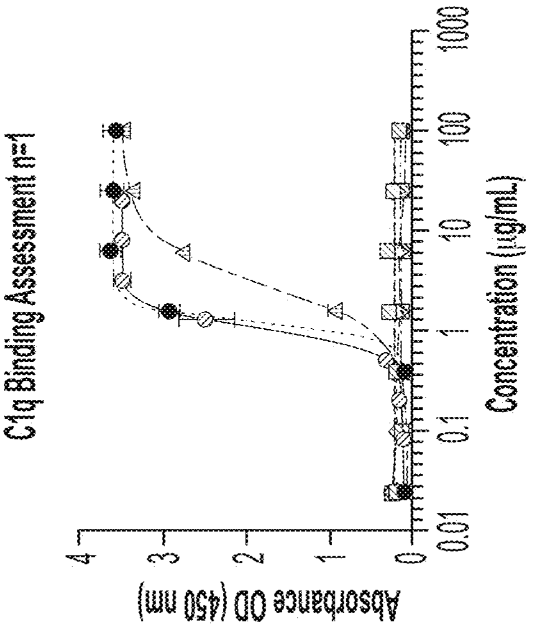

Results from the assay show that Variant D3 and the Fc null molecule, demonstrate no binding to C1q. This is in contrast with WT IgG1 Fc and Variant B3 (FIG. 20).

Testing of Exemplary Molecules for Avidity-Mediated Effects

In this experiment, CHO cells expressing FcγRIIB (CHO-FcγRIIB+) were incubated with exemplary molecules and M22 (an anti-TSHR autoantibody) either at the same molar ratio or at a 4 molar excess (i.e., 1:1 molar ratio of molecule: M22 or 4:1 molar ratio of molecule:M22) with and without 2B6 antibody which is an anti-FcγRIIB antibody that blocks binding of FcγRIIB to antibody Fc domains. The exemplary molecules tested include (i) a molecule that includes a TSHR260 2P2R autoantigen and an Fc domain containing the LALAPG mutation ("Fc null"), and was therefore used as a negative control; (ii) a molecule including a TSHR260 2P2R autoantigen and a wildtype Fc domain WT IgG1 Fc that was used as a positive control; (iii) Variant B3, which contains mutations to enhance binding to FcγRIIB (S267E/L328F); (iv) Variant D3, which contains a mutation that eliminates binding affinity for Fcγ activating receptor FcγRIIA and moderately enhances binding to FcγRIIB; (v) Variant E3, which is the same as Variant D3 but also contains LS mutations to increase half-life; and (vi) Variant F3, which includes a TSHR260 2P2R autoantigen and an IgG1 with only the LS mutations.

Figure 21:
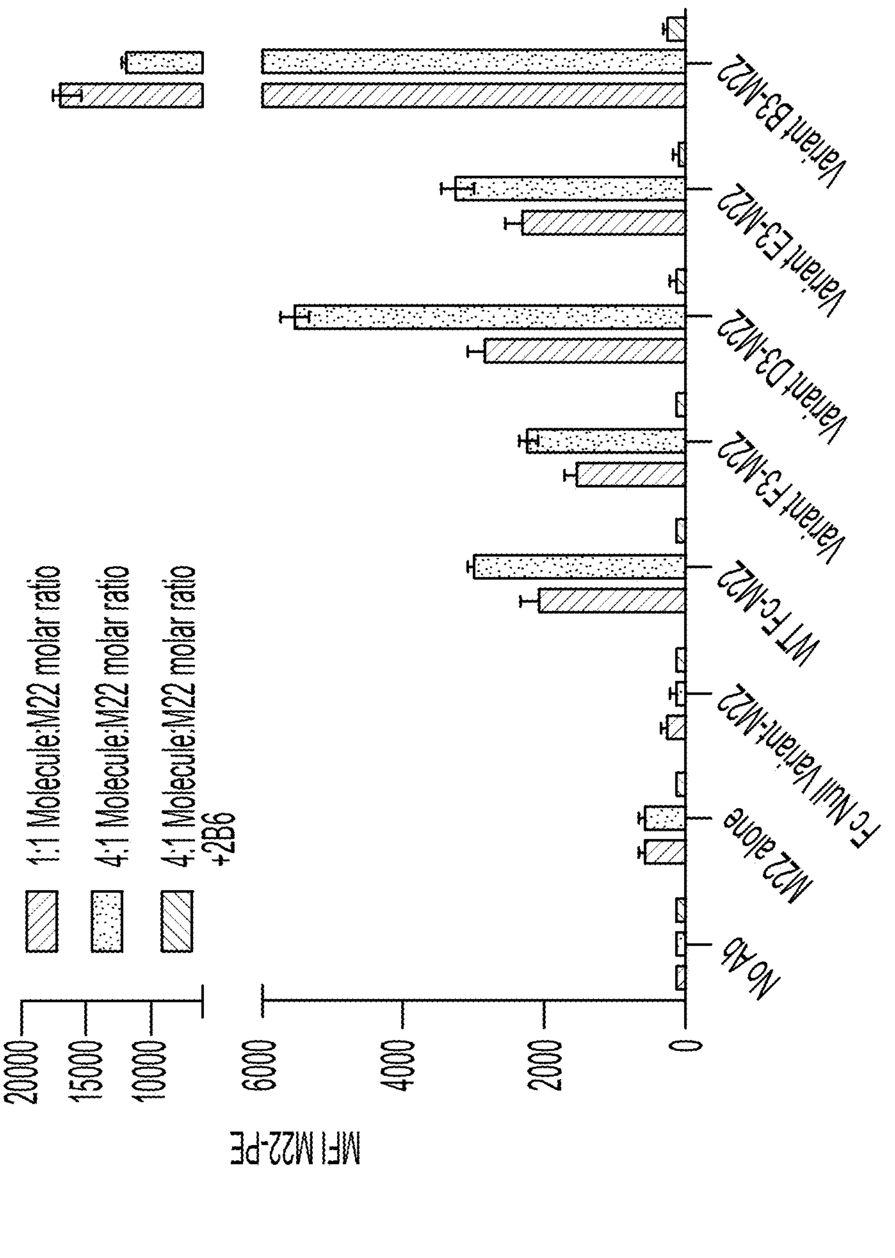
FIG. 21 shows results from a binding assay measuring binding of a TSHR autoantibody (M22) to FcγRIIB expressing CHO cells when M22 was pre-complexed with exemplary molecules such that most M22 was bound to two molecules (when molecules were added at a molar ratio molecule: M22 of "4:1") compared to when M22 was predominantly bound to one molecule (when molecules were added at a molar ratio of molecule: M22 of "1:1"). Results are also shown when 2B6, an anti-FcγRIIB blocking antibody, was included in the 4:1 experiment.

The results show that Variant D3 binds with increased avidity to FcγRIIB-expressing CHO cells (FIG. 21). Specifically, Variant D3 induces a 2-fold increase in binding of M22 to FcγRIIB when pre-complexed such that most M22 is bound to two molecules ("4:1") compared to when M22 is predominantly bound to one molecule ("1:1"). WT IgG1 Fc showed only a 1.5-fold increase and Variant B3 (SE/LF Fc) showed no increase in binding. Variant E3 did not show an increase in avidity compared to WT IgG1. Additionally, binding of the exemplary molecules is fully blocked by the blocking anti-FcγRIIB antibody (clone 2B6). As such, Variant D3 shows a unique and strong avidity-mediated binding effect to FcγRIIB.

Binding Specificity to FcγRIIB-Expressing Cells

Exemplary molecules were also tested for their ability to selectively bind to cells expressing FcγRIIB. Various immune cell types are known to express FcγRIIB at different levels. FcγRIIB is known to be predominantly expressed in B cells and minimally expressed in non-classical monocytes, and is known to not be expressed or expressed at a low level in T cells, NK cells and classical monocytes (FIG. 22B; adapted from Kerntke et al., *Frontiers in immunology* 11:489401, 2020, which is herein incorporated by reference). Each type of cell (monocytes, B cells, NK cells, and T cells) were incubated with the exemplary molecule Variant D3 and M22 (an anti-TSHR autoantibody) at a 4 molar excess of molecule (i.e., 4:1 molecule: M22). Cells were characterized as having specific markers for monocytes, B cell, NK cells, and T cells, namely, CD16, CD19, CD56, and CD3, respectively. Unlabeled cells represent cells that were negative for CD16, CD19, CD56, and CD3 and therefore could not be categorized as monocytes, B cells, NK cells, or T cells. Such cells may be non-classical monocytes or basophils.

Figure 22A:
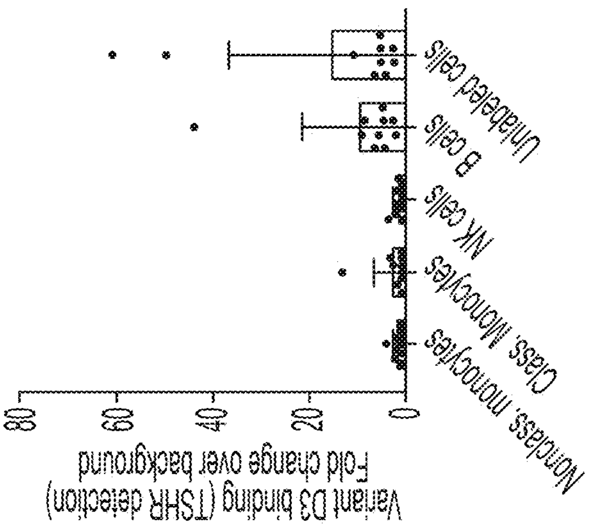
FIGS. 22A-22B relate to FcγRIIB protein expression among various immune cell types.
Figure 22B:
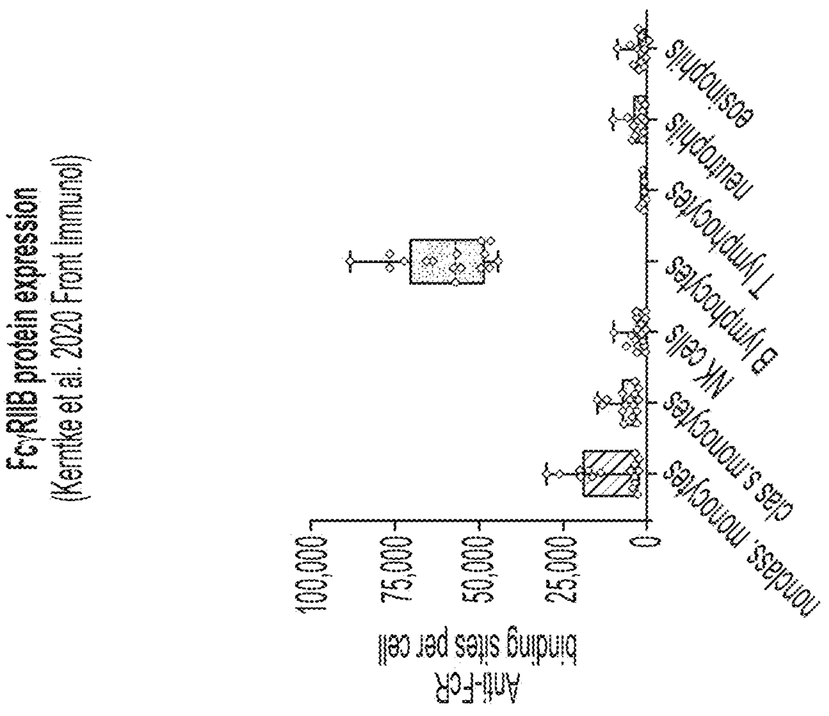

FIG. 22A shows that immune complexes of M22 bound by Variant D3 bind only to primary cells expressing FcγRIIB (i.e., B cells and unlabeled cells which may be non-classical monocytes or basophils).

Further binding studies were performed to compare the selectivity of exemplary molecule Variant D3 and other exemplary molecules including: Variant B3 and the WT IgG1 Fc (with TSHR260 2P2R) compared to Fc null variant (as a negative control) to cells expressing FcγRIIB. Binding was assessed in B cells, T cells, monocytes, non-classical monocytes and NK cells. Each type of cell was incubated with the exemplary molecules and M22 (an anti-TSHR autoantibody) at a 4 molar excess of molecule (i.e., 4:1 of molecule:M22).

Figure 23A:
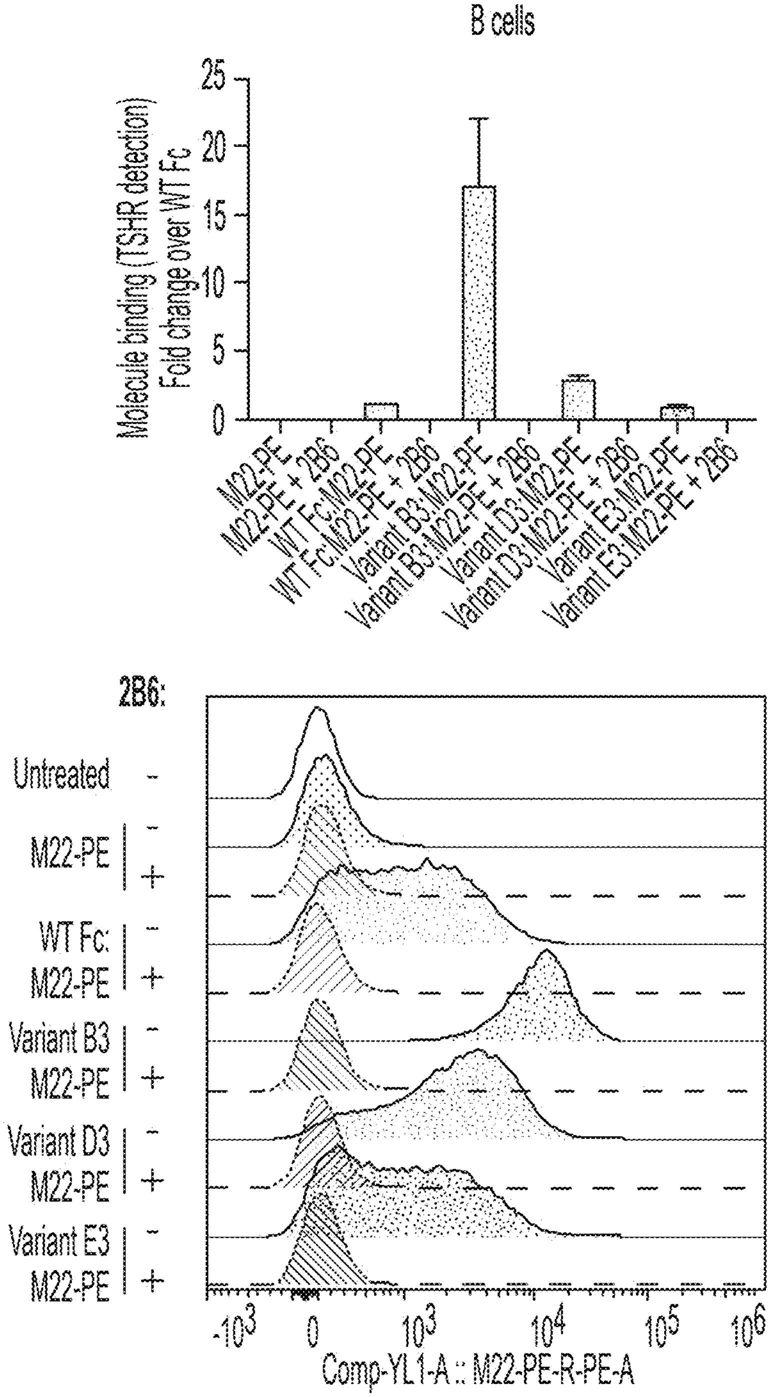
FIGS. 23A-23B show binding of M22 pre-complexed with exemplary molecules to FcγRIIB-expressing cells: B cells (FIG. 23A) and monocytes (FIG. 23B). Results are also shown when 2B6, an anti-FcγRIIB blocking antibody, was included in the experiment.
Figure 23B:
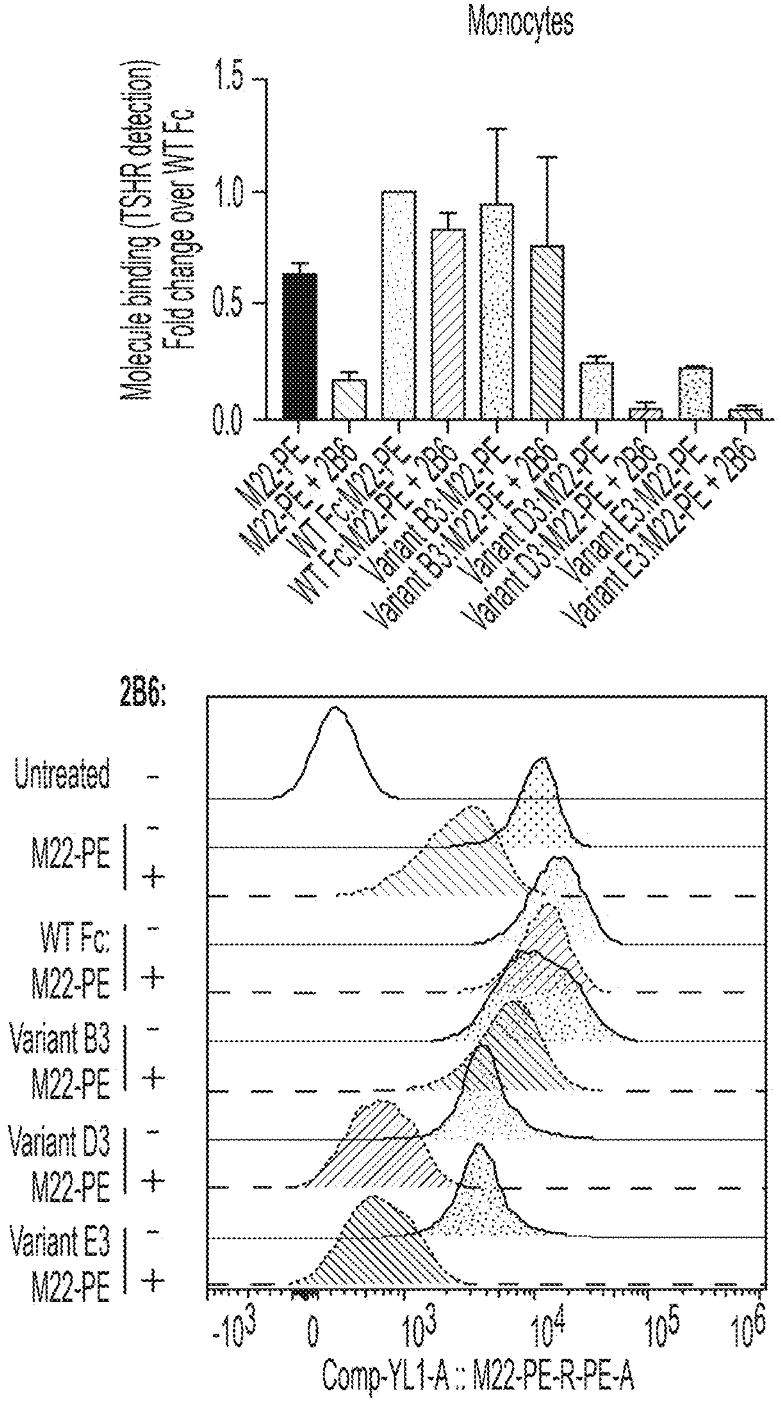
Figure 24A:
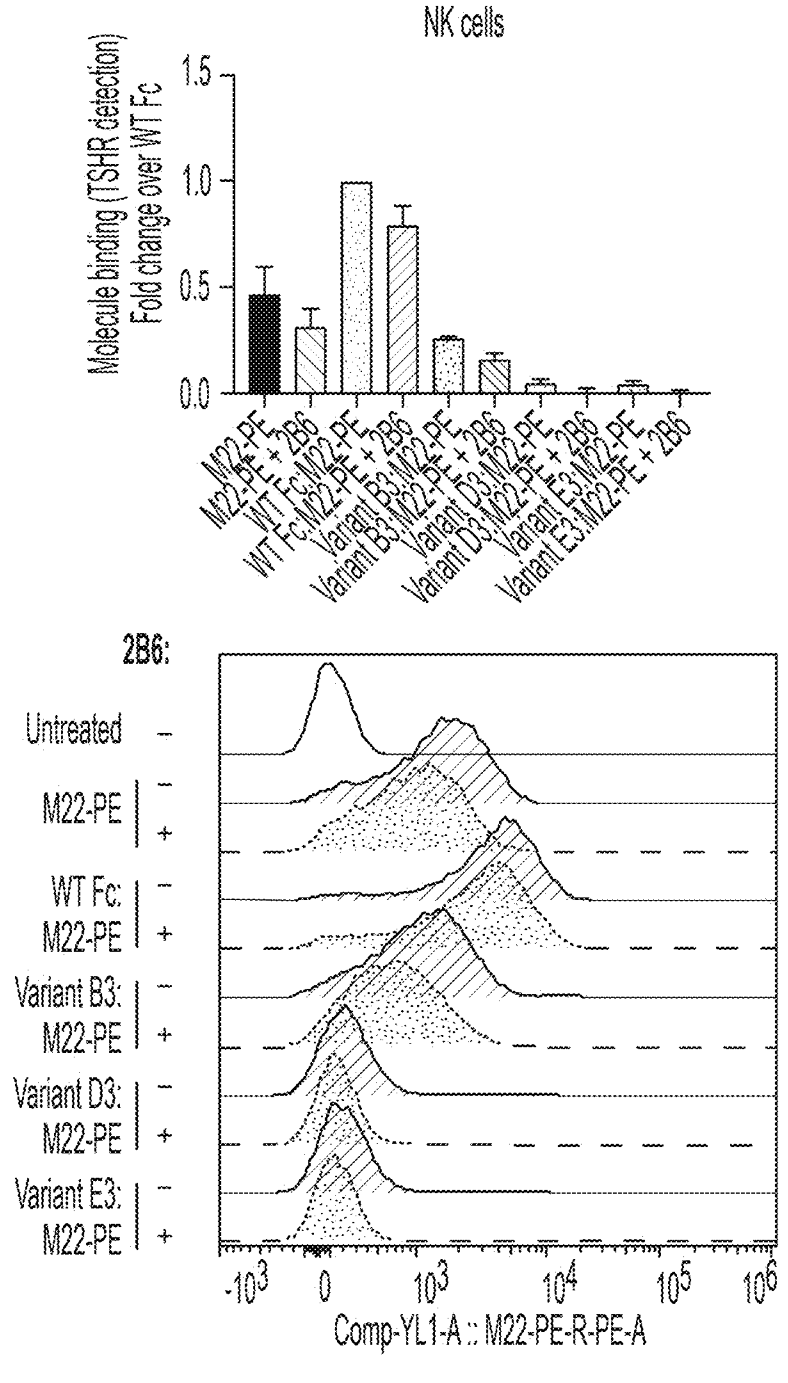
FIGS. 24A-24B show binding of M22 pre-complexed with exemplary molecules to NK cells (FIG. 24A) and unlabeled cells (FIG. 24B). Results are also shown when 2B6, an anti-FcγRIIB blocking antibody, was included in the experiment.
Figure 24B:
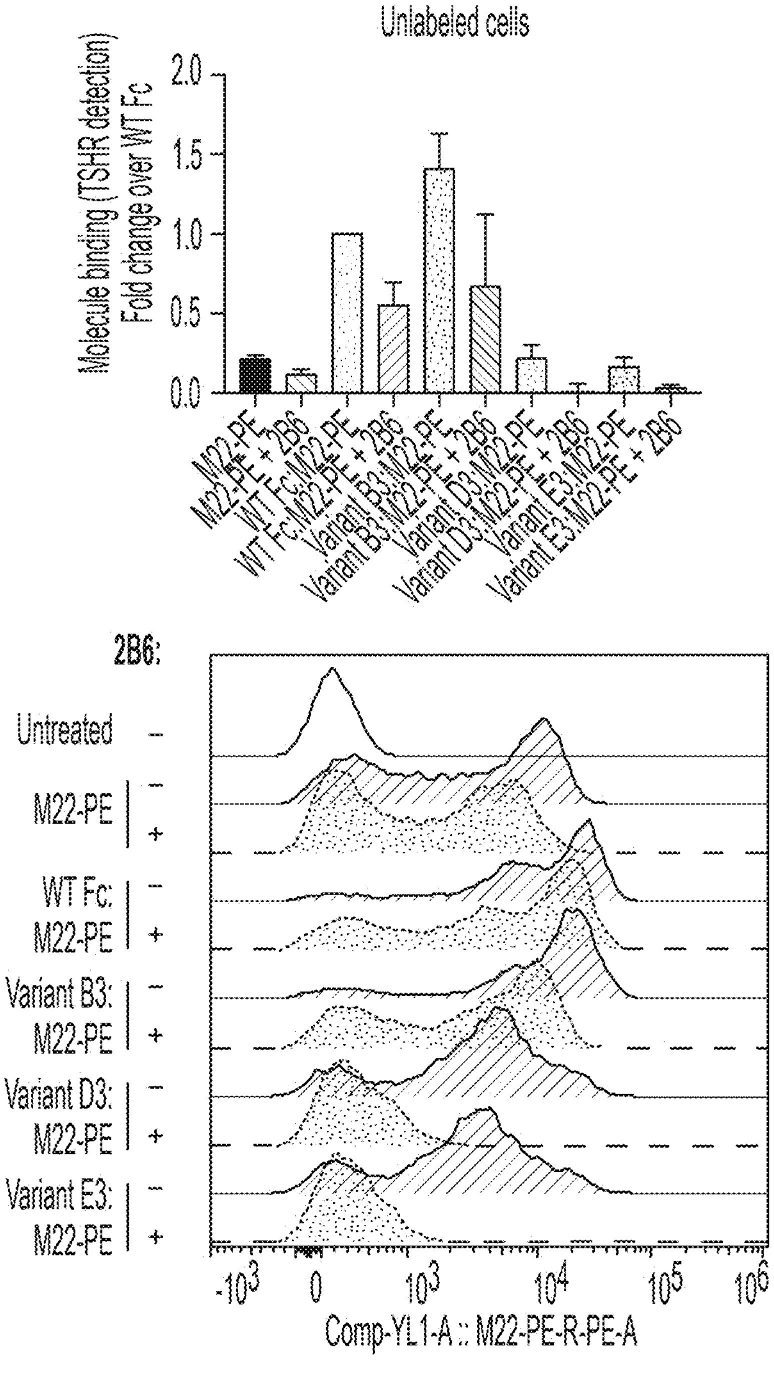

FIGS. 23A-23B (binding of exemplary molecules to B cells (FIG. 23A) and monocytes (FIG. 23B)) and FIGS. 24A-24B (binding of exemplary molecules to NK cells (FIG. 24A) and unlabeled cells (negative for CD3, CD19, CD14, CD56, and CD16, potentially basophils) (FIG. 24B)) show that Variant D3 and Variant E3 exhibit cellular binding that is specific to cells expressing FcγRIIB. Additionally, at a molar ratio of Variant D3:M22 or Variant E3:M22 (4:1), cellular binding is blocked by the anti-FcγRIIB antibody 2B6.

Binding of Free Molecule to FcγRIIB

In this experiment, CHO cells expressing FcγRIIB (CHO-FcγRIIB+) were incubated with exemplary molecules at different concentrations with and without 2B6 antibody (an anti-FcγRIIB antibody that blocks binding of FcγRIIB to antibody Fc domains). The exemplary molecules tested include Variant B3, which contains mutations to enhance binding to FcγRIIB (S267E/L328F; a positive control) and Variant D3, which contains a mutation that eliminates binding affinity for Fcγ activating receptor FcγRIIA and moderately enhances binding to FcγRIIB. Binding of exemplary molecules to CHO-FcγRIIB+ cells was assessed by using an anti-TSHR antibody (CS-17).

Figure 25:
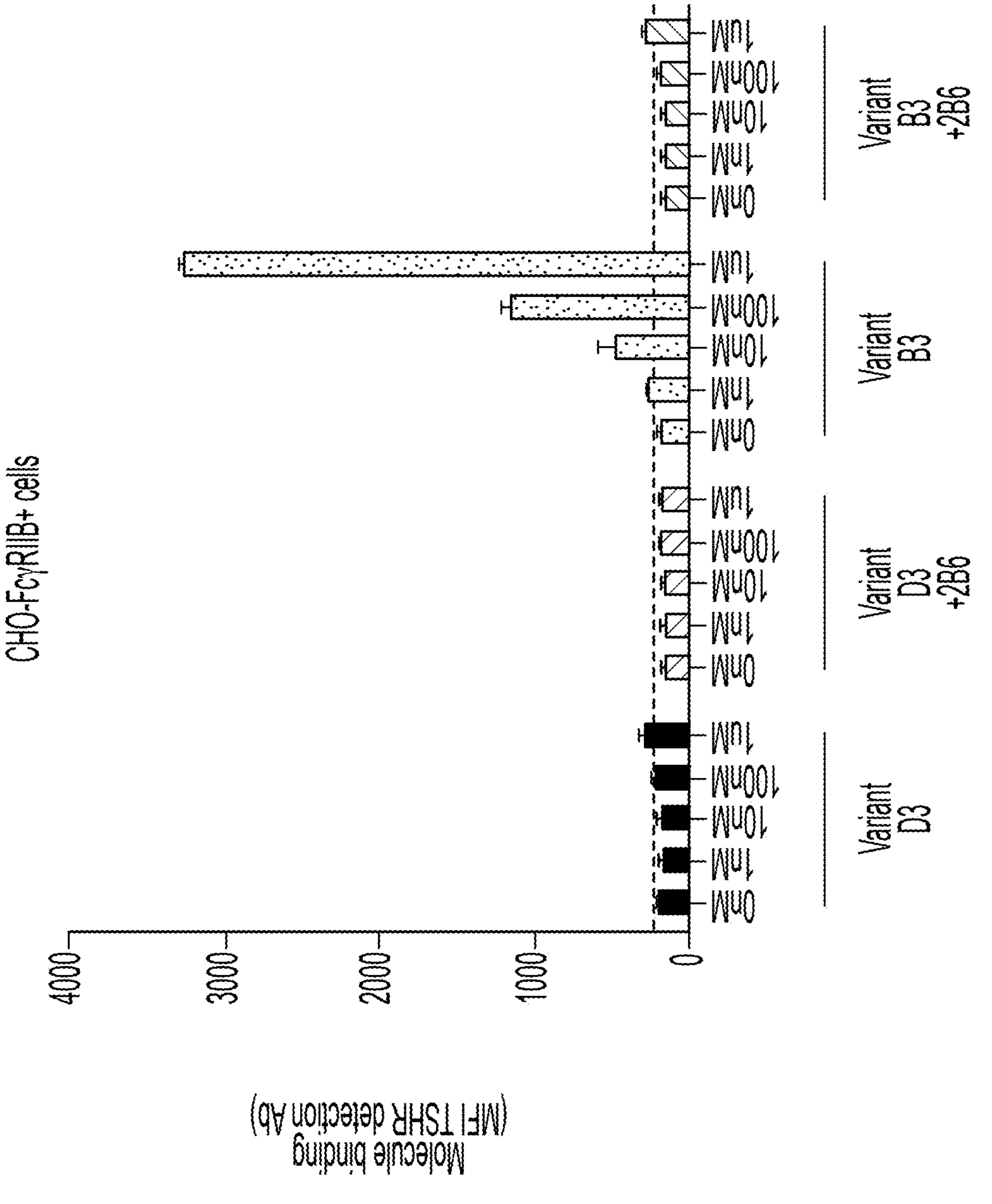
FIG. 25 shows that Variant D3 does not bind strongly to CHO-FcγRIIB+ cells. In contrast, Variant B3 binds to CHO-FcγRIIB+ cells at concentrations as low as 1 nM. Binding of Variant D3 to CHO-FcγRIIB+ cells was only evident at 1 μM. Binding of Variant B3 and D3 is fully blocked by 2B6, an anti-FcγRIIB blocking antibody.

FIG. 25 shows that Variant D3 as a free molecule does not bind strongly to CHO-FcγRIIB+ cells. Variant B3 binds to CHO-FcγRIIB+ cells at concentrations as low as 1 nM. Binding of Variant D3 to CHO-FcγRIIB+ cells was only evident at >1 uM. Binding of Variant D3 is fully blocked by 2B6, the anti-FcγRIIB blocking antibody.

Binding of Free Molecule to FcγRIIB+ Primary Cells

Exemplary molecules were also tested for their ability to bind to primary human cells that express FcγRIIB. Exemplary molecules included a molecule that includes (i) a TSHR260 2P2R autoantigen and an Fc domain containing the LALAPG mutation ("Fc null"), and was therefore used as a negative control; (ii) Variant B3, which contains mutations to enhance binding to FcγRIIB (S267E/L328F); and (iii) Variant D3, which contains a mutation that eliminates binding affinity for FcγRIIA and moderately enhances binding to FcγRIIB.

Molecules were incubated with human PBMCs and then binding was assessed by quantifying the binding of CS-17, an anti-TSHR antibody, to cells bound by exemplary molecules.

Figure 26:
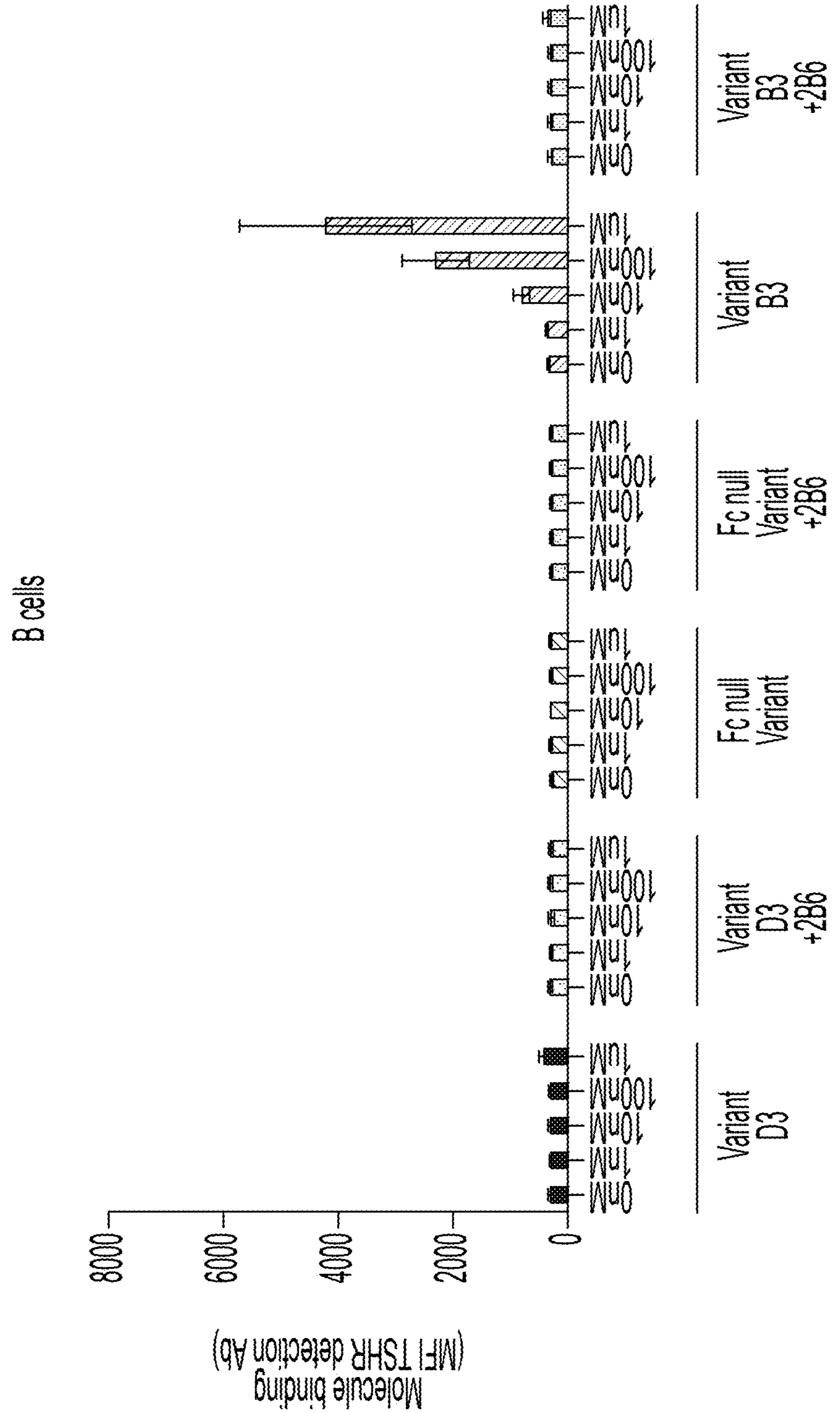
FIG. 26 shows binding of exemplary molecules to B cells.

FIG. 26 shows binding of exemplary molecules to B cells. Similar to FIG. 25, Variant D3 only displays detectable binding to cells at 1 uM, while 1 nM Variant B3 binds B cells.

Figure 27A:
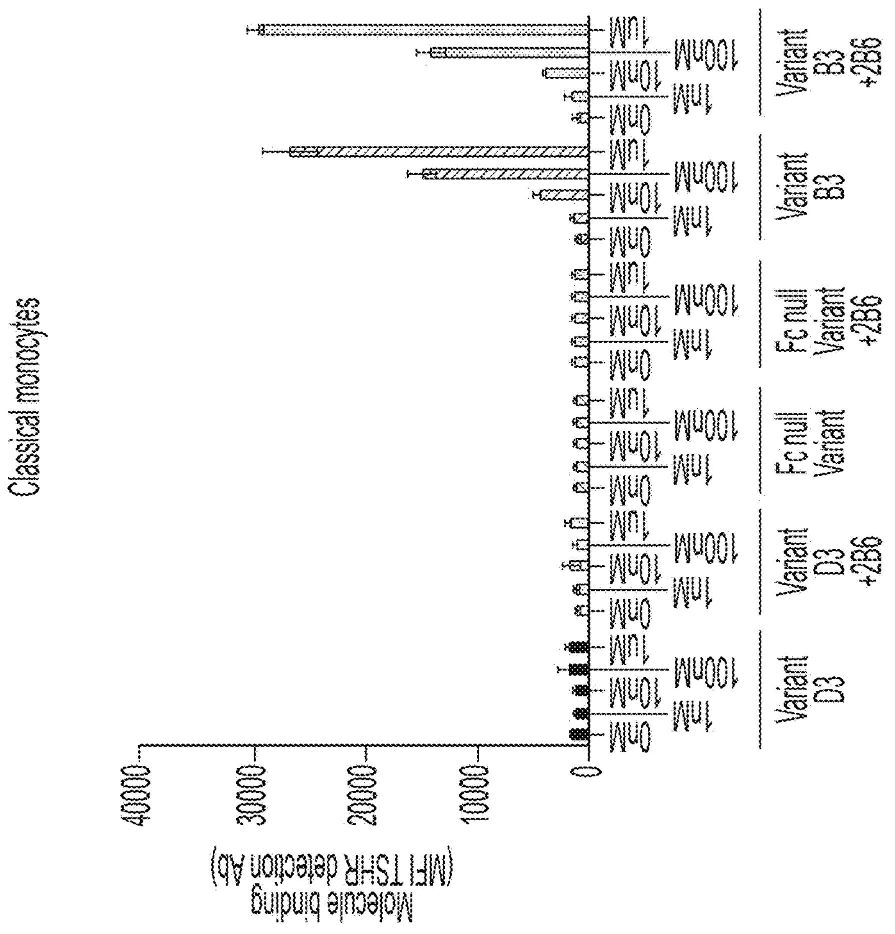
FIGS. 27A-27B shows binding of exemplary molecules to both classical (CD14+) (FIG. 27A) and unlabeled cells (FIG. 27B). Unlabeled cells represent cells that were negative for CD16, CD19, CD56, and CD3 and therefore could not be categorized as monocytes, B cells, NK cells, or T cells. Such cells may be non-classical monocytes or basophils.
Figure 27B:
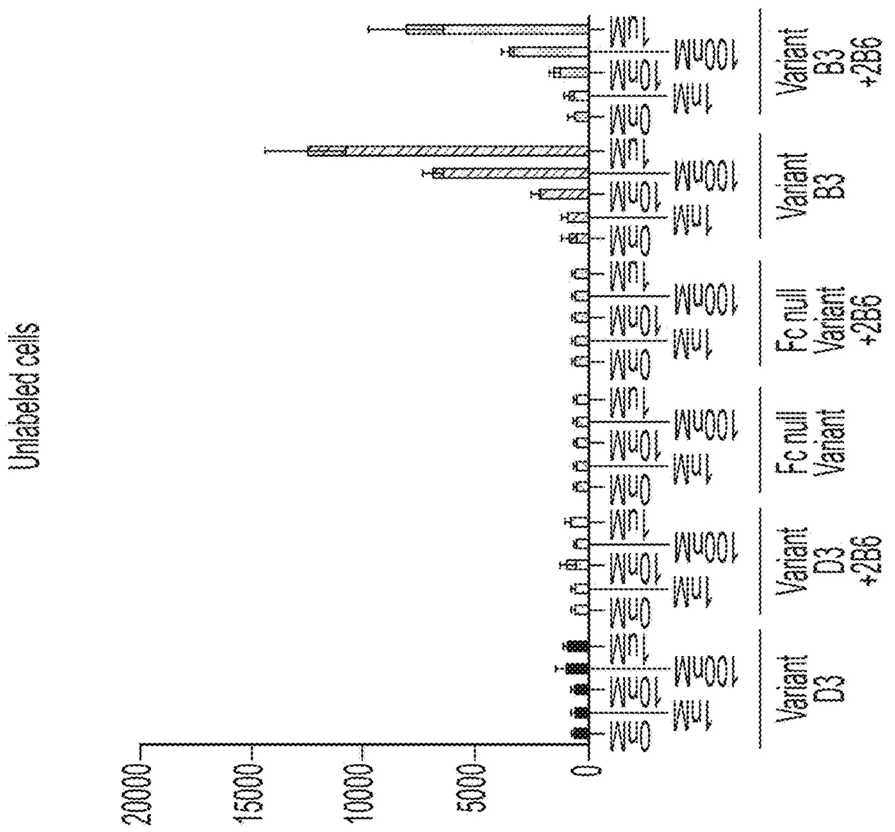

FIG. 27 shows binding of exemplary molecules to classical monocytes (CD14+) and unlabeled cells (negative for CD3, CD19, CD14, CD56, and CD16) that are likely basophils. Similar to FIG. 26 in B cells, 1 uM Variant D3 binds weakly to monocytes, while 10 nM Variant B3 has strong binding for monocytes.

Example 4: In Vivo Testing of Exemplary Molecules

The present Example examines in vivo activity of exemplary molecules described in Example 1. To assess the clearance activity of anti-TSHR monoclonal autoantibodies by exemplary molecules, mouse models are injected with an anti-TSHR monoclonal autoantibody (e.g., M22) followed by injection of molecule or control and anti-TSHR monoclonal autoantibody clearance is assessed over time.

In Vitro Pilot Study to Assess Anti-TSHR Monoclonal Autoantibody and Molecule Detection Using ELISAs.

To test the sensitivity of an Enzyme Linked Immunosorbent Assay (ELISA) for the purpose of detecting molecule in mouse serum, an ELISA detecting anti-TSHR monoclonal autoantibodies (M22) or molecule must first be performed using known concentrations in vitro.

A general ELISA protocol is as follows: capture antibody is coated at 4C overnight. Plates are blocked with blocking buffer (PBS with 5% BSA vol/vol) for 2 hours at room temperature. Plates are washed with washing buffer (PBS+0.05% Tween 20 or similar), and samples are added and incubated for 1 hour at room temperature. Plates are washed, and detection antibody solution is added and incubated for 1 hour at room temperature. Plates are washed and incubated with TMB substrate for 15 minutes at room temperature, protected from light. The reaction is stopped with 2M $H_2SO_4$ and read on a microplate reader set to 450 nm-570 nm.

In Vitro Pilot Study to Assess Labeling and Detection of Anti-TSHR Monoclonal Autoantibodies For the detection of anti-TSHR monoclonal autoantibody M22, varying concentrations of M22 are titrated into buffer, buffer containing 1% mouse serum, or 10% mouse serum, and detected using ELISA. The capture antibody used to bind the anti-TSHR monoclonal autoantibody M22 is goat anti-human Fc, and the detection antibody is HRP-labeled goat anti-human kappa or lambda light chain antibodies, depending on the light chain of the detection antibody.

In addition to using the ELISA method to detect anti-TSHR monoclonal autoantibodies, as described above, anti-TSHR monoclonal autoantibodies can be labeled with biotin for detection. In this in vitro pilot study, anti-TSHR monoclonal autoantibodies are labeled with biotin per manufacturers protocol in PBS. Next, varying concentrations of labeled anti-TSHR monoclonal autoantibodies are titrated into buffer, buffer containing 1% mouse serum, or 10% mouse serum, to assess detection sensitivity. The capture antibody used to bind the anti-TSHR monoclonal autoantibody M22 is goat anti-human Fc, and the detection antibody is Streptavidin Poly-HRP.

In Vitro Pilot Study to Assess Detection of Exemplary Molecules

For the detection of exemplary molecule, varying concentrations of exemplary molecule are titrated into buffer, buffer containing 1% mouse serum, or 10% mouse serum, and detected using ELISA. The capture antibody used to bind the exemplary molecule is goat anti-human Fc, and the detection antibodies are mouse anti-human TSHR CS-17 followed by HRP-labeled anti-mouse IgG.

Pilot Study to Assess pK of Molecule In Vivo

To assess clearance of exemplary molecule in wild-type mice, exemplary molecules are injected at 1 concentration in 20 mM Histidine, 150 mM NaCl, pH 6.0 and serum is collected at 2, 6, 12, 24, 48, 72 hours or 7 days after injection. Exemplary molecule in mouse serum is detected using methods described before, and serum from mice that have not been injected with exemplary molecule is used as a negative control, whereas spiking that serum ex vivo with exemplary molecule is used as a positive control.

Pilot Study to Assess Clearance of Anti-TSHR Monoclonal Autoantibodies In Vivo

To assess clearance of anti-TSHR monoclonal autoantibody M22 in wild-type mice, 1.5 ug, 15 ug or 150 ug of M22 in 20 mM Histidine, 150 mM NaCl pH 6.0 is injected per mouse and serum is collected at 12, 24, 48, 72 hours or 7 days after injection. M22 in mouse serum is detected using methods described before, and serum from mice that have not been injected with anti-TSHR monoclonal autoantibody is used as a negative control, whereas spiking that serum ex vivo with anti-TSHR monoclonal autoantibody is used as a positive control.

Assessing Clearance of Anti-TSHR Monoclonal Autoantibodies by Exemplary Molecules In Vivo Informed by the anti-TSHR monoclonal autoantibody M22 clearance and exemplary molecule clearance assessed in this study, mice are injected with 1 concentration of anti-TSHR monoclonal autoantibody in 20 mM Histidine, 150 mM NaCl, pH 6.0. 24 hours after injection, mice are injected with 4-fold molar excess of molecule or with vehicle as control. Clearance of anti-TSHR monoclonal autoantibodies and exemplary molecule are assessed using methods described above.

Example 5: In Vivo Testing of Exemplary Molecules

The present Example examines in vivo activity of exemplary molecules Variant B3 (TSHR260 2P2R with Fc having S267E/L328F mutations), Variant D3 (TSHR260 2P2R with Fc having P238D mutation), Variant E3 (TSHR260 2P2R with Fc having P238D and LS mutations) and Fc null molecule (TSHR260 2P2R with Fc having LALAPG mutations).

Molecule and M22 Clearance in Wildtype Mice

Figure 28A:
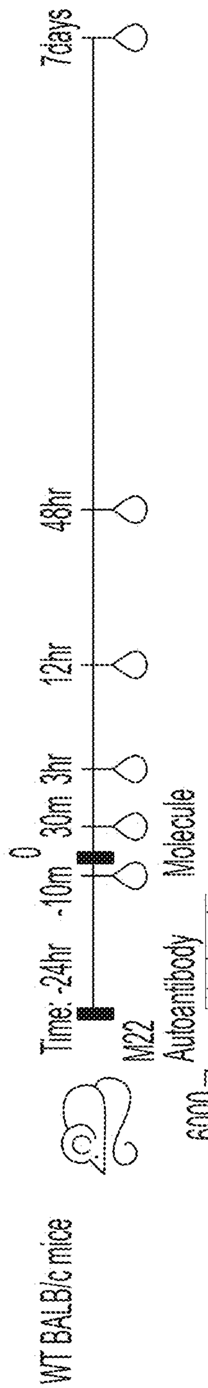
FIGS. 28A-28C show exemplary in vivo activity of exemplary molecules described herein.

In this experiment, wild-type BALBc mice were injected with M22 (TSHR autoantibodies) and 24 hours later the mice were injected with molecule. Serum from the mice was collected and analyzed for concentration of molecule and M22 at timepoints: −10 minutes, 10 minutes, 30 minutes, 3 hours, 12 hours, 48 hours, and 7 days after molecule administration (see dosing schematic in FIGS. 28A and 29A).

Figure 28B:
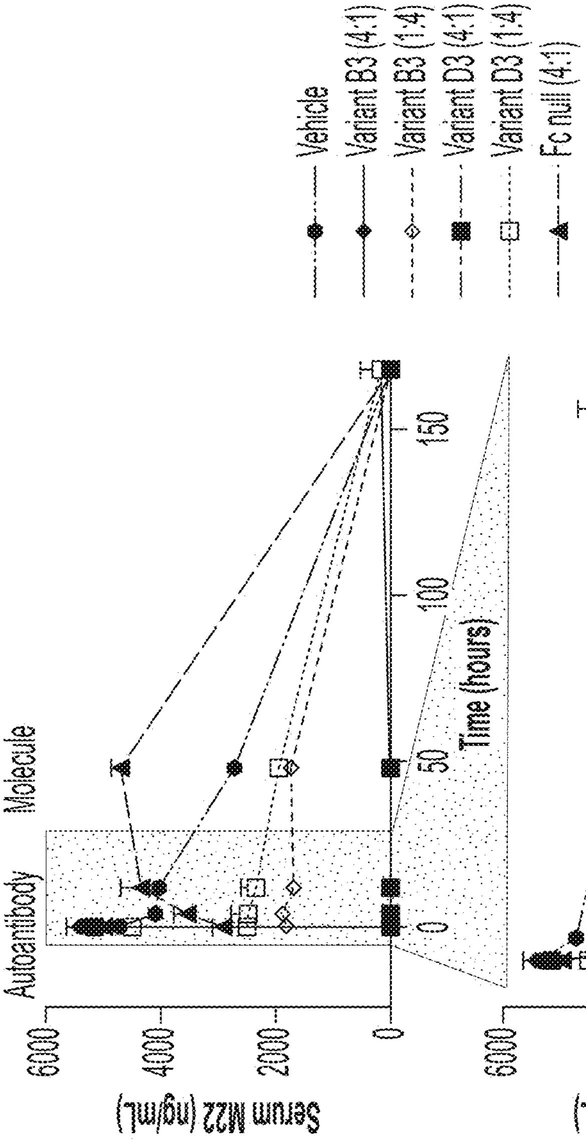
Figure 28C:
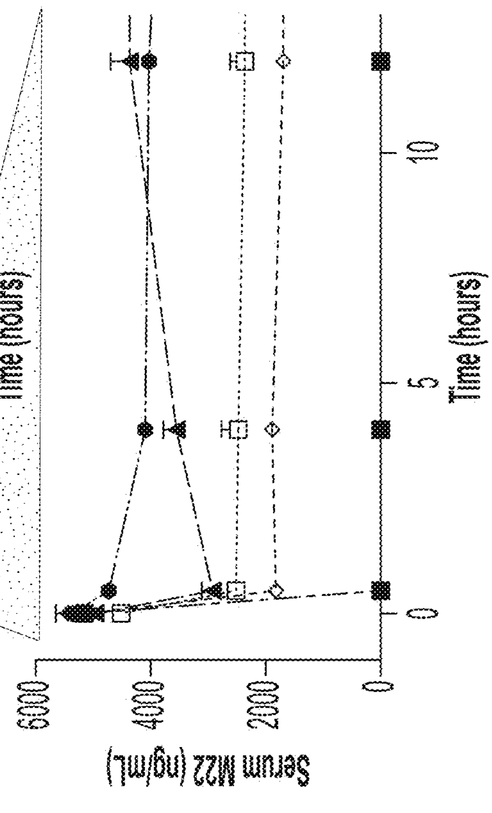
Figures 29A, 29B, 29C:
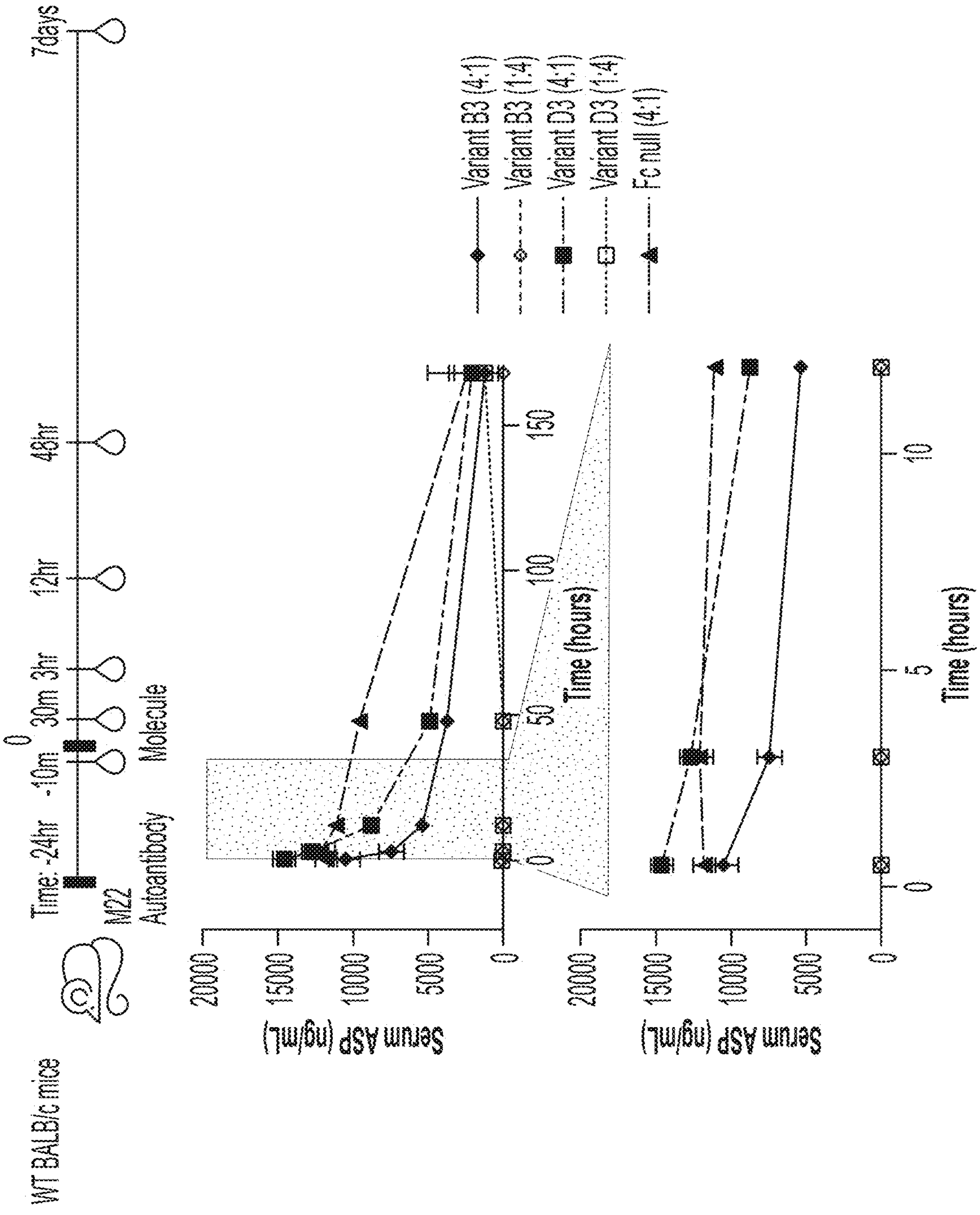
FIGS. 29A-29C show exemplary in vivo activity of exemplary molecules described herein.

Results: FIGS. 28B-28C show levels of M22 at different timepoints. FIGS. 29B-29C show levels of molecule at different timepoints. These results show that M22 is undetectable 30 min after administering Variant D3 in a 4-molar excess (molar ratio of molecule:M22 of 4:1), in contrast to the Fc null molecule (FIGS. 28B-28C). At a 1:4 molar ratio with Variant D3, some M22 remains after all molecule:M22 complex is cleared. This amount is consistent with the unbound fraction of M22 remaining in circulation.

In 4:1 conditions, the molecules persisted out to 7 days, indicating a long half-life of the molecules in serum (FIGS. 29B-29C). This is comparable with pK experiments where the molecules were administered in the absence of M22 as shown in FIG. 30. Additionally, Variant B3 and Variant D3 were undetectable in 1:4 molar ratio conditions FIGS. 29B-29C.

Figure 30A:
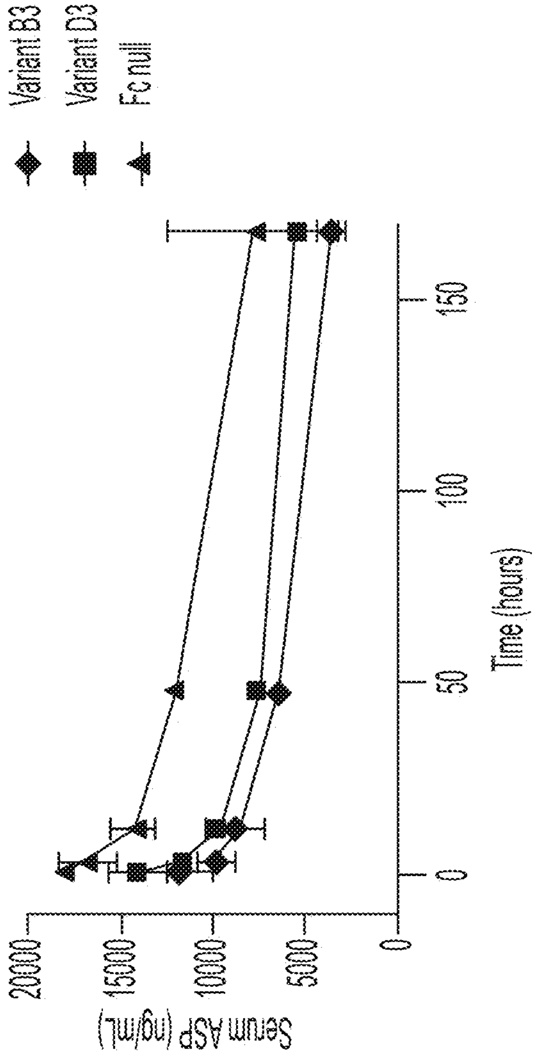
FIGS. 30A-30B show results from pK experiments measuring molecule ("ASP") concentration in serum (ng/mL) over time (FIG. 30A) and mean half-life of molecule, where each point represents the median of 5 mice (wildtype BALB/c mice) and bars represent SEM (FIG. 30B).
Figure 30B:
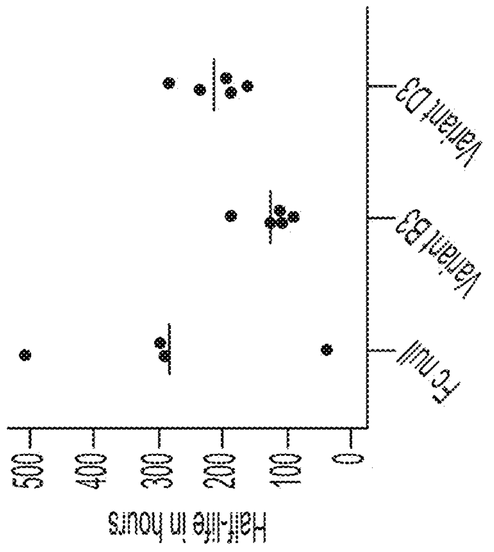

The results from the pK experiments done in the absence of M22 show that Variant B3 has a reduced half-life compared to Variant D3, likely due to its high affinity for FcγRIIA and FcγRIIB (FIG. 30A-30B). The Fc null molecule has reduced volume of distribution due to lack of binding to FcγRs, as well as reduced clearance. Variant D3 has a half-life of about 9 days, similar to most human antibodies in wild-type mice. Points represent median of 5 mice, bars represent SEM (FIG. 30B).

Molecule and M22 Clearance in B-hFcRn Mice

In this experiment, B-hFcRn mice were injected with M22 (TSHR autoantibodies) and 24 hours later the mice were injected with molecule. Serum from the mice was collected and analyzed for concentration of molecule and M22 at timepoints: −10 minutes, 10 minutes, 30 minutes, 3 hours, 12 hours, 48 hours, and 7 days after molecule administration.

Figures 31A, 31B, 31C:
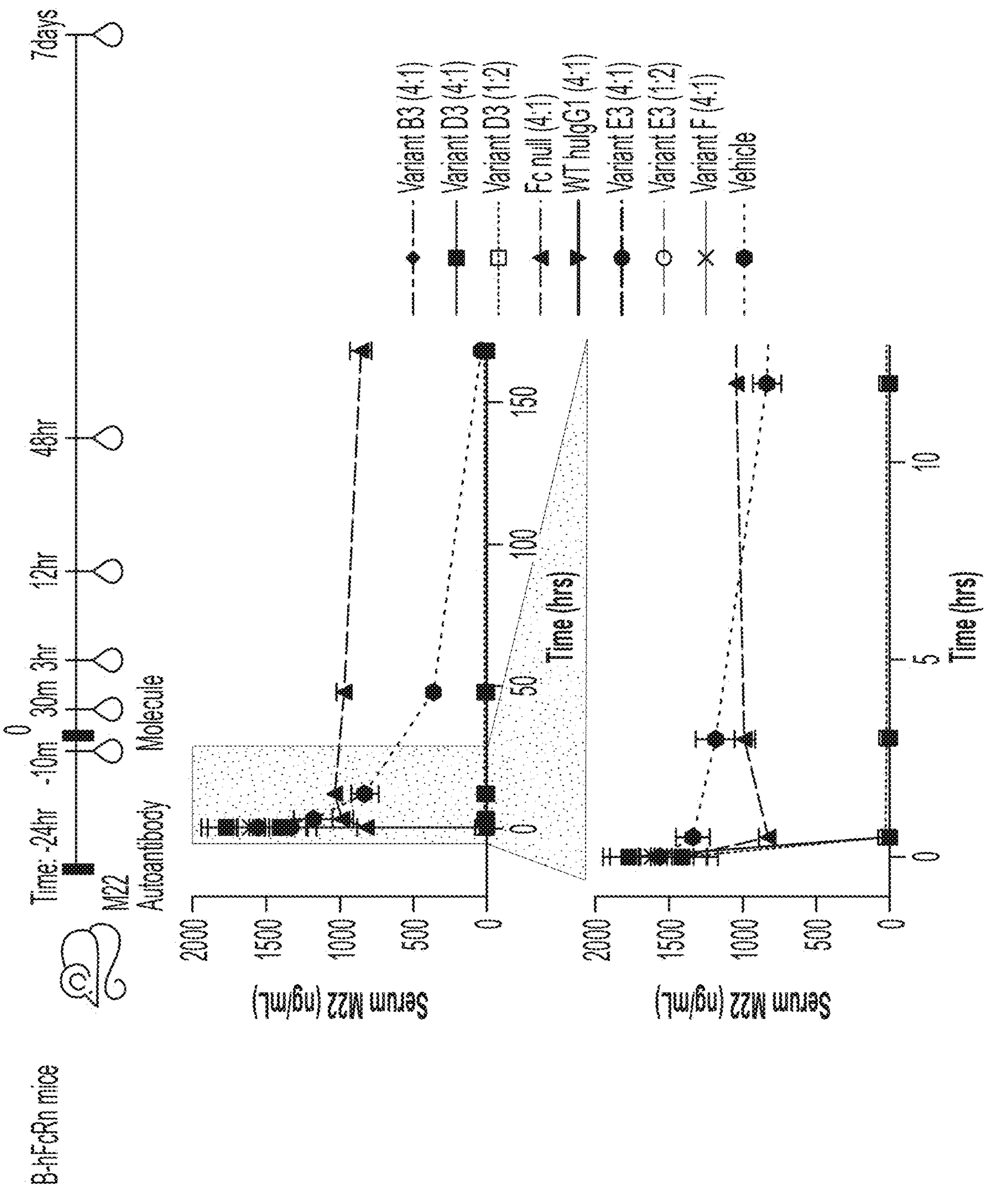
FIGS. 31A-31C show exemplary in vivo activity of exemplary molecules described herein.

Results: Results are shown in FIGS. 31B-31C. These results show that M22 is undetectable 10 min after administering Variant D3 or Variant E3 in a 4-molar excess (molar ratio of molecule:M22 of 4:1), in contrast to the Fc null molecule.

Figures 32A, 32B, 32C:
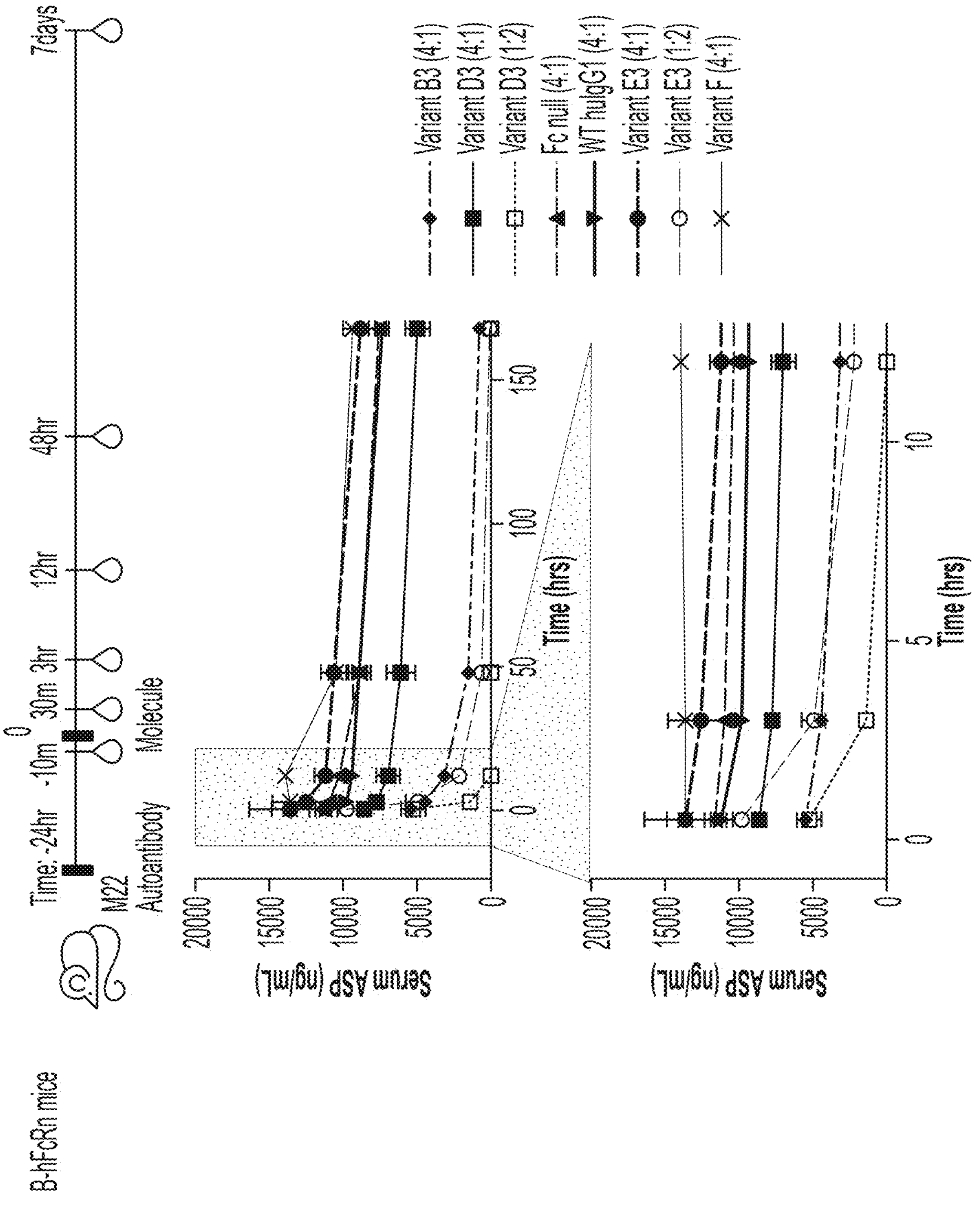
FIGS. 32A-C show exemplary in vivo activity of exemplary molecules described herein.

Additionally, Variants D3 and E3 remain after all molecule:M22 complex is cleared, but all molecules have a long half-life as shown in FIGS. 32B-32C. Variant E3 (with LS mutations) showed an extended half-life compared to Variant D3 (without LS mutations).

Figure 33B:
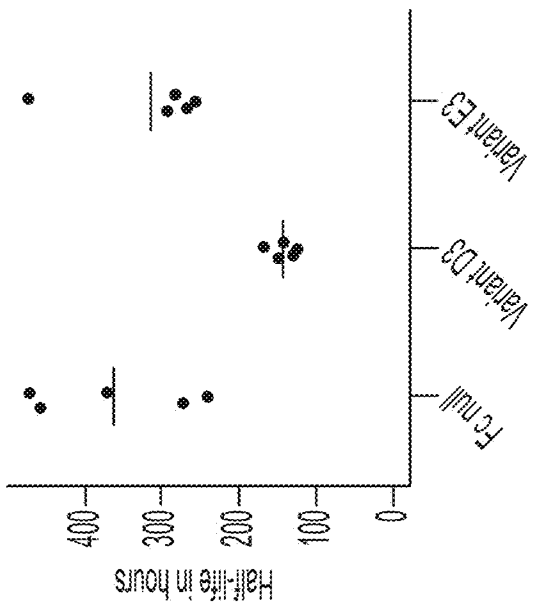
FIGS. 33A-33B show results from pK experiments measuring molecule ("ASP") concentration in serum (ng/mL) over time (FIG. 33A) and mean half-life of molecule, where each point represents median of 5 mice (B-hFcRn) and bars represent SEM (FIG. 33B).
Figure 33A:
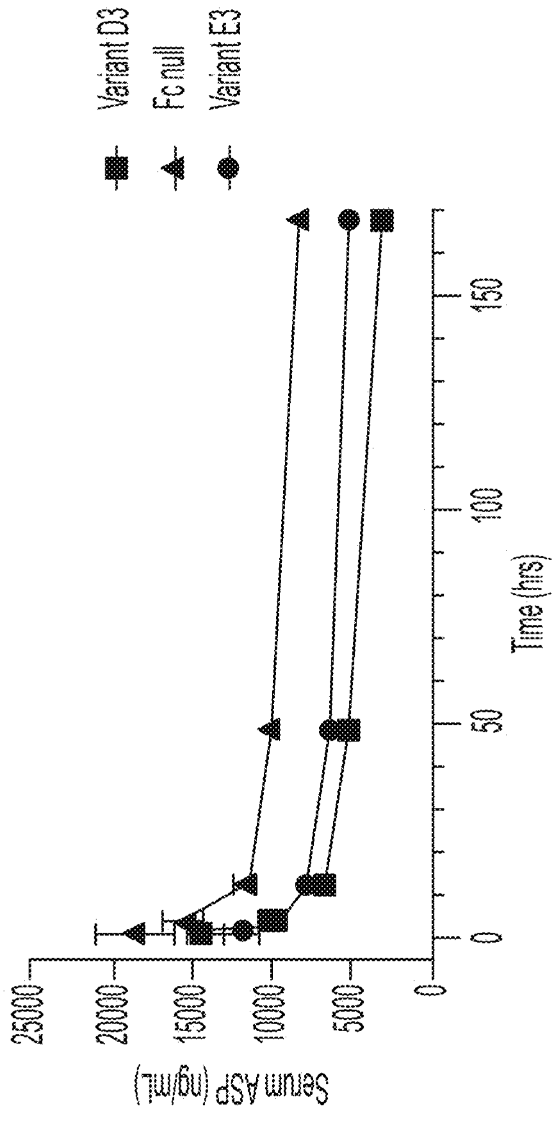

Results from the pK experiment in the absence of M22 are shown in FIGS. 33A-33B. In humanized FcRn mice (B-hFcRn), Variant E3 (with LS mutations) showed an extended half-life compared to Variant D3 (without LS mutations). The Fc null molecule showed reduced volume of distribution due to lack of binding to FcγRs, as well as reduced clearance. Half-lives are likely slightly underestimated due to limited timepoints after the distribution phase. Points represent median of 5 mice and bars represent SEM (FIG. 33B).

Molecule and M22 Clearance in hFcγR/hFcRn Mice

In this experiment, hFcγR/hFcRn mice were injected with M22 (TSHR autoantibodies) and 24 hours later the mice were injected with molecule. Serum from the mice was collected and analyzed for concentration of molecule and M22 at timepoints: −10 minutes, 10 minutes, 30 minutes, 3 hours, 12 hours, 48 hours, and 7 days after molecule administration.

Figure 34A:
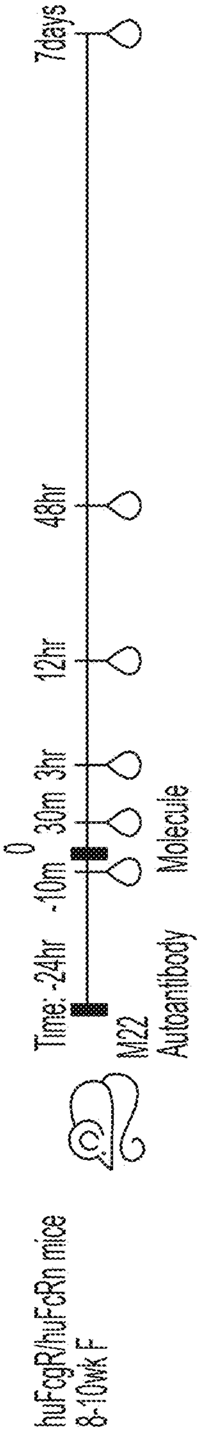
FIGS. 34A-34C show exemplary in vivo activity of exemplary molecules described herein.
Figure 34B:
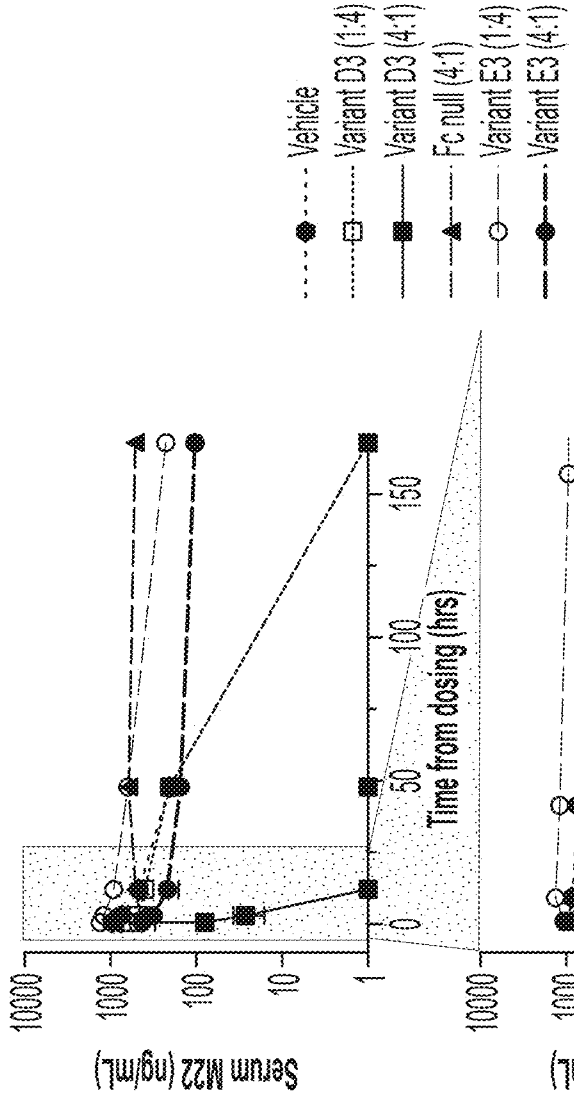
Figure 34C:
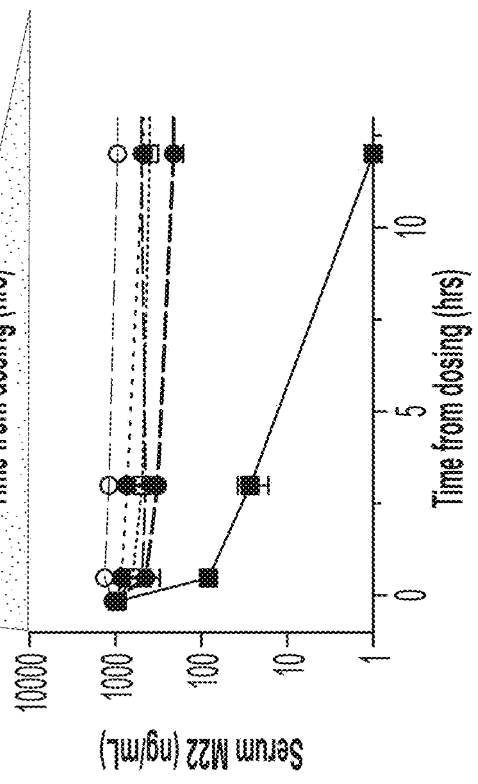
Figure 35A:
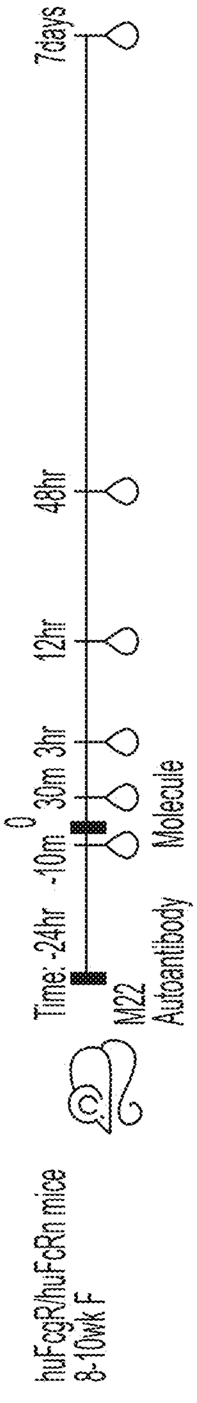
FIGS. 35A-35C show exemplary in vivo activity of exemplary molecules described herein.
Figure 35B:
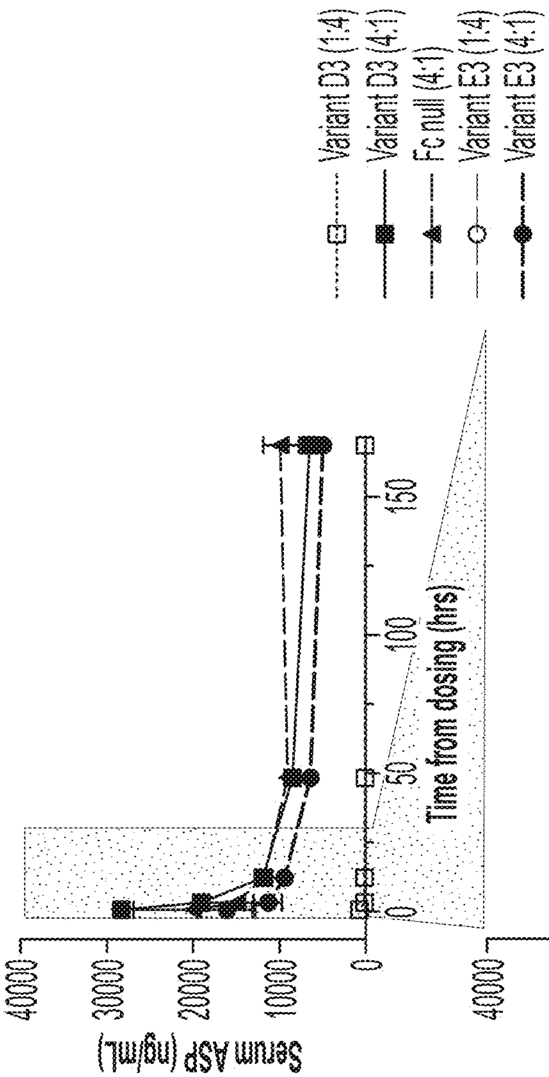
Figure 35C:
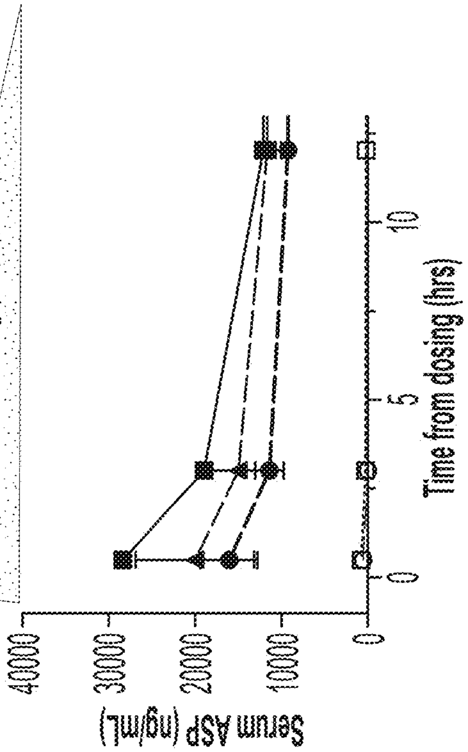

Results: FIGS. 34B-34C show levels of M22 at different timepoints. FIGS. 35B-35C show levels of molecule at different timepoints. These results show that M22 is undetectable 12 hours after administering Variant D3 in a 4-molar excess (molar ratio of molecule:M22 of 4:1), in contrast to the Fc null molecule (FIGS. 34B-34C). Administration of Variant E3 in a 4-molar excess results in much slower clearance of M22 than Variant D3, with some M22 persisting beyond the point observed without administration of molecule (vehicle).

Figure 36A:
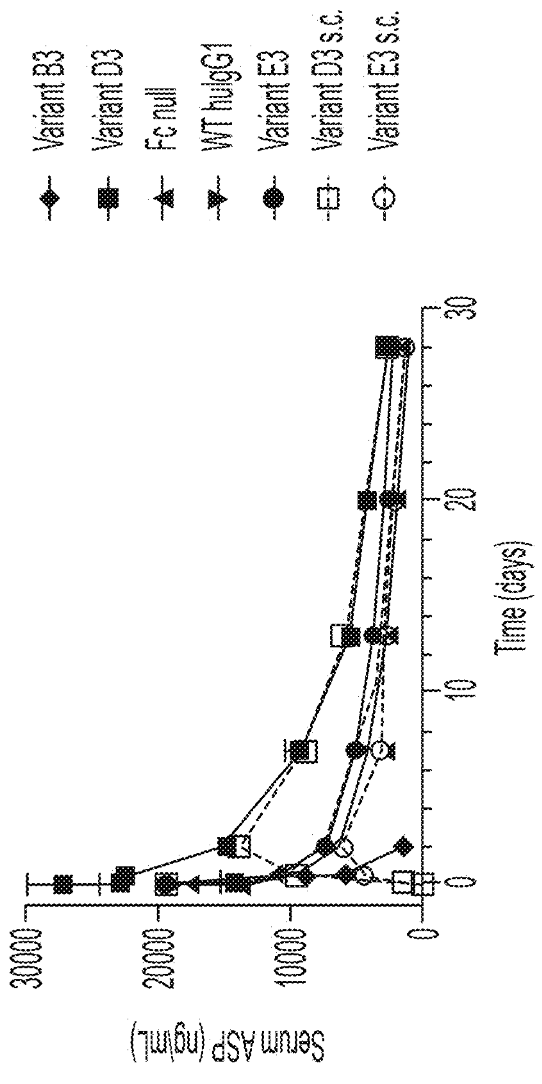
FIGS. 36A-36B show results from pK experiments measuring molecule ("ASP") concentration in serum (ng/mL) over time (FIG. 36A) and mean half-life of molecule, where each point represents median of 5 mice (huFcγR-huFcRn mice) and bars represent SEM (FIG. 36B).
Figure 36B:
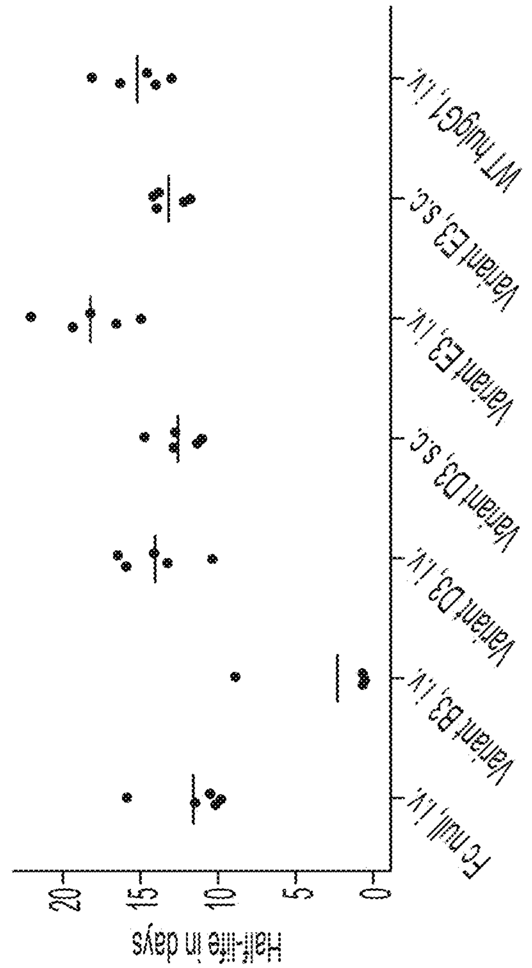

Results from the pK experiment in the absence of M22 are shown in FIGS. 36A-36B. When administered i.v. in hFcγR/hFcRn mice, Variant E3 (with LS mutations) showed an extended half-life of about 18 days compared to Variant D3 (without LS mutations) with a half-life of about 14 days. When administered s.c., Variants E3 and D3 both demonstrate a high level of bioavailability, reaching similar serum concentrations to i.v. administered molecule 48 hours after injection and subsequently following a similar rate of depletion.

Example 6: Additional Studies Examining Activity of Exemplary Molecules

The present Example examines other aspects of exemplary molecules described herein.

Immune Complex Formation: IC Assessment

Figure 37:
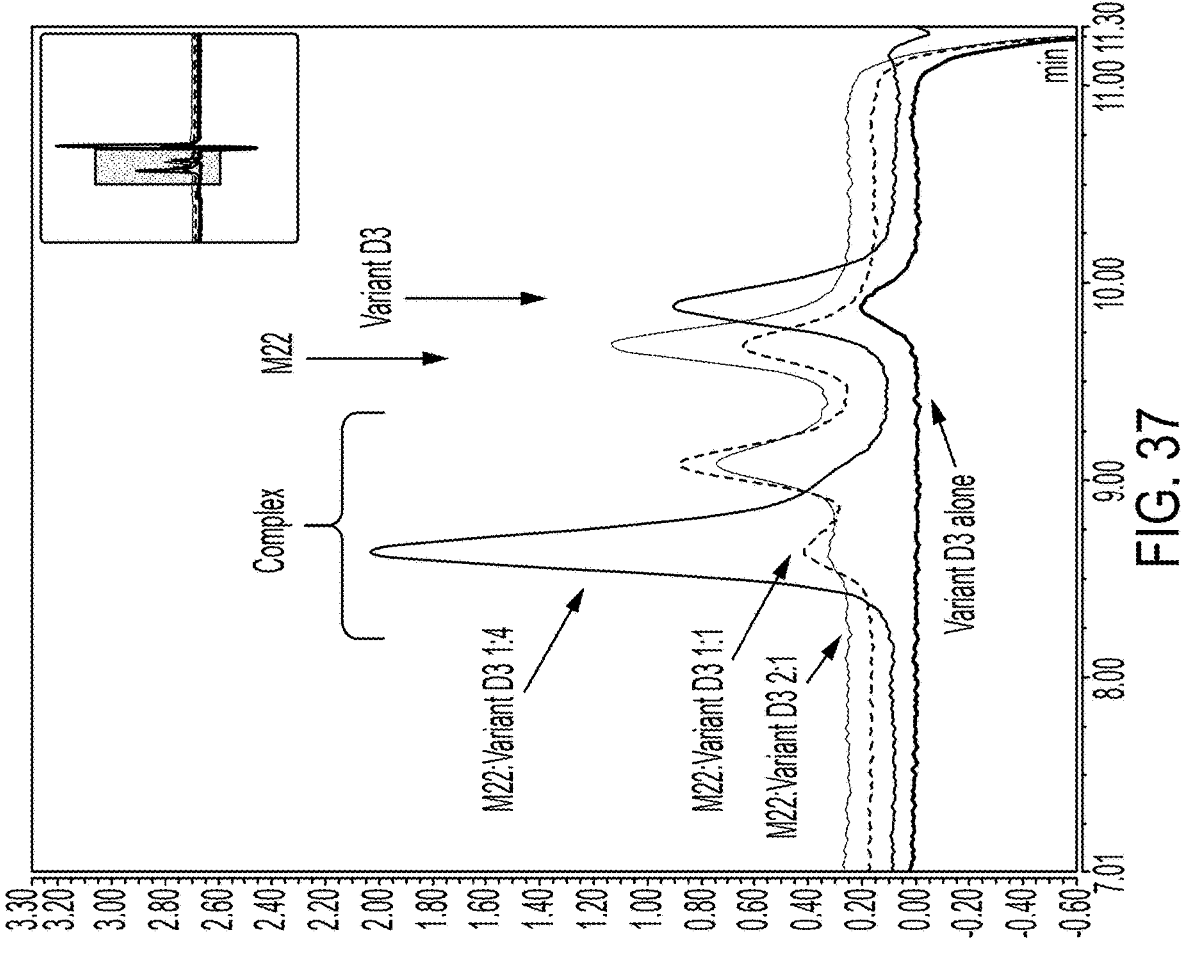
FIG. 37 shows exemplary results from an experiment studying immune complex formation between an exemplary molecule (Variant D3) and M22 antibodies. M22 antibodies and the exemplary molecule were mixed at various ratios and assessed via HPLC-SEC for complex formation.

In this experiment, patient-derived M22, K1-70, and K1-18 recombinant autoantibodies were mixed with Variant D3 (and/or Variant B3) at various ratios and assessed via HPLC-SEC for complex formation. All combinations tested between monoclonal autoantibodies and the exemplary molecules showed at most two peaks representing a 2:1 molecule:autoantibody and a 1:1 molecule:autoantibody complex (Data for Variant D3 and Variant D3:M22 complexes is shown in FIG. 37).

Figure 38:
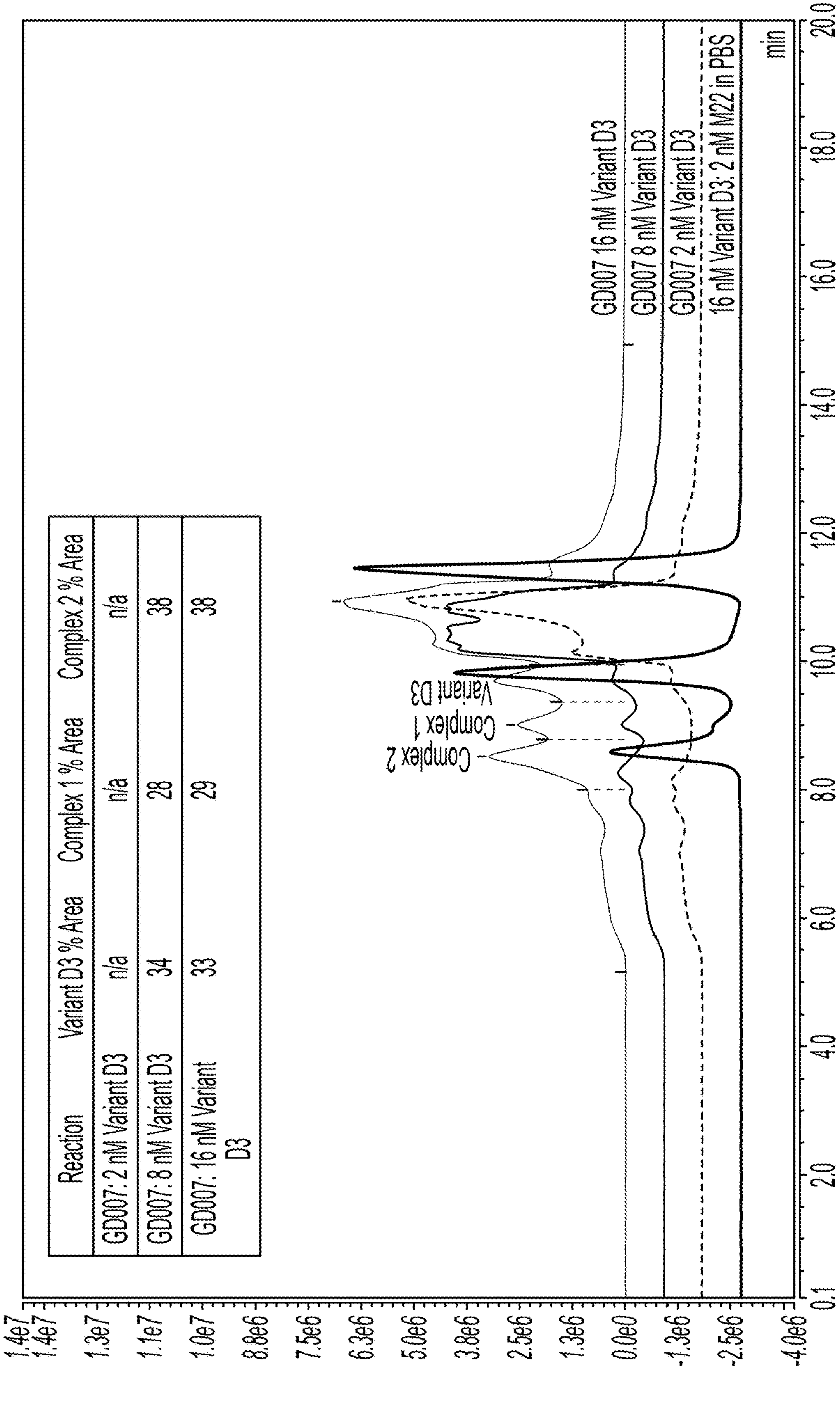
FIG. 38 shows exemplary results from an experiment studying immune complex formation between an exemplary molecule and M22 antibodies. Patient sera samples were incubated with fluorescently labeled molecule and molecules were shown to complex in 2:1 and 1:1 (molecule: autoantibody) complexes (represented by characteristic peaks).

In another experiment, pilot studies using patient sera samples incubated with fluorescently labeled Variant D3 molecule showed a high background due to intrinsic fluorescence from sera. Despite this, however, similar 2:1 and 1:1 complexes and potentially larger complexes were observed (FIG. 38).

Figure 39B:
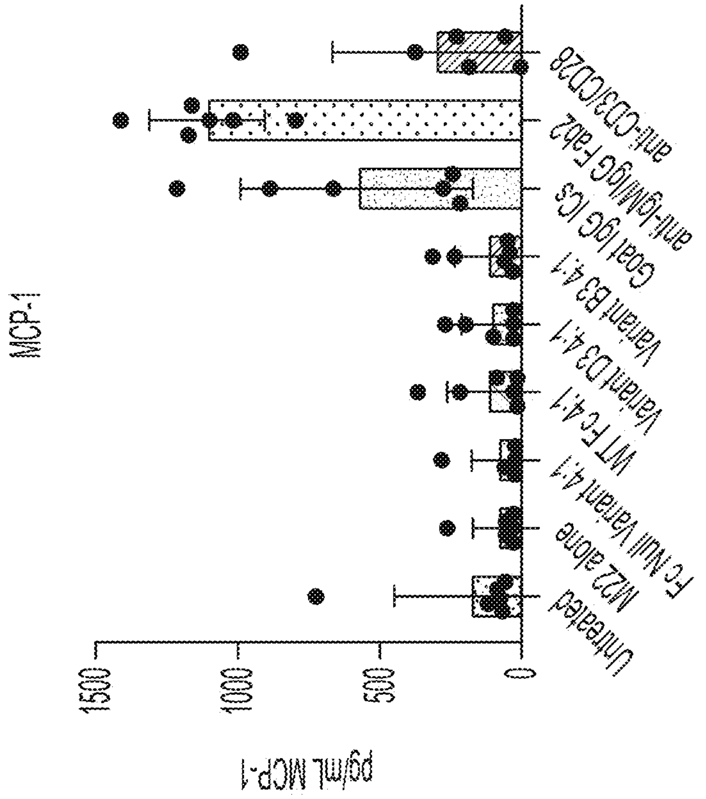
FIGS. 39A-39B show results from an ELISA assay measuring inflammatory cytokines to assess immune response to exemplary molecules.
Figure 39A:
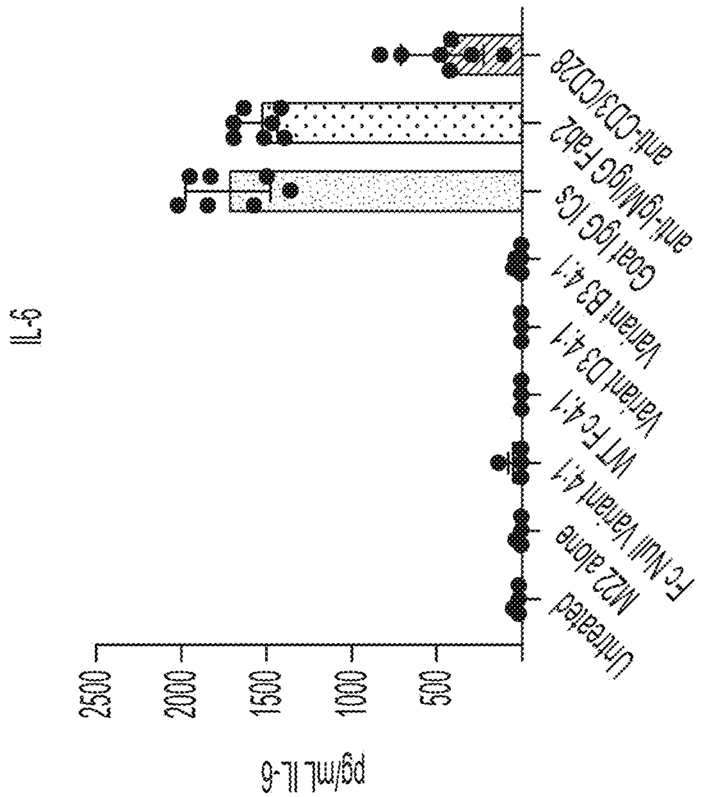

Measuring activation of Inflammatory Cytokines: To assess activity and immune response to the exemplary molecules, human PBMCs were cultured with molecule: M22 complexes at 160 nM molecule:40 nM M22 overnight and levels of IL-6 and MCP-1 were measured in supernatants by ELISA. Results from the assay show that no molecule:M22 complexes led to secretion of pro-inflammatory cytokine IL-6, while positive controls (goat IgG immune complexes, anti-IgM/G Fab2, and an anti-CD3/CD28 antibody) induced cytokine secretion IL-6 or MCP-1 (FIGS. 39A-39B, respectively).

Figure 40A:
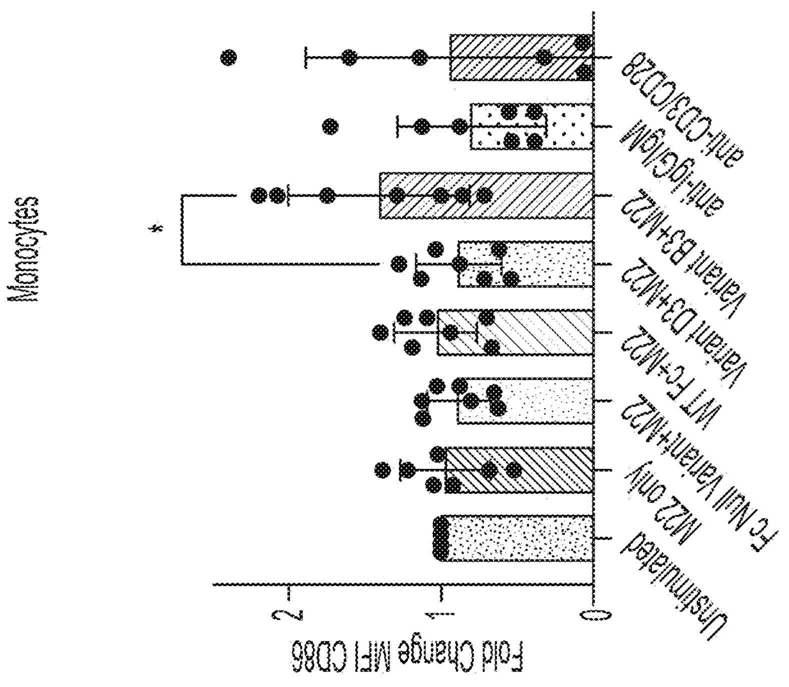
FIGS. 40A-40B show results from an experiment measuring activation of monocytes (FIG. 40A) and NK cells (FIG. 40B) after being cultured with exemplary molecules and M22 antibodies.
Figure 40B:
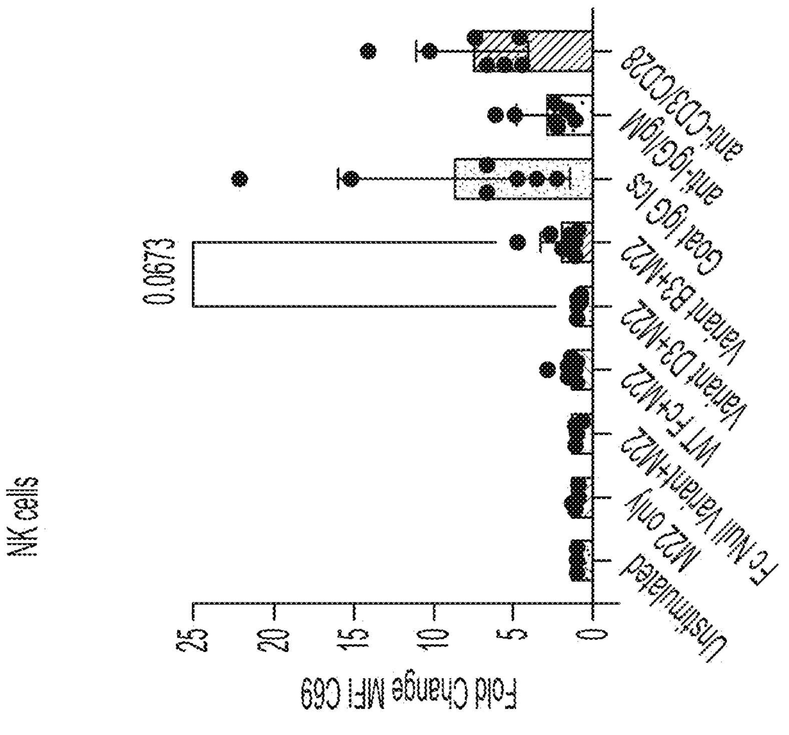

Measuring activation of Monocytes and NK cells: In another experiment, human PBMCs were cultured overnight with molecule:M22 complexes at 160 nM molecule:40 nM M22, and activation of cell types was measured by flow cytometry. Results from this experiment showed that treatment with Variant D3:autoantibody complexes did not lead to activation of monocytes or NK cells (FIG. 40A and FIG. 40B, respectively). Variant B3:autoantibody complexes led to slight, but in some cases statistically significant, increases in activation.

Overall, M22 immune complexes with Variant D3 molecules at 4:1 ratio (double-capped M22, or where one exemplary molecule is bound to each Fab of the M22 antibody) does not lead to activation in PBMCs as measured by secretion of IL-6 or MCP-1 (FIG. 39) and does not lead to activation of immune cells in immune complex with M22, as measured by activation markers in monocytes, NK cells, B cells and T cells (FIG. 40).

Figure 41B:
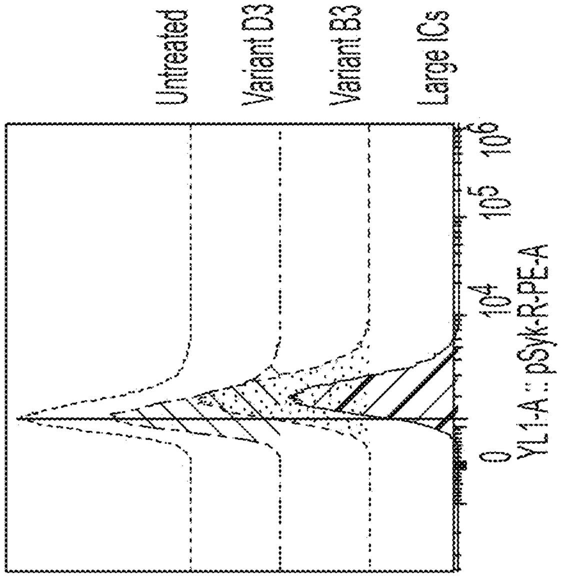
FIGS. 41A-41B show results from an experiment measuring activation of TH-P immune cells cultured with exemplary molecule-M22 immune complexes (molecule:M22 ratio was 4:1).
Figure 41A:
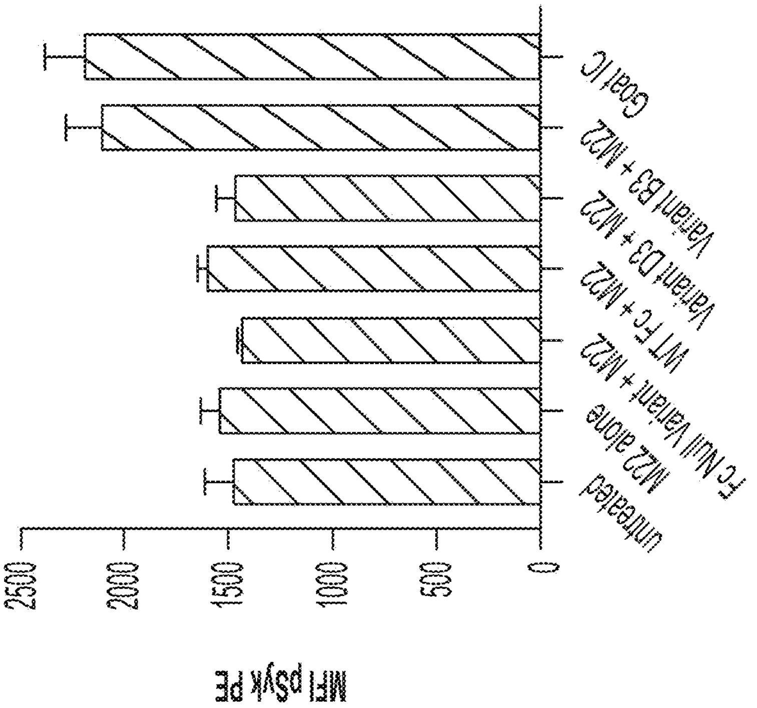

Measuring activation of THP-1 immune cells: In this experiment, THP-1 cells (a monocytic cell line) were cultured with molecule: M22 immune complex at 4:1 ratio (double-capped M22). Phosphorylation of Syk, which is downstream of activating Fc receptors was measured by flow cytometry. Exemplary molecules Variant B3, Variant D3, Fc null molecule, and IgG1 WT Fc, were tested. Results are shown in FIGS. 41A-41B. Results show that Variant D3 does not lead to activation of immune cells in immune complex with M22. Specifically, Variant D3:M22 immune complexes at 4:1 ratio (double-capped M22) do not lead to activation in THP-1 cells. THP-1 cells cultured with Variant D3:M22 complexes had background levels of Syk phosphorylation, while those cultured with Variant B3 had increased levels of pSyk, comparable to activation by large immune complexes ("Large ICs") as formed by human IgG:goat anti-human IgG complexes (positive control). These results indicate that the exemplary molecule Variant D3 in complex with autoantibodies is likely to be well tolerated and not expected to induce a significant immune response.

Developability Assessment of Exemplary Molecules

Developability refers to the likelihood that a biologic candidate will have the potential to become a manufacturable, safe, and efficacious drug. Therefore, assays to assess the developability of exemplary molecules were carried out. Variants D3 and E3 were tested in the following assays: AC-SINS (Sule et al., *Mol. Pharm.* 10(4):1322-1331, 2013) to assess for self-association, BVP-ELISA (Hötzel et al., *MAbs* 4(6):753-760, 2012) to assess for poly-specificity, DSC to assess for thermal stability.

Figure 42:
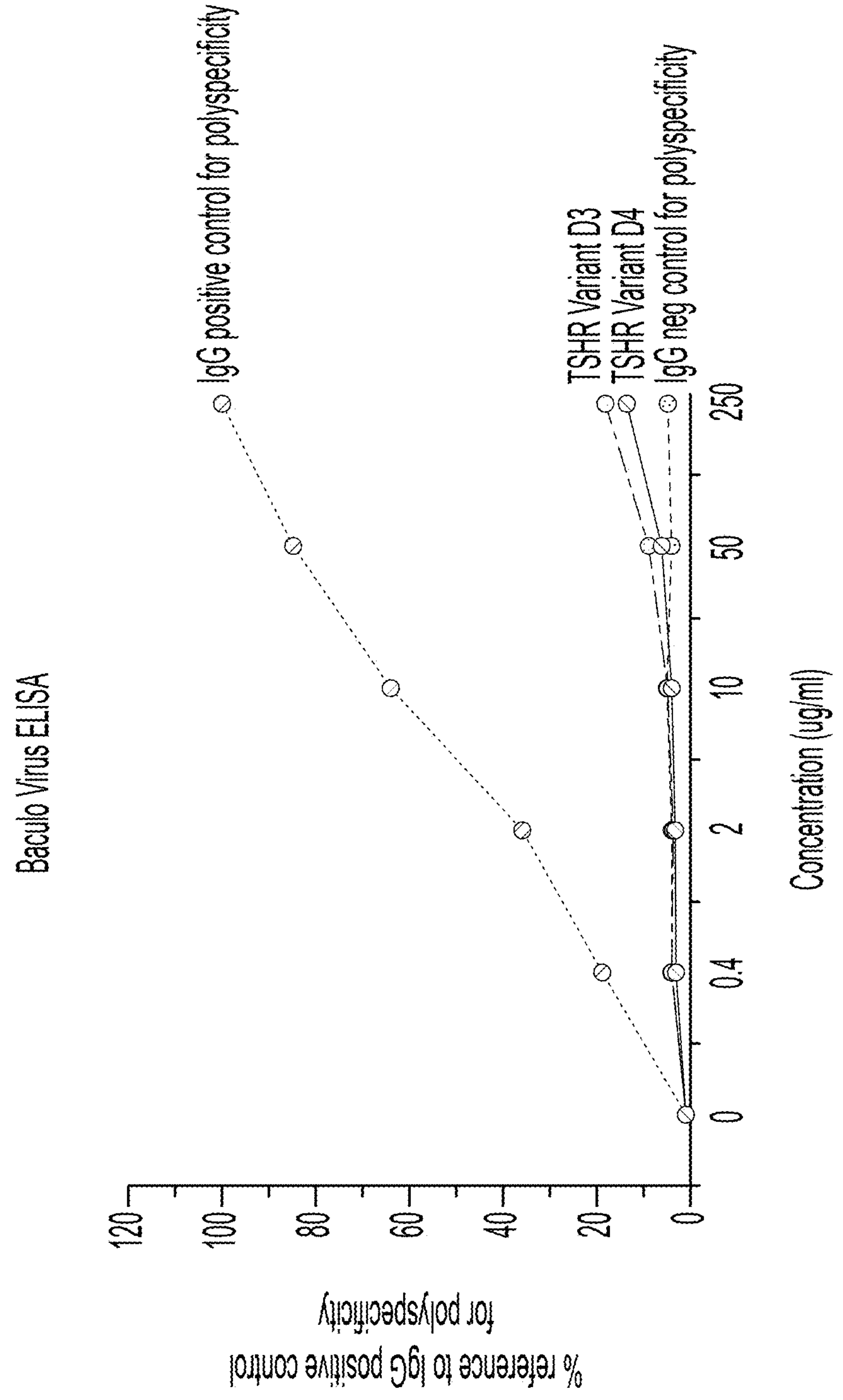
FIG. 42 shows results from an experiment using AC-SINS (affinity-capture self-interaction nanoparticle spectroscopy) to identify self-association propensity of exemplary molecules.

Measuring self-association propensity using AC-SINS: AC-SINS (affinity-capture self-interaction nanoparticle spectroscopy) is capable of identifying antibodies and biologics with low-self-association propensity that is robust even at low concentrations (5-50 ug/mL). Briefly, Variants D3 and E3 (at 50 ug/mL in PBS pH 7.5) were captured on gold nanoparticles and the plasmon wavelength of the TSHR variant-gold conjugates was measured at 25 C. This plasmon wavelength red-shifts as the distance between particles is reduced due to attractive self-interactions. The measured plasmon wavelength shift of Variants D3 and E3 showed a shift of 1 nm (Table 12 below and FIG. 42), indicative of a "well-behaved" molecule that does not exhibit any propensity for self-association (unlike the plasmon wavelength shift of 16 nm for an IgG control known to self-associate and aggregate).

TABLE 12

Testing of Self-Association Propensity of Exemplary Molecules

| Sample | Normalization factor | Normalized Baculovirus score | Referenced to positive control (%) |
|---|---|---|---|
| Variant D3 | 82.30 | 4.9 | 18.22 |
| Variant E3 | 77.82 | 3.7 | 13.66 |
| Negative control IgG for polyspecificity | 104.17 | 1.3 | 4.89 |
| Positive control IgG for polyspecificity | 95.24 | 27.0 | 100.00 |

Figure 43A:
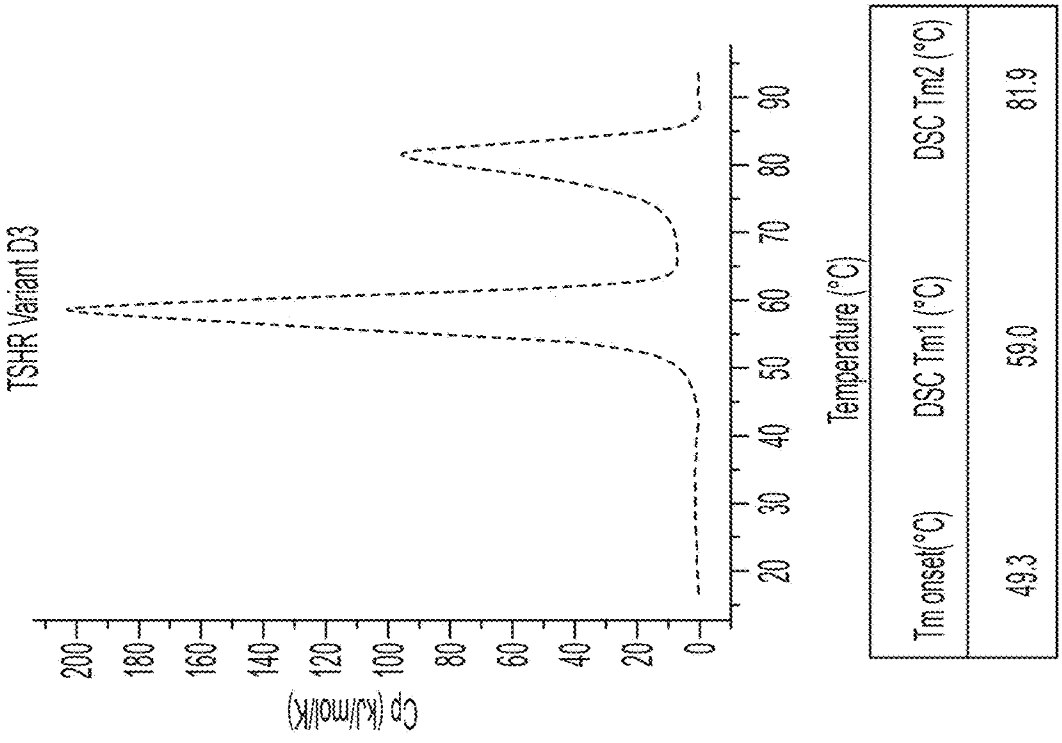
FIGS. 43A-43B show results from an experiment using DSC to measure thermal stability of exemplar molecules Variant D3 (FIG. 43A) and Variant E3 (FIG. 43B).
Figure 43B:
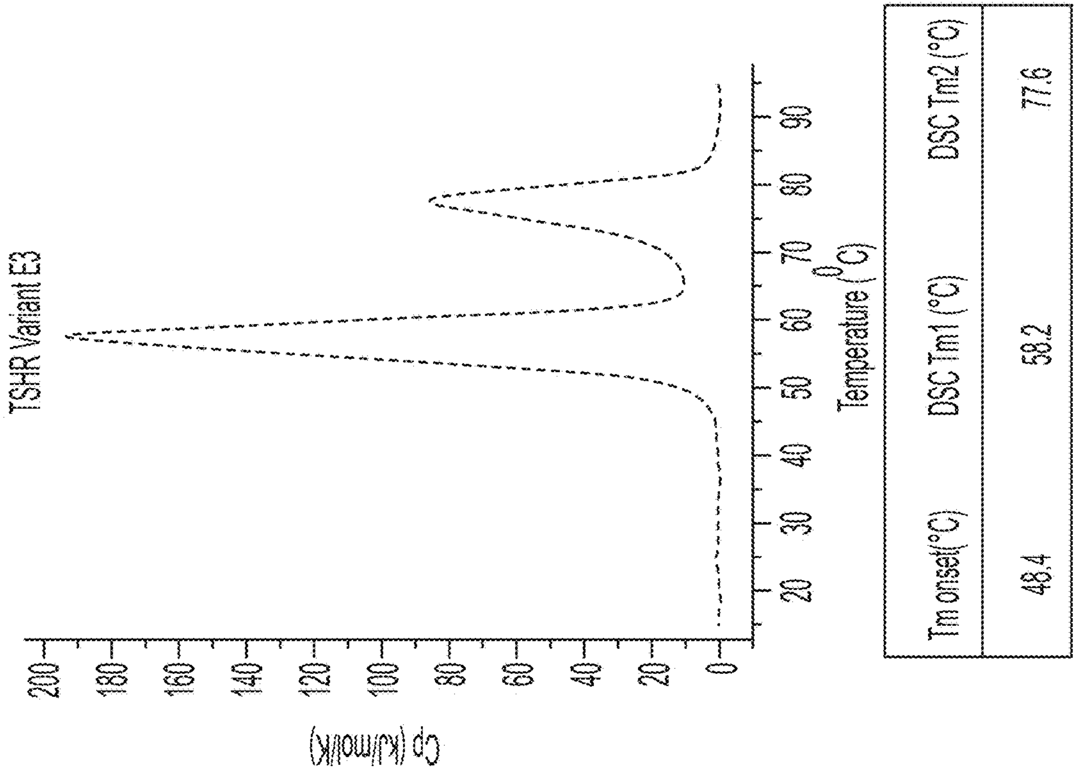

Normalization factor is calculated by: 1/(blank sample OD450-OD620), and Baculovirus score is calculated by: (250 ug/mL sample OD450-OD620)*normalization factor DSC to measure Thermal Stability: To evaluate the thermal stability of the TSHR variants, a MicroCal™ VP-Capillary Differential Scanning Calorimetry (DSC) was used. Briefly, Variants D3 and E3 were tested at 1 mg/mL in 20 mM Histidine, 150 mM NaCl, pH 6.0. Temperature range started from 10C and ended at 95C with a scanning rate of 1.5 C/min. The results show a Tm onset between 48.4-49.3 C, a Tm1 between 58.2-59C, and a Tm2 between 77.6-81.9 C (FIGS. 43A-43B).

Example 7: B Cell Inhibition

Figure 44:
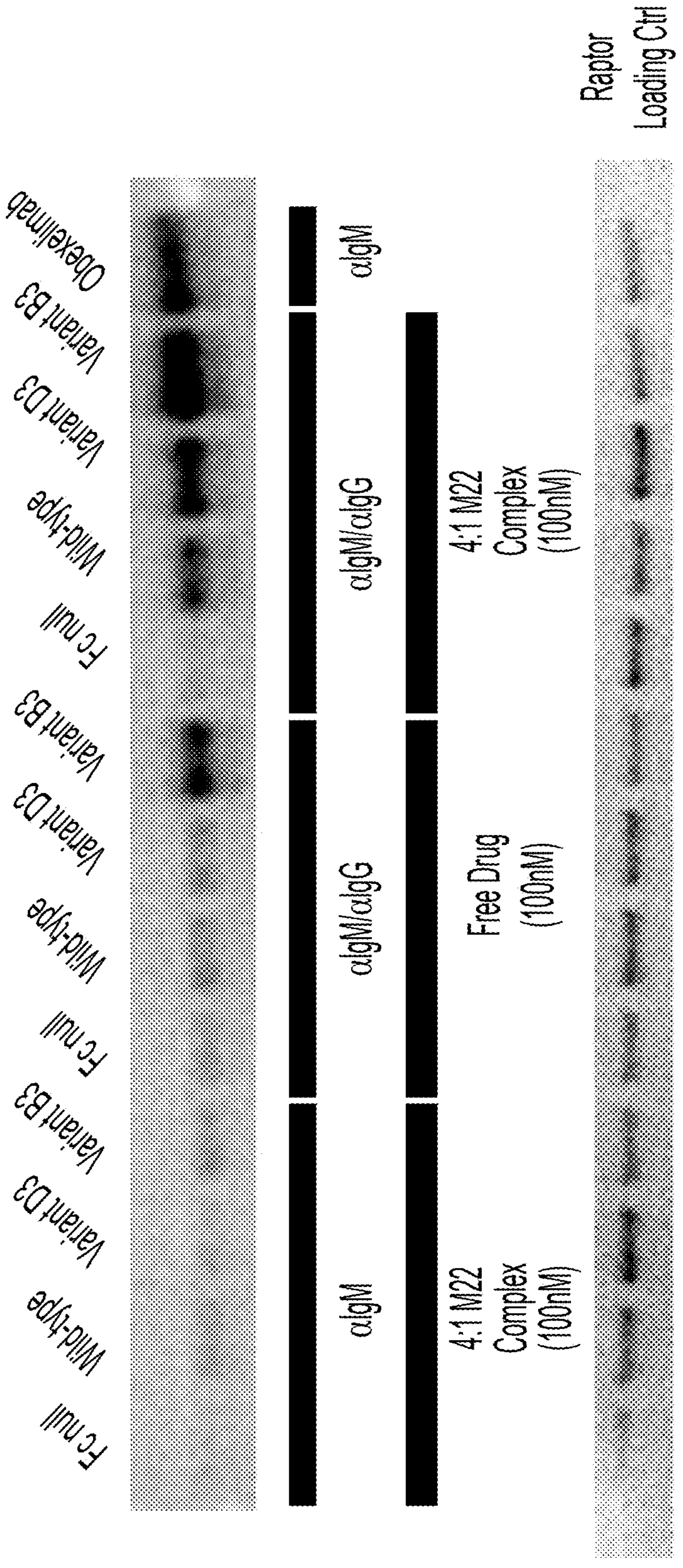
FIG. 44 shows results of western blot analysis measuring phosphorylation of FcγRIIB in B cells incubated with exemplary molecules, pre-complexed (4:1) with M22 or as a free drug in the presence of activating anti-IgG/IgM F(ab)2 or anti-IgM F(ab)2.
Figures 45A, 45B, 45C, 45D, 45E, 45F, 45G:
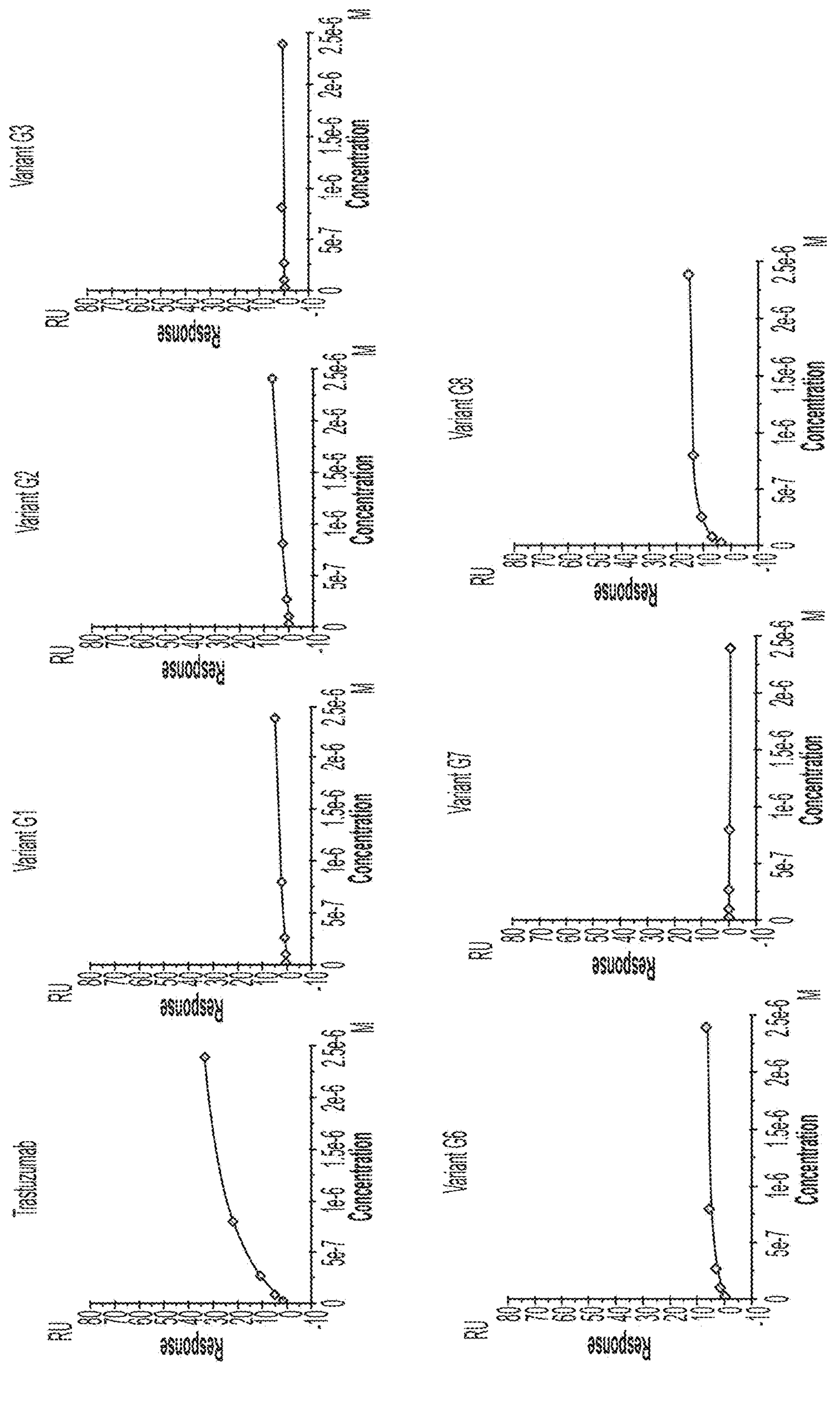
FIGS. 45A-45G show results from binding assays measuring binding activity of Trastuzumab control (FIG. 45A), Variant G1 (FIG. 45B), Variant G2 (FIG. 45C), Variant G3 (FIG. 45D), Variant G6 (FIG. 45E), Variant G7 (FIG. 45F), and Variant G8 (FIG. 45G) to activating receptor FcγRIIA167R when molecules were captured onto an SPR sensor chip and FcγR used as the analyte.

The present Example demonstrates phosphorylation of FcγRIIB in B cells in the presence of an exemplary molecule (Variant D3) pre-complexed with M22. More specifically, the present Example demonstrates effective crosslinking of Variant D3/M22 complex to a B cell receptor (BCR) in the presence of a polyspecific anti-IgG/IgM F(ab)2 activating reagent. FIG. 44 depicts phosphorylation of FcγRIIB when Variant D3 was pre-complexed with M22 but not when Variant D3 was used as a free drug. Without wishing to be bound to any theory, it is believed that phosphorylation of FcγRIIB in B cells requires the simultaneous binding of (i) the Fc domain of Variant D3 to FcγRIIB, the TSHR antigen domain of Variant D3 to M22 antibody, and (iii) the Fc domain of M22 antibody to the activating anti-IgG/IgM F(ab)2, which itself then binds to IgM or IgG BCRs found on the purified naive B cells. No phosphorylation was detected when removing any link in this crosslinking bridge.

The results also show that anti-IgM F(ab)2 alone did not recruit the Variant D3/M22 complex. No phosphorylation was detected when using an exemplary molecule with Fc null mutations (see results with “Fc null” molecule which included LALAPG mutation). Variant B3 which includes the high affinity SE/LF Fc mutation resulted in FcγRIIB phosphorylation even in the absence of complexation with M22.

Methods

Purified primary B cells were thawed and resuspended in cold FACS buffer (PBS+2% FBS) at 1e6/mL. Equal volume of purified primary B cells was distributed to 1.5 mL Eppendorf tubes for separate testing, keeping cells on ice. Test molecules as pre-complexed molecules with M22 (TSHR autoantibodies) (pre-mixed at a 4:1 molar ratio) or free drug (molecule only) were added to the purified primary B cells at 10 μg/mL and the cells were incubated for 10 minutes at room temperature. Primary B cells were activated by adding anti-IgM or anti-IgG/IgM Fab(2) at 50 μg/mL and incubated for 5 minutes at room temperature. Cells were spun for 2 minutes at 600×g prior to cell lysis with 15 μL cold RIPA buffer complete with phosphatase and protease inhibitors. Cells were incubated in RIPA buffer with phosphatase and protease inhibitors for 30 minutes on ice. Lysates were clarified at 10,000×g at 4C for 10 min. 4× NuPage LDS sample buffer (+1% Beta mercaptoethanol) was added to each lysate at 5 μL per sample containing 15 μL of protein.

Proteins were boiled at 95C for 5 minutes using a heat block. Proteins were loaded on a 1.5 mm 15-well 4-12% Tris Bis gel, run at 200 v for 45 minutes. Gels were transferred to a PVDF membrane using Thermo’s iBlot 2, at 20 v for 7 minutes.

Membranes were blocked in 5% milk for 30 minutes shaking at room temperature, cut into separate blots at the 75 kD mark and probed overnight on a rotating platform at 4C with either Raptor (CST, 1:1000) or pCD32b (Abcam, 1:1000), in 5% milk. Next morning, blots were detected with anti-Rabbit IgG-HRP secondary antibody (1:5,000 Southern Biotechnology) in 5% milk shaking for 1 hour at room temperature. Blots were washed three times in TBST prior to detection with a Pierce chemiluminescence kit and read on an iBlot.

Example 8: Testing and Characterization of Exemplary Molecules

Identification of Fc Mutations that Confer Specific Binding to FcγRIIB

Exemplary molecules described above were tested for their ability to selectively bind to FcγRIIB through their Fc domains and to have decreased or no binding affinity for other Fc receptors FcγRIIA167H and FcγRIIA167R.

Binding assays using SPR were performed to determine the binding affinity of the exemplary molecules. Molecules were captured on a CM5 SPR chip. Increasing concentrations of FcγR analyte (FcγRIIA167H, FcγRIIA167R or FcγRIIB) were subsequently injected over the captured molecules and a single dissociation performed using single cycle kinetics. The data was then analyzed using steady state analysis which is suitable for low affinity interactions. In particular, a plot of response at equilibrium against the molecule concentration was generated. The KD value is equal to the concentration that gives 50% of the maximum response. The molecules represented include: a control IgG1 (Trastuzumab antibody), Variant G1, Variant G2, Variant G3, Variant G4, Variant G6, Variant G7, Variant G8, Variant G9, Variant G10, Variant G11, Variant G12, Variant G13, and Variant G14 for various Fc receptors: FcγRIIA167H, FcγRIIA167R and FcγRIIB. Trastuzumab and an exemplary molecule with a wild-type Fc domain (WT IgG1 Fc) were used as positive controls.

Figures 46A, 46B, 46C, 46D, 46E, 46F, 46G:
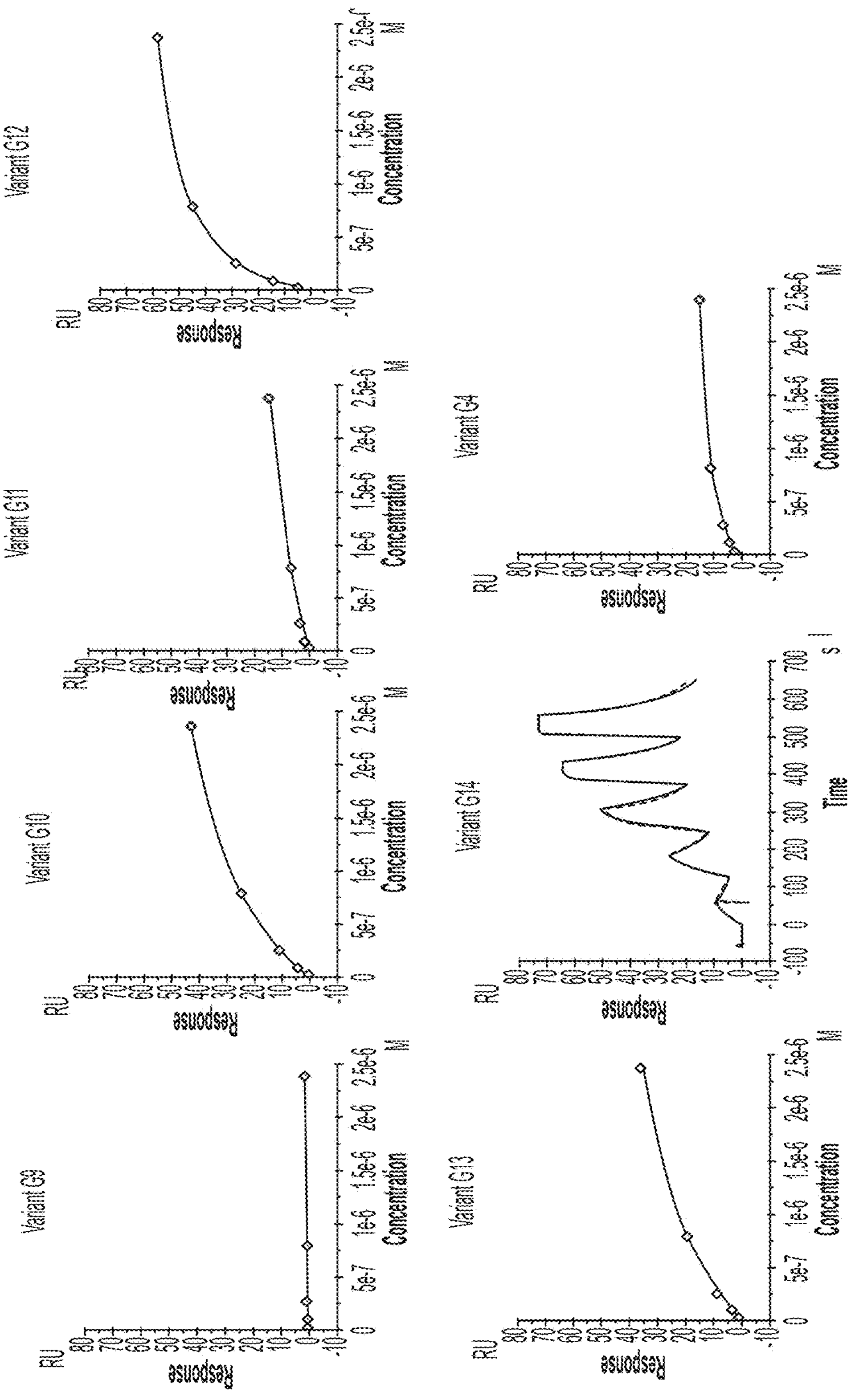
FIGS. 46A-46G show results from binding assays measuring binding activity of Variant G9 (FIG. 46A), Variant G10 (FIG. 46B), Variant G11 (FIG. 46C), Variant G12 (FIG. 46D), Variant G13 (FIG. 46E), Variant G14 (FIG. 46F), and Variant G4 (FIG. 46G) to activating receptor FcγRIIA167R when molecules were captured onto an SPR sensor chip and FcγR used as the analyte.
Figures 49A, 49B, 49C, 49D, 49E, 49F, 49G:
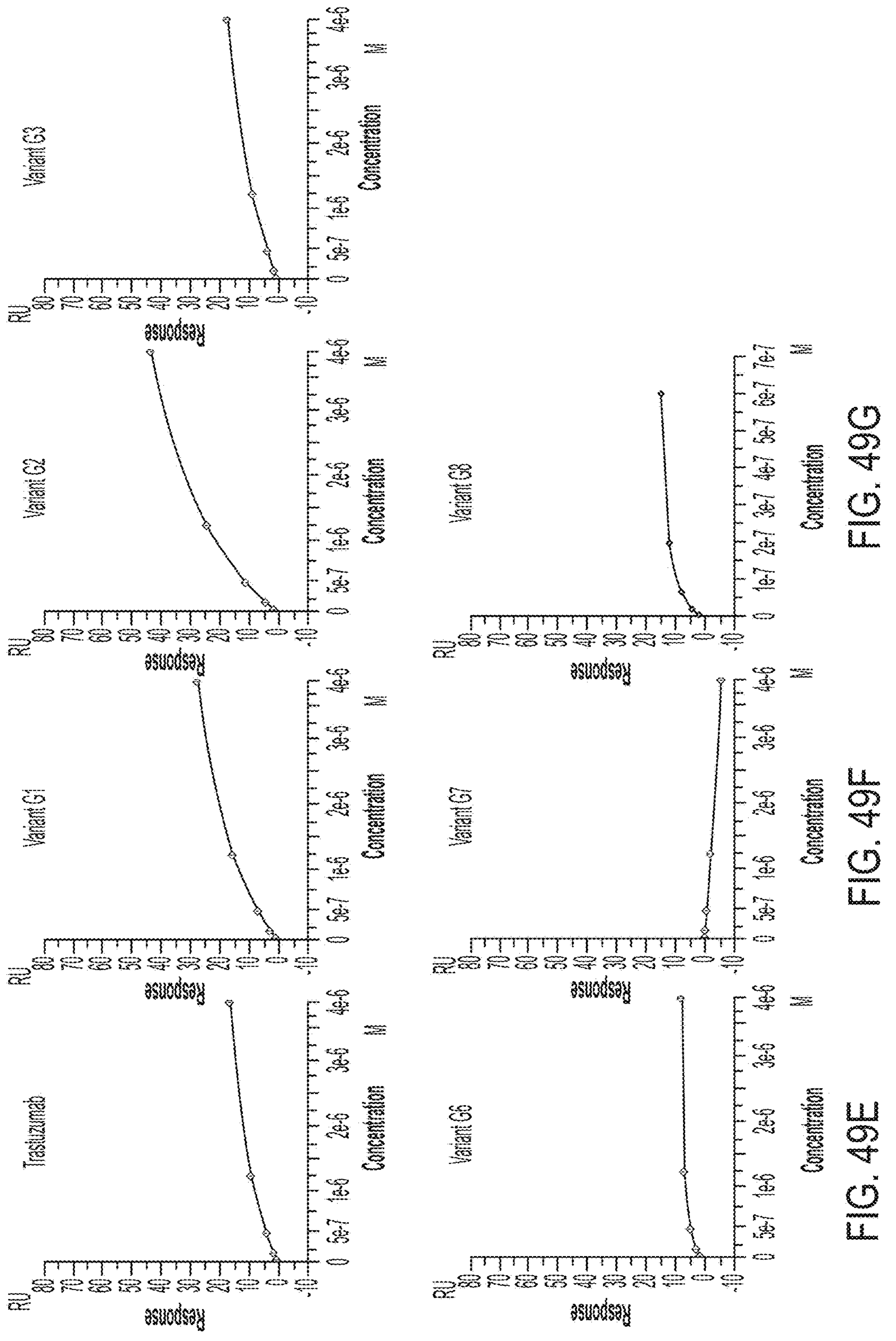
FIGS. 49A-49G show results from binding assays measuring binding activity of Trastuzumab control (FIG. 49A), Variant G1 (FIG. 49B), Variant G2 (FIG. 49C), Variant G3 (FIG. 49D), Variant G6 (FIG. 49E), Variant G7 (FIG. 49F), and Variant G8 (FIG. 49G) to inhibitory receptor FcγRIIB when molecules were captured onto an SPR sensor chip and FcγR used as the analyte.
Figure 50A:
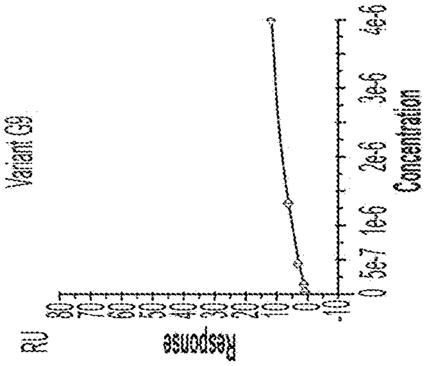
FIGS. 50A-50G show results from binding assays measuring binding activity of Variant G9 (FIG. 50A), Variant G10 (FIG. 50B), Variant G11 (FIG. 50C), Variant G12 (FIG. 50D), Variant G13 (FIG. 50E), Variant G14 (FIG. 50F), and Variant G4 (FIG. 50G) to inhibitory receptor FcγRIIB when molecules were captured onto an SPR sensor chip and FcγR used as the analyte.
Figure 50B:
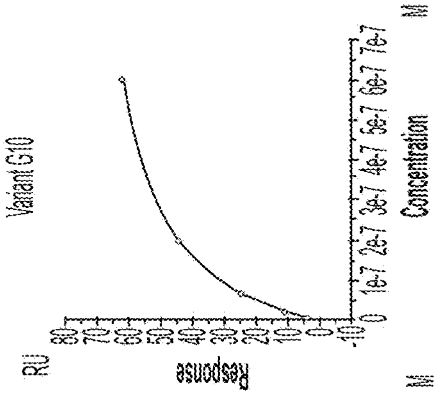
Figure 50C:
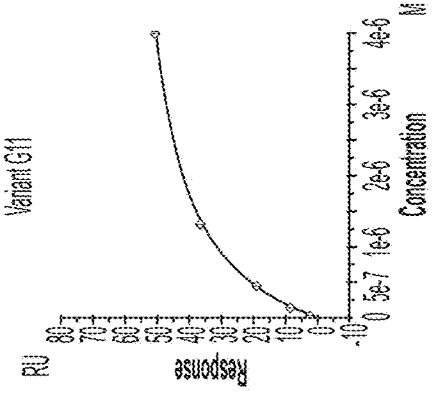
Figure 50D:
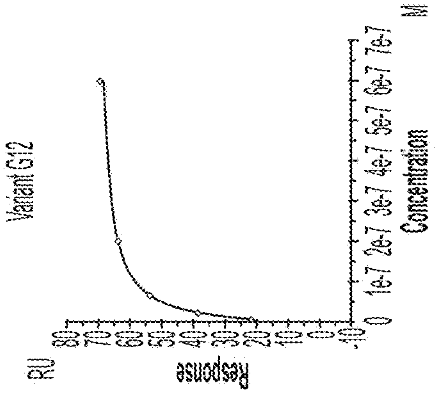
Figure 50E:
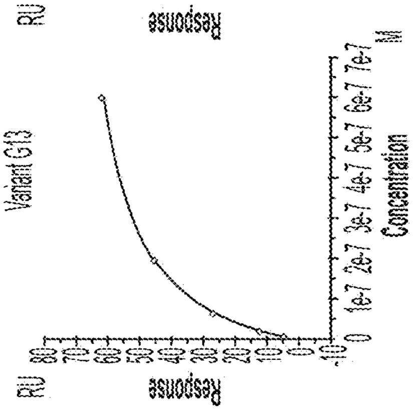
Figure 50F:
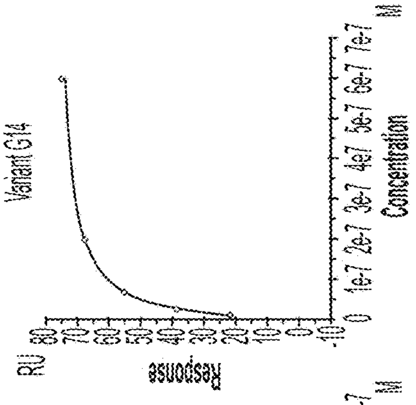
Figure 50G:
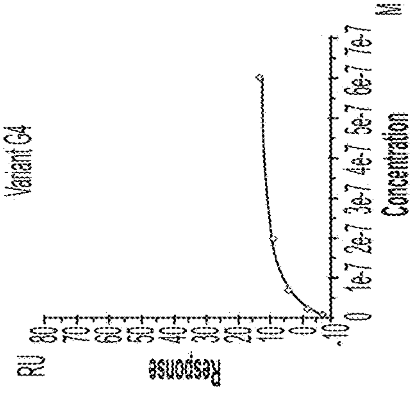

Results from the binding assays are shown in Table 13 below and FIGS. 45-50. Specifically, FIGS. 45A-45G shows binding activity of Trastuzumab (positive control) (FIG. 45A), Variant G1 (FIG. 45B), Variant G2 (FIG. 45C), Variant G3 (FIG. 45D), Variant G6 (FIG. 45E), Variant G7 (FIG. 45F), and Variant G8 (FIG. 45G) to activating receptor FcγRIIA167R, when exemplary molecules were captured onto an SPR sensor chip and FcγR used as the analyte. FIGS. 46 A-46G shows binding activity of Variant G9 (FIG. 46A), Variant G10 (FIG. 46B), Variant G11 (FIG. 46C), Variant G12 (FIG. 46D), Variant G13 (FIG. 46E), Variant G14 (FIG. 46F), and Variant G4 (FIG. 46G) to activating receptor FcγRIIA167R when exemplary molecules were captured onto an SPR sensor chip and FcγR used as the analyte.

FIGS. 47A-47G shows binding activity of Trastuzumab (positive control) (FIG. 47A), Variant G1 (FIG. 47B), Variant G2 (FIG. 47C), Variant G3 (FIG. 47D), Variant G6 (FIG. 47E), Variant G7 (FIG. 47F), and Variant G8 (FIG. 47G) to activating receptor FcγRIIA167H, when exemplary molecules were captured onto an SPR sensor chip and FcγR used as the analyte. FIGS. 48A-48G shows binding activity of Variant G9 (FIG. 48A), Variant G10 (FIG. 48B), Variant G11 (FIG. 48C), Variant G12 (FIG. 48D), Variant G13 (FIG. 48E), Variant G14 (FIG. 48F), and Variant G4 (FIG. 48G) to activating receptor FcγRIIA167H when exemplary molecules were captured onto an SPR sensor chip and FcγR used as the analyte.

FIGS. 49A-49G shows binding activity of Trastuzumab (positive control) (FIG. 49A), Variant G1 (FIG. 49B), Variant G2 (FIG. 49C), Variant G3 (FIG. 49D), Variant G6 (FIG. 49E), Variant G7 (FIG. 49F), and Variant G8 (FIG. 49G) to inhibitory receptor FcγRIIB, when exemplary molecules were captured onto an SPR sensor chip and FcγR used as the analyte. FIGS. 50A-50G shows binding activity of Variant G9 (FIG. 50A), Variant G10 (FIG. 50B), Variant G11 (FIG. 50C), Variant G12 (FIG. 50D), Variant G13 (50E), Variant G14 (FIG. 50F), and Variant G4 (FIG. 50G) to inhibitory receptor FcγRIIB when exemplary molecules were captured onto an SPR sensor chip and FcγR used as the analyte.

Table 13 below shows kinetic parameters for exemplary molecules binding to activating receptors FcγRIIA167R and FcγRIIA167H, and inhibitory receptor FcγRIIB; where KD is dissociation constant, NB indicates non-binding, and UTD indicates a KD was unable to be determined.

TABLE 13

| Molecules captured onto SPR sensor chip and FcγR used as analyte | | | | |
|---|---|---|---|---|
| Molecule Immobilized | Fc mutations | FcγRIIA167R KD(M) | FcγRIIA167H KD(M) | FcγRIIB KD(M) |
| Variant G1 | E233V, L234D, L235F, G236R, G237D, S239L, S267D, H268P, S298G, T299A, A327L, L328A, A330H, E333I | UTD | NB | 2.62E−06 |
| Variant G2 | E233V, L234D, L235F, G236R, G237D, S239L, S267D, H268P, R292Q, S298G, T299A, A327L, L328A, A330H, E333I | UTD | NB | 2.61E−06 |
| Variant G3 | E233V, L234D, L235F, G236R, G237D, S239L, H268P, R292Q, S298G, T299A, A327L, L328A, A330H, E333I | NB | NB | 3.65E−06 |
| Variant G4 | E233D, G237D, P238D, H268D, P271G, A330R | 8.36E−07 | UTD | 5.56E−08 |
| Variant G6 | L234D, G236N, S267E | UTD | NB | 3.35E−07 |
| Variant G7 | L235R | NB | NB | NB |
| Variant G8 | G236N, S267E | 1.48E−07 | UTD | 7.93E−08 |
| Variant G9 | P238D, D270E | NB | NB | 2.96E−06 |
| Variant G10 | P238D, P271G | 1.35E−06 | UTD | 1.45E−07 |
| Variant G11 | P238D, D270E P271G | 3.49E−06 | NB | 9.87E−07 |
| Variant G12 | G237D, P238D, P271G A330R | 3.69E−07 | 3.81E−06 | 2.23E−08 |
| Variant G13 | G237D, P238D, D270E, P271G, A330R | 1.79E−06 | UTD | 1.27E−07 |
| Variant G14 | S239D, H268D, L328W | 4.32E−09 | 1.14E−07 | 3.09E−08 |

Testing of Exemplary Molecules for Avidity-Mediated Effects

In this experiment, CHO cells expressing FcγRIIB (CHO-FcγRIIB+) were incubated with exemplary molecules and M22 (a TSHR autoantibody) with and without 2B6 antibody which is an anti-FcγRIIB antibody that blocks binding of FcγRIIB to antibody Fc domains. The exemplary molecules tested include Variant D3, Variant B3, Variant G1, Variant G2, Variant G5, Variant G10, Variant G11, Variant G12, Variant G13, and Variant G14.

Figure 51:
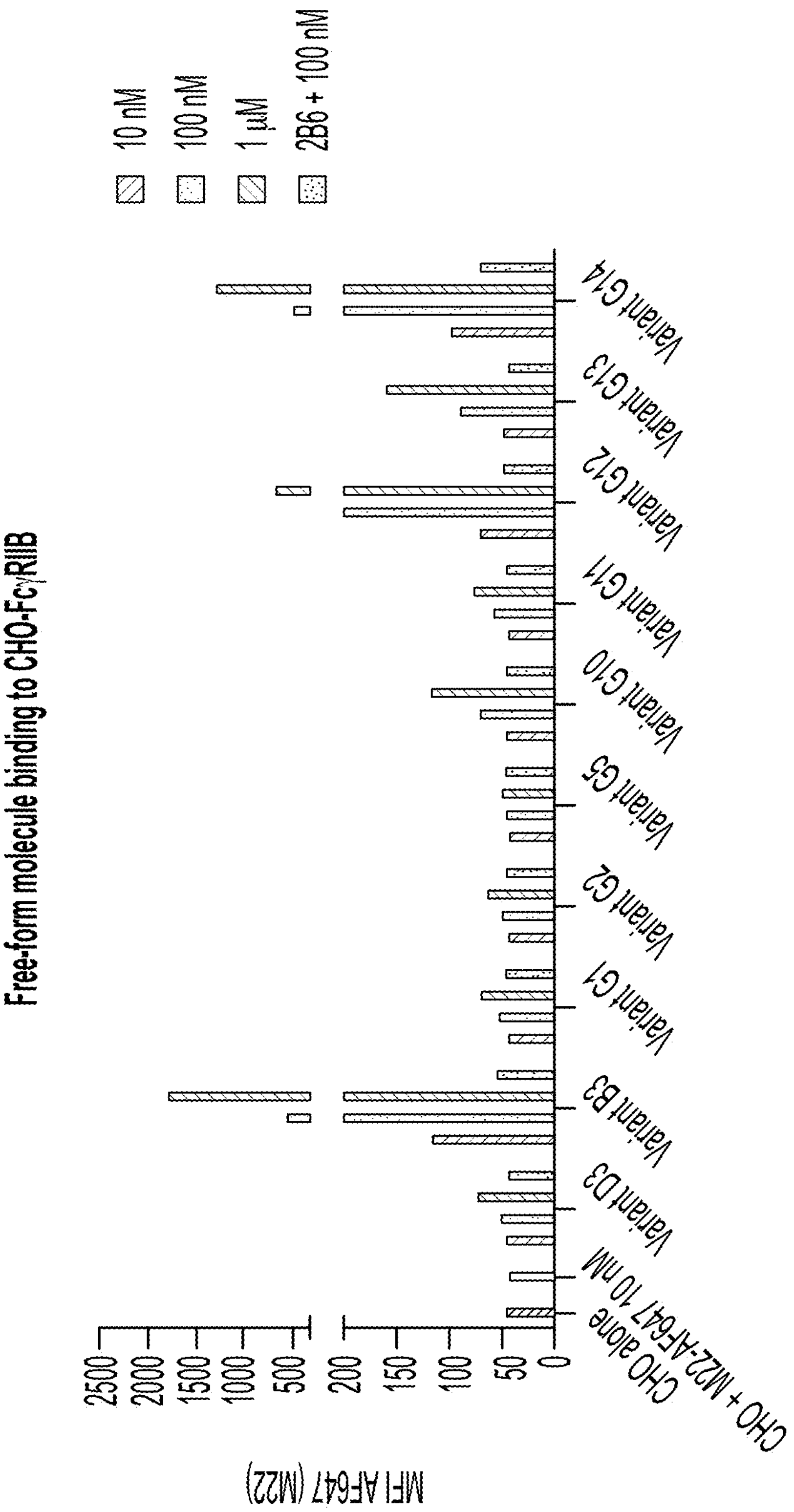
FIG. 51 shows a bar graph of mean fluorescence intensities (MFI) of Alexa Fluor 647-labeled M22 autoantibody detecting, by flow cytometry, binding of free molecules at increasing concentrations to FcγRIIB ectopically expressed in a genetically-engineered CHO-K1 cell line (CHO-FcγRIIB). Pre-treatment of CHO-FcγRIIB cells with anti-FcγRIIB blocking antibody clone 2B6 at 10 μg/mL was used to evaluate FcγRIIB-dependent binding of exemplary molecules. MFI values were calculated from live single cells. Each condition was assessed in singlicate.
Figure 52:
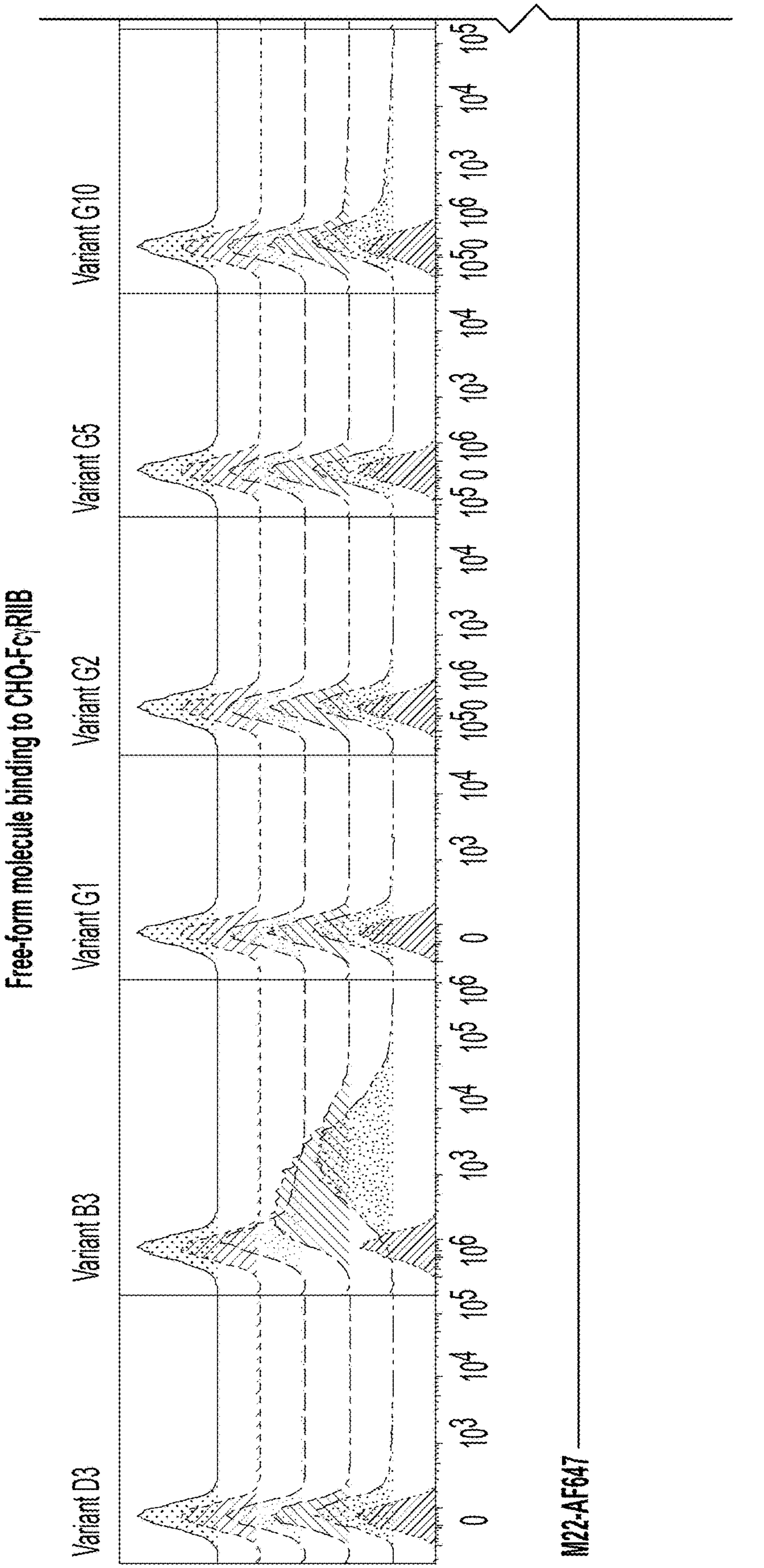
FIG. 52 shows flow cytometry half-offset histograms of Alexa Fluor 647-labeled M22 autoantibody fluorescence signal representing detection of free molecule binding at increasing concentrations to FcγRIIB ectopically expressed in a genetically-engineered CHO-K1 cell line (CHO-FcγRIIB). Pre-treatment of CHO-FcγRIIB cells with anti-FcγRIIB blocking antibody clone 2B6 at 10 μg/mL was used to evaluate FcγRIIB-dependent binding of exemplary molecules. Signal was calculated from live cell singlets. Each condition was assessed in singlicate.
Figure 52:
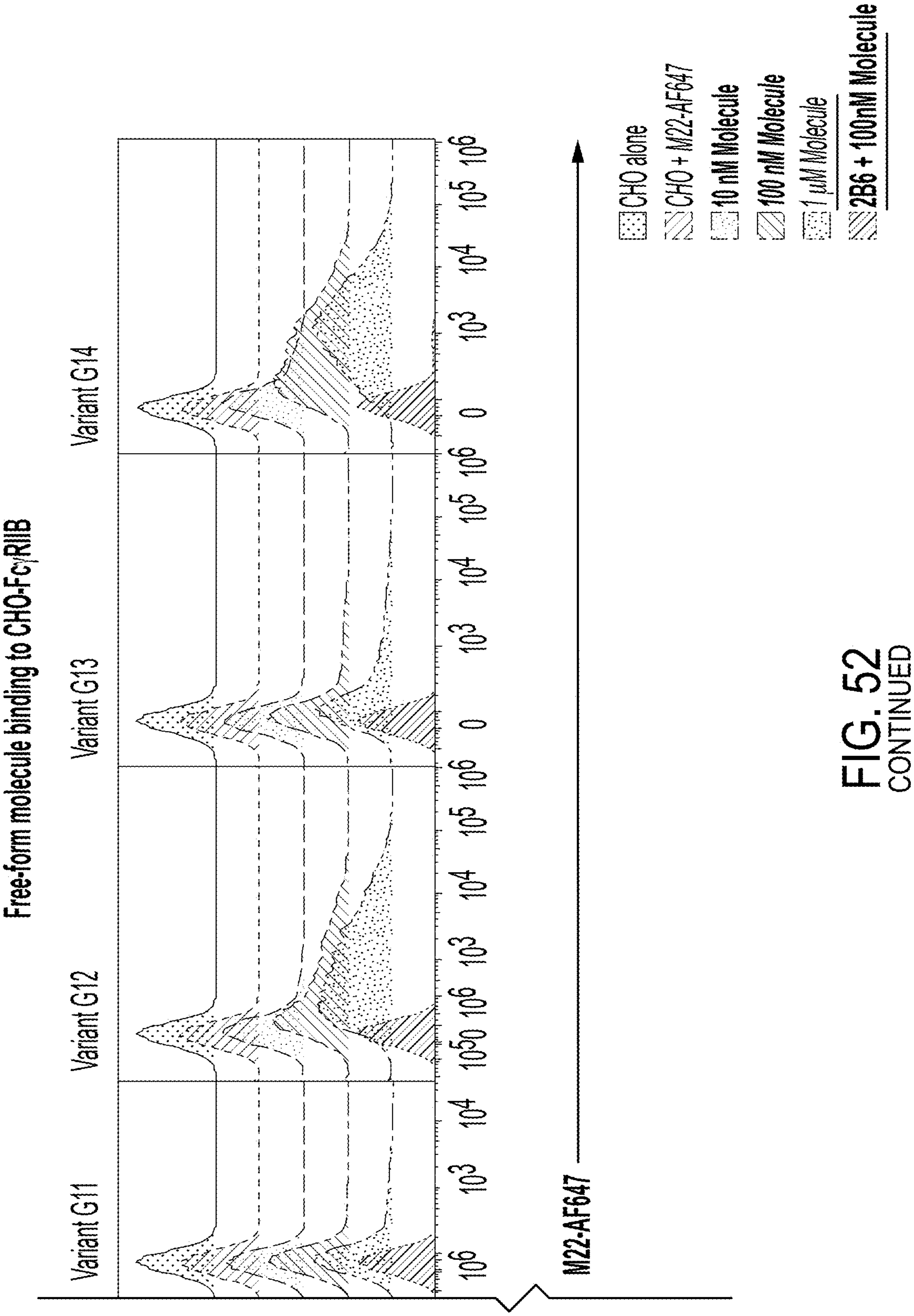

FIGS. 51-52 show that the Fc mutations in Variant G1, Variant G2, Variant G5, and Variant G11 result in comparable lack or very weak binding of free molecule to FcγRIIB compared to Variant D3, which binds weakly to FcγRIIB in free form at only the highest concentration tested (1 μM). In contrast, the Fc mutations in Variant G10, Variant G12, Variant G13, and Variant G14 lead to increased binding to FcγRIIB which is molecule concentration-dependent. Variant G14, specifically, exhibits a similar binding profile to FcγRIIB compared to Variant B3, which binds strongly to FcγRIIB in free form in a concentration-dependent manner. Binding of all molecules tested is shown to be dependent on FcγRIIB as assay signal is diminished upon pre-treatment with anti-FcγRIIB antibody clone 2B6. The Fc mutation D270E confers reduced binding affinity to FcγRIIB as observed in Variant G11 and Variant G13, relative to Variant G10 and Variant G12, respectively, which are the same molecules that do not contain said Fc mutation. These observations are consistent with surface plasmon resonance (SPR) results evaluating binding of the same molecules to FcγRIIB.

Figure 53:
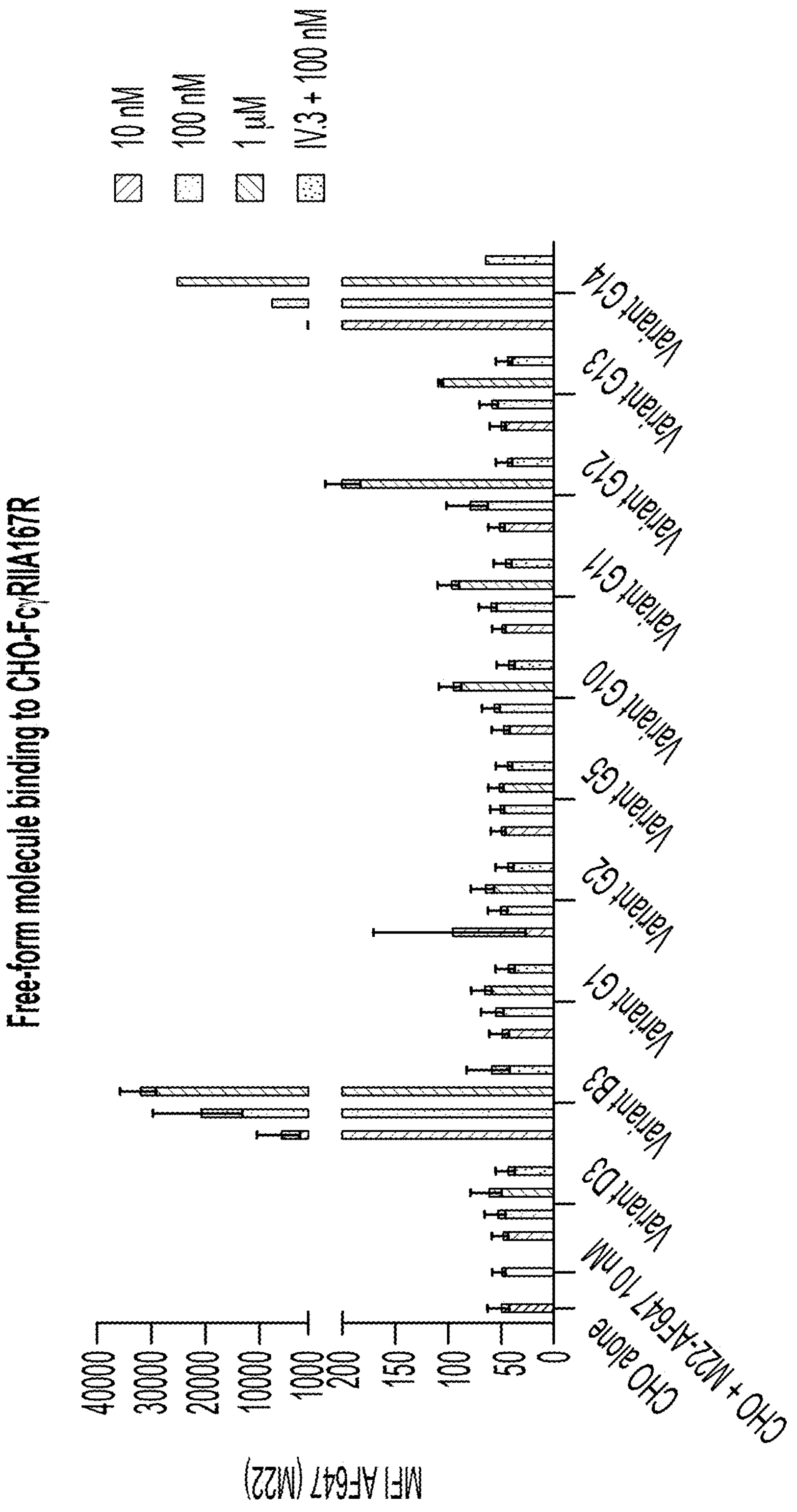
FIG. 53 shows a bar graph of mean fluorescence intensities (MFI) of Alexa Fluor 647-labeled M22 autoantibody detecting, by flow cytometry, binding of free molecules at increasing concentrations to FcγRIIA167R ectopically expressed in a genetically-engineered CHO-K1 cell line (CHO-FcγRIIA167R). Pre-treatment of CHO-FcγRIIA167R cells with anti-FcγRIIA blocking antibody clone IV.3 at 10 μg/mL was used to evaluate FcγRIIA-dependent binding of molecules. MFI values were calculated from live single cells. Each condition was assessed in singlicate. Data represent n=2 biological replicates and mean±s.d.
Figure 54:
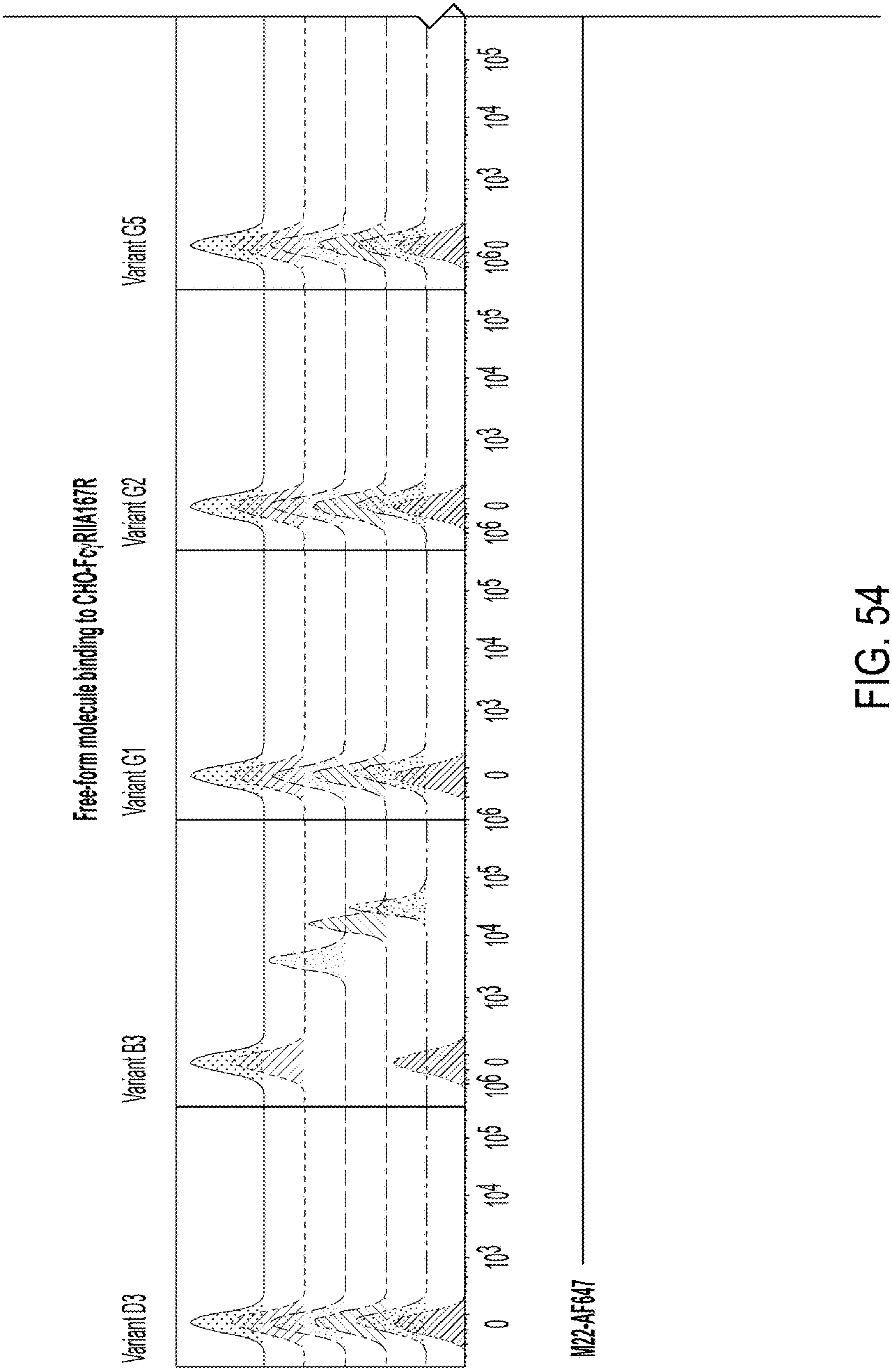
FIG. 54 shows flow cytometry half-offset histograms of Alexa Fluor 647-labeled M22 autoantibody fluorescence signal representing detection of free molecule binding at increasing concentrations to FcγRIIA167R ectopically expressed in a genetically-engineered CHO-K1 cell line (CHO-FcγRIIA167R). Pre-treatment of CHO-FcγRIIA167R cells with anti-FcγRIIA blocking antibody clone IV.3 at 10 μg/mL was used to evaluate FcγRIIA-dependent binding of molecules. Signal was calculated from live cell singlets. Representative data from 1 of two independent experiments.
Figure 54:
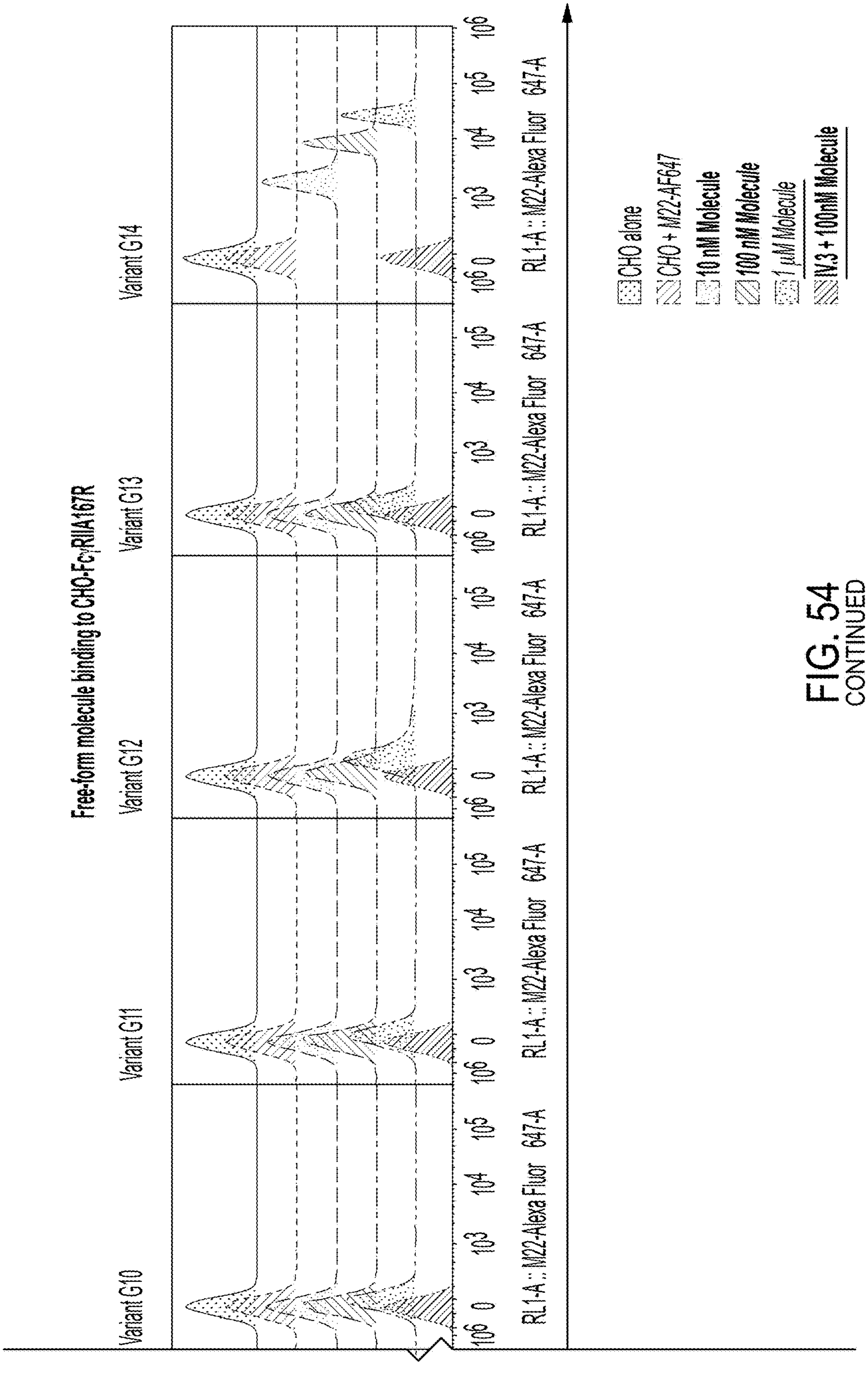

FIGS. 53-54 show that, similar to Variant D3, the Fc mutations in Variant G1, Variant G2, and Variant G5 result in lack of binding to FcγRIIA167R, while the Fc mutations in Variant G10, Variant G11, and Variant G13 demonstrate binding only at the highest concentration tested (1 μM). In contrast, the Fc mutations in Variant G12 and Variant G14 result in stronger, molecule concentration-dependent binding, which for Variant G14 is already detectable at the lowest concentration tested (10 nM). The binding profile of Variant G14 to FcγRIIA167R is similar to Variant B3, which binds strongly to FcγRIIA167R. Binding of all molecules tested is shown to be dependent on FcγRIIA167R as assay signal is diminished upon pre-treatment with anti-FcγRIIA antibody clone IV.3. The Fc mutation D270E confers reduced binding affinity to FcγRIIA167R in the context of Variant G13, relative to Variant G12 which contains the same mutations in the absence of D270E. These observations are consistent with surface plasmon resonance (SPR) results evaluating binding of the same molecules to FcγRIIA167R.

EQUIVALENTS

Those skilled in the art will recognize, or be able to ascertain using no more than routine experimentation, many equivalents to the specific embodiments described herein. The scope is not intended to be limited to the above description, but rather is as set forth in the following claims.

SEQUENCE LISTING

```
Sequence total quantity: 384
SEQ ID NO: 1            moltype = AA  length = 239
FEATURE                 Location/Qualifiers
source                  1..239
                        mol_type = protein
                        organism = synthetic construct
SEQUENCE: 1
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTL   239

SEQ ID NO: 2            moltype = AA  length = 239
FEATURE                 Location/Qualifiers
source                  1..239
                        mol_type = protein
                        organism = synthetic construct
SEQUENCE: 2
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTL   239

SEQ ID NO: 3            moltype = AA  length = 239
FEATURE                 Location/Qualifiers
source                  1..239
                        mol_type = protein
                        organism = synthetic construct
SEQUENCE: 3
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTL   239

SEQ ID NO: 4            moltype = AA  length = 239
FEATURE                 Location/Qualifiers
source                  1..239
                        mol_type = protein
                        organism = synthetic construct
SEQUENCE: 4
MGCSSPPCEC HQEEDFRVTC KDIQRIPSLP PSTQTLKLIE TSLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTL   239

SEQ ID NO: 5            moltype = AA  length = 268
FEATURE                 Location/Qualifiers
source                  1..268
                        mol_type = protein
                        organism = synthetic construct
SEQUENCE: 5
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLK  240
KLPLSLSFLH LTRADLSYPS HCCAFKNQ                                    268

SEQ ID NO: 6            moltype = AA  length = 268
FEATURE                 Location/Qualifiers
source                  1..268
                        mol_type = protein
                        organism = synthetic construct
SEQUENCE: 6
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLK  240
KLPLSLSFLH LTRADLSYPS HCCAFKNQ                                    268

SEQ ID NO: 7            moltype = AA  length = 268
FEATURE                 Location/Qualifiers
source                  1..268
                        mol_type = protein
                        organism = synthetic construct
SEQUENCE: 7
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
```

```
LDAVYLNKNK YLTVIDKDAF GGVYSGPSLL DVSQTSVTAL PSKGLEHLKE LRARNTWTLK  240
KLPLSLSFLH LTRADLSYPS HCCAFKNQ                                     268

SEQ ID NO: 8           moltype = AA  length = 268
FEATURE                Location/Qualifiers
source                 1..268
                       mol_type = protein
                       organism = synthetic construct
SEQUENCE: 8
MGCSSPPCEC HQEEDFRVTC KDIQRIPSLP PSTQTLKLIE TSLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLK  240
KLPLSLSFLH LTRADLSYPS HCCAFKNQ                                     268

SEQ ID NO: 9           moltype = AA  length = 764
FEATURE                Location/Qualifiers
source                 1..764
                       mol_type = protein
                       organism = synthetic construct
SEQUENCE: 9
MRPADLLQLV LLLDLPRDLG GMGCSSPPCE CHQEEDFRVT CKDIQRIPSL PPSTQTLKLI  60
ETHLRTIPSH AFSNLPNISR IYVSIDVTLQ QLESHSFYNL SKVTHIEIRN TRNLTYIDPD  120
ALKELPLLKF LGIFNTGLKM FPDLTKVYST DIFFILEITD NPYMTSIPVN AFQGLCNETL  180
TLKLYNNGFT SVQGYAFNGT KLDAVYLNKN KYLTVIDKDA FGGVYSGPSL LDVSQTSVTA  240
LPSKGLEHLK ELIARNTWTL KKLPLSLSFL HLTRADLSYP SHCCAFKNQK KIRGILESLM  300
CNESSMQSLR QRKSVNALNS PLHQEYEENL GDSIVGYKEK SKFQDTHNNA HYYVFFEEQE  360
DEIIGFGQEL KNPQEETLQA FDSHYDYTIC GDSEDMVCTP KSDEFNPCED IMGYKFLRIV  420
VWFVSLLALL GNVFVLLILL TSHYKLNVPR FLMCNLAFAD FCMGMYLLLI ASVDLYTHSE  480
YYNHAIDWQT GPGCNTAGFF TVFASELSVY TLTVITLERW YAITFAMRLD RKIRLRHACA  540
IMVGGWVCCF LLALLPLVGI SSYAKVSICL PMDTETPLAL AYIVFVLTLN IVAFVIVCCC  600
YVKIYITVRN PQYNPGDKDT KIAKRMAVLI FTDFICMAPI SFYALSAILN KPLITVSNSK  660
ILLVLFYPLN SCANPFLYAI FTKAFQRDVF ILLSKFGICK RQAQAYRGQR VPPKNSTDIQ  720
VQKVTHDMRQ GLHNMEDVYE LIENSHLTPK KQGQISEEYM QTVL                   764

SEQ ID NO: 10          moltype =   length =
SEQUENCE: 10
000

SEQ ID NO: 11          moltype =   length =
SEQUENCE: 11
000

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype =   length =
SEQUENCE: 15
000

SEQ ID NO: 16          moltype =   length =
SEQUENCE: 16
000

SEQ ID NO: 17          moltype =   length =
SEQUENCE: 17
000

SEQ ID NO: 18          moltype =   length =
SEQUENCE: 18
000

SEQ ID NO: 19          moltype =   length =
SEQUENCE: 19
000

SEQ ID NO: 20          moltype =   length =
SEQUENCE: 20
000
```

SEQ ID NO: 21 moltype = length =
SEQUENCE: 21
000

SEQ ID NO: 22 moltype = length =
SEQUENCE: 22
000

SEQ ID NO: 23 moltype = length =
SEQUENCE: 23
000

SEQ ID NO: 24 moltype = length =
SEQUENCE: 24
000

SEQ ID NO: 25 moltype = length =
SEQUENCE: 25
000

SEQ ID NO: 26 moltype = length =
SEQUENCE: 26
000

SEQ ID NO: 27 moltype = length =
SEQUENCE: 27
000

SEQ ID NO: 28 moltype = length =
SEQUENCE: 28
000

SEQ ID NO: 29 moltype = length =
SEQUENCE: 29
000

SEQ ID NO: 30 moltype = length =
SEQUENCE: 30
000

SEQ ID NO: 31 moltype = length =
SEQUENCE: 31
000

SEQ ID NO: 32 moltype = length =
SEQUENCE: 32
000

SEQ ID NO: 33 moltype = length =
SEQUENCE: 33
000

SEQ ID NO: 34 moltype = length =
SEQUENCE: 34
000

SEQ ID NO: 35 moltype = length =
SEQUENCE: 35
000

SEQ ID NO: 36 moltype = length =
SEQUENCE: 36
000

SEQ ID NO: 37 moltype = length =
SEQUENCE: 37
000

SEQ ID NO: 38 moltype = length =
SEQUENCE: 38
000

SEQ ID NO: 39 moltype = length =
SEQUENCE: 39
000

SEQ ID NO: 40 moltype = length =
SEQUENCE: 40
000

SEQ ID NO: 41 moltype = length =
SEQUENCE: 41
000

SEQ ID NO: 42 moltype = length =
SEQUENCE: 42
000

SEQ ID NO: 43 moltype = length =
SEQUENCE: 43
000

SEQ ID NO: 44 moltype = length =
SEQUENCE: 44
000

SEQ ID NO: 45 moltype = length =
SEQUENCE: 45
000

SEQ ID NO: 46 moltype = length =
SEQUENCE: 46
000

SEQ ID NO: 47 moltype = length =
SEQUENCE: 47
000

SEQ ID NO: 48 moltype = length =
SEQUENCE: 48
000

SEQ ID NO: 49 moltype = length =
SEQUENCE: 49
000

SEQ ID NO: 50 moltype = length =
SEQUENCE: 50
000

SEQ ID NO: 51 moltype = length =
SEQUENCE: 51
000

SEQ ID NO: 52 moltype = length =
SEQUENCE: 52
000

SEQ ID NO: 53 moltype = length =
SEQUENCE: 53
000

SEQ ID NO: 54 moltype = length =
SEQUENCE: 54
000

SEQ ID NO: 55 moltype = length =
SEQUENCE: 55
000

SEQ ID NO: 56 moltype = length =
SEQUENCE: 56
000

SEQ ID NO: 57 moltype = length =
SEQUENCE: 57
000

SEQ ID NO: 58 moltype = length =
SEQUENCE: 58
000

SEQ ID NO: 59 moltype = length =
SEQUENCE: 59
000

SEQ ID NO: 60 moltype = length =
SEQUENCE: 60

000

SEQ ID NO: 61 moltype = length =
SEQUENCE: 61
000

SEQ ID NO: 62 moltype = length =
SEQUENCE: 62
000

SEQ ID NO: 63 moltype = length =
SEQUENCE: 63
000

SEQ ID NO: 64 moltype = length =
SEQUENCE: 64
000

SEQ ID NO: 65 moltype = length =
SEQUENCE: 65
000

SEQ ID NO: 66 moltype = length =
SEQUENCE: 66
000

SEQ ID NO: 67 moltype = length =
SEQUENCE: 67
000

SEQ ID NO: 68 moltype = length =
SEQUENCE: 68
000

SEQ ID NO: 69 moltype = length =
SEQUENCE: 69
000

SEQ ID NO: 70 moltype = length =
SEQUENCE: 70
000

SEQ ID NO: 71 moltype = length =
SEQUENCE: 71
000

SEQ ID NO: 72 moltype = length =
SEQUENCE: 72
000

SEQ ID NO: 73 moltype = length =
SEQUENCE: 73
000

SEQ ID NO: 74 moltype = length =
SEQUENCE: 74
000

SEQ ID NO: 75 moltype = length =
SEQUENCE: 75
000

SEQ ID NO: 76 moltype = length =
SEQUENCE: 76
000

SEQ ID NO: 77 moltype = length =
SEQUENCE: 77
000

SEQ ID NO: 78 moltype = length =
SEQUENCE: 78
000

SEQ ID NO: 79 moltype = length =
SEQUENCE: 79
000

SEQ ID NO: 80 moltype = length =

SEQUENCE: 80
000

SEQ ID NO: 81 moltype = length =
SEQUENCE: 81
000

SEQ ID NO: 82 moltype = length =
SEQUENCE: 82
000

SEQ ID NO: 83 moltype = length =
SEQUENCE: 83
000

SEQ ID NO: 84 moltype = length =
SEQUENCE: 84
000

SEQ ID NO: 85 moltype = length =
SEQUENCE: 85
000

SEQ ID NO: 86 moltype = length =
SEQUENCE: 86
000

SEQ ID NO: 87 moltype = length =
SEQUENCE: 87
000

SEQ ID NO: 88 moltype = length =
SEQUENCE: 88
000

SEQ ID NO: 89 moltype = length =
SEQUENCE: 89
000

SEQ ID NO: 90 moltype = length =
SEQUENCE: 90
000

SEQ ID NO: 91 moltype = length =
SEQUENCE: 91
000

SEQ ID NO: 92 moltype = length =
SEQUENCE: 92
000

SEQ ID NO: 93 moltype = length =
SEQUENCE: 93
000

SEQ ID NO: 94 moltype = length =
SEQUENCE: 94
000

SEQ ID NO: 95 moltype = length =
SEQUENCE: 95
000

SEQ ID NO: 96 moltype = length =
SEQUENCE: 96
000

SEQ ID NO: 97 moltype = length =
SEQUENCE: 97
000

SEQ ID NO: 98 moltype = length =
SEQUENCE: 98
000

SEQ ID NO: 99 moltype = length =
SEQUENCE: 99
000

```
SEQ ID NO: 100         moltype =   length =
SEQUENCE: 100
000

SEQ ID NO: 101         moltype =   length =
SEQUENCE: 101
000

SEQ ID NO: 102         moltype =   length =
SEQUENCE: 102
000

SEQ ID NO: 103         moltype = AA  length = 227
FEATURE                Location/Qualifiers
source                 1..227
                       mol_type = protein
                       organism = synthetic construct
SEQUENCE: 103
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALKFHYTQKS LSLSPGK                227

SEQ ID NO: 104         moltype = AA  length = 227
FEATURE                Location/Qualifiers
source                 1..227
                       mol_type = protein
                       organism = synthetic construct
SEQUENCE: 104
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPGK                227

SEQ ID NO: 105         moltype = AA  length = 227
FEATURE                Location/Qualifiers
source                 1..227
                       mol_type = protein
                       organism = synthetic construct
SEQUENCE: 105
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVYT LPPCREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 106         moltype = AA  length = 227
FEATURE                Location/Qualifiers
source                 1..227
                       mol_type = protein
                       organism = synthetic construct
SEQUENCE: 106
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 107         moltype = AA  length = 227
FEATURE                Location/Qualifiers
source                 1..227
                       mol_type = protein
                       organism = synthetic construct
SEQUENCE: 107
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 108         moltype = AA  length = 227
FEATURE                Location/Qualifiers
source                 1..227
                       mol_type = protein
                       organism = synthetic construct
SEQUENCE: 108
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 109         moltype = AA  length = 227
```

```
FEATURE                 Location/Qualifiers
source                  1..227
                        mol_type = protein
                        organism = synthetic construct
SEQUENCE: 109
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVLHE ALHSHYTQKS LSLSPGK               227

SEQ ID NO: 110          moltype = AA  length = 227
FEATURE                 Location/Qualifiers
source                  1..227
                        mol_type = protein
                        organism = synthetic construct
SEQUENCE: 110
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVLHE ALHSHYTQKS LSLSPGK               227

SEQ ID NO: 111          moltype = AA  length = 227
FEATURE                 Location/Qualifiers
source                  1..227
                        mol_type = protein
                        organism = synthetic construct
SEQUENCE: 111
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 112          moltype = AA  length = 227
FEATURE                 Location/Qualifiers
source                  1..227
                        mol_type = protein
                        organism = synthetic construct
SEQUENCE: 112
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALKFHYTQKS LSLSPGK               227

SEQ ID NO: 113          moltype = AA  length = 227
FEATURE                 Location/Qualifiers
source                  1..227
                        mol_type = protein
                        organism = synthetic construct
SEQUENCE: 113
DKTHTCPPCP APVDFRDPLV FLFPPKPKDT LMISRTPEVT CVVVDVDPED PEVKFNWYVD  60
GVEVHNAKTK PREEQYNGAY RVVSVLTVLH QDWLNGKEYK CKVSNKLAPH PIIKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 114          moltype = AA  length = 227
FEATURE                 Location/Qualifiers
source                  1..227
                        mol_type = protein
                        organism = synthetic construct
SEQUENCE: 114
DKTHTCPPCP APVDFRDPLV FLFPPKPKDT LMISRTPEVT CVVVDVDPED PEVKFNWYVD  60
GVEVHNAKTK PREEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 115          moltype = AA  length = 227
FEATURE                 Location/Qualifiers
source                  1..227
                        mol_type = protein
                        organism = synthetic construct
SEQUENCE: 115
DKTHTCPPCP APVDFRDPLV FLFPPKPKDT LMISRTPEVT CVVVDVDPED PEVKFNWYVD  60
GVEVHNAKTK PQEEQYNGAY RVVSVLTVLH QDWLNGKEYK CKVSNKLAPH PIIKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 116          moltype = AA  length = 227
FEATURE                 Location/Qualifiers
source                  1..227
```

```
                        mol_type = protein
                        organism = synthetic construct
SEQUENCE: 116
DKTHTCPPCP APVDFRDPLV FLFPPKPKDT LMISRTPEVT CVVVDVDPED PEVKFNWYVD  60
GVEVHNAKTK PQEEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 117          moltype = AA  length = 227
FEATURE                 Location/Qualifiers
source                  1..227
                        mol_type = protein
                        organism = synthetic construct
SEQUENCE: 117
DKTHTCPPCP APVDFRDPLV FLFPPKPKDT LMISRTPEVT CVVVDVSPED PEVKFNWYVD  60
GVEVHNAKTK PQEEQYNGAY RVVSVLTVLH QDWLNGKEYK CKVSNKLAPH PIIKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 118          moltype = AA  length = 227
FEATURE                 Location/Qualifiers
source                  1..227
                        mol_type = protein
                        organism = synthetic construct
SEQUENCE: 118
DKTHTCPPCP APVDFRDPLV FLFPPKPKDT LMISRTPEVT CVVVDVSPED PEVKFNWYVD  60
GVEVHNAKTK PQEEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 119          moltype = AA  length = 227
FEATURE                 Location/Qualifiers
source                  1..227
                        mol_type = protein
                        organism = synthetic construct
SEQUENCE: 119
DKTHTCPPCP APEYLGGDSV FLFPPKPKDV LMISRTPEVT CVVIDVSHED PEVKFNWYVD  60
GVEVHNAKTK PREEQYNSTY RVVSVLPVLH RDWLNGKEYK CKVSNKALPK PIEKTISKAK  120
GQRREPQVYT LPPCREEMTK NQVSLWCLVK GFYPSDIAVE WESNGQPENN YKTTPPVLDS  180
DGSFFLYSKL TVDKSRWQQG NVFSCSVLHE ALHAHTTRKE LSLSPGK                227

SEQ ID NO: 120          moltype = AA  length = 227
FEATURE                 Location/Qualifiers
source                  1..227
                        mol_type = protein
                        organism = synthetic construct
SEQUENCE: 120
DKTHTCPPCP APEYLGGDSV FLFPPKPKDV LMISRTPEVT CVVIDVSHED PEVKFNWYVD  60
GVEVHNAKTK PREEQYNSTY RVVSVLPVLH RDWLNGKEYK CKVSNKALPK PIEKTISKAK  120
GQRREPQVCT LPPSREEMTK NQVSLSCAVK GFYPSDIAVE WESNGQPENN YKTTPPVLDS  180
DGSFFLVSKL TVDKSRWQQG NVFSCSVLHE ALHAHTTRKE LSLSPGK                227

SEQ ID NO: 121          moltype = AA  length = 227
FEATURE                 Location/Qualifiers
source                  1..227
                        mol_type = protein
                        organism = synthetic construct
SEQUENCE: 121
DKTHTCPPCP APEDLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 122          moltype = AA  length = 227
FEATURE                 Location/Qualifiers
source                  1..227
                        mol_type = protein
                        organism = synthetic construct
SEQUENCE: 122
DKTHTCPPCP APEDLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 123          moltype = AA  length = 227
FEATURE                 Location/Qualifiers
source                  1..227
                        mol_type = protein
                        organism = synthetic construct
```

```
SEQUENCE: 123
DKTHTCPPCP APELRGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 124          moltype = AA  length = 227
FEATURE                 Location/Qualifiers
source                  1..227
                        mol_type = protein
                        organism = synthetic construct
SEQUENCE: 124
DKTHTCPPCP APELRGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 125          moltype = AA  length = 227
FEATURE                 Location/Qualifiers
source                  1..227
                        mol_type = protein
                        organism = synthetic construct
SEQUENCE: 125
DKTHTCPPCP APELLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 126          moltype = AA  length = 227
FEATURE                 Location/Qualifiers
source                  1..227
                        mol_type = protein
                        organism = synthetic construct
SEQUENCE: 126
DKTHTCPPCP APELLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 127          moltype = AA  length = 227
FEATURE                 Location/Qualifiers
source                  1..227
                        mol_type = protein
                        organism = synthetic construct
SEQUENCE: 127
DKTHTCPPCP APELLGGDSV FLFPPKPKDT LMISRTPEVT CVVVDVSHEE PEVKFNWYVD  60
GVEVHNAKTK PREEQYNSTY RVVSVLTVLH QDWLNGKEYK CKVSNKALPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 128          moltype = AA  length = 227
FEATURE                 Location/Qualifiers
source                  1..227
                        mol_type = protein
                        organism = synthetic construct
SEQUENCE: 128
DKTHTCPPCP APELLGGDSV FLFPPKPKDT LMISRTPEVT CVVVDVSHEE PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 129          moltype = AA  length = 227
FEATURE                 Location/Qualifiers
source                  1..227
                        mol_type = protein
                        organism = synthetic construct
SEQUENCE: 129
DKTHTCPPCP APELLGGDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPA PIEKTISKAK  120
GQPREPQVYT LPPCREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 130          moltype = AA  length = 227
FEATURE                 Location/Qualifiers
source                  1..227
                        mol_type = protein
                        organism = synthetic construct
SEQUENCE: 130
DKTHTCPPCP APELLGGDSV FLFPPKPKDT LMISRTPEVT CVVVDVSHED GEVKFNWYVD  60
```

```
GVEVHNAKTK PREEQYNSTY RVVSVLTVLH QDWLNGKEYK CKVSNKALPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 131         moltype = AA  length = 227
FEATURE                Location/Qualifiers
source                 1..227
                       mol_type = protein
                       organism = synthetic construct
SEQUENCE: 131
DKTHTCPPCP APELLGGDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPA PIEKTISKAK  120
GQPREPQVYT LPPCREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 132         moltype = AA  length = 227
FEATURE                Location/Qualifiers
source                 1..227
                       mol_type = protein
                       organism = synthetic construct
SEQUENCE: 132
DKTHTCPPCP APELLGGDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 133         moltype = AA  length = 227
FEATURE                Location/Qualifiers
source                 1..227
                       mol_type = protein
                       organism = synthetic construct
SEQUENCE: 133
DKTHTCPPCP APELLGDDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPR PIEKTISKAK  120
GQPREPQVYT LPPCREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 134         moltype = AA  length = 227
FEATURE                Location/Qualifiers
source                 1..227
                       mol_type = protein
                       organism = synthetic construct
SEQUENCE: 134
DKTHTCPPCP APELLGDDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPR PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 135         moltype = AA  length = 227
FEATURE                Location/Qualifiers
source                 1..227
                       mol_type = protein
                       organism = synthetic construct
SEQUENCE: 135
DKTHTCPPCP APELLGDDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPR PIEKTISKAK  120
GQPREPQVYT LPPCREEMTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 136         moltype = AA  length = 227
FEATURE                Location/Qualifiers
source                 1..227
                       mol_type = protein
                       organism = synthetic construct
SEQUENCE: 136
DKTHTCPPCP APELLGDDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPR PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 137         moltype = AA  length = 227
FEATURE                Location/Qualifiers
source                 1..227
                       mol_type = protein
                       organism = synthetic construct
SEQUENCE: 137
DKTHTCPPCP APDLLGDDSV FLFPPKPKDT LMISRTPEVT CVVVDVSDED GEVKFNWYVD  60
GVEVHNAKTK PREEQYNSTY RVVSVLTVLH QDWLNGKEYK CKVSNKALPR PIEKTISKAK  120
GQPREPQVYT LPPCRDELTK NQVSLWCLVK GFYPSDIAVE WESNGQPENN YKTTPPVLDS  180
```

```
DGSFFLYSKL TVDKSRWQQG NVFSCSVMHE ALHNHYTQKS LSLSPGK              227

SEQ ID NO: 138         moltype = AA  length = 227
FEATURE                Location/Qualifiers
source                 1..227
                       mol_type = protein
                       organism = synthetic construct
SEQUENCE: 138
DKTHTCPPCP APDLLGDDSV FLFPPKPKDT LMISRTPEVT CVVVDVSDED GEVKFNWYVD  60
GVEVHNAKTK PREEQYNSTY RVVSVLTVLH QDWLNGKEYK CKVSNKALPR PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK              227

SEQ ID NO: 139         moltype = AA  length = 227
FEATURE                Location/Qualifiers
source                 1..227
                       mol_type = protein
                       organism = synthetic construct
SEQUENCE: 139
DKTHTCPPCP APVDFRDPLV FLFPPKPKDT LMISRTPEVT CVVVDVDPED PEVKFNWYVD  60
GVEVHNAKTK PREEQYNGAY RVVSVLTVLH QDWLNGKEYK CKVSNKLAPH PIIKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 140         moltype = AA  length = 227
FEATURE                Location/Qualifiers
source                 1..227
                       mol_type = protein
                       organism = synthetic construct
SEQUENCE: 140
DKTHTCPPCP APVDFRDPLV FLFPPKPKDT LMISRTPEVT CVVVDVDPED PEVKFNWYVD  60
GVEVHNAKTK PQEEQYNGAY RVVSVLTVLH QDWLNGKEYK CKVSNKLAPH PIIKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 141         moltype = AA  length = 227
FEATURE                Location/Qualifiers
source                 1..227
                       mol_type = protein
                       organism = synthetic construct
SEQUENCE: 141
DKTHTCPPCP APVDFRDPLV FLFPPKPKDT LMISRTPEVT CVVVDVSPED PEVKFNWYVD  60
GVEVHNAKTK PQEEQYNGAY RVVSVLTVLH QDWLNGKEYK CKVSNKLAPH PIIKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 142         moltype = AA  length = 227
FEATURE                Location/Qualifiers
source                 1..227
                       mol_type = protein
                       organism = synthetic construct
SEQUENCE: 142
DKTHTCPPCP APEYLGGDSV FLFPPKPKDV LMISRTPEVT CVVIDVSHED PEVKFNWYVD  60
GVEVHNAKTK PREEQYNSTY RVVSVLPVLH RDWLNGKEYK CKVSNKALPK PIEKTISKAK  120
GQRREPQVYT LPPSREEMTK NQVSLTCLVK GFYPSDIAVE WESNGQPENN YKTTPPVLDS  180
DGSFFLYSKL TVDKSRWQQG NVFSCSVLHE ALHAHTTRKE LSLSPGK              227

SEQ ID NO: 143         moltype = AA  length = 227
FEATURE                Location/Qualifiers
source                 1..227
                       mol_type = protein
                       organism = synthetic construct
SEQUENCE: 143
DKTHTCPPCP APEDLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227

SEQ ID NO: 144         moltype = AA  length = 227
FEATURE                Location/Qualifiers
source                 1..227
                       mol_type = protein
                       organism = synthetic construct
SEQUENCE: 144
DKTHTCPPCP APELRGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK              227
```

```
SEQ ID NO: 145          moltype = AA  length = 227
FEATURE                 Location/Qualifiers
source                  1..227
                        mol_type = protein
                        organism = synthetic construct
SEQUENCE: 145
DKTHTCPPCP APELLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 146          moltype = AA  length = 227
FEATURE                 Location/Qualifiers
source                  1..227
                        mol_type = protein
                        organism = synthetic construct
SEQUENCE: 146
DKTHTCPPCP APELLGGDSV FLFPPKPKDT LMISRTPEVT CVVVDVSHEE PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 147          moltype = AA  length = 227
FEATURE                 Location/Qualifiers
source                  1..227
                        mol_type = protein
                        organism = synthetic construct
SEQUENCE: 147
DKTHTCPPCP APELLGGDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 148          moltype = AA  length = 227
FEATURE                 Location/Qualifiers
source                  1..227
                        mol_type = protein
                        organism = synthetic construct
SEQUENCE: 148
DKTHTCPPCP APELLGGDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 149          moltype = AA  length = 227
FEATURE                 Location/Qualifiers
source                  1..227
                        mol_type = protein
                        organism = synthetic construct
SEQUENCE: 149
DKTHTCPPCP APELLGDDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPR PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 150          moltype = AA  length = 5
FEATURE                 Location/Qualifiers
source                  1..5
                        mol_type = protein
                        organism = synthetic construct
SEQUENCE: 150
GGGGS                                                              5

SEQ ID NO: 151          moltype = AA  length = 10
FEATURE                 Location/Qualifiers
source                  1..10
                        mol_type = protein
                        organism = synthetic construct
SEQUENCE: 151
GGGGSGGGGS                                                         10

SEQ ID NO: 152          moltype = AA  length = 15
FEATURE                 Location/Qualifiers
source                  1..15
                        mol_type = protein
                        organism = synthetic construct
SEQUENCE: 152
GGGGSGGGGS GGGGS                                                   15
```

```
SEQ ID NO: 153          moltype = AA  length = 18
FEATURE                 Location/Qualifiers
source                  1..18
                        mol_type = protein
                        organism = synthetic construct
SEQUENCE: 153
VDGGGGSGGG GSGGGGSG                                                18

SEQ ID NO: 154          moltype = AA  length = 20
FEATURE                 Location/Qualifiers
source                  1..20
                        mol_type = protein
                        organism = synthetic construct
SEQUENCE: 154
GGGGSGGGGS GGGGSGGGGS                                              20

SEQ ID NO: 155          moltype = AA  length = 26
FEATURE                 Location/Qualifiers
source                  1..26
                        mol_type = protein
                        organism = synthetic construct
SEQUENCE: 155
GGGGSGGGGS GGGGSGGGGS SGGGGS                                       26

SEQ ID NO: 156          moltype = AA  length = 5
FEATURE                 Location/Qualifiers
source                  1..5
                        mol_type = protein
                        organism = synthetic construct
SEQUENCE: 156
GSGGS                                                              5

SEQ ID NO: 157          moltype = AA  length = 4
FEATURE                 Location/Qualifiers
source                  1..4
                        mol_type = protein
                        organism = synthetic construct
SEQUENCE: 157
GGSG                                                               4

SEQ ID NO: 158          moltype = AA  length = 5
FEATURE                 Location/Qualifiers
source                  1..5
                        mol_type = protein
                        organism = synthetic construct
SEQUENCE: 158
GGSGG                                                              5

SEQ ID NO: 159          moltype = AA  length = 5
FEATURE                 Location/Qualifiers
source                  1..5
                        mol_type = protein
                        organism = synthetic construct
SEQUENCE: 159
GSGSG                                                              5

SEQ ID NO: 160          moltype = AA  length = 5
FEATURE                 Location/Qualifiers
source                  1..5
                        mol_type = protein
                        organism = synthetic construct
SEQUENCE: 160
GSGGG                                                              5

SEQ ID NO: 161          moltype = AA  length = 5
FEATURE                 Location/Qualifiers
source                  1..5
                        mol_type = protein
                        organism = synthetic construct
SEQUENCE: 161
GGGSG                                                              5

SEQ ID NO: 162          moltype = AA  length = 5
FEATURE                 Location/Qualifiers
source                  1..5
                        mol_type = protein
                        organism = synthetic construct
SEQUENCE: 162
GSSSG                                                              5
```

```
SEQ ID NO: 163          moltype = AA  length = 227
FEATURE                 Location/Qualifiers
source                  1..227
                        mol_type = protein
                        organism = synthetic construct
SEQUENCE: 163
DKTHTCPPCP APELLGGDDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPR PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 164          moltype = AA  length = 227
FEATURE                 Location/Qualifiers
source                  1..227
                        mol_type = protein
                        organism = synthetic construct
SEQUENCE: 164
DKTHTCPPCP APDLLGGDDSV FLFPPKPKDT LMISRTPEVT CVVVDVSDED GEVKFNWYVD  60
GVEVHNAKTK PREEQYNSTY RVVSVLTVLH QDWLNGKEYK CKVSNKALPR PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 165          moltype =   length =
SEQUENCE: 165
000

SEQ ID NO: 166          moltype =   length =
SEQUENCE: 166
000

SEQ ID NO: 167          moltype =   length =
SEQUENCE: 167
000

SEQ ID NO: 168          moltype =   length =
SEQUENCE: 168
000

SEQ ID NO: 169          moltype =   length =
SEQUENCE: 169
000

SEQ ID NO: 170          moltype =   length =
SEQUENCE: 170
000

SEQ ID NO: 171          moltype =   length =
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype =   length =
SEQUENCE: 174
000

SEQ ID NO: 175          moltype =   length =
SEQUENCE: 175
000

SEQ ID NO: 176          moltype =   length =
SEQUENCE: 176
000

SEQ ID NO: 177          moltype =   length =
SEQUENCE: 177
000

SEQ ID NO: 178          moltype =   length =
SEQUENCE: 178
000
```

SEQ ID NO: 179 moltype = length =
SEQUENCE: 179
000

SEQ ID NO: 180 moltype = length =
SEQUENCE: 180
000

SEQ ID NO: 181 moltype = length =
SEQUENCE: 181
000

SEQ ID NO: 182 moltype = length =
SEQUENCE: 182
000

SEQ ID NO: 183 moltype = length =
SEQUENCE: 183
000

SEQ ID NO: 184 moltype = length =
SEQUENCE: 184
000

SEQ ID NO: 185 moltype = length =
SEQUENCE: 185
000

SEQ ID NO: 186 moltype = length =
SEQUENCE: 186
000

SEQ ID NO: 187 moltype = length =
SEQUENCE: 187
000

SEQ ID NO: 188 moltype = length =
SEQUENCE: 188
000

SEQ ID NO: 189 moltype = length =
SEQUENCE: 189
000

SEQ ID NO: 190 moltype = length =
SEQUENCE: 190
000

SEQ ID NO: 191 moltype = length =
SEQUENCE: 191
000

SEQ ID NO: 192 moltype = length =
SEQUENCE: 192
000

SEQ ID NO: 193 moltype = length =
SEQUENCE: 193
000

SEQ ID NO: 194 moltype = length =
SEQUENCE: 194
000

SEQ ID NO: 195 moltype = length =
SEQUENCE: 195
000

SEQ ID NO: 196 moltype = length =
SEQUENCE: 196
000

SEQ ID NO: 197 moltype = length =
SEQUENCE: 197
000

SEQ ID NO: 198 moltype = length =
SEQUENCE: 198
000

```
SEQ ID NO: 199          moltype =   length =
SEQUENCE: 199
000

SEQ ID NO: 200          moltype =   length =
SEQUENCE: 200
000

SEQ ID NO: 201          moltype =   length =
SEQUENCE: 201
000

SEQ ID NO: 202          moltype =   length =
SEQUENCE: 202
000

SEQ ID NO: 203          moltype =   length =
SEQUENCE: 203
000

SEQ ID NO: 204          moltype =   length =
SEQUENCE: 204
000

SEQ ID NO: 205          moltype =   length =
SEQUENCE: 205
000

SEQ ID NO: 206          moltype =   length =
SEQUENCE: 206
000

SEQ ID NO: 207          moltype =   length =
SEQUENCE: 207
000

SEQ ID NO: 208          moltype =   length =
SEQUENCE: 208
000

SEQ ID NO: 209          moltype = AA  length = 223
FEATURE                 Location/Qualifiers
source                  1..223
                        mol_type = protein
                        organism = synthetic construct
SEQUENCE: 209
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKDF SSRRWYLEYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSC                   223

SEQ ID NO: 210          moltype = AA  length = 215
FEATURE                 Location/Qualifiers
source                  1..215
                        mol_type = protein
                        organism = synthetic construct
SEQUENCE: 210
SSELTQDPAV SVALGQTVRI TCQGDSLRSY YASWYQQKPG QAPVLVIYGK NNRPSGIPDR  60
FSGSSSGNTA SLTITGAQAE DEADYYCNSL ERIGYLSYVF GGGTKLTVLG QPKANPTVTL  120
FPPSSEELQA NKATLVCLIS DFYPGAVTVA WKADGSPVKA GVETTKPSKQ SNNKYAASSY  180
LSLTPEQWKS HRSYSCQVTH EGSTVEKTVA PTECS                            215

SEQ ID NO: 211          moltype = AA  length = 485
FEATURE                 Location/Qualifiers
source                  1..485
                        mol_type = protein
                        organism = synthetic construct
SEQUENCE: 211
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTR NLTYIDPDAL  120
KELPLLKFLG IFNTGLKMFP DLTKVYSTDI FFILEITDNP YMTSIPVNAF QGLCNETLTL  180
KLYNNGFTSV QGYAFNGTKL DAVYLNKNKY LTVIDKDAFG GVYSGPSLLD VSQTSVTALP  240
SKGLEHLKEL IARNTWTLDK THTCPPCPAP ELLRGPSVFL FPPKPKDTLY ITREPEVTCV  300
VVDVSHEDPE VKFNWYVDGV EVHNAKTKPR EEQYNSTYRV VSVLTVLHQD WLNGKEYKCK  360
VSNKARPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL KFHYTQKSLS  480
LSPGK                                                             485
```

```
SEQ ID NO: 212          moltype = AA  length = 485
FEATURE                 Location/Qualifiers
source                  1..485
                        mol_type = protein
                        organism = synthetic construct
SEQUENCE: 212
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLRGPSVFL FPPKPKDTLY ITREPEVTCV  300
VVDVSHEDPE VKFNWYVDGV EVHNAKTKPR EEQYNSTYRV VSVLTVLHQD WLNGKEYKCK  360
VSNKARPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL KFHYTQKSLS  480
LSPGK                                                              485

SEQ ID NO: 213          moltype = AA  length = 485
FEATURE                 Location/Qualifiers
source                  1..485
                        mol_type = protein
                        organism = synthetic construct
SEQUENCE: 213
MGWSCIILFL VATATGVHSM GCSSPPCECH QEEDFRVTCK DIQRIPSLPP STQTLKLIET  60
SLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPVNAF QGLCNETLTL  180
KLYNNGFTSV QGYAFNGTKL DAVYLNKNKY LTVIDKDAFG GVYSGPSLLD VSQTSVTALP  240
SKGLEHLKEL IARNTWTLDK THTCPPCPAP ELLRGPSVFL FPPKPKDTLY ITREPEVTCV  300
VVDVSHEDPE VKFNWYVDGV EVHNAKTKPR EEQYNSTYRV VSVLTVLHQD WLNGKEYKCK  360
VSNKARPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL KFHYTQKSLS  480
LSPGK                                                              485

SEQ ID NO: 214          moltype = AA  length = 485
FEATURE                 Location/Qualifiers
source                  1..485
                        mol_type = protein
                        organism = synthetic construct
SEQUENCE: 214
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTR NLTYIDPDAL  120
KELPLLKFLG IFNTGLKMFP DLTKVYSTDI FFILEITDNP YMTSIPVNAF QGLCNETLTL  180
KLYNNGFTSV QGYAFNGTKL DAVYLNKNKY LTVIDKDAFG GVYSGPSLLD VSQTSVTALP  240
SKGLEHLKEL IARNTWTLDK THTCPPCPAP ELLGGPSVFL FPPKPKDTLM ISRTPEVTCV  300
VVDVEHEDPE VKFNWYVDGV EVHNAKTKPR EEQYNSTYRV VSVLTVLHQD WLNGKEYKCK  360
VSNKAFPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 215          moltype = AA  length = 485
FEATURE                 Location/Qualifiers
source                  1..485
                        mol_type = protein
                        organism = synthetic construct
SEQUENCE: 215
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPVNAF QGLCNETLTL  180
KLYNNGFTSV QGYAFNGTKL DAVYLNKNKY LTVIDKDAFG GVYSGPSLLD VSQTSVTALP  240
SKGLEHLKEL IARNTWTLDK THTCPPCPAP ELLGGPSVFL FPPKPKDTLM ISRTPEVTCV  300
VVDVEHEDPE VKFNWYVDGV EVHNAKTKPR EEQYNSTYRV VSVLTVLHQD WLNGKEYKCK  360
VSNKAFPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 216          moltype = AA  length = 485
FEATURE                 Location/Qualifiers
source                  1..485
                        mol_type = protein
                        organism = synthetic construct
SEQUENCE: 216
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGPSVFL FPPKPKDTLM ISRTPEVTCV  300
VVDVEHEDPE VKFNWYVDGV EVHNAKTKPR EEQYNSTYRV VSVLTVLHQD WLNGKEYKCK  360
VSNKAFPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485
```

```
SEQ ID NO: 217          moltype = AA  length = 485
FEATURE                 Location/Qualifiers
source                  1..485
                        mol_type = protein
                        organism = synthetic construct
SEQUENCE: 217
MGWSCIILFL VATATGVHSM GCSSPPCECH QEEDFRVTCK DIQRIPSLPP STQTLKLIET  60
SLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPVNAF QGLCNETLTL  180
KLYNNGFTSV QGYAFNGTKL DAVYLNKNKY LTVIDKDAFG GVYSGPSLLD VSQTSVTALP  240
SKGLEHLKEL IARNTWTLDK THTCPPCPAP ELLGGPSVFL FPPKPKDTLM ISRTPEVTCV  300
VVDVEHEDPE VKFNWYVDGV EVHNAKTKPR EEQYNSTYRV VSVLTVLHQD WLNGKEYKCK  360
VSNKAFPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 218          moltype = AA  length = 246
FEATURE                 Location/Qualifiers
source                  1..246
                        mol_type = protein
                        organism = synthetic construct
SEQUENCE: 218
MGWSLILLFL VAVATRVLSD KTHTCPPCPA PELLRGPSVF LFPPKPKDTL YITREPEVTC  60
VVVDVSHEDP EVKFNWYVDG VEVHNAKTKP REEQYNSTYR VVSVLTVLHQ DWLNGKEYKC  120
KVSNKARPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LKFHYTQKSL  240
SLSPGK                                                            246

SEQ ID NO: 219          moltype = AA  length = 246
FEATURE                 Location/Qualifiers
source                  1..246
                        mol_type = protein
                        organism = synthetic construct
SEQUENCE: 219
MGWSLILLFL VAVATRVLSD KTHTCPPCPA PELLRGPSVF LFPPKPKDTL YITREPEVTC  60
VVVDVSHEDP EVKFNWYVDG VEVHNAKTKP REEQYNSTYR VVSVLTVLHQ DWLNGKEYKC  120
KVSNKARPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LKFHYTQKSL  240
SLSPGK                                                            246

SEQ ID NO: 220          moltype = AA  length = 246
FEATURE                 Location/Qualifiers
source                  1..246
                        mol_type = protein
                        organism = synthetic construct
SEQUENCE: 220
MGWSLILLFL VAVATRVLSD KTHTCPPCPA PELLRGPSVF LFPPKPKDTL YITREPEVTC  60
VVVDVSHEDP EVKFNWYVDG VEVHNAKTKP REEQYNSTYR VVSVLTVLHQ DWLNGKEYKC  120
KVSNKARPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LKFHYTQKSL  240
SLSPGK                                                            246

SEQ ID NO: 221          moltype = AA  length = 246
FEATURE                 Location/Qualifiers
source                  1..246
                        mol_type = protein
                        organism = synthetic construct
SEQUENCE: 221
MGWSLILLFL VAVATRVLSD KTHTCPPCPA PELLGGPSVF LFPPKPKDTL MISRTPEVTC  60
VVVDVEHEDP EVKFNWYVDG VEVHNAKTKP REEQYNSTYR VVSVLTVLHQ DWLNGKEYKC  120
KVSNKAFPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 222          moltype = AA  length = 246
FEATURE                 Location/Qualifiers
source                  1..246
                        mol_type = protein
                        organism = synthetic construct
SEQUENCE: 222
MGWSLILLFL VAVATRVLSD KTHTCPPCPA PELLGGPSVF LFPPKPKDTL MISRTPEVTC  60
VVVDVEHEDP EVKFNWYVDG VEVHNAKTKP REEQYNSTYR VVSVLTVLHQ DWLNGKEYKC  120
KVSNKAFPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 223          moltype = AA  length = 246
FEATURE                 Location/Qualifiers
```

```
source                  1..246
                        mol_type = protein
                        organism = synthetic construct
SEQUENCE: 223
MGWSLILLFL VAVATRVLSD KTHTCPPCPA PELLGGPSVF LFPPKPKDTL MISRTPEVTC  60
VVVDVEHEDP EVKFNWYVDG VEVHNAKTKP REEQYNSTYR VVSVLTVLHQ DWLNGKEYKC  120
KVSNKAFPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                             246

SEQ ID NO: 224          moltype = AA  length = 246
FEATURE                 Location/Qualifiers
source                  1..246
                        mol_type = protein
                        organism = synthetic construct
SEQUENCE: 224
MGWSLILLFL VAVATRVLSD KTHTCPPCPA PELLGGPSVF LFPPKPKDTL MISRTPEVTC  60
VVVDVEHEDP EVKFNWYVDG VEVHNAKTKP REEQYNSTYR VVSVLTVLHQ DWLNGKEYKC  120
KVSNKAFPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                             246

SEQ ID NO: 225          moltype = AA  length = 485
FEATURE                 Location/Qualifiers
source                  1..485
                        mol_type = protein
                        organism = synthetic construct
SEQUENCE: 225
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGDSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 226          moltype = AA  length = 485
FEATURE                 Location/Qualifiers
source                  1..485
                        mol_type = protein
                        organism = synthetic construct
SEQUENCE: 226
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGDSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVLHEAL HSHYTQKSLS  480
LSPGK                                                              485

SEQ ID NO: 227          moltype = AA  length = 485
FEATURE                 Location/Qualifiers
source                  1..485
                        mol_type = protein
                        organism = synthetic construct
SEQUENCE: 227
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGPSVFL FPPKPKDTLM ISRTPEVTCV  300
VVDVSHEDPE VKFNWYVDGV EVHNAKTKPR EEQYNSTYRV VSVLTVLHQD WLNGKEYKCK  360
VSNKALPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVLHEAL HSHYTQKSLS  480
LSPGK                                                              485

SEQ ID NO: 228          moltype = AA  length = 246
FEATURE                 Location/Qualifiers
source                  1..246
                        mol_type = protein
                        organism = synthetic construct
SEQUENCE: 228
MGWSLILLFL VAVATRVLSD KTHTCPPCPA PELLGGDSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
```

```
ESNGQPENNY KTTPPVLDSD GSFFLVSKLT VDKSRWQQGN VFSCSVMHEA LHNHYTQKSL  240
SLSPGK                                                             246

SEQ ID NO: 229         moltype = AA  length = 246
FEATURE                Location/Qualifiers
source                 1..246
                       mol_type = protein
                       organism = synthetic construct
SEQUENCE: 229
MGWSLILLFL VAVATRVLSD KTHTCPPCPA PELLGGDSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVLHEA LHSHYTQKSL  240
SLSPGK                                                             246

SEQ ID NO: 230         moltype = AA  length = 246
FEATURE                Location/Qualifiers
source                 1..246
                       mol_type = protein
                       organism = synthetic construct
SEQUENCE: 230
MGWSLILLFL VAVATRVLSD KTHTCPPCPA PELLGGDSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVLHEA LHSHYTQKSL  240
SLSPGK                                                             246

SEQ ID NO: 231         moltype = AA  length = 466
FEATURE                Location/Qualifiers
source                 1..466
                       mol_type = protein
                       organism = synthetic construct
SEQUENCE: 231
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLD  240
KTHTCPPCPA PELLRGPSVF LFPPKPKDTL YITREPEVTC VVVDVSHEDP EVKFNWYVDG  300
VEVHNAKTKP REEQYNSTYR VVSVLTVLHQ DWLNGKEYKC KVSNKARPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LKFHYTQKSL SLSPGK                 466

SEQ ID NO: 232         moltype = AA  length = 466
FEATURE                Location/Qualifiers
source                 1..466
                       mol_type = protein
                       organism = synthetic construct
SEQUENCE: 232
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLRGPSVF LFPPKPKDTL YITREPEVTC VVVDVSHEDP EVKFNWYVDG  300
VEVHNAKTKP REEQYNSTYR VVSVLTVLHQ DWLNGKEYKC KVSNKARPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LKFHYTQKSL SLSPGK                 466

SEQ ID NO: 233         moltype = AA  length = 466
FEATURE                Location/Qualifiers
source                 1..466
                       mol_type = protein
                       organism = synthetic construct
SEQUENCE: 233
MGCSSPPCEC HQEEDFRVTC KDIQRIPSLP PSTQTLKLIE TSLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLD  240
KTHTCPPCPA PELLRGPSVF LFPPKPKDTL YITREPEVTC VVVDVSHEDP EVKFNWYVDG  300
VEVHNAKTKP REEQYNSTYR VVSVLTVLHQ DWLNGKEYKC KVSNKARPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LKFHYTQKSL SLSPGK                 466

SEQ ID NO: 234         moltype = AA  length = 466
FEATURE                Location/Qualifiers
source                 1..466
                       mol_type = protein
                       organism = synthetic construct
SEQUENCE: 234
MGCSSPPCEC HQEEDFRVTC KDIQRIPSLP PSTQTLKLIE THLRTIPSHA FSNLPNISRI  60
```

```
YVSIDVTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLD  240
KTHTCPPCPA PELLGGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKAFPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 235          moltype = AA  length = 466
FEATURE                 Location/Qualifiers
source                  1..466
                        mol_type = protein
                        organism = synthetic construct
SEQUENCE: 235
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLD  240
KTHTCPPCPA PELLGGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKAFPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 236          moltype = AA  length = 466
FEATURE                 Location/Qualifiers
source                  1..466
                        mol_type = protein
                        organism = synthetic construct
SEQUENCE: 236
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKAFPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 237          moltype = AA  length = 466
FEATURE                 Location/Qualifiers
source                  1..466
                        mol_type = protein
                        organism = synthetic construct
SEQUENCE: 237
MGCSSPPCEC HQEEDFRVTC KDIQRIPSLP PSTQTLKLIE TSLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTLD  240
KTHTCPPCPA PELLGGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKAFPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 238          moltype = AA  length = 227
FEATURE                 Location/Qualifiers
source                  1..227
                        mol_type = protein
                        organism = synthetic construct
SEQUENCE: 238
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPGK               227

SEQ ID NO: 239          moltype = AA  length = 227
FEATURE                 Location/Qualifiers
source                  1..227
                        mol_type = protein
                        organism = synthetic construct
SEQUENCE: 239
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPGK               227

SEQ ID NO: 240          moltype = AA  length = 227
FEATURE                 Location/Qualifiers
source                  1..227
                        mol_type = protein
```

```
                         organism = synthetic construct
SEQUENCE: 240
DKTHTCPPCP APELLRGPSV FLFPPKPKDT LYITREPEVT CVVVDVSHED PEVKFNWYVD  60
GVEVHNAKTK PREEQYNSTY RVVSVLTVLH QDWLNGKEYK CKVSNKARPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALKFHYTQKS LSLSPGK                227

SEQ ID NO: 241          moltype = AA  length = 227
FEATURE                 Location/Qualifiers
source                  1..227
                         mol_type = protein
                         organism = synthetic construct
SEQUENCE: 241
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 242          moltype = AA  length = 227
FEATURE                 Location/Qualifiers
source                  1..227
                         mol_type = protein
                         organism = synthetic construct
SEQUENCE: 242
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 243          moltype = AA  length = 227
FEATURE                 Location/Qualifiers
source                  1..227
                         mol_type = protein
                         organism = synthetic construct
SEQUENCE: 243
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 244          moltype = AA  length = 227
FEATURE                 Location/Qualifiers
source                  1..227
                         mol_type = protein
                         organism = synthetic construct
SEQUENCE: 244
DKTHTCPPCP APELLGGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKAFPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 245          moltype = AA  length = 466
FEATURE                 Location/Qualifiers
source                  1..466
                         mol_type = protein
                         organism = synthetic construct
SEQUENCE: 245
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGDSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 246          moltype = AA  length = 466
FEATURE                 Location/Qualifiers
source                  1..466
                         mol_type = protein
                         organism = synthetic construct
SEQUENCE: 246
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGDSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
```

```
GSFFLYSKLT VDKSRWQQGN VFSCSVLHEA LHSHYTQKSL SLSPGK                466

SEQ ID NO: 247          moltype = AA  length = 466
FEATURE                 Location/Qualifiers
source                  1..466
                        mol_type = protein
                        organism = synthetic construct
SEQUENCE: 247
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVLHEA LHSHYTQKSL SLSPGK                466

SEQ ID NO: 248          moltype = AA  length = 227
FEATURE                 Location/Qualifiers
source                  1..227
                        mol_type = protein
                        organism = synthetic construct
SEQUENCE: 248
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 249          moltype = AA  length = 227
FEATURE                 Location/Qualifiers
source                  1..227
                        mol_type = protein
                        organism = synthetic construct
SEQUENCE: 249
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVLHE ALHSHYTQKS LSLSPGK               227

SEQ ID NO: 250          moltype = AA  length = 227
FEATURE                 Location/Qualifiers
source                  1..227
                        mol_type = protein
                        organism = synthetic construct
SEQUENCE: 250
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVLHE ALHSHYTQKS LSLSPGK               227

SEQ ID NO: 251          moltype =   length =
SEQUENCE: 251
000

SEQ ID NO: 252          moltype =   length =
SEQUENCE: 252
000

SEQ ID NO: 253          moltype =   length =
SEQUENCE: 253
000

SEQ ID NO: 254          moltype =   length =
SEQUENCE: 254
000

SEQ ID NO: 255          moltype =   length =
SEQUENCE: 255
000

SEQ ID NO: 256          moltype =   length =
SEQUENCE: 256
000

SEQ ID NO: 257          moltype =   length =
SEQUENCE: 257
000

SEQ ID NO: 258          moltype =   length =
```

SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

```
SEQ ID NO: 298          moltype =   length =
SEQUENCE: 298
000

SEQ ID NO: 299          moltype = AA  length = 10
FEATURE                 Location/Qualifiers
source                  1..10
                        mol_type = protein
                        organism = synthetic construct
SEQUENCE: 299
DKTHTCPPCP                                                10

SEQ ID NO: 300          moltype = AA  length = 15
FEATURE                 Location/Qualifiers
source                  1..15
                        mol_type = protein
                        organism = synthetic construct
SEQUENCE: 300
EPKSSDKTHT CPPCP                                          15

SEQ ID NO: 301          moltype = AA  length = 12
FEATURE                 Location/Qualifiers
source                  1..12
                        mol_type = protein
                        organism = synthetic construct
SEQUENCE: 301
ERKCCVECPP CP                                             12

SEQ ID NO: 302          moltype = AA  length = 18
FEATURE                 Location/Qualifiers
source                  1..18
                        mol_type = protein
                        organism = synthetic construct
SEQUENCE: 302
ELKTRPLGDT THTCPPCP                                       18

SEQ ID NO: 303          moltype = AA  length = 63
FEATURE                 Location/Qualifiers
source                  1..63
                        mol_type = protein
                        organism = synthetic construct
SEQUENCE: 303
ELKTRPLGDT THTCPRCPEP KSCDTPPPCP RCPEPKSCDT PPPCPRCPEP KSCDTPPPCP  60
RCP                                                       63

SEQ ID NO: 304          moltype = AA  length = 12
FEATURE                 Location/Qualifiers
source                  1..12
                        mol_type = protein
                        organism = synthetic construct
SEQUENCE: 304
ESKYGPPCPP CP                                             12

SEQ ID NO: 305          moltype =   length =
SEQUENCE: 305
000

SEQ ID NO: 306          moltype =   length =
SEQUENCE: 306
000

SEQ ID NO: 307          moltype = AA  length = 239
FEATURE                 Location/Qualifiers
source                  1..239
                        mol_type = protein
                        organism = synthetic construct
SEQUENCE: 307
MGCSSPPCEC HQEEDFRVTC KDIQRIPSLP PSTQTLKLIE THLRTIPSHA FSNLPNISRI  60
YVSIDVTLQQ LEPHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQGYAFNGTK  180
LDAVYLNKNK YLTVIDKDAF GGVYSGPSLL DVSQTSVTAL PSKGLEHLKE LIARNTWTL   239

SEQ ID NO: 308          moltype = AA  length = 239
FEATURE                 Location/Qualifiers
source                  1..239
                        mol_type = protein
                        organism = synthetic construct
SEQUENCE: 308
```

```
MGCSSPPCEC HQEEDFRVTC KDIQRIPSLP PSTQTLKLIE THLRTIPSHA FSNLPNISRI  60
YVSIDVTLQQ LEPHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDKDAF GGVYSGPSLL DVSQTSVTAL PSKGLEHLKE LIARNTWTL   239

SEQ ID NO: 309         moltype = AA  length = 239
FEATURE                Location/Qualifiers
source                 1..239
                       mol_type = protein
                       organism = synthetic construct
SEQUENCE: 309
MGCSSPPCEC HQEEDFRVTC KDIQRIPSLP PSTQTLKLIE THLRTIPSHA FSNLPNISRI  60
YVSIDVTLQQ LEPHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDPDAF GGVYSGPSLL DVSQTSVTAL PSKGLEHLKE LIARNTWTL   239

SEQ ID NO: 310         moltype = AA  length = 239
FEATURE                Location/Qualifiers
source                 1..239
                       mol_type = protein
                       organism = synthetic construct
SEQUENCE: 310
MGCSSPPCEC HQEEDFRVTC KDIQRIPSLP PSTQTLKLIE THLRTIPSHA FSNLPNISRI  60
YVSIDPTLQQ LEPHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDPDAF GGVYSGPSLL DVSQTSVTAL PSKGLEHLKE LIARNTWTL   239

SEQ ID NO: 311         moltype = AA  length = 239
FEATURE                Location/Qualifiers
source                 1..239
                       mol_type = protein
                       organism = synthetic construct
SEQUENCE: 311
MGCSSPPCEC HQEEDFRVTC KDIQRIPSLP PSTQTLKLIE THLRTIPSHA FSNLPNISRI  60
YVSIDPTLQQ LEPHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDKDAF GGVYSGPSLL DVSQTSVTAL PSKGLEHLKE LIARNTWTL   239

SEQ ID NO: 312         moltype = AA  length = 239
FEATURE                Location/Qualifiers
source                 1..239
                       mol_type = protein
                       organism = synthetic construct
SEQUENCE: 312
MGCSSPPCEC HQEEDFRVTC KDIQRIPSLP PSTQTLKLIE THLRTIPSHA FSNLPNISRI  60
YVSIDPTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDPDAF GGVYSGPSLL DVSQTSVTAL PSKGLEHLKE LIARNTWTL   239

SEQ ID NO: 313         moltype = AA  length = 239
FEATURE                Location/Qualifiers
source                 1..239
                       mol_type = protein
                       organism = synthetic construct
SEQUENCE: 313
MGCSSPPCEC HQEEDFRVTC KDIQRIPSLP PSTQTLKLIE THLRTIPSHA FSNLPNISRI  60
YVSIDPTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDKDAF GGVYSGPSLL DVSQTSVTAL PSKGLEHLKE LIARNTWTL   239

SEQ ID NO: 314         moltype = AA  length = 239
FEATURE                Location/Qualifiers
source                 1..239
                       mol_type = protein
                       organism = synthetic construct
SEQUENCE: 314
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT RNLTYIDPDA LKELPLLKFL GIFNTGLKMF  120
PDLTKVYSTD IFFILEITDN PYMTSIPVNA FQGLCNETLT LKLYNNGFTS VQPYAFNGTK  180
LDAVYLNKNK YLTVIDKDAF GGVYSGPSLL DVSQTSVTAL PSKGLEHLKE LIARNTWTL   239

SEQ ID NO: 315         moltype = AA  length = 239
FEATURE                Location/Qualifiers
source                 1..239
                       mol_type = protein
                       organism = synthetic construct
SEQUENCE: 315
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT RNLTYIDPDA LKELPLLKFL GIFNTGLKMF  120
```

```
PDLTKVYSTD IFFILEITDN PYMTSIPVNA FQGLCNETLT LKLYNNGFTS VQPYAFNGTK  180
LDAVYLNKNK YLTVIDPDAF GGVYSGPSLL DVSQTSVTAL PSKGLEHLKE LIARNTWTL   239

SEQ ID NO: 316         moltype = AA  length = 239
FEATURE                Location/Qualifiers
source                 1..239
                       mol_type = protein
                       organism = synthetic construct
SEQUENCE: 316
MGCSSPPCEC HQEEDFRVTC KDIQRIPSLP PSTQTLKLIE THLRTIPSHA FSNLPNISRI  60
YVSIDPTLQQ LEPHSFYNLS KVTHIEIRNT RNLTYIDPDA LKELPLLKFL GIFNTPLKMF  120
PDLTKVYSTD IFFILEITDN PYMTSIPVNA FQGLCNETLT LKLYNNGFTS VQPYAFNGTK  180
LDAVYLNKNK YLTVIDPDAF GGVYSGPSLL DVSQTSVTAL PSKGLEHLKE LIARNTWTL   239

SEQ ID NO: 317         moltype = AA  length = 239
FEATURE                Location/Qualifiers
source                 1..239
                       mol_type = protein
                       organism = synthetic construct
SEQUENCE: 317
MGCSSPPCEC HQEEDFRVTC KDIQRIPSLP PSTQTLKLIE THLRTIPSHA FSNLPNISRI  60
YVSIDPTLQQ LEPHSFYNLS KVTHIEIRNT RNLTYIDPDA LKELPLLKFL GIFNTPLKMF  120
PDLTKVYSTD IFFILEITDN PYMTSIPVNA FQGLCNETLT LKLYNNPFTS VQPYAFNGTK  180
LDAVYLNKNK YLTVIDPDAF GGVYSGPSLL DVSQTSVTAL PSKGLEHLKE LIARNTWTL   239

SEQ ID NO: 318         moltype = AA  length = 485
FEATURE                Location/Qualifiers
source                 1..485
                       mol_type = protein
                       organism = synthetic construct
SEQUENCE: 318
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP VDFRDPLVFL FPPKPKDTLM ISRTPEVTCV  300
VVDVDPEDPE VKFNWYVDGV EVHNAKTKPR EEQYNGAYRV VSVLTVLHQD WLNGKEYKCK  360
VSNKLAPHPI IKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 319         moltype = AA  length = 485
FEATURE                Location/Qualifiers
source                 1..485
                       mol_type = protein
                       organism = synthetic construct
SEQUENCE: 319
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP VDFRDPLVFL FPPKPKDTLM ISRTPEVTCV  300
VVDVDPEDPE VKFNWYVDGV EVHNAKTKPQ EEQYNGAYRV VSVLTVLHQD WLNGKEYKCK  360
VSNKLAPHPI IKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 320         moltype = AA  length = 485
FEATURE                Location/Qualifiers
source                 1..485
                       mol_type = protein
                       organism = synthetic construct
SEQUENCE: 320
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP VDFRDPLVFL FPPKPKDTLM ISRTPEVTCV  300
VVDVSPEDPE VKFNWYVDGV EVHNAKTKPQ EEQYNGAYRV VSVLTVLHQD WLNGKEYKCK  360
VSNKLAPHPI IKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                              485

SEQ ID NO: 321         moltype = AA  length = 485
FEATURE                Location/Qualifiers
source                 1..485
                       mol_type = protein
                       organism = synthetic construct
SEQUENCE: 321
```

MGWSCIILFL VATATGVHSM GCSSPPCECH QEEDFRVTCK DIQRIPSLPP STQTLKLIET 60
HLRTIPSHAF SNLPNISRIY VSIDVTLQQL ESHSFYNLSK VTHIEIRNTP NLTYIDPDAL 120
KELPLLKFLG IFNTGLKMFP PLTKVYSTDI FFILEITDNP YMTSIPRNAF QGLCNETLTL 180
KLYNNGFTSV QGYAFNGTKL DAVYLNKNKY LTVIDKDAFG GVYSGPSLLD VSQTSVTALP 240
SKGLEHLKEL RARNTWTLDK THTCPPCPAP DLLGDDSVFL FPPKPKDTLM ISRTPEVTCV 300
VVDVSDEDGE VKFNWYVDGV EVHNAKTKPR EEQYNSTYRV VSVLTVLHQD WLNGKEYKCK 360
VSNKALPRPI EKTISKAKGQ PREPQVYTLP PCRDELTKNQ VSLWCLVKGF YPSDIAVEWE 420
SNGQPENNYK TTPPVLDSDG SFFLYSKLTV DKSRWQQGNV FSCSVMHEAL HNHYTQKSLS 480
LSPGK 485

SEQ ID NO: 322 moltype = AA length = 485
FEATURE Location/Qualifiers
source 1..485
mol_type = protein
organism = synthetic construct
SEQUENCE: 322
MGWSCIILFL VATATGVHSM GCSSPPCECH QEEDFRVTCK DIQRIPSLPP STQTLKLIET 60
HLRTIPSHAF SNLPNISRIY VSIDVTLQQL ESHSFYNLSK VTHIEIRNTP NLTYIDPDAL 120
KELPLLKFLG IFNTGLKMFP PLTKVYSTDI FFILEITDNP YMTSIPRNAF QGLCNETLTL 180
KLYNNGFTSV QGYAFNGTKL DAVYLNKNKY LTVIDKDAFG GVYSGPSLLD VSQTSVTALP 240
SKGLEHLKEL RARNTWTLDK THTCPPCPAP EYLGGDSVFL FPPKPKDVLM ISRTPEVTCV 300
VIDVSHEDPE VKFNWYVDGV EVHNAKTKPR EEQYNSTYRV VSVLPVLHRD WLNGKEYKCK 360
VSNKALPKPI EKTISKAKGQ RREPQVYTLP PCREEMTKNQ VSLWCLVKGF YPSDIAVEWE 420
SNGQPENNYK TTPPVLDSDG SFFLYSKLTV DKSRWQQGNV FSCSVLHEAL HAHTTRKELS 480
LSPGK 485

SEQ ID NO: 323 moltype = AA length = 485
FEATURE Location/Qualifiers
source 1..485
mol_type = protein
organism = synthetic construct
SEQUENCE: 323
MGWSCIILFL VATATGVHSM GCSSPPCECH QEEDFRVTCK DIQRIPSLPP STQTLKLIET 60
HLRTIPSHAF SNLPNISRIY VSIDVTLQQL ESHSFYNLSK VTHIEIRNTP NLTYIDPDAL 120
KELPLLKFLG IFNTGLKMFP PLTKVYSTDI FFILEITDNP YMTSIPRNAF QGLCNETLTL 180
KLYNNGFTSV QGYAFNGTKL DAVYLNKNKY LTVIDKDAFG GVYSGPSLLD VSQTSVTALP 240
SKGLEHLKEL RARNTWTLDK THTCPPCPAP EDLNGPSVFL FPPKPKDTLM ISRTPEVTCV 300
VVDVEHEDPE VKFNWYVDGV EVHNAKTKPR EEQYNSTYRV VSVLTVLHQD WLNGKEYKCK 360
VSNKALPAPI EKTISKAKGQ PREPQVYTLP PCRDELTKNQ VSLWCLVKGF YPSDIAVEWE 420
SNGQPENNYK TTPPVLDSDG SFFLYSKLTV DKSRWQQGNV FSCSVMHEAL HNHYTQKSLS 480
LSPGK 485

SEQ ID NO: 324 moltype = AA length = 485
FEATURE Location/Qualifiers
source 1..485
mol_type = protein
organism = synthetic construct
SEQUENCE: 324
MGWSCIILFL VATATGVHSM GCSSPPCECH QEEDFRVTCK DIQRIPSLPP STQTLKLIET 60
HLRTIPSHAF SNLPNISRIY VSIDVTLQQL ESHSFYNLSK VTHIEIRNTP NLTYIDPDAL 120
KELPLLKFLG IFNTGLKMFP PLTKVYSTDI FFILEITDNP YMTSIPRNAF QGLCNETLTL 180
KLYNNGFTSV QGYAFNGTKL DAVYLNKNKY LTVIDKDAFG GVYSGPSLLD VSQTSVTALP 240
SKGLEHLKEL RARNTWTLDK THTCPPCPAP ELRGGPSVFL FPPKPKDTLM ISRTPEVTCV 300
VVDVSHEDPE VKFNWYVDGV EVHNAKTKPR EEQYNSTYRV VSVLTVLHQD WLNGKEYKCK 360
VSNKALPAPI EKTISKAKGQ PREPQVYTLP PCRDELTKNQ VSLWCLVKGF YPSDIAVEWE 420
SNGQPENNYK TTPPVLDSDG SFFLYSKLTV DKSRWQQGNV FSCSVMHEAL HNHYTQKSLS 480
LSPGK 485

SEQ ID NO: 325 moltype = AA length = 485
FEATURE Location/Qualifiers
source 1..485
mol_type = protein
organism = synthetic construct
SEQUENCE: 325
MGWSCIILFL VATATGVHSM GCSSPPCECH QEEDFRVTCK DIQRIPSLPP STQTLKLIET 60
HLRTIPSHAF SNLPNISRIY VSIDVTLQQL ESHSFYNLSK VTHIEIRNTP NLTYIDPDAL 120
KELPLLKFLG IFNTGLKMFP PLTKVYSTDI FFILEITDNP YMTSIPRNAF QGLCNETLTL 180
KLYNNGFTSV QGYAFNGTKL DAVYLNKNKY LTVIDKDAFG GVYSGPSLLD VSQTSVTALP 240
SKGLEHLKEL RARNTWTLDK THTCPPCPAP ELLNGPSVFL FPPKPKDTLM ISRTPEVTCV 300
VVDVEHEDPE VKFNWYVDGV EVHNAKTKPR EEQYNSTYRV VSVLTVLHQD WLNGKEYKCK 360
VSNKALPAPI EKTISKAKGQ PREPQVYTLP PCRDELTKNQ VSLWCLVKGF YPSDIAVEWE 420
SNGQPENNYK TTPPVLDSDG SFFLYSKLTV DKSRWQQGNV FSCSVMHEAL HNHYTQKSLS 480
LSPGK 485

SEQ ID NO: 326 moltype = AA length = 485
FEATURE Location/Qualifiers
source 1..485
mol_type = protein
organism = synthetic construct

```
SEQUENCE: 326
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGDSVFL FPPKPKDTLM ISRTPEVTCV  300
VVDVSHEEPE VKFNWYVDGV EVHNAKTKPR EEQYNSTYRV VSVLTVLHQD WLNGKEYKCK  360
VSNKALPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 327          moltype = AA  length = 485
FEATURE                 Location/Qualifiers
source                  1..485
                        mol_type = protein
                        organism = synthetic construct
SEQUENCE: 327
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGDSVFL FPPKPKDTLM ISRTPEVTCV  300
VVDVSHEDGE VKFNWYVDGV EVHNAKTKPR EEQYNSTYRV VSVLTVLHQD WLNGKEYKCK  360
VSNKALPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 328          moltype = AA  length = 485
FEATURE                 Location/Qualifiers
source                  1..485
                        mol_type = protein
                        organism = synthetic construct
SEQUENCE: 328
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGDSVFL FPPKPKDTLM ISRTPEVTCV  300
VVDVSHEEGE VKFNWYVDGV EVHNAKTKPR EEQYNSTYRV VSVLTVLHQD WLNGKEYKCK  360
VSNKALPAPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 329          moltype = AA  length = 485
FEATURE                 Location/Qualifiers
source                  1..485
                        mol_type = protein
                        organism = synthetic construct
SEQUENCE: 329
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGDDSVFL FPPKPKDTLM ISRTPEVTCV  300
VVDVSHEDGE VKFNWYVDGV EVHNAKTKPR EEQYNSTYRV VSVLTVLHQD WLNGKEYKCK  360
VSNKALPRPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 330          moltype = AA  length = 485
FEATURE                 Location/Qualifiers
source                  1..485
                        mol_type = protein
                        organism = synthetic construct
SEQUENCE: 330
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGDDSVFL FPPKPKDTLM ISRTPEVTCV  300
VVDVSHEEGE VKFNWYVDGV EVHNAKTKPR EEQYNSTYRV VSVLTVLHQD WLNGKEYKCK  360
VSNKALPRPI EKTISKAKGQ PREPQVYTLP PCREEMTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                            485

SEQ ID NO: 331          moltype = AA  length = 485
FEATURE                 Location/Qualifiers
source                  1..485
                        mol_type = protein
```

```
                          organism = synthetic construct
SEQUENCE: 331
MGWSCIILFL VATATGVHSM GCSSPPCECH QEEDFRVTCK DIQRIPSLPP STQTLKLIET  60
HLRTIPSHAF SNLPNISRIY VSIDVTLQQL ESHSFYNLSK VTHIEIRNTP NLTYIDPDAL  120
KELPLLKFLG IFNTGLKMFP PLTKVYSTDI FFILEITDNP YMTSIPRNAF QGLCNETLTL  180
KLYNNGFTSV QGYAFNGTKL DAVYLNKNKY LTVIDKDAFG GVYSGPSLLD VSQTSVTALP  240
SKGLEHLKEL RARNTWTLDK THTCPPCPAP ELLGGPDVFL FPPKPKDTLM ISRTPEVTCV  300
VVDVSDEDPE VKFNWYVDGV EVHNAKTKPR EEQYNSTYRV VSVLTVLHQD WLNGKEYKCK  360
VSNKAWPAPI EKTISKAKGQ PREPQVYTLP PCRDELTKNQ VSLWCLVKGF YPSDIAVEWE  420
SNGQPENNYK TTPPVLDSDG SFFLYSKLTV DKSRWQQGNV FSCSVMHEAL HNHYTQKSLS  480
LSPGK                                                             485

SEQ ID NO: 332            moltype = AA  length = 246
FEATURE                   Location/Qualifiers
source                    1..246
                          mol_type = protein
                          organism = synthetic construct
SEQUENCE: 332
MGWSCIILFL VATATGVHSD KTHTCPPCPA PVDFRDPLVF LFPPKPKDTL MISRTPEVTC  60
VVVDVDPEDP EVKFNWYVDG VEVHNAKTKP REEQYNGAYR VVSVLTVLHQ DWLNGKEYKC  120
KVSNKLAPHP IIKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 333            moltype = AA  length = 246
FEATURE                   Location/Qualifiers
source                    1..246
                          mol_type = protein
                          organism = synthetic construct
SEQUENCE: 333
MGWSCIILFL VATATGVHSD KTHTCPPCPA PVDFRDPLVF LFPPKPKDTL MISRTPEVTC  60
VVVDVDPEDP EVKFNWYVDG VEVHNAKTKP QEEQYNGAYR VVSVLTVLHQ DWLNGKEYKC  120
KVSNKLAPHP IIKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 334            moltype = AA  length = 246
FEATURE                   Location/Qualifiers
source                    1..246
                          mol_type = protein
                          organism = synthetic construct
SEQUENCE: 334
MGWSCIILFL VATATGVHSD KTHTCPPCPA PVDFRDPLVF LFPPKPKDTL MISRTPEVTC  60
VVVDVSPEDP EVKFNWYVDG VEVHNAKTKP QEEQYNGAYR VVSVLTVLHQ DWLNGKEYKC  120
KVSNKLAPHP IIKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 335            moltype = AA  length = 246
FEATURE                   Location/Qualifiers
source                    1..246
                          mol_type = protein
                          organism = synthetic construct
SEQUENCE: 335
MGWSCIILFL VATATGVHSD KTHTCPPCPA PDLLGDDSVF LFPPKPKDTL MISRTPEVTC  60
VVVDVSDEDG EVKFNWYVDG VEVHNAKTKP REEQYNSTYR VVSVLTVLHQ DWLNGKEYKC  120
KVSNKALPRP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 336            moltype = AA  length = 246
FEATURE                   Location/Qualifiers
source                    1..246
                          mol_type = protein
                          organism = synthetic construct
SEQUENCE: 336
MGWSCIILFL VATATGVHSD KTHTCPPCPA PEYLGGDSVF LFPPKPKDVL MISRTPEVTC  60
VVIDVSHEDP EVKFNWYVDG VEVHNAKTKP REEQYNSTYR VVSVLPVLHR DWLNGKEYKC  120
KVSNKALPKP IEKTISKAKG QRREPQVCTL PPSREEMTKN QVSLSCAVKG FYPSDIAVEW  180
ESNGQPENNY KTTPPVLDSD GSFFLVSKLT VDKSRWQQGN VFSCSVMLEA LHAHTTRKEL  240
SLSPGK                                                            246

SEQ ID NO: 337            moltype = AA  length = 246
FEATURE                   Location/Qualifiers
source                    1..246
                          mol_type = protein
                          organism = synthetic construct
SEQUENCE: 337
MGWSCIILFL VATATGVHSD KTHTCPPCPA PEDLNGPSVF LFPPKPKDTL MISRTPEVTC  60
```

```
VVVDVEHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 338          moltype = AA  length = 246
FEATURE                 Location/Qualifiers
source                  1..246
                        mol_type = protein
                        organism = synthetic construct
SEQUENCE: 338
MGWSCIILFL VATATGVHSD KTHTCPPCPA PELRGGPSVF LFPPKPKDTL MISRTPEVTC  60
VVVDVSHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 339          moltype = AA  length = 246
FEATURE                 Location/Qualifiers
source                  1..246
                        mol_type = protein
                        organism = synthetic construct
SEQUENCE: 339
MGWSCIILFL VATATGVHSD KTHTCPPCPA PELLNGPSVF LFPPKPKDTL MISRTPEVTC  60
VVVDVEHEDP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 340          moltype = AA  length = 246
FEATURE                 Location/Qualifiers
source                  1..246
                        mol_type = protein
                        organism = synthetic construct
SEQUENCE: 340
MGWSCIILFL VATATGVHSD KTHTCPPCPA PELLGGDSVF LFPPKPKDTL MISRTPEVTC  60
VVVDVSHEEP EVKFNWYVDG VEVHNAKTKP REEQYNSTYR VVSVLTVLHQ DWLNGKEYKC  120
KVSNKALPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 341          moltype = AA  length = 246
FEATURE                 Location/Qualifiers
source                  1..246
                        mol_type = protein
                        organism = synthetic construct
SEQUENCE: 341
MGWSCIILFL VATATGVHSD KTHTCPPCPA PELLGGDSVF LFPPKPKDTL MISRTPEVTC  60
VVVDVSHEDG EVKFNWYVDG VEVHNAKTKP REEQYNSTYR VVSVLTVLHQ DWLNGKEYKC  120
KVSNKALPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 342          moltype = AA  length = 246
FEATURE                 Location/Qualifiers
source                  1..246
                        mol_type = protein
                        organism = synthetic construct
SEQUENCE: 342
MGWSCIILFL VATATGVHSD KTHTCPPCPA PELLGGDSVF LFPPKPKDTL MISRTPEVTC  60
VVVDVSHEEG EVKFNWYVDG VEVHNAKTKP REEQYNSTYR VVSVLTVLHQ DWLNGKEYKC  120
KVSNKALPAP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 343          moltype = AA  length = 246
FEATURE                 Location/Qualifiers
source                  1..246
                        mol_type = protein
                        organism = synthetic construct
SEQUENCE: 343
MGWSCIILFL VATATGVHSD KTHTCPPCPA PELLGDDSVF LFPPKPKDTL MISRTPEVTC  60
VVVDVSHEDG EVKFNWYVDG VEVHNAKTKP REEQYNSTYR VVSVLTVLHQ DWLNGKEYKC  120
KVSNKALPRP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                            246

SEQ ID NO: 344          moltype = AA  length = 246
FEATURE                 Location/Qualifiers
```

```
source                  1..246
                        mol_type = protein
                        organism = synthetic construct
SEQUENCE: 344
MGWSCIILFL VATATGVHSD KTHTCPPCPA PELLGDDSVF LFPPKPKDTL MISRTPEVTC  60
VVVDVSHEEG EVKFNWYVDG VEVHNAKTKP REEQYNSTYR VVSVLTVLHQ DWLNGKEYKC  120
KVSNKALPRP IEKTISKAKG QPREPQVCTL PPSREEMTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                             246

SEQ ID NO: 345          moltype = AA  length = 246
FEATURE                 Location/Qualifiers
source                  1..246
                        mol_type = protein
                        organism = synthetic construct
SEQUENCE: 345
MGWSCIILFL VATATGVHSD KTHTCPPCPA PELLGGPDVF LFPPKPKDTL MISRTPEVTC  60
VVVDVSDEDP EVKFNWYVDG VEVHNAKTKP REEQYNSTYR VVSVLTVLHQ DWLNGKEYKC  120
KVSNKAWPAP IEKTISKAKG QPREPQVCTL PPSRDELTKN QVSLSCAVKG FYPSDIAVEW  180
ESNGQPENNY KTTPPVLDSD GSFFLVSKLT VDKSRWQQGN VFSCSVMHEA LHNHYTQKSL  240
SLSPGK                                                             246

SEQ ID NO: 346          moltype = AA  length = 466
FEATURE                 Location/Qualifiers
source                  1..466
                        mol_type = protein
                        organism = synthetic construct
SEQUENCE: 346
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PVDFRDPLVF LFPPKPKDTL MISRTPEVTC VVVDVDPEDP EVKFNWYVDG  300
VEVHNAKTKP REEQYNGAYR VVSVLTVLHQ DWLNGKEYKC KVSNKLAPHP IIKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 347          moltype = AA  length = 466
FEATURE                 Location/Qualifiers
source                  1..466
                        mol_type = protein
                        organism = synthetic construct
SEQUENCE: 347
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PVDFRDPLVF LFPPKPKDTL MISRTPEVTC VVVDVDPEDP EVKFNWYVDG  300
VEVHNAKTKP QEEQYNGAYR VVSVLTVLHQ DWLNGKEYKC KVSNKLAPHP IIKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 348          moltype = AA  length = 466
FEATURE                 Location/Qualifiers
source                  1..466
                        mol_type = protein
                        organism = synthetic construct
SEQUENCE: 348
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PVDFRDPLVF LFPPKPKDTL MISRTPEVTC VVVDVSPEDP EVKFNWYVDG  300
VEVHNAKTKP QEEQYNGAYR VVSVLTVLHQ DWLNGKEYKC KVSNKLAPHP IIKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 349          moltype = AA  length = 466
FEATURE                 Location/Qualifiers
source                  1..466
                        mol_type = protein
                        organism = synthetic construct
SEQUENCE: 349
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PDLLGDDSVF LFPPKPKDTL MISRTPEVTC VVVDVSDEDG EVKFNWYVDG  300
VEVHNAKTKP REEQYNSTYR VVSVLTVLHQ DWLNGKEYKC KVSNKALPRP IEKTISKAKG  360
```

```
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 350         moltype = AA  length = 466
FEATURE                Location/Qualifiers
source                 1..466
                       mol_type = protein
                       organism = synthetic construct
SEQUENCE: 350
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PEYLGGDSVF LFPPKPKDVL MISRTPEVTC VVIDVSHEDP EVKFNWYVDG  300
VEVHNAKTKP REEQYNSTYR VVSVLPVLHR DWLNGKEYKC KVSNKALPKP IEKTISKAKG  360
QRREPQVYTL PPCREEMTKN QVSLWCLVKG FYPSDIAVEW ESNGQPENNY KTTPPVLDSD  420
GSFFLYSKLT VDKSRWQQGN VFSCSVLHEA LHAHTTRKEL SLSPGK                466

SEQ ID NO: 351         moltype = AA  length = 466
FEATURE                Location/Qualifiers
source                 1..466
                       mol_type = protein
                       organism = synthetic construct
SEQUENCE: 351
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PEDLNGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 352         moltype = AA  length = 466
FEATURE                Location/Qualifiers
source                 1..466
                       mol_type = protein
                       organism = synthetic construct
SEQUENCE: 352
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELRGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 353         moltype = AA  length = 466
FEATURE                Location/Qualifiers
source                 1..466
                       mol_type = protein
                       organism = synthetic construct
SEQUENCE: 353
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLNGPSVF LFPPKPKDTL MISRTPEVTC VVVDVEHEDP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 354         moltype = AA  length = 466
FEATURE                Location/Qualifiers
source                 1..466
                       mol_type = protein
                       organism = synthetic construct
SEQUENCE: 354
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGDSVF LFPPKPKDTL MISRTPEVTC VVVDVSHEEP EVKFNWYVDG  300
VEVHNAKTKP REEQYNSTYR VVSVLTVLHQ DWLNGKEYKC KVSNKALPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 355         moltype = AA  length = 466
```

```
FEATURE                Location/Qualifiers
source                 1..466
                       mol_type = protein
                       organism = synthetic construct
SEQUENCE: 355
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGDSVF LFPPKPKDTL MISRTPEVTC VVVDVSHEDG EVKFNWYVDG  300
VEVHNAKTKP REEQYNSTYR VVSVLTVLHQ DWLNGKEYKC KVSNKALPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 356         moltype = AA  length = 466
FEATURE                Location/Qualifiers
source                 1..466
                       mol_type = protein
                       organism = synthetic construct
SEQUENCE: 356
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGDSVF LFPPKPKDTL MISRTPEVTC VVVDVSHEEG EVKFNWYVDG  300
VEVHNAKTKP REEQYNSTYR VVSVLTVLHQ DWLNGKEYKC KVSNKALPAP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 357         moltype = AA  length = 466
FEATURE                Location/Qualifiers
source                 1..466
                       mol_type = protein
                       organism = synthetic construct
SEQUENCE: 357
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGDDSVF LFPPKPKDTL MISRTPEVTC VVVDVSHEDG EVKFNWYVDG  300
VEVHNAKTKP REEQYNSTYR VVSVLTVLHQ DWLNGKEYKC KVSNKALPRP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 358         moltype = AA  length = 466
FEATURE                Location/Qualifiers
source                 1..466
                       mol_type = protein
                       organism = synthetic construct
SEQUENCE: 358
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGDDSVF LFPPKPKDTL MISRTPEVTC VVVDVSHEEG EVKFNWYVDG  300
VEVHNAKTKP REEQYNSTYR VVSVLTVLHQ DWLNGKEYKC KVSNKALPRP IEKTISKAKG  360
QPREPQVYTL PPCREEMTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 359         moltype = AA  length = 466
FEATURE                Location/Qualifiers
source                 1..466
                       mol_type = protein
                       organism = synthetic construct
SEQUENCE: 359
MGCSSPPCEC HQEEDFRVTC KDIQRIPSLP PSTQTLKLIE THLRTIPSHA FSNLPNISRI  60
YVSIDVTLQQ LESHSFYNLS KVTHIEIRNT PNLTYIDPDA LKELPLLKFL GIFNTGLKMF  120
PPLTKVYSTD IFFILEITDN PYMTSIPRNA FQGLCNETLT LKLYNNGFTS VQGYAFNGTK  180
LDAVYLNKNK YLTVIDKDAF GGVYSGPSLL DVSQTSVTAL PSKGLEHLKE LRARNTWTLD  240
KTHTCPPCPA PELLGGPDVF LFPPKPKDTL MISRTPEVTC VVVDVSDEDP EVKFNWYVDG  300
VEVHNAKTKP REEQYNSTYR VVSVLTVLHQ DWLNGKEYKC KVSNKAWPAP IEKTISKAKG  360
QPREPQVYTL PPCRDELTKN QVSLWCLVKG FYPSDIAVEW ESNGQPENNY KTTPPVLDSD  420
GSFFLYSKLT VDKSRWQQGN VFSCSVMHEA LHNHYTQKSL SLSPGK                466

SEQ ID NO: 360         moltype = AA  length = 227
FEATURE                Location/Qualifiers
source                 1..227
                       mol_type = protein
                       organism = synthetic construct
```

```
SEQUENCE: 360
DKTHTCPPCP APVDFRDPLV FLFPPKPKDT LMISRTPEVT CVVVDVDPED PEVKFNWYVD  60
GVEVHNAKTK PREEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 361         moltype = AA  length = 227
FEATURE                Location/Qualifiers
source                 1..227
                       mol_type = protein
                       organism = synthetic construct
SEQUENCE: 361
DKTHTCPPCP APVDFRDPLV FLFPPKPKDT LMISRTPEVT CVVVDVDPED PEVKFNWYVD  60
GVEVHNAKTK PQEEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 362         moltype = AA  length = 227
FEATURE                Location/Qualifiers
source                 1..227
                       mol_type = protein
                       organism = synthetic construct
SEQUENCE: 362
DKTHTCPPCP APVDFRDPLV FLFPPKPKDT LMISRTPEVT CVVVDVSPED PEVKFNWYVD  60
GVEVHNAKTK PQEEQYNGAY RVVSVLTVLH QDWLNGKEYK CKVSNKLAPH PIIKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 363         moltype = AA  length = 227
FEATURE                Location/Qualifiers
source                 1..227
                       mol_type = protein
                       organism = synthetic construct
SEQUENCE: 363
DKTHTCPPCP APDLLGDDSV FLFPPKPKDT LMISRTPEVT CVVVDVSDED GEVKFNWYVD  60
GVEVHNAKTK PREEQYNSTY RVVSVLTVLH QDWLNGKEYK CKVSNKALPR PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 364         moltype = AA  length = 227
FEATURE                Location/Qualifiers
source                 1..227
                       mol_type = protein
                       organism = synthetic construct
SEQUENCE: 364
DKTHTCPPCP APEYLGGDSV FLFPPKPKDV LMISRTPEVT CVVIDVSHED PEVKFNWYVD  60
GVEVHNAKTK PREEQYNSTY RVVSVLPVLH RDWLNGKEYK CKVSNKALPK PIEKTISKAK  120
GQRREPQVCT LPPSREEMTK NQVSLSCAVK GFYPSDIAVE WESNGQPENN YKTTPPVLDS  180
DGSFFLVSKL TVDKSRWQQG NVFSCSVMLE ALHAHTTRKE LSLSPGK                227

SEQ ID NO: 365         moltype = AA  length = 227
FEATURE                Location/Qualifiers
source                 1..227
                       mol_type = protein
                       organism = synthetic construct
SEQUENCE: 365
DKTHTCPPCP APEDLNGPSV FLFPPKPKDT LMISRTPEVT CVVVDVEHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 366         moltype = AA  length = 227
FEATURE                Location/Qualifiers
source                 1..227
                       mol_type = protein
                       organism = synthetic construct
SEQUENCE: 366
DKTHTCPPCP APELRGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK                227

SEQ ID NO: 367         moltype = AA  length = 227
FEATURE                Location/Qualifiers
source                 1..227
                       mol_type = protein
                       organism = synthetic construct
SEQUENCE: 367
DKTHTCPPCP APELLNGPSV FLFPPKPKDT LMISRTPEVT CVVVDVEHED PEVKFNWYVD  60
```

```
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 368         moltype = AA  length = 227
FEATURE                Location/Qualifiers
source                 1..227
                       mol_type = protein
                       organism = synthetic construct
SEQUENCE: 368
DKTHTCPPCP APELLGGDSV FLFPPKPKDT LMISRTPEVT CVVVDVSHEE PEVKFNWYVD  60
GVEVHNAKTK PREEQYNSTY RVVSVLTVLH QDWLNGKEYK CKVSNKALPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 369         moltype = AA  length = 227
FEATURE                Location/Qualifiers
source                 1..227
                       mol_type = protein
                       organism = synthetic construct
SEQUENCE: 369
DKTHTCPPCP APELLGGDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 370         moltype = AA  length = 227
FEATURE                Location/Qualifiers
source                 1..227
                       mol_type = protein
                       organism = synthetic construct
SEQUENCE: 370
DKTHTCPPCP APELLGGDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPA PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 371         moltype = AA  length = 227
FEATURE                Location/Qualifiers
source                 1..227
                       mol_type = protein
                       organism = synthetic construct
SEQUENCE: 371
DKTHTCPPCP APELLGDDSV FLFPPKPKDT LMISRTPEVT CVVVDVSHED GEVKFNWYVD  60
GVEVHNAKTK PREEQYNSTY RVVSVLTVLH QDWLNGKEYK CKVSNKALPR PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 372         moltype = AA  length = 227
FEATURE                Location/Qualifiers
source                 1..227
                       mol_type = protein
                       organism = synthetic construct
SEQUENCE: 372
DKTHTCPPCP APELLGDDSV FLFPPKPKDT LMISRTPEVT CVVVDVSHEE GEVKFNWYVD  60
GVEVHNAKTK PREEQYNSTY RVVSVLTVLH QDWLNGKEYK CKVSNKALPR PIEKTISKAK  120
GQPREPQVCT LPPSREEMTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 373         moltype = AA  length = 227
FEATURE                Location/Qualifiers
source                 1..227
                       mol_type = protein
                       organism = synthetic construct
SEQUENCE: 373
DKTHTCPPCP APELLGGPDV FLFPPKPKDT LMISRTPEVT CVVVDVSDED PEVKFNWYVD  60
GVEVHNAKTK PREEQYNSTY RVVSVLTVLH QDWLNGKEYK CKVSNKAWPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 374         moltype = AA  length = 227
FEATURE                Location/Qualifiers
source                 1..227
                       mol_type = protein
                       organism = synthetic construct
SEQUENCE: 374
DKTHTCPPCP APELLGGDSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
```

```
DGSFFLYSKL TVDKSRWQQG NVFSCSVMHE ALHNHYTQKS LSLSPGK               227

SEQ ID NO: 375          moltype = AA  length = 227
FEATURE                 Location/Qualifiers
source                  1..227
                        mol_type = protein
                        organism = synthetic construct
SEQUENCE: 375
DKTHTCPPCP APELLGGPDV FLFPPKPKDT LMISRTPEVT CVVVDVSDED PEVKFNWYVD  60
GVEVHNAKTK PREEQYNSTY RVVSVLTVLH QDWLNGKEYK CKVSNKAWPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 376          moltype = AA  length = 227
FEATURE                 Location/Qualifiers
source                  1..227
                        mol_type = protein
                        organism = synthetic construct
SEQUENCE: 376
DKTHTCPPCP APELLGGPDV FLFPPKPKDT LMISRTPEVT CVVVDVSDED PEVKFNWYVD  60
GVEVHNAKTK PREEQYNSTY RVVSVLTVLH QDWLNGKEYK CKVSNKAWPA PIEKTISKAK  120
GQPREPQVYT LPPCRDELTK NQVSLWCLVK GFYPSDIAVE WESNGQPENN YKTTPPVLDS  180
DGSFFLYSKL TVDKSRWQQG NVFSCSVMHE ALHNHYTQKS LSLSPGK               227

SEQ ID NO: 377          moltype = AA  length = 227
FEATURE                 Location/Qualifiers
source                  1..227
                        mol_type = protein
                        organism = synthetic construct
SEQUENCE: 377
DKTHTCPPCP APELLGGPDV FLFPPKPKDT LMISRTPEVT CVVVDVSDED PEVKFNWYVD  60
GVEVHNAKTK PREEQYNSTY RVVSVLTVLH QDWLNGKEYK CKVSNKAWPA PIEKTISKAK  120
GQPREPQVCT LPPSRDELTK NQVSLSCAVK GFYPSDIAVE WESNGQPENN YKTTPPVLDS  180
DGSFFLVSKL TVDKSRWQQG NVFSCSVMHE ALHNHYTQKS LSLSPGK               227

SEQ ID NO: 378          moltype = AA  length = 232
FEATURE                 Location/Qualifiers
source                  1..232
                        mol_type = protein
                        organism = synthetic construct
SEQUENCE: 378
EPKSSDKTHT CPPCPAPELL GGDSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPCR DELTKNQVSL WCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 379          moltype = AA  length = 232
FEATURE                 Location/Qualifiers
source                  1..232
                        mol_type = protein
                        organism = synthetic construct
SEQUENCE: 379
EPKSSDKTHT CPPCPAPELL GGDSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVCTLPPSR DELTKNQVSL SCAVKGFYPS DIAVEWESNG QPENNYKTTP  180
PVLDSDGSFF LVSKLTVDKS RWQQGNVFSC SVMHEALHNH YTQKSLSLSP GK          232

SEQ ID NO: 380          moltype =   length =
SEQUENCE: 380
000

SEQ ID NO: 381          moltype =   length =
SEQUENCE: 381
000

SEQ ID NO: 382          moltype =   length =
SEQUENCE: 382
000

SEQ ID NO: 383          moltype =   length =
SEQUENCE: 383
000
```

-continued

```
SEQ ID NO: 384          moltype = AA  length = 4
FEATURE                 Location/Qualifiers
source                  1..4
                        mol_type = protein
                        organism = synthetic construct
SEQUENCE: 384
GGGS                                                                    4
```

The invention claimed is:

1. A molecule comprising a first polypeptide and a second polypeptide, wherein the first polypeptide comprises a first Fc domain comprising the amino acid sequence of SEQ ID NO: 107 or a fragment thereof comprising a P238D mutation (according to the EU numbering scheme) and a TSHR autoantigen domain variant comprising the amino acid sequence of SEQ ID NO: 3, and the second polypeptide comprises a second Fc domain comprising the amino acid sequence of SEQ ID NO: 108 or a fragment thereof comprising a P238D mutation (according to the EU numbering scheme); wherein the first Fc domain and the second Fc domain form a heterodimer of the first polypeptide and the second polypeptide.

2. The molecule of claim 1, where the second polypeptide does not comprise a TSHR autoantigen domain variant.

3. The molecule of claim 1, wherein the first polypeptide and/or the second polypeptide comprises a signal peptide.

4. The molecule of claim 3, wherein the first polypeptide comprises the amino acid sequence of SEQ ID NO: 225 and the second polypeptide comprises the amino acid sequence of SEQ ID NO: 228.

5. The molecule of claim 1, wherein the first and/or second Fc domains have increased binding to FcγRIIB, relative to a corresponding wildtype human IgG1 Fc domain.

6. The molecule of claim 1, wherein upon binding of two molecules to an anti-TSHR autoantibody, an immune complex is formed that has enhanced binding kinetics with FcγRIIB relative to an immune complex that comprises the anti-TSHR autoantibody and two corresponding molecules with wild-type human IgG1 Fc domains.

7. The molecule of claim 1, wherein upon binding of two molecules to an anti-TSHR autoantibody, an immune complex is formed that has enhanced binding kinetics with FcγRIIB relative to an immune complex that comprises the anti-TSHR autoantibody bound to only a single molecule.

8. The molecule of claim 7, wherein the enhanced binding kinetics comprise an increase in the rate of association, a decrease in the rate of disassociation, and/or a change in the equilibrium dissociation constant.

9. The molecule of claim 7, wherein the enhanced binding kinetics produce an increase in avidity, stability, strength, frequency, and/or duration of binding between the immune complex and FcγRIIB.

10. The molecule of claim 7, wherein the enhanced binding kinetics comprises at least 30% greater binding affinity of the immune complex to FcγRIIB.

11. The molecule of claim 10, wherein the binding affinity comprises binding affinity to a cell line overexpressing FcγRIIB measured by flow cytometry.

12. The molecule of claim 1, wherein the molecule preferentially binds to immune cells expressing FcγRIIB over immune cells expressing FcγRIIA.

13. The molecule of claim 1, wherein the molecule is capable of selectively depleting anti-TSHR autoantibodies that bind to the TSHR autoantigen domain variant when administered to a human subject.

14. The molecule of claim 13, wherein the anti-TSHR autoantibodies that bind to the TSHR autoantigen domain variant are selectively depleted by uptake into cells and shuttling of the anti-TSHR autoantibodies to the lysosome for degradation.

15. A nucleic acid comprising a first nucleotide sequence encoding a first polypeptide and a second nucleotide sequence encoding a second polypeptide, wherein the first polypeptide comprises a first Fc domain comprising the amino acid sequence of SEQ ID NO: 107 or a fragment thereof comprising a P238D mutation (according to the EU numbering scheme) and a TSHR autoantigen domain variant comprising the amino acid sequence of SEQ ID NO: 3, and the second polypeptide comprises a second Fc domain comprising the amino acid sequence of SEQ ID NO: 108 or a fragment thereof comprising a P238D mutation (according to the EU numbering scheme); wherein the first Fc domain and the second Fc domain form a heterodimer of the first polypeptide and the second polypeptide.

16. A host cell containing the nucleic acid of claim 15.

17. A vector comprising the nucleic acid of claim 15.

18. A pharmaceutical composition comprising the molecule of claim 1 and a pharmaceutically acceptable carrier.

19. A method of making a molecule, the method comprising expressing the nucleic acid of claim 15 in a host cell, and recovering the molecule.

20. A method of treating a human subject suffering from or susceptible to an autoimmune disease, the method comprising administering to the human subject a pharmaceutical composition comprising the molecule of claim 1 and a pharmaceutically acceptable carrier.

21. A method of selectively depleting anti-TSHR autoantibodies in a human subject, the method comprising administering to the human subject a pharmaceutical composition comprising the molecule of claim 1 and a pharmaceutically acceptable carrier.

22. A method of treating a human subject suffering from or susceptible to Graves' Disease (GD), Thyroid Eye Disease, or another autoimmune disease involving anti-TSHR autoantibodies, the method comprising administering to the human subject a pharmaceutical composition comprising the molecule of claim 1 and a pharmaceutically acceptable carrier.

23. The molecule of claim 1, wherein the C-terminus of the TSHR autoantigen domain variant is covalently linked to the N-terminus of the first Fc domain.

24. The molecule of claim 23, where the second polypeptide does not comprise a TSHR autoantigen domain variant.

25. The molecule of claim 1, wherein the first polypeptide comprises the amino acid sequence of SEQ ID NO: 245.

26. The molecule of claim 25, where the second polypeptide does not comprise a TSHR autoantigen domain variant.

27. The nucleic acid of claim 15, wherein the C-terminus of the TSHR autoantigen domain variant is covalently linked to the N-terminus of the first Fc domain.

28. The nucleic acid of claim 27, where the second polypeptide does not comprise a TSHR autoantigen domain variant.

29. The nucleic acid of claim 15, wherein the first polypeptide comprises the amino acid sequence of SEQ ID NO: 245.

30. The nucleic acid of claim 29, where the second polypeptide does not comprise a TSHR autoantigen domain variant.

* * * * *